United States Patent
Williams et al.

(10) Patent No.: US 12,037,407 B2
(45) Date of Patent: Jul. 16, 2024

(54) IMMUNE CELLS HAVING CO-EXPRESSED shRNAS AND LOGIC GATE SYSTEMS

(71) Applicant: Arsenal Biosciences, Inc., South San Francisco, CA (US)

(72) Inventors: Jasper Williams, San Francisco, CA (US); Michelle Nguyen, San Francisco, CA (US); Anzhi Yao, San Francisco, CA (US); Stephen Santoro, Daly City, CA (US); Aaron Cooper, Berkeley, CA (US); John Gagnon, San Francisco, CA (US); Adam Litterman, San Francisco, CA (US); Omar Khan, Philadelphia, PA (US); Natalie Bezman, Foster City, CA (US); Katherine Harris, Newark, CA (US); Harbani Kaur Malik Chaudhry, Oakland, CA (US); Nicole Allen, Fremont, CA (US)

(73) Assignee: Arsenal Biosciences, Inc., South San Francisco, CA (US)

( * ) Notice: Subject to any disclaimer, the term of this patent is extended or adjusted under 35 U.S.C. 154(b) by 0 days.

(21) Appl. No.: 18/311,856

(22) Filed: May 3, 2023

(65) Prior Publication Data

US 2023/0340139 A1 Oct. 26, 2023

Related U.S. Application Data

(63) Continuation of application No. PCT/US2022/078158, filed on Oct. 14, 2022.

(60) Provisional application No. 63/303,422, filed on Jan. 26, 2022, provisional application No. 63/255,889, filed on Oct. 14, 2021, provisional application No. 63/255,887, filed on Oct. 14, 2021, provisional application No. 63/255,891, filed on Oct. 14, 2021.

(51) Int. Cl.
  *C07K 16/28* (2006.01)
  *A61P 35/00* (2006.01)

(52) U.S. Cl.
  CPC .......... *C07K 16/2878* (2013.01); *A61P 35/00* (2018.01); *C07K 16/2896* (2013.01); *C07K 2317/565* (2013.01); *C07K 2317/73* (2013.01); *C07K 2317/76* (2013.01)

(58) Field of Classification Search
  CPC .............................. A61P 35/00; C07K 16/2878
  See application file for complete search history.

(56) References Cited

U.S. PATENT DOCUMENTS

| | | |
|---|---|---|
| 5,081,227 A | 1/1992 | Millan |
| 6,485,961 B1 | 11/2002 | Meserol |
| 6,485,974 B1 | 11/2002 | Popoff |
| 6,773,669 B1 | 8/2004 | Holaday et al. |
| 6,824,978 B1 | 11/2004 | Cox, III et al. |
| 7,029,916 B2 | 4/2006 | Dzekunov et al. |
| 7,081,518 B1 | 7/2006 | Pastan et al. |
| 7,186,559 B2 | 3/2007 | Dzekunov et al. |
| 7,361,752 B2 | 4/2008 | Heidenreich et al. |
| 7,446,190 B2 | 11/2008 | Sadelain et al. |
| 7,771,984 B2 | 8/2010 | Dzekunov et al. |
| 7,991,559 B2 | 8/2011 | Dzekunov et al. |
| 8,133,733 B2 | 3/2012 | Khan |
| 8,252,526 B2 | 8/2012 | Rao |
| 8,586,363 B2 | 11/2013 | Voytas et al. |
| 8,697,359 B1 | 4/2014 | Zhang |
| 8,795,965 B2 | 8/2014 | Zhang |
| 8,829,264 B2 | 9/2014 | Hannon et al. |
| 8,911,993 B2 | 12/2014 | June et al. |
| 9,221,886 B2 | 12/2015 | Liu et al. |
| 9,272,002 B2 | 3/2016 | Powell, Jr. et al. |
| 9,290,748 B2 | 3/2016 | Danos et al. |
| 9,409,992 B2 | 8/2016 | Ho et al. |
| 9,416,190 B2 | 8/2016 | Ho et al. |
| 9,512,446 B1 | 12/2016 | Joung et al. |
| 9,526,784 B2 | 12/2016 | Liu et al. |
| 9,556,431 B2 | 1/2017 | Rao |
| 9,572,836 B2 | 2/2017 | June et al. |
| 9,629,877 B2 | 4/2017 | Cooper et al. |
| 9,714,278 B2 | 7/2017 | June et al. |
| 9,737,604 B2 | 8/2017 | Liu et al. |
| 9,745,368 B2 | 8/2017 | Milone et al. |
| 9,758,775 B2 | 9/2017 | Voytas et al. |
| 9,765,156 B2 | 9/2017 | June et al. |
| 9,783,591 B2 | 10/2017 | June et al. |

(Continued)

FOREIGN PATENT DOCUMENTS

| | | |
|---|---|---|
| AU | 2015339743 A1 | 4/2017 |
| AU | 2015339744 A1 | 4/2017 |

(Continued)

OTHER PUBLICATIONS

McCarthy et al. (J. Immunol. Methods, 251(1-2): 137-149, 2001) (Year: 2001).*

(Continued)

*Primary Examiner* — Gregory S Emch
*Assistant Examiner* — Ashley H. Gao
(74) *Attorney, Agent, or Firm* — Goodwin Procter LLP

(57) ABSTRACT

Provided herein are recombinant nucleic acids encoding chimeric priming receptors that bind ALPG/P, chimeric antigen receptors that bind MSLN, and shRNA that target FAS, PTPN2, and/or TOX. Also provided are systems of chimeric priming receptors that bind ALPG/P, chimeric antigen receptors that bind MSLN, and shRNA that target FAS, PTPN2, and/or TOX, cells expressing such proteins and shRNA, and methods of use thereof.

71 Claims, 59 Drawing Sheets

Specification includes a Sequence Listing.

(56) References Cited

U.S. PATENT DOCUMENTS

| | | |
|---|---|---|
| 9,803,022 B2 | 10/2017 | Ho et al. |
| 9,844,569 B2 | 12/2017 | Gros et al. |
| 9,855,297 B2 | 1/2018 | Duchateau et al. |
| 9,855,298 B2 | 1/2018 | Bot et al. |
| 9,890,393 B2 | 2/2018 | Duchateau et al. |
| 9,944,931 B2 | 4/2018 | Wucherpfennig et al. |
| 9,987,308 B2 | 6/2018 | Riddell et al. |
| 10,040,846 B2 | 8/2018 | Frigault et al. |
| 10,093,717 B2 | 10/2018 | Li et al. |
| 10,105,391 B2 | 10/2018 | Wu et al. |
| 10,117,896 B2 | 11/2018 | Powell, Jr. et al. |
| 10,150,816 B2 | 12/2018 | Abbot et al. |
| 10,155,038 B2 | 12/2018 | Rabinovich et al. |
| 10,183,993 B2 | 1/2019 | Orentas et al. |
| 10,195,274 B2 | 2/2019 | Mumm et al. |
| 10,196,608 B2 | 2/2019 | Poirot et al. |
| 10,208,285 B2 | 2/2019 | Baeuerle et al. |
| 10,239,948 B2 | 3/2019 | Juillerat et al. |
| 10,266,592 B2 | 4/2019 | Jensen |
| 10,287,354 B2 | 5/2019 | Brogdon et al. |
| 10,287,606 B2 | 5/2019 | Valamehr et al. |
| 10,357,514 B2 | 7/2019 | June et al. |
| 10,370,452 B2 | 8/2019 | Themeli et al. |
| 10,377,988 B2 | 8/2019 | Rubinstein et al. |
| 10,391,126 B2 | 8/2019 | Cooper et al. |
| 10,392,446 B2 | 8/2019 | Stephan |
| 10,473,661 B2 | 11/2019 | Geskin et al. |
| 10,501,519 B2 | 12/2019 | June et al. |
| 10,550,179 B2 | 2/2020 | Orentas et al. |
| 10,858,443 B2 | 12/2020 | Ngo |
| 10,876,120 B2 | 12/2020 | Wucherpfennig et al. |
| 11,033,584 B2 | 6/2021 | Roth et al. |
| 11,065,278 B2 | 7/2021 | Riddell et al. |
| 11,067,577 B2 | 7/2021 | Geskin et al. |
| 11,083,753 B1 | 8/2021 | Roth et al. |
| 11,155,616 B2 | 10/2021 | Jensen |
| 11,161,907 B2 | 11/2021 | June et al. |
| 11,202,801 B2 | 12/2021 | Roybal et al. |
| 11,203,758 B2 | 12/2021 | Zhao et al. |
| 11,299,536 B2 | 4/2022 | Frigault et al. |
| 11,331,346 B2 | 5/2022 | Roth et al. |
| 11,332,744 B1 | 5/2022 | Zheng et al. |
| 11,401,332 B2 | 8/2022 | Lim et al. |
| 11,590,171 B2 | 2/2023 | Roth et al. |
| 11,597,754 B2 | 3/2023 | June et al. |
| 11,597,934 B2 | 3/2023 | Wucherpfennig et al. |
| 11,617,766 B2 | 4/2023 | Roybal et al. |
| 11,814,624 B2 | 11/2023 | Roth et al. |
| 11,865,201 B2 | 1/2024 | Kruck et al. |
| 2002/0004490 A1 | 1/2002 | Dean et al. |
| 2002/0064802 A1 | 5/2002 | Raschke et al. |
| 2002/0160940 A1 | 10/2002 | Case et al. |
| 2003/0087817 A1 | 5/2003 | Cox et al. |
| 2003/0165892 A1 | 9/2003 | Park et al. |
| 2003/0232410 A1 | 12/2003 | Liljedahl et al. |
| 2004/0121353 A1 | 6/2004 | Lewis et al. |
| 2005/0048647 A1 | 3/2005 | Taira et al. |
| 2005/0064596 A1 | 3/2005 | Riemen et al. |
| 2005/0136040 A1 | 6/2005 | Hart et al. |
| 2006/0087522 A1 | 4/2006 | Muller-Hartmann et al. |
| 2006/0094095 A1 | 5/2006 | Mueller-Hartmann |
| 2006/0182736 A1 | 8/2006 | Kim et al. |
| 2007/0083334 A1 | 4/2007 | Mintz et al. |
| 2007/0161031 A1 | 7/2007 | Trinklein et al. |
| 2007/0254291 A1 | 11/2007 | Cui et al. |
| 2009/0047211 A1 | 2/2009 | Pastan et al. |
| 2009/0082250 A1 | 3/2009 | Hart et al. |
| 2010/0093617 A1 | 4/2010 | Barrangou et al. |
| 2010/0105134 A1 | 4/2010 | Quay et al. |
| 2011/0145940 A1 | 6/2011 | Voytas et al. |
| 2011/0265198 A1 | 10/2011 | Gregory et al. |
| 2012/0077270 A1 | 3/2012 | Hart et al. |
| 2012/0088842 A1 | 4/2012 | Dzekunov |
| 2012/0110685 A1 | 5/2012 | Bonas et al. |
| 2013/0236504 A1 | 9/2013 | Alexis et al. |
| 2014/0017213 A1 | 1/2014 | Li et al. |
| 2014/0068797 A1 | 3/2014 | Doudna et al. |
| 2014/0189896 A1 | 7/2014 | Zhang et al. |
| 2014/0199767 A1 | 7/2014 | Barrangou et al. |
| 2014/0294773 A1 | 10/2014 | Brouns et al. |
| 2014/0301990 A1 | 10/2014 | Gregory et al. |
| 2014/0349402 A1 | 11/2014 | Cooper et al. |
| 2015/0031624 A1 | 1/2015 | Feldman et al. |
| 2015/0071903 A1 | 3/2015 | Liu et al. |
| 2015/0110762 A1 | 4/2015 | Holmes et al. |
| 2015/0140664 A1 | 5/2015 | Byrne et al. |
| 2015/0164954 A1 | 6/2015 | Bonini et al. |
| 2015/0259704 A1 | 9/2015 | Church et al. |
| 2015/0283265 A1 | 10/2015 | Peyman |
| 2015/0322457 A1 | 11/2015 | Kim et al. |
| 2015/0344912 A1 | 12/2015 | Kim et al. |
| 2015/0344971 A1 | 12/2015 | Geskin et al. |
| 2015/0368360 A1 | 12/2015 | Liang et al. |
| 2016/0002626 A1 | 1/2016 | Zhou et al. |
| 2016/0017366 A1 | 1/2016 | Chen et al. |
| 2016/0024524 A1 | 1/2016 | Joung et al. |
| 2016/0053274 A1 | 2/2016 | D'Halluin |
| 2016/0102322 A1 | 4/2016 | Ravinder et al. |
| 2016/0143953 A1 | 5/2016 | Gregory et al. |
| 2016/0160210 A1 | 6/2016 | Mali et al. |
| 2016/0200779 A1 | 7/2016 | Liu et al. |
| 2016/0264999 A1 | 9/2016 | Rao et al. |
| 2016/0298134 A1 | 10/2016 | Chen et al. |
| 2016/0298135 A1 | 10/2016 | Chen et al. |
| 2016/0298138 A1 | 10/2016 | Chen et al. |
| 2016/0304893 A1 | 10/2016 | Daboussi et al. |
| 2016/0311917 A1 | 10/2016 | Beatty et al. |
| 2016/0354487 A1 | 12/2016 | Zhang et al. |
| 2017/0000743 A1 | 1/2017 | Ghoroghchian et al. |
| 2017/0016027 A1 | 1/2017 | Lee et al. |
| 2017/0044569 A9 | 2/2017 | Church et al. |
| 2017/0051068 A1 | 2/2017 | Pillarisetti et al. |
| 2017/0073705 A1 | 3/2017 | Chen et al. |
| 2017/0175128 A1 | 6/2017 | Welstead et al. |
| 2017/0191082 A1 | 7/2017 | Chen et al. |
| 2017/0211075 A1 | 7/2017 | Lee et al. |
| 2017/0224731 A1 | 8/2017 | Tiganis et al. |
| 2017/0267755 A1 | 9/2017 | Scholler |
| 2017/0290858 A1 | 10/2017 | Zhao et al. |
| 2017/0296676 A1 | 10/2017 | Stephan et al. |
| 2017/0335331 A1 | 11/2017 | Zhao et al. |
| 2017/0362635 A1 | 12/2017 | Chamberlain et al. |
| 2018/0044700 A1 | 2/2018 | Doudna et al. |
| 2018/0127786 A1 | 5/2018 | Bouchon et al. |
| 2018/0161447 A1 | 6/2018 | Watson et al. |
| 2018/0171298 A1 | 6/2018 | Duchateau et al. |
| 2018/0258149 A1 | 9/2018 | Motz et al. |
| 2018/0312848 A1 | 11/2018 | Zhao et al. |
| 2018/0369409 A1 | 12/2018 | Liu et al. |
| 2019/0136230 A1 | 5/2019 | Sather et al. |
| 2019/0136263 A1 | 5/2019 | Kornete et al. |
| 2019/0185849 A1 | 6/2019 | Lundberg et al. |
| 2019/0262399 A1 | 8/2019 | Wang et al. |
| 2019/0309065 A1 | 10/2019 | Freeman et al. |
| 2020/0109400 A1 | 4/2020 | Burge et al. |
| 2020/0208174 A1 | 7/2020 | Cabaniols et al. |
| 2020/0330515 A1 | 10/2020 | Maus et al. |
| 2020/0347386 A1 | 11/2020 | Benson et al. |
| 2020/0352999 A1 | 11/2020 | Rao et al. |
| 2020/0362344 A1 | 11/2020 | Minshull et al. |
| 2020/0384030 A1 | 12/2020 | Emtage et al. |
| 2020/0399383 A1* | 12/2020 | Scholler .............. C07K 16/2878 |
| 2020/0407728 A1 | 12/2020 | Zhao et al. |
| 2021/0052648 A1 | 2/2021 | Tiganis et al. |
| 2021/0107965 A1 | 4/2021 | Lim et al. |
| 2021/0107996 A1 | 4/2021 | Wu et al. |
| 2021/0139914 A1 | 5/2021 | Wucherpfennig et al. |
| 2021/0246186 A1 | 8/2021 | Roybal et al. |
| 2021/0254097 A1 | 8/2021 | O'Dea et al. |
| 2022/0064653 A1 | 3/2022 | Roth et al. |
| 2022/0127616 A1 | 4/2022 | Zheng et al. |
| 2022/0235380 A1 | 7/2022 | Williams et al. |
| 2022/0324982 A1 | 10/2022 | Lim et al. |
| 2022/0348688 A1 | 11/2022 | Wu et al. |

(56) References Cited

U.S. PATENT DOCUMENTS

| | | | |
|---|---|---|---|
| 2023/0104938 A1 | 4/2023 | Boese et al. | |
| 2023/0183709 A1 | 6/2023 | Roybal et al. | |
| 2023/0242612 A1 | 8/2023 | June et al. | |
| 2023/0310502 A1 | 10/2023 | Roth et al. | |

FOREIGN PATENT DOCUMENTS

| | | | | |
|---|---|---|---|---|
| EP | 429242 A | * | 5/1991 | ........... A61K 39/395 |
| EP | 2689010 B1 | | 1/2014 | |
| EP | 3215166 A1 | | 9/2017 | |
| EP | 3215168 A1 | | 9/2017 | |
| EP | 3737765 A1 | | 11/2020 | |
| EP | 3119423 | | 12/2022 | |
| JP | 6879910 B2 | | 6/2021 | |
| WO | WO-1991/007500 A1 | | 5/1991 | |
| WO | WO-1999/032619 A1 | | 7/1999 | |
| WO | WO-2000/001846 A2 | | 1/2000 | |
| WO | WO-2000/041566 A1 | | 7/2000 | |
| WO | WO-2000/044895 A1 | | 8/2000 | |
| WO | WO-2000/044914 A1 | | 8/2000 | |
| WO | WO-2001/029058 A1 | | 4/2001 | |
| WO | WO-2001/036646 A1 | | 5/2001 | |
| WO | WO-2001/083751 A2 | | 11/2001 | |
| WO | WO-2003/033701 A1 | | 4/2003 | |
| WO | WO-2003/080809 A2 | | 10/2003 | |
| WO | WO-2004/030634 A2 | | 4/2004 | |
| WO | WO-2004/092194 A2 | | 10/2004 | |
| WO | WO-2004/108883 A2 | | 12/2004 | |
| WO | WO-2005/123962 A2 | | 12/2005 | |
| WO | WO-2006/001614 A1 | | 1/2006 | |
| WO | WO-2007/025097 A2 | | 3/2007 | |
| WO | WO-2008/021207 A2 | | 2/2008 | |
| WO | WO-2008/109532 A2 | | 9/2008 | |
| WO | WO-2011/059836 A2 | | 5/2011 | |
| WO | WO-2011/072246 A2 | | 6/2011 | |
| WO | WO-2011/139336 A1 | | 11/2011 | |
| WO | WO-2013/134349 A1 | | 9/2013 | |
| WO | WO-2013/176772 A1 | | 11/2013 | |
| WO | WO-2014/031687 A1 | | 2/2014 | |
| WO | WO-2014/089290 A1 | | 6/2014 | |
| WO | WO-2014/093661 A2 | | 6/2014 | |
| WO | WO-2014/144761 A2 | | 9/2014 | |
| WO | WO-2014/153470 A2 | | 9/2014 | |
| WO | WO-2014/161821 A1 | | 10/2014 | |
| WO | WO-2014/164554 A1 | | 10/2014 | |
| WO | WO-2015/035136 A2 | | 3/2015 | |
| WO | WO-2015/048690 A1 | | 4/2015 | |
| WO | WO-2015/057980 A1 | | 4/2015 | |
| WO | WO-2015/073867 A1 | | 5/2015 | |
| WO | WO-2015/086795 A1 | | 6/2015 | |
| WO | WO-2015/089419 A2 | | 6/2015 | |
| WO | WO-2015/089462 A1 | | 6/2015 | |
| WO | WO-2015/089486 A2 | | 6/2015 | |
| WO | WO-2015/115903 A1 | | 8/2015 | |
| WO | WO-2015/117021 A1 | | 8/2015 | |
| WO | WO-2015/142675 A2 | | 9/2015 | |
| WO | WO-2015/157391 A1 | | 10/2015 | |
| WO | WO-2015/089419 A9 | | 11/2015 | |
| WO | WO-2016/036754 A1 | | 3/2016 | |
| WO | WO-2016/049251 A1 | | 3/2016 | |
| WO | WO-2016/057951 A2 | | 4/2016 | |
| WO | WO-2016/097751 A1 | | 6/2016 | |
| WO | WO-2016/118697 A1 | | 7/2016 | |
| WO | WO-2016/123578 A1 | | 8/2016 | |
| WO | WO-2016/118697 A9 | | 9/2016 | |
| WO | WO-2016/135559 A2 | | 9/2016 | |
| WO | WO-2016/172359 A2 | | 10/2016 | |
| WO | WO-2016/196388 A1 | | 12/2016 | |
| WO | WO-2016/205680 A1 | | 12/2016 | |
| WO | WO-2016/205703 A1 | | 12/2016 | |
| WO | WO-2017/004509 A1 | | 1/2017 | |
| WO | WO-2017/011519 A1 | | 1/2017 | |
| WO | WO-2017/035659 A1 | | 3/2017 | |
| WO | WO-2017/053729 A1 | | 3/2017 | |
| WO | WO-2017/058751 A1 | | 4/2017 | |
| WO | WO-2017/062451 A1 | | 4/2017 | |
| WO | WO-2017/070056 A1 | | 4/2017 | |
| WO | WO-2017/070169 A1 | | 4/2017 | |
| WO | WO-2017/070429 A1 | | 4/2017 | |
| WO | WO-2017/079673 A1 | | 5/2017 | |
| WO | WO-2017/091630 A1 | | 6/2017 | |
| WO | WO-2017/115128 A2 | | 7/2017 | |
| WO | WO-2017/156484 A1 | | 9/2017 | |
| WO | WO-2017/177137 A1 | | 10/2017 | |
| WO | WO-2017/180989 A2 | | 10/2017 | |
| WO | WO-2017/181110 A1 | | 10/2017 | |
| WO | WO-2017/186550 A1 | | 11/2017 | |
| WO | WO-2017/189336 A1 | | 11/2017 | |
| WO | WO-2017/210334 A1 | | 12/2017 | |
| WO | WO-2017/220527 A1 | | 12/2017 | |
| WO | WO-2018/035387 A1 | | 2/2018 | |
| WO | WO-2018/039084 A1 | | 3/2018 | |
| WO | WO-2018/068135 A1 | | 4/2018 | |
| WO | WO-2018/073391 A1 | | 4/2018 | |
| WO | WO-2018/073393 A2 | | 4/2018 | |
| WO | WO-2018/094291 A1 | | 5/2018 | |
| WO | WO-2018/208067 A1 | | 11/2018 | |
| WO | WO-2018/232356 A1 | | 12/2018 | |
| WO | WO-2019/084495 A1 | | 5/2019 | |
| WO | WO-2019/084552 A1 | | 5/2019 | |
| WO | WO-2019/104245 A1 | | 5/2019 | |
| WO | WO-2019/169233 A1 | | 9/2019 | |
| WO | WO-2019/178422 A1 | | 9/2019 | |
| WO | WO-2019/226998 A1 | | 11/2019 | |
| WO | WO-2019/240934 A1 | | 12/2019 | |
| WO | WO-2020/014235 A1 | | 1/2020 | |
| WO | WO-2020/043152 A1 | | 3/2020 | |
| WO | WO-2020/057486 A1 | | 3/2020 | |
| WO | WO-2020/113029 A2 | | 6/2020 | |
| WO | WO-2020/123871 A1 | | 6/2020 | |
| WO | WO-2020/132521 A1 | | 6/2020 | |
| WO | WO-2020/072126 A2 | | 7/2020 | |
| WO | WO-2020/150534 A2 | | 8/2020 | |
| WO | WO-2020/163365 A2 | | 8/2020 | |
| WO | WO-2020/186219 A1 | | 9/2020 | |
| WO | WO-2020/219682 A2 | | 10/2020 | |
| WO | WO-2020/221939 A1 | | 11/2020 | |
| WO | 2021/061859 A1 | | 4/2021 | |
| WO | 2021/061862 A1 | | 4/2021 | |
| WO | WO-2021/061872 A1 | | 4/2021 | |
| WO | WO-2021/062227 A2 | | 4/2021 | |
| WO | WO-2021/097521 A1 | | 5/2021 | |
| WO | WO-2021/108650 A1 | | 6/2021 | |
| WO | WO-2021/108665 A1 | | 6/2021 | |
| WO | WO-2021/108671 A1 | | 6/2021 | |
| WO | WO-2021/155071 A1 | | 8/2021 | |
| WO | WO-2021/207526 A1 | | 10/2021 | |
| WO | PCT/US22/13911 | * | 1/2022 | |
| WO | WO-2022/093846 A1 | | 5/2022 | |
| WO | 2022150831 A1 | | 7/2022 | |
| WO | WO-2023/064876 A1 | | 4/2023 | |
| WO | 2023104938 A1 | | 6/2023 | |

OTHER PUBLICATIONS

Lin et al. (African Journal of Biotechnology, 10(79):18294-18302, 2011) (Year: 2011).*
International Search Report and Wirtten Opinion for PCT/US2022/078158 filed Oct. 14, 2022, mailed Jul. 21, 2023. 20 pages.
Jamnani et al. "T cells expressing VHH-directed oligoclonal chimeric HER2 antigen receptors: Towards tumor-directed oligoclonal T cell therapy," Biochimica et Biophysica Acta, 2014, 378-386.
Maher et al. "Human T-lymphocyte cytotoxicity and proliferation directed by a single chimeric TCRζ/CD28 receptor," Nature Biotechnology, 2002, 20:71-75.
Rahbarizadeh et al. "Nanobody, New Agent for Combating Against Breast Cancer Cells," Breat Cancer—Current and Alternative Therapeutic Modalities, 2011, 347-370.
Rahbarizadeh et al. "Nanobody; an Old Concept and New Vehicle for Immunotargeting," Immunological Investigations, 2011, 40:299-338.

(56) References Cited

OTHER PUBLICATIONS

Hegde et al. "Combinatorional Targeting Offsets Antigen Escape and Enhances Effector Functions of Adoptively Transferred T Cells in Glioblastoma," Molecular Therapy, 2013, 21(11):2087-2101.
Sharifzadeh et al. "Genetically engineered T cells bearing chimeric nanoconstructed receptors harboring TAG-72-specific camelid single domain antibodies as targeting agents," Cancer Letters, 2013, 334:237-244.
Ahmed et al. "Immunotherapy for Osteosarcoma: Genetic Modification of T cells Overcomes Low Levels of Tumor Antigen Expression," Molecular Therapy, 17(10):1779-1787.
Dotti et al. "Design and Development of Therapies using Chimeric Antigen Receptor-Expressing T cells," Immunol Rev., 2014, 257(1):1-35.
Duong et al. "Enhancing the specificity of T-cell cultures for adoptive immunotherapy of cancer," Immunotherapy, 2011, 3(1):33-48.
Pirooznia et al. "The Construction of Chimeric T-Cell Receptor with Spacer Base of Modeling Study of VHH and MUC1 Interaction," Journal of Biomedicine and Biotechnology, 2011, 11 pages.
Fedorov et al. "PD-1- and CTLA-4-Based Inhibitory Chimeri Antigen Receptors (iCARs) Divert Off-Target Immunotherapy Responses," Immunotherapy, 2013, 5(215):1-32.
Kunkele et al. "Functional Tuning of CARs Reveals Signaling Threshold above Which CD8+ CTL Antitumor Potency is Attenuated due to Cell Fas-FasL-Dependent AICD," Cancer Immunol Res, 2015, 3(4):368-379.
Kershaw et al. "Gene-engineered T cells for cancer therapy," Nature Reviews, 2013, 13:525-541.
Kakarla et al. "CAR T cells for solid tumors: armed and ready to go?" Cancer J., 2014, 20(2):151-155.
Mao et al. "Immunological research using RNA interference technology," Immunology, 2007, 121:295-307.
Dotti et al. "Design and development of therapies using chimeric antigen receptor-expressing T cells," Immunological Reviews, 2013, 257(1):107-126.
Dotti et al. "Human cytotoxic T lymphocytes with reduced sensitivity to Fas-induced apoptosis," Blood, 205, 105(2):4677-4684.
Altschul, S.F. et al. (Oct. 5, 1990). "Basic local alignment search tool," J Mol Biol 215(3):403-410.
Aznauryan et al., "Discovery and Validation of Novel Human Genomic Safe Harbor Sites for Gene and Cell Therapies," https://doi.org/10.1101/2021.03.04.433856, Mar. 5, 2021, pp. 1-28.
Carbonnel et al. "Extensive small intestinal T-cell lymphoma of Low-Grade Malignancy Associated with a New Chromosomal Translocation," Cancer, 1994, 73:1286-91.
Chylinski et al. "The tracrRNA and Cas9 families of type II CRISPR-Cas immunity systems," RNA Biol., 2013, 10(5):726-37.
Devereux, J. et al. (Jan. 11, 1984). "A comprehensive set of sequence analysis programs for the VAX," Nucleic Acids Res. 12(Pt 1):387-395.
Dobin et al., "STAR: Ultrafast Universal RNA-seq Aligner," Bioinformatics, vol. 29, No. 1, 2013, pp. 15-21.
Du Dani, J.S. et al. (2018). "Harnessing Protease Activity to Improve Cancer Care," Annu. Rev. Cancer Biol. 2:353-376.
EA202090046, Office Action, Sep. 23, 2021, 2 pages.
EP18817563.2, Extended European Search Report, Feb. 12, 2021, 8 pages.
Esvelt et al. "Orthogonal Cas9 proteins for RNA-guided gene regulation and editing," Nat Methods, 2013, 10(11):1116-21.
Eyquem et al., "Targeting a CAR to the TRAC Locus with CRISPR/Cas9 Enhances Tumour Rejection," Letter, Nature, Mar. 2, 2017, vol. 543, pp. 113-131.
Frankel, M.E. et al. (1979). "The rapid determination of binding constants for antiviral antibodies by a radioimmunoassay. An analysis of the interaction between hybridoma proteins and influenza virus," Mol Immunol 16(2):101-106.
Geng et al. "Flow-through electroporation based on constant voltage for large-volume transfection of cells," J Control Release, 2010, 144(1):91-100.
Gordon, W.R. et al. (Jun. 22, 2015, e-published Jun. 4, 2015). "Mechanical Allostery: Evidence for a Force Requirement in the Proteolytic Activation of Notch," Dev Cell 33(6):729-736.
Gordon, W.R. et al. (Oct. 1, 2008). "The molecular logic of Notch signaling—a structural and biochemical perspective," J Cell Sci 121 (Pt 19):3109-3119.
Goudy et al. "Human IL2RA null mutation mediates immunodeficiency with lymphoproliferation and autoimmunity," Clinical Immunology, 2013, 146:248-261.
He et al., "Non-Viral and Viral Delivery Systems for CRISPR-Cas9 Technology in the Biomedical Field," Science China Life Sciences, vol. 60, No. 5, May 2017, pp. 458-467.
Higashimoto et al. "The woodchuck hepatitis virus post-transcriptional regulatory element reduces readthrough transcription from retroviral vectors," Gene Ther., 2007, 14(17):1298-304.
Hou et al. "Efficient genome engineering in human pluripotent stem cells using Cas9 from Neisseria meningitidis," Proc Natl Acad Sci U S A, 2013, 110(39):15644-9.
Hudecek et al. "Receptor affinity and extracellular domain modifications affect tumor recognition by ROR1-specific chimeric antigen receptor T cells," Clin Cancer Res., 2013, 19(12):3153-64.
International Preliminary Report on Patentability mailed on Dec. 26, 2019 for PCT Application No. PCT/US2018/037919, filed Jun. 15, 2018, 5 pages.
International Preliminary Report on Patentability mailed on Jan. 6, 2021 for PCT Application No. PCT/US2020/052327, filed Sep. 23, 2020, 6 pages.
International Search Report and Written Opinion for International Application No. PCT/US2022/078075 filed Oct. 13, 2022. Mailing date Feb. 14, 2023; 14 pages.
International Search Report and Written Opinion mailed on Jan. 6, 2021 for PCT Application No. PCT/US2020/052327, filed Sep. 23, 2020, 9 pages.
International Search Report and Written Opinion mailed on Jun. 29, 2022 for PCT Application No. PCT/US2022/13911, filed Jan. 26, 2022, 22 pages.
International Search Report and Written Opinion mailed on Mar. 2, 2022 for PCT Application No. PCT/US2021/056689, filed Oct. 26, 2021, 19 pages.
International Search Report and Written Opinion mailed on Sep. 18, 2018 for PCT Application No. PCT/US2018/037919, filed Jun. 15, 2018, 8 pages.
Invitation to pay additional fees for International Patent Application No. PCT/US2022/013911 mailed May 3, 2022. 4 pages.
Invitation to pay additional fees for International Patent Application No. PCT/US2022/078158 mailed Apr. 21, 2023. 3 pages.
Irion et al., Identification and Targeting of the ROSA26 Locus in Human Embryonic Stem Cells, Nature Biotechnology, 25(12), 2007, pp. 1477-1482.
Jinek et al. "A programmable dual-RNA-guided DNA endonuclease in adaptive bacterial immunity," Science, 2012, 337(6096):816-21.
Karenko et al. "Primary Cutaneous T-Cell Lymphomas SHow a Deletion or Translocation Affecting NAV3, the Human UNC-53 Homologue," Cancer Res, 2005, 65(18):8101-10.
Kim et al. "A novel electroporation method using a capillary and wire-type electrode," Biosens Bioelectron, 2008, 23(9):1353-60.
Kolb et al., "Site-Directed Genome Modification: Nucleic Acid and Protein Modules for Targeted Integration and Gene Correction," Tends in Biotechnology, vol. 23, Issue 8, Aug. 2005, pp. 399-406.
Kolde et al., "Robust Rank Agregation for Gene List Integration and Meta-Analysis," Bioinformatics, vol. 28, Issue 4, Feb. 15, 2012, pp. 573-580.
Lee et al., "Nanoparticle Delivery of Cas9 Ribonucleoprotein and Donor DNA in Vivo Induces Homology-Directed DNA Repair," Nat. Biomed. Eng., vol. 1, Oct. 2, 2017, pp. 889-901.
Li et al. "Functional dissection of NEAT1 using genome editing reveals substantial localization of the NEAT1_1 isoform outside paraspeckles," RNA, 2017, 23:872-881.
Li et al. "Highly efficient, large volume flow electroporation," Technol Cancer Res Treat, 2002, 1(5):341-50.
Li et al., "Optimization of Genome Engineering Approaches with the CRISPR/Cas9 System," Plos One, vol. 9, Issue 8, Aug. 28, 2014, pp. 1-10.

(56) References Cited

OTHER PUBLICATIONS

Liang et al., "Enhanced CRISPR/Cas9-Mediated Precise Genome Editing by Improved Design and Delivery of gRNA, Cas9 Nuclease, and Donor DNA," Journal of Biotechnology, vol. 241, Jan. 10, 2017, pp. 136-146.

Listgarten et al., "Prediction of Off-Target Activities for the End-to-End Design of CRISPR Guide RNAs," Nat Biomed Eng. Jan. 2018, vol. 2, No. 1, pp. 38-47.

Makarova et al. "Evolution and classification of the CRISPR-Cas systems," Nat Rev Microbiol., 2011, 9(6):467-77.

McCaffrey, A.P. et al. (Jul. 4, 2002). "RNA interference in adult mice," Nature 418(6893):38-39.

Morsut, L. et al. (Feb. 11, 2016, e-published Jan. 28, 2016). "Engineering Customized Cell Sensing and Response Behaviors Using Synthetic Notch Receptors," Cell 164(4):780-791.

Naso, M.F. et al. (Aug. 2017). "Adena-Associated Virus (AAV) as a Vector for Gene Therapy," BioDrugs 31 (4):317-334.

Nasri, M. et al. (Dec. 2014, e-published Mar. 6, 2014). "Production, purification and titration of a lentivirus-based vector for gene delivery purposes," Cytotechnology 66(6):1031-1038.

Nobles et al., "IGUIDE: An Improved Pipeline for Analyzing CRISPR Cleavage Specificity," Genome Biology, 2019, pp. 1-6.

Non-final Office Action for U.S. Appl. No. 17/239,484 mailed Nov. 30, 2021. 36 pages.

Non-final Office Action for U.S. Appl. No. 17/498,531 mailed Mar. 29, 2022. 15 pages.

Papapetrou et al., "Gene Insertion into Genomic Safe Harbors for Human Gene Therapy," Molecular Therapy, vol. 24, No. 4, Apr. 2016, pp. 678-684.

Paques et al., "Meganucleases and DNA Double-Strand Break-Induced Recombination: Perspectives for Gene Therapy," Current Gene Therapy 2007 7:49-66.

Pellenz et al., "New Human Chromosomal Sites with 'Safe Harbor' Potential for Targeted Transgene Insertion," Human Gene Therapy, 30(7), 2019, pp. 814-828.

Porter, D.L. et al. (Aug. 25, 2011, e-published Aug. 10, 2011). "Chimeric antigen receptor-modified T cells in chronic lymphoid leukemia," N. Engl J Med. 365(8): 725-733.

Porteus et al., "Gene Targeting Using Zinc Finger Nucleases," Nat Biotechnol. 23, 2005 23, pp. 967-973.

Putnam, D.A. (Jan. 15, 1996). "Antisense strategies and therapeutic applications," Am. J. Health Syst. Pharm. 53(2):151-160, erratum at Am. J. Health Syst. Pharm. 53:325.

Roth et al., "Reprogramming Human T Cell Function and Specificity with Non-Viral Genome Targeting," Nature, vol. 559, No. 7714, Jul. 19, 2018, 41 pages.

Roth, T. L., et al., "Rapid Discovery of Synthetic DNA Sequences to Rewrite Endogenous T Cell Circuits," Apr. 12, 2019, bioRxiv, 604561, 55 pages.

Roybal, K.T. et al. (Feb. 11, 2016, e-published Jan. 28, 2016). "Precision Tumor Recognition by T Cells With Combinatorial Antigen-Sensing Circuits," Cell 164(4):770-779.

Roybal, K.T. et al. (Oct. 6, 2016, e-published Sep. 29, 2016). "Engineering T Cells with Customized Therapeutic Response Programs Using Synthetic Notch Receptors," Cell 167(2):419-432.

Sadelain, M., Papapetrou, E. P., & Bushman, F. D., "Safe Harbours for the Integration of new DNA in the Human Genome," Nature Reviews—Cancer, 12(1 ), 51-58.

Sakuma, T. et al. (May 1, 2012). "Lentiviral vectors: basic to translational," Biochem J. 443(3):603-618.

Sampson et al. "A CRISPR/Cas system mediates bacterial innate immune evasion and virulence," Nature, 2013, 497(7448):254-7.

Samulski, R.J. et al. (Nov. 2014). "AAV-Mediated Gene Therapy for Research and Therapeutic Purposes," Annu Rev Viral 1 (1):427-451.

Schumann et al. "Generation of knock-in primary human T cells using Cas9 ribonucleoproteins," PNAS, 2015, 12(33):10437-10442.

Suzuki et al., "In Vivo Genome Editing Via CRISPR/Cas9 Mediated Homology-Independent Targeted Integration," Nature, 2016, 540(7631), pp. 144-149.

Vidarsson G. et al. (Oct. 20, 2014). "IgG subclasses and allotypes: from structure to effector functions," Frontiers Immunol. 5:520.

Wallen, Mark C., Thomas Gaj, and Carlos F. Barbas III. "Redesigning recombinase specificity for safe harbor sites in the human genome." PloS one 10.9 (2015): e0139123, pp. 1-16.

Wang et al. "Vortex-assisted DNA delivery," Lab Chip, 2010, 10(16):2057-61.

Watson, D.J. et al. (2003). Lentiviral Vectors for Gene Transfer to the Central Nervous System. Viral vectors for Gene Therapy: Methods and Protocols. Totowa, NJ, USA: Humana Press, pp. 383-404.

Xia, H. et al. (Oct. 2002, e-published Sep. 16, 2002). "SiRNA-mediated gene silencing in vitro and in vivo," Nat Biotechnol 20(10): 1006-1010.

Zetsche et al. "Cpf1 is a single RNA-guided endonuclease of a class 2 CRISPR-Cas system," Cell, 2015, 163(3):759-71.

Zhang et al. "Lipid nanoparticle-mediated efficient delivery of CRISPR/Cas9 for tumor therapy," NPG Asia Materials, 2017, 9:e441.

Zhang, X. et al. (Dec. 11, 2014). "The y-secretase complex: from structure to function," Frontiers Cell Neurosci 8:427.

Zufferey et al. "Woodchuck hepatitis virus posttranscriptional regulatory element enhances expression of transgenes delivered by retroviral vectors," J Virol., 1999, 73(4):2886-92.

\* cited by examiner

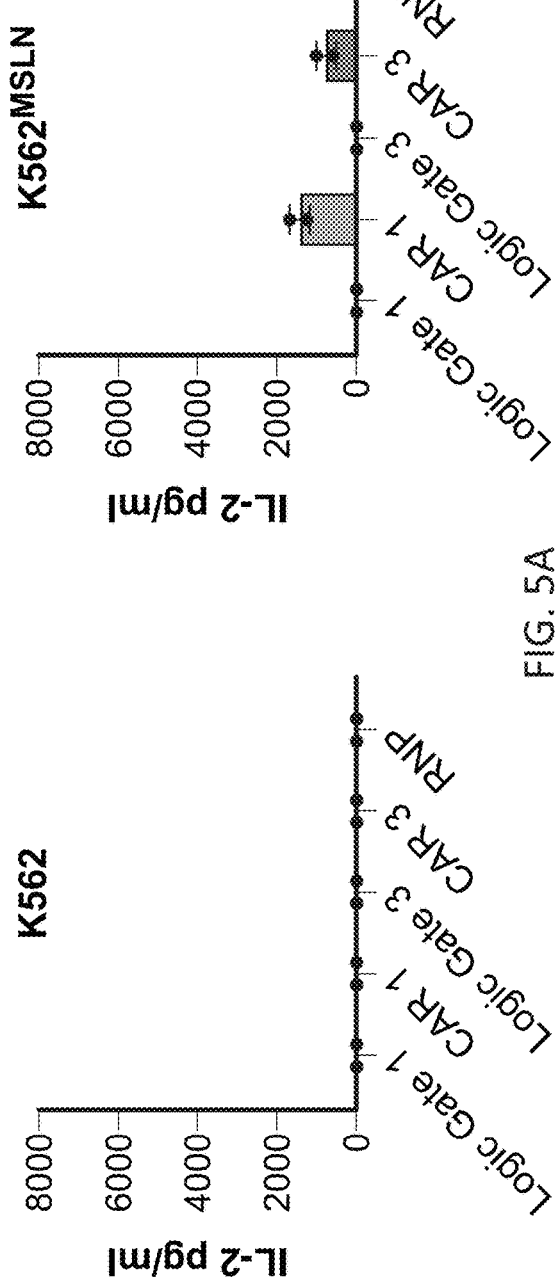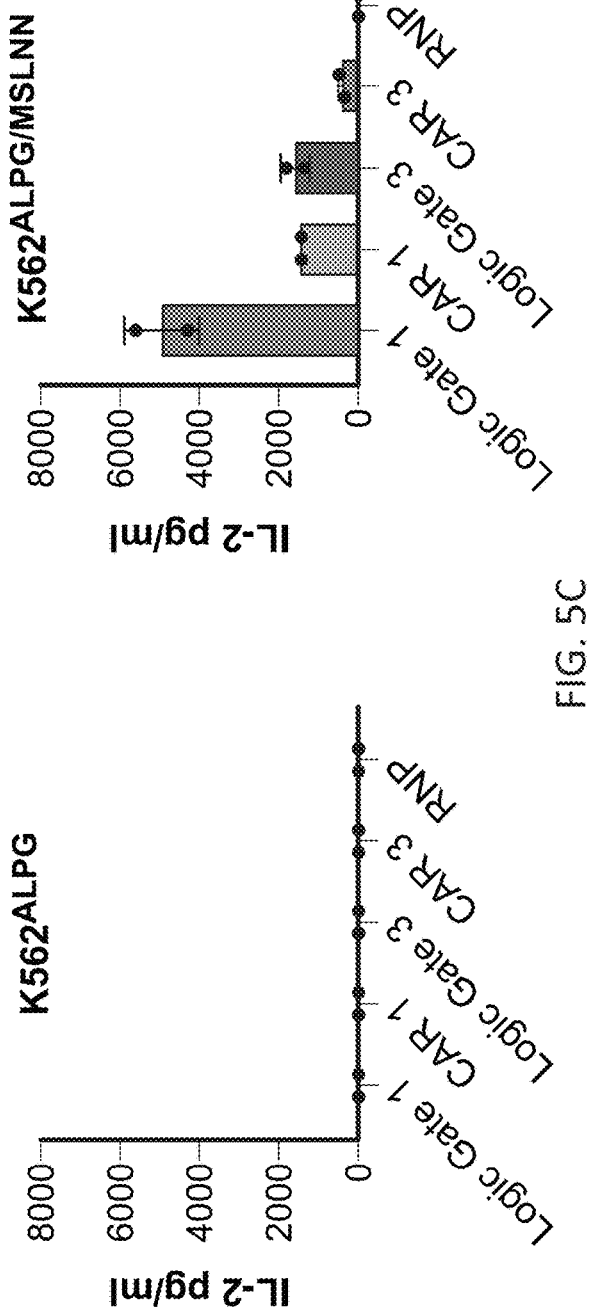
FIG. 5A  FIG. 5B  FIG. 5C  FIG. 5D

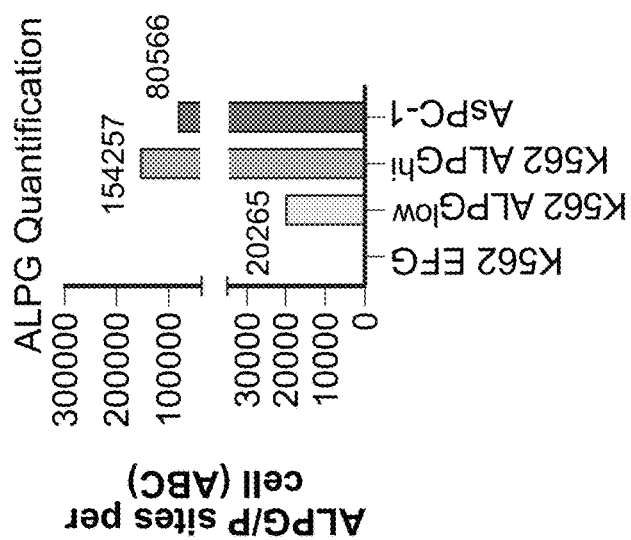
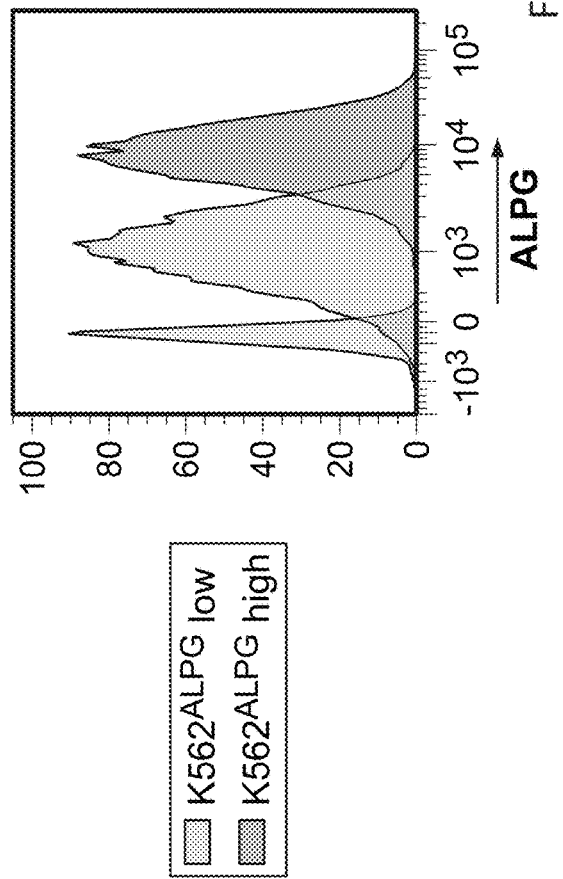
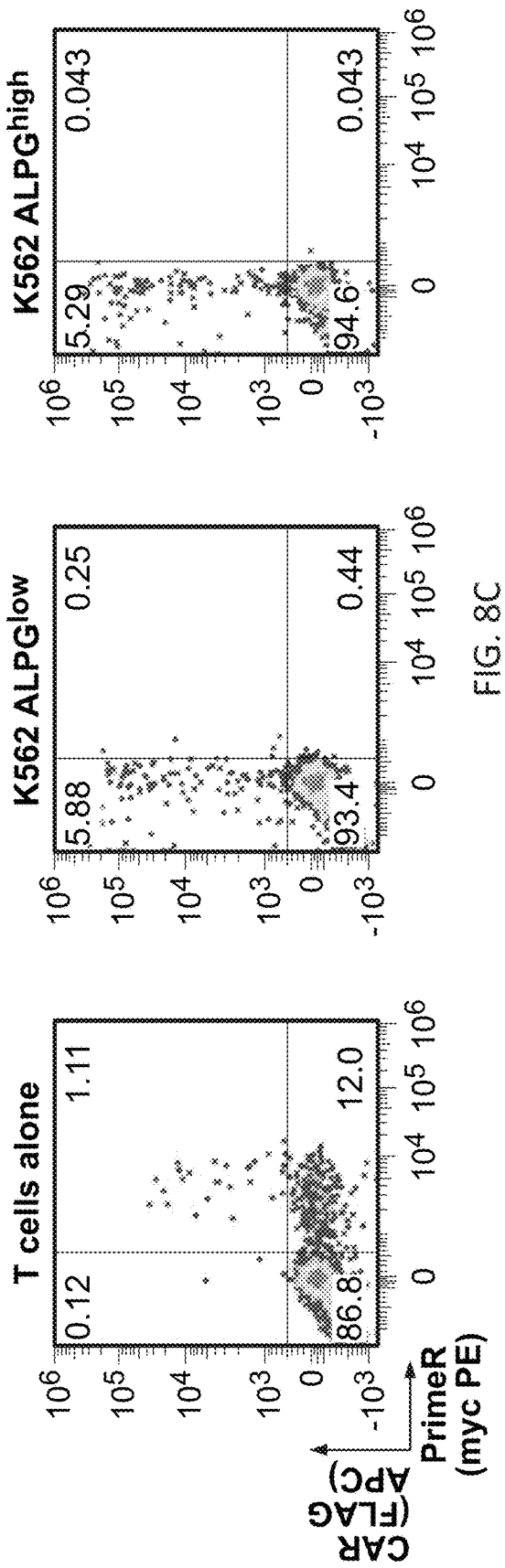
FIG. 8A
FIG. 8B
FIG. 8C

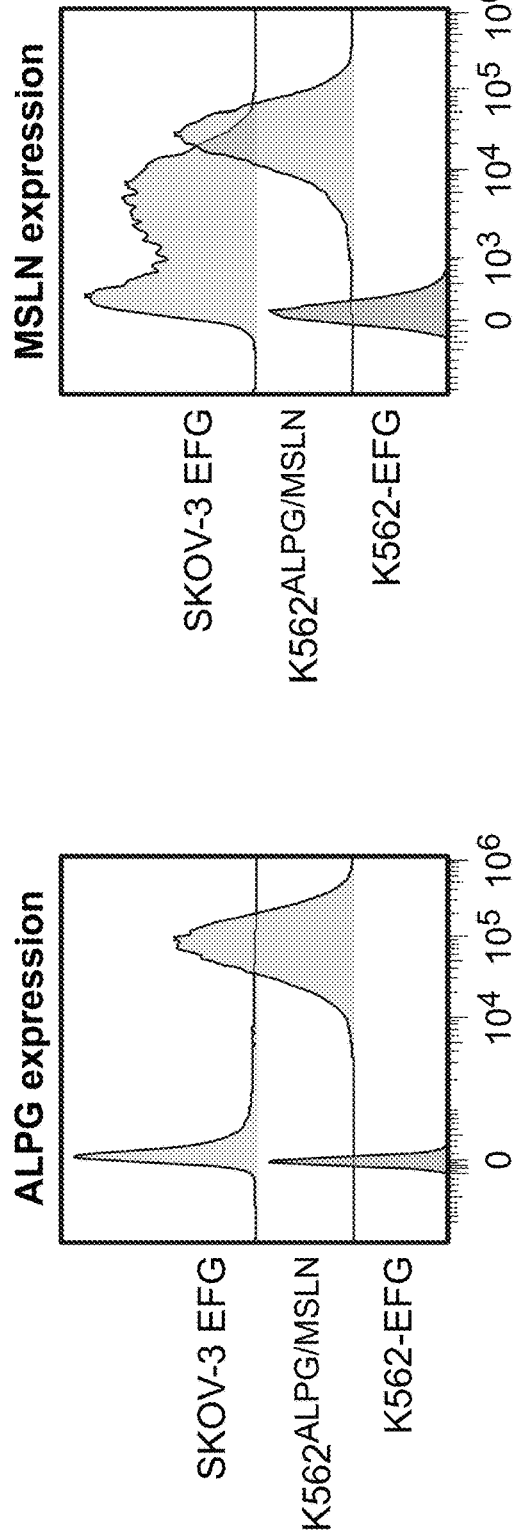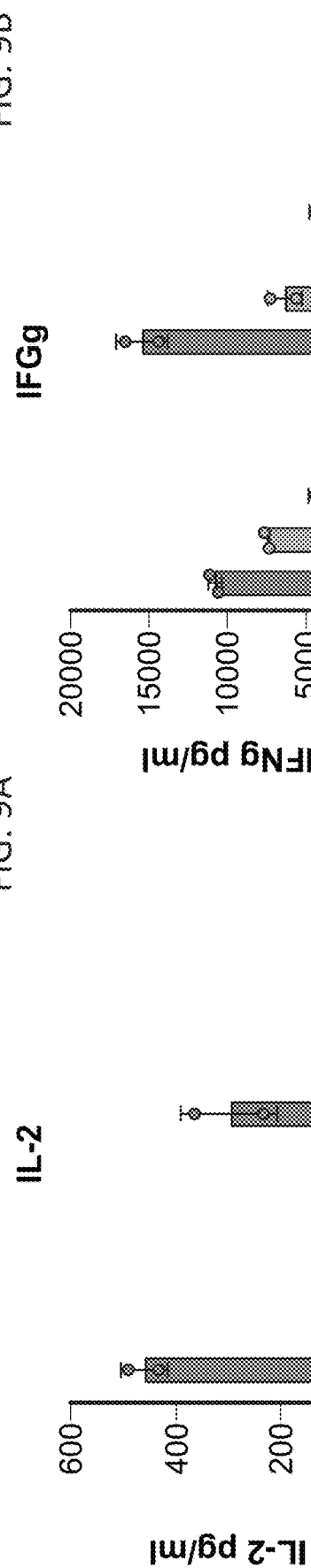

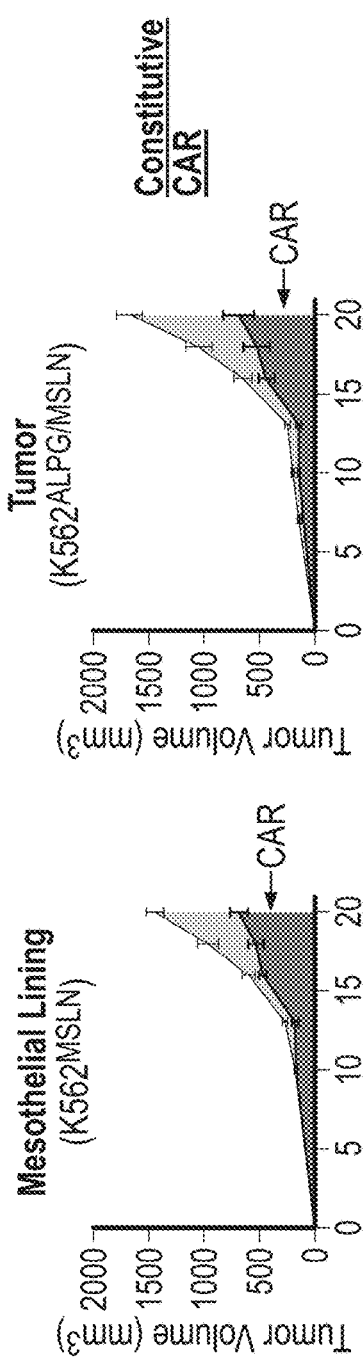
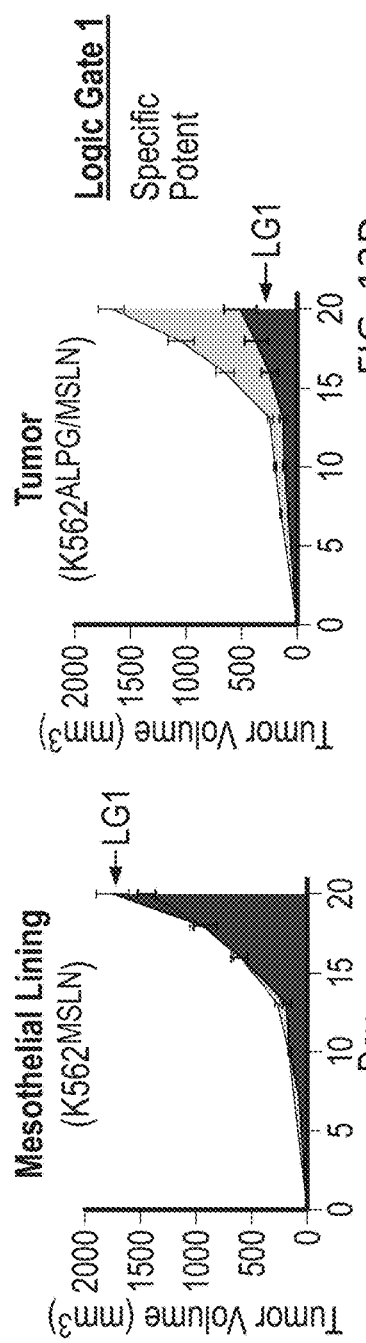
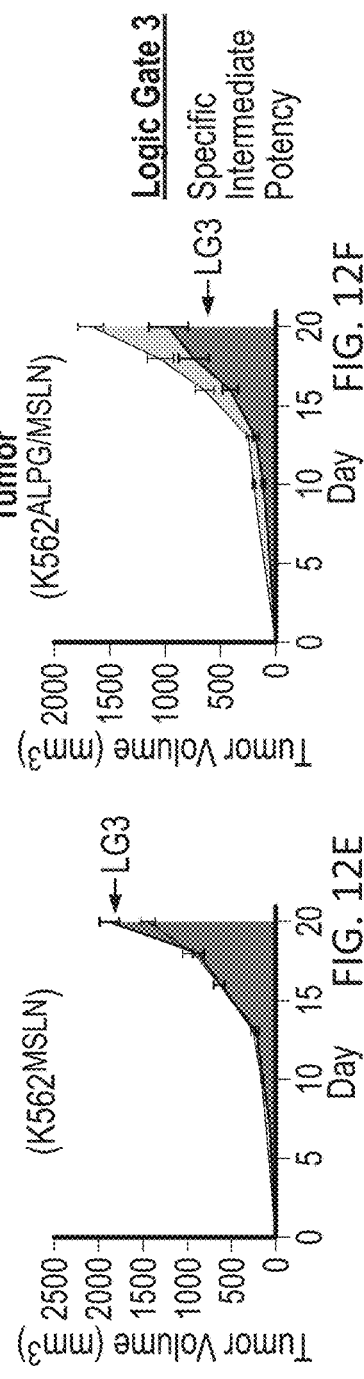

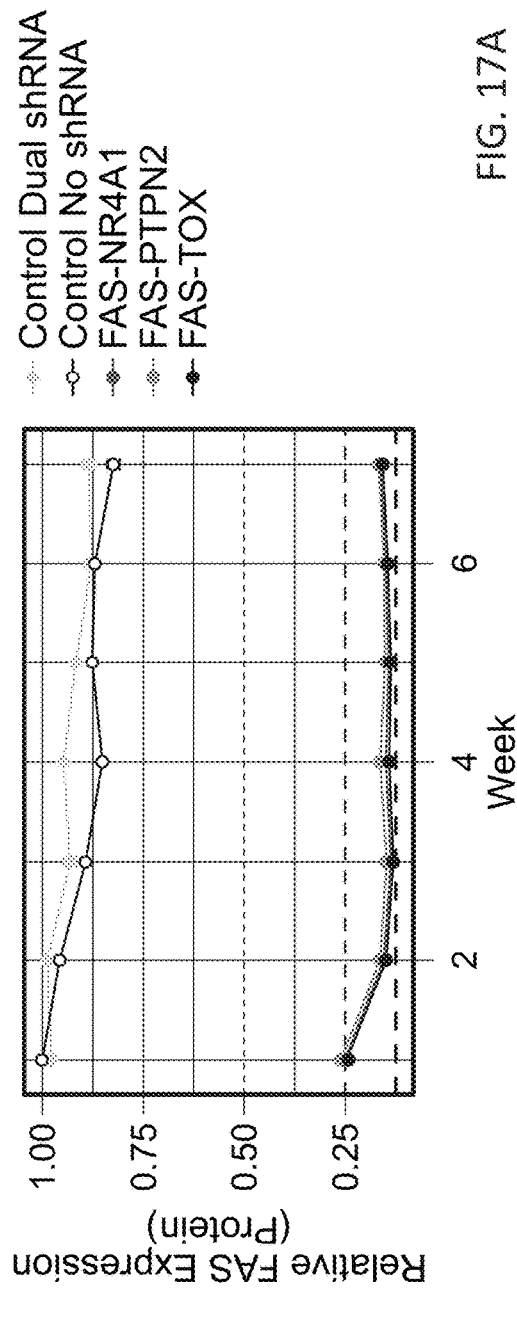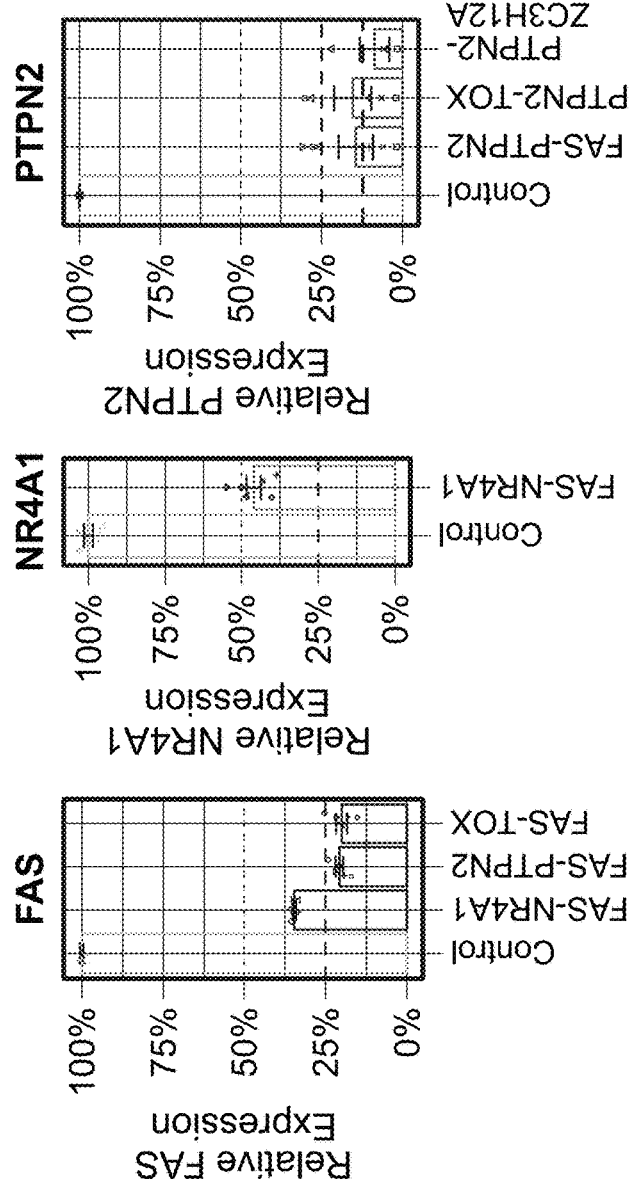
FIG. 17A
FIG. 17B

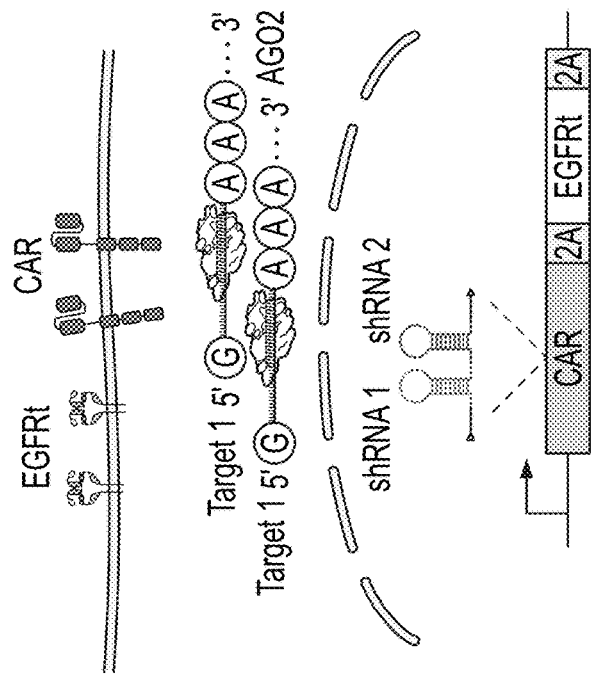
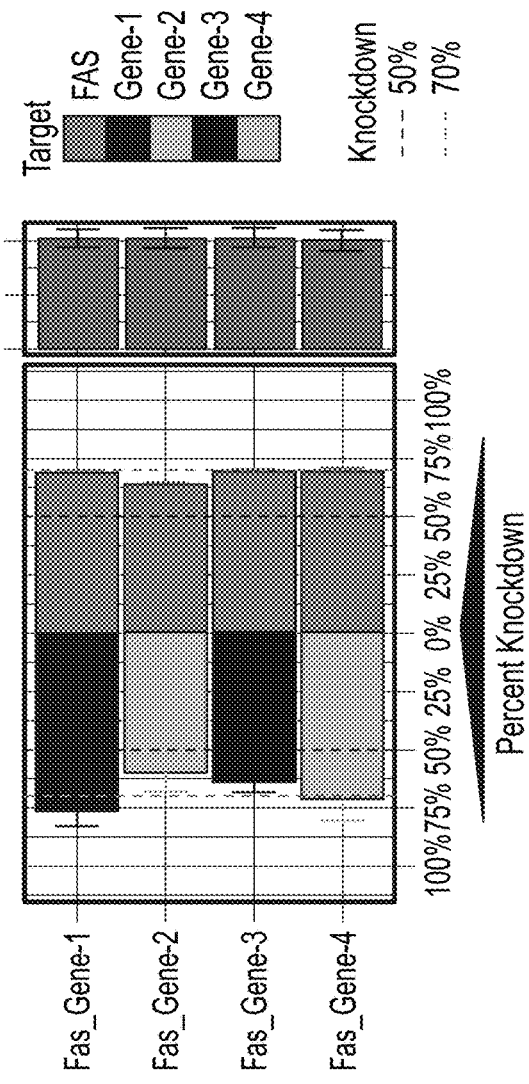
FIG. 39A
FIG. 39B

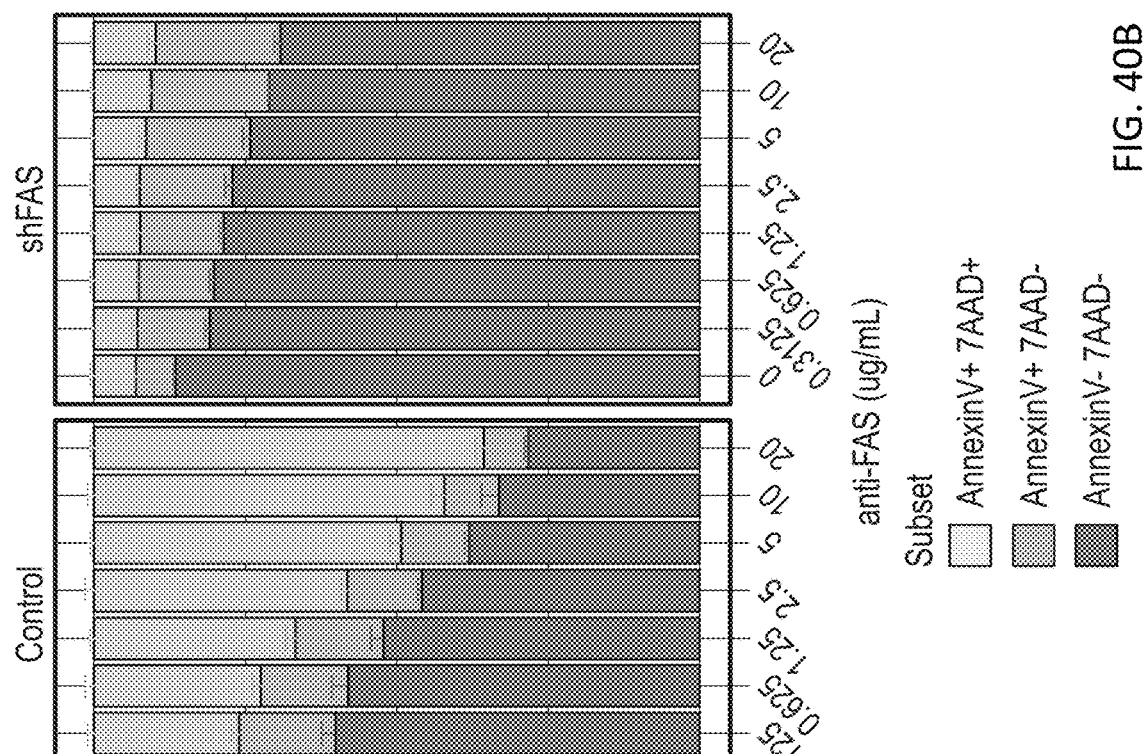
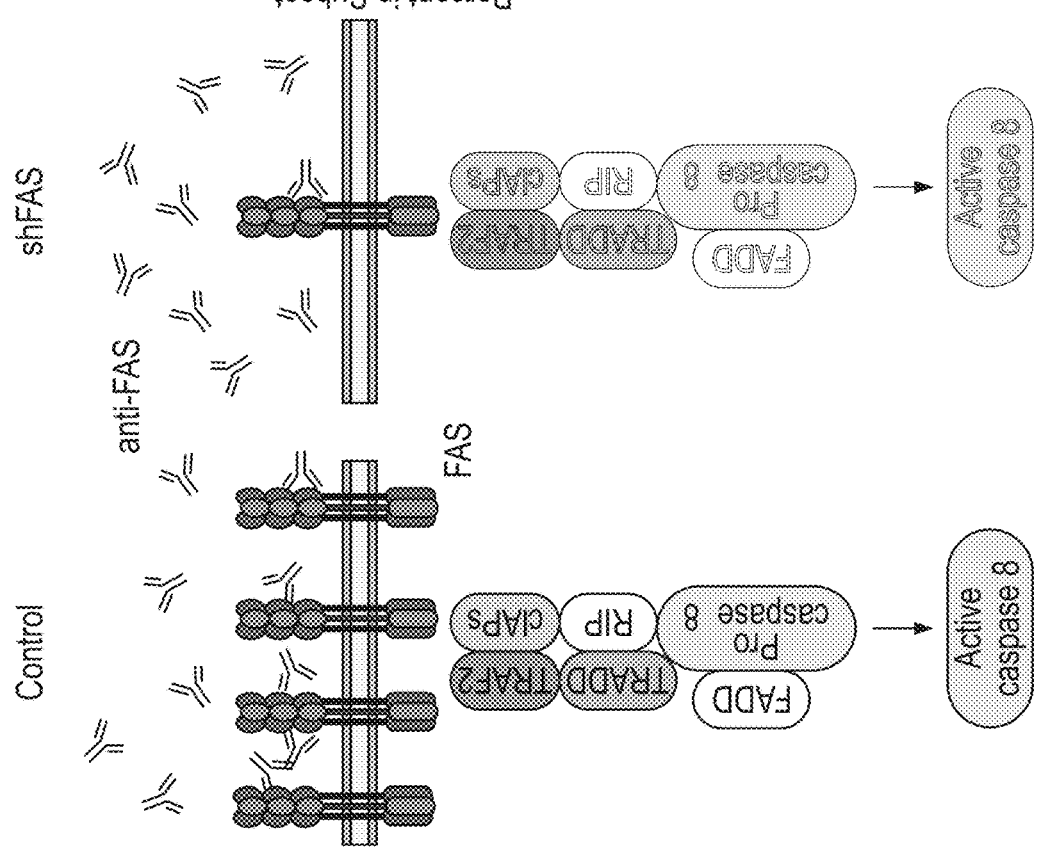
FIG. 40A
FIG. 40B

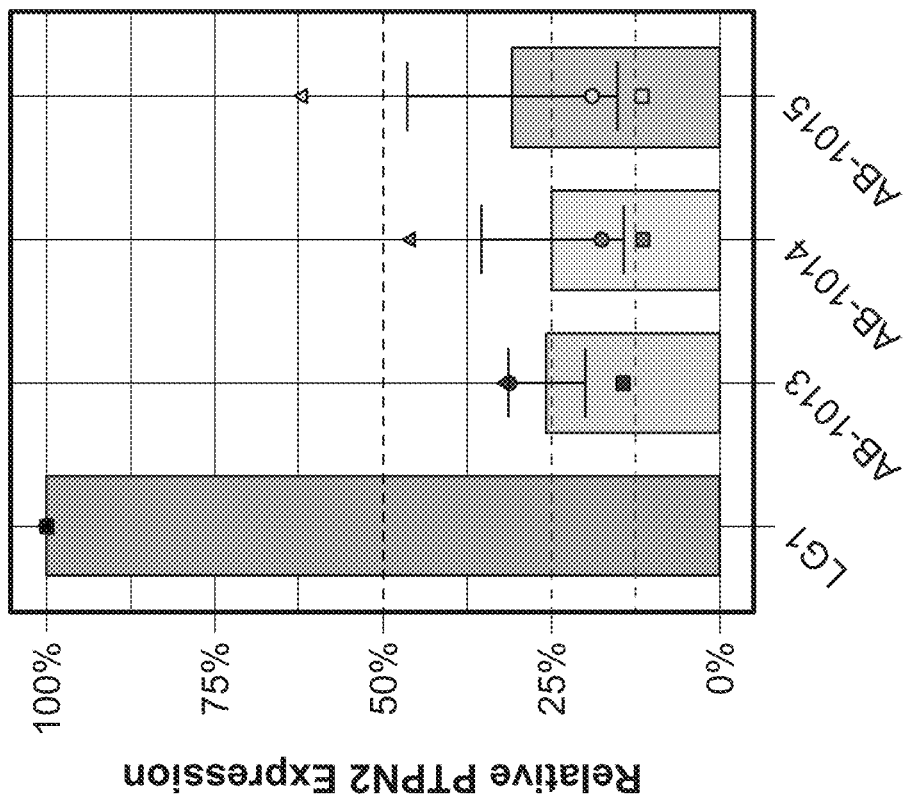
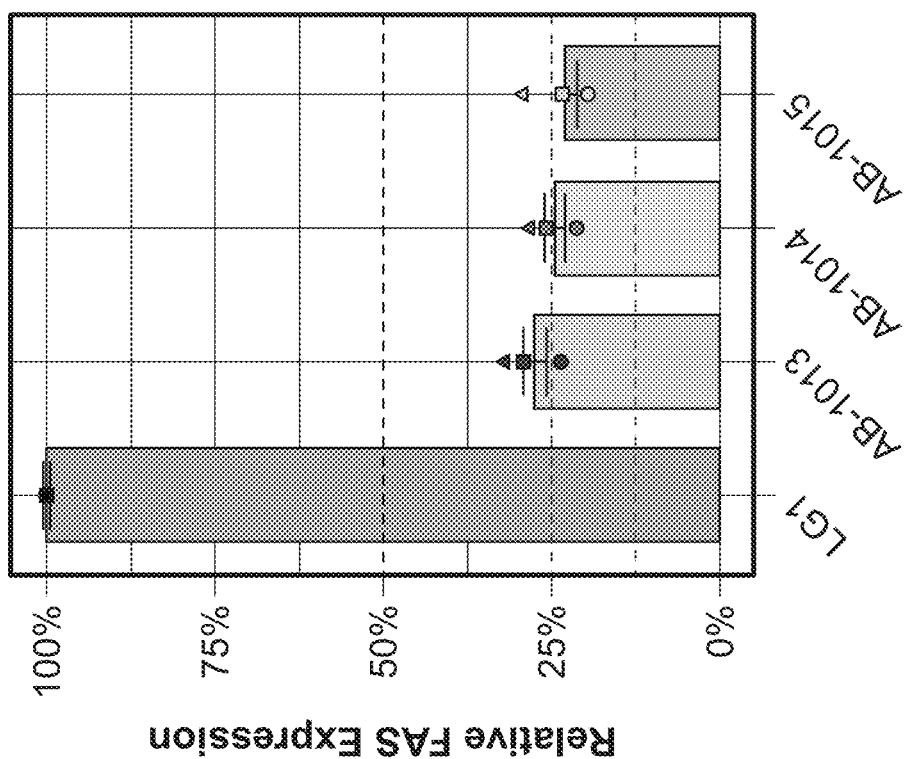
FIG. 44A
FIG. 44B

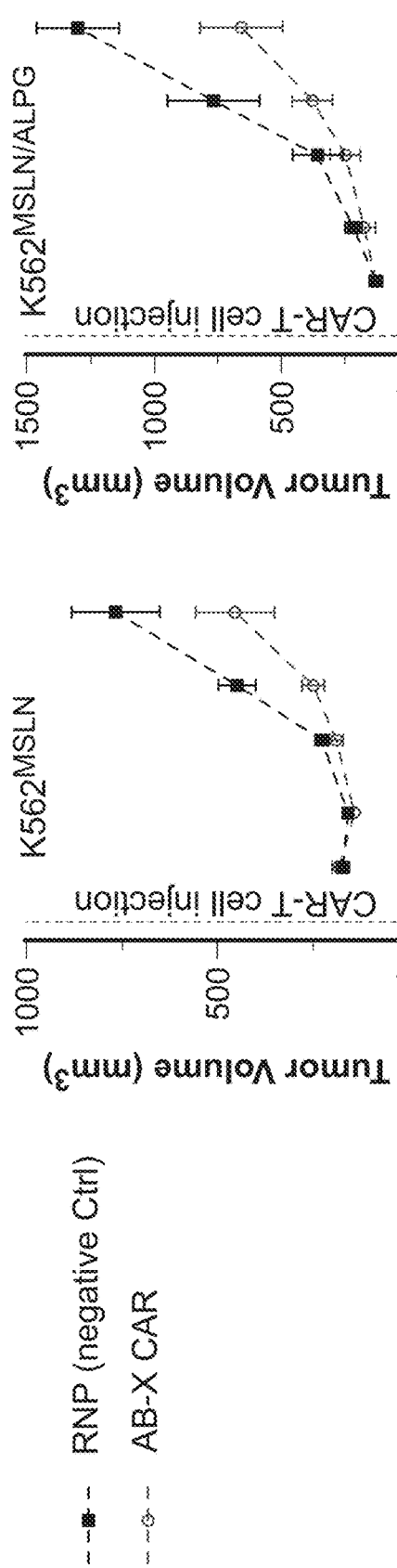
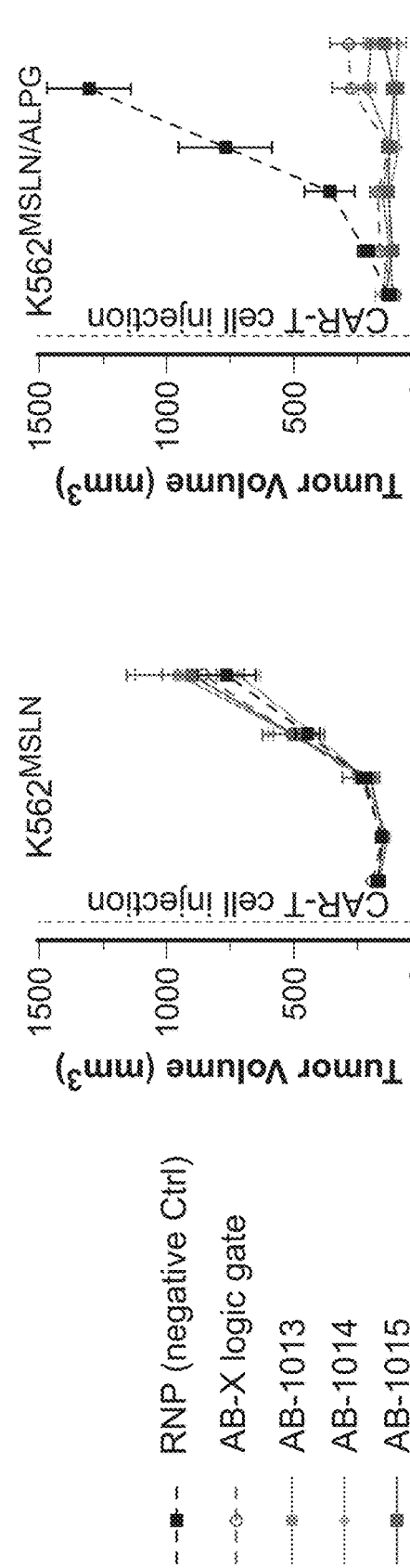

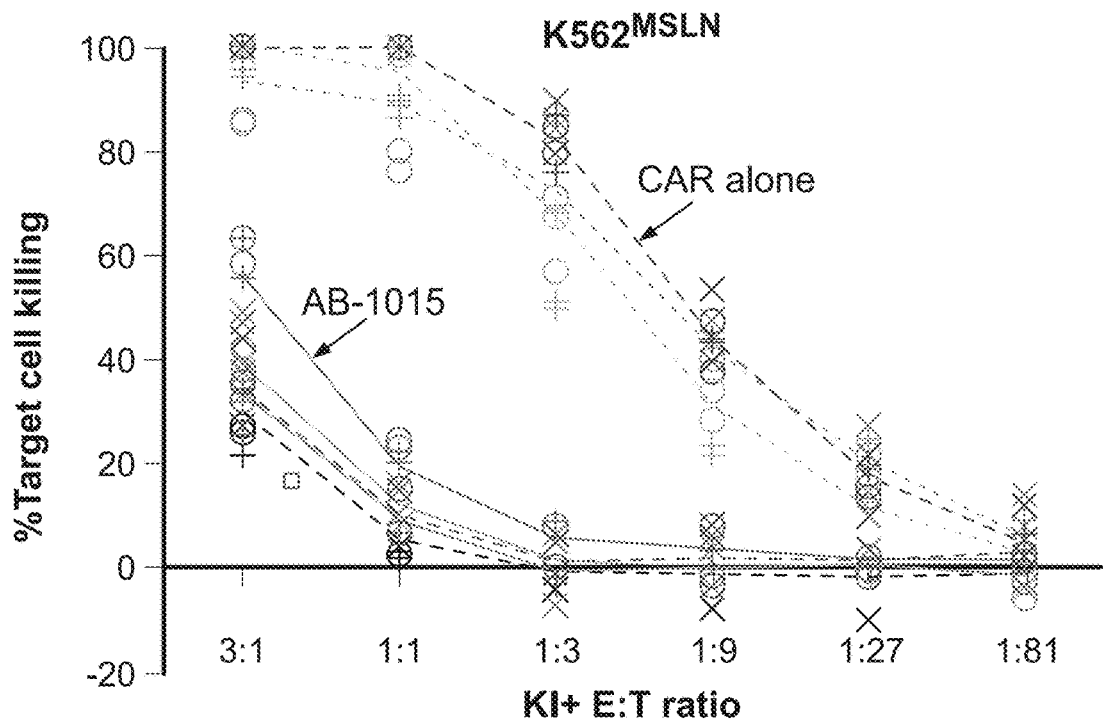
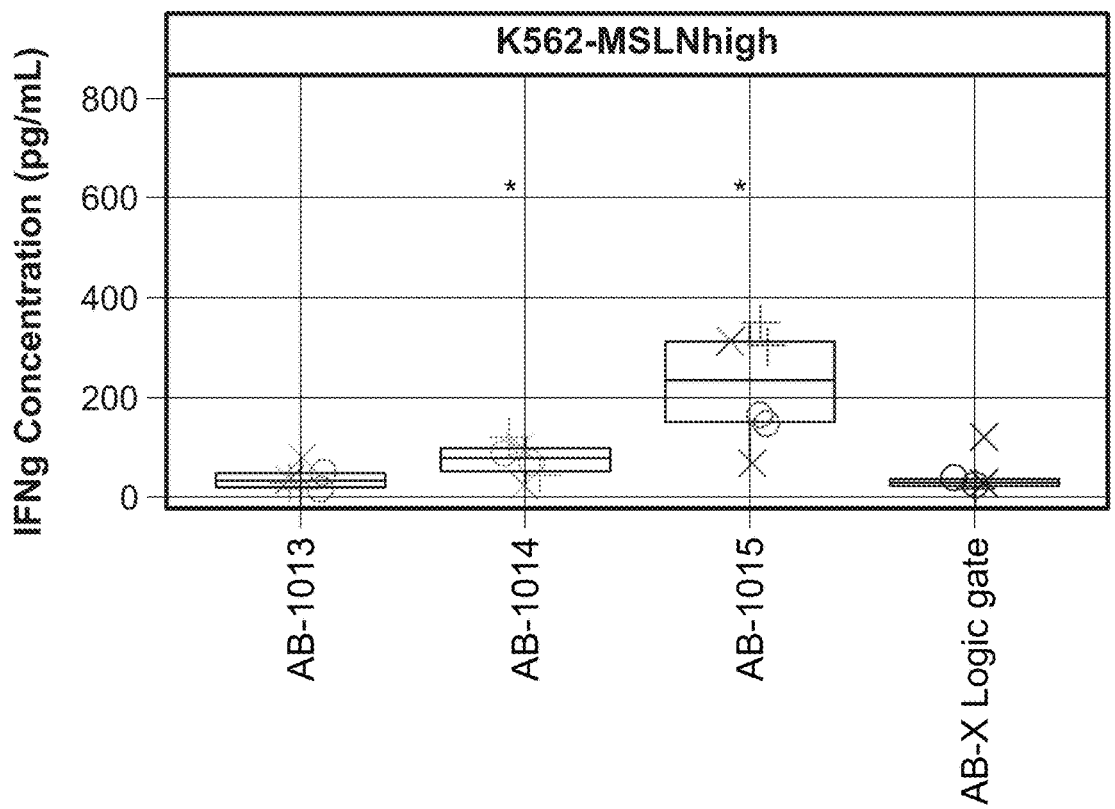
* p-value < 0.05 for ICT versus RNP alone
FIG. 51

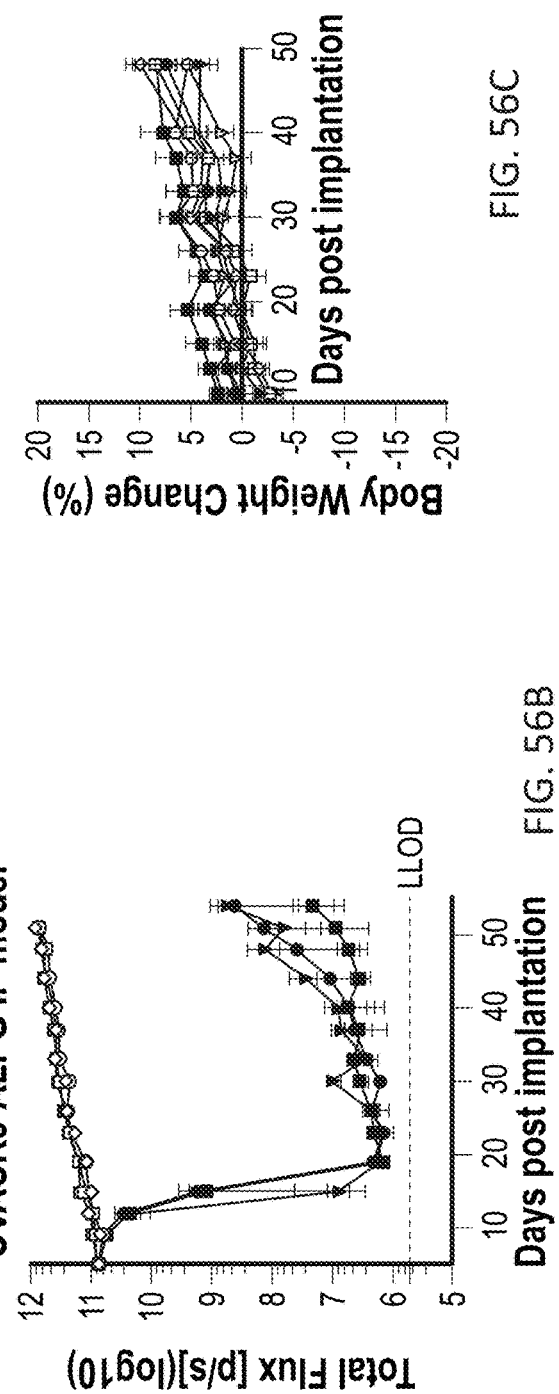
FIG. 56A
FIG. 56B
FIG. 56C

IMMUNE CELLS HAVING CO-EXPRESSED shRNAS AND LOGIC GATE SYSTEMS

CROSS REFERENCE TO RELATED APPLICATIONS

This application is a continuation of PCT/US2022/078158, filed Oct. 14, 2022, which claims priority to and the benefit of U.S. Provisional Application No. 63/255,887, filed Oct. 14, 2021; U.S. Provisional Application No. 63/255,889, filed Oct. 14, 2021; U.S. Provisional Application No. 63/255,891, filed Oct. 14, 2021; and U.S. Provisional Application No. 63/303,422, filed Jan. 26, 2022; each of which is hereby incorporated by reference in its entirety.

SEQUENCE LISTING

The instant application contains a Sequence Listing which has been submitted via Patent Center and is hereby incorporated by reference in its entirety. Said ASCII copy, created on Apr. 25, 2023, is named ANB-207WOC1_sequencelisting.xml, and is 376,116 bytes in size.

BACKGROUND

Cancer is a disease characterized by uncontrollable growth of cells. Many approaches to treating cancer have been tried, including drugs and radiation therapies. Recent cancer treatments have sought to use the body's own immune cells to attack cancer cells. One promising approach uses T cells that are taken from a patient and genetically engineered to produce chimeric antigen receptors, or CARs, receptor proteins that give the T cells a new ability to target a specific protein. The receptors are chimeric because they combine antigen-binding and T-cell activating functions into a single receptor.

Immunotherapy using CAR-T cells is promising because the modified T cells have the potential to recognize cancer cells in order to more effectively target and destroy them. After the T cells are engineered with the CARs, the resulting CAR-T cells are introduced into patients to attack tumor cells. CAR-T cells can be either derived from T cells in a patient's own blood (autologous) or derived from the T cells of another healthy donor (allogeneic). Once CAR-T cells are infused into a patient, they come in contact with their targeted antigen on a cell. The CAR-T cells bind to the antigen and become activated. Upon antigen engagement, CAR T cells can proliferate exponentially, initiate antitumor cytokine production, and target tumor cell killing.

However, there remain some concerns and limitations to CAR T cell-based immunotherapy. Some CART cells may engage with normal cells expressing low levels of target antigens, leading to off target toxicity. However, there remain some limitations to CAR T cell-based immunotherapy. Furthermore, CAR-T cells can lack peripheral survival, can have reduced expansion and effector function, are susceptible to suppression and exhaustion, and may not result in memory T cell persistence. Thus, additional therapies targeting intrinsic pathways and that, e.g., reduce off-target toxicity are needed to address these roadblocks.

SUMMARY

In one aspect, provided herein are one or more recombinant nucleic acids, wherein the one or more recombinant nucleic acids encode: a first chimeric polypeptide comprising a priming receptor; a second chimeric polypeptide comprising a chimeric antigen receptor (CAR); and at least one nucleic acid sequence at least 15 nucleotides in length, wherein the at least one nucleic acid sequence comprises one or more of: (1) a first nucleic acid sequence complementary to nucleotides 1126 to 1364 of an mRNA encoding human Fas Cell Surface Death Receptor (FAS) comprising the sequence set forth in SEQ ID NO: 39, (2) a second nucleic acid sequence complementary to nucleotides 518 to 559 of an mRNA encoding human Protein Tyrosine Phosphatase Non-Receptor Type 2 (PTPN2) comprising the sequence set forth in SEQ ID NO: 40; and (3) a third nucleic acid sequence complementary to nucleotides 1294 to 2141 of an mRNA encoding human Thymocyte Selection Associated High Mobility Group Box (TOX) comprising the sequence set forth in SEQ ID NO: 41.

In some embodiments, the priming receptor comprising a first extracellular antigen-binding domain that specifically binds to Alkaline Phosphatase, Germ Cell (ALPG/P).

In some embodiments, the first extracellular antigen-binding domain comprises a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3, wherein: CDR-H1 comprises the sequence set forth in SEQ ID NO: 1, CDR-H2 comprises the sequence set forth in SEQ ID NO: 2, CDR-H3 comprises the sequence set forth in SEQ ID NO: 3, CDR-L1 comprises the sequence set forth in SEQ ID NO: 4, CDR-L2 comprises the sequence set forth in SEQ ID NO: 5, and CDR-L3 comprises the sequence set forth in SEQ ID NO: 6

In some embodiments, the CAR comprises a second extracellular antigen-binding domain that specifically binds to mesothelin (MSLN), and wherein the second extracellular antigen-binding domain comprises a variable heavy (VH) chain sequence comprising three heavy chain CDR sequences, CDR-H1, CDR-H2, and CDR-H3, wherein: CDR-H1 comprises the sequence set forth in SEQ ID NO: 14, CDR-H2 comprises the sequence set forth in SEQ ID NO: 15, and CDR-H3 comprises the sequence set forth in SEQ ID NO: 16.

In some embodiments, the at least one nucleic acid sequence comprises each of: (1) the first nucleic acid sequence complementary to nucleotides 1126 to 1364 of an mRNA encoding human FAS comprising the sequence set forth in SEQ ID NO: 39; and (2) the second nucleic acid sequence complementary to nucleotides 518 to 559 of an mRNA encoding human PTPN2 comprising the sequence set forth in SEQ ID NO: 40.

In some embodiments, the CAR comprises a second extracellular antigen-binding domain that specifically binds to mesothelin (MSLN).

In some embodiments, the second extracellular antigen-binding domain comprises a variable heavy (VH) chain sequence comprising three heavy chain CDR sequences, CDR-H1, CDR-H2, and CDR-H3, wherein: CDR-H1 comprises the sequence set forth in SEQ ID NO: 14, CDR-H2 comprises the sequence set forth in SEQ ID NO: 15, and CDR-H3 comprises the sequence set forth in SEQ ID NO: 16.

In some embodiments, the second extracellular antigen-binding domain comprises a single domain antibody comprising a variable heavy (VHH) chain sequence comprising three heavy chain CDR sequences, CDR-H1, CDR-H2, and CDR-H3, wherein: CDR-H1 comprises the sequence set forth in SEQ ID NO: 10, CDR-H2 comprises the sequence set forth in SEQ ID NO: 11, and CDR-H3 comprises the sequence set forth in SEQ ID NO: 12.

In one aspect, provided herein are one or more recombinant nucleic acids, wherein the one or more recombinant nucleic acids encode: a first chimeric polypeptide comprising a priming receptor comprising a first extracellular antigen-binding domain that specifically binds Alkaline Phosphatase, Placental/Germ Cell (ALPG/P), wherein the first extracellular antigen-binding domain comprises a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3, wherein: CDR-H1 comprises the sequence set forth in SEQ ID NO: 1, CDR-H2 comprises the sequence set forth in SEQ ID NO: 2, CDR-H3 comprises the sequence set forth in SEQ ID NO: 3, CDR-L1 comprises the sequence set forth in SEQ ID NO: 4, CDR-L2 comprises the sequence set forth in SEQ ID NO: 5, and CDR-L3 comprises the sequence set forth in SEQ ID NO: 6; a second chimeric polypeptide comprising a chimeric antigen receptor (CAR); a first nucleic acid sequence complementary to nucleotides 1126 to 1364 of an mRNA encoding human FAS comprising the sequence set forth in SEQ ID NO: 39, and a second nucleic acid sequence complementary to nucleotides 518 to 559 of an mRNA encoding human PTPN2 comprising the sequence set forth in SEQ ID NO: 40; or complementary to nucleotides 1294 to 2141 of an mRNA encoding human TOX comprising the sequence set forth in SEQ ID NO: 41.

In some embodiments, the first extracellular antigen-binding domain VH chain sequence comprises the sequence set forth in SEQ ID NO: 7.

In some embodiments, the first extracellular antigen-binding domain VL chain sequence comprises the sequence set forth in SEQ ID NO: 8.

In some embodiments, the first extracellular antigen-binding domain comprises the sequence set forth in SEQ ID NO: 9.

In some embodiments, the CAR comprises a second extracellular antigen-binding domain that specifically binds to mesothelin (MSLN).

In some embodiments, the second extracellular antigen-binding domain comprises a variable heavy (VH) chain sequence comprising three heavy chain CDR sequences, CDR-H1, CDR-H2, and CDR-H3, wherein: CDR-H1 comprises the sequence set forth in SEQ ID NO: 14, CDR-H2 comprises the sequence set forth in SEQ ID NO: 15, and CDR-H3 comprises the sequence set forth in SEQ ID NO: 16.

In some embodiments, the second extracellular antigen-binding domain VH comprises the sequence as set forth in SEQ ID NO: 17.

In some embodiments, the second extracellular antigen-binding domain comprises a single domain antibody comprising a variable heavy (VHH) chain sequence comprising three heavy chain CDR sequences, CDR-H1, CDR-H2, and CDR-H3, wherein: CDR-H1 comprises the sequence set forth in SEQ ID NO: 10, CDR-H2 comprises the sequence set forth in SEQ ID NO: 11, and CDR-H3 comprises the sequence set forth in SEQ ID NO: 12.

In some embodiments, the second extracellular antigen-binding domain VHH chain sequence comprises the sequence set forth in SEQ ID NO: 13.

In some embodiments, the second nucleic acid sequence is complementary to nucleotides 518 to 559 of an mRNA encoding human PTPN2 comprising the sequence set forth in SEQ ID NO: 40.

In some embodiments, the recombinant nucleic acid comprises a sequence selected from the group consisting of the sequences set forth in SEQ ID NOs: 168, 167, or 166.

In some embodiments, the second nucleic acid sequence is complementary to nucleotides 1294 to 2141 of an mRNA encoding human TOX comprising the sequence set forth in SEQ ID NO: 41.

In one aspect, provided herein are recombinant nucleic acids comprising a nucleic acid sequence at least 15 nucleotides in length complementary to nucleotides 1126 to 1364 of an mRNA encoding human FAS comprising the sequence set forth in SEQ ID NO: 39.

In one aspect, provided herein are recombinant nucleic acids comprising a nucleic acid sequence at least 15 nucleotides in length complementary to nucleotides 518 to 559 of an mRNA encoding human Protein Tyrosine Phosphatase Non-Receptor Type 2 (PTPN2) comprising the sequence set forth in SEQ ID NO: 40.

In one aspect, provided herein are recombinant nucleic acid comprising a nucleic acid sequence at least 15 nucleotides in length complementary to nucleotides 1294 to 2141 of an mRNA encoding human thymocyte selection associated high mobility group box (TOX) comprising the sequence set forth in SEQ ID NO: 41.

In one aspect, provided herein are one or more recombinant nucleic acids comprising a first nucleic acid sequence at least 15 nucleotides in length complementary to nucleotides 1126 to 1364 of an mRNA encoding human FAS comprising the sequence set forth in SEQ ID NO: 39 and a second nucleic acid sequence at least 15 nucleotides in length complementary to nucleotides 518 to 559 of an mRNA encoding human PTPN2 comprising the sequence set forth in SEQ ID NO: 40.

In one aspect, provided herein are one or more recombinant nucleic acids comprising a first nucleic acid at least 15 nucleotides in length complementary to nucleotides 1126 to 1364 of an mRNA encoding human FAS comprising the sequence set forth in SEQ ID NO: 39; and a second nucleic acid at least 15 nucleotides in length complementary to nucleotides 1294 to 2141 of an mRNA encoding human TOX comprising the sequence set forth in SEQ ID NO: 41.

In some embodiments, the first, second, and third nucleic acid sequences are at least 16, 17, 18, 19, 20, 21, or 22 nucleotides in length.

In some embodiments, the first, second, and third nucleic acid sequences are a short hairpin RNA (shRNA), a small interfering RNA (siRNA), a double stranded RNA (dsRNA), or an antisense oligonucleotide.

In some embodiments, the first, second, and third nucleic acid sequences are shRNA.

In some embodiments, the first nucleic acid sequence comprises a sequence selected from the group consisting of the sequences set forth in SEQ ID NOs: 42-71.

In some embodiments, the first nucleic acid sequence comprises the sequence set forth in SEQ ID NO: 49.

In some embodiments, the first nucleic acid reduces expression of FAS in the immune cell by at least 50%, 55%, 60%, 65%, 75%, 80%, 85%, 90%, 95%, or 99% as compared to a control cell that does not comprise the nucleic acid.

In some embodiments, the second nucleic acid sequence comprises a sequence selected from the group consisting of the sequences set forth in SEQ ID NOs: 72-97.

In some embodiments, the second nucleic acid sequence comprises the sequence set forth in SEQ ID NO: 82.

In some embodiments, the first nucleic acid sequence comprises a sequence selected from the group consisting of the sequences set forth in SEQ ID NOs: 42 to 71; and the second nucleic acid sequence comprises a sequence selected from the group consisting of the sequences set forth in SEQ ID NOs: 72 to 97.

In some embodiments, the first nucleic acid sequence comprises the sequence set forth in SEQ ID NO: 49 and the second nucleic acid sequence comprises the sequence set forth in SEQ ID NO: 82.

In some embodiments, the second nucleic acid reduces expression of PTPN2 in the immune cell by at least 50%, 55%, 60%, 65%, 75%, 80%, 85%, 90%, 95%, or 99% as compared to a control cell that does not comprise the nucleic acid.

In some embodiments, the second nucleic acid sequence comprises a sequence selected from the group consisting of the sequences set forth in SEQ ID NOs: 98-125.

In some embodiments, the second nucleic acid sequence comprises the sequence set forth in SEQ ID NO: 99 or 104.

In some embodiments, the first nucleic acid sequence comprises a sequence selected from the group consisting of the sequences set forth in SEQ ID NOs: 42 to 71; and the second nucleic acid sequence comprises a sequence selected from the group consisting of the sequences set forth in SEQ ID NOs: 98 to 125.

In some embodiments, the first nucleic acid sequence comprises the sequence set forth in SEQ ID NO: 49 and the second nucleic acid sequence comprises the sequence set forth in SEQ ID NO: SEQ ID NOs: 99 or 104

In some embodiments, the second nucleic acid reduces expression of TOX in the immune cell by at least 50%, 55%, 60%, 65%, 75%, 80%, 85%, 90%, 95%, or 99% as compared to a control cell that does not comprise the nucleic acid.

In one aspect, provided herein are one or more recombinant nucleic acids, wherein the one or more recombinant nucleic acids encode: a first chimeric polypeptide comprises a priming receptor, a second chimeric polypeptide comprises a chimeric antigen receptor (CAR) comprising an extracellular antigen-binding domain that specifically binds to mesothelin (MSLN), wherein the extracellular antigen-binding domain comprises a single domain antibody comprising a variable heavy (VHH) chain sequence comprising three heavy chain CDR sequences, CDR-H1, CDR-H2, and CDR-H3, wherein: CDR-H1 comprises the sequence set forth in SEQ ID NO: 10, CDR-H2 comprises the sequence set forth in SEQ ID NO: 11, and CDR-H3 comprises the sequence set forth in SEQ ID NO: 12; and a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and a second nucleic acid sequence, wherein the second nucleic acid sequence is complementary to nucleotides 518 to 559 of an mRNA encoding human PTPN2 comprising the sequence set forth in SEQ ID NO: 40; or is complementary to nucleotides 1294 to 2141 of an mRNA encoding human TOX comprising the sequence set forth in SEQ ID NO: 41.

In some embodiments, the VHH chain sequence comprises the sequence set forth in SEQ ID NO: 13.

In one aspect, provided herein are one or more recombinant nucleic acids, wherein the one or more recombinant nucleic acids encode: a first chimeric polypeptide comprises a priming receptor, a second chimeric polypeptide comprises a chimeric antigen receptor (CAR) comprising an extracellular antigen-binding domain that specifically binds to mesothelin (MSLN), wherein the second extracellular antigen-binding domain comprises a variable heavy (VH) chain sequence comprising three heavy chain CDR sequences, CDR-H1, CDR-H2, and CDR-H3, wherein: CDR-H1 comprises the sequence set forth in SEQ ID NO: 14, CDR-H2 comprises the sequence set forth in SEQ ID NO: 15, and CDR-H3 comprises the sequence set forth in SEQ ID NO: 16; and a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and a second nucleic acid sequence, wherein the second nucleic acid sequence is complementary to nucleotides 518 to 559 of an mRNA encoding human PTPN2 comprising the sequence set forth in SEQ ID NO: 40; or is complementary to nucleotides 1294 to 2141 of an mRNA encoding human TOX comprising the sequence set forth in SEQ ID NO: 41.

In some embodiments, the VH comprises the sequence as set forth in SEQ ID NO: 17.

In one aspect, provided herein are one or more recombinant nucleic acids, wherein the one or more recombinant nucleic acids encode: a first chimeric polypeptide comprises a priming receptor comprising a first extracellular antigen-binding domain that specifically binds to Alkaline Phosphatase, Germ Cell (ALPG/P); and a second chimeric polypeptide comprises a CAR comprising a second extracellular antigen-binding domain that specifically binds to mesothelin (MSLN); a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and a second nucleic acid sequence, wherein the second nucleic acid sequence is complementary to nucleotides 518 to 559 of an mRNA encoding human PTPN2 comprising the sequence set forth in SEQ ID NO: 40; or is complementary to nucleotides 1294 to 2141 of an mRNA encoding human TOX comprising the sequence set forth in SEQ ID NO: 41.

In some embodiments, the second nucleic acid sequence is complementary to nucleotides 518 to 559 of an mRNA encoding human PTPN2 comprising the sequence set forth in SEQ ID NO: 40.

In some embodiments, the recombinant nucleic acid comprises a sequence selected from the group consisting of the sequences set forth in SEQ ID NOs: 168, 167, or 166.

In some embodiments, the second nucleic acid sequence is complementary to nucleotides 1294 to 2141 of an mRNA encoding human TOX comprising the sequence set forth in SEQ ID NO: 41.

In some embodiments, the first and second nucleic acid sequences are at least 16, 17, 18, 19, 20, 21, or 22 nucleotides in length.

In some embodiments, the first and second nucleic acids are a short hairpin RNA (shRNA), a small interfering RNA (siRNA), a double stranded RNA (dsRNA), or an antisense oligonucleotide.

In some embodiments, the first and second nucleic acids are shRNA.

In some embodiments, the first nucleic acid sequence comprises a sequence selected from the group consisting of the sequences set forth in SEQ ID NOs: 42-71.

In some embodiments, the first nucleic acid sequence comprises the sequence set forth in SEQ ID NO: 49.

In some embodiments, the first nucleic acid reduces expression of FAS in the immune cell by at least 50%, 55%, 60%, 65%, 75%, 80%, 85%, 90%, 95%, or 99% as compared to a control cell that does not comprise the nucleic acid.

In some embodiments, the second nucleic acid sequence comprises a sequence selected from the group consisting of the sequences set forth in SEQ ID NOs: 72-97.

In some embodiments, the second nucleic acid sequence comprises the sequence set forth in SEQ ID NO: 82.

In some embodiments, the second nucleic acid reduces expression of PTPN2 in the immune cell by at least 50%, 55%, 60%, 65%, 75%, 80%, 85%, 90%, 95%, or 99% as compared to a control cell that does not comprise the nucleic acid.

In some embodiments, the second nucleic acid sequence comprises a sequence selected from the group consisting of the sequences set forth in SEQ ID NOs: 98-125.

In some embodiments, the second nucleic acid sequence comprises the sequence set forth in SEQ ID NO: 99 or 104.

In some embodiments, the second nucleic acid reduces expression of TOX in the immune cell by at least 50%, 55%, 60%, 65%, 75%, 80%, 85%, 90%, 95%, or 99% as compared to a control cell that does not comprise the nucleic acid.

In some embodiments, the priming receptor comprises, from N-terminus to C-terminus, the first extracellular antigen-binding domain; a first transmembrane domain comprising one or more ligand-inducible proteolytic cleavage sites; and an intracellular domain comprising a human or humanized transcriptional effector, wherein binding of ALPG/P by the first extracellular antigen-binding domain results in cleavage at the one or more ligand-inducible proteolytic cleavage sites.

In some embodiments, the priming receptor further comprises a first hinge domain positioned between the first extracellular antigen-binding domain and the first transmembrane domain.

In some embodiments, the first hinge domain comprises a CD8α or a truncated CD8α hinge domain.

In some embodiments, the first hinge comprises the sequence as set forth in SEQ ID NO: 18.

In some embodiments, the first transmembrane domain comprises a Notch1 transmembrane domain.

In some embodiments, the first transmembrane domain comprises the sequence as set forth in SEQ ID NO: 19.

In some embodiments, the intracellular domain comprises an HNF1a/p65 domain or a Gal4/VP64 domain.

In some embodiments, the intracellular domain comprises the sequence as set forth in SEQ ID NO: 23.

In some embodiments, the priming receptor further comprises a stop-transfer-sequence between the first transmembrane domain and the intracellular domain.

In some embodiments, the stop-transfer-sequence comprises the sequence as set forth in SEQ ID NO: 20.

In some embodiments, the priming receptor comprises a sequence as set forth in SEQ ID NO: 24.

In some embodiments, the CAR comprises, from N-terminus to C-terminus, a second extracellular antigen-binding domain; a second transmembrane domain; an intracellular co-stimulatory domain; and an intracellular activation domain.

In some embodiments, the second extracellular antigen-binding domain specifically binds to mesothelin (MSLN), wherein the second extracellular antigen-binding domain comprises a single domain antibody comprising a variable heavy (VHH) chain sequence comprising three heavy chain CDR sequences, CDR-H1, CDR-H2, and CDR-H3, wherein: CDR-H1 comprises the sequence set forth in SEQ ID NO: 10, CDR-H2 comprises the sequence set forth in SEQ ID NO: 11, and CDR-H3 comprises the sequence set forth in SEQ ID NO: 12.

In some embodiments, the VHH chain sequence comprises the sequence set forth in SEQ ID NO: 13.

In some embodiments, the second extracellular antigen-binding domain specifically binds to mesothelin (MSLN), wherein the extracellular antigen-binding domain comprises a variable heavy (VH) chain sequence comprising three heavy chain CDR sequences, CDR-H1, CDR-H2, and CDR-H3, wherein: CDR-H1 comprises the sequence set forth in SEQ ID NO: 14, CDR-H2 comprises the sequence set forth in SEQ ID NO: 15, and CDR-H3 comprises the sequence set forth in SEQ ID NO: 16.

In some embodiments, the VH chain sequence comprises the sequence set forth in SEQ ID NO: 17.

In some embodiments, the CAR comprises a second hinge domain.

In some embodiments, the second hinge domain comprises a CD8α or a truncated CD8α hinge domain.

In some embodiments, the second transmembrane domain comprises a CD8α transmembrane domain.

In some embodiments, the intracellular co-stimulatory domain comprises a 4-1BB domain.

In some embodiments, the intracellular activation domain comprises a CD3ζ domain.

In some embodiments, the CAR comprises a sequence as set forth in SEQ ID NO: 30 or 31.

In some embodiments, the priming receptor and the CAR are capable of binding to a single target cell if the target cell expresses each of ALPG/P and MSLN.

In some embodiments, the target cell is a human cell.

In some embodiments, the target cell is a cancer cell.

In some embodiments, the cancer cell is a solid cancer cell or a liquid cancer cell.

In some embodiments, the cancer cell is ovarian cancer, fallopian cancer, primary peritoneal cancer, uterine cancer, mesothelioma, cervical cancer, or pancreatic cancer.

In some embodiments, the recombinant nucleic acid comprises two or more nucleic acid fragments.

In some embodiments, the recombinant nucleic acid further comprises an inducible promoter operably linked to the nucleotide sequence encoding the CAR.

In some embodiments, the recombinant nucleic acid further comprises a first constitutive promoter operably linked to the nucleotide sequence encoding the priming receptor.

In some embodiments, the recombinant nucleic acid further comprises an inducible promoter operably linked to the nucleotide sequence encoding the chimeric antigen receptor and a constitutive promoter operably linked to the nucleotide sequence encoding the priming receptor.

In some embodiments, the recombinant nucleic acid further comprises a second constitutive promoter operably linked to the nucleotide sequence encoding the first nucleic acid complementary to human FAS.

In some embodiments, the recombinant nucleic acid further comprises a second constitutive promoter operably linked to the nucleotide sequence encoding the second nucleic acid complementary to human PTPN2 or TOX.

In some embodiments, the recombinant nucleic acid further comprises a second constitutive promoter operably linked to the nucleotide sequence encoding the first nucleic acid complementary to human FAS or the second nucleic acid complementary to human PTPN2 or TOX.

In some embodiments, the recombinant nucleic acid comprises, in a 5' to 3' direction, the first constitutive promoter; the nucleotide sequence encoding the priming receptor; the second constitutive promoter; the nucleotide sequence encoding the first nucleic acid complementary to human FAS, human PTPN2, or human TOX; the inducible promoter; and the nucleotide sequence encoding the chimeric antigen receptor.

In some embodiments, the recombinant nucleic acid comprises, in a 5' to 3' direction, the first constitutive promoter; the nucleotide sequence encoding the priming receptor; the second constitutive promoter; the nucleotide sequence encoding the first nucleic acid complementary to human FAS; the nucleotide sequence encoding the second first nucleic acid complementary to human PTPN2 or TOX; the inducible promoter; and the nucleotide sequence encoding the chimeric antigen receptor.

In some embodiments, the recombinant nucleic acid comprises, in a 5' to 3' direction, the inducible promoter; the nucleotide sequence encoding the chimeric antigen receptor; the second constitutive promoter; the nucleotide sequence encoding the first nucleic acid complementary to human FAS; the nucleotide sequence encoding the second first nucleic acid complementary to human PTPN2 or TOX; the first constitutive promoter; and the nucleotide sequence encoding the priming receptor.

In some embodiments, the nucleotide sequence encoding the priming receptor comprises the sequence set forth in SEQ ID NO: 36.

In some embodiments, the nucleotide sequence encoding the chimeric antigen receptor comprises the sequence set forth in SEQ ID NO: 37 or 38.

In some embodiments, the recombinant nucleic acid further comprises a 5' homology directed repair arm and a 3' homology directed repair arm complementary to an insertion site in a host cell chromosome.

In some embodiments, the recombinant nucleic acid further comprises a nucleotide sequence encoding a self-excising 2A peptide (P2A).

In some embodiments, the P2A is at the 3' end of the nucleotide sequence encoding chimeric antigen receptor.

In some embodiments, the P2A is at the 3' end of the nucleotide sequence encoding priming receptor.

In some embodiments, the recombinant nucleic acid further comprises a woodchuck hepatitis virus post-translational regulatory element (WPRE).

In some embodiments, the WPRE is at the 3' end of the nucleotide sequence encoding chimeric antigen receptor and at the 5' end of the nucleotide sequence encoding priming receptor or wherein the WPRE is at the 3' end of the nucleotide sequence encoding priming receptor and at the 5' end of the nucleotide sequence encoding chimeric antigen receptor.

In some embodiments, the recombinant nucleic acid further comprises an SV40 polyA element.

In some embodiments, the nucleic acid is incorporated into an expression cassette or an expression vector.

In some embodiments, the expression vector is a non-viral vector.

In one aspect, provided herein are expression vector comprising the recombinant nucleic acid disclosed herein.

In some embodiments, the 5' and 3' ends of the recombinant nucleic acid comprise nucleotide sequences that are homologous to genomic sequences flanking an insertion site in a genome of a primary cell.

In some embodiments, the insertion site is located at a T Cell Receptor Alpha Constant (TRAC) locus or a genomic safe harbor (GSH) locus.

In some embodiments, the GHS locus is a GS94 locus.

In one aspect, provided herein are immune cell comprising: at least one recombinant nucleic acid(s) disclosed herein; and/or the vector disclosed herein.

In some embodiments, the immune cell is a primary human immune cell.

In some embodiments, the primary human immune cell is an autologous immune cell.

In some embodiments, the primary immune cell is a natural killer (NK) cell, a T cell, a CD8+ T cell, a CD4+ T cell, a primary T cell, or a T cell progenitor.

In some embodiments, the primary immune cell is a primary T cell.

In some embodiments, the primary immune cell is a primary human T cell.

In some embodiments, the primary immune cell is virus-free.

In some embodiments, the immune cell is an autologous immune cell.

In some embodiments, the immune cell is an allogeneic immune cell.

In one aspect, provided herein are primary immune cell comprising at least one recombinant nucleic acid comprising a priming receptor comprising a first extracellular antigen-binding domain that specifically binds to ALPG/P; a chimeric antigen receptor comprising a second extracellular antigen-binding domain that specifically binds to MSLN; a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and a second nucleic acid sequence at least 15 nucleotides in length, wherein the second nucleic acid sequence is complementary to nucleotides 518 to 559 of an mRNA encoding human PTPN2 comprising the sequence set forth in SEQ ID NO: 40; or complementary to nucleotides 1294 to 2141 of an mRNA encoding human TOX comprising the sequence set forth in SEQ ID NO: 41; wherein the recombinant nucleic acid is inserted into a target region of the genome of the primary immune cell, and wherein the primary immune cell does not comprise a viral vector for introducing the recombinant nucleic acid into the primary immune cell.

In one aspect, provided herein are primary immune cell comprising at least one recombinant nucleic acid(s) comprising a first nucleic acid comprising the sequence set forth in SEQ ID NO: 49; and a second nucleic acid comprising the sequence set forth in SEQ ID NO: 82, inserted into a target region of the genome of the primary immune cell, and wherein the primary immune cell does not comprise a viral vector for introducing the recombinant nucleic acid(s) into the primary immune cell.

In one aspect, provided herein are primary immune cell comprising at least one recombinant nucleic acid(s) comprising a first nucleic acid comprising the sequence set forth in SEQ ID NO: 49; and a second nucleic acid comprising the sequence set forth in SEQ ID NO: SEQ ID NOs: 99 or 104, inserted into a target region of the genome of the primary immune cell, and wherein the primary immune cell does not comprise a viral vector for introducing the recombinant nucleic acid into the primary immune cell.

In one aspect, provided herein are viable, virus-free, primary cell comprising a ribonucleoprotein (RNP)-recombinant nucleic acid complex, wherein the RNP comprises a nuclease domain and a guide RNA, and wherein the recombinant nucleic acid encodes: a priming receptor comprising a first extracellular antigen-binding domain that specifically binds to ALPG/P; a chimeric antigen receptor comprising a second extracellular antigen-binding domain that specifically binds to MSLN; a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and a second nucleic acid sequence at least 15 nucleotides in length, wherein the second nucleic acid sequence is complementary to nucleotides 518 to 559 of an mRNA encoding human PTPN2 comprising the sequence set forth in SEQ ID NO: 40; or complementary to nucleotides 1294 to 2141 of an mRNA encoding human TOX comprising the sequence set forth in SEQ ID NO: 41; and wherein the 5' and 3' ends of the recombinant nucleic acid comprise nucleotide sequences that are homologous to genomic sequences flanking an insertion site in the genome of the primary cell.

In one aspect, provided herein are viable, virus-free, primary cell comprising a ribonucleoprotein complex (RNP)-recombinant nucleic acid(s) complex, wherein the RNP comprises a nuclease domain and a guide RNA, wherein recombinant nucleic acid(s) comprises a first nucleic acid comprising the sequence set forth in SEQ ID NO: 49; and a second nucleic acid comprising the sequence set forth in SEQ ID NO: 82, and wherein the 5' and 3' ends of the recombinant nucleic acid(s) comprise nucleotide sequences that are homologous to genomic sequences flanking an insertion site in the genome of the primary cell.

In one aspect, provided herein are viable, virus-free, primary cell comprising a ribonucleoprotein complex (RNP)-recombinant nucleic acid(s) complex, wherein the RNP comprises a nuclease domain and a guide RNA, wherein recombinant nucleic acid(s) comprises a first nucleic acid comprising the sequence set forth in SEQ ID NO: 49; and a second nucleic acid comprising the sequence set forth in SEQ ID NO: SEQ ID NOs: 99 or 104, and wherein the 5' and 3' ends of the recombinant nucleic acid(s) comprise nucleotide sequences that are homologous to genomic sequences flanking an insertion site in the genome of the primary cell.

In some embodiments, the cell comprises a sequence selected from the group consisting of the sequences set forth in SEQ ID NOs: 168, 167, or 166.

In some embodiments, the first nucleic acid reduces expression of FAS in the immune cell by at least 50%, 55%, 60%, 65%, 75%, 80%, 85%, 90%, 95%, or 99% as compared to a control cell that does not comprise the first nucleic acid.

In some embodiments, expression of FAS in the immune cell is reduced by at least 50%, 55%, 60%, 65%, 75%, 80%, 85%, 90%, 95%, or 99% as compared to a control cell that does not comprise the first nucleic acid.

In some embodiments, the second nucleic acid reduces expression of PTPN2 in the immune cell by at least 50%, 55%, 60%, 65%, 75%, 80%, 85%, 90%, 95%, or 99% as compared to a control cell that does not comprise the second nucleic acid.

In some embodiments, expression of PTPN2 in the immune cell is reduced by at least 50%, 55%, 60%, 65%, 75%, 80%, 85%, 90%, 95%, or 99% as compared to a control cell that does not comprise the second nucleic acid In some embodiments, the second nucleic acid reduces expression of TOX in the immune cell by at least 50%, 55%, 60%, 65%, 75%, 80%, 85%, 90%, 95%, or 99% as compared to a control cell that does not comprise the second nucleic acid.

In some embodiments, expression of TOX in the immune cell is reduced by at least 50%, 55%, 60%, 65%, 75%, 80%, 85%, 90%, 95%, or 99% as compared to a control cell that does not comprise the second nucleic acid.

In some embodiments, expression of FAS, PTPN2, and/or TOX is determined by a nucleic acid assay or a protein assay.

In some embodiments, the nucleic acid assay comprises at least one of polymerase chain reaction (PCR), quantitative PCR (qPCR), RT-qPCR, microarray, gene array, or RNAseq.

In some embodiments, the protein assay comprises at least one of immunoblotting, fluorescence activated cell sorting, flow-cytometry, magnetic-activated cell sorting, or affinity-based cell separation.

In one aspect, provided herein are population of cells comprising a plurality of immune cells disclosed herein.

In one aspect, provided herein are pharmaceutical composition comprising the immune cell disclosed herein or the population of cells disclosed herein, and a pharmaceutically acceptable excipient.

In one aspect, provided herein are pharmaceutical composition comprising the recombinant nucleic acid disclosed herein or the vector disclosed herein, and a pharmaceutically acceptable excipient.

In one aspect, provided herein are method of editing an immune cell, comprising providing a ribonucleoprotein (RNP)-recombinant nucleic acid complex, wherein the RNP comprises a nuclease domain and a guide RNA, wherein the recombinant nucleic acid comprises the recombinant nucleic acid disclosed herein, and wherein the 5' and 3' ends of the recombinant nucleic acid comprise nucleotide sequences that are homologous to genomic sequences flanking an insertion site in the genome of the immune cell; non-virally introducing the RNP-recombinant nucleic acid complex into the immune cell, wherein the guide RNA specifically hybridizes to a target region of the genome of the primary immune cell, and wherein the nuclease domain cleaves the target region to create the insertion site in the genome of the immune cell; and editing the immune cell via insertion of the recombinant nucleic acid disclosed herein into the insertion site in the genome of the immune cell.

In some embodiments, non-virally introducing comprises electroporation.

In some embodiments, the nuclease domain comprises a CRISPR-associated endonuclease (Cas), optionally a Cas9 nuclease.

In some embodiments, the target region of the genome of the cell is a T Cell Receptor Alpha Constant (TRAC) locus or a genomic safe harbor (GSH) locus.

In some embodiments, the GSH locus is the GS94 locus.

In some embodiments, the recombinant nucleic acid is a double-stranded recombinant nucleic acid or a single-stranded recombinant nucleic acid.

In some embodiments, the recombinant nucleic acid is a linear recombinant nucleic acid or a circular recombinant nucleic acid, optionally wherein the circular recombinant nucleic acid is a plasmid.

In some embodiments, the immune cell is a primary human immune cell.

In some embodiments, the immune cell is an allogeneic immune cell.

In some embodiments, the immune cell is an autologous immune cell.

In some embodiments, the immune cell is a natural killer (NK) cell, a T cell, a CD8+ T cell, a CD4+ T cell, a primary T cell, or a T cell progenitor.

In some embodiments, the immune cell is a primary T cell.

In some embodiments, the immune cell is a primary human T cell.

In some embodiments, the immune cell is virus-free.

In some embodiments, the method further comprising obtaining the immune cell from a patient and introducing the recombinant nucleic acid in vitro.

In one aspect, provided herein are method of treating a disease in a subject comprising administering the immune cell disclosed herein or the pharmaceutical composition disclosed herein to the subject.

In some embodiments, the disease is cancer.

In some embodiments, the cancer is a solid cancer or a liquid cancer.

In some embodiments, the cancer is ovarian cancer, fallopian cancer, primary peritoneal cancer, uterine cancer, mesothelioma, cervical cancer, or pancreatic cancer.

In some embodiments, the administration of the immune cell enhances an immune response in the subject.

In some embodiments, the enhanced immune response is an adaptive immune response.

In some embodiments, the enhanced immune response is an innate immune response.

In some embodiments, the enhanced immune response is an increased expression of at least one cytokine or chemokine.

In some embodiments, the at least one cytokine or chemokine is IL-2 or IFNγ.

In some embodiments, the method further comprising administering an immunotherapy to the subject concurrently with the immune cell or subsequently to the immune cell.

In one aspect, provided herein are method of inhibiting a target cell in a subject comprising administering the immune cell disclosed herein to the subject, wherein the immune cell inhibits the target cell.

In some embodiments, the target cell expresses ALPG/P and MSLN.

In some embodiments, the target cell is a cancer cell.

In one aspect, provided herein are method of inducing expression of a chimeric antigen receptor with a priming receptor in an immune cell comprising obtaining an immune cell comprising the recombinant nucleic acid disclosed herein; and/or the vector disclosed herein; and contacting the immune cell with a target cell expressing ALPG/P and MSLN, wherein binding of the priming receptor to ALPG/P on the target cell induces activation of the priming receptor and expression of the chimeric antigen receptor.

In one aspect, provided herein are method of modulating the activity of an immune cell comprising: obtaining an immune cell comprising the recombinant nucleic acid disclosed herein; and/or the vector disclosed herein; and contacting the immune cell with a target cell expressing ALPG/P and MSLN, wherein binding of the priming receptor to ALPG/P on the target cell induces activation of the priming receptor and expression of the chimeric antigen receptor and wherein binding of the chimeric antigen receptor to MSLN on the target cell modulates the activity of the immune cell.

In some embodiments, the modulation of the immune cell activity comprises enhancing an immune response.

In some embodiments, the enhanced immune response is an adaptive immune response.

In some embodiments, the enhanced immune response is an innate immune response.

In some embodiments, the immune cell activity is an increased expression of at least one cytokine or chemokine.

In some embodiments, the at least one cytokine or chemokine is IL-2 or IFNγ.

In some embodiments, expression of FAS in the immune cell is reduced by at least 50%, 55%, 60%, 65%, 75%, 80%, 85%, 90%, 95%, or 99% as compared to a control cell that does not comprise the first nucleic acid.

In some embodiments, expression of PTPN2 in the immune cell is reduced by at least 50%, 55%, 60%, 65%, 75%, 80%, 85%, 90%, 95%, or 99% as compared to a control cell that does not comprise the second nucleic acid.

In some embodiments, expression of TOX in the immune cell is reduced by at least 50%, 55%, 60%, 65%, 75%, 80%, 85%, 90%, 95%, or 99% as compared to a control cell that does not comprise the second nucleic acid.

In some embodiments, expression of FAS, PTPN2, and/or TOX in the immune cell is determined by a nucleic acid assay or a protein assay.

In some embodiments, the nucleic acid assay comprises at least one of polymerase chain reaction (PCR), quantitative PCR (qPCR), RT-qPCR, microarray, gene array, or RNAseq.

In some embodiments, the protein assay comprises at least one of immunoblotting, fluorescence activated cell sorting, flow-cytometry, magnetic-activated cell sorting, or affinity-based cell separation.

BRIEF DESCRIPTION OF THE SEVERAL VIEWS OF THE DRAWINGS

These and other features, aspects, and advantages of the present invention will become better understood with regard to the following description, and accompanying drawings, where:

FIG. 5A shows cytokine production by the logic gate-expressing T cells (LG1 and LG3), CAR-expressing-T cells, or negative control cells after incubation with the K562 cell line. FIG. 5B shows cytokine production by the logic gate-expressing T cells (LG1 and LG3), CAR-expressing-T cells, or negative control cells after incubation with the K562$^{MSLN}$ cell line. FIG. 5C shows cytokine production by the logic gate-expressing T cells (LG1 and LG3), CAR-expressing-T cells, or negative control cells after incubation with the K562$^{ALPG}$ cell line, FIG. 5D shows cytokine production by the logic gate-expressing T cells (LG1 and LG3), CAR-expressing-T cells, or negative control cells after incubation with the K562$^{ALPG/MSLN}$ cell line.

FIG. 8A shows ALPG expression in K562$^{ALPG}$ low and high expressing cells. FIG. 8B shows ALPG expression in K562$^{ALPG}$ low and high expressing cells, AsPC-1 cells, and K562-EFG cells. FIG. 8C shows priming receptor and CAR expression on engineered T cells before and after incubation with K562$^{ALPG}$ low and high expressing cells.

FIG. 9A shows ALPG expression in SKOV3-EFG cells, K562$^{ALPG/MSLN}$ cells, and K562 EFG cells. FIG. 9B shows MSLN expression in SKOV3-WT cells, K562$^{ALPG/MSLN}$ cells, and K562 EFG cells. FIG. 9C shows IL-2 cytokine production after incubation of T cells expressing the indicated LG or CAR with the SKOV3-EFG cells. FIG. 9D shows IFNγ cytokine production after incubation of T cells expressing the indicated LG or CAR with the SKOV3-EFG cells

FIG. 12A shows tumor volume in the K562 dual-flank model in K562$^{MSLN}$ tumor, modeling the healthy mesothelial lining, after treatment with the constitutive CAR. FIG. 12B shows tumor volume in the K562$^{ALPG/MSLN}$ tumor, modeling an on-target tumor, after treatment with the constitutive CAR. FIG. 12C shows tumor volume in the K562$^{MSLN}$ tumor after treatment with the Logic Gate 1 T cells. FIG. 12D shows tumor volume in the K562$^{ALPG/MSLN}$ tumor after treatment with the Logic Gate 1 T cells. FIG. 12E shows tumor volume in the K562$^{MSLN}$ tumor after treatment with the Logic Gate 3 T cells. FIG. 12F shows tumor volume in the K562$^{ALPG/MSLN}$ tumor after treatment with the Logic Gate 3 T cells. In each figure, the lower line shows the tumor volume after treatment with the indicated T cells, and the higher line shows the tumor volume after treatment with control T cells.

FIG. 13A shows tumor volume after treatment with a high dose of the indicated engineered T cells.

FIG. 17A shows that shRNA module targeting FAS, PTPN2, and TOX provides stable knockdown of FAS for at least 7 weeks after editing under resting conditions. FIG. 17B shows that FAS, PTPN2, and NR4A1 protein levels were also significantly reduced 6 days post editing.

FIG. 39A provides a diagram of the knockdown system and a diagram of an exemplary shRNA-CAR dual construct. FIG. 39B shows robust dual knockdown (>50%) of FAS and additional targets using shRNA.

FIG. 40A provides a diagram of an exemplary control and shFAS system. FIG. 40B shows that FAS knockdown provided >2-fold improved protection from FAS-mediated apoptosis.

FIG. 44A shows shRNA knockdown of FAS. FIG. 44B shows shRNA knockdown of PTPN2.

FIG. 47A shows that the CAR only T cells inhibited the growth of $K526^{MSLN}$ tumor cells. FIG. 47B shows that the CAR only T cells inhibited the growth of $K526^{MSLN/ALPG}$ tumor cells. FIG. 47C shows that the AB-1013, AB-1014, and AB-1015 shRNA+ logic gate circuit T cells did not inhibit growth of the $K526^{MSLN}$ tumor cells. FIG. 47D shows that the AB-1013, AB-1014, and AB-1015 shRNA+ logic gate circuit T cells inhibited growth of the $K526^{MSLN/ALGP}$ tumor cells.

FIG. 51 shows that AB-1015 was associated with a modest increase in ALPG-independent killing activity in $K562^{MSLN}$ cells and increased IFNγ expression as compared to AB-1013 and AB-1014.

FIG. 56A shows randomization of mouse groups 5 days post implantation. FIG. 56B shows that AB-1015 T cells reduced tumor volume in an in vivo ovarian cancer model. FIG. 56C shows the mouse weight post tumor implantation after treatment with AB-1015 T cells. Treatment with AB-1015 T cells did not result in body weight loss.

DETAILED DESCRIPTION OF THE INVENTION

Definitions

Figure 1:
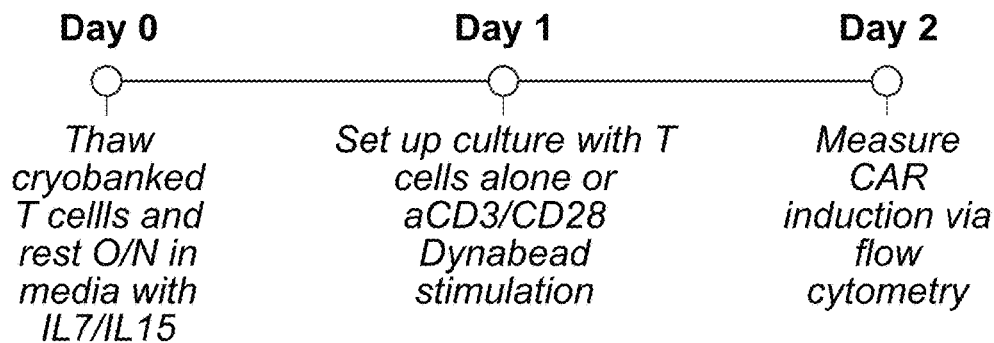
FIG. 1 shows a schematic of the logic gate expression with T cell activation assay.

Terms used in the claims and specification are defined as set forth below unless otherwise specified.

As used herein, the term "gene" refers to the basic unit of heredity, consisting of a segment of DNA arranged along a chromosome, which codes for a specific protein or segment of protein. A gene typically includes a promoter, a 5' untranslated region, one or more coding sequences (exons), optionally introns, and a 3' untranslated region. The gene may further comprise a terminator, enhancers and/or silencers.

As used herein, the term "locus" refers to a specific, fixed physical location on a chromosome where a gene or genetic marker is located.

The term "safe harbor locus" refers to a locus at which genes or genetic elements can be incorporated without disruption to expression or regulation of adjacent genes. These safe harbor loci are also referred to as safe harbor sites (SHS) or genomic safe harbor (GSH) sites. As used herein, a safe harbor locus refers to an "integration site" or "knock-in site" at which a sequence encoding a transgene, as defined herein, can be inserted. In some embodiments the insertion occurs with replacement of a sequence that is located at the integration site. In some embodiments, the insertion occurs without replacement of a sequence at the integration site. Examples of integration sites contemplated are provided in Table D.

As used herein, the term "insert" refers to a nucleotide sequence that is integrated (inserted) at a target locus or safe harbor site. The insert can be used to refer to the genes or genetic elements that are incorporated at the target locus or safe harbor site using, for example, homology-directed repair (HDR) CRISPR/Cas9 genome-editing or other methods for inserting nucleotide sequences into a genomic region known to those of ordinary skill in the art.

The term "inserting" refers to a manipulation of a nucleotide sequence to introduce a non-native sequence. This is done, for example, via the use of restriction enzymes and ligases whereby the DNA sequence of interest, usually encoding the gene of interest, can be incorporated into another nucleic acid molecule by digesting both molecules with appropriate restriction enzymes in order to create compatible overlaps and then using a ligase to join the molecules together. One skilled in the art is very familiar with such manipulations and examples may be found in Sambrook et al. (Sambrook, Fritsch, & Maniatis, "Molecular Cloning: A Laboratory Manual", 2nd ed., Cold Spring Harbor Laboratory, 1989), which is hereby incorporated by reference in its entirety including any drawings, figures and tables.

The "CRISPR/Cas" system refers to a widespread class of bacterial systems for defense against foreign nucleic acid. CRISPR/Cas systems are found in a wide range of eubacterial and archaeal organisms. CRISPR/Cas systems include type I, II, and III sub-types. Wild-type type II CRISPR/Cas systems utilize an RNA-mediated nuclease, Cas9 in complex with guide and activating RNA to recognize and cleave foreign nucleic acid. Guide RNAs having the activity of both a guide RNA and an activating RNA are also known in the art. In some cases, such dual activity guide RNAs are referred to as a small guide RNA (sgRNA).

Cas9 homologs are found in a wide variety of eubacteria, including, but not limited to bacteria of the following taxonomic groups: *Actinobacteria, Aquificae, Bacteroidetes-Chlorobi, Chlamydiae-Verrucomicrobia, Chlroflexi, Cyanobacteria, Firmicutes, Proteobacteria, Spirochaetes,* and *Thermotogae*. An exemplary Cas9 protein is the *Streptococcus pyogenes* Cas9 protein. Additional Cas9 proteins and homologs thereof are described in, e.g., Chylinksi, et al., RNA Biol. 2013 May 1; 10(5): 726-737; Nat. Rev. Microbiol. 2011 June; 9(6): 467-477; Hou, et al., Proc Natl Acad Sci USA. 2013 Sep. 24; 110(39):15644-9; Sampson et al., Nature. 2013 May 9; 497(7448):254-7; and Jinek, et al., Science. 2012 Aug. 17; 337(6096):816-21. The Cas9 nuclease domain can be optimized for efficient activity or enhanced stability in the host cell.

As used herein, the term "Cas9" refers to an RNA-mediated nuclease (e.g., of bacterial or archaeal origin, or derived therefrom). Exemplary RNA-mediated nucleases include the foregoing Cas9 proteins and homologs thereof, and include but are not limited to, CPF1 (See, e.g., Zetsche et al., Cell, Volume 163, Issue 3, p 759-771, 22 Oct. 2015). Similarly, as used herein, the term "Cas9 ribonucleoprotein" complex and the like refers to a complex between the Cas9 protein, and a crRNA (e.g., guide RNA or small guide RNA), the Cas9 protein and a trans-activating crRNA (tracrRNA), the Cas9 protein and a small guide RNA, or a combination thereof (e.g., a complex containing the Cas9 protein, a tracrRNA, and a crRNA guide RNA).

As used herein, the phrase "immune cell" is inclusive of all cell types that can give rise to immune cells, including hematopoietic cells such hematopoietic stem cells, pluripotent stem cells, and induced pluripotent stem cells (iPSCs). In some embodiments, the immune cell is a B cell, macrophage, a natural killer (NK) cell, an induced pluripotent stem cell (iPSC), a human pluripotent stem cell (HSPC), a T cell or a T cell progenitor or dendritic cell. In some embodiments, the cell is an innate immune cell.

As used herein, the term "primary" in the context of a primary cell or primary stem cell refers to a cell that has not been transformed or immortalized. Such primary cells can be cultured, sub-cultured, or passaged a limited number of times (e.g., cultured 0, 1, 2, 3, 4, 5, 6, 7, 8, 9, 10, 11, 12, 13, 14, 15, 16, 17, 18, 19, or 20 times). In some cases, the primary cells are adapted to in vitro culture conditions. In some cases, the primary cells are isolated from an organism, system, organ, or tissue, optionally sorted, and utilized, e.g., directly without culturing or sub-culturing. In some cases, the primary cells are stimulated, activated, or differentiated. For example, primary T cells can be activated by contact with (e.g., culturing in the presence of) CD3, CD28 agonists, IL-2, IFN-γ, or a combination thereof.

As used herein, the terms "T lymphocyte" and "T cell" are used interchangeably and refer to cells that have completed maturation in the thymus, and identify certain foreign antigens in the body. The terms also refer to the major leukocyte types that have various roles in the immune system, including activation and deactivation of other immune cells. The T cell can be any T cell such as a cultured T cell, e.g., a primary T cell, or a T cell derived from a cultured T cell line, e.g., a Jurkat, SupT1, etc., or a T cell obtained from a mammal. T cells include, but are not limited to, naïve T cells, stimulated T cells, primary T cells (e.g., uncultured), cultured T cells, immortalized T cells, helper T cells, cytotoxic T cells, memory T cells, regulatory T cells, natural killer T cells, combinations thereof, or sub-populations thereof. The T cell can be a CD3+ cell. T cells can be $CD4^+$, $CD8^+$, or $CD4^+$ and $CD8^+$. The T cell can be any type of T cell, CD4+/CD8+ double positive T cells, CD4+ helper T cells (e.g. Th1 and Th2 cells), CD8+ T cells (e.g. cytotoxic T cells), peripheral Including but not limited to blood mononuclear cells (PBMC), peripheral blood leukocytes (PBL), tumor infiltrating lymphocytes (TIL), memory T cells, naive T cells, regulatory T cells, γδ T cells, etc. It can be any T cell at any stage of development. Additional types of helper T cells include Th3 (Treg) cells, Th17 cells, Th9 cells, or Tfh cells. Additional types of memory T cells include cells such as central memory T cells (Tcm cells), effector memory T cells (Tem cells and TEMRA cells). A T cell can also refer to a genetically modified T cell, such as a T cell that has been modified to express a T cell receptor (TCR) or a chimeric antigen receptor (CAR). T cells can also be differentiated from stem cells or progenitor cells.

"CD4+ T cells" refers to a subset of T cells that express CD4 on their surface and are associated with a cellular immune response. CD4+ T cells are characterized by a post-stimulation secretion profile that can include secretion of cytokines such as IFN-γ, TNF-α, IL-2, IL-4 and IL-10. "CD4" is a 55 kD glycoprotein originally defined as a differentiation antigen on T lymphocytes, but was also found on other cells including monocytes/macrophages. The CD4 antigen is a member of the immunoglobulin superfamily and has been implicated as an associative recognition element in MHC (major histocompatibility complex) class II restricted immune responses. On T lymphocytes, the CD4 antigen defines a helper/inducer subset.

"CD8+ T cells" refers to a subset of T cells that express CD8 on their surface, are MHC class I restricted, and function as cytotoxic T cells. The "CD8" molecule is a differentiation antigen present on thymocytes, as well as on cytotoxic and suppressor T lymphocytes. The CD8 antigen is a member of the immunoglobulin superfamily and is an associative recognition element in major histocompatibility complex class I restriction interactions.

As used herein, the phrase "hematopoietic stem cell" refers to a type of stem cell that can give rise to a blood cell. Hematopoietic stem cells can give rise to cells of the myeloid or lymphoid lineages, or a combination thereof. Hematopoietic stem cells are predominantly found in the bone marrow, although they can be isolated from peripheral blood, or a fraction thereof. Various cell surface markers can be used to identify, sort, or purify hematopoietic stem cells. In some cases, hematopoietic stem cells are identified as c-kit$^+$ and lin$^-$. In some cases, human hematopoietic stem cells are identified as CD34$^+$, CD59$^+$, Thy1/CD90$^+$, CD38$^{lo/-}$, C-kit/CD117$^+$, lin$^-$. In some cases, human hematopoietic stem cells are identified as CD34$^-$, CD59$^+$, Thy1/CD90$^+$, CD38$^{lo/-}$, C-kit/CD117$^+$, lin$^-$. In some cases, human hematopoietic stem cells are identified as CD133$^+$, CD59$^+$, Thy1/CD90$^+$, CD38$^{lo/-}$, C-kit/CD117$^+$, lin$^-$. In some cases, mouse hematopoietic stem cells are identified as CD34$^{lo/-}$, SCA-1$^+$, Thy1$^{+/lo}$, CD38$^+$, C-kit$^+$, lin$^-$. In some cases, the hematopoietic stem cells are CD150$^+$CD48$^-$CD244$^-$.

As used herein, the phrase "hematopoietic cell" refers to a cell derived from a hematopoietic stem cell. The hematopoietic cell may be obtained or provided by isolation from an organism, system, organ, or tissue (e.g., blood, or a fraction thereof). Alternatively, an hematopoietic stem cell can be isolated and the hematopoietic cell obtained or provided by differentiating the stem cell. Hematopoietic cells include cells with limited potential to differentiate into further cell types. Such hematopoietic cells include, but are not limited to, multipotent progenitor cells, lineage-restricted progenitor cells, common myeloid progenitor cells, granulocyte-macrophage progenitor cells, or megakaryocyte-erythroid progenitor cells. Hematopoietic cells include cells of the lymphoid and myeloid lineages, such as lymphocytes, erythrocytes, granulocytes, monocytes, and thrombocytes.

As used herein, the term "construct" refers to a complex of molecules, including macromolecules or polynucleotides.

As used herein, the term "integration" refers to the process of stably inserting one or more nucleotides of a construct into the cell genome, i.e., covalently linking to a nucleic acid sequence in the chromosomal DNA of the cell. It may also refer to nucleotide deletions at a site of integration. Where there is a deletion at the insertion site, "integration" may further include substitution of the endogenous sequence or nucleotide deleted with one or more inserted nucleotides.

As used herein, the term "exogenous" refers to a molecule or activity that has been introduced into a host cell and is not native to that cell. The molecule can be introduced, for example, by introduction of the encoding nucleic acid into host genetic material, such as by integration into a host chromosome, or as non-chromosomal genetic material, such as a plasmid. Thus, the term, when used in connection with expression of an encoding nucleic acid, refers to the introduction of the encoding nucleic acid into a cell in an expressible form. The term "endogenous" refers to a molecule or activity that is present in a host cell under natural, unedited conditions. Similarly, the term, when used in connection with expression of the encoding nucleic acid, refers to expression of the encoding nucleic acid that is contained within the cell and not introduced exogenously.

The term "heterologous" refers to a nucleic acid or polypeptide sequence or domain which is not native to a flanking sequence, e.g., wherein the heterologous sequence is not found in nature coupled to the nucleic acid or polypeptide sequences occurring at one or both ends.

The term "homologous" refers to a nucleic acid or polypeptide sequence or domain which is native to a flanking sequence, e.g., wherein the homologous sequence is found in nature coupled to the nucleic acid or polypeptide sequences occurring at one or both ends.

As used herein, a "polynucleotide donor construct" refers to a nucleotide sequence (e.g. DNA sequence) that is genetically inserted into a polynucleotide and is exogenous to that polynucleotide. The polynucleotide donor construct is transcribed into RNA and optionally translated into a polypeptide. The polynucleotide donor construct can include prokaryotic sequences, cDNA from eukaryotic mRNA, genomic DNA sequences from eukaryotic (e.g., mammalian) DNA, and synthetic DNA sequences. For example, the polynucleotide donor construct can be a miRNA, shRNA, natural polypeptide (i.e., a naturally occurring polypeptide) or fragment thereof or a variant polypeptide (e.g. a natural polypeptide having less than 100% sequence identity with the natural polypeptide) or fragments thereof.

As used herein, the term "complementary" or "complementarity" refers to specific base pairing between nucleotides or nucleic acids. Complementary nucleotides are, generally, A and T (or A and U), and G and C. The guide RNAs described herein can comprise sequences, for example, DNA targeting sequence that are perfectly complementary or substantially complementary (e.g., having 1-4 mismatches) to a genomic sequence in a cell.

The term "encode" refers to protein coding sequences or non-protein coding sequences. Non-protein coding sequences include, but are not limited to, short hairpin RNA (shRNA), small interfering RNA (siRNA), double stranded RNA (dsRNA), or antisense oligonucleotides.

As used herein, the term "transgene" refers to a polynucleotide that has been transferred naturally, or by any of a number of genetic engineering techniques from one organism to another. It is optionally translated into a polypeptide. It is optionally translated into a recombinant protein. A "recombinant protein" is a protein encoded by a gene—recombinant DNA—that has been cloned in a system that supports expression of the gene and translation of messenger RNA (see expression system). The recombinant protein can be a therapeutic agent, e.g. a protein that treats a disease or disorder disclosed herein. As used, transgene can refer to a polynucleotide that encodes a polypeptide.

The terms "protein," "polypeptide," and "peptide" are used herein interchangeably.

As used herein, the term "operably linked" or "operatively linked" refers to the binding of a nucleic acid sequence to a single nucleic acid fragment such that one function is affected by the other. For example, if a promoter is capable of affecting the expression of a coding sequence or functional RNA (i.e., the coding sequence or functional RNA is under transcriptional control by the promoter), the promoter is operably linked thereto. Coding sequences can be operably linked to control sequences in both sense and antisense orientation.

As used herein, the term "developmental cell states" refers to, for example, states when the cell is inactive, actively expressing, differentiating, senescent, etc. developmental cell state may also refer to a cell in a precursor state (e.g., a T cell precursor).

As used, the term "encoding" refers to a sequence of nucleic acids which codes for a protein or polypeptide of interest. The nucleic acid sequence may be either a molecule of DNA or RNA. In preferred embodiments, the molecule is a DNA molecule. In other preferred embodiments, the molecule is a RNA molecule. When present as a RNA molecule, it will comprise sequences which direct the ribosomes of the host cell to start translation (e.g., a start codon, ATG) and direct the ribosomes to end translation (e.g., a stop codon). Between the start codon and stop codon is an open reading frame (ORF). Such terms are known to one of ordinary skill in the art.

As used herein, the term "subject" refers to a mammalian subject. Exemplary subjects include humans, monkeys, dogs, cats, mice, rats, cows, horses, camels, goats, rabbits, pigs and sheep. In certain embodiments, the subject is a human. In some embodiments the subject has a disease or condition that can be treated with an engineered cell provided herein or population thereof. In some aspects, the disease or condition is a cancer.

As used herein, the term "promoter" refers to a nucleotide sequence (e.g. DNA sequence) capable of controlling the expression of a coding sequence or functional RNA. The promoter sequence consists of proximal and more distal upstream elements, the latter elements often referred to as enhancers. A promoter can be derived from natural genes in its entirety, can be composed of different elements from different promoters found in nature, and/or may comprise synthetic DNA segments. A promoter, as contemplated herein, can be endogenous to the cell of interest or exogenous to the cell of interest. It is appreciated by those skilled in the art that different promoters can induce gene expression in different tissue or cell types, or at different developmental stages, or in response to different environmental conditions. As is known in the art, a promoter can be selected according to the strength of the promoter and/or the conditions under which the promoter is active, e.g., constitutive promoter, strong promoter, weak promoter, inducible/repressible promoter, tissue specific promoter Or developmentally regulated promoters, cell cycle-dependent promoters, and the like.

A promoter can be an inducible promoter (e.g., a heat shock promoter, tetracycline-regulated promoter, steroid-regulated promoter, metal-regulated promoter, estrogen receptor-regulated promoter, etc.). The promoter can be a constitutive promoter (e.g., CMV promoter, UBC promoter). In some embodiments, the promoter can be a spatially restricted and/or temporally restricted promoter (e.g., a tissue specific promoter, a cell type specific promoter, etc.). See for example US Publication 20180127786, the disclosure of which is herein incorporated by reference in its entirety.

Gene editing, as contemplated herein, may involve a gene (or nucleotide sequence) knock-in or knock-out. As used herein, the term "knock-in" refers to an addition of a DNA sequence, or fragment thereof into a genome. Such DNA sequences to be knocked-in may include an entire gene or genes, may include regulatory sequences associated with a gene or any portion or fragment of the foregoing. For example, a polynucleotide donor construct encoding a recombinant protein may be inserted into the genome of a cell carrying a mutant gene. In some embodiments, a knock-in strategy involves substitution of an existing sequence with the provided sequence, e.g., substitution of a mutant allele with a wild-type copy. On the other hand, the term "knock-out" refers to the elimination of a gene or the expression of a gene. For example, a gene can be knocked out by either a deletion or an addition of a nucleotide sequence that leads to a disruption of the reading frame. As another example, a gene may be knocked out by replacing a part of the gene with an irrelevant (e.g., non-coding) sequence.

As used herein, the term "non-homologous end joining" or NHEJ refers to a cellular process in which cut or nicked ends of a DNA strand are directly ligated without the need for a homologous template nucleic acid. NHEJ can lead to the addition, the deletion, substitution, or a combination thereof, of one or more nucleotides at the repair site.

As used herein, the term "homology directed repair" or HDR refers to a cellular process in which cut or nicked ends of a DNA strand are repaired by polymerization from a homologous template nucleic acid. Thus, the original sequence is replaced with the sequence of the template. The homologous template nucleic acid can be provided by homologous sequences elsewhere in the genome (sister chromatids, homologous chromosomes, or repeated regions on the same or different chromosomes). Alternatively, an exogenous template nucleic acid can be introduced to obtain a specific HDR-induced change of the sequence at the target site. In this way, specific mutations can be introduced at the cut site.

As used herein, a single-stranded DNA template or a double-stranded DNA template refers to a DNA oligonucleotide that can be used by a cell as a template for HDR. Generally, the single-stranded DNA template or a double-stranded DNA template has at least one region of homology to a target site. In some cases, the single-stranded DNA template or double-stranded DNA template has two homologous regions flanking a region that contains a heterologous sequence to be inserted at a target cut site.

The terms "vector" and "plasmid" are used interchangeably and as used herein refer to polynucleotide vehicles useful to introduce genetic material into a cell. Vectors can be linear or circular. Vectors can integrate into a target genome of a host cell or replicate independently in a host cell. Vectors can comprise, for example, an origin of replication, a multicloning site, and/or a selectable marker. An expression vector typically comprises an expression cassette. Vectors and plasmids include, but are not limited to, integrating vectors, prokaryotic plasmids, eukaryotic plasmids, plant synthetic chromosomes, episomes, cosmids, and artificial chromosomes.

As used herein, the phrase "introducing" in the context of introducing a nucleic acid or a complex comprising a nucleic acid, for example, an RNP-DNA template complex, refers to the translocation of the nucleic acid sequence or the RNP-DNA template complex from outside a cell to inside the cell. In some cases, introducing refers to translocation of the nucleic acid or the complex from outside the cell to inside the nucleus of the cell. Various methods of such translocation are contemplated, including but not limited to, electroporation, contact with nanowires or nanotubes, receptor mediated internalization, translocation via cell penetrating peptides, liposome mediated translocation, and the like.

As used herein the term "expression cassette" is a polynucleotide construct, generated recombinantly or synthetically, comprising regulatory sequences operably linked to a selected polynucleotide to facilitate expression of the selected polynucleotide in a host cell. For example, the regulatory sequences can facilitate transcription of the selected polynucleotide in a host cell, or transcription and translation of the selected polynucleotide in a host cell. An expression cassette can, for example, be integrated in the genome of a host cell or be present in an expression vector.

As used herein, the phrase "subject in need thereof" refers to a subject that exhibits and/or is diagnosed with one or more symptoms or signs of a disease or disorder as described herein.

A "chemotherapeutic agent" refers to a chemical compound useful in the treatment of cancer. Chemotherapeutic agents include "anti-hormonal agents" or "endocrine therapeutics" which act to regulate, reduce, block, or inhibit the effects of hormones that can promote the growth of cancer.

The term "composition" refers to a mixture that contains, e.g., an engineered cell or protein contemplated herein. In some embodiments, the composition may contain additional components, such as adjuvants, stabilizers, excipients, and the like. The term "composition" or "pharmaceutical composition" refers to a preparation which is in such form as to permit the biological activity of an active ingredient contained therein to be effective in treating a subject, and which contains no additional components which are unacceptably toxic to the subject in the amounts provided in the pharmaceutical composition.

The term "in situ" refers to processes that occur in a living cell growing separate from a living organism, e.g., growing in tissue culture.

The term "in vivo" refers to processes that occur in a living organism.

As used herein, the term "ex vivo" generally includes experiments or measurements made in or on living tissue, preferably in an artificial environment outside the organism, preferably with minimal differences from natural conditions.

The term "mammal" as used herein includes both humans and non-humans and include but is not limited to humans, non-human primates, canines, felines, murines, bovines, equines, and porcines.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease.

The term "ameliorating" refers to any therapeutically beneficial result in the treatment of a disease state, e.g., a cancer disease state, lessening in the severity or progression, remission, or cure thereof.

As used herein, the term "effective amount" refers to the amount of a compound (e.g., a compositions described herein, cells described herein) sufficient to effect beneficial or desired results. An effective amount can be administered in one or more administrations, applications or dosages and is not intended to be limited to a particular formulation or administration route.

As used herein, the term "treating" includes any effect, e.g., lessening, reducing, modulating, ameliorating or eliminating, that results in the improvement of the condition, disease, disorder, and the like, or ameliorating a symptom thereof.

The terms "modulate" and "modulation" refer to reducing or inhibiting or, alternatively, activating or increasing, a recited variable.

The terms "increase" and "activate" refer to an increase of 10%, 20%, 30%, 40%, 50%, 60%, 70%, 75%, 80%, 85%, 90%, 95%, 100%, 2-fold, 3-fold, 4-fold, 5-fold, 10-fold, 20-fold, 50-fold, 100-fold, or greater in a recited variable.

The terms "reduce" and "inhibit" refer to a decrease of 10%, 20%, 30%, 40%, 50%, 60%, 70%, 75%, 80%, 85%, 90%, 95%, 2-fold, 3-fold, 4-fold, 5-fold, 10-fold, 20-fold, 50-fold, 100-fold, or greater in a recited variable.

It must be noted that, as used in the specification and the appended claims, the singular forms "a," "an" and "the" include plural referents unless the context clearly dictates otherwise.

Logic Gate Systems

As used herein, a "logic gate," "circuit," "circuit receptor," "system" or "system receptor" refers to a two part protein expression system comprising a priming receptor and a chimeric antigen receptor. The system can be encoded on at least one nucleic acid inserted into a cell, where the priming receptor is expressed in the cell. The intracellular domain of the priming receptor is cleaved from the transmembrane domain upon binding of the priming receptor to its target antigen. The intracellular domain is then capable of translocating into a cell nucleus where it induces expression of the chimeric antigen receptor.

In one aspect, provided herein are systems comprising a priming receptor that binds to ALPG/P and a chimeric antigen receptor that binds to MSLN, wherein the transcription factor of the intracellular domain of the priming receptor is capable of inducing expression of the CAR. Such systems are alternatively termed "logic gates" or "circuits." In some aspects, the system is encoded by nucleic acid transgenes inserted into an immune cell. The system can be encoded on a single nucleic acid insert or fragment that comprises both transgenes, or can be encoded on two nucleic acids that encode the system transgenes individually. The priming receptor and CAR of the system can be placed in any order on the single nucleic acid. For example, the priming receptor can be at the 5' end and the CAR can be at the 3' end, or the CAR can be at the 5' end and the priming receptor can be at the 3' end.

A first constitutive promoter can be operably linked to the nucleotide sequence encoding the priming receptor. An inducible promoter can also be operably linked to the nucleotide sequence encoding the CAR. A second constitutive promoter can be operably linked to the first nucleic acid complementary to an mRNA encoding human FAS comprising the sequence set forth in SEQ ID NO: 39. A third constitutive promoter can be operably linked to the second nucleic acid complementary to an mRNA encoding human PTPN2 comprising the sequence set forth in SEQ ID NO: 40 or encoding human TOX comprising the sequence set forth in SEQ ID NO: 41.

In some embodiments, when the system is encoded on a single recombinant nucleic acid insert or fragment that comprises both transgenes and nucleic acid(s), the recombinant nucleic acid insert can comprise, in a 5' to 3' direction, the first constitutive promoter; the nucleotide sequence encoding priming receptor; the second constitutive promoter; the nucleotide sequence encoding a first nucleic acid complementary to human FAS mRNA, human PTPN2 mRNA, or human TOX mRNA; the inducible promoter; and the nucleotide sequence encoding chimeric antigen receptor.

In some embodiments, when the system is encoded on a single recombinant nucleic acid insert or fragment that comprises both transgenes and nucleic acid(s), the recombinant nucleic acid insert can comprise, in a 5' to 3' direction, the first constitutive promoter; the nucleotide sequence encoding priming receptor; the nucleotide sequence encoding a first nucleic acid complementary to human FAS mRNA, human PTPN2 mRNA, or human TOX mRNA; the inducible promoter; and the nucleotide sequence encoding chimeric antigen receptor.

In some embodiments, when the system is encoded on a single recombinant nucleic acid insert or fragment that comprises both transgenes and nucleic acid(s), the recombinant nucleic acid insert can comprise, in a 5' to 3' direction, the first constitutive promoter; the nucleotide sequence encoding priming receptor; the nucleotide sequence encoding a first nucleic acid complementary to human FAS mRNA, human PTPN2 mRNA, or human TOX mRNA; the nucleotide sequence encoding a second nucleic acid complementary to human FAS mRNA, human PTPN2 mRNA, or human TOX mRNA; the inducible promoter; and the nucleotide sequence encoding chimeric antigen receptor.

In some embodiments, when the system is encoded on a single recombinant nucleic acid insert or fragment that comprises both transgenes and nucleic acid(s), the recombinant nucleic acid insert can comprise, in a 5' to 3' direction, the inducible promoter, and the nucleotide sequence encoding chimeric antigen receptor; the second constitutive promoter; the nucleotide sequence encoding a first nucleic acid complementary to human FAS mRNA, human PTPN2 mRNA, or human TOX mRNA; and the first constitutive promoter; the nucleotide sequence encoding priming receptor.

In some embodiments, when the system is encoded on a single recombinant nucleic acid insert or fragment that comprises both transgenes and nucleic acid(s), the recombinant nucleic acid insert can comprise, in a 5' to 3' direction, the inducible promoter, and the nucleotide sequence encoding chimeric antigen receptor; the first constitutive promoter; the nucleotide sequence encoding a first nucleic acid complementary to human FAS mRNA, human PTPN2 mRNA, or human TOX mRNA; the nucleotide sequence encoding priming receptor.

In some embodiments, when the system is encoded on a single recombinant nucleic acid insert or fragment that comprises both transgenes and nucleic acid(s), the recombinant nucleic acid insert can comprise, in a 5' to 3' direction, the inducible promoter, and the nucleotide sequence encoding chimeric antigen receptor; the first constitutive promoter; the nucleotide sequence encoding a first nucleic acid complementary to human FAS mRNA, human PTPN2 mRNA, or human TOX mRNA; the nucleotide sequence encoding a second nucleic acid complementary to human FAS mRNA, human PTPN2 mRNA, or human TOX mRNA; the nucleotide sequence encoding priming receptor.

In some embodiments, when the system is encoded on a single recombinant nucleic acid insert or fragment that comprises both transgenes and nucleic acids, the recombinant nucleic acid insert can comprise, in a 5' to 3' direction, the first constitutive promoter; the nucleotide sequence encoding priming receptor; the second constitutive promoter; the nucleotide sequence encoding the first nucleic acid complementary to human FAS mRNA; the nucleotide sequence encoding the second nucleic acid complementary to human PTPN2 mRNA or TOX mRNA; the inducible promoter; and the nucleotide sequence encoding chimeric antigen receptor.

In another embodiments, the recombinant nucleic acid insert can comprise, in a 5' to 3' direction, the first constitutive promoter; the nucleotide sequence encoding priming receptor; the second constitutive promoter; the nucleotide sequence encoding the second first nucleic acid complementary to human PTPN2 mRNA or TOX mRNA; the nucleotide sequence encoding the first nucleic acid complementary to human FAS mRNA; the inducible promoter; and the nucleotide sequence encoding chimeric antigen receptor.

In another embodiments, the recombinant nucleic acid insert can comprise, in a 5' to 3' direction, the inducible promoter; the nucleotide sequence encoding chimeric antigen receptor; the second constitutive promoter; the nucleotide sequence encoding the first nucleic acid complementary to human FAS mRNA; the nucleotide sequence encoding the second first nucleic acid complementary to human PTPN2 mRNA or TOX mRNA; the second constitutive promoter; the nucleotide sequence encoding priming receptor.

In another embodiments, the recombinant nucleic acid insert can comprise, in a 5' to 3' direction, the inducible promoter; the nucleotide sequence encoding chimeric antigen receptor; the second constitutive promoter; the nucleotide sequence encoding the second first nucleic acid complementary to human PTPN2 mRNA or TOX mRNA; the nucleotide sequence encoding the first nucleic acid complementary to human FAS mRNA; the second constitutive promoter; the nucleotide sequence encoding priming receptor.

In some embodiments, the recombinant nucleic acid comprises a sequence selected from the group consisting of SEQ ID NOs; 166, 167, 168, 169, 170, or 171. In some embodiments, the recombinant nucleic acid comprises the sequence as set forth in SEQ ID NO: 166. In some embodiments, the recombinant nucleic acid comprises the sequence as set forth in SEQ ID NO: 167. In some embodiments, the recombinant nucleic acid comprises the sequence as set forth in SEQ ID NO: 168. In some embodiments, the recombinant nucleic acid comprises the sequence as set forth in SEQ ID NO: 169. In some embodiments, the recombinant nucleic acid comprises the sequence as set forth in SEQ ID NO: 170. In some embodiments, the recombinant nucleic acid comprises the sequence as set forth in SEQ ID NO: 171.

Priming Receptors

Provided herein are priming receptors comprising an extracellular antigen-binding domain that specifically binds Alkaline Phosphatase, Placental/Germ Cell (ALPG/P); ALPP: NCBI Entrez Gene: 250, UniProtKB/Swiss-Prot: P05187; ALPG: NCBI Entrez Gene: 251, UniProtKB/Swiss-Prot: P10696). In some embodiments, the priming receptor comprises an extracellular antigen-binding domain that specifically binds Alkaline Phosphatase, Placental (ALPP). In some embodiments, the priming receptor comprises an extracellular antigen-binding domain that specifically binds Alkaline Phosphatase, Germ Cell (ALPG). As used herein, "Alkaline Phosphatase, Placental/Germ Cell (ALPG/P)" refers to both Alkaline Phosphatase, Placental (ALPP) and Alkaline Phosphatase, Germ Cell (ALPG). An antigen binding domain that specifically binds ALPG/P is capable of specifically binding ALPG and/or ALPP.

In some embodiments, the priming receptor comprises a sequence as set forth in SEQ ID NO: 24. In some embodiments, the priming receptor comprises a sequence as set forth in SEQ ID NO: 25.

In certain aspects of the present disclosure, the priming receptor is a synthetic receptor based on the Notch protein. Binding of a natural Notch receptor to a cognate ligand, such as those from the Delta family of proteins, causes intramembrane proteolysis that cleaves an intracellular fragment of the Notch protein. This intracellular fragment is a transcriptional regulator that only functions when cleaved from Notch. Cleavage may occur by sequential proteolysis by ADAM metalloprotease and the gamma-secretase complex. This intracellular fragment enters the nucleus of a cell and activates cell-cell signaling genes. In contrast to a natural Notch protein, a synthetic notch priming receptor replaces the natural Notch intracellular fragment with one that causes a gene encoding a protein of choice, such as a CAR, to be transcribed upon release of the intracellular fragment from the priming receptor.

Notch receptors have a modular domain organization. The ectodomains of Notch receptors consist of a series of N-terminal epidermal growth factor (EGF)-like repeats that are responsible for ligand binding. In synthetic Notch receptors or priming receptors, the Notch ligand-binding domain is replaced with a ligand binding domain that binds a selected target ligand or antigen. The EGF repeats are followed by three LIN-12/Notch repeat (LNR) modules, which are unique to Notch receptors, and are widely reported to participate in preventing premature receptor activation. The heterodimerization (HD) domain of Notch1 is divided by furin cleavage, so that its N-terminal part terminates the extracellular subunit, and its C-terminal half constitutes the beginning of the transmembrane subunit. Following the extracellular region, the receptor has a transmembrane segment and an intracellular domain (ICD), which includes a transcriptional regulator.

Multiple forms of priming receptors can be used in the methods, cells, and nucleic acids as described herein. One type of priming receptor contemplated for use in the methods and cells herein comprise a heterologous extracellular ligand binding domain, a linking polypeptide having substantial sequence identity with a Notch receptor including the NRR, a TMD, and an ICD. "Fn Notch" receptors comprise a heterologous extracellular ligand binding domain, a linking polypeptide having substantial sequence identity with a Robo receptor (such as a mammalian Robo1, Robo2, Robo3, or Robo4), followed by 1, 2, or 3 fibronectin repeats ("Fn"), a TMD, and an ICD. "Mini Notch" receptors comprise a heterologous extracellular ligand binding domain, a linking polypeptide having substantial sequence identity with a Notch receptor (lacking the NRR), a TMD, and an ICD. "Minimal Linker Notch" receptors comprise a heterologous extracellular ligand binding domain, a linking polypeptide lacking substantial sequence identity with a Notch receptor (e.g., a synthetic (GGS)n polypeptide sequence), a TMD, and an ICD. "Hinge Notch" receptors comprise a heterologous extracellular ligand binding domain, a hinge sequence comprising an oligomerization domain (i.e., a domain that promotes dimerization, trimerization, or higher order multimerization with a synthetic receptor and/or an existing host receptor), a TMD, and an ICD. All of these receptor classes are synthetic, recombinant, and do not occur in nature. In some embodiments, the non-naturally occurring receptors disclosed herein bind a target cell-surface displayed ligand, which triggers proteolytic cleavage of the receptors and release of a transcriptional regulator that modulates a custom transcriptional program in the cell. In some embodiments, the priming receptor does not include a LIN-12-Notch repeat (LNR) and/or a heterodimerization domain (HD) of a Notch receptor.

Priming Receptor Extracellular Domain

The priming receptor disclosed herein comprises an extracellular domain that specifically binds Alkaline Phosphatase, Placental/Germ Cell (ALPG/P; ALPP: NCBI Entrez Gene: 250, UniProtKB/Swiss-Prot: P05187; ALPG: NCBI Entrez Gene: 251, UniProtKB/Swiss-Prot: P10696). In some embodiments, the extracellular domain includes the ligand-binding portion of a receptor. In some embodiments, the extracellular domain includes an antigen-binding moiety that binds to one or more target antigens. In some embodiments, the antigen-binding moiety includes one or more antigen-binding determinants of an antibody or a functional antigen-binding fragment thereof. In some embodiments, the antigen-binding moiety is selected from the group consisting of an antibody, a nanobody, a diabody, a triabody, or a minibody, a F(ab')2 fragment, a Fab fragment, a single chain variable fragment (scFv), and a single domain antibody (sdAb), or a functional fragment thereof. In some embodiments, the antigen-binding moiety comprises an scFv. The antigen-binding moiety can include naturally-occurring amino acid sequences or can be engineered, designed, or modified so as to provide desired and/or improved properties, e.g., increased binding affinity.

With regard to the binding of an antibody to a target molecule, the terms "bind," "specific binding," "specifically binds to," "specific for," "selectively binds," and "selective for" a particular antigen (e.g., a polypeptide target) or an epitope on a particular antigen mean binding that is measurably different from a non-specific or non-selective interaction (e.g., with a non-target molecule). For example, an antibody that "selectively binds" or "specifically binds" an antigen is an antigen-binding moiety that binds the antigen with high affinity and does not significantly bind other unrelated antigens. Specific binding can be measured, for example, by measuring binding to a target molecule and comparing it to binding to a non-target molecule. Specific binding can also be determined by competition with a control molecule that mimics the epitope recognized on the target molecule. In that case, specific binding is indicated if the binding of the antibody to the target molecule is competitively inhibited by the control molecule. In some embodiments, the extracellular antigen-binding domain specifically binds to Alkaline phosphatase, Germ Cell type (ALPG). In some embodiments, the extracellular domain includes an antigen-binding moiety that binds to Alkaline phosphatase, Placenta (ALPP).

"Affinity" refers to the strength of the sum total of non-covalent interactions between a single binding site of a molecule (e.g., an antibody) and its binding partner (e.g., an antigen or epitope). Unless indicated otherwise, as used herein, "affinity" refers to intrinsic binding affinity, which reflects a 1:1 interaction between members of a binding pair (e.g., antibody and antigen or epitope). The affinity of a molecule X for its partner Y can be represented by the dissociation equilibrium constant ($K_D$). The kinetic components that contribute to the dissociation equilibrium constant are described in more detail below. Affinity can be measured by common methods known in the art, including, but not limited to, surface plasmon resonance (SPR) technology (e.g., BIACORE®) or biolayer interferometry (e.g., FORTEBIO®).

The term "hypervariable region" or "HVR", as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the complementarity determining regions (CDRs), the latter being of highest sequence variability and/or involved in antigen recognition. With the exception of CDR1 in VH, CDRs generally comprise the amino acid residues that form the hypervariable loops. Hypervariable regions (HVRs) are also referred to as "complementarity determining regions" (CDRs), and these terms are used herein interchangeably in reference to portions of the variable region that form the antigen-binding regions. This particular region has been described by Kabat et al., U.S. Dept. of Health and Human Services, Sequences of Proteins of Immunological Interest (1983) and by Chothia et al., J Mol Biol 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The exact residue numbers which encompass a particular CDR will vary depending on the sequence and size of the CDR. Those skilled in the art can routinely determine which residues comprise a particular CDR given the variable region amino acid sequence of the antibody.

The amino acid sequence boundaries of a CDR can be determined by one of skill in the art using any of a number of known numbering schemes, including those described by Kabat et al., supra ("Kabat" numbering scheme); Al-Lazikani et al., 1997, J. Mol. Biol., 273:927-948 ("Chothia" numbering scheme); MacCallum et al., 1996, J. Mol. Biol. 262:732-745 ("Contact" numbering scheme); Lefranc et al., Dev. Comp. Immunol., 2003, 27:55-77 ("IMGT" numbering scheme); and Honegge and Plückthun, J. Mol. Biol., 2001, 309:657-70 ("AHo" numbering scheme); each of which is incorporated by reference in its entirety.

Table A provides the positions of CDR-L1, CDR-L2, CDR-L3, CDR-H1, CDR-H2, and CDR-H3 as identified by the Kabat and Chothia schemes. For CDR-H1, residue numbering is provided using both the Kabat and Chothia numbering schemes.

CDRs may be assigned, for example, using antibody numbering software, such as Abnum, available at bioinforg.uk/abs/abnum/, and described in Abhinandan and Martin, Immunology, 2008, 45:3832-3839, incorporated by reference in its entirety.

TABLE A

Residues in CDRs according to Kabat and Chothia numbering schemes.

| CDR | Kabat | Chothia |
|---|---|---|
| L1 | L24-L34 | L24-L34 |
| L2 | L50-L56 | L50-L56 |
| L3 | L89-L97 | L89-L97 |
| H1 (Kabat Numbering) | H31-H35B | H26-H32 or H34* |
| H1 (Chothia Numbering) | H31-H35 | H26-H32 |
| H2 | H50-H65 | H52-H56 |
| H3 | H95-H102 | H95-H102 |

*The C-terminus of CDR-H1, when numbered using the Kabat numbering convention, varies between H32 and H34, depending on the length of the CDR.

The "EU numbering scheme" is generally used when referring to a residue in an antibody heavy chain constant region (e.g., as reported in Kabat et al., supra). Unless stated otherwise, the EU numbering scheme is used to refer to residues in antibody heavy chain constant regions described herein.

TABLE A1

Example Conservative Substitutions

| Original | Example Substitutions | Specific Example Substitutions |
|---|---|---|
| Ala (A) | Val, Leu, Ile | Val |
| Arg (R) | Lys, Gln, Asn | Lys |
| Asn (N) | Gln, His, Asp, Lys, Arg | Gln |
| Asp (D) | Glu, Asn | Glu |
| Cys (C) | Ser, Ala | Ser |
| Gln (Q) | Asn, Glu | Asn |
| Glu (E) | Asp, Gln | Asp |
| Gly (G) | Ala | Ala |
| His (H) | Asn, Gln, Lys, Arg | Arg |
| Ile (I) | Leu, Val, Met, Ala, Phe | Leu |
| Leu (L) | Norleucine, Ile, Val, Met, Ala | Ile |
| Lys (K) | Arg, Gln, Asn | Arg |
| Met (M) | Leu, Phe, Ile | Leu |
| Phe (F) | Leu, Val, Ile, Ala, Tyr | Tyr |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala | Leu |

As used herein, the term "single-chain" refers to a molecule comprising amino acid monomers linearly linked by peptide bonds. In a particular such embodiment, the C-terminus of the Fab light chain is connected to the N-terminus of the Fab heavy chain in the single-chain Fab molecule. As described in more detail herein, an scFv has a variable domain of light chain (VL) connected from its C-terminus to the N-terminal end of a variable domain of heavy chain (VH) by a polypeptide chain. Alternately the scFv comprises of polypeptide chain where in the C-terminal end of the VH is connected to the N-terminal end of VL by a polypeptide chain.

The "Fab fragment" (also referred to as fragment antigen-binding) contains the constant domain (CL) of the light chain and the first constant domain (CH1) of the heavy chain along with the variable domains VL and VH on the light and heavy chains respectively. The variable domains comprise the complementarity determining loops (CDR, also referred to as hypervariable region) that are involved in antigen-binding. Fab' fragments differ from Fab fragments by the addition of a few residues at the carboxy terminus of the heavy chain CH1 domain including one or more cysteines from the antibody hinge region.

"F(ab')$_2$" fragments contain two Fab' fragments joined, near the hinge region, by disulfide bonds. F(ab')$_2$ fragments may be generated, for example, by recombinant methods or by pepsin digestion of an intact antibody. The F(ab') fragments can be dissociated, for example, by treatment with ß-mercaptoethanol.

"Fv" fragments comprise a non-covalently-linked dimer of one heavy chain variable domain and one light chain variable domain.

The "Single-chain Fv" or "scFv" includes the VH and VL domains of an antibody, wherein these domains are present in a single polypeptide chain. In one embodiment, the Fv polypeptide further comprises a polypeptide linker between the VH and VL domains which enables the scFv to form the desired structure for antigen-binding. For a review of scFv see Pluckthun in *The Pharmacology of Monoclonal Antibodies*, vol. 113, Rosenburg and Moore eds., Springer-Verlag, New York, pp. 269-315 (1994). HER2 antibody scFv fragments are described in WO93/16185; U.S. Pat. Nos. 5,571,894; and 5,587,458.

The term "single domain antibody" or "sdAb" refers to a molecule in which one variable domain of an antibody specifically binds to an antigen without the presence of the other variable domain. Single domain antibodies, and fragments thereof, are described in Arabi Ghahroudi et al., *FEBS Letters*, 1998, 414:521-526 and Muyldermans et al., *Trends in Biochem. Sci.*, 2001, 26:230-245, each of which is incorporated by reference in its entirety. Single domain antibodies are also known as sdAbs or nanobodies. Sdabs are fairly stable and easy to express as fusion partner with the Fc chain of an antibody (Harmsen M M, De Haard H J (2007). "Properties, production, and applications of camelid single-domain antibody fragments". Appl. Microbiol Biotechnol. 77(1): 13-22).

Priming Receptor CDRs, VH, VL Domains

In some aspects, the priming receptor extracellular antigen-binding domain comprises a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3, wherein: CDR-H1 comprises the sequence set forth in SEQ ID NO: 1, CDR-H2 comprises the sequence set forth in SEQ ID NO: 2, CDR-H3 comprises the sequence set forth in SEQ ID NO: 3, CDR-L1 comprises the sequence set forth in SEQ ID NO: 4, CDR-L2 comprises the sequence set forth in SEQ ID NO: 5; and CDR-L3 comprises the sequence set forth in SEQ ID NO: 6. In some embodiments, the VH chain sequence comprises the sequence set forth in SEQ ID NO: 7. In some embodiments, the VL comprises the sequence set forth in SEQ ID NO: 8. In some embodiments, the extracellular domain comprises the sequence set forth in SEQ ID NO: 9

In some embodiments, the priming receptor extracellular antigen-binding domain CDR-H3 has at least about 50%, 75%, 80%, 85%, 90%, or 95% identity with a CDR-H3 of SEQ ID NO: 3, the CDR-H2 has at least about 50%, 75%, 80%, 85%, 90%, or 95% identity with a CDR-H2 of SEQ ID NO: 2, the CDR-H1 has at least about 50%, 75%, 80%, 85%, 90%, or 95% identity with a CDR-H1 of SEQ ID NO: 1, the CDR-L3 has at least about 50%, 75%, 80%, 85%, 90%, or 95% identity with a CDR-L3 of SEQ ID NO: 6, the CDR-L2 has at least about 50%, 75%, 80%, 85%, 90%, or 95% identity with a CDR-L2 of SEQ ID NO: 5, and the CDR-L1 has at least about 50%, 75%, 80%, 85%, 90%, or 95% identity with a CDR-L1 of SEQ ID NO: 4. In some embodiments, the CDR-H3 is a CDR-H3 of SEQ ID NO: 3, with up to 1, 2, 3, 4, 5, 6, 7, or 8 amino acid substitutions; the CDR-H2 is a CDR-H2 of SEQ ID NO: 2, with up to 1, 2, 3, 4, 5, 6, 7, or 8 amino acid substitutions; the CDR-H1 is a CDR-H1 of SEQ ID NO: 1, with up to 1, 2, 3, 4, or 5 amino acid substitutions; the CDR-L3 is a CDR-L3 of SEQ ID NO: 6, with up to 1, 2, 3, 4, or 5 amino acid substitutions; the CDR-L2 is a CDR-L2 of SEQ ID NO: 5, with up to 1, 2, 3, or 4 amino acid substitutions; and the CDR-L1 is a CDR-L1 of SEQ ID NO: 4 with up to 1, 2, 3, 4, 5, or 6 amino acid substitutions.

In some embodiments, a priming receptor extracellular antigen-binding domain provided herein comprises one to three CDRs of a VH domain as set forth in SEQ ID NO: 7. In some embodiments, an antigen-binding domain provided herein comprises two to three CDRs of a VH domain as set forth in SEQ ID Ns: 7. In some embodiments, an antigen-binding domain provided herein comprises three CDRs of a VH domain as set forth in SEQ ID NO: 7. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, a priming receptor extracellular antigen-binding domain provided herein comprises a VH sequence having at least about 50%, 60%, 70%, 80%, 90%, 95%, or 99% identity to an VH sequence set forth in SEQ ID NO: 7. In some embodiments, an antigen-binding domain provided herein comprises a VH sequence provided in SEQ ID NO: 7, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antigen-binding domains described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies or antigen-binding domains.

In some embodiments, a priming receptor extracellular antigen-binding domain provided herein comprises one to three CDRs of a VL domain as set forth in SEQ ID NO: 8. In some embodiments, an antigen-binding domain provided herein comprises two to three CDRs of a VL domain as set forth in SEQ ID NO: 8. In some embodiments, an antigen-binding domain provided herein comprises three CDRs of a VL domain as set forth in SEQ ID NO: 8. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, a priming receptor extracellular antigen-binding domain provided herein comprises a VL sequence having at least about 50%, 60%, 70%, 80%, 90%, 95%, or 99% identity to an VL sequence set forth in SEQ ID NO: 8. In some embodiments, a antigen-binding domain provided herein comprises a VL sequence provided in SEQ ID NO: 8, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antibodies described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies or antigen-binding domains.

Table B provides the CDR sequences of the VH and VL of an illustrative ALPG/P antigen binding domain according to the indicated numbering schemes.

TABLE B

| SEQ ID NO | Name | Numbering scheme | Sequence |
|---|---|---|---|
| 1 | CDR-H1 | Chothia | GFSLTSY--- |
| 173 | | AbM | GFSLTSYGVS |
| 174 | | Kabat | -----SYGVS |
| 175 | | Contact | ----TSYGVS |
| 176 | | IMGT | GFSLTSYG-- |
| 2 | CDR-H2 | Chothia | -----WEDGS--------- |
| 177 | | AbM | ---VIWEDGSTN------- |
| 178 | | Kabat | ---VIWEDGSTNYHSALIS |
| 179 | | Contact | WIGVIWEDGSTN------- |
| 180 | | IMGT | ----IWEDGST-------- |
| 3 | CDR-H3 | Chothia | --PHYGSSYVGAMEY |
| 3 | | AbM | --PHYGSSYVGAMEY |
| 3 | | Kabat | --PHYGSSYVGAMEY |
| 181 | | Contact | ARPHYGSSYVGAME- |
| 182 | | IMGT | ARPHYGSSYVGAMEY |
| 4 | CDR-L1 | Chothia | RASENTYSYVA-- |
| 4 | | AbM | RASENTYSYVA-- |
| 4 | | Kabat | RASENTYSYVA-- |
| 183 | | Contact | ------YSYVAWY |
| 184 | | IMGT | ---ENIYSY---- |
| 5 | CDR-L2 | Chothia | ----NAKSLAS |
| 5 | | AbM | ----NAKSLAS |
| 5 | | Kabat | ----NAKSLAS |
| 185 | | Contact | LLIYNAKSLA- |
| 186 | | IMGT | ----NA----- |
| 6 | CDR-L3 | Chothia | QHHYVSPWT |
| 6 | | AbM | QHHYVSPWT |
| 6 | | Kabat | QHHYVSPWT |

TABLE B-continued

| SEQ ID NO | Name | Numbering scheme | Sequence |
|---|---|---|---|
| 187 | | Contact | QHHYVSPW- |
| 6 | | IMGT | QHHYVSPWT |

Transmembrane Domain

As described above, the priming receptor comprises a transmembrane domain (TMD) comprising one or more ligand-inducible proteolytic cleavage sites.

In some embodiments, the TMD comprises a Notch1 transmembrane domain. In some embodiments, the transmembrane domain comprises the sequence as set forth in SEQ ID NO: 19.

Generally, the TMD suitable for the chimeric receptors disclosed herein can be any transmembrane domain of a Type 1 transmembrane receptor including at least one gamma-secretase cleavage site. Detailed description of the structure and function of the gamma-secretase complex as well as its substrate proteins, including amyloid precursor protein (APP) and Notch, can, for example, be found in a recent review by Zhang et al, Frontiers Cell Neurosci (2014). Non limiting suitable TMDs from Type 1 transmembrane receptors include those from CLSTN1, CLSTN2, APLP1, APLP2, LRP8, APP, BTC, TGBR3, SPN, CD44, CSF1R, CXCL16, CX3CL1, DCC, DLL1, DSG2, DAG1, CDH1, EPCAM, EPHA4, EPHB2, EFNB1, EFNB2, ErbB4, GHR, HLA-A, and IFNAR2, wherein the TMD includes at least one gamma secretase cleavage site. Additional TMDs suitable for the compositions and methods described herein include, but are not limited to, transmembrane domains from Type 1 transmembrane receptors IL1R1, IL1R2, IL6R, INSR, ERN1, ERN2, JAG2, KCNE1, KCNE2, KCNE3, KCNE4, KL, CHL1, PTPRF, SCN1B, SCN3B, NPR3, NGFR, PLXDC2, PAM, AGER, ROBO1, SORCS3, SORCS1, SORL1, SDC1, SDC2, SPN, TYR, TYRP1, DCT, YASN, FLT1, CDH5, PKHD1, NECTIN1, PCDHGC3, NRG1, LRP1B, CDH2, NRG2, PTPRK, SCN2B, Nradd, and PTPRM. In some embodiments, the TMD of the chimeric polypeptides or Notch receptors of the disclosure is a TMD derived from the TMD of a member of the calsyntenin family, such as, alcadein alpha and alcadein gamma. In some embodiments, the TMD of the chimeric polypeptides or Notch receptors of the disclosure is a TMD known for Notch receptors. In some embodiments, the TMD of the chimeric polypeptides or Notch receptors of the disclosure is a TMD derived from a different Notch receptor. For example, in a Mini Notch based on human Notch1, the Notch1 TMD can be substituted with a Notch2 TMD, Notch3 TMD, Notch4 TMD, or a Notch TMD from a non-human animal such as *Danio rerio, Drosophila melanogaster, Xenopus laevis*, or *Gallus gallus*.

In some embodiments, the priming receptor comprises a Notch cleavage site, such as S2 or S3. Additional proteolytic cleavage sites suitable for the compositions and methods disclosed herein include, but are not limited to, ADAM10, a metalloproteinase cleavage site for a MMP selected from collagenase-1, -2, and -3 (MMP-1, -8, and -13), gelatinase A and B (MMP-2 and -9), stromelysin 1, 2, and 3 (MMP-3, -10, and -11), matrilysin (MMP-7), and membrane metalloproteinases (MT1-MMP and MT2-MMP). Another example of a suitable protease cleavage site is a plasminogen activator cleavage site, e.g., a urokinase plasminogen activator (uPA) or a tissue plasminogen activator (tPA) cleavage site.

Another example of a suitable protease cleavage site is a prolactin cleavage site. Specific examples of cleavage sequences of uPA and tPA include sequences comprising Yal-Gly-Arg. Another example of a protease cleavage site that can be included in a proteolytically cleavable linker is a tobacco etch virus (TEV) protease cleavage site, e.g., Glu-Asn-Leu-Tyr-Thr-Gln-Ser (SEQ ID NO: 188), where the protease cleaves between the glutamine and the serine. Another example of a protease cleavage site that can be included in a proteolytically cleavable linker is an enterokinase cleavage site, e.g., Asp-Asp-Asp-Asp-Lys (SEQ ID NO: 189), where cleavage occurs after the lysine residue. Another example of a protease cleavage site that can be included in a proteolytically cleavable linker is a thrombin cleavage site, e.g., Leu-Val-Pro-Arg (SEQ ID NO: 190). Additional suitable linkers comprising protease cleavage sites include sequences cleavable by the following proteases: a PreScission™ protease (a fusion protein comprising human rhinovirus 3C protease and glutathione-S-transferase), a thrombin, cathepsin B, Epstein-Barr virus protease, MMP-3 (stromelysin), MMP-7 (matrilysin), MMP-9; thermolysin-like MMP, matrix metalloproteinase 2 (MMP-2), cathepsin L; cathepsin D, matrix metalloproteinase 1 (MMP-1), urokinase-type plasminogen activator, membrane type 1 matrixmetalloprotemase (MT-MMP), stromelysin 3 (or MMP-11), thermo lysine, fibroblast collagenase and stromelysin-1, matrix metalloproteinase 13 (collagenase-3), tissue-type plasminogen activator (tPA), human prostate-specific antigen, kallikrein (hK3), neutrophil elastase, and calpain (calcium activated neutral protease). Proteases that are not native to the host cell in which the receptor is expressed (for example, TEV) can be used as a further regulatory mechanism, in which activation of the receptor is reduced until the protease is expressed or otherwise provided. Additionally, a protease may be tumor-associated or disease-associated (expressed to a significantly higher degree than in normal tissue), and serve as an independent regulatory mechanism. For example, some matrix metalloproteases are highly expressed in certain cancer types.

In some embodiments, the amino acid substitution(s) within the TMD includes one or more substitutions within a "GV" motif of the TMD. In some embodiments, at least one of such substitution(s) comprises a substitution to alanine. Additional sequences and substitutions are described in WO2021061872, hereby incorporated by reference in its entirety.

Intracellular Domain

In some embodiments, the priming receptor comprises one or more intracellular domains from or derived from a transcriptional regulator and/or a DNA-binding domain. In some embodiments, the intracellular domain comprises an HNF1a/p65 domain or a Gal4/VP64 domain. In some embodiments, the intracellular domain comprises the sequence as set forth in SEQ ID NO: 23.

Transcriptional regulators either activate or repress transcription from cognate promoters. Transcriptional activators typically bind nearby to transcriptional promoters and recruit RNA polymerase to directly initiate transcription. Transcriptional repressors bind to transcriptional promoters and sterically hinder transcriptional initiation by RNA polymerase. Other transcriptional regulators serve as either an activator or a repressor depending on where it binds and cellular conditions. Accordingly, as used herein, a "transcriptional activation domain" refers to the domain of a transcription factor that interacts with transcriptional control elements and/or transcriptional regulatory proteins (i.e., transcription factors, RNA polymerases, etc.) to increase and/or activate transcription of one or more genes. Non-limiting examples of transcriptional activation domains include: a herpes simplex virus VP16 activation domain, VP64 (which is a tetrameric derivative of VP16), HIV TAT, a NFkB p65 activation domain, p53 activation domains 1 and 2, a CREB (cAMP response element binding protein) activation domain, an E2A activation domain, NFAT (nuclear factor of activated T-cells) activation domain, yeast Gal4, yeast GCN4, yeast HAP1, MLL, RTG3, GLN3, OAF1, PIP2, PDR1, PDR3, PHO4, LEU3 glucocorticoid receptor transcription activation domain, B-cell POU homeodomain protein Oct2, plant Ap2, or any others known to one or ordinary skill in the art. In some embodiments, the transcriptional regulator is selected from Gal4-VP16, Gal4-VP64, tetR-VP64, ZFHD1-YP64, Gal4-KRAB, and HAP1-VP16. In some embodiments, the transcriptional regulator is Gal4-VP64. A transcriptional activation domain can comprise a wild-type or naturally occurring sequence, or it can be a modified, mutant, or derivative version of the original transcriptional activation domain that has the desired ability to increase and/or activate transcription of one or more genes. In some embodiments, the transcriptional regulator can further include a nuclear localization signal.

In some embodiments, the priming receptor comprises one or more intracellular "DNA-binding domains" (or "DB domains"). Such "DNA-binding domains" refer to sequence-specific DNA binding domains that bind a particular DNA sequence element. Accordingly, as used herein, a "sequence-specific DNA-binding domain" refers to a protein domain portion that has the ability to selectively bind DNA having a specific, predetermined sequence. A sequence-specific DNA binding domain can comprise a wild type or naturally occurring sequence, or it can be a modified, mutant, or derivative version of the original domain that has the desired ability to bind to a desired sequence. In some embodiments, the sequence-specific DNA binding domain is engineered to bind a desired sequence. Non-limiting examples of proteins having sequence-specific DNA binding domains that can be used in synthetic proteins described herein include HNF1a, Gal4, GCN4, reverse tetracycline receptor, THY1, SYN1, NSE/RU5', AGRP, CALB2, CAMK2A, CCK, CHAT, DLX6A, EMX1, zinc finger proteins or domains thereof, CRISPR/Cas proteins, such as Cas9, Cas3, Cas4, Cas5, Cas5e (or CasD), Cash, Cas6e, Cas6f, Cas7, Cas8a1, Cas8a2, Cas8b, Cas8c, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, and Cu196, and TALES.

In those embodiments where a CRISPR/Cas-like protein is used, the CRISPR/Cas-like protein can be a wild type CRISPR/Cas protein, a modified CRISPR/Cas protein, or a fragment of a wild type or modified CRISPR/Cas protein. The CRISPR/Cas-like protein can be modified to increase nucleic acid binding affinity and/or specificity, alter an enzymatic activity, and/or change another property of the protein. For example, nuclease (i.e., DNase, RNase) domains of the CRISPR/Cas-like protein can be modified, deleted, or inactivated. Alternatively, the CRISPR/Cas-like protein can be truncated to remove domains that are not essential for the functions of the systems described herein. For example, a CRISPR enzyme that is used as a DNA binding protein or domain thereof can be mutated with respect to a corresponding wild-type enzyme such that the mutated CRISPR or domain thereof lacks the ability to cleave a nucleic acid sequence containing a DNA binding domain target site. For example, a D10A mutation can be combined with one or more of H840A, N854A, or N863A mutations to produce a Cas9 enzyme substantially lacking all DNA cleavage activity.

Juxtamembrane Domain

The ECD and the TMD, or the TMD and the ICD, can be linked to each other with a linking polypeptide, such as a juxtamembrane domain. "SynNotch" or synthetic notch receptors comprise a heterologous extracellular ligand-binding domain, a linking polypeptide having substantial sequence identity with a Notch receptor JMD (including the NRR), a TMD, and an ICD. "Fn Notch" receptors comprise a heterologous extracellular ligand binding domain, a linking polypeptide having substantial sequence identity with a Robo receptor (such as a mammalian Robo1, Robo2, Robo3, or Robo4), followed by 1, 2, or 3 fibronectin repeats ("Fn"), a TMD, and an ICD. "Mini Notch" receptors comprise a heterologous extracellular ligand binding domain, a linking polypeptide having substantial sequence identity with a Notch receptor JMD but lacking the NRR (the LIN-12-Notch repeat (LNR) modules, and the heterodimerization domain), a TMD, and an ICD. "Minimal Linker Notch" receptors comprise a heterologous extracellular ligand-binding domain, a linking polypeptide lacking substantial sequence identity with a Notch receptor (for example, without limitation, having a synthetic $(GGS)_n$ polypeptide sequence), a TMD, and an ICD. "Hinge Notch" receptors comprise a heterologous extracellular ligand-binding domain, a hinge sequence comprising an oligomerization domain (i.e., a domain that promotes dimerization, trimerization, or higher order multimerization with a synthetic receptor and/or an existing host receptor), a TMD, and an ICD.

In some embodiments, the priming receptor comprises a juxtamembrane domain (JMD) peptide in between the extracellular domain and the transmembrane domain. In some embodiments, the priming receptor comprises a juxtamembrane domain (JMD) peptide in between the transmembrane domain and the intracellular domain. In some embodiments, the JMD peptide comprises an LWF motif. The use of LWF motifs in receptor constructs is described in U.S. Pat. No. 10,858,443, hereby incorporated by reference in its entirety. In some embodiments, the JMD peptide has substantial sequence identity to the JMD of Notch1, Notch2, Notch3, and/or Notch4. In some embodiments, the JMD peptide has substantial sequence identity to the Notch1, Notch2, Notch3, and/or Notch4 JMD, but does not include a LIN-12-Notch repeat (LNR) and/or a heterodimerization domain (HD) of a Notch receptor. In some embodiments, the JMD peptide does not have substantial sequence identity to the Notch1, Notch2, Notch3, and/or Notch4 JMD. In some embodiments, the JMD peptide includes an oligomerization domain which promotes formation of dimers, trimers, or higher order assemblages of the receptor. Such JMD peptides are described in WO2021061872, hereby incorporated by reference in its entirety.

In the Mini Notch receptor, the linking polypeptide is derived from a Notch JMD sequence after deletion of the NRR and HD domain. The Notch JMD sequence may be the sequence from Notch1, Notch2, Notch3, or Notch4, and can be derived from a non-human homolog, such as those from Drosophila, Gallus, Danio, and the like. Four to 50 amino acid residues of the remaining Notch sequence can be used as a polypeptide linker. In some embodiments, the length and amino acid composition of the linker polypeptide sequence are varied to alter the orientation and/or proximity of the ECD and the TMD relative to one another to achieve a desired activity of the chimeric polypeptide, such as the signal transduction level when ligand induced or in the absence of ligand.

In the Minimal Linker Notch receptor, the linking polypeptide does not have substantial sequence identity to a Notch JMD sequence, including the Notch JMD sequence from Notch1, Notch2, Notch3, or Notch4, or a non-human homolog thereof. Four to 50 amino acid residues can be used as a polypeptide linker. In some embodiments, the length and amino acid composition of the linker polypeptide sequence are varied to alter the orientation and/or proximity of the ECD and the TMD relative to one another to achieve a desired activity of the chimeric polypeptide of the disclosure. The Minimal Linker sequence can be designed to include or omit a protease cleavage site, and can include or omit a glycosylation site or sites for other types of post-translational modification. In some embodiments, the Minimal Linker does not comprise a protease cleavage site or a glycosylation site.

In some embodiments, the priming receptor further comprises a hinge. Hinge linkers that can be used in the priming receptor can include an oligomerization domain (e.g., a hinge domain) containing one or more polypeptide motifs that promote oligomer formation of the chimeric polypeptides via intermolecular disulfide bonding. In these instances, within the chimeric receptors disclosed herein, the hinge domain generally includes a flexible polypeptide connector region disposed between the ECD and the TMD. Thus, the hinge domain provides flexibility between the ECD and TMD and also provides sites for intermolecular disulfide bonding between two or more chimeric polypeptide monomers to form an oligomeric complex. In some embodiments, the hinge domain includes motifs that promote dimer formation of the chimeric polypeptides disclosed herein. In some embodiments, the hinge domain includes motifs that promote trimer formation of the chimeric polypeptides disclosed herein (e.g., a hinge domain derived from OX40). Hinge polypeptide sequences suitable for the compositions and methods of the disclosure can be naturally-occurring hinge polypeptide sequences (e.g., those from naturally-occurring immunoglobulins) or can be engineered, designed, or modified so as to provide desired and/or improved properties, e.g., modulating transcription. Suitable hinge polypeptide sequences include, but are not limited to, those derived from IgA, IgD, and IgG subclasses, such as IgG1 hinge domain, IgG2 hinge domain, IgG3 hinge domain, and IgG4 hinge domain, or a functional variant thereof. In some embodiments, the hinge polypeptide sequence contains one or more CXXC motifs. In some embodiments, the hinge polypeptide sequence contains one or more CPPC motifs (SEQ ID NO: 191).

Hinge polypeptide sequences can also be derived from a CD8α hinge domain, a CD28 hinge domain, a CD152 hinge domain, a PD-1 hinge domain, a CTLA4 hinge domain, an OX40 hinge domain, and functional variants thereof. In some embodiments, the hinge domain includes a hinge polypeptide sequence derived from a CD8 α hinge domain or a functional variant thereof. In some embodiments, the hinge domain includes a hinge polypeptide sequence derived from a CD28 hinge domain or a functional variant thereof. In some embodiments, the hinge domain includes a hinge polypeptide sequence derived from an OX40 hinge domain or a functional variant thereof. In some embodiments, the hinge domain includes a hinge polypeptide sequence derived from an IgG4 hinge domain or a functional variant thereof.

The Fn Notch linking polypeptide is derived from the Robo1 JMD, which contains a fibronectin repeat (Fn) domain, with a short polypeptide sequence between the Fn repeats and the TMD. The Fn Notch linking polypeptide does not contain a Notch negative regulatory region (NRR), or the Notch HD domain. The Fn linking polypeptide can contain 1, 2, 3, 4, or 5 Fn repeats. In some embodiments, the chimeric receptor comprises a Fn linking polypeptide having about 1 to about 5 Fn repeats, about 1 to about 3 Fn repeats, or about 2 to about 3 Fn repeats. The short polypeptide sequence between the Fn repeats and the TMD can be from about 2 to about 30 amino acid residues. In some embodiments, the short polypeptide sequence can be between about 5 and about 20 amino acids, of any sequence. In some embodiments, the short polypeptide sequence can be between about 5 and about 20 naturally-occurring amino acids, of any sequence. In some embodiments, the short polypeptide sequence can be between about 5 and about 20 amino acids, of any sequence but having no more than one proline. In some embodiments, the short polypeptide sequence can be between about 5 and about 20 amino acids, and about 50% or more of the amino acids are glycine. In some embodiments, the short polypeptide sequence can be between about 5 and about 20 amino acids, where the amino acids are selected from glycine, serine, threonine, and alanine. In some embodiments, the length and amino acid composition of the Fn linking polypeptide sequence can be varied to alter the orientation and/or proximity of the ECD and the TMD relative to one another to achieve a desired activity of the chimeric polypeptide of the disclosure.

Stop-Transfer Sequence

In some embodiments, the priming receptor further comprises a stop-transfer sequence (STS) in between the transmembrane domain and the intracellular domains. The STS comprises a charged, lipophobic sequence. Without being bound by any theory, the STS serves as a membrane anchor, and is believed to prevent passage of the intracellular domain into the plasma membrane. The use of STS domains in priming receptors is described in WO2021061872, hereby incorporated by reference in its entirety. Non-limiting exemplary STS sequences include APLP1, APLP2, APP, TGBR3, CSF1R, CXCL16, CX3CL1, DAG1, DCC, DNER, DSG2, CDH1, GHR, HLA-A, IFNAR2, IGF1R, IL1R1, ERN2, KCNE1, KCNE2, CHL1, LRP1, LRP2, LRP18, PTPRF, SCN1B, SCN3B, NPR3, NGFR, PLXDC2, PAM, AGER, ROBO1, SORCS3, SORCS1, SORL1, SDC1, SDC2, SPN, TYR, TYRP1, DCT, VASN, FLT1, CDH5, PKTFD1, NECTIN1, KL, IL6R, EFNB1, CD44, CLSTN1, LRP8, PCDHGC3, NRG1, LRP1B, JAG2, EFNB2, DLL1, CLSTN2, EPCAM, ErbB4, KCNE3, CDH2, NRG2, PTPRK, BTC, EPHA4, IL1R2, KCNE4, SCN2B, Nradd, PTPRM, Notch1, Notch2, Notch3, and Notch4 STS sequences. In some embodiments, the STS is heterologous to the transmembrane domain. In some embodiments, the STS is homologous to the transmembrane domain. STS sequences are described in WO2021061872, hereby incorporated by reference in its entirety.

In some embodiments, the stop-transfer-sequence comprises the sequence as set forth in SEQ ID NO: 20.

ALPG/P Antibodies and Antigen Binding Fragments

In some aspects, provided herein are Alkaline Phosphatase, Placental/Germ Cell (ALPG/P) antibodies or antigen binding fragments. In some embodiments, the ALPG/P antigen-binding moiety is selected from the group consisting of an antibody, a nanobody, a diabody, a triabody, or a minibody, a F(ab')2 fragment, a Fab fragment, a single chain variable fragment (scFv), and a single domain antibody (sdAb), or a functional fragment thereof. In some embodiments, the antigen-binding moiety comprises an scFv. The antigen-binding moiety can include naturally-occurring amino acid sequences or can be engineered, designed, or modified so as to provide desired and/or improved properties, e.g., increased binding affinity.

In one aspect, provided herein are isolated antibodies or antigen binding fragments thereof that binds to Alkaline Phosphatase, Placental/Germ Cell (ALPG/P), comprising a variable heavy (VH) chain sequence comprising three heavy chain CDR sequences, CDR-H1, CDR-H2, and CDR-H3, wherein: CDR-H1 comprises a sequence as set forth in SEQ ID NOs: 1, 173, 174, 175, or 176, CDR-H2 comprises a sequence as set forth in SEQ ID NOs: 2, 177, 178, 179, or 180, and CDR-H3 comprises a sequence as set forth in SEQ ID NOs: 3, 181, or 182, and a variable light (VL) chain sequence comprising three light chain CDR sequences, CDR-L1, CDR-L2, and CDR-L3, wherein: CDR-L1 comprises a sequence as set forth in SEQ ID NOs: 4, 183, or 184, CDR-L2 comprises a sequence as set forth in SEQ ID NOs: 5, 185, or 186, and CDR-L3 comprises a sequence as set forth in SEQ ID NOs: 6 or 187.

In some embodiments, the ALPG/P antibody or antigen binding fragment comprises a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3. In some embodiments, the VH chain sequence comprises the sequence set forth in SEQ ID NO: 7. In some embodiments, the VL chain sequence comprises the sequence set forth in SEQ ID NO: 8.

In some embodiments, the ALPG/P antibody or antigen binding fragment CDR-H3 has at least about 50%, 75%, 80%, 85%, 90%, or 95% identity with a CDR-H3 of SEQ ID NO: 3, 181, or 182; the CDR-H2 has at least about 50%, 75%, 80%, 85%, 90%, or 95% identity with a CDR-H2 of SEQ ID NO: 2, 177, 178, 179, or 180; the CDR-H1 has at least about 50%, 75%, 80%, 85%, 90%, or 95% identity with a CDR-H1 of SEQ ID NO: 1, 173, 174, 175, or 176. In some embodiments, the CDR-H3 is a CDR-H3 of SEQ ID NO: 3, 181, or 182, with up to 1, 2, 3, 4, 5, 6, 7, or 8 amino acid substitutions; the CDR-H2 is a CDR-H2 of SEQ ID NO: 2, 177, 178, 179, or 180, with up to 1, 2, 3, 4, 5, 6, 7, or 8 amino acid substitutions; and the CDR-H1 is a CDR-H1 of SEQ ID NO: 1, 173, 174, 175, or 176, with up to 1, 2, 3, 4, or 5 amino acid substitutions.

In some embodiments, the ALPG/P antibody or antigen binding fragment CDR-L3 has at least about 50%, 75%, 80%, 85%, 90%, or 95% identity with a CDR-L3 of SEQ ID NO: 6 or 187; the CDR-L2 has at least about 50%, 75%, 80%, 85%, 90%, or 95% identity with a CDR-L2 of SEQ ID NO: 5, 185, or 186; the CDR-L1 has at least about 50%, 75%, 80%, 85%, 90%, or 95% identity with a CDR-L1 of SEQ ID NO: 4, 183, or 184. In some embodiments, the CDR-L3 is a CDR-L3 of SEQ ID NO: 6 or 187, with up to 1, 2, 3, 4, 5, 6, 7, or 8 amino acid substitutions; the CDR-L2 is a CDR-L2 of SEQ ID NO: 5, 185, or 186, with up to 1, 2, 3, 4, 5, 6, 7, or 8 amino acid substitutions; and the CDR-L1 is a CDR-L1 of SEQ ID NO: 4, 183, or 184, with up to 1, 2, 3, 4, or 5 amino acid substitutions.

In some embodiments, an ALPG/P antibody or antigen binding fragment provided herein comprises one to three CDRs of a VH domain as set forth in SEQ ID NO: 7. In some embodiments, an antigen-binding domain provided herein comprises two to three CDRs of a VH domain as set forth in SEQ ID NOs: 7. In some embodiments, an antigen-binding domain provided herein comprises three CDRs of a VH domain as set forth in SEQ ID NO: 7. In some embodiments, an ALPG/P antibody or antigen binding fragment provided herein comprises one to three CDRs of a VL domain as set forth in SEQ ID NO: 8. In some embodiments, an antigen-binding domain provided herein comprises two to three CDRs of a VL domain as set forth in SEQ ID NO: 8. In some embodiments, an antigen-binding domain provided herein comprises three CDRs of a VL domain as set forth in SEQ ID NO: 8. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, an ALPG/P antibody or antigen binding fragment provided herein comprises a VH sequence having at least about 50%, 60%, 70%, 80%, 90%, 95%, or 99% identity to an VH sequence set forth in SEQ ID NO: 7. In some embodiments, an antigen-binding domain provided herein comprises a VH sequence provided in SEQ ID NO: 7, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some embodiments, an ALPG/P antibody or antigen binding fragment provided herein comprises a VL sequence having at least about 50%, 60%, 70%, 80%, 90%, 95%, or 99% identity to an VL sequence set forth in SEQ ID NO: 8. In some embodiments, an ALPG/P antigen-binding domain provided herein comprises a VL sequence provided in SEQ ID NO: 8, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antigen-binding domains described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies or antigen-binding domains.

In some embodiments, the ALPG/P antibody or antigen binding fragment comprises a heavy chain variable (VH) region in which the full set of VH CDRs 1, 2, and 3 (combined) has at least 80% (such as, e.g., 80%, 85%, 90%, 95%, at least 85%, at least 90%, at least 95%) sequence identity to the CDRs 1, 2, and 3 of SEQ ID NO: 7. In some embodiments, the ALPG/P antibody or antigen binding fragment comprises a heavy chain variable (VH) region in which the full set of VH CDRs 1, 2, and 3 (combined) has at least 85% (such as, e.g., 85%, 90%, 95%, at least 90%, at least 95%) sequence identity to the CDRs 1, 2, and 3 of SEQ ID NO: 7. In some embodiments, the ALPG/P antibody or antigen binding fragment comprises a heavy chain variable (VH) region in which the full set of VH CDRs 1, 2, and 3 (combined) has at least 90% (such as, e.g., 90%, 95%, at least 95%) sequence identity to the CDRs 1, 2, and 3 of SEQ ID NO: 7. In some embodiments, the ALPG/P antibody or antigen binding fragment comprises a heavy chain variable (VH) region in which the full set of VH CDRs 1, 2, and 3 (combined) has at least 95% sequence identity to the CDRs 1, 2, and 3 of SEQ ID NO: 7.

In some embodiments, the ALPG/P antibody or antigen binding fragment comprises a light chain variable (VL) region in which the full set of VL CDRs 1, 2, and 3 (combined) has at least 80% (such as, e.g., 80%, 85%, 90%, 95%, at least 85%, at least 90%, at least 95%) sequence identity to the CDRs 1, 2, and 3 of SEQ ID NO: 8. In some embodiments, the ALPG/P antibody or antigen binding fragment comprises a light chain variable (VL) region in which the full set of VL CDRs 1, 2, and 3 (combined) has at least 85% (such as, e.g., 85%, 90%, 95%, at least 90%, at least 95%) sequence identity to the CDRs 1, 2, and 3 of SEQ ID NO: 8. In some embodiments, the ALPG/P antibody or antigen binding fragment comprises a light chain variable (VL) region in which the full set of VL CDRs 1, 2, and 3 (combined) has at least 90% (such as, e.g., 90%, 95%, at least 95%) sequence identity to the CDRs 1, 2, and 3 of SEQ ID NO: 8. In some embodiments, the ALPG/P antibody or antigen binding fragment comprises a light chain variable (VL) region in which the full set of VL CDRs 1, 2, and 3 (combined) has at least 95% sequence identity to the CDRs 1, 2, and 3 of SEQ ID NO: 8.

In some embodiments, the ALPG/P antibody or antigen binding fragment comprises a heavy chain variable (VH) region in which the full set of VH CDRs 1, 2, and 3 (combined) has at least 80% (such as, e.g., 80%, 85%, 90%, 95%, at least 85%, at least 90%, at least 95%) sequence identity to the CDRs 1, 2, and 3 of SEQ ID NO: 7. In some embodiments, the ALPG/P antibody or antigen binding fragment comprises a light chain variable (VL) region in which the full set of VL CDRs 1, 2, and 3 (combined) has at least 80% (such as, e.g., 80%, 85%, 90%, 95%, at least 85%, at least 90%, at least 95%) sequence identity to the CDRs 1, 2, and 3 of SEQ ID NO: 8.

In some embodiments, the ALPG/P antibody or antigen binding fragment comprises a heavy chain variable (VH) region comprising:
(i) a VH complementarity determining region one (CDR1) comprising a sequence having at most two (e.g., one, two, zero) amino acid modifications relative to SEQ ID NO: 1, 173, 174, 175, or 176;
(ii) a VH CDR2 comprising a sequence having at most two (e.g., one, two, zero) amino acid modifications relative to SEQ ID NO: 2, 177, 178, 179, or 180;
(iii) a VH CDR3 comprising a sequence having at most two (e.g., one, two, zero) amino acid modifications relative to SEQ ID NO: 3, 181, or 182;
(iv) a VL CDR1 comprising a sequence having at most two (e.g., one, two, zero) amino acid modifications relative to SEQ ID NO: 4, 183, or 184;
(v) a VL CDR2 comprising a sequence having at most two (e.g., one, two, zero) amino acid modifications relative to SEQ ID NO: 5, 185, or 186; and
(vi) a VL CDR3 comprising a sequence having at most two (e.g., one, two, zero) amino acid modifications relative to SEQ ID NO: 6 or 187.

In some embodiments, each amino acid modification, if any, is a conservative amino acid substitution. In some embodiments, each amino acid modification, if any, is a conservative amino acid substitution listed in Table A1.

In some embodiments, the VH CDR1 comprises a sequence having at most one amino acid modification relative to SEQ ID NO: 1, 173, 174, 175, or 176. In some embodiments, the VH CDR2 comprises a sequence having at most one amino acid modification relative to SEQ ID NO: 2, 177, 178, 179, or 180. In some embodiments, the VH CDR3 comprises a sequence having at most one amino acid modification relative to SEQ ID NO: 3, 181, or 182. In some embodiments, the VL CDR1 comprises a sequence having at most one amino acid modification relative to SEQ ID NO: 4, 183, or 184. In some embodiments, the VL CDR2 comprises a sequence having at most one amino acid modification relative to SEQ ID NO: 5, 185, or 186. In some embodiments, the VL CDR3 comprises a sequence having at most one amino acid modification relative to SEQ ID NO: 6 or 187. In some embodiments, the at most one amino acid modification is an amino acid substitution. In some embodiments, the at most one amino acid modification is a conservative amino acid substitution. In some embodiments, the at most one amino acid modification is an amino acid deletion. In some embodiments, the at most one amino acid modification is an amino acid addition.

In some embodiments, the VH CDR1 comprises a sequence as set forth in SEQ ID NO: 1. In some embodiments, the VH CDR2 comprises a sequence as set forth in SEQ ID NO: 2. In some embodiments, the VH CDR3 comprises a sequence as set forth in SEQ ID NO: 3.

In some embodiments, the VL CDR1 comprises a sequence as set forth in SEQ ID NO: 4. In some embodiments, the VL CDR2 comprises a sequence as set forth in SEQ ID NO: 5. In some embodiments, the VL CDR3 comprises a sequence as set forth in SEQ ID NO: 6.

In some embodiments, the ALPG/P antibody or antigen binding fragment comprises a heavy chain variable (VH) region comprising:
  (i) a VH complementarity determining region one (CDR1) comprising the sequence set forth in SEQ ID NO: 1;
  (ii) a VH CDR2 comprising the sequence set forth in SEQ ID NO: 2;
  (iii) a VH CDR3 comprising the sequence set forth in SEQ ID NO: 3;
  (iv) a VL complementarity determining region one (CDR1) comprising the sequence set forth in SEQ ID NO: 4;
  (v) a VL CDR2 comprising the sequence set forth in SEQ ID NO: 5; and
  (ivi) a VL CDR3 comprising the sequence set forth in SEQ ID NO: 6.

In some embodiments, the ALPG/P antibody or antigen binding fragment comprises a heavy chain variable (VH) region comprising a VH CDR1, a VH CDR2, and a VH CDR3 comprising the sequences of SEQ ID NOs: 1, 2, and 3, respectively, and a light chain variable (VL) region comprising a VL CDR1, a VL CDR2, and a VL CDR3 comprising the sequences of SEQ ID NOs: 4, 5, and 6, respectively.

In some embodiments, the ALPG/P antibody or antigen binding fragment comprises a heavy chain variable (VH) region comprising the CDR1, CDR2, and CDR3 of SEQ ID NOs: 7 and a light chain variable (VL) region comprising the CDR1, CDR2, and CDR3 of SEQ ID NO: 8.

In some embodiments, the VH CDR1, VH CDR2, and VH CDR3 sequences are present in a human VH framework.

In some embodiments, the ALPG/P antibody or antigen binding fragment comprises a heavy chain variable (VH) region having at least 80% (such as, e.g., 80%, 85%, 90%, 95%, at least 85%, at least 90%, at least 95%) sequence identity to SEQ ID NO: 7. In some embodiments, the ALPG/P antibody or antigen binding fragment comprises a heavy chain variable (VH) region having at least 85% (such as, e.g., 85%, 90%, 95%, at least 90%, at least 95%) sequence identity to SEQ ID NO: 7. In some embodiments, the ALPG/P antibody or antigen binding fragment comprises a heavy chain variable (VH) region having at least 90% (such as, e.g., 90%, 95%, at least 95%) sequence identity to SEQ ID NO: 7. In some embodiments, the ALPG/P antibody or antigen binding fragment comprises a heavy chain variable (VH) region having at least 95% sequence identity to SEQ ID NO: 7.

In some embodiments, the ALPG/P antibody or antigen binding fragment comprises a light chain variable (VL) region having at least 80% (such as, e.g., 80%, 85%, 90%, 95%, at least 85%, at least 90%, at least 95%) sequence identity to SEQ ID NO: 8. In some embodiments, the ALPG/P antibody or antigen binding fragment comprises a light chain variable (VL) region having at least 85% (such as, e.g., 85%, 90%, 95%, at least 90%, at least 95%) sequence identity to SEQ ID NO: 8. In some embodiments, the ALPG/P antibody or antigen binding fragment comprises a light chain variable (VL) region having at least 90% (such as, e.g., 90%, 95%, at least 95%) sequence identity to SEQ ID NO: 8. In some embodiments, the ALPG/P antibody or antigen binding fragment comprises a light chain variable (VL) region having at least 95% sequence identity to SEQ ID NO: 8.

In some embodiments, the ALPG/P antibody or antigen binding fragment comprises a heavy chain variable (VH) region having at least 80% (such as, e.g., 80%, 85%, 90%, 95%, at least 85%, at least 90%, at least 95%) sequence identity to SEQ ID NO: 7. In some embodiments, the ALPG/P antibody or antigen binding fragment comprises a light chain variable (VL) region having at least 80% (such as, e.g., 80%, 85%, 90%, 95%, at least 85%, at least 90%, at least 95%) sequence identity to SEQ ID NO: 8.

In some embodiments, the ALPG/P antibody or antigen binding fragment comprises the heavy chain variable (VH) region of SEQ ID NO: 7. In some embodiments, ALPG/P antibody or antigen binding fragment comprises the light chain variable (VL) region of SEQ ID NO: 8.

In some embodiments, the ALPG/P antibody or antigen binding fragment specifically binds to human ALPG/P.

In some embodiments, the ALPG/P antibody or antigen binding fragment binds to human ALPG/P with a $K_D$ of from about $10^{-9}$ M to about $10^{-6}$ M. In some embodiments, the ALPG/P antibody or antigen binding fragment binds to human ALPG/P with a $K_D$ of $\leq 5\times 10^{-7}$ M. In some embodiments, the ALPG/P antibody or antigen binding fragment binds to human ALPG/P with a $K_D$ of $\leq 1\times 10^{-7}$ M. In some embodiments, the ALPG/P antibody or antigen binding fragment binds to human ALPG/P with a $K_D$ of $\leq 5\times 10^{-8}$ M. In some embodiments, the ALPG/P antibody or antigen binding fragment binds to human ALPG/P with a $K_D$ of $\leq 2\times 10^{-8}$ M. In some embodiments, the ALPG/P antibody or antigen binding fragment binds to human ALPG/P with a $K_D$ of $\leq 1\times 10^{-8}$ M. In some embodiments, the ALPG/P antibody or antigen binding fragment binds to human ALPG/P with a $K_D$ of $\leq 1\times 10^{-9}$ M.

Chimeric Receptors

In one aspect, provided herein are chimeric receptors that binds to mesothelin (MSLN), comprising a variable heavy (VH) chain sequence comprising three heavy chain CDR sequences, CDR-H1, CDR-H2, and CDR-H3, wherein: CDR-H1 comprises the sequence set forth in SEQ ID NO: 14, 202, 203, 204, or 205, CDR-H2 comprises the sequence set forth in SEQ ID NO: 15, 206, 207, 208, or 209, and CDR-H3 comprises the sequence set forth in SEQ ID NO: 16, 210, or 211.

In some embodiments, the MSLN chimeric receptor comprises a variable heavy (VH) chain sequence comprising three heavy chain CDR sequences, CDR-H1, CDR-H2, and CDR-H3. In some embodiments, the VH chain sequence comprises the sequence set forth in SEQ ID NO: 17. In some embodiments, the VH chain sequence comprises the sequence set forth in SEQ ID NO: 17.

In some embodiments, the MSLN chimeric receptor CDR-H3 has at least about 50%, 75%, 80%, 85%, 90%, or 95% identity with a CDR-H3 of SEQ ID NO: 16, 210, or 211; the CDR-H2 has at least about 50%, 75%, 80%, 85%, 90%, or 95% identity with a CDR-H2 of SEQ ID NO: 15, 206, 207, 208 or 209; the CDR-H1 has at least about 50%, 75%, 80%, 85%, 90%, or 95% identity with a CDR-H1 of SEQ ID NO: 14, 202, 203, 204, or 205. In some embodiments, the CDR-H3 is a CDR-H3 of SEQ ID NO: 16, 210, or 211, with up to 1, 2, 3, 4, 5, 6, 7, or 8 amino acid substitutions; the CDR-H2 is a CDR-H2 of SEQ ID NO: 15, 206, 207, 208 or 209, with up to 1, 2, 3, 4, 5, 6, 7, or 8 amino acid substitutions; and the CDR-H1 is a CDR-H1 of SEQ ID NO: 14, 202, 203, 204, or 205, with up to 1, 2, 3, 4, or 5 amino acid substitutions.

In some embodiments, an MSLN chimeric receptor provided herein comprises one to three CDRs of a VH domain as set forth in SEQ ID NO: 17. In some embodiments, an MSLN chimeric receptor provided herein comprises two to three CDRs of a VH domain as set forth in SEQ ID NO: 17. In some embodiments, an MSLN chimeric receptor provided herein comprises three CDRs of a VH domain as set forth in SEQ ID NO: 17. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, an MSLN chimeric receptor provided herein comprises a VH sequence having at least about 50%, 60%, 70%, 80%, 90%, 95%, or 99% identity to an VH sequence set forth in SEQ ID NO: 17. In some embodiments, an MSLN chimeric receptor provided herein comprises a VH sequence provided in SEQ ID NO: 17, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antigen-binding domains described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies or antigen-binding domains.

In some aspects, provided herein are chimeric receptors that binds to mesothelin (MSLN), comprising a variable heavy (VHH) chain sequence comprising three heavy chain CDR sequences, CDR-H1, CDR-H2, and CDR-H3, wherein: CDR-H1 comprises the sequence set forth in SEQ ID NO: 10, CDR-H2 comprises the sequence set forth in SEQ ID NO: 11, and CDR-H3 comprises the sequence set forth in SEQ ID NO: 12.

In some aspects, an MSLN chimeric receptor comprises a variable heavy (VHH) chain sequence comprising three heavy chain CDR sequences, CDR-H1, CDR-H2, and CDR-H3. In some embodiments, the VHH chain sequence comprises the sequence set forth in SEQ ID NO: 13.

In some embodiments, an MSLN chimeric receptor CDR-H3 has at least about 50%, 75%, 80%, 85%, 90%, or 95% identity with a CDR-H3 of SEQ ID NO: 12, 200, or 201; the CDR-H2 has at least about 50%, 75%, 80%, 85%, 90%, or 95% identity with a CDR-H2 of SEQ ID NO: 11, 196, 197, 198, or 199; the CDR-H1 has at least about 50%, 75%, 80%, 85%, 90%, or 95% identity with a CDR-H1 of SEQ ID NO: 10, 192, 193, 194, or 195. In some embodiments, the CDR-H3 is a CDR-H3 of SEQ ID NO: 12, 200, or 201, with up to 1, 2, 3, 4, 5, 6, 7, or 8 amino acid substitutions; the CDR-H2 is a CDR-H2 of SEQ ID NO: 11, 196, 197, 198, or 199, with up to 1, 2, 3, 4, 5, 6, 7, or 8 amino acid substitutions; and the CDR-H1 is a CDR-H1 of SEQ ID NO: 10, 192, 193, 194, or 195, with up to 1, 2, 3, 4, or 5 amino acid substitutions.

In some embodiments, an MSLN chimeric receptor provided herein comprises one to three CDRs of a VHH domain as set forth in SEQ ID NO: 13. In some embodiments, an MSLN chimeric receptor provided herein comprises two to three CDRs of a VHH domain as set forth in SEQ ID NO: 13. In some embodiments, an antigen-binding domain provided herein comprises three CDRs of a VHH domain as set forth in SEQ ID NO: 13. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, an MSLN chimeric receptor provided herein comprises a VHH sequence having at least about 50%, 60%, 70%, 80%, 90%, 95%, or 99% identity to an VHH sequence set forth in SEQ ID NO: 13. In some embodiments, an antigen-binding domain provided herein comprises a VHH sequence provided in SEQ ID NO: 13, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antigen-binding domains described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies or antigen-binding domains.

In some embodiments, an MSLN chimeric receptor comprises a heavy chain variable (VH) region in which the full set of VH CDRs 1, 2, and 3 (combined) has at least 80% (such as, e.g., 80%, 85%, 90%, 95%, at least 85%, at least 90%, at least 95%) sequence identity to the CDRs 1, 2, and 3 of one of SEQ ID NOs: 13 or 17. In some embodiments, the MSLN chimeric receptor comprises a heavy chain variable (VH) region in which the full set of VH CDRs 1, 2, and 3 (combined) has at least 85% (such as, e.g., 85%, 90%, 95%, at least 90%, at least 95%) sequence identity to the CDRs 1, 2, and 3 of one of SEQ ID NOs: 13 or 17. In some embodiments, the MSLN chimeric receptor comprises a heavy chain variable (VH) region in which the full set of VH CDRs 1, 2, and 3 (combined) has at least 90% (such as, e.g., 90%, 95%, at least 95%) sequence identity to the CDRs 1, 2, and 3 of one of SEQ ID NOs: 13 or 17. In some embodiments, the MSLN chimeric receptor comprises a heavy chain variable (VH) region in which the full set of VH CDRs 1, 2, and 3 (combined) has at least 95% sequence identity to the CDRs 1, 2, and 3 of one of SEQ ID NOs: 13 or 17.

In some embodiments, the MSLN chimeric receptor comprises a heavy chain variable (VH) region in which the full set of VH CDRs 1, 2, and 3 (combined) has at least 80% (such as, e.g., 80%, 85%, 90%, 95%, at least 85%, at least 90%, at least 95%) sequence identity to the CDRs 1, 2, and 3 of SEQ ID NO: 13. In some embodiments, the MSLN chimeric receptor comprises a heavy chain variable (VH) region in which the full set of VH CDRs 1, 2, and 3 (combined) has at least 80% (such as, e.g., 80%, 85%, 90%, 95%, at least 85%, at least 90%, at least 95%) sequence identity to the CDRs 1, 2, and 3 of SEQ ID NO: 17.

In some embodiments, the MSLN chimeric receptor comprises a heavy chain variable (VH) region comprising:
(i) a VH complementarity determining region one (CDR1) comprising a sequence having at most two (e.g., one, two, zero) amino acid modifications relative to SEQ ID NO: 10, 192, 193, 194, or 195;
(ii) a VH CDR2 comprising a sequence having at most two (e.g., one, two, zero) amino acid modifications relative to SEQ ID NO: 11, 196, 197, 198, or 199; and
(iii) a VH CDR3 comprising a sequence having at most two (e.g., one, two, zero) amino acid modifications relative to SEQ ID NO: 12, 200, or 201.

In some embodiments, the MSLN chimeric receptor comprises a heavy chain variable (VH) region comprising:
(i) a VH complementarity determining region one (CDR1) comprising a sequence having at most two (e.g., one, two, zero) amino acid modifications relative to SEQ ID NO: 14, 202, 203, 204, or 205;
(ii) a VH CDR2 comprising a sequence having at most two (e.g., one, two, zero) amino acid modifications relative to SEQ ID NO: 15, 206, 207, 208, or 209; and
(iii) a VH CDR3 comprising a sequence having at most two (e.g., one, two, zero) amino acid modifications relative to SEQ ID NO: 16, 210, or 211.

In some embodiments, each amino acid modification, if any, is a conservative amino acid substitution. In some embodiments, each amino acid modification, if any, is a conservative amino acid substitution listed in Table A1.

In some embodiments, the MSLN chimeric receptor VH CDR1 comprises a sequence having at most one amino acid modification relative to SEQ ID NO: 10, 192, 193, 194, or 195. In some embodiments, the MSLN chimeric receptor VH CDR2 comprises a sequence having at most one amino acid modification relative to SEQ ID NO: 11, 196, 197, 198, or 199. In some embodiments, the MSLN chimeric receptor VH CDR3 comprises a sequence having at most one amino acid modification relative to SEQ ID NO: 12, 200, or 201. In some embodiments, the MSLN chimeric receptor VH CDR1 comprises a sequence having at most one amino acid modification relative to SEQ ID NO: 14, 202, 203, 204, or 205. In some embodiments, the MSLN chimeric receptor VH CDR2 comprises a sequence having at most one amino acid modification relative to SEQ ID NO: 15, 206, 207, 208, or 209. In some embodiments, the MSLN chimeric receptor VH CDR3 comprises a sequence having at most one amino acid modification relative to SEQ ID NO: 16, 210, or 211. In some embodiments, the at most one amino acid modification is an amino acid substitution. In some embodiments, the at most one amino acid modification is a conservative amino acid substitution. In some embodiments, the at most one amino acid modification is an amino acid deletion. In some embodiments, the at most one amino acid modification is an amino acid addition.

In some embodiments, the MSLN chimeric receptor VH CDR1 comprises a sequence as set forth in SEQ ID NO: 10. In some embodiments, the MSLN chimeric receptor VH CDR2 comprises a sequence as set forth in SEQ ID NO: 11. In some embodiments, the MSLN chimeric receptor VH CDR3 comprises a sequence as set forth in SEQ ID NO: 12.

In some embodiments, the MSLN chimeric receptor VH CDR1 comprises a sequence as set forth in SEQ ID NO: 14. In some embodiments, the MSLN chimeric receptor VH CDR2 comprises a sequence as set forth in SEQ ID NO: 15. In some embodiments, the MSLN chimeric receptor VH CDR3 comprises a sequence as set forth in SEQ ID NO: 16.

In some embodiments, the MSLN chimeric receptor comprises a heavy chain variable (VH) region comprising:
(i) a VH complementarity determining region one (CDR1) comprising the sequence set forth in SEQ ID NO: 10;
(ii) a VH CDR2 comprising the sequence set forth in SEQ ID NO: 11; and
(iii) a VH CDR3 comprising the sequence set forth in SEQ ID NO: 12.

In some embodiments, the MSLN chimeric receptor comprises a heavy chain variable (VH) region comprising:
(i) a VH complementarity determining region one (CDR1) comprising the sequence set forth in SEQ ID NO: 14;
(ii) a VH CDR2 comprising the sequence set forth in SEQ ID NO: 15; and
(iii) a VH CDR3 comprising the sequence set forth in SEQ ID NO: 16.

In some embodiments, the MSLN chimeric receptor comprises a heavy chain variable (VH) region comprising a VH CDR1, a VH CDR2, and a VH CDR3 comprising the sequences of SEQ ID NOs: 10, 11, and 12, respectively. In some embodiments, the MSLN chimeric receptor comprises a heavy chain variable (VH) region comprising a VH CDR1, a VH CDR2, and a VH CDR3 comprising the sequences of SEQ ID NOs: 14, 15, and 16, respectively.

In some embodiments, the MSLN chimeric receptor comprises a heavy chain variable (VH) region comprising the CDR1, CDR2, and CDR3 of one of SEQ ID NOs: 13 or 17. In some embodiments, the MSLN chimeric receptor comprises a heavy chain variable (VH) region comprising the CDR1, CDR2, and CDR3 of SEQ ID NO: 13. In some embodiments, the MSLN chimeric receptor comprises a heavy chain variable (VH) region comprising the CDR1, CDR2, and CDR3 of SEQ ID NO: 17.

In some embodiments, the VH CDR1, VH CDR2, and VH CDR3 sequences are present in a human VH framework.

In some embodiments, the MSLN chimeric receptor comprises a heavy chain variable (VH) region having at least 80% (such as, e.g., 80%, 85%, 90%, 95%, at least 85%, at least 90%, at least 95%) sequence identity to one of SEQ ID NOs: 13 or 17. In some embodiments, the MSLN chimeric receptor comprises a heavy chain variable (VH) region having at least 85% (such as, e.g., 85%, 90%, 95%, at least 90%, at least 95%) sequence identity to one of SEQ ID NOs: 13 or 17. In some embodiments, the MSLN chimeric receptor comprises a heavy chain variable (VH) region having at least 90% (such as, e.g., 90%, 95%, at least 95%) sequence identity to one of SEQ ID NOs: 13 or 17. In some embodiments, the MSLN chimeric receptor comprises a heavy chain variable (VH) region having at least 95% sequence identity to one of SEQ ID NOs: 13 or 17.

In some embodiments, the MSLN chimeric receptor comprises a heavy chain variable (VH) region having at least 80% (such as, e.g., 80%, 85%, 90%, 95%, at least 85%, at least 90%, at least 95%) sequence identity to SEQ ID NO: 13. In some embodiments, the MSLN chimeric receptor comprises a heavy chain variable (VH) region having at least 80% (such as, e.g., 80%, 85%, 90%, 95%, at least 85%, at least 90%, at least 95%) sequence identity to SEQ ID NO: 17

In some embodiments, the MSLN chimeric receptor comprises the heavy chain variable (VH) region of SEQ ID NO: 13. In some embodiments, MSLN chimeric receptor comprises the heavy chain variable (VH) region of SEQ ID NO: 17.

In some embodiments, the MSLN chimeric receptor specifically binds to human MSLN.

In some embodiments, the MSLN chimeric receptor binds to human MSLN with a $K_D$ of from about $10^{-9}$ M to about $10^{-6}$ M. In some embodiments, the MSLN chimeric receptor to human MSLN with a $K_D$ of $\leq 5\times10^{-7}$ M. In some embodiments, the MSLN chimeric receptor binds to human MSLN with a $K_D$ of $\leq 1\times10^{-7}$ M. In some embodiments, the MSLN chimeric receptor binds to human MSLN with a $K_D$ of $\leq 5\times10^{-8}$ M. In some embodiments, the MSLN chimeric receptor binds to human MSLN with a $K_D$ of $\leq 2\times10^{-8}$ M. In some embodiments, the MSLN chimeric receptor binds to human MSLN with a $K_D$ of $\leq 1\times10^{-8}$ M. In some embodiments, the MSLN chimeric receptor binds to human MSLN with a $K_D$ of $\leq 1\times10^{-9}$ M.

In some embodiments, the MSLN chimeric receptor is a chimeric antigen receptor or a priming receptor.

Chimeric Antigen Receptors

In another aspect, provided herein are chimeric antigen receptors comprising an extracellular antigen-binding domain that specifically binds to mesothelin (MSLN; NCBI Entrez Gene: 10232; UniProtKB/Swiss-Prot: Q13421). The recombinant CAR may be a human CAR, comprising fully human sequences, e.g., natural human sequences.

In some embodiments, the chimeric antigen receptor includes an extracellular portion comprising an antigen binding domain. The antigen recognition domain of a receptor such as a CAR can be linked to one or more intracellular signaling components, such as signaling components that mimic activation through an antigen receptor complex, such as a TCR complex, in the case of a CAR, and/or signal via another cell surface receptor. Thus, in some embodiments, the extracellular binding component (e.g., ligand-binding or antigen-binding domain) is linked to one or more transmembrane and intracellular signaling domains. In some embodiments, the transmembrane domain is fused to the extracellular domain. In one embodiment, a transmembrane domain that naturally is associated with one of the domains in the receptor, e.g., CAR, is used. In some instances, the transmembrane domain is selected or modified by amino acid substitution to avoid binding of such domains to the transmembrane domains of the same or different surface membrane proteins to minimize interactions with other members of the receptor complex.

In some aspects, the chimeric antigen receptor includes an extracellular portion comprising an antigen binding domain described herein and an intracellular signaling domain. In some embodiments, an antibody or fragment includes an scFv, a VH, or a single-domain VH antibody and the intracellular domain contains an ITAM. In some aspects, the intracellular signaling domain includes a signaling domain of a zeta chain of a CD3-zeta (CD3) chain. In some embodiments, the chimeric antigen receptor includes a transmembrane domain linking the extracellular domain and the intracellular signaling domain.

In some aspects, the transmembrane domain contains a transmembrane portion of CD8a or CD28. The extracellular domain and transmembrane can be linked directly or indirectly. In some embodiments, the extracellular domain and transmembrane are linked by a spacer, such as any described herein. In some embodiments, the chimeric antigen receptor contains an intracellular domain of a T cell costimulatory molecule, such as between the transmembrane domain and intracellular signaling domain. In some aspects, the T cell costimulatory molecule is CD28 or 41BB.

Chimeric Antigen Receptor CDRs, VH, VL Domains

In some aspects, the chimeric antigen receptor extracellular antigen-binding domain comprises an MSLN antibody or antigen binding fragment thereof.

In some aspects, the chimeric antigen receptor extracellular antigen-binding domain comprises a variable heavy (VH) chain sequence comprising three heavy chain CDR sequences, CDR-H1, CDR-H2, and CDR-H3. In some embodiments, the VH chain sequence comprises the sequence set forth in SEQ ID NO: 17.

In some embodiments, the chimeric antigen receptor extracellular antigen-binding domain CDR-H3 has at least about 50%, 75%, 80%, 85%, 90%, or 95% identity with a CDR-H3 of SEQ ID NO: 16, the CDR-H2 has at least about 50%, 75%, 80%, 85%, 90%, or 95% identity with a CDR-H2 of SEQ ID NO: 15, the CDR-H1 has at least about 50%, 75%, 80%, 85%, 90%, or 95% identity with a CDR-H1 of SEQ ID NO: 14. In some embodiments, the CDR-H3 is a CDR-H3 of SEQ ID NO: 16, with up to 1, 2, 3, 4, 5, 6, 7, or 8 amino acid substitutions; the CDR-H2 is a CDR-H2 of SEQ ID NO: 15, with up to 1, 2, 3, 4, 5, 6, 7, or 8 amino acid substitutions; and the CDR-H1 is a CDR-H1 of SEQ ID NO: 14, with up to 1, 2, 3, 4, or 5 amino acid substitutions.

In some embodiments, a chimeric antigen receptor extracellular antigen-binding domain provided herein comprises one to three CDRs of a VH domain as set forth in SEQ ID NO: 17. In some embodiments, an antigen-binding domain provided herein comprises two to three CDRs of a VH domain as set forth in SEQ ID NO: 17. In some embodiments, an antigen-binding domain provided herein comprises three CDRs of a VH domain as set forth in SEQ ID NO: 17. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, a chimeric antigen receptor extracellular antigen-binding domain provided herein comprises a VH sequence having at least about 50%, 60%, 70%, 80%, 90%, 95%, or 99% identity to an VH sequence set forth in SEQ ID NO: 17. In some embodiments, an antigen-binding domain provided herein comprises a VH sequence provided in SEQ ID NO: 17, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antigen-binding domains described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies or antigen-binding domains.

In some aspects, the chimeric antigen receptor extracellular antigen-binding domain comprises a single antibody variable heavy (VHH) chain sequence comprising three heavy chain CDR sequences, CDR-H1, CDR-H2, and CDR-H3. In some embodiments, the VHH chain sequence comprises the sequence set forth in SEQ ID NO: 13.

In some embodiments, the chimeric antigen receptor extracellular antigen-binding domain CDR-H3 has at least about 50%, 75%, 80%, 85%, 90%, or 95% identity with a CDR-H3 of SEQ ID NO: 12, the CDR-H2 has at least about 50%, 75%, 80%, 85%, 90%, or 95% identity with a CDR-H2 of SEQ ID NO: 11, the CDR-H1 has at least about 50%, 75%, 80%, 85%, 90%, or 95% identity with a CDR-H1 of SEQ ID NO: 10. In some embodiments, the CDR-H3 is a CDR-H3 of SEQ ID NO: 12, with up to 1, 2, 3, 4, 5, 6, 7, or 8 amino acid substitutions; the CDR-H2 is a CDR-H2 of SEQ ID NO: 11, with up to 1, 2, 3, 4, 5, 6, 7, or 8 amino acid substitutions; and the CDR-H1 is a CDR-H1 of SEQ ID NO: 10, with up to 1, 2, 3, 4, or 5 amino acid substitutions.

In some embodiments, a chimeric antigen receptor extracellular antigen-binding domain provided herein comprises one to three CDRs of a VHH domain as set forth in SEQ ID NO: 13. In some embodiments, an antigen-binding domain provided herein comprises two to three CDRs of a VHH domain as set forth in SEQ ID NO: 13. In some embodiments, an antigen-binding domain provided herein comprises three CDRs of a VHH domain as set forth in SEQ ID NO: 13. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, a chimeric antigen receptor extracellular antigen-binding domain provided herein comprises a VHH sequence having at least about 50%, 60%, 70%, 80%, 90%, 95%, or 99% identity to an VHH sequence set forth in SEQ ID NO: 13. In some embodiments, an antigen-binding domain provided herein comprises a VHH sequence provided in SEQ ID NO: 13, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antigen-binding domains described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies or antigen-binding domains.

Table C provides illustrative MSLN antigen binding domain CDR sequences of the VHH of SEQ ID NO: 13 and the VHH of SEQ ID NO: 17, according to the indicated numbering schemes.

TABLE C

| SEQ ID NO | Name | Numbering scheme | Sequence |
|---|---|---|---|
| 10 | CDR-H1 | Chothia | GIDESLY--- |
| 192 | | AbM | GIDLSLYRMR |
| 193 | | Kabat | -----LYRMR |
| 194 | | Contact | ----SLYRMR |
| 195 | | IMGT | GIDLSLYR-- |
| 11 | CDR-H2 | Chothia | -----TDDGT--------- |
| 196 | | ADM | ---LITDDGTSY------- |
| 197 | | Kabat | ---LITDDGTSYYADSVKG |
| 198 | | Contact | LVALITDDGTSY------- |

TABLE C-continued

| SEQ ID NO | Name | Numbering scheme | Sequence |
|---|---|---|---|
| 199 | | IMGT | ----ITDDGTS-------- |
| 12 | CDR-H3 | Chothia | --ETPLSPVNY |
| 12 | | AbM | --ETPLSPVNY |
| 12 | | Kabat | --ETPLSPVNY |
| 200 | | Contact | NAETPLSPVN- |
| 201 | | IMGT | NAETPLSPVNY |
| 14 | CDR-H1 | Chothia | GGSISNSY--- |
| 202 | | ADM | GGSISNSYYWG |
| 203 | | Kabat | -----NSYYWG |
| 204 | | Contact | ----SNSYYWG |
| 205 | | IMGT | GGSISNSYY-- |
| 15 | CDR-H2 | Chothia | -----YHSGN--------- |
| 206 | | AbM | ---SIYHSGNTY------- |
| 207 | | Kabat | ---SIYHSGNTYYNPSLKS |
| 208 | | Contact | WIGSIYHSGNTY------- |
| 209 | | IMGT | ----IYHSGNT-------- |
| 16 | CDR-H3 | Chothia | --QDGVGATTTEEY |
| 16 | | AbM | --QDGVGATTTEEY |
| 16 | | Kabat | --QDGVGATTTEEY |
| 210 | | Contact | VTQDGVGATTTEE- |
| 211 | | IMGT | VTQDGVGATTTEEY |

CAR Transmembrane Domain

The transmembrane domain in some embodiments is derived either from a natural or from a synthetic source. Where the source is natural, the domain in some aspects is derived from any membrane-bound or transmembrane protein. Transmembrane regions include those derived from (i.e. comprise at least the transmembrane region(s) of) the alpha, beta or zeta chain of the T-cell receptor, CD28, CD3 epsilon, CD45, CD4, CD5, CDS, CD9, CD16, CD22, CD33, CD37, CD64, CD80, CD86, CD 134, CD137, and/or CD154. Alternatively the transmembrane domain in some embodiments is synthetic. In some aspects, the synthetic transmembrane domain comprises predominantly hydrophobic residues such as leucine and valine. In some aspects, a triplet of phenylalanine, tryptophan and valine will be found at each end of a synthetic transmembrane domain. In some embodiments, the linkage is by linkers, spacers, and/or transmembrane domain(s).

In some embodiments, the transmembrane domain of the receptor, e.g., the CAR, is a transmembrane domain of human CD28 or variant thereof, e.g., a 27-amino acid transmembrane domain of a human CD28 (Accession No.: P10747.1).

In some embodiments, the CAR comprises a CD8a TMD. In some embodiments, the CD8a TMD comprises the sequence set forth in SEQ ID NO: 27.

CAR Hinge

In some embodiments, the CAR further includes a spacer, which may be or include at least a portion of an immunoglobulin constant region or variant or modified version thereof, such as a hinge region, e.g., a CD8a hinge, an IgG4 hinge region, and/or a CH1/CL and/or Fc region. In some embodiments, the constant region or portion is of a human IgG, such as IgG4 or IgG1. In some aspects, the portion of the constant region serves as a spacer region between the antigen-recognition component, e.g., scFv, and transmembrane domain. The spacer can be of a length that provides for increased responsiveness of the cell following antigen binding, as compared to in the absence of the spacer. In some examples, the spacer is at or about 12 amino acids in length or is no more than 12 amino acids in length. Exemplary spacers include those having at least about 10 to 229 amino acids, about 10 to 200 amino acids, about 10 to 175 amino acids, about 10 to 150 amino acids, about 10 to 125 amino acids, about 10 to 100 amino acids, about 10 to 75 amino acids, about 10 to 50 amino acids, about 10 to 40 amino acids, about 10 to 30 amino acids, about 10 to 20 amino acids, or about 10 to 15 amino acids, and including any integer between the endpoints of any of the listed ranges. In some embodiments, a spacer region has about 12 amino acids or less, about 119 amino acids or less, or about 229 amino acids or less. Exemplary spacers include CD8a hinge, IgG4 hinge alone, IgG4 hinge linked to CH2 and CH3 domains, or IgG4 hinge linked to the CH3 domain. Exemplary spacers include, but are not limited to, those described in Hudecek et al. (2013) Clin. Cancer Res., 19:3153 or international patent application publication number WO2014031687. In some embodiments, the CAR hinge comprises a CD8a hinge. In some embodiments, the CD8a hinge comprises the sequence set forth in SEQ ID NO: 26.

Among the intracellular signaling domains are those that mimic or approximate a signal through a natural antigen receptor, a signal through such a receptor in combination with a costimulatory receptor, and/or a signal through a costimulatory receptor alone. In some embodiments, a short oligo- or polypeptide linker, for example, a linker of between 2 and 10 amino acids in length, such as one containing glycines and serines, e.g., glycine-serine doublet, is present and forms a linkage between the transmembrane domain and the cytoplasmic signaling domain of the receptor.

CAR Intracellular Domain

In some embodiments, upon ligation of the CAR, the cytoplasmic domain or intracellular signaling domain of the receptor activates at least one of the normal effector functions or responses of the immune cell, e.g., T cell engineered to express the receptor. For example, in some contexts, the receptor induces a function of a T cell such as cytolytic activity or T-helper activity, such as secretion of cytokines or other factors. In some embodiments, a truncated portion of an intracellular signaling domain of an antigen receptor component or costimulatory molecule is used in place of an intact immunostimulatory chain, for example, if it transduces the effector function signal. In some embodiments, the intracellular signaling domain or domains include the cytoplasmic sequences of the T cell receptor (TCR), and in some aspects also those of co-receptors that in the natural context act in concert with such receptor to initiate signal transduction following antigen receptor engagement, and/or any derivative or variant of such molecules, and/or any synthetic sequence that has the same functional capability.

In some aspects, the receptor includes a primary cytoplasmic signaling sequence that regulates primary activation of the TCR complex. Primary cytoplasmic signaling sequences that act in a stimulatory manner may contain signaling motifs which are known as immunoreceptor tyrosine-based activation motifs or ITAMs. Examples of ITAM containing primary cytoplasmic signaling sequences include those derived from TCR or CD3 zeta, FcR gamma, FcR beta, CD3 gamma, CD3 delta, CD3 epsilon, CD5, CD22, CD79a, CD79b, and CD66d. In some embodiments, cytoplasmic signaling molecule(s) in the CAR contain(s) a cytoplasmic signaling domain, portion thereof, or sequence derived from CD3 zeta.

In some embodiments, the intracellular signaling domain comprises a human CD3 zeta stimulatory signaling domain or functional variant thereof, such as a 112 AA cytoplasmic domain of isoform 3 of human CD3.zeta. (Accession No.: P20963.2) or a CD3 zeta signaling domain as described in U.S. Pat. No. 7,446,190 or U.S. Pat. No. 8,911,993.

The receptor, e.g., the CAR, can include at least one intracellular signaling component or components. In some embodiments, the receptor includes an intracellular component of a TCR complex, such as a TCR CD3 chain that mediates T-cell activation and cytotoxicity, e.g., CD3 zeta chain. Thus, in some aspects, the extracellular domain is linked to one or more cell signaling modules. In some embodiments, cell signaling modules include CD3 transmembrane domain, CD3 intracellular signaling domains, and/or other CD transmembrane domains. In some embodiments, the receptor, e.g., CAR, further includes a portion of one or more additional molecules such as Fc receptor-gamma, CD8, CD4, CD25, or CD16. For example, in some aspects, the CAR includes a chimeric molecule between CD3-zeta or Fc receptor-gamma and CD8, CD4, CD25 or CD16. In some embodiments, the CAR comprises a CD3-zeta activation domain comprising the sequence set forth in SEQ ID NO: 29.

In some embodiments, the intracellular domain comprises an intracellular costimulatory signaling domain of 41BB or functional variant or portion thereof, such as a 42-amino acid cytoplasmic domain of a human 4-1BB (Accession No. Q07011.1) or functional variant or portion thereof.

In some embodiments, the receptor encompasses one or more, e.g., two or more, costimulatory domains and an activation domain, e.g., primary activation domain, in the cytoplasmic portion. Exemplary receptors include intracellular components of CD3-zeta, CD28, and 4-1BB. In some embodiments, the chimeric antigen receptor contains an intracellular domain of a T cell costimulatory molecule. In some aspects, the T cell costimulatory molecule is 4-1BB.

In some embodiments, the receptor includes a signaling domain and/or transmembrane portion of a costimulatory receptor, such as CD28, 4-1BB, OX40, DAP10, and ICOS. In some aspects, the same receptor includes both the activating and costimulatory components.

In certain embodiments, the intracellular signaling domain comprises a CD8a transmembrane and signaling domain linked to a CD3 (e.g., CD3-zeta) intracellular domain. In some embodiments, the intracellular signaling domain comprises a 4-1BB (CD137, TNFRSF9) co-stimulatory domains, linked to a CD3 zeta intracellular domain. In some embodiments, the CAR comprises a 4-1BB co-stimulatory domain. In some embodiments, the 4-1BB co-stimulatory domain comprises the sequence as set forth in SEQ ID NO: 28.

In some embodiments, the CAR comprises a sequence as set forth in SEQ ID NO: 30, 31, 32, or 33. In some embodiments, the CAR comprises a sequence as set forth in SEQ ID NO: 30.

In some embodiments, the CAR or other antigen receptor further includes a marker, such as a cell surface marker, which may be used to confirm transduction or engineering of the cell to express the receptor, such as a truncated version of a cell surface receptor, such as truncated EGFR (tEGFR). In some aspects, the marker includes all or part (e.g., truncated form) of CD34, a nerve growth factor receptor (NGFR), or epidermal growth factor receptor (e.g., tEGFR). In some embodiments, the nucleic acid encoding the marker is operably linked to a polynucleotide encoding for a linker sequence, such as a cleavable linker sequence or a ribosomal skip sequence, e.g., T2A. See WO2014031687. In some embodiments, introduction of a construct encoding the CAR and EGFRt separated by a T2A ribosome switch can express two proteins from the same construct, such that the EGFRt can be used as a marker to detect cells expressing such construct. In some embodiments, a marker, and optionally a linker sequence, can be any as disclosed in published patent application No. WO2014031687. For example, the marker can be a truncated EGFR (tEGFR) that is, optionally, linked to a linker sequence, such as a T2A ribosomal skip sequence.

In some embodiments, the marker is a molecule, e.g., cell surface protein, not naturally found on T cells or not naturally found on the surface of T cells, or a portion thereof.

In some embodiments, the molecule is a non-self molecule, e.g., non-self protein, i.e., one that is not recognized as "self" by the immune system of the host into which the cells will be adoptively transferred.

In some embodiments, the marker serves no therapeutic function and/or produces no effect other than to be used as a marker for genetic engineering, e.g., for selecting cells successfully engineered. In other embodiments, the marker may be a therapeutic molecule or molecule otherwise exerting some desired effect, such as a ligand for a cell to be encountered in vivo, such as a costimulatory or immune checkpoint molecule to enhance and/or dampen responses of the cells upon adoptive transfer and encounter with ligand.

The CAR may comprise one or modified synthetic amino acids in place of one or more naturally-occurring amino acids. Exemplary modified amino acids include, but are not limited to, aminocyclohexane carboxylic acid, norleucine, α-amino n-decanoic acid, homoserine, S-acetylaminomethylcysteine, trans-3- and trans-4-hydroxyproline, 4-aminophenylalanine, 4-nitrophenylalanine, 4-chlorophenylalanine, 4-carboxyphenylalanine, (3-phenylserine (3-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N,N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbomane)-carboxylic acid, α,γ-diaminobutyric acid, α,γ-diaminopropionic acid, homophenylalanine, and α-tertbutylglycine.

For example, in some embodiments, the CAR includes an antibody or fragment thereof, including single chain antibodies (sdAbs, e.g. containing only the VH region), VH domains, and scFvs, described herein, a spacer such as a CD8a hinge, a CD8a transmembrane domain, a 4-1BB intracellular signaling domain, and a CD3 zeta signaling domain. In some embodiments, the CAR includes an antibody or fragment, including sdAbs and scFvs described herein, a spacer such as a CD8a hinge, a CD8a transmembrane domain, a 4-1BB intracellular signaling domain, and a CD3 zeta signaling domain.

MSLN Antibodies and Antigen Binding Fragments

In some aspects, provided herein are MSLN antibodies or antigen binding fragments thereof. In some embodiments, the MSLN antigen-binding moiety is selected from the group consisting of an antibody, a nanobody, a diabody, a triabody, or a minibody, a F(ab')2 fragment, a Fab fragment, a single chain variable fragment (scFv), and a single domain antibody (sdAb), or a functional fragment thereof. In some embodiments, the antigen-binding moiety comprises an scFv. The antigen-binding moiety can include naturally-occurring amino acid sequences or can be engineered, designed, or modified so as to provide desired and/or improved properties, e.g., increased binding affinity.

In some aspects, provided herein are isolated antibodies or antigen binding fragments thereof that binds to mesothelin (MSLN), comprising a single domain antibody comprising a variable heavy (VM) chain sequence comprising three heavy chain CDR sequences, CDR-H1, CDR-H2, and CDR-H3, wherein: CDR-H1 comprises the sequence set forth in SEQ ID NO: 10, CDR-H2 comprises the sequence set forth in SEQ ID NO: 11, and CDR-H3 comprises the sequence set forth in SEQ ID NO: 12.

In some aspects, an MSLN antibody or antigen binding fragment comprises a single domain antibody variable heavy (VHH) chain sequence comprising three heavy chain CDR sequences, CDR-H1, CDR-H2, and CDR-H3. In some embodiments, the VHH chain sequence comprises the sequence set forth in SEQ ID NO: 13.

In some embodiments, the MSLN antibody or antigen binding fragment CDR-H3 has at least about 50%, 75%, 80%, 85%, 90%, or 95% identity with a CDR-H3 of SEQ ID NO: 12, 200, or 201; the CDR-H2 has at least about 50%, 75%, 80%, 85%, 90%, or 95% identity with a CDR-H2 of SEQ ID NO: 11, 196, 197, 198, or 199; the CDR-H1 has at least about 50%, 75%, 80%, 85%, 90%, or 95% identity with a CDR-H1 of SEQ ID NO: 10, 192, 193, 194, or 195. In some embodiments, the CDR-H3 is a CDR-H3 of SEQ ID NO: 12, 200, or 201, with up to 1, 2, 3, 4, 5, 6, 7, or 8 amino acid substitutions; the CDR-H2 is a CDR-H2 of SEQ ID NO: 11, 196, 197, 198, or 199, with up to 1, 2, 3, 4, 5, 6, 7, or 8 amino acid substitutions; and the CDR-H1 is a CDR-H1 of SEQ ID NO: 10, 192, 193, 194, or 195, with up to 1, 2, 3, 4, or 5 amino acid substitutions.

In some embodiments, an MSLN antibody or antigen binding fragment provided herein comprises one to three CDRs of a VHH domain as set forth in SEQ ID NO: 13. In some embodiments, an antigen-binding domain provided herein comprises two to three CDRs of a VHH domain as set forth in SEQ ID NO: 13. In some embodiments, an antigen-binding domain provided herein comprises three CDRs of a VHH domain as set forth in SEQ ID NO: 13. In some aspects, the CDRs are Kabat CDRs. In some aspects, the CDRs are Chothia CDRs. In some aspects, the CDRs are AbM CDRs. In some aspects, the CDRs are Contact CDRs. In some aspects, the CDRs are IMGT CDRs.

In some embodiments, an MSLN antibody or antigen binding fragment provided herein comprises a VHH sequence having at least about 50%, 60%, 70%, 80%, 90%, 95%, or 99% identity to an VHH sequence set forth in SEQ ID NO: 13. In some embodiments, an antigen-binding domain provided herein comprises a VHH sequence provided in SEQ ID NO: 13, with up to 1, 2, 3, 4, 5, 6, 7, 8, 9, 10, 11, 12, 13, 14, 15, 16, 17, 18, 19, 20, 21, 22, 23, 24, or 25 amino acid substitutions. In some aspects, the amino acid substitutions are conservative amino acid substitutions. In some embodiments, the antigen-binding domains described in this paragraph are referred to herein as "variants." In some embodiments, such variants are derived from a sequence provided herein, for example, by affinity maturation, site directed mutagenesis, random mutagenesis, or any other method known in the art or described herein. In some embodiments, such variants are not derived from a sequence provided herein and may, for example, be isolated de novo according to the methods provided herein for obtaining antibodies or antigen-binding domains.

In some embodiments, the MSLN antibody or antigen binding fragment comprises a heavy chain variable (VH) region in which the full set of VH CDRs 1, 2, and 3 (combined) has at least 80% (such as, e.g., 80%, 85%, 90%, 95%, at least 85%, at least 90%, at least 95%) sequence identity to the CDRs 1, 2, and 3 of SEQ ID NO: 13. In some embodiments, the MSLN antibody or antigen binding fragment comprises a heavy chain variable (VH) region in which the full set of VH CDRs 1, 2, and 3 (combined) has at least 85% (such as, e.g., 85%, 90%, 95%, at least 90%, at least 95%) sequence identity to the CDRs 1, 2, and 3 of SEQ ID NO: 13. In some embodiments, the MSLN antibody or antigen binding fragment comprises a heavy chain variable (VH) region in which the full set of VH CDRs 1, 2, and 3 (combined) has at least 90% (such as, e.g., 90%, 95%, at least 95%) sequence identity to the CDRs 1, 2, and 3 of SEQ ID NO: 13. In some embodiments, the MSLN antibody or antigen binding fragment comprises a heavy chain variable (VH) region in which the full set of VH CDRs 1, 2, and 3 (combined) has at least 95% sequence identity to the CDRs 1, 2, and 3 of SEQ ID NO: 13.

In some embodiments, the MSLN antibody or antigen binding fragment comprises a heavy chain variable (VH) region comprising:
  (i) a VH complementarity determining region one (CDR1) comprising a sequence having at most two (e.g., one, two, zero) amino acid modifications relative to SEQ ID NO: 10, 192, 193, 194, or 195;
  (ii) a VH CDR2 comprising a sequence having at most two (e.g., one, two, zero) amino acid modifications relative to SEQ ID NO: 11, 196, 197, 198, or 199; and
  (iii) a VH CDR3 comprising a sequence having at most two (e.g., one, two, zero) amino acid modifications relative to SEQ ID NO: 12, 200, or 201.

In some embodiments, each amino acid modification, if any, is a conservative amino acid substitution. In some embodiments, each amino acid modification, if any, is a conservative amino acid substitution listed in Table A1.

In some embodiments, the VH CDR1 comprises a sequence having at most one amino acid modification relative to SEQ ID NO: 10, 192, 193, 194, or 195. In some embodiments, the VH CDR2 comprises a sequence having at most one amino acid modification relative to SEQ ID NO: 11, 196, 197, 198, or 199. In some embodiments, the VH CDR3 comprises a sequence having at most one amino acid modification relative to SEQ ID NO: 12, 200, or 201. In some embodiments, the at most one amino acid modification is an amino acid substitution. In some embodiments, the at most one amino acid modification is a conservative amino acid substitution. In some embodiments, the at most one amino acid modification is an amino acid deletion. In some embodiments, the at most one amino acid modification is an amino acid addition.

In some embodiments, the VH CDR1 comprises a sequence as set forth in SEQ ID NO: 10. In some embodiments, the VH CDR2 comprises a sequence as set forth in SEQ ID NO: 11. In some embodiments, the VH CDR3 comprises a sequence as set forth in SEQ ID NO: 12.

In some embodiments, the MSLN antibody or antigen binding fragment comprises a heavy chain variable (VH) region comprising:
  (i) a VH complementarity determining region one (CDR1) comprising the sequence set forth in SEQ ID NO: 10;
  (ii) a VH CDR2 comprising the sequence set forth in SEQ ID NO: 11; and
  (iii) a VH CDR3 comprising the sequence set forth in SEQ ID NO: 12.

In some embodiments, the MSLN antibody or antigen binding fragment comprises a heavy chain variable (VH) region comprising a VH CDR1, a VH CDR2, and a VH CDR3 comprising the sequences of SEQ ID NOs: 10, 11, and 12, respectively.

In some embodiments, the MSLN antibody or antigen binding fragment comprises a heavy chain variable (VH) region comprising the CDR1, CDR2, and CDR3 of SEQ ID NO: 13.

In some embodiments, the VH CDR1, VH CDR2, and VH CDR3 sequences are present in a human VH framework.

In some embodiments, the MSLN antibody or antigen binding fragment comprises a heavy chain variable (VH) region having at least 80% (such as, e.g., 80%, 85%, 90%, 95%, at least 85%, at least 90%, at least 95%) sequence identity to SEQ ID NO: 13. In some embodiments, the MSLN antibody or antigen binding fragment comprises a heavy chain variable (VH) region having at least 85% (such as, e.g., 85%, 90%, 95%, at least 90%, at least 95%) sequence identity to SEQ ID NO: 13. In some embodiments, the MSLN antibody or antigen binding fragment comprises a heavy chain variable (VH) region having at least 90% (such as, e.g., 90%, 95%, at least 95%) sequence identity to SEQ ID NO: 13. In some embodiments, the MSLN antibody or antigen binding fragment comprises a heavy chain variable (VH) region having at least 95% sequence identity to SEQ ID NO: 13.

In some embodiments, the MSLN antibody or antigen binding fragment comprises a heavy chain variable (VH) region having at least 80% (such as, e.g., 80%, 85%, 90%, 95%, at least 85%, at least 90%, at least 95%) sequence identity to SEQ ID NO: 13.

In some embodiments, the MSLN antibody or antigen binding fragment specifically binds to human MSLN.

In some embodiments, the MSLN antibody or antigen binding fragment binds to human MSLN with a $K_D$ of from about $10^{-9}$ M to about $10^{-6}$ M. In some embodiments, the MSLN antibody or antigen binding fragment binds to human MSLN with a $K_D$ of $\leq 5 \times 10^{-7}$ M. In some embodiments, the MSLN antibody or antigen binding fragment binds to human MSLN with a $K_D$ of $\leq 1 \times 10^{-7}$ M. In some embodiments, the MSLN antibody or antigen binding fragment binds to human MSLN with a $K_D$ of $\leq 5 \times 10^{-8}$ M. In some embodiments, the MSLN antibody or antigen binding fragment binds to human MSLN with a $K_D$ of $\leq 2 \times 10^{-8}$ M. In some embodiments, the MSLN antibody or antigen binding fragment binds to human MSLN with a $K_D$ of $\leq 1 \times 10^{-8}$ M. In some embodiments, the MSLN antibody or antigen binding fragment binds to human MSLN with a $K_D$ of $\leq 1 \times 10^{-9}$ M.

In some embodiments, the MSLN antibody or antigen binding fragment is a single domain antibody.

In some embodiments, the MSLN antibody or antigen binding fragment is a human single domain antibody.

In some embodiments, the MSLN antibody or antigen binding fragment is an isolated single domain antibody. In some embodiments, the MSLN antibody or antigen binding fragment is an isolated, human single domain antibody.

Recombinant Nucleic Acids and Vectors

In one aspect, provided herein are recombinant nucleic acids wherein the one or more recombinant nucleic acids encode: a first chimeric polypeptide comprising a priming receptor comprising a first extracellular antigen-binding domain that specifically binds to Alkaline Phosphatase, Germ Cell (ALPG/P); a second chimeric polypeptide comprising a CAR comprising a second extracellular antigen-binding domain that specifically binds to mesothelin (MSLN); and a nucleic acid sequence at least 15 nucleotides in length, wherein the nucleic acid sequence is selected from the group consisting of: a nucleic acid sequence complementary to nucleotides 1126 to 1364 of an mRNA encoding human FAS comprising the sequence set forth in SEQ ID NO: 39, a nucleic acid sequence complementary to nucleotides 518 to 559 of an mRNA encoding human PTPN2 comprising the sequence set forth in SEQ ID NO: 40; and a nucleic acid sequence complementary to nucleotides 1294 to 2141 of an mRNA encoding human TOX comprising the sequence set forth in SEQ ID NO: 41.

In another aspect, provided herein are recombinant nucleic acids wherein the one or more recombinant nucleic acids encode: a first chimeric polypeptide comprises a priming receptor comprising a first extracellular antigen-binding domain that specifically binds Alkaline Phosphatase, Placental/Germ Cell (ALPG/P), wherein the first extracellular antigen-binding domain comprises a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3, wherein: CDR-H1 comprises the sequence set forth in SEQ ID NO: 1, CDR-H2 comprises the sequence set forth in SEQ ID NO: 2, CDR-H3 comprises the sequence set forth in SEQ ID NO: 3, CDR-L1 comprises the sequence set forth in SEQ ID NO: 4, CDR-L2 comprises the sequence set forth in SEQ ID NO: 5, and CDR-L3 comprises the sequence set forth in SEQ ID NO: 6; a second chimeric polypeptide comprising a chimeric antigen receptor (CAR); and a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and a second nucleic acid sequence at least 15 nucleotides in length, wherein the second nucleic acid sequence is complementary to nucleotides 518 to 559 of an mRNA encoding human PTPN2 comprising the sequence set forth in SEQ ID NO: 40; or complementary to nucleotides 1294 to 2141 of an mRNA encoding human TOX comprising the sequence set forth in SEQ ID NO: 41.

In another aspect, provided herein are recombinant nucleic acids wherein the one or more recombinant nucleic acids encode: a first chimeric polypeptide comprises a priming receptor; a second chimeric polypeptide comprising a chimeric antigen receptor (CAR) comprising an extracellular antigen-binding domain that specifically binds to mesothelin (MSLN), wherein the extracellular antigen-binding domain comprises a variable heavy (VH) chain sequence comprising three heavy chain CDR sequences, CDR-H1, CDR-H2, and CDR-H3, wherein: CDR-H1 comprises the sequence set forth in SEQ ID NO: 14, CDR-H2 comprises the sequence set forth in SEQ ID NO: 15, and CDR-H3 comprises the sequence set forth in SEQ ID NO: 16; and a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and a second nucleic acid sequence at least 15 nucleotides in length, wherein the second nucleic acid sequence is complementary to nucleotides 518 to 559 of an mRNA encoding human PTPN2 comprising the sequence set forth in SEQ ID NO: 40; or complementary to nucleotides 1294 to 2141 of an mRNA encoding human TOX comprising the sequence set forth in SEQ ID NO: 41.

In another aspect, provided herein are recombinant nucleic acids wherein the one or more recombinant nucleic acids encode: a first chimeric polypeptide comprising a priming receptor; a second chimeric polypeptide comprising a chimeric antigen receptor (CAR) comprising an extracellular antigen-binding domain that specifically binds to mesothelin (MSLN), wherein the extracellular antigen-binding domain comprises a single domain antibody comprising a variable heavy (VHH) chain sequence comprising three heavy chain CDR sequences, CDR-H1, CDR-H2, and CDR-H3, wherein: CDR-H1 comprises the sequence set forth in SEQ ID NO: 10, CDR-H2 comprises the sequence set forth in SEQ ID NO: 11, and CDR-H3 comprises the sequence set forth in SEQ ID NO: 12; and a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and a second nucleic acid sequence at least 15 nucleotides in length, wherein the second nucleic acid sequence is complementary to nucleotides 518 to 559 of an mRNA encoding human PTPN2 comprising the sequence set forth in SEQ ID NO: 40; or complementary to nucleotides 1294 to 2141 of an mRNA encoding human TOX comprising the sequence set forth in SEQ ID NO: 41.

In some embodiments, the recombinant nucleic acid comprises a sequence selected form the group consisting of the sequences shown in SEQ ID NOs: 156-165.

RNA Interference Molecules

Fas Cell Surface Death Receptor (FAS) is an apoptosis-inducing TNF receptor superfamily member. Protein Tyrosine Phosphatase Non-Receptor Type 2 (PTPN2) is a phosphatase that regulates interferon and many other signaling pathways. Thymocyte selection associated high mobility group box (TOX) is a transcription factor that regulates differentiation of exhausted T cells.

As used herein, "target gene" refers to a nucleic acid sequence in a cell, wherein the expression of the sequence may be specifically and effectively modulated using the recombinant nucleic acid molecules and methods described herein. In certain embodiments, the target gene may be implicated in the growth (proliferation), maintenance (survival), and/or immune behavior of an individual's immune cells. In some embodiments, the target gene is FAS. In some embodiments, the target gene is PTPN2. In some embodiments, the target gene is TOX. In some embodiments, more than one target gene is modulated using a recombinant nucleic acid molecule and methods described herein. In some embodiments, at least two target gene are modulated using the recombinant nucleic acid molecules and methods described herein. In some embodiments, the recombinant nucleic acid molecule(s) is an shRNA. In some embodiments, the target genes are at least FAS and PTPN2. In some embodiments, the target genes are at least FAS and TOX.

In some embodiments, the recombinant nucleic acid comprises a nucleic acid sequence at least 15 nucleotides in length complementary to nucleotides 1126 to 1364 of an mRNA encoding human FAS comprising the sequence set forth in SEQ ID NO: 39.

In some embodiments, the recombinant nucleic acid comprises a nucleic acid sequence at least 15 nucleotides in length complementary to nucleotides 518 to 559 of an mRNA encoding human Protein Tyrosine Phosphatase Non-Receptor Type 2 (PTPN2) comprising the sequence set forth in SEQ ID NO: 40.

In some embodiments, the recombinant nucleic acid comprises a nucleic acid sequence at least 15 nucleotides in length complementary to nucleotides 1294 to 2141 of an mRNA encoding human thymocyte selection associated high mobility group box (TOX) comprising the sequence set forth in SEQ ID NO: 41.

In some embodiments, the recombinant nucleic acid comprises a first nucleic acid sequence at least 15 nucleotides in length complementary to nucleotides 1126 to 1364 of an mRNA encoding human FAS comprising the sequence set forth in SEQ ID NO: 39 and a second nucleic acid sequence at least 15 nucleotides in length complementary to nucleotides 518 to 559 of an mRNA encoding human Protein Tyrosine Phosphatase Non-Receptor Type 2 (PTPN2) comprising the sequence set forth in SEQ ID NO: 40.

In some embodiments, the recombinant nucleic acid comprises a first nucleic acid sequence at least 15 nucleotides in length complementary to nucleotides 1126 to 1364 of an mRNA encoding human FAS comprising the sequence set forth in SEQ ID NO: 39 and a and a second nucleic acid sequence at least 15 nucleotides in length complementary to nucleotides 1294 to 2141 of an mRNA encoding human thymocyte selection associated high mobility group box (TOX) comprising the sequence set forth in SEQ ID NO: 41.

In some embodiments, the recombinant nucleic acid comprises a first nucleic acid sequence at least 15 nucleotides in length complementary to nucleotides 518 to 559 of an mRNA encoding human Protein Tyrosine Phosphatase Non-Receptor Type 2 (PTPN2) comprising the sequence set forth in SEQ ID NO: 40 and a second nucleic acid sequence at least 15 nucleotides in length complementary to nucleotides 1294 to 2141 of an mRNA encoding human thymocyte selection associated high mobility group box (TOX) comprising the sequence set forth in SEQ ID NO: 41.

In some embodiments, the nucleic acid comprises a sequence selected from the group consisting of the sequences set forth in SEQ ID NOs: 42-56. In some embodiments, the nucleic acid comprises the sequence set forth in SEQ ID NO: 45. In some embodiments, the nucleic acid is capable of reducing expression of FAS in the immune cell by at least 50%, 55%, 60%, 65%, 75%, 80%, 85%, 90%, 95%, or 99% as compared to a control cell that does not comprise the nucleic acid.

In some embodiments, the nucleic acid comprises a sequence selected from the group consisting of the sequences set forth in SEQ ID NOs: 72-84. In some embodiments, the nucleic acid comprises the sequence set forth in SEQ ID NO: 82. In some embodiments, the nucleic acid is capable of reducing expression of PTPN2 in the immune cell by at least 50%, 55%, 60%, 65%, 75%, 80%, 85%, 90%, 95%, or 99% as compared to a control cell that does not comprise the nucleic acid.

In some embodiments, the nucleic acid comprises a sequence selected from the group consisting of the sequences set forth in SEQ ID NOs: 98-111. In some embodiments, the nucleic acid comprises the sequence set forth in SEQ ID NO: 99 or 104. In some embodiments, the nucleic acid is capable of reducing expression of TOX in the immune cell by at least 50%, 55%, 60%, 65%, 75%, 80%, 85%, 90%, 95%, or 99% as compared to a control cell that does not comprise the nucleic acid.

In some embodiments, the nucleic acid sequence is at least 16, 17, 18, 19, 20, 21, or 22 nucleotides in length.

In some embodiments, the nucleic acid is an RNA interference (RNAi) molecule. Exemplary RNAi molecules include short hairpin RNA (shRNA), a small interfering RNA (siRNA), a double stranded RNA (dsRNA), or an antisense oligonucleotide. In some embodiments, the nucleic acid is a short hairpin RNA (shRNA), a small interfering RNA (siRNA), a double stranded RNA (dsRNA), or an antisense oligonucleotide. In some embodiments, the nucleic acid is an shRNA.

Single-stranded hairpin ribonucleic acids (shRNAs) are short duplexes where the sense and antisense strands are linked by a hairpin loop. They consist of a stem-loop structure that can be transcribed in cells from an RNA polymerase II or RNA polymerase III promoter on a plasmid construct. Once expressed, shRNAs are processed into RNAi species. Expression of shRNA from a plasmid is known to be relatively stable, thereby providing strong advantages over, for example, the use of synthetic siRNAs. shRNA expression units may be incorporated into a variety of plasmids, liposomes, viral vectors, and other vehicles for delivery and integration into a target cell. Expression of shRNA from a plasmid can be stably integrated for constitutive expression. shRNAs are synthesized in the nucleus of cells, further processed and transported to the cytoplasm, and then incorporated into the RNA-induced silencing complex (RISC) for activity. The shRNAs are converted into active siRNA molecules (which are capable of binding to, sequestering, and/or preventing the translation of mRNA transcripts encoded by target genes).

The Argonaute family of proteins is the major component of RISC. Within the Argonaute family of proteins, only Ago2 contains endonuclease activity that is capable of cleaving and releasing the passenger strand from the stem portion of the shRNA molecule. The remaining three members of Argonaute family, Ago1, Ago3 and Ago4, which do not have identifiable endonuclease activity, are also assembled into RISC and are believed to function through a cleavage-independent manner. Thus, RISC can be characterized as having cleavage-dependent and cleavage-independent pathways.

RNAi (e.g., antisense RNA, siRNA, microRNA, shRNA, etc.) are described in International Publication Nos. WO2018232356A1, WO2019084552A1, WO2019226998A1, WO2020014235A1, WO2020123871A1, and WO2020186219A1, each of which is herein incorporated by reference for all purposes.

Antisense oligonucleotide structure and chemical modifications are described in International PCT Publication No. WO20/132521, which is hereby incorporated by reference.

dsRNA and shRNA molecules and methods of use and production are described in U.S. Pat. Nos. 8,829,264; 9,556,431; and 8,252,526, each of which are hereby incorporated by reference siRNA molecules and methods of use and production are described in U.S. Pat. No. 7,361,752 and US Patent Application No. US20050048647, both of which are hereby incorporated by reference.

Additional methods and compositions for RNA interference such as shRNA, siRNA, dsRNA, and antisense oligonucleotides are generally known in the art, and are further described in U.S. Pat. Nos. 7,361,752; 8,829,264; 9,556,431; 8,252,526, International PCT Publication No. WO00/44895; International PCT Publication No. WO01/36646; International PCT Publication No. WO99/32619; International PCT Publication No. WO00/01846; International PCT Publication No. WO01/29058; and International PCT Publication No. WO00/44914; International PCT Publication No. WO04/030634; each of which are hereby incorporated by reference.

The nucleic acid sequences (or constructs) that may be used to encode the RNAi molecules, such as an shRNA described herein, may comprise a promoter, which is operably linked (or connected), directly or indirectly, to a sequence encoding the RNAi molecules. Such promoters may be selected based on the host cell and the effect sought. Non-limiting examples of suitable promoters include constitutive and inducible promoters, such as EF1α or inducible RNA polymerase II (pol II)-based promoters. Non-limiting examples of suitable promoters further include the tetracycline inducible or repressible promoter, RNA polymerase I or III-based promoters, the pol II dependent viral promoters, such as the CMV-IE promoter, and the pol III U6 and H1 promoters. The bacteriophage T7 promoter may also be used (in which case it will be appreciated that the T7 polymerase must also be present). The nucleic acid sequences need not be restricted to the use of any single promoter, especially since the nucleic acid sequences may comprise two or more shRNAs (i.e., a combination of effectors), including but not limited to incorporated shRNA molecules. Each incorporated promoter may control one, or any combination of, the shRNA molecule components.

In certain embodiments, the promoter may be preferentially active in the targeted cells, e.g., it may be desirable to preferentially express at least one recombinant nucleic acid in immune cells using an immune cell-specific promoter. Introduction of such constructs into host cells may be effected under conditions whereby the two or more recombinant nucleic acids that are contained within the recombinant nucleic acid precursor transcript initially reside within a single primary transcript, such that the separate RNA molecules (for example, shRNA each comprising its own stem-loop structure) are subsequently excised from such precursor transcript by an endogenous ribonuclease. The resulting mature recombinant nucleic acids (e.g., shRNAs) may then induce degradation, and/or translation repression, of target gene mRNA transcripts produced in the cell. Alternatively, each of the precursor stem-loop structures may be produced as part of a separate transcript, in which case each recombinant nucleic acid sequence will preferably include its own promoter and transcription terminator sequences. Additionally, the multiple recombinant nucleic acid precursor transcripts may reside within a single primary transcript.

The stem-loop structures of the shRNA recombinant nucleic acids described herein may be about 40 to 100 nucleotides long or, preferably, about 50 to 75 nucleotides long. The stem region may be about 15-45 nucleotides in length (or more), or about 20-30 nucleotides in length. In some embodiments, the stem region is 22 nucleotides in length. In some embodiments, the stem region is 15, 16, 17, 18, 19, 20, 21, 22, 23, 24, 25, 26, 27 28 29, 30, 31, 32, 33, 34, 35, 36, 37, 38, 39, 40, 41, 42, 43, 44, or 45 nucleotides in length.

The stem may comprise a perfectly complementary duplex (but for any 3' tail), however, bulges or interior loops may be present on either arm of the stem. The number of such bulges and asymmetric interior loops are preferably few in number (e.g., 1, 2 or 3) and are about 3 nucleotides or less in size. The terminal loop portion may comprise about 4 or more nucleotides, but preferably not more than about 25. The loop portion will preferably be 6-15 nucleotides in size.

As described herein, the stem regions of the shRNAs comprise passenger strands and guide strands, whereby the guide strands contain sequences complementary to the target mRNA transcript encoded by the target gene(s). Preferably, the G-C content and matching of guide strand and passenger strand is carefully designed for thermodynamically-favorable strand unwind activity with or without endonuclease cleavage. Furthermore, the specificity of the guide strand is preferably confirmed via a BLAST search (www.ncbi.nlm.nih.qov/BLAST).

The invention provides that the expression level of multiple target genes may be modulated using the methods and recombinant nucleic acids described herein. For example, the invention provides that a first set of recombinant nucleic acids may be designed to include a sequence (a guide strand) that is designed to reduce the expression level of a first target gene, whereas a second set of recombinant nucleic acids may be designed to include a sequence (a guide strand) that is designed to reduce the expression level of a second target gene. The different sets of recombinant nucleic acids may be expressed and reside within the same, or separate, preliminary transcripts. In certain embodiments, such multiplex approach, i.e., the use of the recombinant nucleic acids described herein to modulate the expression level of two or more target genes, may have an enhanced therapeutic effect on a patient. For example, if a patient is provided with cells expressing the recombinant nucleic acid molecules described herein to treat, prevent, or ameliorate the effects of cancer, it may be desirable to provide the patient with two or more types of recombinant nucleic acid molecules, which are designed to reduce the expression level of multiple genes that are implicated in activation or repression of immune cells.

The recombinant nucleic acid molecule(s) described herein may be capable of reducing target gene expression in a cell by at least more than about 50% as compared to a control cell that does not comprise the recombinant nucleic acid molecule(s). For example, the recombinant nucleic acid molecule(s) (e.g., shRNA) can be capable of reducing expression of a target gene selected from the group consisting of FAS, PTPN2, and TOX in the immune cell by at least 50%, 55%, 60%, 65%, 75%, 80%, 85%, 90%, 95%, 97%, 98%, 99%, or more as compared to a control cell that does not comprise the recombinant nucleic acid molecule(s). The recombinant nucleic acid molecule(s) can be capable of reducing expression of a target gene selected from the group consisting of FAS, PTPN2, and TOX in the immune cell by at least between about 50-100%, 50-99%, 50-95%, 50-90%, 50-85%, 50-80%, 50-75%, 50-70%, 50-65%, 50-60%, 50-55%, or as compared to a control cell that does not comprise the recombinant nucleic acid molecule(s). In some embodiments, the recombinant nucleic acid molecule(s) is capable of reducing expression of FAS in the immune cell by at least 50%, 55%, 60%, 65%, 75%, 80%, 85%, 90%, 95%, or 99% as compared to a control cell that does not comprise the recombinant nucleic acid molecule(s). In some embodiments, the recombinant nucleic acid molecule(s) is capable of reducing expression of PTPN2 in the immune cell by at least 50%, 55%, 60%, 65%, 75%, 80%, 85%, 90%, 95%, or 99% as compared to a control cell that does not comprise the recombinant nucleic acid molecule(s). In some embodiments, the recombinant nucleic acid molecule(s) is capable of reducing expression of TOX in the immune cell by at least 50%, 55%, 60%, 65%, 75%, 80%, 85%, 90%, 95%, or 99% as compared to a control cell that does not comprise the recombinant nucleic acid molecule(s).

The recombinant nucleic acid molecule(s) may be chemically synthesized, or in vitro transcribed, and may further include one or more modifications to phosphate-sugar backbone or nucleosides residues.

Other methods known in the art for introducing nucleic acids to cells may be used, such as lipid-mediated carrier transport, chemical mediated transport, such as calcium phosphate, and the like. Thus, the recombinant nucleic acid molecule(s) construct may be introduced along with components that perform one or more of the following activities: enhance RNA uptake by the cell, promote annealing of the duplex strands for shRNA, stabilize the annealed shRNA strands, or otherwise increase inhibition of the target gene.

Additional Elements

In some embodiments, the one or more recombinant nucleic acid(s) further comprises a 5' homology directed repair arm and/or a 3' homology directed repair arm complementary to an insertion site in a host cell chromosome. In some embodiments, the one or more recombinant nucleic acid(s) comprises the 5' homology directed repair arm and the 3' homology directed repair arm. In some embodiments, the one or more recombinant nucleic acid(s) is incorporated into an expression cassette or an expression vector. In some embodiments, the expression cassette or the expression vector further comprises a constitutive promoter upstream of the one or more recombinant nucleic acid(s).

In some embodiments, the priming receptor, CAR, first nucleic acid, and the second nucleic acid are incorporated into a single expression cassette or a single expression vector. In some embodiments, the priming receptor, CAR, first nucleic acid, and the second nucleic acid are incorporated into two or more expression cassettes or expression vectors. In some embodiments, the expression vector(s) is a non-viral vector.

The one or more interfering nucleic acid sequences (e.g., one or more shRNA) can be encoded in the intron regions of the recombinant nucleic acid insert, DNA template, single expression cassette, or a single expression vector that also encodes the priming receptor and/or the CAR. For example, if the DNA template includes promoters, such as EF1α or inducible promoters described herein, to drive expression of the CAR or priming receptor, the one or more nucleic acid sequences (e.g., shRNA sequences) can be encoded in the promoter intronic region. In some embodiments, the one or more nucleic acid sequences is encoded in at least one intron region of the recombinant nucleic acid insert or DNA template. In some embodiments, the one or more nucleic acid sequences is encoded in at least one EF1α intron region of the recombinant nucleic acid insert or DNA template.

In some embodiments, the present disclosure contemplates recombinant nucleic acid DNA template inserts that comprise one or more transgenes encoding the priming receptors and/or CARs as described herein. In some embodiments, the DNA template insert encodes a priming receptor transgene. In some embodiments, the DNA template insert encodes a chimeric antigen receptor transgene. In some embodiments, the DNA template insert encodes a first nucleic acid complementary to at least 15 nucleotides of a human FAS mRNA sequence, and a second nucleic acid complementary to at least 15 nucleotides of a human PTPN2 or TOX mRNA sequence. In some embodiments, the DNA template insert comprises a priming receptor transgene and a chimeric antigen receptor transgene. In some embodiments, the DNA template insert comprises a priming receptor transgene, a chimeric antigen receptor transgene, a first nucleic acid complementary to at least 15 nucleotides of a human FAS mRNA sequence, and a second nucleic acid complementary to at least 15 nucleotides of a human PTPN2 or TOX mRNA sequence. In some embodiments, the DNA template insert comprises a priming receptor transgene, a chimeric antigen receptor transgene, a first nucleic acid complementary to at least 15 nucleotides of a human FAS mRNA sequence, and a second nucleic acid complementary to at least 15 nucleotides of a human PTPN2 mRNA sequence.

In some embodiments, the one or more recombinant nucleic acid(s) are encoded on a single DNA template insert. In some embodiments, the one or more recombinant nucleic acid(s) are encoded on multiple DNA template inserts. For example, the one or more recombinant nucleic acid(s) can be encoded on two, three, or four DNA template inserts.

The DNA template insert can also comprise a self-cleaving peptide. Examples of self-cleaving peptides include, but are not limited to, self-cleaving viral 2A peptides, for example, a porcine teschovirus-1 (P2A) peptide, a Thosea asigna virus (T2A) peptide, an equine rhinitis A virus (E2A) peptide, or a foot-and-mouth disease virus (F2A) peptide. Self-cleaving 2A peptides allow expression of multiple gene products from a single construct. (See, for example, Chang et al. "Cleavage efficient 2A peptides for high level monoclonal antibody expression in CHO cells," *MAbs* 7(2): 403-412 (2015)).

The DNA template insert can also comprise a WPRE element. WPRE elements are generally described in Higashimoto, T., et al. Gene Ther 14, 1298-1304 (2007); and Zufferey, R., et al. J Virol. 1999 April; 73(4):2886-92, both of which are hereby incorporated by reference.

The DNA template insert can also comprise an SV40 polyA tail.

Recombinant Cells

Transgenes expressing the priming receptor and CAR system may be introduced into cells, such as a T cell, using, for example, a site-specific technique. With site specific integration of the transgenes (e.g. priming receptor and CAR), the transgenes may be targeted to a safe harbor locus or TRAC. Examples of site-specific techniques for integration into the safe harbor loci include, without limitation, homology-dependent engineering using nucleases and homology independent targeted insertion using Cas9.

The engineered recombinant cells have applications to immune-oncology. The priming receptor and CAR, for example, can be selected to target different specific tumor antigens. Examples of cancers that can be effectively targeted using such cells are blood cancers or solid cancers. In some embodiments, immune cell therapy can be used to treat solid tumors.

Provide herein is a modified cell, wherein the cell is modified to have reduced expression of a FAS gene and/or reduced function of a product of the FAS gene relative to a corresponding unmodified cell, optionally wherein the modified cell is a hematopoietic cell. In some aspects, the modified cell is further modified to have reduced expression of at least one second gene and/or reduced function of a product of the at least one second gene relative to a corresponding unmodified cell.

Also provided herein is a modified engineered cell, wherein the engineered cell is modified to have reduced expression of a FAS gene and/or reduced function of a product of the FAS gene relative to a corresponding unmodified engineered cell, optionally wherein the modified engineered cell is engineered to express a heterologous immune receptor. In some aspects, the modified engineered cell is further modified to have reduced expression of at least one second gene and/or reduced function of a product of the at least one second gene relative to a corresponding unmodified engineered cell.

Also provided herein is a modified cell, wherein the cell is modified to have: (a) reduced expression of a FAS gene and/or reduced function of a product of the FAS gene; and (b) reduced expression of at least one second gene and/or reduced function of a product of the at least one second gene; wherein the reduced expression of each gene is relative to a corresponding unmodified cell, optionally wherein the modified cell is a hematopoietic cell.

In some aspects, the modification to reduce expression comprises genetically engineering the genome of the cell to disrupt the FAS gene and optionally the at least one second gene. In some aspects, the genetic engineering comprises nuclease-mediated editing, optionally wherein the nuclease-mediated editing comprises CRISPR/Cas9-mediated editing.

In some aspects, the modification to reduce expression comprises RNAi-mediated targeting of the FAS gene and optionally the at least one second gene, optionally wherein the RNAi-mediated targeting comprises short hairpin RNA (shRNA)-mediated knockdown. In some aspects, the RNAi-mediated targeting comprises engineering the cell to express an RNA polynucleotide capable of mediating knockdown of the FAS gene and optionally the at least one second gene.

In some aspects, the modified cell comprises a hematopoietic cell. In some aspects, the hematopoietic cell comprises a hematopoietic stem cell. In some aspects, the hematopoietic cell comprises an immune cell. In some aspects, the immune cell comprises a adaptive immune cell, an innate immune cell, a T cell, an NK cell, a macrophage.

In some aspects, the modified cell comprises an engineered cell. In some aspects, the engineered cell is engineered to express a heterologous receptor. In some aspects, the heterologous receptor comprises an immune receptor. In some aspects, the heterologous immune receptor comprises a chimeric antigen receptor (CAR), a T cell receptor, or an NK cell receptor. In some aspects, the engineered cell comprises a T cell or a cell capable of differentiation into a T cell, and wherein the heterologous receptor is inserted into an endogenous TCR locus, optionally the T cell receptor alpha (TRAC) locus. In some aspects, the heterologous receptor comprises one or more antigen binding domains, optionally wherein the one or more antigen binding domains are capable of binding to a tumor antigen or an antigen associated with cancer.

In some aspects, the reduced expression and/or function of the FAS gene or its expression product improves at least one property of the modified cell relative to the corresponding unmodified cell.

In some aspects, when the modified cell is further modified to have reduced expression and/or function of the at least one second gene, the reduced expression and/or function of the FAS gene or its expression product and the reduced expression and/or function of the at least one second gene or its expression product improves at least one property of the modified cell relative to a corresponding cell modified to only reduce expression and/or function of the FAS gene.

In some aspects, when the modified cell is further modified to have reduced expression and/or function of the at least one second gene, the reduced expression and/or function of the FAS gene or its expression product and the reduced expression and/or function of the at least one second gene or its expression product improves at least one property of the modified cell relative to a corresponding cell modified to only reduce expression and/or function of the at least one second gene.

In some aspects, the at least one property comprises improved proliferative capacity. In some aspects, the at least one property comprises improved protection from FAS-mediated apoptosis. In some aspects, the modified cell comprises an immune cell and the at least one property comprises an improved immune effector cell function. In some aspects, the improved immune effector cell function comprises increased relative effector molecule expression, production, and/or secretion. In some aspects, the immune cell comprises a T cell and the effector molecule comprises one or more molecules selected from the group consisting of: IFNγ, TNF-alpha, Granzyme B, and FASL.

In some aspects, the modified cell is engineered to express a heterologous surface antigen, optionally wherein the heterologous surface antigen is capable of mediating targeted depletion of the engineered modified cell relative to a corresponding modified cell not engineered to express the heterologous surface antigen.

Also provided herein is a method of stimulating an immune response in a subject, wherein the method comprises administering to the subject any one of the modified cells as disclosed herein. Also provided herein is a method of treating cancer in a subject, wherein the method comprises administering to the subject any one of the modified as disclosed herein. In some aspects, the modified cell is autologous with reference to the subject. In some aspects, the modified cell is allogenic with reference to the subject.

Also provided herein are recombinant immune cells comprising one or more recombinant nucleic acid(s), wherein the one or more recombinant nucleic acids encode: a first chimeric polypeptide comprising a priming receptor; a second chimeric polypeptide comprising a CAR; and a nucleic acid sequence at least 15 nucleotides in length, wherein the nucleic acid sequence is selected from the group consisting of: a nucleic acid sequence complementary to nucleotides 1126 to 1364 of an mRNA encoding human FAS comprising the sequence set forth in SEQ ID NO: 39, a nucleic acid sequence complementary to nucleotides 518 to 559 of an mRNA encoding human PTPN2 comprising the sequence set forth in SEQ ID NO: 40; and a nucleic acid sequence complementary to nucleotides 1294 to 2141 of an mRNA encoding human TOX comprising the sequence set forth in SEQ ID NO: 41.

In some embodiments, the nucleic acid sequence is complementary to nucleotides 1126 to 1364 of an mRNA encoding human FAS comprising the sequence set forth in SEQ ID NO: 39. In some embodiments, the nucleic acid sequence is complementary to nucleotides 518 to 559 of an mRNA encoding human PTPN2 comprising the sequence set forth in SEQ ID NO: 40. In some embodiments, the nucleic acid sequence is complementary to nucleotides 1294 to 2141 of an mRNA encoding human TOX comprising the sequence set forth in SEQ ID NO: 41.

Also provided herein are recombinant immune cells comprising one or more recombinant nucleic acid(s) non-virally inserted into a target region of the genome of the cell, wherein the one or more recombinant nucleic acid(s) encodes the priming receptor, CAR, a first nucleic acid sequence at least 15 nucleotides in length complementary to an mRNA encoding human FAS comprising the sequence set forth in SEQ ID NO: 39, and a second nucleic acid sequence at least 15 nucleotides in length complementary to an mRNA encoding human PTPN2 comprising the sequence set forth in SEQ ID NO: 40; or complementary to an mRNA encoding human TOX comprising the sequence set forth in SEQ ID NO: 41 as described herein. Also provided herein are recombinant immune cells comprising the priming receptor that specifically binds Alkaline Phosphatase, Placental/Germ Cell (ALPG/P), the chimeric antigen receptor that specifically binds MSLN, a first nucleic acid sequence at least 15 nucleotides in length complementary to an mRNA encoding human FAS comprising the sequence set forth in SEQ ID NO: 39, and a second nucleic acid sequence at least 15 nucleotides in length complementary to an mRNA encoding human PTPN2 comprising the sequence set forth in SEQ ID NO: 40; or complementary to an mRNA encoding human TOX comprising the sequence set forth in SEQ ID NO: 41.

A cell comprising a DNA template insert at a target locus or safe harbor site as described in the present disclosure can be referred to as an engineered cell. In some embodiments, the immune cell is any cell that can give rise to a pluripotent immune cell. In some embodiments, the immune cell is a primary immune cell. In some embodiments, the immune cell can be an induced pluripotent stem cell (iPSC) or a human pluripotent stem cell (HSPC). In some embodiments, the immune cell comprises primary hematopoietic cells or primary hematopoietic stem cells. In some embodiments, that engineered cell is a stem cell, a human cell, a primary cell, an hematopoietic cell, an adaptive immune cell, an innate immune cell, a natural killer (NK) cell, a T cell, a CD8+ cell, a CD4+ cell, or a T cell progenitor. In some embodiments, the immune cells are T cells. In some embodiments, the T cells are regulatory T cells, effector T cells, or naïve T cells. In some embodiments, the T cells are CD8$^+$ T cells. In some embodiments, the T cells are CD4$^+$ T cells. In some embodiments, the T cells are CD4$^+$CD8$^+$ T cells.

In some embodiments, the engineered cell is a stem cell, a human cell, a primary cell, an hematopoietic cell, an hematopoietic stem cell, an adaptive immune cell, an innate immune cell, a T cell or a T cell progenitor. Non-limiting examples of immune cells that are contemplated in the present disclosure include T cell, B cell, natural killer (NK) cell, NKT/iNKT cell, macrophage, myeloid cell, and dendritic cells. Non-limiting examples of stem cells that are contemplated in the present disclosure include pluripotent stem cells (PSCs), embryonic stem cells (ESCs), induced pluripotent stem cells (iPSCs), embryo-derived embryonic stem cells obtained by nuclear transfer (ntES; nuclear transfer ES), male germline stem cells (GS cells), embryonic germ cells (EG cells), hematopoietic stem/progenitor stem cells (HSPCs), somatic stem cells (adult stem cells), hemangioblasts, neural stem cells, mesenchymal stem cells and stem cells of other cells (including osteocyte, chondrocyte, myocyte, cardiac myocyte, neuron, tendon cell, adipocyte, pancreocyte, hepatocyte, nephrocyte and follicle cells and so on). In some embodiments, the engineered cells is a T cell, NK cells, iPSC, and HSPC. In some embodiments, the engineered cells used in the present disclosure are human cell lines grown in vitro (e.g. deliberately immortalized cell lines, cancer cell lines, etc.).

Also provided herein are populations of cells comprising a plurality of the immune cell. In some embodiments, the genome of at least 20%, 30%, 40%, 50%, 60%, 70%, 80%, 90%, 95%, 99% or greater of the cells comprises the priming receptor, CAR, and first and second nucleic acids as described herein.

Method of Treating Cancer

In another aspect, the invention provides methods of treating an immune-related condition (e.g., cancer) in an individual comprising administering to the individual an effective amount of a composition comprising a system comprising a priming receptor that specifically binds to ALPG/P, a chimeric antigen receptor that specifically binds to MSLN, a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and a second nucleic acid sequence at least 15 nucleotides in length, wherein the second nucleic acid sequence is complementary to nucleotides 518 to 559 of an mRNA encoding human PTPN2 comprising the sequence set forth in SEQ ID NO: 40; or complementary to nucleotides 1294 to 2141 of an mRNA encoding human TOX comprising the sequence set forth in SEQ ID NO: 41.

In another aspect, the invention provides methods of enhancing an immune response in an individual comprising administering to the individual an effective amount of a composition comprising a system comprising a priming receptor that specifically binds to ALPG/P, a chimeric antigen receptor that specifically binds to MSLN, a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and a second nucleic acid sequence at least 15 nucleotides in length, wherein the second nucleic acid sequence is complementary to nucleotides 518 to 559 of an mRNA encoding human PTPN2 comprising the sequence set forth in SEQ ID NO: 40; or complementary to nucleotides 1294 to 2141 of an mRNA encoding human TOX comprising the sequence set forth in SEQ ID NO: 41.

In some embodiments, the recombinant nucleic acid is an shRNA molecule. In some embodiments, the shRNA is selected from the group consisting of a FAS shRNA molecule, a PTPN2 shRNA molecule, and a TOX shRNA molecule. In some embodiments, the cell comprises at least a FAS shRNA molecule. In some embodiments, the cell comprises at least a PTPN2 shRNA molecule. In some embodiments, the cell comprises at least a TOX shRNA molecule. In some embodiments, the cell comprises at least a FAS shRNA molecule and a PTPN2 shRNA molecule. In some embodiments, the cell comprises at least a FAS shRNA molecule and a TOX shRNA molecule. In some embodiments, the cell comprises at least a PTPN2 shRNA molecule and a TOX shRNA molecule. In another aspect, the invention provides methods of enhancing an immune response in an individual comprising administering to the individual an effective amount of a composition comprising a cell comprising at least one shRNA molecule, wherein the shRNA molecule is selected from the group consisting of a FAS shRNA molecule, a PTPN2 shRNA molecule, and a TOX shRNA molecule.

In some embodiments, the methods provided herein are useful for the treatment of an immune-related condition in an individual. In one embodiment, the individual is a human.

In some embodiments, the methods provided herein (such as methods of enhancing an immune response) are useful for the treatment of cancer and as such an individual receiving the system described herein has cancer. In some embodiments, the cancer is a solid cancer. In some embodiments, the cancer is a liquid cancer. In some embodiments, the cancer is immunoevasive. In some embodiments, the cancer is immunoresponsive. In particular embodiments, the cancer is ovarian cancer, fallopian cancer, primary peritoneal cancer, uterine cancer, mesothelioma, cervical cancer, or pancreatic cancers. In particular embodiments, the cancer is ovarian cancer.

In some embodiments, the treatment results in a decrease in the cancer volume or size. In some embodiments, the treatment is effective at reducing a cancer volume as compared to the cancer volume prior to administration of the antibody. In some embodiments, the treatment results in a decrease in the cancer growth rate. In some embodiments, the treatment is effective at reducing a cancer growth rate as compared to the cancer growth rate prior to administration of the antibody. In some embodiments, the treatment is effective at eliminating the cancer.

In some embodiments, MSLN and ALPG or ALPP is expressed at a higher level in the cancer as compared to a non-cancer cell. Levels of MSLN, ALPG, and ALPP can be assessed by any technique known in the field, including, but not limited to, protein assays or nucleic assays such as FACS, Western blot, ELISA, immunoprecipitation, immunohistochemistry, immunofluorescence, radioimmunoassay, dot blotting, immunodetection methods, HPLC, surface plasmon resonance, optical spectroscopy, mass spectrometry, HPLC, qPCR, RT-qPCR, multiplex qPCR or RT-qPCR, RNA-seq, microarray analysis, SAGE, MassARRAY technique, and FISH, and combinations thereof.

Method of Immune Modulation

Methods of administration of a cell comprising a system comprising a priming receptor that specifically binds to ALPG/P, a chimeric antigen receptor that specifically binds to MSLN, a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and a second nucleic acid sequence at least 15 nucleotides in length, wherein the second nucleic acid sequence is complementary to nucleotides 518 to 559 of an mRNA encoding human PTPN2 comprising the sequence set forth in SEQ ID NO: 40; or complementary to nucleotides 1294 to 2141 of an mRNA encoding human TOX comprising the sequence set forth in SEQ ID NO: 41 as described herein can result in modulation of an immune response. Modulation can be an increase or decrease in an immune response. In some embodiments, modulation is an increase in an immune response.

In one aspect, administration of a cell comprising a system comprising a priming receptor that specifically binds to ALPG/P and a chimeric antigen receptor that specifically binds to MSLN as described herein can result in induction of pro-inflammatory molecules, such as cytokines or chemokines. Generally, induced pro-inflammatory molecules are present at levels greater than that achieved with isotype control. Such pro-inflammatory molecules in turn result in activation of anti-tumor immunity, including, but not limited to, T cell activation, T cell proliferation, T cell differentiation, M1-like macrophage activation, and NK cell activation. Thus, the administration of a system comprising a priming receptor that specifically binds to ALPG/P and a chimeric antigen receptor that specifically binds to MSLN can induce multiple anti-tumor immune mechanisms that lead to tumor destruction.

In another aspect, provided herein are methods of increasing an immune response in an individual comprising administering to the individual an effective amount of a cell comprising a system comprising a priming receptor that specifically binds to ALPG/P and a chimeric antigen receptor that specifically binds to MSLN. In some embodiments, the method of increasing an immune response in a subject comprises administering to the subject a cell comprising a system comprising a priming receptor that specifically binds to ALPG/P and a chimeric antigen receptor that specifically binds to MSLN.

In some embodiments, the cell is present in a pharmaceutical composition further comprising a pharmaceutically acceptable excipient.

In any and all aspects of increasing an immune response as described herein, any increase or decrease or alteration of an aspect of characteristic(s) or function(s) is as compared to a cell not comprising a composition comprising a system comprising a priming receptor that specifically binds to ALPG/P and a chimeric antigen receptor that specifically binds to MSLN.

Increasing an immune response can be both enhancing an immune response or inducing an immune response. For instance, increasing an immune response encompasses both the start or initiation of an immune response, or ramping up or amplifying an on-going or existing immune response. In some embodiments, the treatment induces an immune response. In some embodiments, the induced immune response is an adaptive immune response. In some embodiments, the induced immune response is an innate immune response. In some embodiments, the treatment enhances an immune response. In some embodiments, the enhanced immune response is an adaptive immune response. In some embodiments, the enhanced immune response is an innate immune response. In some embodiments, the treatment increases an immune response. In some embodiments, the increased immune response is an adaptive immune response. In some embodiments, the increased immune response is an innate immune response. In some embodiments, the immune response is started or initiated by administration of a cell comprising a system comprising a priming receptor that specifically binds to ALPG/P and a chimeric antigen receptor that specifically binds to MSLN. In some embodiments, the immune response is enhanced by administration of cell comprising a system comprising a priming receptor that specifically binds to ALPG/P and a chimeric antigen receptor that specifically binds to MSLN.

In another aspect, the present application provides methods of genetically editing a cell with a system comprising a priming receptor that specifically binds to ALPG/P, a chimeric antigen receptor that specifically binds to MSLN, a first nucleic acid sequence at least 15 nucleotides in length complementary to an mRNA encoding human FAS comprising the sequence set forth in SEQ ID NO: 39, and a second nucleic acid sequence at least 15 nucleotides in length complementary to an mRNA encoding human PTPN2 comprising the sequence set forth in SEQ ID NO: 40; or complementary to an mRNA encoding human TOX comprising the sequence set forth in SEQ ID NO: 41, which results in the modulation of the immune function of the cell. The modulation can be increasing an immune response. In some embodiments, the modulation is an increase in immune function. In some embodiments, the modulation of function leads to the expression of an MSLN CAR. In some embodiments, the modulation of function leads to the activation of a cell comprising the system.

In some embodiments, the cell is a natural killer (NK) cell, a T cell, a CD8+ T cell, a CD4+ T cell, a primary T cell, or a T cell progenitor.

In some embodiments, the modulation of function of the cells comprising the priming receptor and CAR system as described herein leads to an increase in the cells' abilities to stimulate both native and activated T-cells, for example, by increasing cytokine or chemokine secretion by the cells expressing the priming receptor and CAR system. In some embodiments, the modulation of function enhances or increases the cells' ability to produce cytokines, chemokines, CARs, or costimulatory or activating receptors. In some embodiments, the modulation increases the T-cell stimulatory function of the cells expressing the priming receptor and CAR system, including, for example, the cells' abilities to trigger T-cell receptor (TCR) signaling, T-cell proliferation, or T-cell cytokine production.

In some embodiments, the increased immune response is secretion of cytokines and chemokines. In some embodiments, the priming receptor and CAR system induces increased expression of at least one cytokine or chemokine in a cell as compared to an isotype control cell. In some embodiments, the at least one cytokine or chemokine is selected from the group consisting of: IL-2 and IFNγ. In some embodiments, the cytokine or chemokine is IL-2. In some embodiments, the cytokine or chemokine is IFNγ. In some embodiments, the cytokine or chemokine secretion is increased a between bout 1-100-fold 1, 5, 10, 20, 30, 40, 50, 60, 70, 80, 90, 100, 1-10, 10-20, 20-30, 30-40, 40-50, 50-60, 60-70, 70-80, 80-90, or 90-100 fold as compared to an untreated cell or a cell treated with an isotype control antibody. In some embodiments, the chemokine is IL-2 and the secretion is increased between about 1-100-fold, 1-fold, 5-fold, 10-fold, 20-fold, 30-fold, 40-fold, 50-fold, 60-fold, 70-fold, 80-fold, 90-fold, 100-fold, 1-10-fold, 10-20-fold, 20-30-fold, 30-40-fold, 40-50-fold, 50-60-fold, 60-70-fold, 70-80-fold, 80-90-fold, or 90-100-fold as compared to an untreated cell or a cell treated with an isotype control antibody. In some embodiments, the cytokine is IFNγ and the secretion is increased between about 1-100-fold, 1-fold, 5-fold, 10-fold, 20-fold, 30-fold, 40-fold, 50-fold, 60-fold, 70-fold, 80-fold, 90-fold, 100-fold, 1-10-fold, 10-20-fold, 20-30-fold, 30-40-fold, 40-50-fold, 50-60-fold, 60-70-fold, 70-80-fold, 80-90-fold, or 90-100-fold as compared to an untreated cell or a cell treated with an isotype control antibody.

In some embodiments, the enhanced immune response is anti-tumor immune cell recruitment and activation.

In some embodiments, the cell expressing the priming receptor and CAR system induces a memory immune response as compared to an isotype control cell. In general, a memory immune response is a protective immune response upon a subsequent exposure to pathogens or antigens that the immune system encountered previously. Exemplary memory immune responses include the immune response after infection or vaccination with an antigen. In general, memory immune responses are mediated by lymphocytes such as T cells or B cells. In some embodiments, the memory immune response is a protective immune response to cancer, including cancer cell growth, proliferation, or metastasis. In some embodiments, the memory immune response inhibits, prevents, or reduces cancer cell growth, proliferation, or metastasis.

Methods of Reducing Gene Expression

Another aspect of the invention provides a method for attenuating expression of a target gene in mammalian cells, comprising introducing into the mammalian cells a recombinant nucleic acid complementary to the target gene mRNA, such as a single-stranded hairpin ribonucleic acid (shRNA), siRNA, dsRNA, or antisense oligonucleotide. In some embodiments, the recombinant nucleic acid complementary to the target gene mRNA is an shRNA. In some embodiments, the shRNA comprises self-complementary sequences of 19 to 100 nucleotides that form a duplex region, which self-complementary sequences hybridize under intracellular conditions to a target gene mRNA transcript. In some embodiments, the shRNA comprises self-complementary sequences of 22 nt. In some embodiments, the shRNA: (i) is a substrate for cleavage by a RNaseIII enzyme to produce a double-stranded RNA product, (ii) does not produce a general sequence-independent killing of the mammalian cells, and (iii) reduces expression of said target gene in a manner dependent on the sequence of said complementary regions. In some embodiments, the target gene is FAS. In some embodiments, the target gene is human FAS. In some embodiments, the target gene is PTPN2. In some embodiments, the target gene is human PTPN2. In some embodiments, the target gene is TOX. In some embodiments, the target gene is human TOX.

The immune cell comprising the recombinant nucleic acid can have reduced or decreased expression of a target gene selected from the group consisting of FAS, PTPN2, and TOX. In some embodiments, the immune cell has reduced FAS, PTPN2, and/or TOX expression of between about 50-100%, 50-99%, 50-95%, 50-90%, 50-85%, 50-80%, 50-75%, 50-70%, 50-65%, 50-60%, 50-55%, as compared to a control cell that does not comprise the recombinant nucleic acid molecule(s). In some embodiments, the immune cell has reduced FAS expression in the immune cell by at least 50%, 55%, 60%, 65%, 75%, 80%, 85%, 90%, 95%, or 99% as compared to a control cell that does not comprise the recombinant nucleic acid molecule(s). In some embodiments, the immune cell has reduced PTPN2 expression in the immune cell by at least 50%, 55%, 60%, 65%, 75%, 80%, 85%, 90%, 95%, or 99% as compared to a control cell that does not comprise the recombinant nucleic acid molecule(s). In some embodiments, the immune cell has reduced TOX expression in the immune cell by at least 50%, 55%, 60%, 65%, 75%, 80%, 85%, 90%, 95%, or 99% as compared to a control cell that does not comprise the recombinant nucleic acid molecule(s).

In some embodiments, expression of FAS in the immune cell is reduced by at least 50%, 55%, 60%, 65%, 75%, 80%, 85%, 90%, 95%, or 99% as compared to a control cell that does not comprise the first nucleic acid. In some embodiments, the second nucleic acid is capable of reducing expression of PTPN2 in the immune cell by at least 50%, 55%, 60%, 65%, 75%, 80%, 85%, 90%, 95%, or 99% as compared to a control cell that does not comprise the second nucleic acid. In some embodiments, expression of PTPN2 in the immune cell is reduced by at least 50%, 55%, 60%, 65%, 75%, 80%, 85%, 90%, 95%, or 99% as compared to a control cell that does not comprise the second nucleic acid.

In some embodiments, the second nucleic acid is capable of reducing expression of TOX in the immune cell by at least 50%, 55%, 60%, 65%, 75%, 80%, 85%, 90%, 95%, or 99% as compared to a control cell that does not comprise the second nucleic acid. In some embodiments, expression of TOX in the immune cell is reduced by at least 50%, 55%, 60%, 65%, 75%, 80%, 85%, 90%, 95%, or 99% as compared to a control cell that does not comprise the second nucleic acid.

In some embodiments, expression of FAS, PTPN2, and/or TOX is determined by a nucleic acid assay or a protein assay. In some embodiments, the nucleic acid assay comprises at least one of polymerase chain reaction (PCR), quantitative PCR (qPCR), RT-qPCR, microarray, gene array, or RNAseq Methods of Editing Cells The terms "genetic engineering," "gene editing," or "genome editing", as used herein, refer to a type of genetic manipulation in which DNA is inserted, replaced, or removed from the genome using artificially manipulated nucleases or "molecular scissors". It is a useful tool for elucidating the function and effect of sequence-specific genes or proteins or altering cell behavior (e.g. for therapeutic purposes).

Currently available genome editing tools include zinc finger nucleases (ZFN) and transcription activator-like effector nucleases (TALENs) to incorporate genes at safe harbor loci (e.g. the adeno-associated virus integration site 1 (AAVS1) safe harbor locus). The DICE (dual integrase cassette exchange) system utilizing phiC31 integrase and Bxb1 integrase is a tool for target integration. Additionally, clustered regularly interspaced short palindromic repeat/ Cas9 (CRISPR/Cas9) techniques can be used for targeted gene insertion.

Site specific gene editing approaches can include homology dependent mechanisms or homology independent mechanisms.

All methods known in the art for targeted insertion of gene sequences are contemplated in the methods described herein to insert constructs at gene targets or safe harbor loci.

Provided herein are methods of inserting nucleotide sequences greater than about 5 kilobases in length into the genome of a cell, in the absence of a viral vector. In some embodiments, the nucleotide sequence greater than about 5 kilobase in length can be inserted into the genome of a primary immune cell, in the absence of a viral vector Integration of large nucleic acids, for example nucleic acids greater than 5 kilobase in size, into cells, can be limited by low efficiency of integration, off-target effects and/or loss of cell viability. Described herein are methods and compositions for achieving integration of a nucleotide sequence, for example, a nucleotide sequence greater than about 5 kilobases in size, into the genome of a cell. In some methods the efficiency of integration is increased, off-target effects are reduced and/or loss of cell viability is reduced.

The plasmid can be introduced into an immune cell with a nuclease, such as a CRISPR-associated system (Cas). The nuclease can be introduced in a ribonucleoprotein format with a guide RNA (gRNA) that targets a specific site on the genome of the immune cell. The nuclease cuts the genomic DNA at this specific site. The specific site may be a portion of the genome that encodes an endogenous immune cell receptor. Thus, cutting the genome at this site will cause the immune cell to no longer express an endogenous immune cell receptor.

The plasmid may include 5' and 3' homology-directed repair arms complementary to sequences at a specific site on the genome of the immune cell. The complementary sequences are on either side of the site cut by the nuclease, which allows the plasmid to be incorporated at a specified insertion site on the immune cell's genome. Once the plasmid is incorporated, the cell will express the priming receptor. However, as explained, the design of the transgene cassette ensures that non-virally delivered circuit system receptors do not express CAR until the priming receptor binds to its cognate ligand and releases the cleavable transcription factor.

Initially, a T cell is activated. The T cell may be obtained from a patient. Thus, the present disclosure provides methods in which immune cells, such as T cells, are harvested from a patient. Then, the plasmid that encodes the CAR and priming receptor are introduced into a T cell. Advantageously, the plasmids of the present disclosure can be introduced using electroporation. When introducing the plasmid via electroporation, the nuclease may also be introduced. By using electroporation, methods of the present disclosure avoid the use of viral vectors for introducing transgenes, which is a known bottleneck in immune cell engineering. The T cells are then expanded and co-cultured to create a sufficient quantity of engineered immune cells to be used as a therapeutic treatment.

Methods for editing the genome of a cell can include a) providing a Cas9 ribonucleoprotein complex (RNP)-DNA template complex comprising: (i) the RNP, wherein the RNP comprises a Cas9 nuclease domain and a guide RNA, wherein the guide RNA specifically hybridizes to a target region of the genome of the cell, and wherein the Cas9 nuclease domain cleaves the target region to create an insertion site in the genome of the cell; and (ii) a double-stranded or single-stranded DNA template, wherein the size of the DNA template is greater than about 200 nucleotides, wherein the 5' and 3' ends of the DNA template comprise nucleotide sequences that are homologous to genomic sequences flanking the insertion site, and wherein the molar ratio of RNP to DNA template in the complex is from about 3:1 to about 100:1; and b) introducing the RNP-DNA template complex into the cell.

In some embodiments, the methods described herein provide an efficiency of delivery of the RNP-DNA template complex of at least about 20%, 25%, 30%, 35%, 40%, 45%, 50%, 55%, 60%, 65%, 70%, 75%, 80%, 85%, 90%, 95%, 97.5%, 99%, 99.5%, 99%, or higher. In some cases, the efficiency is determined with respect to cells that are viable after introducing the RNP-DNA template into the cell. In some cases, the efficiency is determined with respect to the total number of cells (viable or non-viable) in which the RNP-DNA template is introduced into the cell.

As another example, the efficiency of delivery can be determined by quantifying the number of genome edited cells in a population of cells (as compared to total cells or total viable cells obtained after the introducing step). Various methods for quantifying genome editing can be utilized. These methods include, but are not limited to, the use of a mismatch-specific nuclease, such as T7 endonuclease I; sequencing of one or more target loci (e.g., by Sanger sequencing of cloned target locus amplification fragments); and high-throughput deep sequencing.

In some embodiments, loss of cell viability is reduced as compared to loss of cell viability after introduction of naked DNA into a cell or introduction of DNA into a cell using a viral vector. The reduction can be a reduction of at least 10%, 20%, 30%, 40%, 50%, 60%, 70%, 80%, 90%, 100% or any percentage in between these percentages. In some embodiments, off-target effects of integration are reduced as compared to off-target integration after introduction of naked DNA into a cell or introduction of DNA into a cell using a viral vector. The reduction can be a reduction of at least 10%, 20%, 30%, 40%, 50%, 60%, 70%, 80%, 90%, 100% or any percentage in between these percentages.

In some cases, the methods described herein provide for high cell viability of cells to which the RNP-DNA template has been introduced. In some cases, the viability of the cells to which the RNP-DNA template has been introduced is at least about 20%, 25%, 30%, 35%, 40%, 45%, 50%, 55%, 60%, 65%, 70%, 75%, 80%, 85%, 90%, 95%, 97.5%, 99%, 99.5%, 99%, or higher. In some cases, the viability of the cells to which the RNP-DNA template has been introduced is from about 20% to about 99%, from about 30% to about 90%, from about 35% to about 85% or 90% or higher, from about 40% to about 85% or 90% or higher, from about 50% to about 85% or 90% or higher, from about 50% to about 85% or 90% or higher, from about 60% to about 85% or 90% or higher, or from about 70% to about 85% or 90% or higher.

In the methods provided herein, the molar ratio of RNP to DNA template can be from about 3:1 to about 100:1. For example, the molar ratio can be from about 5:1 to 10:1, from about 5:1 to about 15:1, 5:1 to about 20:1; 5:1 to about 25:1; from about 8:1 to about 12:1; from about 8:1 to about 15:1, from about 8:1 to about 20:1, or from about 8:1 to about 25:1.

In some embodiments, the DNA template is at a concentration of about 2.5 pM to about 25 pM. For example, the concentration of DNA template can be about 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25 pM or any concentration in between these concentrations.

In some embodiments, the size or length of the DNA template is greater than about 4.5 kb, 5.0 kb, 5.1 kb, 5.2 kb, 5.3 kb, 5.4 kb, 5.5 kb, 5.6 kb, 5.7 kb, 5.8 kb, 5.9 kb, 6.0 kb, 6.1 kb, 6.2 kb, 6.3 kb, 6.4 kb, 6.5 kb, 6.6 kb, 6.7 kb, 6.8 kb, 6.9 kb, 7.0 kb, 7.1 kb, 7.2 kb, 7.3 kb, 7.4 kb, 7.5 kb, 7.6 kb, 7.7 kb, 7.8 kb, 7.9 kb, 8.0 kb, 8.1 kb, 8.2 kb, 8.3 kb, 8.4 kb, 8.5 kb, 8.6 kb, 8.7 kb, 8.8 kb, 8.9 kb, 9.0 kb, 9.1 kb, 9.2 kb, 9.3 kb, 9.4 kb, 9.5 kb, 9.6 kb, 9.7 kb, 9.8 kb, 9.9 kb, or 10 kb or any size of DNA template in between these sizes. For example, the size of the DNA template can be about 4.5 kb to about 10 kb, about 5 kb to about 10 kb, about 5 kb to about 9 kb, about 5 kb to about 8 kb, about 5 kb to about 7 kb, about 5 kb to about 6 kb, about kb 6 to about 10 kb, about 6 kb to about 9 kb, about 6 kb to about 8 kb, about 6 kb to about 7 kb, about 7 kb to about 10 kb, about 7 kb to about 9 kb, about 7 kb to about 8 kb, about 8 kb to about 10 kb, about 8 kb to about 9 kb, or about 9 kb to about 10 kb.

In some embodiments, the amount of DNA template is about 1 μg to about 10 μg. For example, the amount of DNA template can be about 1 μg to about 2 μg, about 1 μg to about 3 μg, about 1 μg to about 4 μg, about 1 μg to about 5 μg, about 1 μg to about 6 μg, about 1 μg to about 7 μg, about 1 μg to about 8 μg, about 1 μg to about 9 μg, about 1 μg to about 10 μg. In some embodiments the amount of DNA template is about 2 μg to about 3 μg, about 2 μg to about 4 μg, about 2 μg to about 5 μg, about 2 μg to about 6 μg, about 2 μg to about 7 μg, about 2 μg to about 8 μg, about 2 μg to about 9 μg, or 2 μg to about 10 μg. In some embodiments the amount of DNA template is about 3 μg to about 4 μg, about 3 μg to about 5 μg, about 3 μg to about 6 μg, about 3 μg to about 7 μg, about 3 μg to about 8 μg, about 3 μg to about 9 μg, or about 3 μg to about 10 μg. In some embodiments, the amount of DNA template is about 4 μg to about 5 μg, about 4 μg to about 6 μg, about 4 μg to about 7 μg, about 4 μg to about 8 μg, about 4 μg to about 9 μg, or about 4 μg to about 10 μg. In some embodiments, the amount of DNA template is about 5 μg to about 6 μg, about 5 μg to about 7 μg, about 5 μg to about 8 μg, about 5 μg to about 9 μg, or about 5 μg to about 10 μg. In some embodiments, the amount of DNA template is about 6 μg to about 7 μg, about 6 μg to about 8 μg, about 6 μg to about 9 μg, or about 6 μg to about 10 μg. In some embodiments, the amount of DNA template is about 7 μg to about 8 μg, about 7 μg to about 9 μg, or about 7 μg to about 10 μg. In some embodiments, the amount of DNA template is about 8 μg to about 9 μg, or about 8 μg to about 10 μg. In some embodiments, the amount of DNA template is about 9 μg to about 10 μg.

In some cases, the size of the DNA template is large enough and in sufficient quantity to be lethal as naked DNA. In some embodiments, the DNA template encodes a heterologous protein or a fragment thereof. In some embodiments, the DNA template encodes at least one gene. In some embodiments, the DNA template encodes at least two genes.

In some embodiments, the DNA template encodes one, two, three, four, five, six, seven, eight, nine, ten, or more genes.

In some embodiments, the DNA template includes regulatory sequences, for example, a promoter sequence and/or an enhancer sequence to regulate expression of the heterologous protein or fragment thereof after insertion into the genome of a cell.

In some cases, the DNA template is a linear DNA template. In some cases, the DNA template is a single-stranded DNA template. In some cases, the single-stranded DNA template is a pure single-stranded DNA template. As used herein, by "pure single-stranded DNA" is meant single-stranded DNA that substantially lacks the other or opposite strand of DNA. By "substantially lacks" is meant that the pure single-stranded DNA lacks at least 100-fold more of one strand than another strand of DNA.

In some cases, the RNP-DNA template complex is formed by incubating the RNP with the DNA template for less than about one minute to about thirty minutes, at a temperature of about 20° C. to about 25° C. For example, the RNP can be incubated with the DNA template for about 5 seconds, 10 seconds, 15 seconds, 20 seconds, 25 seconds, 30 seconds, 35 seconds, 40 seconds, 45 seconds, 50 seconds, 55 seconds, 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes or 30 minutes or any amount of time in between these times, at a temperature of about 20° C., 21° C., 22° C., 23° C., 24° C. or 25° C. In another example, the RNP can be incubated with the DNA template for less than about one minute to about one minute, for less than about one minute to about 5 minutes, for less than about 1 minute to about 10 minutes, for about 5 minutes to 10 minutes, for about 5 minutes to 15 minutes, for about 10 to about 15 minutes, for about 10 minutes to about 20 minutes, or for about 10 minutes to about 30 minutes, at a temperature of about 20° C. to about 25° C. In some embodiments, the RNP-DNA template complex and the cell are mixed prior to introducing the RNP-DNA template complex into the cell.

In some embodiments introducing the RNP-DNA template complex comprises electroporation. Methods, compositions, and devices for electroporating cells to introduce a RNP-DNA template complex can include those described in the examples herein. Additional or alternative methods, compositions, and devices for electroporating cells to introduce a RNP-DNA template complex can include those described in WO/2006/001614 or Kim, J. A. et al. Biosens. Bioelectron. 23, 1353-1360 (2008). Additional or alternative methods, compositions, and devices for electroporating cells to introduce a RNP-DNA template complex can include those described in U.S. Patent Appl. Pub. Nos. 2006/0094095; 2005/0064596; or 2006/0087522. Additional or alternative methods, compositions, and devices for electroporating cells to introduce a RNP-DNA template complex can include those described in Li, L. H. et al. Cancer Res. Treat. 1, 341-350 (2002); U.S. Pat. Nos. 6,773,669; 7,186,559; 7,771,984; 7,991,559; 6,485,961; 7,029,916; and U.S. Patent Appl. Pub. Nos: 2014/0017213; and 2012/0088842, all of which are hereby incorporated by reference. Additional or alternative methods, compositions, and devices for electroporating cells to introduce a RNP-DNA template complex can include those described in Geng, T. et al. J.

Control Release 144, 91-100 (2010); and Wang, J., et al. Lab. Chip 10, 2057-2061 (2010), all of which are hereby incorporated by reference.

In some embodiments, the Cas9 protein can be in an active endonuclease form, such that when bound to target nucleic acid as part of a complex with a guide RNA or part of a complex with a DNA template, a double strand break is introduced into the target nucleic acid. The double strand break can be repaired by NHEJ to introduce random mutations, or HDR to introduce specific mutations. Various Cas9 nucleases can be utilized in the methods described herein. For example, a Cas9 nuclease that requires an NGG protospacer adjacent motif (PAM) immediately 3' of the region targeted by the guide RNA can be utilized. Such Cas9 nucleases can be targeted to any region of a genome that contains an NGG sequence. As another example, Cas9 proteins with orthogonal PAM motif requirements can be utilized to target sequences that do not have an adjacent NGG PAM sequence. Exemplary Cas9 proteins with orthogonal PAM sequence specificities include, but are not limited to, CFP1, those described in Nature Methods 10, 1116-1121 (2013), and those described in Zetsche et al., Cell, Volume 163, Issue 3, p 759-771, 22 Oct. 2015, both of which are hereby incorporated by reference.

In some cases, the Cas9 protein is a nickase, such that when bound to target nucleic acid as part of a complex with a guide RNA, a single strand break or nick is introduced into the target nucleic acid. A pair of Cas9 nickases, each bound to a structurally different guide RNA, can be targeted to two proximal sites of a target genomic region and thus introduce a pair of proximal single stranded breaks into the target genomic region. Nickase pairs can provide enhanced specificity because off-target effects are likely to result in single nicks, which are generally repaired without lesion by base-excision repair mechanisms. Exemplary Cas9 nickases include Cas9 nucleases having a D10A or H840A mutation.

In some embodiments, the RNP comprises a Cas9 nuclease. In some embodiments, the RNP comprises a Cas9 nickase. In some embodiments, the RNP-DNA template complex comprises at least two structurally different RNP complexes. In some embodiments, the at least two structurally different RNP complexes contain structurally different Cas9 nuclease domains In some embodiments, the at least two structurally different RNP complexes contain structurally different guide RNAs. In some embodiments, wherein the at least two structurally different RNP complexes contain structurally different guide RNAs, each of the structurally different RNP complexes comprises a Cas9 nickase, and the structurally different guide RNAs hybridize to opposite strands of the target region.

In some cases, a plurality of RNP-DNA templates comprising structurally different ribonucleoprotein complexes is introduced into the cell. For example a Cas9 protein can be complexed with a plurality (e.g., 2, 3, 4, 5, or more, e.g., 2-10, 5-100, 20-100) of structurally different guide RNAs to target insertion of a DNA template at a plurality of structurally different target genomic regions.

In the methods and compositions provided herein, cells include, but are not limited to, eukaryotic cells, prokaryotic cells, animal cells, plant cells, fungal cells and the like. Optionally, the cell is a mammalian cell, for example, a human cell. The cell can be in vitro, ex vivo or in vivo. The cell can also be a primary cell, a germ cell, a stem cell or a precursor cell. The precursor cell can be, for example, a pluripotent stem cell, or a hematopoietic stem cell. In some embodiments, the cell is a primary hematopoietic cell or a primary hematopoietic stem cell. In some embodiments, the primary hematopoietic cell is an immune cell. In some embodiments, the immune cell is a T cell. In some embodiments, the T cell is a regulatory T cell, an effector T cell, or a naïve T cell. In some embodiments, the T cell is a $CD4^+$ T cell. In some embodiments, the T cell is a $CD8^+$ T cell. In some embodiments, the T cell is a $CD4^+CD8^+$ T cell. In some embodiments, the T cell is a $CD4^-CD8^-$ T cell. Populations of any of the cells modified by any of the methods described herein are also provided. In some embodiments, the methods further comprise expanding the population of modified cells.

In some cases, the cells are removed from a subject, modified using any of the methods described herein and administered to the patient. In other cases, any of the constructs described herein is delivered to the patient in vivo. See, for example, U.S. Pat. No. 9,737,604 and Zhang et al. "Lipid nanoparticle-mediated efficient delivery of CRISPR/Cas9 for tumor therapy," *NPG Asia Materials* Volume 9, page e441 (2017), both of which are hereby incorporated by reference.

In some embodiments, the RNP-DNA template complex is introduced into about $1\times10^5$ to about $2\times10^6$ cells. For example, the RNP-DNA template complex can be introduced into about $1\times10^5$ to about $5\times10^5$ cells, about $1\times10^5$ to about $1\times10^6$, $1\times10^5$ to about $1.5\times10^6$, $1\times10^5$ to about $2\times10^6$, about $1\times10^6$ to about $1.5\times10^6$ cells or about $1\times10^6$ to about $2\times10^6$.

In some cases, the methods and compositions described herein can be used for generation, modification, use, or control of recombinant T cells, such as chimeric antigen receptor T cells (CAR T cells). Such CAR T cells can be used to treat or prevent cancer, an infectious disease, or autoimmune disease in a subject. For example, in some embodiments, one or more gene products are inserted or knocked-in to a T cell to express a heterologous protein (e.g., a chimeric antigen receptor (CAR) or a priming receptor).

Genetic engineering (e.g., genome editing, nuclease-mediated editing, CRISPR/Cas9-mediated editing, etc.), engineering expression of heterologous receptors (e.g., CAR and/or TCRs), and RNAi (e.g., antisense RNA, siRNA, microRNA, shRNA, etc.) are described in International Publication Nos. WO2018232356A1, WO2019084552A1, WO2019226998A1, WO2020014235A1, WO2020123871A1, and WO2020186219A1, each of which is herein incorporated by reference for all purposes.

Insertion Sites

Methods for editing the genome of a T cell, specifically, include a method of editing the genome of a human T cell comprise inserting a nucleic acid sequence or construct into a target region in exon 1 of the TCR-α subunit (TRAC) gene in the human T cell. In some embodiments, the target region is in exon 1 of the constant domain of TRAC gene. In other embodiments, the target region is in exon 1, exon 2 or exon 3, prior to the start of the sequence encoding the TCR-α transmembrane domain.

Methods for editing the genome of a T cell also include a method of editing the genome of a human T cell comprise inserting a nucleic acid sequence or construct into a target region in exon 1 of a TCR-β subunit (TRBC) gene in the human T cell. In some embodiments, the target region is in exon 1 of the TRBC1 or TRBC2 gene.

Methods for editing the genome of a T cell, specifically, include a method of editing the genome of a human T cell comprise inserting a nucleic acid sequence or construct into a target region of a genomic safe harbor (GSH) site.

Methods for editing the genome of a T cell also include a method of editing the genome of a human T cell comprise inserting a nucleic acid sequence or construct into a GS94 target region (locus chr11:128340000-128350000).

In some embodiments, the target region is the GS94 locus.

Gene editing therapies include, for example, vector integration and site specific integration. Site-specific integration is a promising alternative to random integration of viral vectors, as it mitigates the risks of insertional mutagenesis or insertional oncogenesis (Kolb et al. Trends Biotechnol. 2005 23:399-406; Porteus et al. Nat Biotechnol. 2005 23:967-973; Paques et al. Curr Gen Ther. 2007 7:49-66). However, site specific integration continues to face challenges such as poor knock-in efficiency, risk of insertional oncogenesis, unstable and/or anomalous expression of adjacent genes or the transgene, low accessibility (e.g. within 20 kB of adjacent genes), etc. These challenges can be addressed, in part, through the identification and use of safe harbor loci or safe harbor sites (SHS), which are sites in which genes or genetic elements can be incorporated without disruption to expression or regulation of adjacent genes.

The most widely used of the putative human safe harbor sites is the AAVS1 site on chromosome 19q, which was initially identified as a site for recurrent adenoassociated virus insertion. Other potential SHS have been identified on the basis of homology, with sites first identified in other species (e.g., the human homolog of the permissive murine Rosa26 locus) or among the growing number of human genes that appear non-essential under some circumstances. One putative SHS of this type is the CCR5 chemokine receptor gene, which, when disrupted, confers resistance to human immunodeficiency virus infection. Additional potential genomic SHS have been identified in human and other cell types on the basis of viral integration site mapping or gene-trap analyses, as was the original murine Rosa26 locus. The three top SHS, AAVS1, CCR5, and Rosa26, are in close proximity to many protein coding genes and regulatory elements. (See Sadelain, M., et al. (2012). Safe harbours for the integration of new DNA in the human genome. Nature reviews Cancer, 12(1), 51-58, the relevant disclosures of which are herein incorporated by reference in their entirety).

The AAVS1 (also known as the PPP1R12C locus) on human chromosome 19 is a known SHS for hosting transgenes (e.g. DNA transgenes) with expected function. It is at position 19q13.42. It has an open chromatin structure and is transcription-competent. The canonical SHS locus for AAVS1 is chr19: 55,625,241-55,629,351. See Pellenz et al. "New Human Chromosomal Sites with "Safe Harbor" Potential for Targeted Transgene Insertion." Human gene therapy vol. 30, 7 (2019): 814-828, the relevant disclosures of which are herein incorporated by reference. An exemplary AAVS1 target gRNA and target sequence are provided below:

```
AAVS1-gRNA sequence:
                              (SEQ ID NO: 212)
ggggccactagggacaggatGTTTTAGAGCTAGAAATAGC

AAGTTAAAATAAGGCTAGTCCGTTATCAACTTGAAAAAGT

GGCACCGAGTCGGTGCTTTTTT

AAVS1 target sequence:
                              (SEQ ID NO: 213)
ggggccactagggacaggat
```

CCR5, which is located on chromosome 3 at position 3p21.31, encodes the major co-receptor for HIV-1. Disruption at this site in the CCR5 gene has been beneficial in HIV/AIDS therapy and prompted the development of zinc-finger nucleases that target its third exon. The canonical SHS locus for CCR5 is chr3: 46,414,443-46,414,942. See Pellenz et al. "New Human Chromosomal Sites with "Safe Harbor" Potential for Targeted Transgene Insertion." Human gene therapy vol. 30, 7 (2019): 814-828, the relevant disclosures of which are herein incorporated by reference.

The mouse Rosa26 locus is particularly useful for genetic modification as it can be targeted with high efficiency and is expressed in most cell types tested. Irion et al. 2007 ("Identification and targeting of the ROSA26 locus in human embryonic stem cells." Nature biotechnology 25.12 (2007): 1477-1482, the relevant disclosure of which are herein incorporated by reference) identified the human homolog, human ROSA26, in chromosome 3 (position 3p25.3). The canonical SHS locus for human Rosa26 (hRosa26) is chr3: 9,415,082-9,414,043. See Pellenz et al. "New Human Chromosomal Sites with "Safe Harbor" Potential for Targeted Transgene Insertion." Human gene therapy vol. 30, 7 (2019): 814-828, the relevant disclosures of which are herein incorporated by reference.

Additional examples of safe harbor sites are provided in Pellenz et al. "New Human Chromosomal Sites with "Safe Harbor" Potential for Targeted Transgene Insertion." Human gene therapy vol. 30, 7 (2019): 814-828, the relevant disclosures of which are herein incorporated by reference. Examples of additional integration sites are provided in Table D.

In some embodiments, the safe harbor sites allow for high transgene expression (sufficient to allow for transgene functionality or treatment of a disease of interest) and stable expression of the transgene over several days, weeks or months. In some embodiments, knockout of the gene at the safe harbor locus confers benefit to the function of the cell, or the gene at the safe harbor locus has no known function within the cell. In some embodiments the safe harbor locus results in stable transgene expression in vitro with or without CD3/CD28 stimulation, negligible off-target cleavage as detected by iGuide-Seq or CRISPR-Seq, less off-target cleavage relative to other loci as detected by iGuide-Seq or CRISPR-Seq, negligible transgene-independent cytotoxicity, negligible transgene-independent cytokine expression, negligible transgene-independent chimeric antigen receptor expression, negligible deregulation or silencing of nearby genes, and positioned outside of a cancer-related gene.

As used, a "nearby gene" can refer to a gene that is within about 100 kB, about 125 kB, about 150 kB, about 175 kB, about 200 kB, about 225 kB, about 250 kB, about 275 kB, about 300 kB, about 325 kB, about 350 kB, about 375 kB, about 400 kB, about 425 kB, about 450 kB, about 475 kB, about 500 kB, about 525 kB, about 550 kB away from the safe harbor locus (integration site).

In some embodiments, the present disclosure contemplates inserts that comprise one or more transgenes. The transgene can encode a therapeutic protein, an antibody, a peptide, or any other gene of interest. The transgene integration can result in, for example, enhanced therapeutic properties. These enhanced therapeutic properties, as used herein, refer to an enhanced therapeutic property of a cell when compared to a typical immune cell of the same normal cell type. For example, a T cell having "enhanced therapeutic properties" has an enhanced, improved, and/or increased treatment outcome when compared to a typical, unmodified and/or naturally occurring T cell. The therapeutic properties of immune cells can include, but are not limited to, cell transplantation, transport, homing, viability, self-renewal, persistence, immune response control and regulation, survival, and cytotoxicity. The therapeutic properties of immune cells are also manifested by: antigen targeted receptor expression; HLA presentation or lack thereof; tolerance to the intratumoral microenvironment; induction of bystander immune cells and immune regulation; improved target specificity with reduction; resistance to treatments such as chemotherapy.

As used herein, the term "insert size" refers to the length of the nucleotide sequence being integrated (inserted) at the target locus or safe harbor site. In some embodiments, the insert size comprises at least about 4.5 kilobasepairs (kb) to about 10 kilobasepairs (kb). In some embodiments, the insert size comprises about 5000 nucleotides or more basepairs. In some embodiments, the insert size comprises up to 4.5, 4.8, 5, 6, 7, 8, 9, 10, 11, 12, 13, 14, 15, 16, 17, 18, 19, 20 kbp (kilo basepairs) or the sizes in between. In some embodiments, the insert size is greater than 4.5, 4.8, 5, 6, 7, 8, 9, 10, 11, 12, 13, 14, 15, 16, 17, 18, 19, 20 kbp or the sizes in between. In some embodiments, the insert size is within the range of 4.5-15 kbp or is any number in that range. In some embodiments, the insert size is within the range of 4.8-8.3 kbp or is any number in that range. In some embodiments, the insert size is within the range of 5-8.3 kbp or is any number in that range. In some embodiments, the insert size is within the range of 5-15 kbp or is any number in that range. In some embodiments, the insert size is within the range of 4.5-20 kbp or is any number in that range. In some embodiments, the insert size is 5-10 kbp. In some embodiments, the insert size is 4.5-10, 5-10, 6-10, 7-10, 8-10, 9-10 kbp. In some embodiments, the insert size is 4.5-11, 6-11, 7-11, 8-11, 9-11, or 10-11 kbp. In some embodiments, the insert size is 4.5-12, 6-12, 7-12, 8-12, 9-12, 10-12, or 11-12 kbp. In some embodiments, the insert size is 4.5-13, 6-13, 7-13, 8-13, 9-13, 10-13, 11-13, or 12-13 kbp. In some embodiments, the insert size is 4.5-14, 6-14, 7-14, 8-14, 9-14, 10-14, 11-14, 12-14 or 13-14 kbp. In some embodiments, the insert size is 4.5-15, 6-15, 7-15, 8-15, 9-15, 10-15, 11-15, 12-15, 13-15, or 14-15 kbp. In some embodiments, the insert size is 4.5-16, 6-16, 7-16, 8-16, 9-16, 10-16, 11-16, 12-16, 13-16, 14-16 or 15-16 kbp. In some embodiments, the insert size is 4.5-17, 6-17, 7-17, 8-17, 9-17, 10-17, 11-17, 12-17, 13-17, or 14-17, 15-17 or 16-17 kbp. In some embodiments, the insert size is 4.5-18, 6-18, 7-18, 8-18, 9-18, 10-18, 11-18, 12-18, 13-18, 14-18, 15-18, 16-18 or 17-18 kbp. In some embodiments, the insert size is 4.5-19, 6-19, 7-19, 8-19, 9-19, 10-19, 11-19, 12-19, 13-19, 14-19, 15-19, 16-19, 17-19, or 18-19 kbp. In some embodiments, the insert size is 4.5-20, 6-20, 7-20, 8-20, 9-20, 10-20, 11-20, 12-20, 13-20, 14-20, 15-20, 16-20, 17-20, 18-20, or 19-20 kbp.

The inserts of the present disclosure refer to nucleic acid molecules or polynucleotide inserted at a target locus or safe harbor site. In some embodiments, the nucleotide sequence is a DNA molecule, e.g., genomic DNA, or comprises deoxy-ribonucleotides. In some embodiments, the insert comprises a smaller fragment of DNA, such as a plastid DNA, mitochondrial DNA, or DNA isolated in the form of a plasmid, a fosmid, a cosmid, a bacterial artificial chromosome (BAC), a yeast artificial chromosome (YAC), and/or any other sub-genome segment of DNA. In some embodiments, the insert is an RNA molecule or comprises ribonucleotides. The nucleotides in the insert are contemplated as naturally occurring nucleotides, non-naturally occurring, and modified nucleotides. Nucleotides may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications. The polynucleotides can be in any topological conformation, including single-stranded, double-stranded, partially duplexed, triplexed, hairpinned, circular conformations, and other three-dimension conformations contemplated in the art.

The inserts can have coding and/or non-coding regions. The insert can comprises a non-coding sequence (e.g., control elements, e.g., a promoter sequence). In some embodiments, the insert encodes transcription factors. In some embodiments, the insert encodes an antigen binding receptors such as single receptors, T-cell receptors (TCRs), priming receptors, CARs, mAbs, etc. In some embodiments, the insert is a human sequence. In some embodiments, the insert is chimeric. In some embodiments, the insert is a multi-gene/multi-module therapeutic cassette. A multi-gene/multi-module therapeutic cassette refers to an insert or cassette having one or more than one receptor (e.g., synthetic receptors), other exogenous protein coding sequences, non-coding RNAs, transcriptional regulatory elements, and/or insulator sequences, etc.

In some embodiments, the nucleic acid sequence is inserted into the genome of the T cell via non-viral delivery. In non-viral delivery methods, the nucleic acid can be naked DNA, or in a non-viral plasmid or vector. Non-viral delivery techniques can be site-specific integration techniques, as described herein or known to those of ordinary skill in the art. Examples of site-specific techniques for integration into the safe harbor loci include, without limitation, homology-dependent engineering using nucleases and homology independent targeted insertion using Cas9 or other CRISPR endonucleases.

In some embodiments, the insert is integrated at a safe harbor site by introducing into the engineered cell, (a) a targeted nuclease that cleaves a target region in the safe harbor site to create the insertion site; and (b) the nucleic acid sequence (insert), wherein the insert is incorporated at the insertion site by, e.g., HDR. Examples of non-viral delivery techniques that can be used in the methods of the present disclosure are provided in U.S. application Ser. Nos. 16/568,116 and 16/622,843, the relevant disclosures of which are herein incorporated by reference in their entirety.

Examples of integration sites contemplated are provided in Table D.

TABLE D

| | | sgRNA sequences | | | | |
|---|---|---|---|---|---|---|
| sgRNA ID | SEQ ID NO: | sgRNA Sequence | sgRNA start coor GRCH38 | sgRNA Target Loci | Integration Site | Median (% Modified), summarized from 2 donors, 2 primersets |
| sgRNA_1 | 214 | GCACCTGAATACCACGCCTG | chr16:88811818 | APRT | APRT | 79.28 |
| sgRNA_2 | 215 | CGCCTGCGATGTAGTCGATG | chr16:88811551 | APRT | APRT | 78.60 |

TABLE D-continued sgRNA sequences

| sgRNA ID | SEQ ID NO: | sgRNA Sequence | sgRNA start coor GRCH38 | sgRNA Target Loci | Integration Site | Median (% Modified), summarized from 2 donors, 2 primersets |
|---|---|---|---|---|---|---|
| sgRNA_3 | 216 | CAGGACGGGCGAGATGTCCC | chr16:88811640 | APRT | APRT | 85.25 |
| sgRNA_4 | 217 | CTGAATCTTTGGAGTACCTG | chr15:44715425 | B2M | B2M | 78.51 |
| sgRNA_5 | 218 | GGCCACGGAGCGAGACATCT | chr15:44711550 | B2M | B2M | 94.75 |
| sgRNA_6 | 219 | AAGTCAACTTCAATGTCGGA | chr15:44715515 | B2M | B2M | 70.97 |
| sgRNA_7 | 220 | GCTTGGAGGCCTGATCAGCG | chr19:36141111 | CAPNS1 | CAPNS1 | 89.34 |
| sgRNA_8 | 221 | CTTATCTCTTCGCAGCGAGG | chr19:36142301 | CAPNS1 | CAPNS1 | 91.09 |
| sgRNA_9 | 222 | CACACATTACTCCAACATTG | chr19:36142676 | CAPNS1 | CAPNS1 | 71.98 |
| sgRNA_10 | 223 | TTCCGCAAAATAGAGCCCCA | chr3:105746019 | CBLB | CBLB | 91.55 |
| sgRNA_11 | 224 | TGCACAGAACTATCGTACCA | chr3:105751622 | CBLB | CBLB | 91.43 |
| sgRNA_12 | 225 | GCAATAAGACTCTTTAAAGA | chr3:105853470 | CBLB | CBLB | 76.18 |
| sgRNA_13 | 226 | CAAAGAGATTACGAATGCCT | chr1:116754658 | CD2 | CD2 | 89.80 |
| sgRNA_14 | 227 | CAAGGCACCCCAGGTTTCCA | chr1:116754663 | CD2 | CD2 | 92.70 |
| sgRNA_15 | 228 | TTACGAATGCCTTGGAAACC | chr1:116754666 | CD2 | CD2 | 92.82 |
| sgRNA_16 | 229 | CAGAGACGCATCTGACCCTC | chr11:118315540 | CD3E | CD3E | 90.96 |
| sgRNA_17 | 230 | CATGCAGTTCTCACACACTG | chr11:118313715 | CD3E | CD3E | 87.47 |
| sgRNA_18 | 231 | GTGTGAGAACTGCATGGAGA | chr11:118313715 | CD3E | CD3E | 86.65 |
| sgRNA_19 | 232 | TCTCATTTCAGGAAACCACT | chr11:118349748 | CD3G | CD3G | 87.24 |
| sgRNA_20 | 233 | AGTCATACACCTTAACCAAG | chr11:118349754 | CD3G | CD3G | 87.99 |
| sgRNA_21 | 234 | TTCAAGGAA ACCAGTTGAGG | chr11:118352458 | CD3G | CD3G | 86.55 |
| sgRNA_22 | 235 | GAGCCTTGCCTGGAAATCTG | chr11:61118177 | CD5 | CD5 | 84.03 |
| sgRNA_23 | 236 | AAGCGTCAAAAGTCTGCCAG | chr11:61118324 | CD5 | CD5 | 89.19 |
| sgRNA_24 | 237 | CGTTCCAACTCGAAGTGCCA | chr11:61118121 | CD5 | CD5 | 83.11 |
| sgRNA_25 | 238 | GAGCGACTGGGACACGGTGA | chr9:136866246 | EDF1 | EDF 1 | 88.84 |

TABLE D-continued sgRNA sequences

| sgRNA ID | SEQ ID NO: | sgRNA Sequence | sgRNA start coor GRCH38 | sgRNA Target Loci | Integration Site | Median (% Modified), summarized from 2 donors, 2 primersets |
|---|---|---|---|---|---|---|
| sgRNA_26 | 239 | GCTGCGCAAGAAGGGCCCTA | chr9: 136866211 | EDF1 | EDF 1 | 91.04 |
| sgRNA_27 | 240 | TTGTTCTGGCCAGCAGCCCC | chr9: 136863433 | EDF1 | EDF 1 | 85.98 |
| sgRNA_28 | 241 | CTTCCAGAGCCACATCATCG | chr19: 48965791 | FTL | FTL | 93.10 |
| sgRNA_29 | 242 | GGGACTCACCAGAGAGAGGT | chr19: 48965601 | FTL | FTL | 88.86 |
| sgRNA_30 | 243 | CGGTCGAAATAGAAGCCCTA | chr19: 48965770 | FTL | FTL | 93.14 |
| sgRNA_31 | 244 | AAAAGGATATTGTGCAACTG | chr10: 87933015 | PTEN | PTEN | 92.37 |
| sgRNA_32 | 245 | TGTGCATATTTATTACATCG | chr10: 87933183 | PTEN | PTEN | 90.64 |
| sgRNA_33 | 246 | TTTGTGAAGATCTTGACCAA | chr10: 87933087 | PTEN | PTEN | 85.36 |
| sgRNA_34 | 247 | TGTCATGCTGAACCGCATTG | chr18: 12830972 | PTPN2 | PTPN2 | 87.94 |
| sgRNA_35 | 248 | CCACTCTATGAGGATAGTCA | chr18: 12859219 | PTPN2 | PTPN2 | 92.45 |
| sgRNA_36 | 249 | TTGACATAGAAGAGGCACAA | chr18: 12836828 | PTPN2 | PTPN2 | 93.96 |
| sgRNA_37 | 250 | GAGTACTACACTCAGCAGCA | chr12: 6952098 | PTPN6 | PTPN6 | 89.61 |
| sgRNA_38 | 251 | TCACGCACAAGAAACGTCCA | chr12: 6954872 | PTPN6 | PTPN6 | 82.74 |
| sgRNA_39 | 252 | AGGTCTCGGTGAAACCACCT | chr12: 6951610 | PTPN6 | PTPN6 | 91.27 |
| sgRNA_40 | 253 | AGCATTATCCAAAGAGTCCG | chr1: 198696873 | PTPRC | PTPRC | 88.88 |
| sgRNA_41 | 254 | ATATTAATTCTTACCAGTGG | chr1: 198692370 | PTPRC | PTPRC | 88.95 |
| sgRNA_42 | 255 | AGCTTTAAATCAAGGTTCAT | chr1: 198756176 | PTPRC | PTPRC | 96.89 |
| sgRNA_43 | 256 | ATCCCGAGCCCTAAGGTGCA | chr11: 67436325 | PTPRCAP | PTPRCAP | 84.08 |
| sgRNA_44 | 257 | GGCAGCGCGGAGGACAGCGT | chr11: 67436285 | PTPRCAP | PTPRCAP | 97.74 |
| sgRNA_45 | 258 | CTCAGGGGCTACTACCACC | chr11: 67436170 | PTPRCAP | PTPRCAP | 91.50 |
| sgRNA_46 | 259 | GTCACCGACGAGACCAGAAG | chr5: 82277810 | RPS23 | RPS23 | 79.40 |
| sgRNA_47 | 260 | GTCGTGGACTTCGTACTGCT | chr5: 82277843 | RPS23 | RPS23 | 83.07 |
| sgRNA_48 | 261 | TAATTTTAGGCAAGTGTCG | chr5: 82277860 | RPS23 | RPS23 | 61.94 |

TABLE D-continued sgRNA sequences

| sgRNA ID | SEQ ID NO: | sgRNA Sequence | sgRNA start coor GRCH38 | sgRNA Target Loci | Integration Site | Median (% Modified), summarized from 2 donors, 2 primersets |
|---|---|---|---|---|---|---|
| sgRNA_49 | 262 | TTAGCTGTTAGACTTGAATA | chr14: 51993810 | RTRAF | RTRAF | 85.50 |
| sgRNA_50 | 263 | CGAGAGCCGTCAACTTGCGT | chr14: 51989652 | RTRAF | RTRAF | 85.64 |
| sgRNA_51 | 264 | CGGCTTCAACTGCAAAGGTG | chr14: 51989700 | RTRAF | RTRAF | 88.77 |
| sgRNA_52 | 265 | TATGAAAAGCAGAGCGACT | chr15: 43793025 | SERF2 | SERF2 | 89.61 |
| sgRNA_53 | 266 | TCTGGCGGGCGAGCTCACGC | chr15: 43792989 | SERF2 | SERF2 | 86.73 |
| sgRNA_54 | 267 | CTCACGCTGGTTACCGCCTA | chr15: 43792977 | SERF2 | SERF2 | 80.57 |
| sgRNA_55 | 268 | AAAGATTACGAACTTCCCTG | chr12: 46207559 | SLC38A1 | SLC38A1 | 92.24 |
| sgRNA_56 | 269 | GTTAAAAACAGACATGCCTA | chr12: 46229232 | SLC38A1 | SLC38A1 | 91.51 |
| sgRNA_57 | 270 | ATGCCTAAGGAGGTTGTAcc | chr12: 46229246 | SLC38A1 | SLC38A1 | 79.48 |
| sgRNA_58 | 271 | CTCCAGGTATCCCATCGAAA | chr18: 47869418 | SMAD2 | SMAD2 | 79.53 |
| sgRNA_59 | 272 | CACCAAATACGATAGATCAG | chr18: 47870532 | SMAD2 | SMAD2 | 86.61 |
| sgRNA_60 | 273 | TGGCGGCGTGAATGGCAAGA | chr18: 47896729 | SMAD2 | SMAD2 | 82.91 |
| sgRNA_61 | 274 | TAGGATGGTAGCACACAAcc | chr16: 11255478 | SOCS1 | SOCS1 | 92.25 |
| sgRNA_62 | 275 | CAGCAGCAGAGCCCCGACGG | chr16: 11255432 | SOCS1 | SOCS1 | 83.79 |
| sgRNA_63 | 276 | CGGCGTGCGAACGGAATGTG | chr16: 11255296 | SOCS1 | SOCS1 | 84.24 |
| sgRNA_64 | 277 | TATAGACGCTGCCCGACGTC | chr15: 40038895 | SRP14 | SRP14 | 95.12 |
| sgRNA_65 | 278 | TCCAAAGAAGGGTACTGTGG | chr15: 40038368 | SRP14 | SRP14 | 92.14 |
| sgRNA_66 | 279 | ACAGTACCCTTCTTTGGAAT | chr15: 40038358 | SRP14 | SRP14 | 65.82 |
| sgRNA_67 | 280 | GCGACGGGCGCATCTACGTG | chr12: 120469572 | SRSF9 | SRSF9 | 83.68 |
| sgRNA_68 | 281 | CCCGACCTCCATAAGTCCTG | chr12: 120465700 | SRSF9 | SRSF9 | 92.56 |
| sgRNA_69 | 282 | GGGGTCCTCGAAGCGCACGA | chr12: 120469426 | SRSF9 | SRSF9 | 89.94 |
| sgRNA_70 | 283 | TGCTCTGTTTAGAAGATGAC | chr5: 32591641 | SUB1 | SUB1 | 79.36 |
| sgRNA_71 | 284 | ATATTCTTTTCTAGTTAAAG | chr5: 32591566 | SUB1 | SUB1 | 70.93 |

TABLE D-continued sgRNA sequences

| sgRNA ID | SEQ ID NO: | sgRNA Sequence | sgRNA start coor GRCH38 | sgRNA Target Loci | Integration Site | Median (% Modified), summarized from 2 donors, 2 primersets |
| --- | --- | --- | --- | --- | --- | --- |
| sgRNA_72 | 285 | CCTGTAAAGAAACAAAGAC | chr5: 32591614 | SUB1 | SUB1 | 93.66 |
| sgRNA_73 | 286 | TGGAGAAAGACGTAACTTCG | chr4: 105234315 | TET2 | TET2 | 83.53 |
| sgRNA_74 | 287 | TCTGCCCTGAGGTATGCGAT | chr4: 105234747 | TET2 | TET2 | 90.97 |
| sgRNA_75 | 288 | ATTCCGCTTGGTGAAAACGA | chr4: 105235656 | TET2 | TET2 | 89.62 |
| sgRNA_76 | 289 | CAGGCACAATAGAAACAACG | chr3: 114295571 | TIGIT | TIGIT | 92.65 |
| sgRNA_77 | 290 | CCATTTGTAATGCTGACTTG | chr3: 114295700 | TIGIT | TIGIT | 60.75 |
| sgRNA_78 | 291 | CTGGGTCACTTGTGCCGTGG | chr3: 311429564 | TIGIT | TIGIT | 87.99 |
| sgRNA_79 | 292 | GTCAGGGTTCTGGATATCTG | chr14: 22547508 | TRAC | TRAC | 98.20 |
| sgRNA_80 | 293 | TGGATTTAGAGTCTCTCAGC | chr14: 22547541 | TRAC | TRAC | 88.15 |
| sgRNA_81 | 294 | CTGCGGCTGTGGTCCAGCTG | chr14: 22550661 | TRAC | TRAC | 94.77 |
| sgRNA_82 | 295 | ACAAAACTGTGCTAGACATG | chr14: 22547658 | TRAC | TRAC | 87.86 |
| sgRNA_83 | 296 | TTCTTCCCCAGCCCAGGTAA | chr14: 22547778 | TRAC | TRAC | 89.85 |
| sgRNA_84 | 297 | CGTCATGAGCAGATTAAACC | chr14: 22550625 | TRAC | TRAC | 95.81 |
| sgRNA_85 | 298 | GAGAGCGCCTGCGACCCGAG | chr19: 58544980 | TRIM28 | TRIM28 | 89.44 |
| sgRNA_86 | 299 | CCAGCGGGTGAAGTACACCA | chr19: 58544869 | TRIM28 | TRIM28 | 94.79 |
| sgRNA_87 | 300 | GGAGCGCTTTTCGCCGCCAG | chr19: 58544839 | TRIM28 | TRIM28 | 91.81 |
| sgRNA_88 | 301 | TGAGGCCTGGACCTTATGCA | chr10: 33134193 | chr10:33130000-33140000 | desert_1 (GS88) | 69.44 |
| sgRNA_89 | 302 | CCTGGTGGAGTGAACCATGA | chr10: 33132917 | chr10:33130000-33140000 | desert_1 (GS89) | 95.25 |
| sgRNA_90 | 303 | CAAGCACTTAGGTTCCCCTG | chr10: 33134633 | chr10:33130000-33140000 | desert_1 (GS90) | 91.13 |
| sgRNA_91 | 304 | GGTCTCCCTACAATTCAGCG | chr10: 72294568 | chr10:72290000-72300000 | desert_2 (GS91) | 92.02 |
| sgRNA_92 | 305 | CACAGCGCGTGACTGCAATG | chr10: 72298268 | chr10:72290000-72300000 | desert_2 (GS92) | 90.22 |
| sgRNA_93 | 306 | TCTGGGGCACCAATTCTAGG | chr10: 72292786 | chr10:72290000-72300000 | desert_2 (GS93) | 86.35 |
| sgRNA_94 | 307 | GAGCCATGCTTGGCTTACGA | chr11: 128342576 | chr11: 128340000-128350000 | desert_3 (GS94) | 91.24 |

TABLE D-continued sgRNA sequences

| sgRNA ID | SEQ ID NO: | sgRNA Sequence | sgRNA start coor GRCH38 | sgRNA Target Loci | Integration Site | Median (% Modified), summarized from 2 donors, 2 primersets |
|---|---|---|---|---|---|---|
| sgRNA_95 | 308 | GTACAAGTACTTATCTCATG | chr11: 128343592 | chr11: 128340000-128350000 | desert_3 (GS95) | 89.02 |
| sgRNA_96 | 309 | GAGATAACAACATAACAACA | chr11: 128347170 | chr11: 128340000-128350000 | desert_3 (GS96) | 96.47 |
| sgRNA_97 | 310 | CATATTCCATAGTCTTTGGG | chr11: 65425000 | chr11:65425000-65427000 (NEAT1) | desert_4 (GS97) | 88.54 |
| sgRNA_98 | 311 | CTGCCCCTTAGCAACTTAGG | chr11: 65425507 | chr11:65425000-65427000 (NEAT1) | desert_4 (GS98) | 92.76 |
| sgRNA_99 | 312 | TGTTTAAAAATATGTTGACA | chr11: 65426264 | chr11:65425000-65427000 (NEAT1) | desert_4 (GS99) | 90.76 |
| sgRNA_100 | 313 | CCAGGAATGGAAACTCACGC | chr15: 92830315 | chr15:92830000-92840000 | desert_5 (GS100) | 87.84 |
| sgRNA_101 | 314 | GAGGCCGCTGAATTAACCCG | chr15: 92831850 | chr15:92830000-92840000 | desert_5 (GS101) | 85.32 |
| sgRNA_102 | 315 | ATACACGCACACTTGCAGAA | chr15: 92831131 | chr15:92830000-92840000 | desert_5 (GS102) | 99.92 |
| sgRNA_103 | 316 | GAGCAGACAGAAACCCAGGG | chr16: 11225670 | chr16:11220000-11230000 | desert_6 (GS103) | 87.92 |
| sgRNA_104 | 317 | TGAGTCTCCAAACAGAACAG | chr16: 11226284 | chr16:11220000-11230000 | desert_6 (GS104) | 88.53 |
| sgRNA_105 | 318 | TAATATCACTGACTTCACGG | chr16: 11225029 | chr16:11220000-11230000 | desert_6 (GS105) | 87.65 |
| sgRNA_106 | 319 | TACACACAATGTAAGCAGCA | chr2: 87467461 | chr2:87460000-87470000 | desert_7 (GS106) | 71.79 |
| sgRNA_107 | 320 | GGGAGCTCAATTCGAAACCA | chr2: 87468809 | chr2:87460000-87470000 | desert_7 (GS107) | 65.89 |
| sgRNA_108 | 321 | TTGGACAGGTGAGACAGTCG | chr2: 87467001 | chr2:87460000-87470000 | desert_7 (GS108) | 72.64 |
| sgRNA_109 | 322 | AAGCTCACTCAGATAGTGTG | chr3: 186511316 | chr3: 186510000-186520000 | desert_8 (GS109) | 76.89 |
| sgRNA_110 | 323 | CAGGAGAACCACCTTACACG | chr3: 186515260 | chr3: 186510000-186520000 | desert_8 (GS110) | 86.31 |
| sgRNA_111 | 324 | GGACAGACCCTGATTCACAA | chr3: 186519655 | chr3: 186510000-186520000 | desert_8 (GS111) | 85.47 |
| sgRNA_112 | 325 | ACATGGCAGTCTATGAACAG | chr3: 59451154 | chr3:59450000-59460000 | desert_9 (GS112) | 87.77 |
| sgRNA_113 | 326 | CCTATAGAGAGTACTACTTG | chr3: 59456416 | chr3:59450000-59460000 | desert_9 (GS113) | 79.33 |
| sgRNA_114 | 327 | CCAACCGGGTCTTCATTACG | chr3: 59457029 | chr3:59450000-59460000 | desert_9 (GS114) | 92.21 |
| sgRNA_115 | 328 | TCAAGCGTAGAGTTCCGAGT | chr8: 127993006 | chr8: 127980000-128000000 | desert_10 (GS115) | 93.07 |

TABLE D-continued sgRNA sequences

| sgRNA ID | SEQ ID NO: | sgRNA Sequence | sgRNA start coor GRCH38 | sgRNA Target Loci | Integration Site | Median (% Modified), summarized from 2 donors, 2 primersets |
|---|---|---|---|---|---|---|
| sgRNA_116 | 329 | TCATGCAATTATGGACCCAG | chr8: 127994663 | chr8: 127980000-128000000 | desert_10 (GS116) | 89.40 |
| sgRNA_117 | 330 | CGGGAAAGTGACTGGCCATG | chr8: 127996766 | chr8: 127980000-128000000 | desert_10 (GS117) | 87.45 |
| sgRNA_118 | 331 | TGAGATTGA AATCAAATCGG | chr9: 7974159 | chr9: 7970000-7980000 | desert_11 (GS118) | 84.84 |
| sgRNA_119 | 332 | TATGCAATATTCATCACGCG | chr9: 7977914 | chr9: 7970000-7980000 | desert_11 (GS119) | 85.44 |
| sgRNA_120 | 333 | AATGTGTTAAATCAAATGCA | chr9: 7976895 | chr9:7970000-7980000 | desert_11 (GS120) | 83.48 |

CRISPR-Cas Editing

One effective example of gene editing is the CRISPR-Cas approach (e.g. CRISPR-Cas9). This approach incorporates the use of a guide polynucleotide (e.g. guide ribonucleic acid or gRNA) and a cas endonuclease (e.g. Cas9 endonuclease).

As used herein, a polypeptide referred to as a "Cas endonuclease" or having "Cas endonuclease activity" refers to a CRISPR-related (Cas) polypeptide encoded by a Cas gene, wherein a Cas polypeptide is a target DNA sequence that can be cleaved when operably linked to one or more guide polynucleotides (see, e.g., U.S. Pat. No. 8,697,359). Also included in this definition are variants of Cas endonuclease that retain guide polynucleotide-dependent endonuclease activity. The Cas endonuclease used in the donor DNA insertion method detailed herein is an endonuclease that introduces double-strand breaks into DNA at the target site (e.g., within the target locus or at the safe harbor site).

As used herein, the term "guide polynucleotide" relates to a polynucleotide sequence capable of complexing with a Cas endonuclease and allowing the Cas endonuclease to recognize and cleave a DNA target site. The guide polynucleotide can be a single molecule or a double molecule. The guide polynucleotide sequence can be an RNA sequence, a DNA sequence, or a combination thereof (RNA-DNA combination sequence). A guide polynucleotide comprising only ribonucleic acid is also referred to as "guide RNA". In some embodiments, a polynucleotide donor construct is inserted at a safe harbor locus using a guide RNA (gRNA) in combination with a cas endonuclease (e.g. Cas9 endonuclease).

The guide polynucleotide includes a first nucleotide sequence domain (also referred to as a variable targeting domain or VT domain) that is complementary to a nucleotide sequence in the target DNA, and a second nucleotide that interacts with a Cas endonuclease polypeptide. It can be a double molecule (also referred to as a double-stranded guide polynucleotide) comprising a sequence domain (referred to as a Cas endonuclease recognition domain or CER domain). The CER domain of this double molecule guide polynucleotide comprises two separate molecules that hybridize along the complementary region. The two separate molecules can be RNA sequences, DNA sequences and/or RNA-DNA combination sequences.

Genome editing using CRISPR-Cas approaches relies on the repair of site-specific DNA double-strand breaks (DSBs) induced by the RNA-guided Cas endonuclease (e.g. Cas 9 endonuclease). Homology-directed repair (HDR) of these DSBs enables precise editing of the genome by introducing defined genomic changes, including base substitutions, sequence insertions, and deletions. Conventional HDR-based CRISPR/Cas9 genome-editing involves transfecting cells with Cas9, gRNA and donor DNA containing homologous arms matching the genomic locus of interest.

HITI (homology independent targeted insertion) uses a non-homologous end joining (NHEJ)-based homology-independent strategy and the method can be more efficient than HDR. Guide RNAs (gRNAs) target the insertion site. For HITI, donor plasmids lack homology arms and DSB repair does not occur through the HDR pathway. The donor polynucleotide construct can be engineered to include Cas9 cleavage site(s) flanking the gene or sequence to be inserted. This results in Cas9 cleavage at both the donor plasmid and the genomic target sequence. Both target and donor have blunt ends and the linearized donor DNA plasmid is used by the NHEJ pathway resulting integration into the genomic DSB site. (See, for example, Suzuki, K., et al. (2016). In vivo genome editing via CRISPR/Cas9 mediated homology-independent targeted integration. Nature, 540(7631), 144-149, the relevant disclosures of which are herein incorporated in their entirety).

Methods for conducing gene editing using CRISPR-Cas approaches are known to those of ordinary skill in the art. (See, for example, U.S. application Ser. Nos. 16/312,676, 15/303,722, and 15/628,533, the disclosures of which are herein incorporated by reference in their entirety). Additionally, uses of endonucleases for inserting transgenes into safe harbor loci are described, for example, in U.S. application Ser. No. 13/036,343, the disclosures of which are herein incorporated by reference in their entirety.

The guide RNAs and/or mRNA (or DNA) encoding an endonuclease can be chemically linked to one or more moieties or conjugates that enhance the activity, cellular distribution, or cellular uptake of the oligonucleotide. Non-limiting examples of such moieties include lipid moieties such as a cholesterol moiety, cholic acid, a thioether, a thiocholesterol, an aliphatic chain (e.g., dodecandiol or undecyl residues), a phospholipid, e.g., di-hexadecyl-rac-glycerol or triethylammonium 1,2-di-O-hexadecyl-rac-glycero-3-H-phosphonate, a polyamine or a polyethylene glycol chain, adamantane acetic acid, a palmityl moiety and an octadecylamine or hexylamino-carbonyl-t oxycholesterol moiety. See for example US Patent Publication No. 20180127786, the disclosure of which is herein incorporated by reference in its entirety.

Therapeutic Applications

For therapeutic applications, the engineered cells, populations thereof, or compositions thereof are administered to a subject, generally a mammal, generally a human, in an effective amount. The engineered cells may be administered to a subject by infusion (e.g., continuous infusion over a period of time) or other modes of administration known to those of ordinary skill in the art.

The engineered cells provided herein not only find use in gene therapy but also in non-pharmaceutical uses such as, e.g., production of animal models and production of recombinant cell lines expressing a protein of interest.

The engineered cells of the present disclosure can be any cell, generally a mammalian cell, generally a human cell that has been modified by integrating a transgene at a safe harbor locus described herein. Exemplary cells are provided in the Recombinant Cells section.

The engineered cells, compositions and methods of the present disclosure are useful for therapeutic applications such as CAR T cell therapy and TCR T cell therapy. In some embodiments, the insertion of a sequence encoding a transgene within a safe harbor locus maintains the TCR expression relative to instances when there is no insertion and enables transgene expression while maintaining TCR function.

In some embodiments, the present disclosure provides methods of treating a subject in need of treatment by administering to the subject a composition comprising any of the engineered cells described herein. In some embodiments, administration of the engineered cell composition results in a desired pharmacological and/or physiological effect. That effect can be partial or complete cure of the disease and/or adverse effects resulting from the disease. In some embodiments, treatment encompasses any treatment of a disease in a subject (e.g., mammal, e.g., human). Further, treatment may stabilize or reduce undesirable clinical symptoms in subjects (e.g., patients). The cells provided herein populations thereof, or compositions thereof may be administered during or after the occurrence of the disease.

In certain embodiments, the subject has a disease, condition, and/or injury that can be treated and/or ameliorated by cell therapy. In some embodiments, the subject in need of cell therapy is a subject having an injury, disease, or condition, thereby causing cell therapy (e.g., therapy in which cellular material is administered to the subject). However, it is contemplated that it is possible to treat, ameliorate and/or reduce the severity of at least one symptom associated with the injury, disease or condition.

Method of Administration

An effective amount of the immune cell comprising the system may be administered for the treatment of cancer. The appropriate dosage of the immune cell comprising the system may be determined based on the type of cancer to be treated, the type of the immune cell comprising the system, the severity and course of the cancer, the clinical condition of the individual, the individual's clinical history and response to the treatment, and the discretion of the attending physician.

Pharmaceutical Compositions

The engineered recombinant cells provided herein can be administered as part of a pharmaceutical compositions. These compositions can comprise, in addition to one or more of the recombinant cells, a pharmaceutically acceptable excipient, carrier, buffer, stabiliser or other materials well known to those skilled in the art. Such materials should be non-toxic and should not interfere with the efficacy of the active ingredient. The precise nature of the carrier or other material can depend on the route of administration, e.g. oral, intravenous, cutaneous or subcutaneous, nasal, intramuscular, intraperitoneal routes. The pharmaceutical composition may comprise one or more pharmaceutical excipients. Any suitable pharmaceutical excipient may be used, and one of ordinary skill in the art is capable of selecting suitable pharmaceutical excipients. Accordingly, the pharmaceutical excipients provided below are intended to be illustrative, and not limiting. Additional pharmaceutical excipients include, for example, those described in the *Handbook of Pharmaceutical Excipients*, Rowe et al. (Eds.) 6th Ed. (2009), incorporated by reference in its entirety.

Various modes of administering the additional therapeutic agents are contemplated herein. In some embodiments, the additional therapeutic agent is administered by any suitable mode of administration.

A composition can be administered alone or in combination with other treatments, either simultaneously or sequentially dependent upon the condition to be treated.

Kits and Articles of Manufacture

The present application provides kits comprising any one or more of the system or cell compositions described herein along with instructions for use. The instructions for use can be present in the kits as a package insert, in the labeling of the container of the kit or components thereof, or can be in digital form (e.g. on a CD-ROM, via a link on the internet). A kit can include one or more of a genome-targeting nucleic acid, a polynucleotide encoding a genome-targeting nucleic acid, a site-directed polypeptide, and/or a polynucleotide encoding a site-directed polypeptide. Additional components within the kits are also contemplated, for example, buffer (such as reconstituting buffer, stabilizing buffer, diluting buffer), and/or one or more control vectors.

In some embodiments, the kits further contain a component selected from any of secondary antibodies, reagents for immunohistochemistry analysis, pharmaceutically acceptable excipient and instruction manual and any combination thereof. In one specific embodiment, the kit comprises a pharmaceutical composition comprising any one or more of the antibody compositions described herein, with one or more pharmaceutically acceptable excipients.

The present application also provides articles of manufacture comprising any one of the antibody compositions or kits described herein. Examples of an article of manufacture include vials (including sealed vials).

Additional Embodiments

Embodiment 1 One or more recombinant nucleic acids, wherein the one or more recombinant nucleic acids encode:
a first chimeric polypeptide comprising a priming receptor;

a second chimeric polypeptide comprising a chimeric antigen receptor (CAR); and at least one nucleic acid sequence at least 15 nucleotides in length, wherein the at least one nucleic acid sequence comprises one or more of: (1) a first nucleic acid sequence complementary to nucleotides 1126 to 1364 of an mRNA encoding human Fas Cell Surface Death Receptor (FAS) comprising the sequence set forth in SEQ ID NO: 39, (2) a second nucleic acid sequence complementary to nucleotides 518 to 559 of an mRNA encoding human Protein Tyrosine Phosphatase Non-Receptor Type 2 (PTPN2) comprising the sequence set forth in SEQ ID NO: 40; and (3) a third nucleic acid sequence complementary to nucleotides 1294 to 2141 of an mRNA encoding human Thymocyte Selection Associated High Mobility Group Box (TOX) comprising the sequence set forth in SEQ ID NO: 41.

Embodiment 2 The recombinant nucleic acid(s) of embodiment 1, wherein the priming receptor comprising a first extracellular antigen-binding domain that specifically binds to Alkaline Phosphatase, Germ Cell (ALPG/P).

Embodiment 3 The recombinant nucleic acid(s) of embodiment 2, wherein the first extracellular antigen-binding domain comprises a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3, wherein:
CDR-H1 comprises the sequence set forth in SEQ ID NO: 1,
CDR-H2 comprises the sequence set forth in SEQ ID NO: 2,
CDR-H3 comprises the sequence set forth in SEQ ID NO: 3,
CDR-L1 comprises the sequence set forth in SEQ ID NO: 4,
CDR-L2 comprises the sequence set forth in SEQ ID NO: 5, and
CDR-L3 comprises the sequence set forth in SEQ ID NO: 6

Embodiment 4 The recombinant nucleic acid(s) of embodiment 3, wherein the CAR comprises a second extracellular antigen-binding domain that specifically binds to mesothelin (MSLN), and wherein the second extracellular antigen-binding domain comprises a variable heavy (VH) chain sequence comprising three heavy chain CDR sequences, CDR-H1, CDR-H2, and CDR-H3, wherein:
CDR-H1 comprises the sequence set forth in SEQ ID NO: 14,
CDR-H2 comprises the sequence set forth in SEQ ID NO: 15, and
CDR-H3 comprises the sequence set forth in SEQ ID NO: 16.

Embodiment 5 The recombinant nucleic acid(s) of embodiment 4, wherein the at least one nucleic acid sequence comprises each of: (1) the first nucleic acid sequence complementary to nucleotides 1126 to 1364 of an mRNA encoding human FAS comprising the sequence set forth in SEQ ID NO: 39; and (2) the second nucleic acid sequence complementary to nucleotides 518 to 559 of an mRNA encoding human PTPN2 comprising the sequence set forth in SEQ ID NO: 40.

Embodiment 6 The recombinant nucleic acid(s) of any one embodiments 1-3, wherein the CAR comprises a second extracellular antigen-binding domain that specifically binds to mesothelin (MSLN).

Embodiment 7 The recombinant nucleic acid(s) of embodiment 6, wherein the second extracellular antigen-binding domain comprises a variable heavy (VH) chain sequence comprising three heavy chain CDR sequences, CDR-H1, CDR-H2, and CDR-H3, wherein:
CDR-H1 comprises the sequence set forth in SEQ ID NO: 14,
CDR-H2 comprises the sequence set forth in SEQ ID NO: 15, and
CDR-H3 comprises the sequence set forth in SEQ ID NO: 16.

Embodiment 8 The recombinant nucleic acid(s) of embodiment 6, wherein the second extracellular antigen-binding domain comprises a single domain antibody comprising a variable heavy (VHH) chain sequence comprising three heavy chain CDR sequences, CDR-H1, CDR-H2, and CDR-H3, wherein:
CDR-H1 comprises the sequence set forth in SEQ ID NO: 10,
CDR-H2 comprises the sequence set forth in SEQ ID NO: 11, and
CDR-H3 comprises the sequence set forth in SEQ ID NO: 12.

Embodiment 9 One or more recombinant nucleic acids, wherein the one or more recombinant nucleic acids encode:
a first chimeric polypeptide comprising a priming receptor comprising a first extracellular antigen-binding domain that specifically binds Alkaline Phosphatase, Placental/Germ Cell (ALPG/P), wherein the first extracellular antigen-binding domain comprises a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3, wherein:
CDR-H1 comprises the sequence set forth in SEQ ID NO: 1,
CDR-H2 comprises the sequence set forth in SEQ ID NO: 2,
CDR-H3 comprises the sequence set forth in SEQ ID NO: 3,
CDR-L1 comprises the sequence set forth in SEQ ID NO: 4,
CDR-L2 comprises the sequence set forth in SEQ ID NO: 5, and
CDR-L3 comprises the sequence set forth in SEQ ID NO: 6;
a second chimeric polypeptide comprising a chimeric antigen receptor (CAR);
a first nucleic acid sequence complementary to nucleotides 1126 to 1364 of an mRNA encoding human FAS comprising the sequence set forth in SEQ ID NO: 39, and
a second nucleic acid sequence complementary to nucleotides 518 to 559 of an mRNA encoding human PTPN2 comprising the sequence set forth in SEQ ID NO: 40; or complementary to nucleotides 1294 to 2141 of an mRNA encoding human TOX comprising the sequence set forth in SEQ ID NO: 41.

Embodiment 10 The recombinant nucleic acid(s) of any one of embodiments 3-9, wherein the first extracellular antigen-binding domain VH chain sequence comprises the sequence set forth in SEQ ID NO: 7.

Embodiment 11 The recombinant nucleic acid(s) of any one of embodiments 3-10, wherein the first extracellular antigen-binding domain VL chain sequence comprises the sequence set forth in SEQ ID NO: 8.

Embodiment 12 The recombinant nucleic acid(s) of any one of embodiments 3-11, wherein the first extracellular antigen-binding domain comprises the sequence set forth in SEQ ID NO: 9.

Embodiment 13 The recombinant nucleic acid(s) of any one of embodiments 9-12, wherein the CAR comprises a second extracellular antigen-binding domain that specifically binds to mesothelin (MSLN).

Embodiment 14 The recombinant nucleic acid(s) of embodiment 13, wherein the second extracellular antigen-binding domain comprises a variable heavy (VH) chain sequence comprising three heavy chain CDR sequences, CDR-H1, CDR-H2, and CDR-H3, wherein:
CDR-H1 comprises the sequence set forth in SEQ ID NO: 14,
CDR-H2 comprises the sequence set forth in SEQ ID NO: 15, and
CDR-H3 comprises the sequence set forth in SEQ ID NO: 16.

Embodiment 15 The recombinant nucleic acid(s) of any one of embodiments 4-8 and 13-14, wherein the second extracellular antigen-binding domain VH comprises the sequence as set forth in SEQ ID NO: 17.

Embodiment 16 The recombinant nucleic acid(s) of embodiment 13, wherein the second extracellular antigen-binding domain comprises a single domain antibody comprising a variable heavy (VHH) chain sequence comprising three heavy chain CDR sequences, CDR-H1, CDR-H2, and CDR-H3, wherein:
CDR-H1 comprises the sequence set forth in SEQ ID NO: 10,
CDR-H2 comprises the sequence set forth in SEQ ID NO: 11, and
CDR-H3 comprises the sequence set forth in SEQ ID NO: 12.

Embodiment 17 The recombinant nucleic acid(s) of any one of embodiments 4-8, 13, and 16, wherein the second extracellular antigen-binding domain VHH chain sequence comprises the sequence set forth in SEQ ID NO: 13.

Embodiment 18 The recombinant nucleic acid of any one of embodiments 1 to 17, wherein the second nucleic acid sequence is complementary to nucleotides 518 to 559 of an mRNA encoding human PTPN2 comprising the sequence set forth in SEQ ID NO: 40.

Embodiment 19 The recombinant nucleic acid of any one of embodiments 1 to 17, wherein the recombinant nucleic acid comprises a sequence selected from the group consisting of the sequences set forth in SEQ ID NOs: 168, 167, or 166.

Embodiment 20 The recombinant nucleic acid of any one of embodiments 1 to 17, wherein the second nucleic acid sequence is complementary to nucleotides 1294 to 2141 of an mRNA encoding human TOX comprising the sequence set forth in SEQ ID NO: 41.

Embodiment 21 A recombinant nucleic acid comprising a nucleic acid sequence at least 15 nucleotides in length complementary to nucleotides 1126 to 1364 of an mRNA encoding human FAS comprising the sequence set forth in SEQ ID NO: 39.

Embodiment 22 A recombinant nucleic acid comprising a nucleic acid sequence at least 15 nucleotides in length complementary to nucleotides 518 to 559 of an mRNA encoding human Protein Tyrosine Phosphatase Non-Receptor Type 2 (PTPN2) comprising the sequence set forth in SEQ ID NO: 40.

Embodiment 23 A recombinant nucleic acid comprising a nucleic acid sequence at least 15 nucleotides in length complementary to nucleotides 1294 to 2141 of an mRNA encoding human thymocyte selection associated high mobility group box (TOX) comprising the sequence set forth in SEQ ID NO: 41.

Embodiment 24 One or more recombinant nucleic acids comprising a first nucleic acid sequence at least 15 nucleotides in length complementary to nucleotides 1126 to 1364 of an mRNA encoding human FAS comprising the sequence set forth in SEQ ID NO: 39 and a second nucleic acid sequence at least 15 nucleotides in length complementary to nucleotides 518 to 559 of an mRNA encoding human PTPN2 comprising the sequence set forth in SEQ ID NO: 40.

Embodiment 25 One or more recombinant nucleic acids comprising a first nucleic acid at least 15 nucleotides in length complementary to nucleotides 1126 to 1364 of an mRNA encoding human FAS comprising the sequence set forth in SEQ ID NO: 39; and a second nucleic acid at least 15 nucleotides in length complementary to nucleotides 1294 to 2141 of an mRNA encoding human TOX comprising the sequence set forth in SEQ ID NO: 41.

Embodiment 26 The recombinant nucleic acid of any one of embodiments 1 to 25, wherein the first and second nucleic acid sequences are at least 16, 17, 18, 19, 20, 21, or 22 nucleotides in length.

Embodiment 27 The recombinant nucleic acid of any one of embodiments 1 to 26, wherein the first and second nucleic acids are a short hairpin RNA (shRNA), a small interfering RNA (siRNA), a double stranded RNA (dsRNA), or an antisense oligonucleotide.

Embodiment 28 The recombinant nucleic acid of embodiment 27, wherein the first and second nucleic acids are shRNA.

Embodiment 29 The recombinant nucleic acid of any one of embodiments 1-28, wherein the first nucleic acid sequence comprises a sequence selected from the group consisting of the sequences set forth in SEQ ID NOs: 42-71.

Embodiment 30 The recombinant nucleic acid of embodiment 29, wherein the first nucleic acid sequence comprises the sequence set forth in SEQ ID NO: 49.

Embodiment 31 The recombinant nucleic acid of any one of embodiments 1-30, wherein the first nucleic acid reduces expression of FAS in the immune cell by at least 50%, 55%, 60%, 65%, 75%, 80%, 85%, 90%, 95%, or 99% as compared to a control cell that does not comprise the nucleic acid.

Embodiment 32 The recombinant nucleic acid of any one of embodiments 1-31, wherein the second nucleic acid sequence comprises a sequence selected from the group consisting of the sequences set forth in SEQ ID NOs: 72-97.

Embodiment 33 The recombinant nucleic acid of embodiment 32, wherein the second nucleic acid sequence comprises the sequence set forth in SEQ ID NO: 82.

Embodiment 34 The recombinant nucleic acid of any one of embodiments 1-33, wherein the first nucleic acid sequence comprises a sequence selected from the group consisting of the sequences set forth in SEQ ID NOs: 42 to 71; and the second nucleic acid sequence comprises a sequence selected from the group consisting of the sequences set forth in SEQ ID NOs: 72 to 97.

Embodiment 35 The recombinant nucleic acid of any one of embodiments 1-34, wherein the first nucleic acid sequence comprises the sequence set forth in SEQ ID NO: 49 and the second nucleic acid sequence comprises the sequence set forth in SEQ ID NO: 82.

Embodiment 36 The recombinant nucleic acid of any one of embodiments 1-35, wherein the second nucleic acid reduces expression of PTPN2 in the immune cell by at least 50%, 55%, 60%, 65%, 75%, 80%, 85%, 90%, 95%, or 99% as compared to a control cell that does not comprise the nucleic acid.

Embodiment 37 The recombinant nucleic acid of any one of embodiments 1-31, wherein the second nucleic acid sequence comprises a sequence selected from the group consisting of the sequences set forth in SEQ ID NOs: 98-125.

Embodiment 38 The recombinant nucleic acid of embodiment 37, wherein the second nucleic acid sequence comprises the sequence set forth in SEQ ID NO: 99 or 104.

Embodiment 39 The recombinant nucleic acid of any one of embodiments 1-31, or 37-38, wherein the first nucleic acid sequence comprises a sequence selected from the group consisting of the sequences set forth in SEQ ID NOs: 42 to 71; and the second nucleic acid sequence comprises a sequence selected from the group consisting of the sequences set forth in SEQ ID NOs: 98 to 125.

Embodiment 40 The recombinant nucleic acid of embodiment 39, wherein the first nucleic acid sequence comprises the sequence set forth in SEQ ID NO: 49 and the second nucleic acid sequence comprises the sequence set forth in SEQ ID NO: SEQ ID NOs: 99 or 104

Embodiment 41 The recombinant nucleic acid of any one of embodiments 1-31 or 37-40, wherein the second nucleic acid reduces expression of TOX in the immune cell by at least 50%, 55%, 60%, 65%, 75%, 80%, 85%, 90%, 95%, or 99% as compared to a control cell that does not comprise the nucleic acid.

Embodiment 42 The recombinant nucleic acid of any one of embodiments 1-41, wherein the first, second, and/or third nucleic acid sequence is encoded in at least one intron region of the recombinant nucleic acid.

Embodiment 43 One or more recombinant nucleic acids, wherein the one or more recombinant nucleic acids encode:
  a first chimeric polypeptide comprises a priming receptor,
  a second chimeric polypeptide comprises a chimeric antigen receptor (CAR) comprising an extracellular antigen-binding domain that specifically binds to mesothelin (MSLN), wherein the extracellular antigen-binding domain comprises a single domain antibody comprising a variable heavy (VHH) chain sequence comprising three heavy chain CDR sequences, CDR-H1, CDR-H2, and CDR-H3, wherein:
    CDR-H1 comprises the sequence set forth in SEQ ID NO: 10,
    CDR-H2 comprises the sequence set forth in SEQ ID NO: 11, and
    CDR-H3 comprises the sequence set forth in SEQ ID NO: 12; and
  a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and
  a second nucleic acid sequence, wherein the second nucleic acid sequence is complementary to nucleotides 518 to 559 of an mRNA encoding human PTPN2 comprising the sequence set forth in SEQ ID NO: 40; or is complementary to nucleotides 1294 to 2141 of an mRNA encoding human TOX comprising the sequence set forth in SEQ ID NO: 41.

Embodiment 44 The recombinant nucleic acid(s) of embodiment 43, wherein the VHH chain sequence comprises the sequence set forth in SEQ ID NO: 13.

Embodiment 45 One or more recombinant nucleic acids, wherein the one or more recombinant nucleic acids encode:
  a first chimeric polypeptide comprises a priming receptor,
  a second chimeric polypeptide comprises a chimeric antigen receptor (CAR) comprising an extracellular antigen-binding domain that specifically binds to mesothelin (MSLN), wherein the second extracellular antigen-binding domain comprises a variable heavy (VH) chain sequence comprising three heavy chain CDR sequences, CDR-H1, CDR-H2, and CDR-H3, wherein:
    CDR-H1 comprises the sequence set forth in SEQ ID NO: 14,
    CDR-H2 comprises the sequence set forth in SEQ ID NO: 15, and
    CDR-H3 comprises the sequence set forth in SEQ ID NO: 16; and
  a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and
  a second nucleic acid sequence, wherein the second nucleic acid sequence is complementary to nucleotides 518 to 559 of an mRNA encoding human PTPN2 comprising the sequence set forth in SEQ ID NO: 40; or is complementary to nucleotides 1294 to 2141 of an mRNA encoding human TOX comprising the sequence set forth in SEQ ID NO: 41.

Embodiment 46 The recombinant nucleic acid(s) of embodiment 45, wherein the VH comprises the sequence as set forth in SEQ ID NO: 17.

Embodiment 47 One or more recombinant nucleic acids, wherein the one or more recombinant nucleic acids encode:
  a first chimeric polypeptide comprises a priming receptor comprising a first extracellular antigen-binding domain that specifically binds to Alkaline Phosphatase, Germ Cell (ALPG/P); and
  a second chimeric polypeptide comprises a CAR comprising a second extracellular antigen-binding domain that specifically binds to mesothelin (MSLN);
  a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and
  a second nucleic acid sequence, wherein the second nucleic acid sequence is complementary to nucleotides 518 to 559 of an mRNA encoding human PTPN2 comprising the sequence set forth in SEQ ID NO: 40; or is complementary to nucleotides 1294 to 2141 of an mRNA encoding human TOX comprising the sequence set forth in SEQ ID NO: 41.

Embodiment 48 The recombinant nucleic acid(s) of any one of embodiments 43-47, wherein the second nucleic acid sequence is complementary to nucleotides 518 to 559 of an mRNA encoding human PTPN2 comprising the sequence set forth in SEQ ID NO: 40.

Embodiment 49 The recombinant nucleic acid(s) of any one of embodiments 43-48, wherein the recombinant nucleic acid comprises a sequence selected from the group consisting of the sequences set forth in SEQ ID NOs: 168, 167, or 166.

Embodiment 50 The recombinant nucleic acid(s) of any one of embodiments 43-47, wherein the second nucleic acid sequence is complementary to nucleotides 1294 to 2141 of an mRNA encoding human TOX comprising the sequence set forth in SEQ ID NO: 41.

Embodiment 51 The recombinant nucleic acid of any one of embodiments 43 to 50, wherein the first and second nucleic acid sequences are at least 16, 17, 18, 19, 20, 21, or 22 nucleotides in length.

Embodiment 52 The recombinant nucleic acid of any one of embodiments 43 to 51, wherein the first and second nucleic acids are a short hairpin RNA (shRNA), a small interfering RNA (siRNA), a double stranded RNA (dsRNA), or an antisense oligonucleotide.

Embodiment 53 The recombinant nucleic acid of embodiment 52, wherein the first and second nucleic acids are shRNA.

Embodiment 54 The recombinant nucleic acid of any one of embodiments 43-53, wherein the first nucleic acid sequence comprises a sequence selected from the group consisting of the sequences set forth in SEQ ID NOs: 42-71.

Embodiment 55 The recombinant nucleic acid of embodiment 54, wherein the first nucleic acid sequence comprises the sequence set forth in SEQ ID NO: 49.

Embodiment 56 The recombinant nucleic acid of any one of embodiments 43-55, wherein the first nucleic acid reduces expression of FAS in the immune cell by at least 50%, 55%, 60%, 65%, 75%, 80%, 85%, 90%, 95%, or 99% as compared to a control cell that does not comprise the nucleic acid.

Embodiment 57 The recombinant nucleic acid of any one of embodiments 43-56, wherein the second nucleic acid sequence comprises a sequence selected from the group consisting of the sequences set forth in SEQ ID NOs: 72-97.

Embodiment 58 The recombinant nucleic acid of embodiment 57, wherein the second nucleic acid sequence comprises the sequence set forth in SEQ ID NO: 82.

Embodiment 59 The recombinant nucleic acid of any one of embodiments 43-58, wherein the second nucleic acid reduces expression of PTPN2 in the immune cell by at least 50%, 55%, 60%, 65%, 75%, 80%, 85%, 90%, 95%, or 99% as compared to a control cell that does not comprise the nucleic acid.

Embodiment 60 The recombinant nucleic acid of any one of embodiments 43-56, wherein the second nucleic acid sequence comprises a sequence selected from the group consisting of the sequences set forth in SEQ ID NOs: 98-125.

Embodiment 61 The recombinant nucleic acid of embodiment 60, wherein the second nucleic acid sequence comprises the sequence set forth in SEQ ID NO: 99 or 104.

Embodiment 62 The recombinant nucleic acid of any one of embodiments 43-56, 60, or 61, wherein the second nucleic acid reduces expression of TOX in the immune cell by at least 50%, 55%, 60%, 65%, 75%, 80%, 85%, 90%, 95%, or 99% as compared to a control cell that does not comprise the nucleic acid.

Embodiment 63 The recombinant nucleic acid of any one of embodiments 43-62, wherein the first, second, and/or third nucleic acid sequence is encoded in at least one intron region of the recombinant nucleic acid.

Embodiment 64 The recombinant nucleic acid(s) of embodiments 1-63, wherein the priming receptor comprises, from N-terminus to C-terminus,
the first extracellular antigen-binding domain;
a first transmembrane domain comprising one or more ligand-inducible proteolytic cleavage sites; and
an intracellular domain comprising a human or humanized transcriptional effector, wherein binding of ALPG/P by the first extracellular antigen-binding domain results in cleavage at the one or more ligand-inducible proteolytic cleavage sites.

Embodiment 65 The recombinant nucleic acid(s) of embodiment 64, wherein the priming receptor further comprises a first hinge domain positioned between the first extracellular antigen-binding domain and the first transmembrane domain.

Embodiment 66 The recombinant nucleic acid(s) of embodiment 65, wherein the first hinge domain comprises a CD8α or a truncated CD8α hinge domain.

Embodiment 67 The recombinant nucleic acid(s) of embodiment 66, wherein the first hinge comprises the sequence as set forth in SEQ ID NO: 18.

Embodiment 68 The recombinant nucleic acid(s) of embodiments 1-67, wherein the first transmembrane domain comprises a Notch1 transmembrane domain.

Embodiment 69 The recombinant nucleic acid(s) of embodiment 68, wherein the first transmembrane domain comprises the sequence as set forth in SEQ ID NO: 19.

Embodiment 70 The recombinant nucleic acid(s) of any one of embodiments 64-69, wherein the intracellular domain comprises an HNF1a/p65 domain or a Gal4/VP64 domain.

Embodiment 71 The recombinant nucleic acid(s) of embodiment 70, wherein the intracellular domain comprises the sequence as set forth in SEQ ID NO: 23.

Embodiment 72 The recombinant nucleic acid(s) of any one of embodiments 1-71, wherein the priming receptor further comprises a stop-transfer-sequence between the first transmembrane domain and the intracellular domain.

Embodiment 73 The recombinant nucleic acid(s) of embodiment 72, wherein the stop-transfer-sequence comprises the sequence as set forth in SEQ ID NO: 20.

Embodiment 74 The recombinant nucleic acid(s) of any one of embodiments 1-73, wherein the priming receptor comprises a sequence as set forth in SEQ ID NO: 24.

Embodiment 75 The recombinant nucleic acid(s) of any one of embodiments 1 to 74, wherein the CAR comprises, from N-terminus to C-terminus,
a second extracellular antigen-binding domain;
a second transmembrane domain;
an intracellular co-stimulatory domain; and
an intracellular activation domain.

Embodiment 76 The recombinant nucleic acid(s) of embodiment 75, wherein the second extracellular antigen-binding domain specifically binds to mesothelin (MSLN), wherein the second extracellular antigen-binding domain comprises a single domain antibody comprising a variable heavy (VHH) chain sequence comprising three heavy chain CDR sequences, CDR-H1, CDR-H2, and CDR-H3, wherein:
CDR-H1 comprises the sequence set forth in SEQ ID NO: 10,
CDR-H2 comprises the sequence set forth in SEQ ID NO: 11, and
CDR-H3 comprises the sequence set forth in SEQ ID NO: 12.

Embodiment 77 The recombinant nucleic acid(s) of embodiment 76, wherein the VHH chain sequence comprises the sequence set forth in SEQ ID NO: 13.

Embodiment 78 The recombinant nucleic acid(s) of embodiment 75, wherein the second extracellular antigen-binding domain specifically binds to mesothelin (MSLN), wherein the extracellular antigen-binding domain comprises a variable heavy (VH) chain sequence comprising three heavy chain CDR sequences, CDR-H1, CDR-H2, and CDR-H3, wherein:

CDR-H1 comprises the sequence set forth in SEQ ID NO: 14,

CDR-H2 comprises the sequence set forth in SEQ ID NO: 15, and

CDR-H3 comprises the sequence set forth in SEQ ID NO: 16.

Embodiment 79 The recombinant nucleic acid(s) of embodiment 78, wherein the VH chain sequence comprises the sequence set forth in SEQ ID NO: 17.

Embodiment 80 The recombinant nucleic acid(s) of any one of embodiments 1-79, wherein the CAR comprises a second hinge domain.

Embodiment 81 The recombinant nucleic acid(s) of embodiment 80, wherein the second hinge domain comprises a CD8α or a truncated CD8α hinge domain.

Embodiment 82 The recombinant nucleic acid(s) of any one of embodiments 75-81, wherein the second transmembrane domain comprises a CD8α transmembrane domain.

Embodiment 83 The recombinant nucleic acid(s) of any one of embodiments 75-82, wherein the intracellular co-stimulatory domain comprises a 4-1 BB domain.

Embodiment 84 The recombinant nucleic acid(s) of any one of embodiments 75-83, wherein the intracellular activation domain comprises a CD3ζ domain.

Embodiment 85 The recombinant nucleic acid(s) of any one of embodiments 1-84, wherein the CAR comprises a sequence as set forth in SEQ ID NO: 30 or 31.

Embodiment 86 The recombinant nucleic acid(s) of any one of embodiments 1-72, wherein the priming receptor and the CAR are capable of binding to a single target cell if the target cell expresses each of ALPG/P and MSLN.

Embodiment 87 The recombinant nucleic acid(s) of embodiment 86, wherein the target cell is a human cell.

Embodiment 88 The recombinant nucleic acid(s) of embodiment 86 or 87, wherein the target cell is a cancer cell.

Embodiment 89 The recombinant nucleic acid(s) of any one of embodiments 88, wherein the cancer cell is a solid cancer cell or a liquid cancer cell.

Embodiment 90 The recombinant nucleic acid(s) of any one of embodiments 88-89, wherein the cancer cell is ovarian cancer, fallopian cancer, primary peritoneal cancer, uterine cancer, mesothelioma, cervical cancer, or pancreatic cancer.

Embodiment 01 The recombinant nucleic acid(s) of any one of embodiments 1-90, wherein the recombinant nucleic acid comprises two or more nucleic acid fragments.

Embodiment 92 The recombinant nucleic acid of any one of embodiments 1-91, wherein the recombinant nucleic acid further comprises an inducible promoter operably linked to the nucleotide sequence encoding the CAR.

Embodiment 93 The recombinant nucleic acid of any one of embodiments 1-92, wherein the recombinant nucleic acid further comprises a first constitutive promoter operably linked to the nucleotide sequence encoding the priming receptor.

Embodiment 94 The recombinant nucleic acid of any one of embodiments 1-93, wherein the recombinant nucleic acid further comprises an inducible promoter operably linked to the nucleotide sequence encoding the chimeric antigen receptor and a constitutive promoter operably linked to the nucleotide sequence encoding the priming receptor.

Embodiment 95 The recombinant nucleic acid of any one of embodiments 1-94, wherein the recombinant nucleic acid further comprises a second constitutive promoter operably linked to the nucleotide sequence encoding the first nucleic acid complementary to human FAS.

Embodiment 96 The recombinant nucleic acid of any one of embodiments 1-94, wherein the recombinant nucleic acid further comprises a second constitutive promoter operably linked to the nucleotide sequence encoding the second nucleic acid complementary to human PTPN2 or TOX.

Embodiment 97 The recombinant nucleic acid of any one of embodiments 1-96, wherein the recombinant nucleic acid further comprises a second constitutive promoter operably linked to the nucleotide sequence encoding the first nucleic acid complementary to human FAS or the second nucleic acid complementary to human PTPN2 or TOX.

Embodiment 98 The recombinant nucleic acid of any one of embodiment 1-97, wherein the recombinant nucleic acid comprises, in a 5' to 3' direction, the first constitutive promoter;
the nucleotide sequence encoding the priming receptor;
the second constitutive promoter;
the nucleotide sequence encoding the first nucleic acid complementary to human FAS, human PTPN2, or human TOX;
the inducible promoter; and
the nucleotide sequence encoding the chimeric antigen receptor.

Embodiment 99 The recombinant nucleic acid of any one of embodiment 1-97, wherein the recombinant nucleic acid comprises, in a 5' to 3' direction, the first constitutive promoter;
the nucleotide sequence encoding the priming receptor;
the second constitutive promoter;
the nucleotide sequence encoding the first nucleic acid complementary to human FAS;
the nucleotide sequence encoding the second first nucleic acid complementary to human PTPN2 or TOX;
the inducible promoter; and
the nucleotide sequence encoding the chimeric antigen receptor.

Embodiment 100 The recombinant nucleic acid of any one of embodiment 1-97, wherein the recombinant nucleic acid comprises, in a 5' to 3' direction,
the inducible promoter;
the nucleotide sequence encoding the chimeric antigen receptor,
the second constitutive promoter;
the nucleotide sequence encoding the first nucleic acid complementary to human FAS;
the nucleotide sequence encoding the second first nucleic acid complementary to human PTPN2 or TOX;
the first constitutive promoter; and
the nucleotide sequence encoding the priming receptor.

Embodiment 101 The recombinant nucleic acid of any one of embodiment 1-100, wherein the nucleotide sequence encoding the priming receptor comprises the sequence set forth in SEQ ID NO: 36.

Embodiment 102 The recombinant nucleic acid of any one of embodiment 1-101, wherein the nucleotide sequence encoding the chimeric antigen receptor comprises the sequence set forth in SEQ ID NO: 37 or 38.

Embodiment 103 The recombinant nucleic acid of embodiment of any one of embodiment 1-102, wherein the recombinant nucleic acid further comprises a 5' homology directed repair arm and a 3' homology directed repair arm complementary to an insertion site in a host cell chromosome.

Embodiment 104 The recombinant nucleic acid of any one of embodiments 1-103, wherein the recombinant nucleic acid further comprises a nucleotide sequence encoding a self-excising 2A peptide (P2A).

Embodiment 105 The recombinant nucleic acid of any one of embodiments 1-104, wherein the P2A is at the 3' end of the nucleotide sequence encoding chimeric antigen receptor.

Embodiment 106 The recombinant nucleic acid of any one of embodiments 1-104, wherein the P2A is at the 3' end of the nucleotide sequence encoding priming receptor.

Embodiment 107 The recombinant nucleic acid of any one of embodiments 1-106, wherein the recombinant nucleic acid further comprises a woodchuck hepatitis virus post-translational regulatory element (WPRE).

Embodiment 108 The recombinant nucleic acid of embodiment 107, wherein the WPRE is at the 3' end of the nucleotide sequence encoding chimeric antigen receptor and at the 5' end of the nucleotide sequence encoding priming receptor or wherein the WPRE is at the 3' end of the nucleotide sequence encoding priming receptor and at the 5' end of the nucleotide sequence encoding chimeric antigen receptor.

Embodiment 109 The recombinant nucleic acid of any one of embodiments 1-107, wherein the recombinant nucleic acid further comprises an SV40 polyA element.

Embodiment 110 The recombinant nucleic acid of any one of embodiments 1 to 109, wherein the nucleic acid is incorporated into an expression cassette or an expression vector.

Embodiment 111 The recombinant nucleic acid of embodiment 110, wherein the expression vector is a non-viral vector.

Embodiment 112 An expression vector comprising the recombinant nucleic acid of any one of embodiments 1-111.

Embodiment 113 The vector of embodiment 112, wherein the 5' and 3' ends of the recombinant nucleic acid comprise nucleotide sequences that are homologous to genomic sequences flanking an insertion site in a genome of a primary cell.

Embodiment 114 The vector of embodiment 113, wherein the insertion site is located at a T Cell Receptor Alpha Constant (TRAC) locus or a genomic safe harbor (GSH) locus.

Embodiment 115 The vector of embodiment 114, wherein the GHS locus is a GS94 locus.

Embodiment 116 An isolated antibody or antigen binding fragment thereof that binds to Alkaline Phosphatase, Placental/Germ Cell (ALPG/P) comprising a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3, wherein:
  CDR-H1 comprises the sequence set forth in SEQ ID NO: 1,
  CDR-H2 comprises the sequence set forth in SEQ ID NO: 2,
  CDR-H3 comprises the sequence set forth in SEQ ID NO: 3,
  CDR-L1 comprises the sequence set forth in SEQ ID NO: 4,
  CDR-L2 comprises the sequence set forth in SEQ ID NO: 5; and
  CDR-L3 comprises the sequence set forth in SEQ ID NO: 6.

Embodiment 117 The isolated antibody or antigen binding fragment thereof of embodiment 116, wherein the VH chain sequence comprises the sequence set forth in SEQ ID NO: 7.

Embodiment 118 The isolated antibody or antigen binding fragment thereof of embodiment 116 or 117, wherein the VL comprises the sequence set forth in SEQ ID NO: 8.

Embodiment 119 The isolated antibody or antigen binding fragment thereof of any one of embodiments 116-118, wherein the extracellular domain comprises the sequence set forth in SEQ ID NO: 9.

Embodiment 120 A priming receptor comprising an extracellular antigen-binding domain that specifically binds Alkaline Phosphatase, Placental/Germ Cell (ALPG/P), a transmembrane domain comprising one or more ligand-inducible proteolytic cleavage sites; and an intracellular domain comprising a human or humanized transcriptional effector, wherein the extracellular antigen-binding domain comprises a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3, wherein:
  CDR-H1 comprises the sequence set forth in SEQ ID NO: 1,
  CDR-H2 comprises the sequence set forth in SEQ ID NO: 2,
  CDR-H3 comprises the sequence set forth in SEQ ID NO: 3,
  CDR-L1 comprises the sequence set forth in SEQ ID NO: 4,
  CDR-L2 comprises the sequence set forth in SEQ ID NO: 5; and
  CDR-L3 comprises the sequence set forth in SEQ ID NO: 6.

Embodiment 121 The priming receptor of embodiment 120, wherein the VH chain sequence comprises the sequence set forth in SEQ ID NO: 7.

Embodiment 122 The priming receptor of embodiment 120 or 121, wherein the VL comprises the sequence set forth in SEQ ID NO: 8.

Embodiment 123 The priming receptor of any one of embodiments 120-122, wherein the extracellular domain comprises the sequence set forth in SEQ ID NO: 9.

Embodiment 124 A chimeric antigen receptor (CAR) comprising an extracellular antigen-binding domain that specifically binds to mesothelin (MSLN), wherein the extracellular antigen-binding domain comprises a variable heavy (VH) chain sequence comprising three heavy chain CDR sequences, CDR-H1, CDR-H2, and CDR-H3, wherein:
  CDR-H1 comprises the sequence set forth in SEQ ID NO: 14,
  CDR-H2 comprises the sequence set forth in SEQ ID NO: 15, and
  CDR-H3 comprises the sequence set forth in SEQ ID NO: 16.

Embodiment 125 The chimeric antigen receptor of embodiment 124, wherein the VH chain sequence comprises the sequence set forth in SEQ ID NO: 17.

Embodiment 126 A chimeric antigen receptor (CAR) comprising an extracellular antigen-binding domain that specifically binds to mesothelin (MSLN), wherein the extracellular antigen-binding domain comprises a single domain antibody comprising a variable heavy (VHH) chain sequence comprising three heavy chain CDR sequences, CDR-H1, CDR-H2, and CDR-H3, wherein:
  CDR-H1 comprises the sequence set forth in SEQ ID NO: 10,
  CDR-H2 comprises the sequence set forth in SEQ ID NO: 11, and CDR-H3 comprises the sequence set forth in SEQ ID NO: 12.

Embodiment 127 The chimeric antigen receptor of embodiment 126, wherein the VHH chain sequence comprises the sequence set forth in SEQ ID NO: 13.

Embodiment 128 A system comprising a first chimeric polypeptide and a second chimeric polypeptide, wherein
the first chimeric polypeptide comprises a priming receptor comprising a first extracellular antigen-binding domain that specifically binds Alkaline Phosphatase, Placental/Germ Cell (ALPG/P), wherein the first extracellular antigen-binding domain comprises a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3, wherein:
CDR-H1 comprises the sequence set forth in SEQ ID NO: 1,
CDR-H2 comprises the sequence set forth in SEQ ID NO: 2,
CDR-H3 comprises the sequence set forth in SEQ ID NO: 3,
CDR-L1 comprises the sequence set forth in SEQ ID NO: 4,
CDR-L2 comprises the sequence set forth in SEQ ID NO: 5, and
CDR-L3 comprises the sequence set forth in SEQ ID NO: 6; and
the second chimeric polypeptide comprises a chimeric antigen receptor (CAR).

Embodiment 129 The system of embodiment 128, wherein the VH chain sequence comprises the sequence set forth in SEQ ID NO: 7.

Embodiment 130 The system of embodiment 128 or 129, wherein the VL chain sequence comprises the sequence set forth in SEQ ID NO: 8.

Embodiment 131 The system of embodiment 128, wherein the first extracellular antigen-binding domain comprises the sequence set forth in SEQ ID NO: 9.

Embodiment 132 The system of embodiment 128, wherein the CAR comprises a second extracellular antigen-binding domain that specifically binds to mesothelin (MSLN).

Embodiment 133 The system of embodiment 132, wherein the second extracellular antigen-binding domain comprises a variable heavy (VH) chain sequence comprising three heavy chain CDR sequences, CDR-H1, CDR-H2, and CDR-H3, wherein:
CDR-H1 comprises the sequence set forth in SEQ ID NO: 14,
CDR-H2 comprises the sequence set forth in SEQ ID NO: 15, and
CDR-H3 comprises the sequence set forth in SEQ ID NO: 16.

Embodiment 134 The system of embodiment 133, wherein the VH comprises the sequence as set forth in SEQ ID NO: 17.

Embodiment 135 The system of embodiment 132, wherein the second extracellular antigen-binding domain comprises a single domain antibody comprising a variable heavy (VHH) chain sequence comprising three heavy chain CDR sequences, CDR-H1, CDR-H2, and CDR-H3, wherein:
CDR-H1 comprises the sequence set forth in SEQ ID NO: 10,
CDR-H2 comprises the sequence set forth in SEQ ID NO: 11, and
CDR-H3 comprises the sequence set forth in SEQ ID NO: 12.

Embodiment 136 The system of embodiment 135, wherein the VHH chain sequence comprises the sequence set forth in SEQ ID NO: 13.

Embodiment 137 A system comprising a first chimeric polypeptide and a second chimeric polypeptide, wherein
the first chimeric polypeptide comprises a priming receptor, and
the second chimeric polypeptide comprises a chimeric antigen receptor (CAR) comprising an extracellular antigen-binding domain that specifically binds to mesothelin (MSLN), wherein the extracellular antigen-binding domain comprises a single domain antibody comprising a variable heavy (VHH) chain sequence comprising three heavy chain CDR sequences, CDR-H1, CDR-H2, and CDR-H3, wherein:
CDR-H1 comprises the sequence set forth in SEQ ID NO: 10,
CDR-H2 comprises the sequence set forth in SEQ ID NO: 11, and
CDR-H3 comprises the sequence set forth in SEQ ID NO: 12.

Embodiment 138 The system of embodiment 137, wherein the VHH chain sequence comprises the sequence set forth in SEQ ID NO: 13.

Embodiment 139 A system comprising a first chimeric polypeptide and a second chimeric polypeptide, wherein
the first chimeric polypeptide comprises a priming receptor, and
the second chimeric polypeptide comprises a chimeric antigen receptor (CAR) comprising an extracellular antigen-binding domain that specifically binds to mesothelin (MSLN), wherein the second extracellular antigen-binding domain comprises a variable heavy (VH) chain sequence comprising three heavy chain CDR sequences, CDR-H1, CDR-H2, and CDR-H3, wherein:
CDR-H1 comprises the sequence set forth in SEQ ID NO: 14,
CDR-H2 comprises the sequence set forth in SEQ ID NO: 15, and
CDR-H3 comprises the sequence set forth in SEQ ID NO: 16.

Embodiment 140 The system of embodiment 138, wherein the VH comprises the sequence as set forth in SEQ ID NO: 17.

Embodiment 141 A system comprising a first chimeric polypeptide and a second chimeric polypeptide, wherein
the first chimeric polypeptide comprises a priming receptor comprising a first extracellular antigen-binding domain that specifically binds to Alkaline Phosphatase, Germ Cell (ALPG/P); and
the second chimeric polypeptide comprises a CAR comprising a second extracellular antigen-binding domain that specifically binds to mesothelin (MSLN).

Embodiment 142 The system of anyone of embodiments 128-141, wherein the priming receptor comprises, from N-terminus to C-terminus,
the first extracellular antigen-binding domain;
a first transmembrane domain comprising one or more ligand-inducible proteolytic cleavage sites; and
an intracellular domain comprising a human or humanized transcriptional effector, wherein binding of ALPG/P by the first extracellular antigen-binding domain results in cleavage at the one or more ligand-inducible proteolytic cleavage sites.

Embodiment 143 The system of embodiment 142, wherein the priming receptor further comprises a first hinge domain positioned between the first extracellular antigen-binding domain and the first transmembrane domain.

Embodiment 144 The system of embodiment 142, wherein the first hinge domain comprises a CD8α or a truncated CD8α hinge domain.

Embodiment 145 The system of embodiment 144, wherein the first hinge comprises the sequence as set forth in SEQ ID NO: 18.

Embodiment 146 The system of any one of embodiments 142-145, wherein the first transmembrane domain comprises a Notch1 transmembrane domain.

Embodiment 147 The system of embodiment 146, wherein the first transmembrane domain comprises the sequence as set forth in SEQ ID NO: 19.

Embodiment 148 The system of any one of embodiments 142-147, wherein the intracellular domain comprises an HNF1a/p65 domain or a Gal4/VP64 domain.

Embodiment 149 The system of embodiment 148, wherein the intracellular domain comprises the sequence as set forth in SEQ ID NO: 23.

Embodiment 150 The system of any one of embodiments 128-149, wherein the priming receptor further comprises a stop-transfer-sequence between the first transmembrane domain and the intracellular domain.

Embodiment 151 The system of embodiment 150, wherein the stop-transfer-sequence comprises the sequence as set forth in SEQ ID NO: 20.

Embodiment 152 The system of any one of embodiments 128-151, wherein the priming receptor comprises a sequence as set forth in SEQ ID NO: 24.

Embodiment 153 The system of any one of embodiments 128-152, wherein the CAR comprises, from N-terminus to C-terminus,
  a second extracellular antigen-binding domain;
  a second transmembrane domain;
  an intracellular co-stimulatory domain; and
  an intracellular activation domain.

Embodiment 154 The system of embodiment 153, wherein the second extracellular antigen-binding domain specifically binds to mesothelin (MSLN), wherein the second extracellular antigen-binding domain comprises a single domain antibody comprising a variable heavy (VHH) chain sequence comprising three heavy chain CDR sequences, CDR-H1, CDR-H2, and CDR-H3, wherein:
  CDR-H1 comprises the sequence set forth in SEQ ID NO: 10,
  CDR-H2 comprises the sequence set forth in SEQ ID NO: 11, and
  CDR-H3 comprises the sequence set forth in SEQ ID NO: 12.

Embodiment 155 The system of embodiment 154, wherein the VHH chain sequence comprises the sequence set forth in SEQ ID NO: 13.

Embodiment 156 The system of embodiment 153, wherein the second extracellular antigen-binding domain specifically binds to mesothelin (MSLN), wherein the extracellular antigen-binding domain comprises a variable heavy (VH) chain sequence comprising three heavy chain CDR sequences, CDR-H1, CDR-H2, and CDR-H3, wherein:
  CDR-H1 comprises the sequence set forth in SEQ ID NO: 14,
  CDR-H2 comprises the sequence set forth in SEQ ID NO: 15, and
  CDR-H3 comprises the sequence set forth in SEQ ID NO: 16.

Embodiment 157 The chimeric antigen receptor of embodiment 156, wherein the VH chain sequence comprises the sequence set forth in SEQ ID NO: 17.

Embodiment 158 The system of any one of embodiments 128-157, wherein the CAR comprises a second hinge domain.

Embodiment 159 The system of embodiment 158, wherein the second hinge domain comprises a CD8α or a truncated CD8α hinge domain.

Embodiment 160 The system of any one of embodiments 153-159, wherein the second transmembrane domain comprises a CD8α transmembrane domain.

Embodiment 161 The system of any one of embodiments 153-160, wherein the intracellular co-stimulatory domain comprises a 4-1BB domain.

Embodiment 162 The system of any one of embodiments 153-161, wherein the intracellular activation domain comprises a CD3ζ domain.

Embodiment 163 The system of any one of embodiments 128-162, wherein the CAR comprises a sequence as set forth in SEQ ID NO: 30 or 31.

Embodiment 164 The system of any one of embodiments 128-163, wherein the priming receptor and the CAR are capable of binding to a same target cell if the target cell expresses ALPG/P and MSLN.

Embodiment 165 The system of embodiment 164, wherein the target cell is a human cell.

Embodiment 166 The system of embodiment 164 or 165, wherein the target cell is a cancer cell.

Embodiment 167 The system of any one of embodiments 166, wherein the cancer cell is a solid cancer cell or a liquid cancer cell.

Embodiment 168 The system of embodiments 166 or 167, wherein the cancer cell is ovarian cancer, fallopian cancer, primary peritoneal cancer, uterine cancer, mesothelioma, cervical cancer, or pancreatic cancer.

Embodiment 169 An immune cell comprising:
  at least one recombinant nucleic acid(s) of any one of embodiments 1 to 111; and/or
  the antibody or antigen-binding fragment, priming reception, CAR or system of any one of embodiments 116-168; and/or
  the vector of any one of embodiments 112-114.

Embodiment 170 The cell of embodiment 169, wherein the immune cell is a primary human immune cell.

Embodiment 171 The cell of embodiment 170, wherein the primary human immune cell is an autologous immune cell.

Embodiment 172 The cell of any one of embodiments 169-171, wherein the primary immune cell is a natural killer (NK) cell, a T cell, a CD8+ T cell, a CD4+ T cell, a primary T cell, or a T cell progenitor.

Embodiment 173 The cell of any one of embodiments 169-172, wherein the primary immune cell is a primary T cell.

Embodiment 174 The cell of any one of embodiments 169-173, wherein the primary immune cell is a primary human T cell.

Embodiment 175 The cell of any one of embodiments 169-174, wherein the primary immune cell is virus-free.

Embodiment 176 The cell of any one of embodiments 169-174, wherein the immune cell is an autologous immune cell.

Embodiment 177 The cell of any one of embodiments 169-174, wherein the immune cell is an allogeneic immune cell.

Embodiment 178 A primary immune cell comprising at least one recombinant nucleic acid comprising
  a priming receptor comprising a first extracellular antigen-binding domain that specifically binds to ALPG/P;
  a chimeric antigen receptor comprising a second extracellular antigen-binding domain that specifically binds to MSLN;
  a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and a second nucleic acid sequence at least 15 nucleotides in length, wherein the second nucleic acid sequence is:
    complementary to nucleotides 518 to 559 of an mRNA encoding human PTPN2 comprising the sequence set forth in SEQ ID NO: 40; or
    complementary to nucleotides 1294 to 2141 of an mRNA encoding human TOX comprising the sequence set forth in SEQ ID NO: 41;
  wherein the recombinant nucleic acid is inserted into a target region of the genome of the primary immune cell, and wherein the primary immune cell does not comprise a viral vector for introducing the recombinant nucleic acid into the primary immune cell.

Embodiment 179 A primary immune cell comprising at least one recombinant nucleic acid(s) comprising a first nucleic acid comprising the sequence set forth in SEQ ID NO: 49; and a second nucleic acid comprising the sequence set forth in SEQ ID NO: 82, inserted into a target region of the genome of the primary immune cell, and wherein the primary immune cell does not comprise a viral vector for introducing the recombinant nucleic acid(s) into the primary immune cell.

Embodiment 180 A primary immune cell comprising at least one recombinant nucleic acid(s) comprising a first nucleic acid comprising the sequence set forth in SEQ ID NO: 49; and a second nucleic acid comprising the sequence set forth in SEQ ID NO: SEQ ID NOs: 99 or 104, inserted into a target region of the genome of the primary immune cell, and wherein the primary immune cell does not comprise a viral vector for introducing the recombinant nucleic acid into the primary immune cell.

Embodiment 181 A viable, virus-free, primary cell comprising a ribonucleoprotein (RNP)-recombinant nucleic acid complex, wherein the RNP comprises a nuclease domain and a guide RNA, and wherein the recombinant nucleic acid encodes:
  a priming receptor comprising a first extracellular antigen-binding domain that specifically binds to ALPG/P;
  a chimeric antigen receptor comprising a second extracellular antigen-binding domain that specifically binds to MSLN;
  a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and a second nucleic acid sequence at least 15 nucleotides in length, wherein the second nucleic acid sequence is:
    complementary to nucleotides 518 to 559 of an mRNA encoding human PTPN2 comprising the sequence set forth in SEQ ID NO: 40; or
    complementary to nucleotides 1294 to 2141 of an mRNA encoding human TOX comprising the sequence set forth in SEQ ID NO: 41; and
  wherein the 5' and 3' ends of the recombinant nucleic acid comprise nucleotide sequences that are homologous to genomic sequences flanking an insertion site in the genome of the primary cell.

Embodiment 182 A viable, virus-free, primary cell comprising a ribonucleoprotein complex (RNP)-recombinant nucleic acid(s) complex, wherein the RNP comprises a nuclease domain and a guide RNA, wherein recombinant nucleic acid(s) comprises a first nucleic acid comprising the sequence set forth in SEQ ID NO: 49; and a second nucleic acid comprising the sequence set forth in SEQ ID NO: 82, and wherein the 5' and 3' ends of the recombinant nucleic acid(s) comprise nucleotide sequences that are homologous to genomic sequences flanking an insertion site in the genome of the primary cell.

Embodiment 183 A viable, virus-free, primary cell comprising a ribonucleoprotein complex (RNP)-recombinant nucleic acid(s) complex, wherein the RNP comprises a nuclease domain and a guide RNA, wherein recombinant nucleic acid(s) comprises a first nucleic acid comprising the sequence set forth in SEQ ID NO: 49; and a second nucleic acid comprising the sequence set forth in SEQ ID NO: SEQ ID NOs: 99 or 104, and wherein the 5' and 3' ends of the recombinant nucleic acid(s) comprise nucleotide sequences that are homologous to genomic sequences flanking an insertion site in the genome of the primary cell.

Embodiment 184 The cell of any one of embodiments 169-183, wherein the cell comprises a sequence selected from the group consisting of the sequences set forth in SEQ ID NOs: 168, 167, or 166.

Embodiment 185 The cell of any one of embodiments 169-184, wherein the first nucleic acid reduces expression of FAS in the immune cell by at least 50%, 55%, 60%, 65%, 75%, 80%, 85%, 90%, 95%, or 99% as compared to a control cell that does not comprise the first nucleic acid.

Embodiment 186 The cell of embodiment 184, wherein expression of FAS in the immune cell is reduced by at least 50%, 55%, 60%, 65%, 75%, 80%, 85%, 90%, 95%, or 99% as compared to a control cell that does not comprise the first nucleic acid.

Embodiment 187 The cell of any one of embodiments 169-186, wherein the second nucleic acid reduces expression of PTPN2 in the immune cell by at least 50%, 55%, 60%, 65%, 75%, 80%, 85%, 90%, 95%, or 99% as compared to a control cell that does not comprise the second nucleic acid.

Embodiment 188 The cell of embodiment 187, wherein expression of PTPN2 in the immune cell is reduced by at least 50%, 55%, 60%, 65%, 75%, 80%, 85%, 90%, 95%, or 99% as compared to a control cell that does not comprise the second nucleic acid Embodiment 189 The cell of any one of embodiments 169-186, wherein the second nucleic acid reduces expression of TOX in the immune cell by at least 50%, 55%, 60%, 65%, 75%, 80%, 85%, 90%, 95%, or 99% as compared to a control cell that does not comprise the second nucleic acid.

Embodiment 190 The cell of embodiment 189, wherein expression of TOX in the immune cell is reduced by at least 50%, 55%, 60%, 65%, 75%, 80%, 85%, 90%, 95%, or 99% as compared to a control cell that does not comprise the second nucleic acid.

Embodiment 191 The cell of any one of embodiments 184-190, wherein expression of FAS, PTPN2, and/or TOX is determined by a nucleic acid assay or a protein assay.

Embodiment 192 The cell of embodiment 191, wherein the nucleic acid assay comprises at least one of polymerase chain reaction (PCR), quantitative PCR (qPCR), RT-qPCR, microarray, gene array, or RNAseq.

Embodiment 193 The cell of embodiment 191, wherein the protein assay comprises at least one of immunoblotting, fluorescence activated cell sorting, flow-cytometry, magnetic-activated cell sorting, or affinity-based cell separation.

Embodiment 194 A population of cells comprising a plurality of immune cells of any one of embodiments 169-193.

Embodiment 195 A pharmaceutical composition comprising the immune cell of any one of embodiments 169 to 193 or the population of cells of embodiment 194, and a pharmaceutically acceptable excipient.

Embodiment 196 A pharmaceutical composition comprising the recombinant nucleic acid of any one of embodiments 1-111 or the vector of any one of embodiments 112-114, and a pharmaceutically acceptable excipient.

Embodiment 197 A method of editing an immune cell, comprising:
  providing a ribonucleoprotein (RNP)-recombinant nucleic acid complex, wherein the RNP comprises a nuclease domain and a guide RNA, wherein the recombinant nucleic acid comprises the recombinant nucleic acid of any one of embodiments 1 to 111, and wherein the 5' and 3' ends of the recombinant nucleic acid comprise nucleotide sequences that are homologous to genomic sequences flanking an insertion site in the genome of the immune cell;
  non-virally introducing the RNP-recombinant nucleic acid complex into the immune cell, wherein the guide RNA specifically hybridizes to a target region of the genome of the primary immune cell, and wherein the nuclease domain cleaves the target region to create the insertion site in the genome of the immune cell; and editing the immune cell via insertion of the recombinant nucleic acid of any one of embodiments 1 to 111 into the insertion site in the genome of the immune cell.

Embodiment 198 The method of embodiment 197, wherein non-virally introducing comprises electroporation.

Embodiment 199 The method of embodiment 197 or 198, wherein the nuclease domain comprises a CRISPR-associated endonuclease (Cas), optionally a Cas9 nuclease.

Embodiment 200 The method of any one of embodiments 197 to 199, wherein the target region of the genome of the cell is a T Cell Receptor Alpha Constant (TRAC) locus or a genomic safe harbor (GSH) locus.

Embodiment 201 The method of embodiment 200, wherein the GSH locus is the GS94 locus.

Embodiment 202 The method of any one of embodiments 197 to 201, wherein the recombinant nucleic acid is a double-stranded recombinant nucleic acid or a single-stranded recombinant nucleic acid.

Embodiment 203 The method of any one of embodiments 197 to 202, wherein the recombinant nucleic acid is a linear recombinant nucleic acid or a circular recombinant nucleic acid, optionally wherein the circular recombinant nucleic acid is a plasmid.

Embodiment 204 The method of any one of embodiments 197 to 203, wherein the immune cell is a primary human immune cell.

Embodiment 205 The method of any one of embodiments 197 to 204, wherein the immune cell is an allogeneic immune cell.

Embodiment 206 The method of any one of embodiments 197 to 204, wherein the immune cell is an autologous immune cell.

Embodiment 207 The method of any one of embodiments 197 to 206, wherein the immune cell is a natural killer (NK) cell, a T cell, a CD8+ T cell, a CD4+ T cell, a primary T cell, or a T cell progenitor.

Embodiment 208 The method of any one of embodiments 197 to 207, wherein the immune cell is a primary T cell.

Embodiment 209 The method of any one of embodiments 197 to 208, wherein the immune cell is a primary human T cell.

Embodiment 210 The method of any one of embodiments 197 to 209, wherein the immune cell is virus-free.

Embodiment 211 The method of any one of embodiments 197 to 210, further comprising obtaining the immune cell from a patient and introducing the recombinant nucleic acid in vitro.

Embodiment 212 A method of treating a disease in a subject comprising administering the immune cell of any one of embodiments 169-194 or the pharmaceutical composition of embodiments 195 or 196 to the subject.

Embodiment 213 The method of embodiment 212, wherein the disease is cancer.

Embodiment 214 The method of embodiment 213, wherein the cancer is a solid cancer or a liquid cancer.

Embodiment 215 The method of embodiment 213 or 214, wherein the cancer is ovarian cancer, fallopian cancer, primary peritoneal cancer, uterine cancer, mesothelioma, cervical cancer, or pancreatic cancer.

Embodiment 216 The method of any one of embodiments 213-215, wherein the administration of the immune cell enhances an immune response in the subject.

Embodiment 217 The method of embodiment 216, wherein the enhanced immune response is an adaptive immune response.

Embodiment 218 The method of embodiment 216, wherein the enhanced immune response is an innate immune response.

Embodiment 219 The method of any one of embodiments 213-218, wherein the enhanced immune response is an increased expression of at least one cytokine or chemokine.

Embodiment 220 The method of embodiment 219, wherein the at least one cytokine or chemokine is IL-2 or IFNγ.

Embodiment 221 The method of any one of embodiments 212-215, further comprising administering an immunotherapy to the subject concurrently with the immune cell or subsequently to the immune cell.

Embodiment 222 A method of inhibiting a target cell in a subject comprising administering the immune cell of any one of embodiments 169-194 to the subject, wherein the immune cell inhibits the target cell.

Embodiment 223 The method of embodiment 222, wherein the target cell expresses ALPG/P and MSLN.

Embodiment 224 The method of embodiment 222 or 223, wherein the target cell is a cancer cell.

Embodiment 225 A method of inducing expression of a chimeric antigen receptor with a priming receptor in an immune cell comprising:
  obtaining an immune cell comprising
    the recombinant nucleic acid of any one of embodiments 1-111; and/or
    the antibody or antigen-binding fragment, priming reception, CAR or system of any one of embodiments 116-168; and/or
    the vector of any one of embodiments 112-114; and contacting the immune cell with a target cell expressing ALPG/P and MSLN, wherein binding of the priming receptor to ALPG/P on the target cell induces activation of the priming receptor and expression of the chimeric antigen receptor.

Embodiment 226 A method of modulating the activity of an immune cell comprising:
obtaining an immune cell comprising
the recombinant nucleic acid of any one of embodiments 1-111; and/or
the antibody or antigen-binding fragment, priming reception, CAR or system of any one of embodiments 116-168; and/or
the vector of any one of embodiments 112-114; and
contacting the immune cell with a target cell expressing ALPG/P and MSLN, wherein binding of the priming receptor to ALPG/P on the target cell induces activation of the priming receptor and expression of the chimeric antigen receptor and wherein binding of the chimeric antigen receptor to MSLN on the target cell modulates the activity of the immune cell.

Embodiment 227 The method of embodiment 226, wherein the modulation of the immune cell activity comprises enhancing an immune response.

Embodiment 228 The method of embodiment 227, wherein the enhanced immune response is an adaptive immune response.

Embodiment 229 The method of embodiment 227, wherein the enhanced immune response is an innate immune response.

Embodiment 230 The method of any one of embodiments 226-229, wherein the immune cell activity is an increased expression of at least one cytokine or chemokine.

Embodiment 231 The method of embodiment 230, wherein the at least one cytokine or chemokine is IL-2 or IFNγ.

Embodiment 232 The method of any one of embodiments 197-231, wherein expression of FAS in the immune cell is reduced by at least 50%, 55%, 60%, 65%, 75%, 80%, 85%, 90%, 95%, or 99% as compared to a control cell that does not comprise the first nucleic acid.

Embodiment 233 The method of any one of embodiments 197-232, wherein expression of PTPN2 in the immune cell is reduced by at least 50%, 55%, 60%, 65%, 75%, 80%, 85%, 90%, 95%, or 99% as compared to a control cell that does not comprise the second nucleic acid Embodiment 234 The method of any one of embodiments 197-232, wherein expression of TOX in the immune cell is reduced by at least 50%, 55%, 60%, 65%, 75%, 80%, 85%, 90%, 95%, or 99% as compared to a control cell that does not comprise the second nucleic acid.

Embodiment 235 The method of any one of embodiments 232-234, wherein expression of FAS, PTPN2, and/or TOX in the immune cell is determined by a nucleic acid assay or a protein assay.

Embodiment 236 The method of embodiment 235, wherein the nucleic acid assay comprises at least one of polymerase chain reaction (PCR), quantitative PCR (qPCR), RT-qPCR, microarray, gene array, or RNAseq.

Embodiment 237 The method of embodiment 235, wherein the protein assay comprises at least one of immunoblotting, fluorescence activated cell sorting, flow-cytometry, magnetic-activated cell sorting, or affinity-based cell separation.

In one aspect, provided herein are priming receptors comprising an extracellular antigen-binding domain that specifically binds Alkaline Phosphatase, Placental/Germ Cell (ALPG/P), a transmembrane domain comprising one or more ligand-inducible proteolytic cleavage sites; and an intracellular domain comprising a human or humanized transcriptional effector, wherein the extracellular antigen-binding domain comprises a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3, wherein:
CDR-H1 comprises the sequence set forth in SEQ ID NO: 1,
CDR-H2 comprises the sequence set forth in SEQ ID NO: 2,
CDR-H3 comprises the sequence set forth in SEQ ID NO: 3,
CDR-L1 comprises the sequence set forth in SEQ ID NO: 4,
CDR-L2 comprises the sequence set forth in SEQ ID NO: 5; and
CDR-L3 comprises the sequence set forth in SEQ ID NO: 6.

In some embodiments, the VH chain sequence comprises the sequence set forth in SEQ ID NO: 7.

In some embodiments, the VL comprises the sequence set forth in SEQ ID NO: 8.

In some embodiments, the extracellular domain comprises the sequence set forth in SEQ ID NO: 9.

In another aspect, provided herein are chimeric antigen receptors (CAR) comprising an extracellular antigen-binding domain that specifically binds to mesothelin (MSLN), wherein the extracellular antigen-binding domain comprises a variable heavy (VH) chain sequence comprising three heavy chain CDR sequences, CDR-H1, CDR-H2, and CDR-H3, wherein:
CDR-H1 comprises the sequence set forth in SEQ ID NO: 14,
CDR-H2 comprises the sequence set forth in SEQ ID NO: 15, and
CDR-H3 comprises the sequence set forth in SEQ ID NO: 16.

In some embodiments, the VH chain sequence comprises the sequence set forth in SEQ ID NO: 17.

In another aspect, provided herein are chimeric antigen receptors (CAR) comprising an extracellular antigen-binding domain that specifically binds to mesothelin (MSLN), wherein the extracellular antigen-binding domain comprises a single domain antibody comprising a variable heavy (VHH) chain sequence comprising three heavy chain CDR sequences, CDR-H1, CDR-H2, and CDR-H3, wherein:
CDR-H1 comprises the sequence set forth in SEQ ID NO: 10,
CDR-H2 comprises the sequence set forth in SEQ ID NO: 11, and
CDR-H3 comprises the sequence set forth in SEQ ID NO: 12.

In some embodiments, the VHH chain sequence comprises the sequence set forth in SEQ ID NO: 13.

In another aspect, provided herein are systems comprising a first chimeric polypeptide and a second chimeric polypeptide, wherein the first chimeric polypeptide comprises a priming receptor comprising a first extracellular antigen-binding domain that specifically binds Alkaline Phosphatase, Placental/Germ Cell (ALPG/P), wherein the first extracellular antigen-binding domain comprises a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3, wherein:
   CDR-H1 comprises the sequence set forth in SEQ ID NO: 1,
   CDR-H2 comprises the sequence set forth in SEQ ID NO: 2,
   CDR-H3 comprises the sequence set forth in SEQ ID NO: 3,
   CDR-L1 comprises the sequence set forth in SEQ ID NO: 4,
   CDR-L2 comprises the sequence set forth in SEQ ID NO: 5, and
   CDR-L3 comprises the sequence set forth in SEQ ID NO: 6; and
   the second chimeric polypeptide comprises a chimeric antigen receptor (CAR).

In some embodiments, the VH chain sequence comprises the sequence set forth in SEQ ID NO: 7.

In some embodiments, the VL chain sequence comprises the sequence set forth in SEQ ID NO: 8.

In some embodiments, the first extracellular antigen-binding domain comprises the sequence set forth in SEQ ID NO: 9.

In some embodiments, the CAR comprises a second extracellular antigen-binding domain that specifically binds to mesothelin (MSLN).

In some embodiments, the second extracellular antigen-binding domain comprises a variable heavy (VH) chain sequence comprising three heavy chain CDR sequences, CDR-H1, CDR-H2, and CDR-H3, wherein:
   CDR-H1 comprises the sequence set forth in SEQ ID NO: 14,
   CDR-H2 comprises the sequence set forth in SEQ ID NO: 15, and
   CDR-H3 comprises the sequence set forth in SEQ ID NO: 16.

In some embodiments, the VH comprises the sequence as set forth in SEQ ID NO: 17.

In some embodiments, the second extracellular antigen-binding domain comprises a single domain antibody comprising a variable heavy (VHH) chain sequence comprising three heavy chain CDR sequences, CDR-H1, CDR-H2, and CDR-H3, wherein:
   CDR-H1 comprises the sequence set forth in SEQ ID NO: 10,
   CDR-H2 comprises the sequence set forth in SEQ ID NO: 11, and
   CDR-H3 comprises the sequence set forth in SEQ ID NO: 12.

In some embodiments, the VHH chain sequence comprises the sequence set forth in SEQ ID NO: 13.

In another aspect, provided herein are systems comprising a first chimeric polypeptide and a second chimeric polypeptide, wherein:
   the first chimeric polypeptide comprises a priming receptor, and
   the second chimeric polypeptide comprises a chimeric antigen receptor (CAR) comprising an extracellular antigen-binding domain that specifically binds to mesothelin (MSLN), wherein the extracellular antigen-binding domain comprises a single domain antibody comprising a variable heavy (VHH) chain sequence comprising three heavy chain CDR sequences, CDR-H1, CDR-H2, and CDR-H3, wherein:
   CDR-H1 comprises the sequence set forth in SEQ ID NO: 10,
   CDR-H2 comprises the sequence set forth in SEQ ID NO: 11, and
   CDR-H3 comprises the sequence set forth in SEQ ID NO: 12.

In some embodiments, the VHH chain sequence comprises the sequence set forth in SEQ ID NO: 13.

In another aspect, provided herein are systems comprising a first chimeric polypeptide and a second chimeric polypeptide, wherein
   the first chimeric polypeptide comprises a priming receptor, and
   the second chimeric polypeptide comprises a chimeric antigen receptor (CAR) comprising an extracellular antigen-binding domain that specifically binds to mesothelin (MSLN), wherein the second extracellular antigen-binding domain comprises a variable heavy (VH) chain sequence comprising three heavy chain CDR sequences, CDR-H1, CDR-H2, and CDR-H3, wherein:
   CDR-H1 comprises the sequence set forth in SEQ ID NO: 14,
   CDR-H2 comprises the sequence set forth in SEQ ID NO: 15, and
   CDR-H3 comprises the sequence set forth in SEQ ID NO: 16.

In some embodiments, the VH comprises the sequence as set forth in SEQ ID NO: 17.

In another aspect, provided herein are systems comprising a first chimeric polypeptide and a second chimeric polypeptide, wherein
   the first chimeric polypeptide comprises a priming receptor comprising a first extracellular antigen-binding domain that specifically binds to Alkaline Phosphatase, Germ Cell (ALPG/P); and
   the second chimeric polypeptide comprises a CAR comprising a second extracellular antigen-binding domain that specifically binds to mesothelin (MSLN).

In some embodiments, the priming receptor comprises, from N-terminus to C-terminus,
   the first extracellular antigen-binding domain;
   a first transmembrane domain comprising one or more ligand-inducible proteolytic cleavage sites; and
   an intracellular domain comprising a human or humanized transcriptional effector,
   wherein binding of ALPG/P by the first extracellular antigen-binding domain results in cleavage at the one or more ligand-inducible proteolytic cleavage sites.

In some embodiments, the priming receptor further comprises a first hinge domain positioned between the first extracellular antigen-binding domain and the first transmembrane domain.

In some embodiments, the first hinge domain comprises a CD8α or a truncated CD8α hinge domain.

In some embodiments, the first hinge comprises the sequence as set forth in SEQ ID NO: 18.

In some embodiments, the first transmembrane domain comprises a Notch1 transmembrane domain.

In some embodiments, the first transmembrane domain comprises the sequence as set forth in SEQ ID NO: 19.

In some embodiments, the intracellular domain comprises an HNF1a/p65 domain or a Gal4/VP64 domain.

In some embodiments, the intracellular domain comprises the sequence as set forth in SEQ ID NO: 23.

In some embodiments, the priming receptor further comprises a stop-transfer-sequence between the first transmembrane domain and the intracellular domain.

In some embodiments, the stop-transfer-sequence comprises the sequence as set forth in SEQ ID NO: 20.

In some embodiments, the priming receptor comprises a sequence as set forth in SEQ ID NO: 24.

In some embodiments, the CAR comprises, from N-terminus to C-terminus,
 a second extracellular antigen-binding domain;
 a second transmembrane domain;
 an intracellular co-stimulatory domain; and
 an intracellular activation domain.

In some embodiments, the second extracellular antigen-binding domain specifically binds to mesothelin (MSLN), wherein the second extracellular antigen-binding domain comprises a single domain antibody comprising a variable heavy (VHH) chain sequence comprising three heavy chain CDR sequences, CDR-H1, CDR-H2, and CDR-H3, wherein:
 CDR-H1 comprises the sequence set forth in SEQ ID NO: 10,
 CDR-H2 comprises the sequence set forth in SEQ ID NO: 11, and
 CDR-H3 comprises the sequence set forth in SEQ ID NO: 12.

In some embodiments, the VHH chain sequence comprises the sequence set forth in SEQ ID NO: 13.

In some embodiments, the second extracellular antigen-binding domain specifically binds to mesothelin (MSLN), wherein the extracellular antigen-binding domain comprises a variable heavy (VH) chain sequence comprising three heavy chain CDR sequences, CDR-H1, CDR-H2, and CDR-H3, wherein:
 CDR-H1 comprises the sequence set forth in SEQ ID NO: 14,
 CDR-H2 comprises the sequence set forth in SEQ ID NO: 15, and
 CDR-H3 comprises the sequence set forth in SEQ ID NO: 16.

In some embodiments, the VH chain sequence comprises the sequence set forth in SEQ ID NO: 17.

In some embodiments, the CAR comprises a second hinge domain.

In some embodiments, the second hinge domain comprises a CD8α or a truncated CD8α hinge domain.

In some embodiments, the second transmembrane domain comprises a CD8α transmembrane domain.

In some embodiments, the intracellular co-stimulatory domain comprises a 4-1BB domain.

In some embodiments, the intracellular activation domain comprises a CD3ζ domain.

In some embodiments, the CAR comprises a sequence as set forth in SEQ ID NO: 30 or 31.

In some embodiments, the priming receptor and the CAR are capable of binding to a same target cell if the target cell expresses ALPG/P and MSLN.

In some embodiments, the target cell is a human cell.

In some embodiments, the target cell is a cancer cell.

In some embodiments, the cancer cell is a solid cancer cell or a liquid cancer cell.

In some embodiments, the cancer cell is ovarian cancer, fallopian cancer, primary peritoneal cancer, uterine cancer, mesothelioma, cervical cancer, or pancreatic cancer.

In another aspect, provided herein are isolated antibodies or antigen binding fragments thereof that binds to mesothelin (MSLN), comprising a single domain antibody comprising a variable heavy (VHH) chain sequence comprising three heavy chain CDR sequences, CDR-H1, CDR-H2, and CDR-H3, wherein: CDR-H1 comprises the sequence set forth in SEQ ID NO: 10, CDR-H2 comprises the sequence set forth in SEQ ID NO: 11, and CDR-H3 comprises the sequence set forth in SEQ ID NO: 12.

In some embodiments, the VHH chain sequence comprises the sequence set forth in SEQ ID NO: 13.

In one aspect, provided herein are recombinant nucleic acids comprising a nucleic acid sequence at least 15 nucleotides in length complementary to nucleotides 1126 to 1364 of an mRNA encoding human FAS comprising the sequence set forth in SEQ ID NO: 39.

In one aspect, provided herein are recombinant nucleic acids comprising a nucleic acid sequence at least 15 nucleotides in length complementary to nucleotides 518 to 559 of an mRNA encoding human Protein Tyrosine Phosphatase Non-Receptor Type 2 (PTPN2) comprising the sequence set forth in SEQ ID NO: 40.

In one aspect, provided herein are recombinant nucleic acids comprising a nucleic acid sequence at least 15 nucleotides in length complementary to nucleotides 1294 to 2141 of an mRNA encoding human thymocyte selection associated high mobility group box (TOX) comprising the sequence set forth in SEQ ID NO: 41.

In some embodiments, the nucleic acid sequence is at least 16, 17, 18, 19, 20, 21, or 22 nucleotides in length.

In some embodiments, the nucleic acid is a short hairpin RNA (shRNA), a small interfering RNA (siRNA), a double stranded RNA (dsRNA), or an antisense oligonucleotide.

In some embodiments, the nucleic acid is shRNA.

In some embodiments, the nucleic acid comprises a sequence selected from the group consisting of the sequences set forth in SEQ ID NOs: 42 to 71.

In some embodiments, the nucleic acid comprises the sequence set forth in SEQ ID NO: 49.

In some embodiments, the nucleic acid reduces expression of FAS in the immune cell by at least 50%, 55%, 60%, 65%, 75%, 80%, 85%, 90%, 95%, or 99% as compared to a control cell that does not comprise the nucleic acid.

In some embodiments, the nucleic acid comprises a sequence selected from the group consisting of the sequences set forth in SEQ ID NOs: 72 to 97.

In some embodiments, the nucleic acid comprises the sequence set forth in SEQ ID NO: 82.

In some embodiments, the nucleic acid reduces expression of PTPN2 in the immune cell by at least 50%, 55%, 60%, 65%, 75%, 80%, 85%, 90%, 95%, or 99% as compared to a control cell that does not comprise the nucleic acid.

In some embodiments, the nucleic acid comprises a sequence selected from the group consisting of the sequences set forth in SEQ ID NOs: 98 to 125.

In some embodiments, the nucleic acid comprises the sequence set forth in SEQ ID NO: SEQ ID NOs: 99 or 104.

In some embodiments, the nucleic acid reduces expression of TOX in the immune cell by at least 50%, 55%, 60%, 65%, 75%, 80%, 85%, 90%, 95%, or 99% as compared to a control cell that does not comprise the nucleic acid.

In some embodiments, the recombinant nucleic acid further comprises a nucleotide sequence encoding a priming receptor comprising a first extracellular antigen-binding domain that specifically binds to a first antigen and a nucleotide sequence encoding a chimeric antigen receptor (CAR) comprising a second extracellular antigen-binding domain that specifically binds to a second antigen, wherein the first antigen and the second antigen are distinct.

In some embodiments, the recombinant nucleic acid comprises, in a 5' to 3' direction, the CAR; the nucleic as disclosed herein; and the priming receptor.

In some embodiments, the nucleic acid comprises, in a 5' to 3' direction; the priming receptor; the nucleic as disclosed herein; and the CAR.

In some embodiments, the recombinant nucleic acid further comprises a 5' homology directed repair arm and/or a 3' homology directed repair arm complementary to an insertion site in a host cell chromosome.

In some embodiments, the recombinant nucleic acid comprises the 5' homology directed repair arm and the 3' homology directed repair arm.

In some embodiments, the recombinant nucleic acid is incorporated into an expression cassette or an expression vector.

In some embodiments, the expression cassette or the expression vector further comprises a constitutive promoter upstream of the recombinant nucleic acid.

In one aspect, provided herein are one or more recombinant nucleic acids comprising a first nucleic acid sequence at least 15 nucleotides in length complementary to nucleotides 1126 to 1364 of an mRNA encoding human FAS comprising the sequence set forth in SEQ ID NO: 39 and a second nucleic acid sequence at least 15 nucleotides in length complementary to nucleotides 518 to 559 of an mRNA encoding human PTPN2 comprising the sequence set forth in SEQ ID NO: 40.

In one aspect, provided herein are one or more recombinant nucleic acids comprising a first nucleic acid at least 15 nucleotides in length complementary to nucleotides 1126 to 1364 of an mRNA encoding human FAS comprising the sequence set forth in SEQ ID NO: 39; and a second nucleic acid at least 15 nucleotides in length complementary to nucleotides 1294 to 2141 of an mRNA encoding human TOX comprising the sequence set forth in SEQ ID NO: 41.

In some embodiments, the first and second nucleic acids are an shRNA, an siRNA, a dsRNA, or an antisense oligonucleotide.

In some embodiments, the first and second nucleic acids are each shRNA.

In some embodiments, the first nucleic acid comprises a sequence selected from the group consisting of the sequences set forth in SEQ ID NOs: 42 to 71.

In some embodiments, the first nucleic acid comprises the sequence set forth in SEQ ID NO: 49.

In some embodiments, the first nucleic acid reduces expression of FAS in the immune cell by at least 50%, 55%, 60%, 65%, 75%, 80%, 85%, 90%, 95%, or 99% as compared to a control cell that does not comprise the first nucleic acid.

In some embodiments, the second nucleic acid comprises a sequence selected from the group consisting of the sequences set forth in SEQ ID NOs: 72 to 97.

In some embodiments, the second nucleic acid comprises the sequence set forth in SEQ ID NO: 82.

In some embodiments, the second nucleic acid reduces expression of PTPN2 in the immune cell by at least 50%, 55%, 60%, 65%, 75%, 80%, 85%, 90%, 95%, or 99% as compared to a control cell that does not comprise the second nucleic acid.

In some embodiments, the first nucleic acid comprises a sequence selected from the group consisting of the sequences set forth in SEQ ID NOs: 42 to 71; and the second nucleic acid comprises a sequence selected from the group consisting of the sequences set forth in SEQ ID NOs: 72 to 97.

In some embodiments, the first nucleic acid comprises the sequence set forth in SEQ ID NO: 49 and the second nucleic acid comprises the sequence set forth in SEQ ID NO: 82.

In some embodiments, the second nucleic acid comprises a sequence selected from the group consisting of the sequences set forth in SEQ ID NOs: 98 to 125.

In some embodiments, the second nucleic acid comprises the sequence set forth in SEQ ID NO: SEQ ID NOs: 99 or 104.

In some embodiments, the second nucleic acid reduces expression of PTPN2 in the immune cell by at least 50%, 55%, 60%, 65%, 75%, 80%, 85%, 90%, 95%, or 99% as compared to a control cell that does not comprise the second nucleic acid.

In some embodiments, the first nucleic acid comprises a sequence selected from the group consisting of the sequences set forth in SEQ ID NOs: 42 to 71; and the second nucleic acid comprises a sequence selected from the group consisting of the sequences set forth in SEQ ID NOs: 98 to 125.

In some embodiments, the first nucleic acid comprises the sequence set forth in SEQ ID NO: 49 and the second nucleic acid comprises the sequence set forth in SEQ ID NO: SEQ ID NOs: 99 or 104.

In some embodiments, the first nucleic acid further comprises a 5' homology directed repair arm and/or a 3' homology directed repair arm complementary to an insertion site in a host cell chromosome.

In some embodiments, the second nucleic acid comprises the 5' homology directed repair arm and/or the 3' homology directed repair arm.

In some embodiments, the first nucleic acid and the second nucleic acid are encoded on a single nucleic acid.

In some embodiments, the first nucleic acid comprises the 5' homology directed repair arm and the second nucleic acid comprises the 3' homology directed repair arm.

In some embodiments, the first nucleic acid and the second nucleic acid are encoded on different nucleic acids.

In some embodiments, the nucleic acid further comprises a nucleotide sequence encoding a priming receptor comprising a first extracellular antigen-binding domain that specifically binds to a first antigen and a nucleotide sequence encoding a chimeric antigen receptor (CAR) comprising a second extracellular antigen-binding domain that specifically binds to a second antigen, wherein the first antigen and the second antigen are distinct.

In some embodiments, the nucleic acid comprises, in a 5' to 3' direction: the CAR; the first nucleic acid; the second nucleic acid; and the priming receptor.

In some embodiments, the first nucleic acid is incorporated into an expression cassette or an expression vector.

In some embodiments, the second nucleic acid is incorporated into an expression cassette or an expression vector.

In some embodiments, the first nucleic acid and the second nucleic acid are incorporated into a single expression cassette or a single expression vector.

In some embodiments, the expression cassette or the expression vector further comprises a constitutive promoter upstream of the first nucleic acid and/or upstream of the second nucleic acid.

In some embodiments, the expression vector is a non-viral vector.

In one aspect, provided herein are expression vectors comprising the recombinant nucleic acid(s) as disclosed herein.

In some embodiments, the expression vector is a non-viral vector.

In some embodiments, the 5' and 3' ends of the recombinant nucleic acid(s) comprise one or more nucleotide sequences that are homologous to genomic sequences flanking an insertion site in a genome of a primary cell.

In some embodiments, the insertion site is located at a T Cell Receptor Alpha Constant (TRAC) locus or a genomic safe harbor (GSH) locus.

In some embodiments, the GSH locus is the GS94 locus.

In one aspect, provided herein are immune cells comprising a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and a second nucleic acid sequence at least 15 nucleotides in length, wherein the second nucleic acid sequence is complementary to nucleotides 518 to 559 of an mRNA encoding human PTPN2 comprising the sequence set forth in SEQ ID NO: 40; or complementary to nucleotides 1294 to 2141 of an mRNA encoding human TOX comprising the sequence set forth in SEQ ID NO: 41.

In some embodiments, the second nucleic acid sequence is complementary to nucleotides 518 to 559 of an mRNA encoding human PTPN2 comprising the sequence set forth in SEQ ID NO: 40.

In some embodiments, the second nucleic acid sequence is complementary to nucleotides 1294 to 2141 of an mRNA encoding human TOX comprising the sequence set forth in SEQ ID NO: 41.

In one aspect, provided herein are immune cells comprising a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and a second nucleic acid sequence at least 15 nucleotides in length, wherein the second nucleic acid sequence is complementary to nucleotides 518 to 559 of an mRNA encoding human PTPN2 comprising the sequence set forth in SEQ ID NO: 40.

In one aspect, provided herein are immune cells comprising a first nucleic acid sequence at least 15 nucleotides in length, wherein the first nucleic acid sequence is complementary to nucleotides 1126 to 1364 of an mRNA encoding human FAS comprising the sequence set forth in SEQ ID NO: 39, and a second nucleic acid sequence at least 15 nucleotides in length, wherein the second nucleic acid sequence is complementary to nucleotides 1294 to 2141 of an mRNA encoding human TOX comprising the sequence set forth in SEQ ID NO: 41.

In some embodiments, the first and second nucleic acids are an shRNA, an siRNA, a dsRNA, or an antisense oligonucleotide.

In some embodiments, the first and second nucleic acids are shRNA.

In some embodiments, the first nucleic acid comprises a sequence selected from the group consisting of the sequences set forth in SEQ ID NOs: 42 to 71.

In some embodiments, the first nucleic acid comprises the sequence set forth in SEQ ID NO: 49.

In some embodiments, the second nucleic acid comprises a sequence selected from the group consisting of the sequences set forth in SEQ ID NOs: 72 to 97.

In some embodiments, the second nucleic acid comprises the sequence set forth in SEQ ID NO: 82.

In some embodiments, the first nucleic acid comprises a sequence selected from the group consisting of the sequences set forth in SEQ ID NOs: 42 to 71; and the second nucleic acid sequence comprises a sequence selected from the group consisting of the sequences set forth in SEQ ID NOs: 72 to 97.

In some embodiments, the first nucleic acid comprises the sequence set forth in SEQ ID NO: 49; and the second nucleic acid comprises the sequence set forth in SEQ ID NO: 82.

In some embodiments, the second nucleic acid comprises a sequence selected from the group consisting of the sequences set forth in SEQ ID NOs: 98 to 125.

In some embodiments, the second nucleic acid comprises the sequence set forth in SEQ ID NO: SEQ ID NOs: 99 or 104.

In some embodiments, the first nucleic acid comprises a sequence selected from the group consisting of the sequences set forth in SEQ ID NOs: 42 to 71; and the second nucleic acid comprises a sequence selected from the group consisting of the sequences set forth in SEQ ID NOs: 98 to 125.

In some embodiments, the first nucleic acid comprises the sequence set forth in SEQ ID NO: 49; and the second nucleic acid comprises the sequence set forth in SEQ ID NO: SEQ ID NOs: 99 or 104.

In some embodiments, the first nucleic acid reduces expression of FAS in the immune cell by at least 50%, 55%, 60%, 65%, 75%, 80%, 85%, 90%, 95%, or 99% as compared to a control cell that does not comprise the first nucleic acid.

In some embodiments, expression of FAS in the immune cell is reduced by at least 50%, 55%, 60%, 65%, 75%, 80%, 85%, 90%, 95%, or 99% as compared to a control cell that does not comprise the first nucleic acid.

In some embodiments, the second nucleic acid reduces expression of PTPN2 in the immune cell by at least 50%, 55%, 60%, 65%, 75%, 80%, 85%, 90%, 95%, or 99% as compared to a control cell that does not comprise the second nucleic acid.

In some embodiments, expression of PTPN2 in the immune cell is reduced by at least 50%, 55%, 60%, 65%, 75%, 80%, 85%, 90%, 95%, or 99% as compared to a control cell that does not comprise the second nucleic acid In some embodiments, the second nucleic acid reduces expression of TOX in the immune cell by at least 50%, 55%, 60%, 65%, 75%, 80%, 85%, 90%, 95%, or 99% as compared to a control cell that does not comprise the second nucleic acid.

In some embodiments, expression of TOX in the immune cell is reduced by at least 50%, 55%, 60%, 65%, 75%, 80%, 85%, 90%, 95%, or 99% as compared to a control cell that does not comprise the second nucleic acid.

In some embodiments, expression of FAS, PTPN2, and/or TOX is determined by a nucleic acid assay or a protein assay.

In some embodiments, the nucleic acid assay comprises at least one of polymerase chain reaction (PCR), quantitative PCR (qPCR), RT-qPCR, microarray, gene array, or RNAseq.

In some embodiments, the protein assay comprises at least one of immunoblotting, fluorescence activated cell sorting, flow-cytometry, magnetic-activated cell sorting, or affinity-based cell separation.

In some embodiments, the cell further comprises a priming receptor comprising a first extracellular antigen-binding domain that specifically binds to a first antigen and a chimeric antigen receptor (CAR) comprising a second extracellular antigen-binding domain that specifically binds to a second antigen.

In some embodiments, the immune cell is a primary human immune cell.

In some embodiments, the primary immune cell is a natural killer (NK) cell, a natural killer T (NKT) cell, a T cell, a γδ T cell, a CD8+ T cell, a CD4+ T cell, a primary T cell, a T cell progenitor, or an induced pluripotent stem cell (iPSC).

In some embodiments, the primary immune cell is a primary T cell.

In some embodiments, the primary immune cell is a primary human T cell.

In some embodiments, the immune cell is virus-free.

In some embodiments, the immune cell is an autologous immune cell.

In some embodiments, the immune cell is an allogeneic immune cell.

In one aspect, provided herein are primary immune cells comprising at least one recombinant nucleic acid(s) comprising a first nucleic acid comprising the sequence set forth in SEQ ID NO: 49; and a second nucleic acid comprising the sequence set forth in SEQ ID NO: 82, inserted into a target region of the genome of the primary immune cell, and wherein the primary immune cell does not comprise a viral vector for introducing the recombinant nucleic acid(s) into the primary immune cell.

In one aspect, provided herein are primary immune cells comprising at least one recombinant nucleic acid(s) comprising a first nucleic acid comprising the sequence set forth in SEQ ID NO: 49; and a second nucleic acid comprising the sequence set forth in SEQ ID NO: SEQ ID NOs: 99 or 104, inserted into a target region of the genome of the primary immune cell, and wherein the primary immune cell does not comprise a viral vector for introducing the recombinant nucleic acid into the primary immune cell.

In one aspect, provided herein are viable, virus-free, primary cells comprising a ribonucleoprotein complex (RNP)-recombinant nucleic acid(s) complex, wherein the RNP comprises a nuclease domain and a guide RNA, wherein recombinant nucleic acid(s) comprises a first nucleic acid comprising the sequence set forth in SEQ ID NO: 49; and a second nucleic acid comprising the sequence set forth in SEQ ID NO: 82, and wherein the 5' and 3' ends of the recombinant nucleic acid(s) comprise nucleotide sequences that are homologous to genomic sequences flanking an insertion site in the genome of the primary cell.

In one aspect, provided herein are viable, virus-free, primary cells comprising a ribonucleoprotein complex (RNP)-recombinant nucleic acid(s) complex, wherein the RNP comprises a nuclease domain and a guide RNA, wherein recombinant nucleic acid(s) comprises a first nucleic acid comprising the sequence set forth in SEQ ID NO: 49; and a second nucleic acid comprising the sequence set forth in SEQ ID NO: SEQ ID NOs: 99 or 104, and wherein the 5' and 3' ends of the recombinant nucleic acid(s) comprise nucleotide sequences that are homologous to genomic sequences flanking an insertion site in the genome of the primary cell.

In some embodiments, the cell further comprises a priming receptor comprising a first extracellular antigen-binding domain that specifically binds to a first antigen and a chimeric antigen receptor (CAR) comprising a second extracellular antigen-binding domain that specifically binds to a second antigen, wherein the first antigen and the second antigen are distinct.

In one aspect, provided herein are population of cells comprising a plurality of immune cells as disclosed herein.

In one aspect, provided herein are pharmaceutical compositions comprising the immune cell as disclosed herein or the population of cells as disclosed herein, and a pharmaceutically acceptable excipient.

In one aspect, provided herein are pharmaceutical compositions comprising the recombinant nucleic acid as disclosed herein, the one or more recombinant nucleic acids as disclosed herein, or the vector as disclosed herein, and a pharmaceutically acceptable excipient.

In one aspect, provided herein are methods of editing an immune cell, comprising: providing a ribonucleoprotein (RNP)-recombinant nucleic acid(s) complex, wherein the RNP comprises a nuclease domain and a guide RNA, wherein the recombinant nucleic acid(s) comprises the recombinant nucleic acid(s) as disclosed herein, and wherein the 5' and 3' ends of the recombinant nucleic acid(s) comprise nucleotide sequences that are homologous to genomic sequences flanking an insertion site in the genome of the immune cell; non-virally introducing the RNP-recombinant nucleic acid(s) complex into the immune cell, wherein the guide RNA specifically hybridizes to a target region of the genome of the primary immune cell, and wherein the nuclease domain cleaves the target region to create the insertion site in the genome of the immune cell; and editing the immune cell via insertion of the recombinant nucleic acid(s) as disclosed herein into the insertion site in the genome of the immune cell.

In some embodiments, non-virally introducing comprises electroporation.

In some embodiments, the nuclease domain comprises a CRISPR-associated endonuclease (Cas), optionally a Cas9 nuclease.

In some embodiments, the target region of the genome of the cell is a T Cell Receptor Alpha Constant (TRAC) locus or a genomic safe harbor (GSH) locus.

In some embodiments, the recombinant nucleic acid(s) is a double-stranded recombinant nucleic acid(s) or a single-stranded recombinant nucleic acid(s).

In some embodiments, the recombinant nucleic acid(s) is a linear recombinant nucleic acid(s) or a circular recombinant nucleic acid(s), optionally wherein the circular recombinant nucleic acid(s) is a plasmid.

In some embodiments, the immune cell is a primary human immune cell.

In some embodiments, the immune cell is an autologous immune cell.

In some embodiments, the immune cell is an allogeneic immune cell.

In some embodiments, the immune cell is a natural killer (NK) cell, a natural killer T (NKT) cell, a T cell, a γδ T cell, a CD8+ T cell, a CD4+ T cell, a primary T cell, a T cell progenitor, or an induced pluripotent stem cell (iPSC).

In some embodiments, the immune cell is a primary T cell.

In some embodiments, the immune cell is a primary human T cell.

In some embodiments, the immune cell is virus-free.

In some embodiments, the method further comprises obtaining the immune cell from a patient and introducing the recombinant nucleic acid in vitro.

In one aspect, provided herein are methods of treating a disease in a subject comprising administering the immune cell(s) as disclosed herein or the pharmaceutical composition as disclosed herein to the subject.

In some embodiments, the disease is cancer.

In some embodiments, the cancer is a solid cancer or a liquid cancer.

In some embodiments, the cancer is ovarian cancer, fallopian cancer, primary peritoneal cancer, uterine cancer, mesothelioma, cervical cancer, or pancreatic cancer.

In some embodiments, the administration of the cell(s) enhances an immune response.

In some embodiments, the enhanced immune response is an adaptive immune response.

In some embodiments, the enhanced immune response is an innate immune response.

In one aspect, provided herein are methods of enhancing an immune response in a subject comprising administering the immune cell(s) as disclosed herein or the pharmaceutical composition as disclosed herein to the subject.

In some embodiments, the enhanced immune response is an adaptive immune response.

In some embodiments, the enhanced immune response is an innate immune response.

In some embodiments, expression of FAS in the immune cell is reduced by at least 50%, 55%, 60%, 65%, 75%, 80%, 85%, 90%, 95%, or 99% as compared to a control cell that does not comprise the first nucleic acid.

In some embodiments, expression of PTPN2 in the immune cell is reduced by at least 50%, 55%, 60%, 65%, 75%, 80%, 85%, 90%, 95%, or 99% as compared to a control cell that does not comprise the second nucleic acid.

In some embodiments, expression of TOX in the immune cell is reduced by at least 50%, 55%, 60%, 65%, 75%, 80%, 85%, 90%, 95%, or 99% as compared to a control cell that does not comprise the second nucleic acid.

In some embodiments, expression of FAS, PTPN2, and/or TOX in the immune cell is determined by a nucleic acid assay or a protein assay.

In some embodiments, the nucleic acid assay comprises at least one of polymerase chain reaction (PCR), quantitative PCR (qPCR), RT-qPCR, microarray, gene array, or RNAseq.

In some embodiments, the protein assay comprises at least one of immunoblotting, fluorescence activated cell sorting, flow-cytometry, magnetic-activated cell sorting, or affinity-based cell separation.

In some embodiments, the method further comprises administering an immunotherapy to the subject concurrently with the immune cell or subsequently to the immune cell.

In one aspect, provided herein are modified cells, wherein the cell is modified to have reduced expression of a FAS gene and/or reduced function of a product of the FAS gene relative to a corresponding unmodified cell, optionally wherein the modified cell is a hematopoietic cell.

In some embodiments, the modified cell is further modified to have reduced expression of at least one second gene and/or reduced function of a product of the at least one second gene relative to a corresponding unmodified cell.

In one aspect, provided herein are modified engineered cells, wherein the engineered cell is modified to have reduced expression of a FAS gene and/or reduced function of a product of the FAS gene relative to a corresponding unmodified engineered cell, optionally wherein the modified engineered cell is engineered to express a heterologous immune receptor.

In some embodiments, the modified engineered cell is further modified to have reduced expression of at least one second gene and/or reduced function of a product of the at least one second gene relative to a corresponding unmodified engineered cell.

In one aspect, provided herein are modified cells, wherein the cell is modified to have: (a) reduced expression of a FAS gene and/or reduced function of a product of the FAS gene; and (b) reduced expression of at least one second gene and/or reduced function of a product of the at least one second gene; wherein the reduced expression of each gene is relative to a corresponding unmodified cell, optionally wherein the modified cell is a hematopoietic cell.

In some embodiments, the modification to reduce expression comprises genetically engineering the genome of the cell to disrupt the FAS gene and optionally the at least one second gene.

In some embodiments, the genetic engineering comprises nuclease-mediated editing, optionally wherein the nuclease-mediated editing comprises CRISPR/Cas9-mediated editing.

In some embodiments, the modification to reduce expression comprises RNAi-mediated targeting of the FAS gene and optionally the at least one second gene, optionally wherein the RNAi-mediated targeting comprises short hairpin RNA (shRNA)-mediated knockdown.

In some embodiments, the RNAi-mediated targeting comprises engineering the cell to express an RNA polynucleotide capable of mediating knockdown of the FAS gene and optionally the at least one second gene.

In some embodiments, the modified cell comprises a hematopoietic cell.

In some embodiments, the hematopoietic cell comprises a hematopoietic stem cell.

In some embodiments, the hematopoietic cell comprises an immune cell.

In some embodiments, the immune cell comprises a adaptive immune cell, an innate immune cell, a T cell, an NK cell, a macrophage.

In some embodiments, the modified cell comprises an engineered cell.

In some embodiments, the engineered cell is engineered to express a heterologous receptor.

In some embodiments, the heterologous receptor comprises an immune receptor.

In some embodiments, the heterologous immune receptor comprises a chimeric antigen receptor (CAR), a T cell receptor, or an NK cell receptor.

In some embodiments, the engineered cell comprises a T cell or a cell capable of differentiation into a T cell, and wherein the heterologous receptor is inserted into an endogenous TCR locus, optionally the T cell receptor alpha (TRAC) locus.

In some embodiments, the heterologous receptor comprises one or more antigen binding domains, optionally wherein the one or more antigen binding domains are capable of binding to a tumor antigen or an antigen associated with cancer.

In some embodiments, the reduced expression and/or function of the FAS gene or its expression product improves at least one property of the modified cell relative to the corresponding unmodified cell.

In some embodiments, when the modified cell is further modified to have reduced expression and/or function of the at least one second gene, the reduced expression and/or function of the FAS gene or its expression product and the reduced expression and/or function of the at least one second gene or its expression product improves at least one property of the modified cell relative to a corresponding cell modified to only reduce expression and/or function of the FAS gene.

In some embodiments, when the modified cell is further modified to have reduced expression and/or function of the at least one second gene, the reduced expression and/or function of the FAS gene or its expression product and the reduced expression and/or function of the at least one second gene or its expression product improves at least one property of the modified cell relative to a corresponding cell modified to only reduce expression and/or function of the at least one second gene.

In some embodiments, the at least one property comprises improved proliferative capacity.

In some embodiments, the at least one property comprises improved protection from FAS-mediated apoptosis.

In some embodiments, the modified cell comprises an immune cell and the at least one property comprises an improved immune effector cell function.

In some embodiments, the improved immune effector cell function comprises increased relative effector molecule expression, production, and/or secretion.

In some embodiments, the immune cell comprises a T cell and the effector molecule comprises one or more molecules selected from the group consisting of: IFNγ, TNF-alpha, Granzyme B, and FASL.

In some embodiments, the modified cell is engineered to express a heterologous surface antigen, optionally wherein the heterologous surface antigen is capable of mediating targeted depletion of the engineered modified cell relative to a corresponding modified cell not engineered to express the heterologous surface antigen.

In one aspect, provided herein are methods of stimulating an immune response in a subject, wherein the method comprises administering to the subject any one of the modified cells as disclosed herein.

In one aspect, provided herein are methods of treating cancer in a subject, wherein the method comprises administering to the subject any one of the modified cells as disclosed herein.

In some embodiments, the modified cell is autologous with reference to the subject.

In some embodiments, the modified cell is allogenic with reference to the subject.

In one aspect, provided herein are one or more recombinant nucleic acids, wherein the one or more recombinant nucleic acids encode: a first chimeric polypeptide comprising a priming receptor comprising a first extracellular antigen-binding domain that specifically binds to Alkaline Phosphatase, Germ Cell (ALPG/P); and a second chimeric polypeptide comprising a chimeric antigen receptor (CAR) comprising a second extracellular antigen-binding domain that specifically binds to mesothelin (MSLN).

In some embodiments, the first extracellular antigen-binding domain comprises a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3, wherein: CDR-H1 comprises the sequence set forth in SEQ ID NO: 1, CDR-H2 comprises the sequence set forth in SEQ ID NO: 2, CDR-H3 comprises the sequence set forth in SEQ ID NO: 3, CDR-L1 comprises the sequence set forth in SEQ ID NO: 4, CDR-L2 comprises the sequence set forth in SEQ ID NO: 5, and CDR-L3 comprises the sequence set forth in SEQ ID NO: 6.

In some embodiments, the second extracellular antigen-binding domain comprises a variable heavy (VH) chain sequence comprising three heavy chain CDR sequences, CDR-H1, CDR-H2, and CDR-H3, wherein: CDR-H1 comprises the sequence set forth in SEQ ID NO: 14, CDR-H2 comprises the sequence set forth in SEQ ID NO: 15, and CDR-H3 comprises the sequence set forth in SEQ ID NO: 16.

In one aspect, provided herein are one or more recombinant nucleic acids, wherein the one or more recombinant nucleic acids encode at least one nucleic acid sequence at least 15 nucleotides in length, wherein the at least one nucleic acid sequence comprises one or more of: (1) a first nucleic acid sequence complementary to nucleotides 1126 to 1364 of an mRNA encoding human Fas Cell Surface Death Receptor (FAS) comprising the sequence set forth in SEQ ID NO: 39, (2) a second nucleic acid sequence complementary to nucleotides 518 to 559 of an mRNA encoding human Protein Tyrosine Phosphatase Non-Receptor Type 2 (PTPN2) comprising the sequence set forth in SEQ ID NO: 40; and (3) a third nucleic acid sequence complementary to nucleotides 1294 to 2141 of an mRNA encoding human Thymocyte Selection Associated High Mobility Group Box (TOX) comprising the sequence set forth in SEQ ID NO: 41.

In some embodiments, the one or more recombinant nucleic acid sequences are at least 16, 17, 18, 19, 20, 21, or 22 nucleotides in length.

In some embodiments, wherein the one or more recombinant nucleic acid sequences are a short hairpin RNA (shRNA), a small interfering RNA (siRNA), a double stranded RNA (dsRNA), or an antisense oligonucleotide.

In some embodiments, the one or more recombinant nucleic acids comprise the first nucleic acid sequence complementary to nucleotides 1126 to 1364 of an mRNA encoding human FAS comprising the sequence set forth in SEQ ID NO: 39, and the second nucleic acid sequence complementary to nucleotides 518 to 559 of an mRNA encoding human PTPN2 comprising the sequence set forth in SEQ ID NO: 40.

In some embodiments, the first nucleic acid sequence comprises a sequence selected from the group consisting of the sequences set forth in SEQ ID NOs: 42-71.

In some embodiments, the first nucleic acid sequence comprises the sequence set forth in SEQ ID NO: 49.

In some embodiments, the first nucleic acid sequence reduces expression of FAS in an immune cell by at least 50%, 55%, 60%, 65%, 75%, 80%, 85%, 90%, 95%, or 99% as compared to a control immune cell that does not comprise the first nucleic acid sequence.

In some embodiments, the second nucleic acid sequence comprises a sequence selected from the group consisting of the sequences set forth in SEQ ID NOs: 72-97.

In some embodiments, the second nucleic acid sequence comprises the sequence set forth in SEQ ID NO: 82.

In some embodiments, the second nucleic acid sequence reduces expression of PTPN2 in an immune cell by at least 50%, 55%, 60%, 65%, 75%, 80%, 85%, 90%, 95%, or 99% as compared to a control immune cell that does not comprise the second nucleic acid sequence.

In some embodiments, the first nucleic acid sequence comprises a sequence selected from the group consisting of the sequences set forth in SEQ ID NOs: 42 to 71; and the second nucleic acid sequence comprises a sequence selected from the group consisting of the sequences set forth in SEQ ID NOs: 72 to 97.

In some embodiments, the first nucleic acid sequence comprises the sequence set forth in SEQ ID NO: 49 and the second nucleic acid sequence comprises the sequence set forth in SEQ ID NO: 82.

In some embodiments, the nucleic acid(s) comprises a sequence selected from the group consisting of the sequences set forth in SEQ ID NOs: 168, 167, and 166.

In some embodiments, the third nucleic acid sequence comprises a sequence selected from the group consisting of the sequences set forth in SEQ ID NOs: 98-125.

In one aspect, provided herein are one or more expression vector(s) comprising the recombinant nucleic acid(s) disclosed herein.

In one aspect, provided herein are cells comprising the one or more recombinant nucleic acid(s) of disclosed herein.

In some embodiments, the cell is a primary human immune cell.

In one aspect, provided herein are pharmaceutical compositions comprising the recombinant nucleic acid(s) disclosed herein, and a pharmaceutically acceptable excipient.

In one aspect, provided herein are methods of inhibiting a target cell in a subject comprising administering a cell comprising: a first chimeric polypeptide comprising a priming receptor comprising a first extracellular antigen-binding domain that specifically binds Alkaline Phosphatase, Placental/Germ Cell (ALPG/P); and a second chimeric polypeptide comprising a chimeric antigen receptor (CAR) wherein the CAR comprises a second extracellular antigen-binding domain that specifically binds to mesothelin (MSLN).

In one aspect, provided herein are methods of inhibiting a target cell in a subject comprising administering a cell comprising at least one nucleic acid sequence at least 15 nucleotides in length, wherein the at least one nucleic acid sequence comprises one or more of: (1) a first nucleic acid sequence complementary to nucleotides 1126 to 1364 of an mRNA encoding human Fas Cell Surface Death Receptor (FAS) comprising the sequence set forth in SEQ ID NO: 39, (2) a second nucleic acid sequence complementary to nucleotides 518 to 559 of an mRNA encoding human Protein Tyrosine Phosphatase Non-Receptor Type 2 (PTPN2) comprising the sequence set forth in SEQ ID NO: 40; and (3) a third nucleic acid sequence complementary to nucleotides 1294 to 2141 of an mRNA encoding human Thymocyte Selection Associated High Mobility Group Box (TOX) comprising the sequence set forth in SEQ ID NO: 41.

In some embodiments, the target cell is a cancer cell, optionally a solid cancer cell or a liquid cancer cell.

In one aspect, provided herein are methods of treating a disease in a subject comprising administering a cell disclosed herein to the subject.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pennsylvania: Mack Publishing Company, 1990); Carey and Sundberg *Advanced Organic Chemistry* 3$^{rd}$ Ed. (Plenum Press) Vols A and B (1992).

Example 1: Production and In Vitro Characterization of ALPG/P and MSLN Logic Gates Materials and Methods Non-Viral T Cell Engineering for In Vitro Studies.

T-cells were enriched from peripheral blood mononuclear cells (PBMCs) obtained from normal donor Leukopaks (STEMCELL Technologies) using Lymphoprep (STEMCELL Technologies) and the EasySep Human T-Cell Isolation Kit (STEMCELL Technologies). T-cells were subsequently activated with CD3/CD28 Dynabeads at 1:1 bead to cell ratio (ThermoFisher, 40203D) in TexMACS medium (Miltenyi 130-197-196) supplemented with 3% human AB serum (Gemini Bio) and 12.5 ng/ml human IL-7 and IL-15 (Miltenyi premium grade) and cultured at 37° C., 5% CO2 for 48 hours before electroporation.

CRISPR RNP were prepared by combining 120 µM sgRNA (Synthego) targeting DNA sequence GAGC-CATGCTTGGCTTACGA (GS94, SEQ ID NO: 307), 62.5 µM sNLS-SpCas9-sNLS (Aldevron) and P3 buffer (Lonza) at a volume ratio of 5:1:3:6, and incubated for 15 minutes at room temperature. An optimized amount of plasmid DNA, determined by dose titration experiments (ranging from 0.25-3 micrograms) was mixed with 3.5 µl of RNP. T-cells were counted, debeaded, centrifuged at 90×G for 10 minutes and resuspended at 10^6 cells/14.5 µl of P3 with supplement added (Lonza). 14.5 µl of T-cell suspension was added to the DNA/RNP mixture, transferred to Lonza 384-well nucleocuvette plate, and pulsed in a Lonza HT Nucleofector System with code EH-115. Cells were allowed to rest for 15 minutes at room temperature before transfer to 96-well plates (Sarstedt) in TexMACS medium supplemented with 12.5 ng/ml human IL-7 and IL-15 (Miltenyi premium grade).

Transgene expression was detected by staining with anti-Myc antibody (Cell Signaling Technology clone 9B11) and anti-Flag antibody (RnD systems, clone 1042E) and analyzed on an Attune NxT Flow Cytometer. Other antibodies used were live/dead Fixable Near-IR (Thermo Fisher), TCRalpha/beta antibody (BioLegend clone IP26), CD4 antibody (BioLegend clone RPA-T4), CD8 antibody (BioLegend clone SKI).

FLAG-tag MSLN CAR 1: anti-MSLN human VH-CD8a hinge-CD8a-TMD-4-1BB costimulatory domain-CD3z activation domain.

FLAG-tag MSLN CAR 3: anti-MSLN human VHH-CD8a hinge-CD8a-TMD-4-1BB costimulatory domain-CD3z activation domain.

Myc-tag ALPG/P priming receptor: anti-ALPG/P scFv-CD8a hinge-Notch1 TMD-Notch1 STS-HNF1aDBD-p65 activation domain.

T Cell Stimulation

T cells from two donors were engineered to express a logic gate system of two different MSLN binders in CAR format combination with an ALPG/P priming receptor using the in vitro method manufacturing process. LG1 is MSLN CAR1 in combination with the ALPG/P priming receptor and LG3 is MSLN CAR3 in combination with an ALPG/P priming receptor. T cells were frozen and cryobanked at Day 9 after initial activation. Prior to the assay, engineered T cells were thawed and rested overnight in media including 12.5 ng/mL human IL-7 and IL-15. On the day of the assay, T cells expressing LG1 or LG3 were counted and 2e4 total T cells were plated per well of a 96-well round-bottom plate in 200 uL media without IL-7 and IL-15. Engineered T cells were plated either alone ("Resting T cells" condition) or with anti-CD3/anti-CD28 Dynabeads at a 1:5 bead:cell ratio ("+ TCR stimulation" condition) in technical duplicates. Prepared plates with T cells were spun down for 2 min at 300 g prior to incubation at 37° C. for 24 hours. Following the 24 hour co-culture, the T cells are stained for PrimeR and CAR expression using anti-myc PE and anti-FLAG APC, respectively, and analyzed by flow cytometry on an Attune NxT.

Dual Antigen-Dependent Killing In Vitro Assay

T cells from two donors were engineered to express LG1 or LG3 (or matched constitutive CAR controls) using the non-viral manufacturing process and were frozen and cryobanked at Day 9 after initial activation. Prior to the assay, engineered T cells and RNP only control T cells from the same donors were thawed and rested overnight in media including 12.5 ng/mL human IL-7 and IL-15. On the day of the assay, engineered T cells were counted and stained for PrimeR and CAR expression using anti-myc PE and anti-FLAG APC, respectively, and analyzed by flow cytometry. For each donor, all engineered T cell populations were normalized to the lowest KI % within that donor by adding RNP only cells to dilute engineered populations that were above the lowest KM, After normalization, T cells were resuspended in medium without IL-7 and IL-15 and serially diluted prior to being added to 96-well flat-bottom, white-walled assay plates. The serial dilution of T cells results in the following co-culture KI+ effector:target (E:T) ratios once 1e4 target cells were added/well: 3:1, 1:1, 1:3, 1:9, 1:27, and 1:81 in technical duplicates. Each T cell population was co-cultured with four different K562s that had the different combinations of priming antigen ALPG and cytolytic antigen MSLN expression: K562. K562-ALPG, K562-MSLN, and K562-ALPG/MSLN. Prepared plates with T cells and target cells were spun down for 2 min at 300 g prior to incubation at 37° C. for 72 hours with a breathable membrane on each plate. Cytotoxicity at the end of the 72 hour co-culture was measured using an end-point luciferase assay.

Cytotoxicity Kinetics

T cells from three donors were engineered to express LG1 or LG3 (or matched constitutive CAR controls) using the non-viral manufacturing process and were frozen and cryobanked at Day 9 after initial activation. Prior to the assay, engineered T cells and RNP only control T cells from the same donors were thawed and rested overnight in media including 12.5 ng/mL human IL-7 and IL-15. On the day of the assay, engineered T cells were counted and stained for PrimeR and CAR expression using anti-myc PE and anti-FLAG APC, respectively, and analyzed by flow cytometry. For each donor, all engineered T cell populations were normalized to the lowest KI % within that donor by adding RNP only cells to dilute engineered populations that were above the lowest KI %. After normalization, T cells were resuspended in medium without IL-7 and IL-15 and serially diluted prior to being added to 96-well flat-bottom, clear assay plates that had been pre-coated with poly-L-lysine (50 uL/well at room temperature, aspirate and dry for 30 minutes). The serial dilution of T cells resulted in the following co-culture KI+ effector:target (E:T) ratios once 6e3 K562-ALPG/MSLN target cells were gently added to each well: 3:1, 1:1, and 1:3 in technical duplicates. An AnnexinV dye was included in the assay medium to mark apoptotic cells. Prepared plates with T cells and target cells were allowed to settle undisturbed for 30 minutes at room temperature prior to being covered with breath easy films. The plates were then loaded in Incucyte live cell imager and imaged every 2 hours for 72 hours to track cytotoxic activity over time by measuring GFP signal in the K562s and the AnnexinV apoptotic marker.

Cytokine Production

Cytokine production was evaluated in supernatants taken from co-culture wells of the cytotoxicity assay with K562 tumor cells engineered to express different combinations of ALPG and MSLN (See "dual antigen-dependent killing in vitro"). Supernatants collected at 72 hours from the 1:1 KI+ E:T wells in the cytotoxicity assay described above were analyzed for IL-2 production using a Luminex assay.

Model Cell Lines Engineering for Patient-Relevant Levels of ALPG and MSLN

K562 target cells used in all co-culture experiments with logic gate T cells were engineered via lentivirus to express constructs with target antigens and proteins. Cell expression was matched to the level of priming antigen ALPG and cytolytic antigen MSLN expression to levels typically found in ovarian cancer primary tumor samples. Parental K562 cells were sourced from ATCC. Pantropic VSV-G pseudo-typed lentivirus was produced via transfection of Lenti-X 293T cells with a transgene expression vector and the viral packaging plasmids psPAX2 and pMD2.G using Fugene HD (Promega #E2312). Lentivirus was further concentrated using Lenti-X Concentrator (Takara Bio #631231). All K562 cells used in assays were transduced with lentivirus containing an "EFG" construct expressing both GFP and luciferase. The GFP was used as a sort marker to generate a pure population of transduced cells via FACS sorting with a FACS ARIA II as well as a marker for target cells in flow- or Incucyte-based assays, and the luciferase gene was used for reading out cytotoxicity assays.

After sorting and banking the K562-EFG line, the cell line was further transduced to express combinations of the priming antigen ALPG and the cytolytic antigen MSLN. Lentiviral constructs expressing ALPG, MSLN, or ALPG and MSLN together separated by a 2A sequence for bicistronic expression were utilized to transduce the K562-EFG line.

Priming Receptor Sensitivity Assay for CAR Expression Induction

T cells from one donor were engineered to express LG1, which has the same exact PrimeR as LG3, using the engineering method as described above. On Day 9 post-activation, LG1 T cells were counted and 2e4 total T cells were plated per well of a 96-well round-bottom plate in 200 uL media without IL-7 and IL-15. Engineered T cells were plated either alone ("T cells alone" condition), with K562-ALPG$^{low}$, or with K562-ALPG$^{high}$ cells at 1:1 KI+E:T in technical duplicates. Prepared plates with T cells were spun down for 2 min at 300 g prior to incubation at 37° C. for 72 hours. Following the 72 hour co-culture, the T cells are stained for PrimeR and CAR expression using anti-myc PE and anti-FLAG APC, respectively, and analyzed by flow cytometry on an Attune NxT. To specifically analyze live T cells in flow analysis using FlowJo, a viability dye and GFP expression in the K562s were used to exclude dead cells and target cells in gating.

Next, an in vitro stress model using SKOV3-WT cells was used. T cells from two donors were engineered to express LG1 or LG3 (or matched constitutive CAR controls) using the engineering method as described above. Cells were cryobanked at Day 9 after initial activation. Prior to the assay, engineered T cells and RNP only control T cells from the same donors were thawed and rested overnight in media including 12.5 ng/mL human IL-7 and IL-15. On the day of the assay, engineered T cells were counted and stained for PrimeR and CAR expression using anti-myc PE and anti-FLAG APC, respectively, and analyzed by flow cytometry. For each donor, all engineered T cell populations were normalized to the lowest KI % within that donor by adding RNP only cells to dilute engineered populations that were above the lowest KI %. After normalization, T cells were resuspended in medium without IL-7 and IL-15 and added to 96-well flat-bottom, white-walled assay plates at 1:1 KI+E:T with 1e4 SKOV3 ovarian cancer cells that endogenously express ALPG and MSLN. Prepared plates with T cells and target cells were spun down for 2 min at 300 g prior to incubation at 37° C. for 72 hours with a breathable membrane on each plate. Supernatants were collected at 72 hours and analyzed for IFNγ and IL-2 production using a Luminex assay.

Expression in Primary and Metastatic Cancer Samples

To assess antigen levels in indication specific samples, expression of logic gate target antigens ALPG (priming antibody) and MSLN (cytolytic antigen) in primary and metastatic ovarian cancer tumor samples was evaluated via IHC analysis. Primary ovarian cancer tumor samples (n=22) and metastases (n=11) were analyzed via IHC for ALPG and MSLN expression, and each sample was scored for percent of tumor cells positive for each antigen in addition to the intensity of antigen expression.

Heterogeneity Cytotoxicity Assay

To assess the minimum proportion of prime antigen positive cells necessary to induce full tumor clearance by circuit T cells, a cytotoxicity assay was developed in which tumor antigen heterogeneity was directly controlled. T cells from two donors were engineered to express LG1 or LG3 (or matched constitutive CAR controls) using the engineering method as described above. Cells were frozen and cryobanked at Day 9 after initial activation. Prior to the assay, engineered T cells and RNP only control T cells from the same donors were thawed and rested overnight in media including 12.5 ng/mL human IL-7 and IL-15. On the day of the assay, engineered T cells were counted and stained for PrimeR and CAR expression using anti-myc PE and anti-FLAG APC, respectively, and analyzed by flow cytometry. For each donor, all engineered T cell populations were normalized to the lowest KI % within that donor by adding RNP only cells to dilute engineered populations that were above the lowest KI %. After normalization, T cells were resuspended in medium without IL-7 and IL-15 and added to 96-well round-bottom, clear assay plates at 1:1 KI+E:T with 1e4 K562-MSLN and K562-ALPG/MSLN mixed at various ratios to model different levels of priming antigen heterogeneity. Prepared plates with T cells and target cells were spun down for 2 min at 300 g prior to incubation at 37° C. for 72 hours with a breathable membrane on each plate. Cytotoxicity at the end of the 72 hour co-culture was measured using an end-point luciferase assay.

Soluble Protein Inhibition Assay

MSLN is shed from cells in a soluble form (sMSLN) that can act as a sink and inhibit binding by anti-MSLN CAR T cells to MSLN presented on the surface of cancer cells, and therefore inhibit target cell killing. Additionally, the soluble protein CA125 is known to interact with MSLN and can block the binding of anti-MSLN binders and CARs if they target an epitope that can be occluded by CA125 binding. Candidate anti-MSLN CAR designs can be screened for the ability to resist inhibition by sMSLN and CA125 found at physiologically-relevant levels using assays that titrate increasing levels of soluble proteins into co-culture with CAR T cells and MSLN positive target cancer cells and measure T cell activation/target killing. An assay utilizing K562-ALPG/MSLN target cells and IL-2 cytokine production as a measure of T cell activation was developed to detect anti-MSLN CAR T cell inhibition by soluble protein, with the M912 CAR showing inhibition by CA125. After validating the soluble protein CAR inhibition assay using constitutive CART cell controls, the assay was then used to test logic gates LG1 and LG3.

T cells from two donors were engineered to express LG1 or LG3 (or matched constitutive CAR controls) using the engineering method as described above. Cells were frozen and cryobanked at Day 9 after initial activation. Prior to the assay, engineered T cells and RNP only control T cells from the same donors were thawed and rested overnight in media including 12.5 ng/mL human IL-7 and IL-15. On the day of the assay, engineered T cells were counted and stained for PrimeR and CAR expression using anti-myc PE and anti-FLAG APC, respectively, and analyzed by flow cytometry. For each donor, all engineered T cell populations were normalized to the lowest KI % within that donor by adding RNP only cells to dilute engineered populations that were above the lowest KI %. After normalization, T cells were resuspended in medium without IL-7 and IL-15 and added to 96-well flat-bottom, clear assay plates at 1:1 KI+E:T with 2e4 K562-ALPG/MSLN target cells in the presence of variable concentrations of soluble CA125 or sMSLN. Prepared plates with T cells and target cells were spun down for 2 min at 300 g prior to incubation at 37° C. for 48 hours. Supernatants were collected at 48 hours and analyzed for IL-2 production using a Luminex assay.

Results

T Cell Editing and Stimulation

Figure 2:
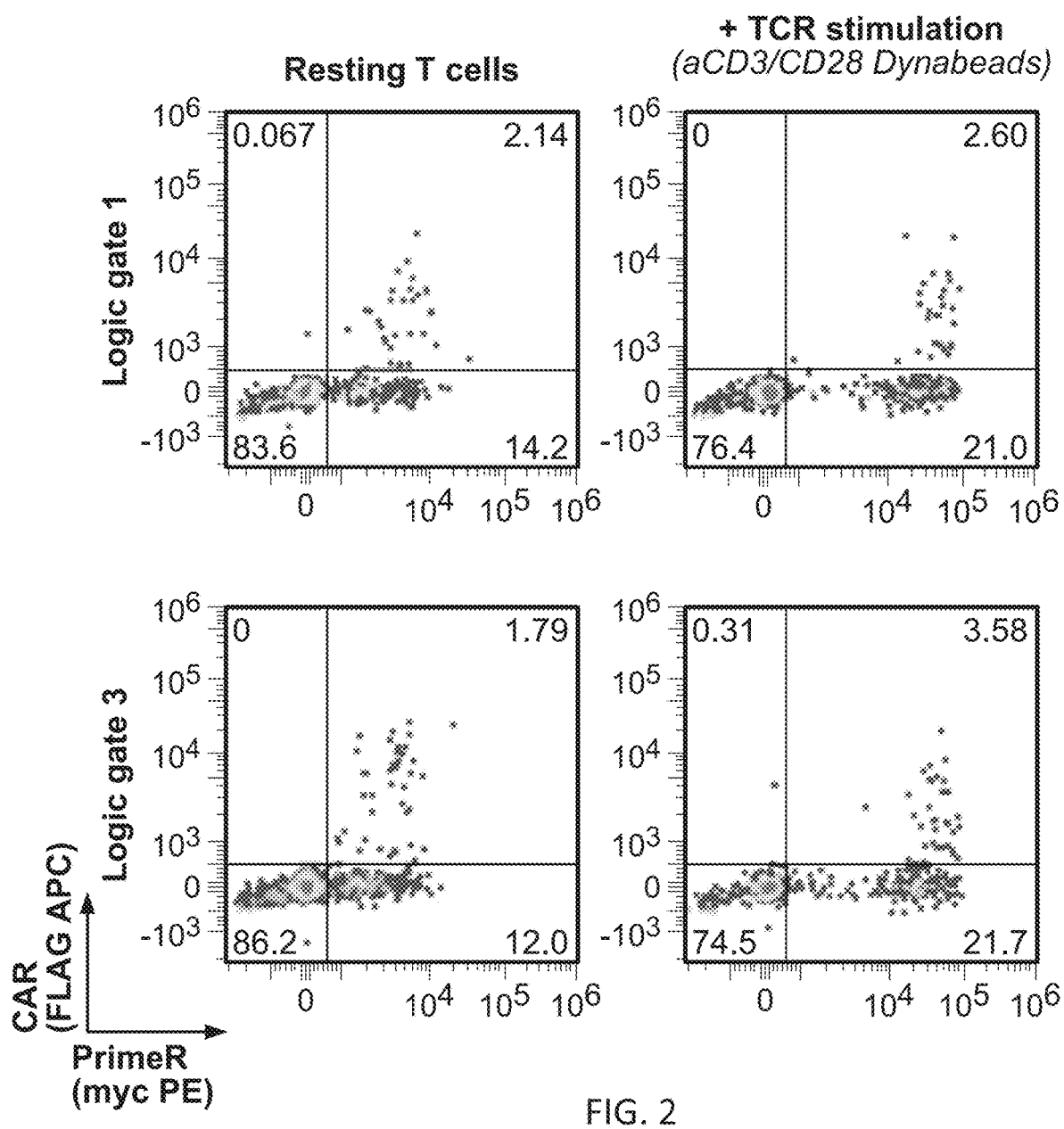
FIG. 2 provides flow cytometry data showing that T cells expressing both logic gates (LG1 and LG3) showed priming receptor expression but minimal CAR expression in the absence of priming antigen stimulation and in the presence of T cell activation stimulation.

A diagram of the assay is shown in FIG. 1. The results are shown in FIG. 2. In the "Resting T cells" condition, T cells expressing both logic gates (LG1 and LG3) showed PrimeR expression but minimal CAR expression in the absence of stimulation (FIG. 2). Upon TCR stimulation through the anti-CD3/anti-CD28 Dynabeads, the now activated T cells showed increased PrimeR MFI and % PrimeR+ relative to the same T cells in the "Resting T cells" condition (FIG. 2). However, TCR stimulation did not increase the percent of PrimeR+ cells that also express CAR. These results indicate that expression of a CAR from LG1 and LG3 is dependent on binding to the PrimeR antigen, even in the context of strong TCR and co-stimulatory signaling.

Dual Antigen-Dependent Killing In Vitro

Figure 3A:
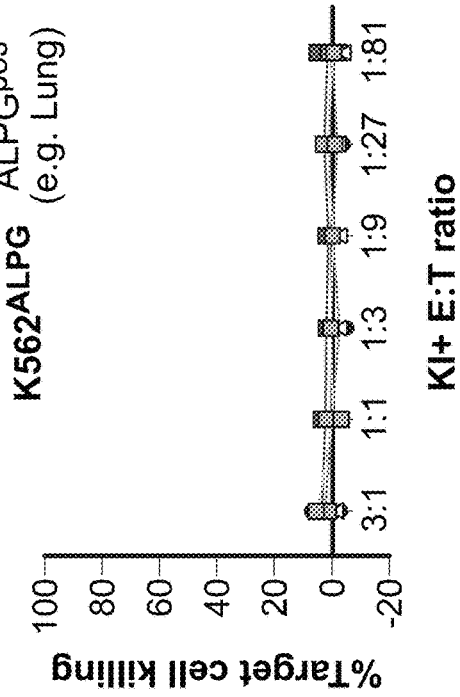
FIG. 3A shows no cytotoxicity was observed from negative control RNP-only T cells.
Figure 3B:
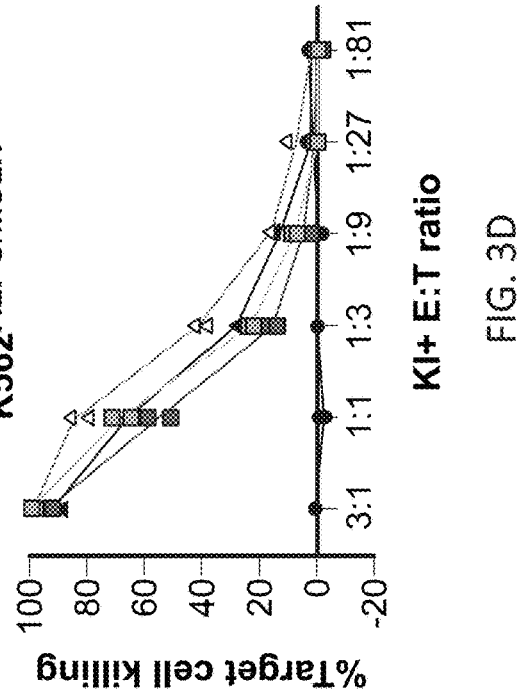
FIG. 3B shows minimal logic gate expressing-T cell activity against the single antigen positive K562-ALPG cells.
Figure 3C:
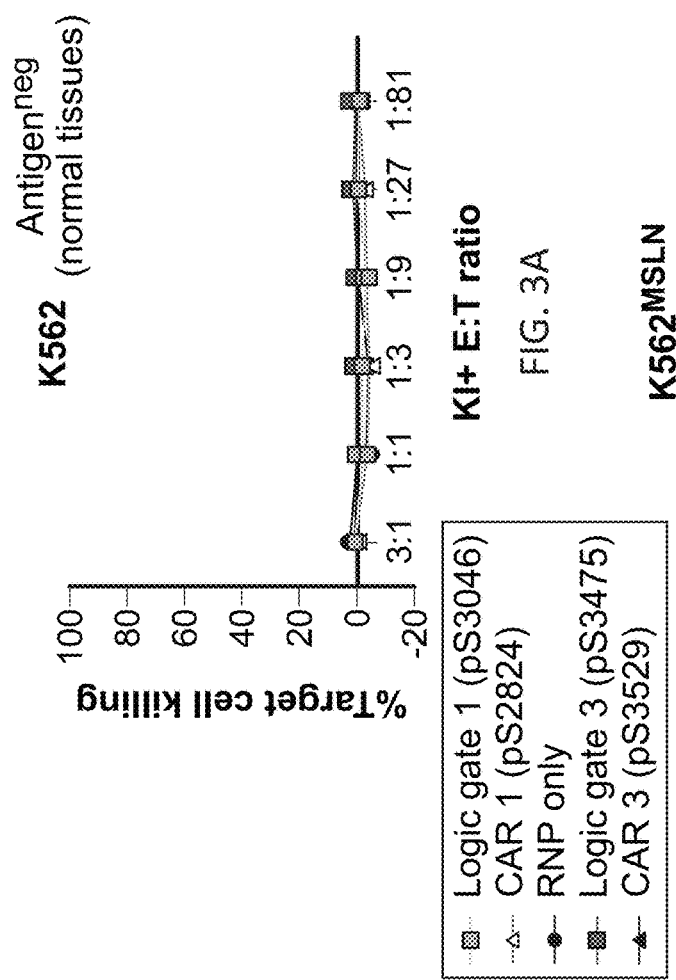
FIG. 3C shows no logic gate expressing-T cell activity against the single antigen positive K562-MSLN.
Figure 3D:
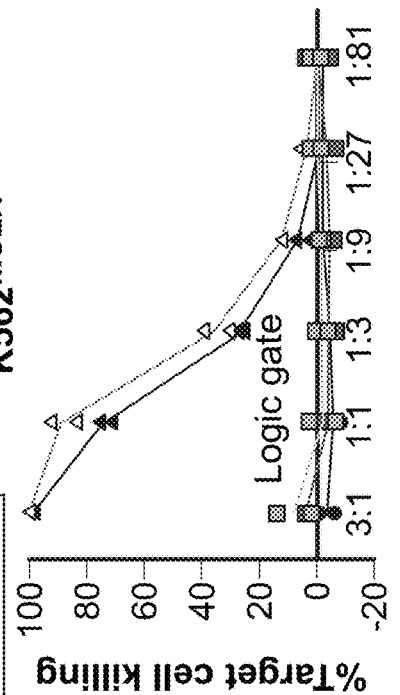
FIG. 3D shows tumor-specific activity in the logic gate-expressing T cells.

Both logic gates demonstrate dual antigen-dependent killing in vitro. T cells engineered with logic gate 1 or logic gate 3 were programmed to specifically recognize and activate a cytotoxic response to cancer cells that express both the priming antigen ALPG and the cytolytic antigen MSLN. The dual-antigen specificity of the logic gate T cells is in contrast to conventional constitutive CAR T cells that can cause toxicities due to ON-target OFF-tumor cross-reaction with healthy tissues that express the cytolytic antigen. While T cells expressing the constitutive anti-MSLN CARs killed both K562-MSLN and K562-ALPG/MSLN cells (FIGS. 3C and 3D), cytotoxicity from logic gate-expressing T cells was specific for dual-antigen K562-ALPG/MSLN (FIG. 3D), and demonstrated minimal activity against the single antigen positive K562-ALPG or K562-MSLN cell lines even at the highest E:T ratios (FIGS. 3B and 3C). No cytotoxicity was observed from the negative control RNP-only T cells (FIG. 3A). Tumor-specific activity was observed in the logic gate-expressing T cells (FIG. 3D). On-target, off-tissue toxicity was observed in the CAR only T cells against the K562-MSLN cell line (FIG. 3C). Together, this data demonstrates that cytotoxicity from the logic gate T cells against cytolytic antigen positive cells was restricted to co-culture conditions where the priming antigen ALPG is also present.

Cytotoxicity Kinetics

Figure 4:
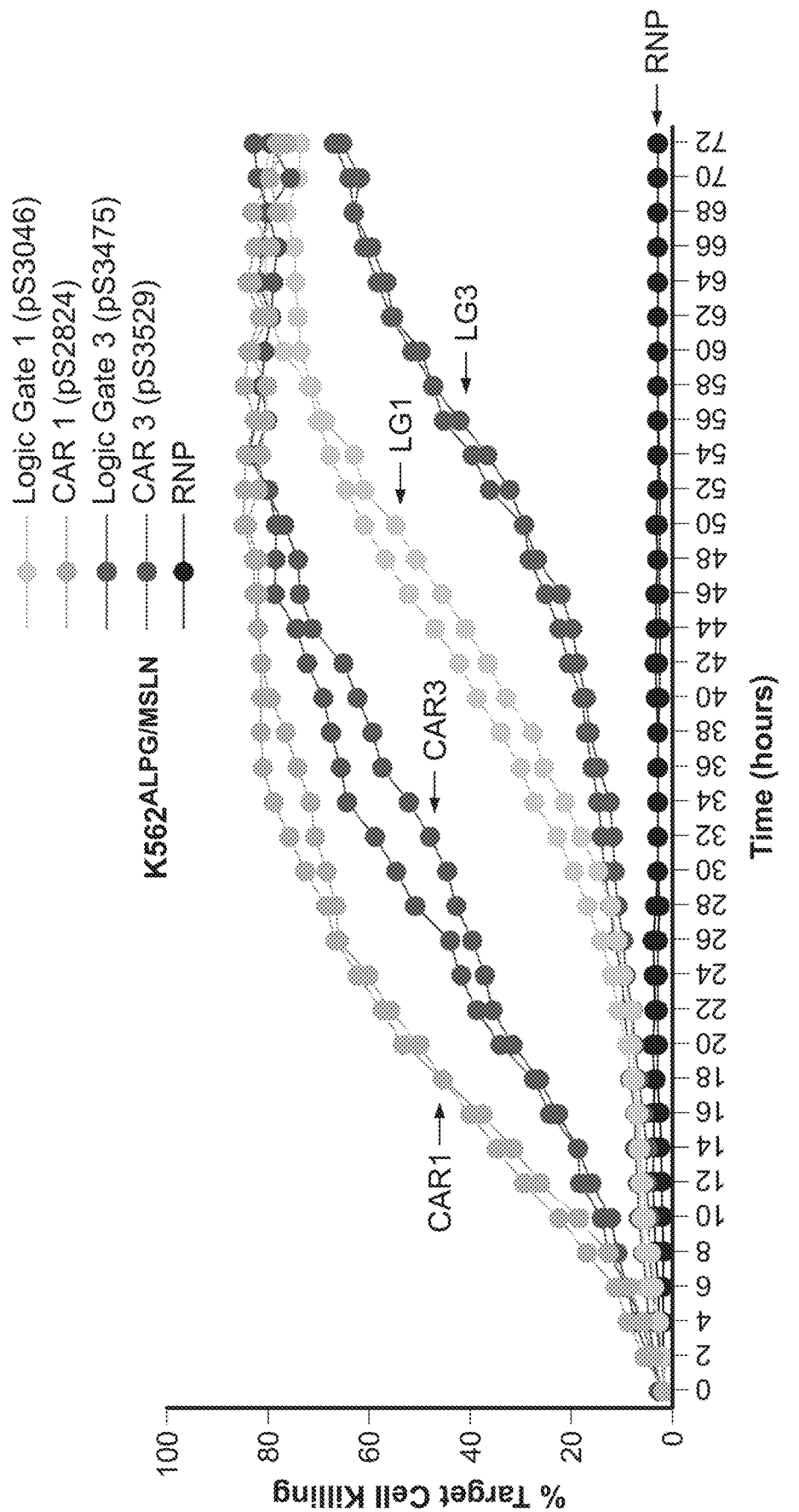
FIG. 4 shows that Logic Gate 1 T cells showed both more rapid and more complete K562-ALPG/MSLN target cell killing relative to Logic Gate 3 T cells.

Logic gate 1 demonstrated faster killing kinetics than logic gate 3 in vitro. Dynamic imaging of T cell co-cultures with K562-ALPG/MSLN target cells revealed that T cells engineered with different logic gates or matched constitutive CAR controls killed their targets with different kinetics. T cells engineered with constitutive CAR 1 or CAR 3 showed a rapid onset of cytotoxic activity upon plating with the target cells, with CAR 1 having the fastest rate of killing. Logic gate T cell cytotoxicity began approximately 24 hours after the start of cytotoxicity by constitutive CAR controls. Without wishing to be bound by theory, the delayed cytotoxicity by logic gates was likely based on their mechanism of the PrimeR first needing to bind its antigen before the T cells can trigger CAR expression sufficient to reach surface levels capable of inducing cytotoxicity. Logic Gate 1 T cells showed both more rapid and more complete K562-ALPG/MSLN target cell killing relative to Logic Gate 3 T cells (FIG. 4). No cytotoxicity was observed from the negative control RNP-only T cells. The faster kinetics of killing by Logic Gate 1 T cells relative to Logic Gate 3 T cells corresponds well with other measures of T cell activation and target killing that indicate Logic Gate 1 to be the more potent candidate.

Cytokine Production

To further demonstrate the specificity and functional activity of the logic gate T cells, cytokine production was assessed. In agreement with the cytotoxicity data, cytokine production from logic gate cells was limited to wells where the dual-antigen K562-ALPG/MSLN target cells were present (FIG. 5D). In contrast, T cells bearing the constitutive CAR control produced IL-2 when co-cultured with either K562-MSLN (FIG. 5B) or K562-ALPG/MSLN (FIG. 5D) target cells. Neither logic gate nor constitutive CAR T cells produced IL-2 in response to K562 (FIG. 5A) or K562-ALPG (FIG. 5C) target cell lines that did not express the cytolytic antigen. Negative control RNP-only T cells did not produce cytokine when co-cultured with any target cell line (FIG. 5A). Without wishing to be hound by theory, these data further support the hypothesis that the functional output of the logic gate T cells is limited to conditions where both the priming and cytolytic antigens are present.

Model Cell Lines Engineering for Patient-Relevant Levels of ALPG and MSLN

Figures 6A, 6B:
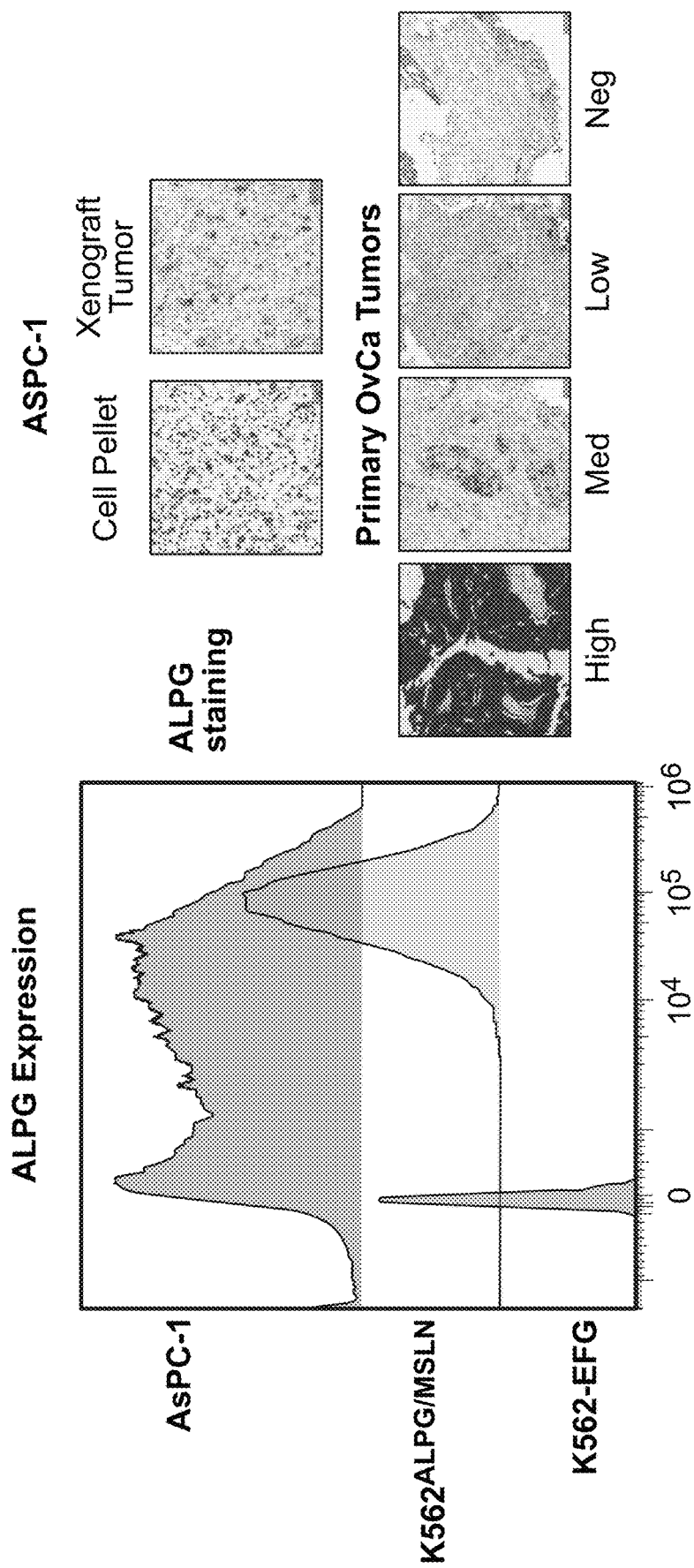
FIG. 6A shows ALPG expression in AsPC-1 cells, K562$^{ALPG/MSLN}$ cells and K562-EFG cells.
FIG. 6B shows ALPG IHC staining in AsPC-1 cells and primary ovarian cancer tumors.
Figures 7A, 7B:
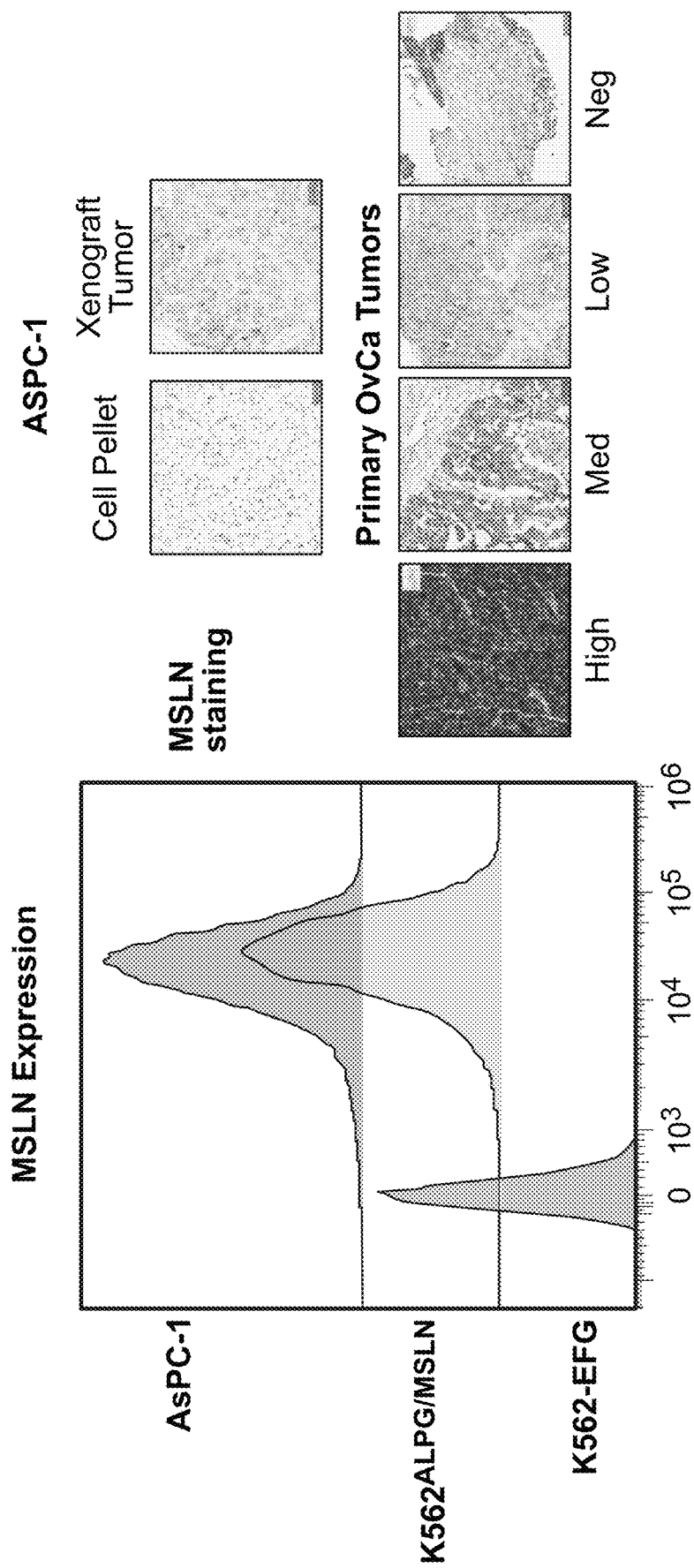
FIG. 7A shows MSLN expression in AsPC-1 cells, K562$^{ALPG/MSLN}$ cells and K562-EFG cells.
FIG. 7B shows ALPG IHC staining in AsPC-1 cells and primary ovarian cancer tumors.

The K562-ALPG, K562-MSLN, and K562-ALPG/MSLN lines were generated via FACS to have matched antigen expression levels to the ASPC-1 cell lines, a pancreatic cancer cell line sourced from ATCC with endogenous antigen expression of both ALPG and MSLN. Flow cytometry-based assessment of ALPG and MSLN expression on post-sort, established K562 lines and the ASPC-1 cell line control shows that FACS successfully generated engineered K562 lines with expression matching the control (FIGS. 6A and 7A). Importantly, IHC analysis of ALPG and MSLN expression in ASPC-1 cells both Cell Pellet and Xenograft Tumor samples (take from NSG mice and formalin fixed) was found to match low-medium expression levels of these antigens in primary ovarian cancer tumor samples analyzed in the same experiments (FIGS. 6B and 7B). Taken together, this data supports that the K562 target lines utilized in these assays express physiologically-relevant levels of target antigens ALPG and MSLN that match the levels found in typical ovarian cancer patient tumor samples.

Priming Receptor Sensitivity Assay for CAR Expression Induction

Next, a CAR induction assay was used to assess the sensitivity of this PrimeR to low density ALPG. The anti-ALPG binder PrimeR was sensitive to ALPG levels 4-fold lower than the AsPC-1 reference line. Both LG1 and LG3 utilize the same PrimeR with the anti-ALPG binder. K562-ALPG$^{high}$ and K562-ALPG$^{low}$ cell lines were generated to match the antigen expression of the AsPC-1 reference tumor cell line. The K562-ALPG/MSLN target cells used in the functional assays were sorted to have matched ALPG expression to the K562-ALPG$^{high}$ line used in the CAR induction assay. Quantification of ALPG surface molecules on the K562-ALPG$^{high}$ line shows that there is a greater number of antigens present on these cells as compared to the reference cell line (FIG. 8A, 8B, 8C). In contrast, the K562-ALPG$^{low}$ line shows distinctly lower ALPG expression than the "high" line, and antigen quantification shows that the K562-ALPG$^{low}$ line has 4-fold lower ALPG expression than the reference ASPC-1 cell line (FIG. 8A, 8B, 8C). Therefore, the K562-ALPG$^{low}$ line has ALPG expression that is physiologically-relevant and likely below the levels of that found in ovarian cancer tumors in human cancer patients. Importantly, T cells engineered with LG1 and the anti-ALPG binder PrimeR show equivalent prime-dependent CAR induction levels in response to both K562-ALPG$^{low}$ and K562-ALPG$^{high}$ cells (FIG. 8C). Without wishing to be bound by theory, these results demonstrate that LG1 T cells are capable of inducing CAR expression in response to ALPG levels at or below the level of expression typically found in ovarian cancer tumor samples from human cancer patients, and suggest that tumor ALPG density will not be a limiting factor to LG1 T cells' ability to clear ALP G+/MSLN+ cancer cells.

Next, an in vitro stress model using SKOV3-WT cells was used to evaluate how T cells engineered with the two candidate logic gates respond to SKOV3 ovarian cancer cell lines with low and heterogenous ALPG and MSLN expression (FIGS. 9A and 9B). Without wishing to be hound by theory, given that LG1 and LG3 utilize the same PrimeR but each induces expression of a 41BBζ-based CAR built with a different MSLN binder, differences in response by these logic gate T cells to different dual-antigen positive target cells may be driven by different activity of the two MSLN CARs within the distinct circuits. Interestingly, in both donors tested LG1 T cells produced significantly more cytokine in response to SKOV3 target cells than did LG3 T cells, with the effect particularly striking for IL-2 (FIGS. 9C and 9D). Additionally, cells expressing LG1 produced significantly more cytokine than did constitutive CAR1 T cells (again, more dramatically for IL-2) (FIGS. 9C and 9D). Without wishing to be bound by theory, this data suggests that LG1 T cells are capable of inducing strong cytokine production in response to ovarian cancer target cells with low and heterogenous ALPG and MSLN expression.

Expression in Primary and Metastatic Cancer Samples

Figure 10A:
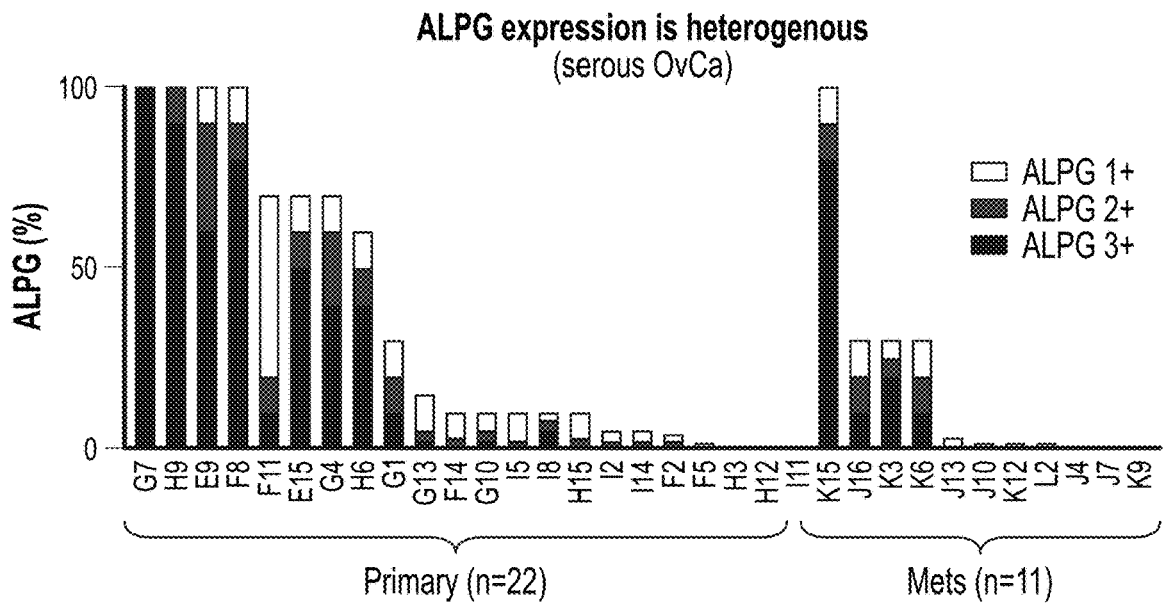
FIG. 10A shows ALPG expression on ovarian cancer samples.
Figure 10B:
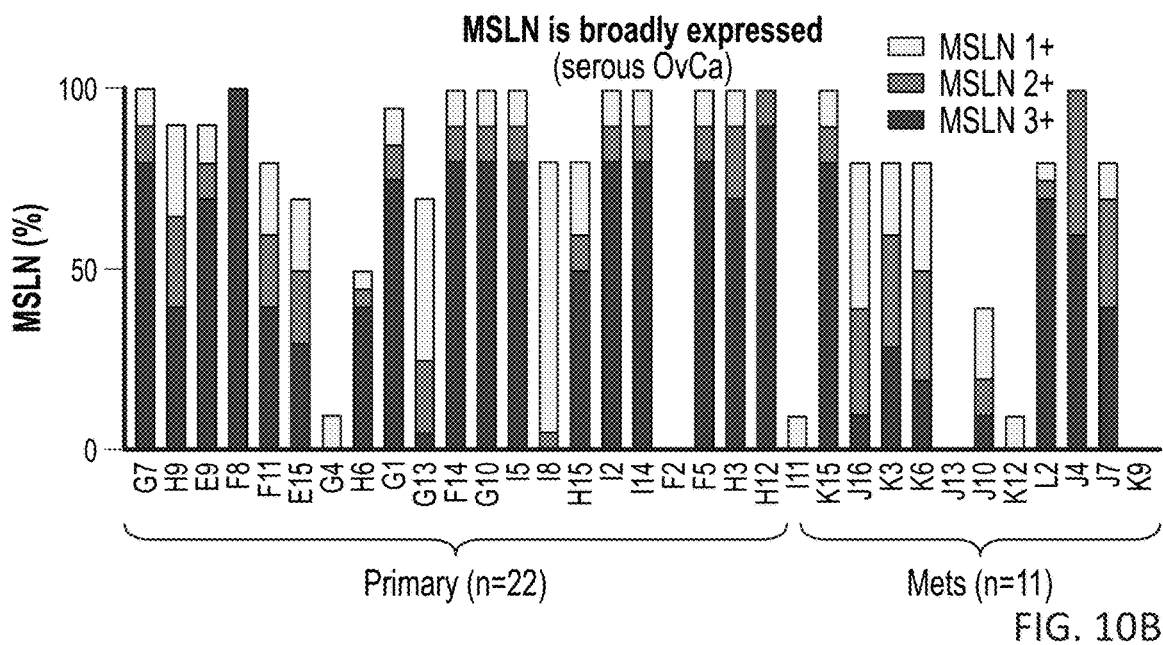
FIG. 10B shows MSLN expression on ovarian cancer samples.

Almost all samples, both primary and metastatic ovarian cancer, were found to express MSLN, and the vast majority of primary tumor samples expressed MSLN on 100% of cancer cells (FIG. 10B). Expression of the priming antigen ALPG was also found in the vast majority of patient samples, although not in all metastases (FIG. 10A). While ALPG was present in most ovarian cancer samples, the percent of cancer cells within each sample that express ALPG was found to be more heterogenous than MSLN for many patients. Samples that were positive for ALPG were all >5% ALPG+, with most containing at least 10% ALPG+ cancer cells. Thus, ALPG and MSLN are co-expressed in the vast majority of ovarian cancer patient samples, with MSLN expression appearing more homogeneously on all cells in many samples and ALPG being present but more heterogeneously expressed.

Heterogeneity Cytotoxicity Assay

Figure 10C:
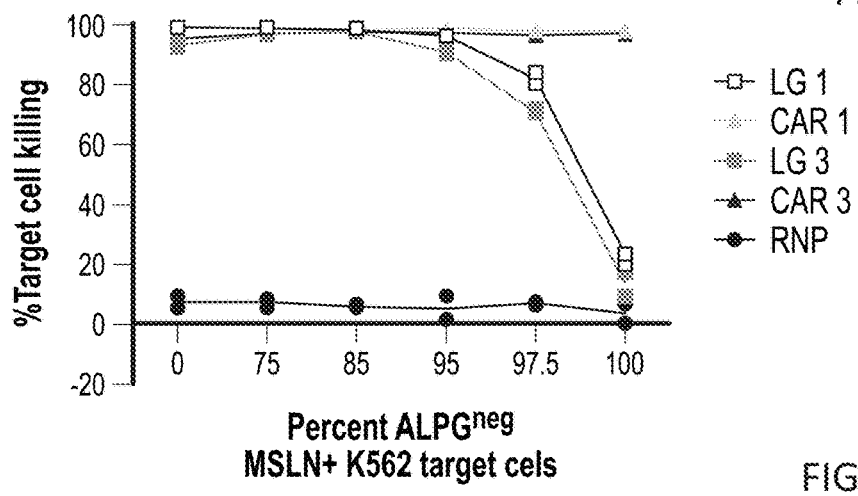
FIG. 10C shows a dose assay for percent target cell killing with increasing percentage of ALPG negative cells incubated with T cells expressing the indicated logic gate or CAR.

Tumors are heterogeneous mixtures of cancer cells, and this heterogeneity extends to antigen expression. By targeting two antigens in an AND-gate fashion, the primeR/CAR logic gate circuit has the potential to significantly reduce toxic side effects relative to existing cancer therapies by improving the precision of tumor targeting versus healthy tissue. However, with this more specific targeting it has been a question whether these circuits are capable of clearing heterogeneous tumors that only express the priming antigen on a minority of the cells, which will likely be the case in many patient tumors. The results of this assay demonstrate that both logic gates demonstrate complete target cell clearance down to only 5% priming antigen positive cancer cells (ALPG), with LG1 showing the most potent response in the presence of the least priming antigen (FIG. 10C). The constitutive CAR control T cells killed all MSLN+ target cell conditions equally well regardless of ALPG expression. No cytotoxicity was observed from the negative control RNP-only T cells. Taken together with the IHC data analyzing antigen expression in ovarian cancer patient samples, the results of the priming antigen heterogeneity cytotoxicity assay demonstrate that logic gate T cells are capable of eliminating heterogenous populations of cancer cells that express the priming antigen on only a small minority of cells.

Soluble Protein Assay

Figure 11A:
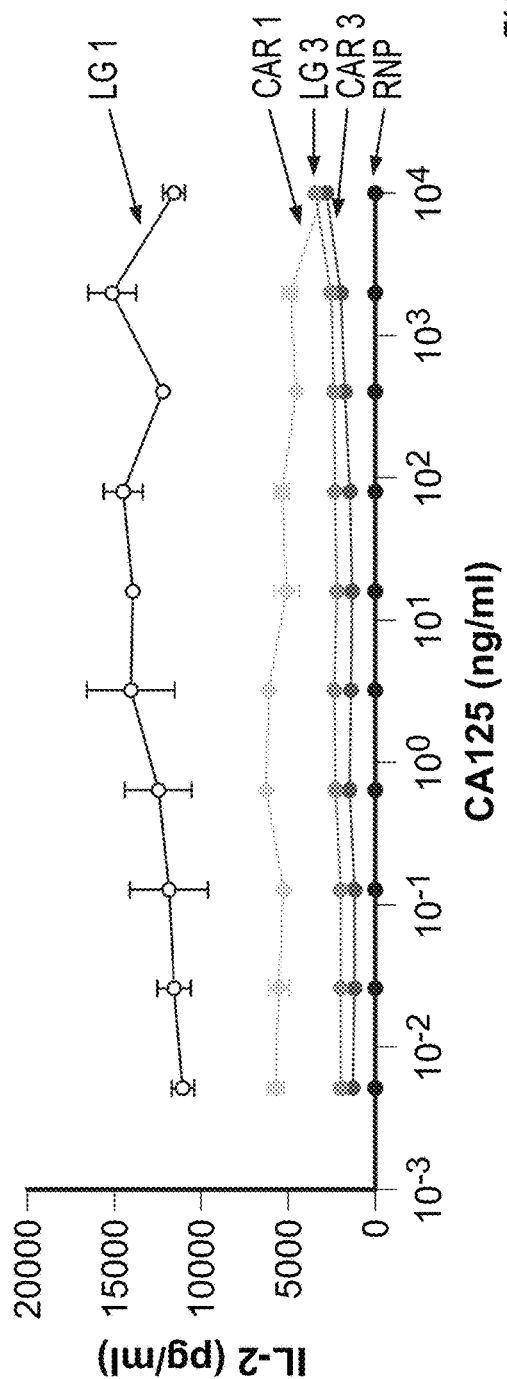
FIG. 11A shows IL-2 cytokine production after incubation of logic gate-expressing T cells or CAR-expressing T cells with target cells in the presence of CA125.
Figure 11B:
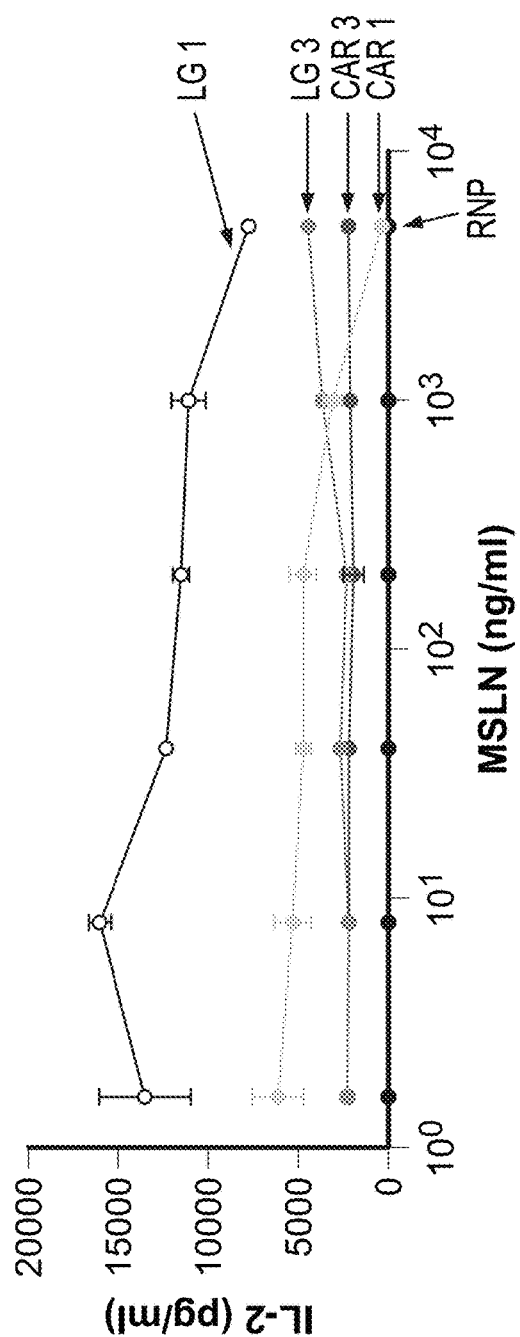
FIG. 11B shows IL-2 cytokine production after incubation of logic gate-expressing T cells or CAR-expressing T cells with target cells in the presence of MSLN.

Neither LG1 nor LG3 (or their matched constitutive CAR controls) were inhibited by physiologically-relevant levels of soluble CA125 or sMSLN (FIGS. 11A and 11B). The RNP T cells showed no cytokine release as expected for the negative control. These results indicate that both LG1 and LG3 contain CARs that are resistant to inhibition by levels of soluble CA125 and sMSLN that could be encountered in ovarian cancer patients.

Example 2: In Vivo Characterization of ALPG/P and MSLN Logic Gates

Materials and Methods

T cells from two donors were engineered to express LG1 or LG3 (or matched constitutive CAR controls) using the engineering methods described above in Example 1. Cells were frozen and cryobanked at Day 9 after initial activation. For quality control (QC) assays, engineered T cells and RNP only control T cells from the same donors were thawed and rested overnight in media including 12.5 ng/mL human IL-7 and IL-15. Next, engineered T cells were counted and stained for PrimeR and CAR expression using anti-myc PE and anti-FLAG APC, respectively, and analyzed by flow cytometry to assess KI %.

K526 Dual Flank In Vivo Study

NSG double MHC KO (NSG DKO) strain (Jackson Laboratories, 025216) were implanted with 1e6 each of K562-MSLN cells on the left flank and K562-ALPG/MSLN cells on the right flank, both in 50% Matrigel solution. Three days after K562 cell inoculation, mice were randomly assigned to treatment groups with matched tumor sizes using bioluminescent imaging (BLI) to measure luciferase signal to quantify engineered tumor cells, with 7 mice assigned per treatment condition. The same day of staging and normalization, engineered T cells and matched RNP controls were thawed and rested overnight in media including 12.5 ng/mL human IL-7 and IL-15. On Day 4 after K562 implantation, for each donor all engineered T cell populations were normalized to the lowest KI % within that donor by adding RNP only cells to dilute engineered populations that were above the lowest KI %. Mice were injected with 5e6 KI+ T cells i.v. via the tail vein. Bilateral tumor volumes were monitored twice weekly via caliper along with body weight.

MSTO

NSG double MHC KO (NSG DKO) strain (Jackson Laboratories, 025216) were implanted with 1e6 each of MSTO-211H cells engineered to express ALPG and MSLN at levels matching the ASPC-1 reference line in 50% Matrigel solution. Nine days after MSTO cell inoculation, mice were randomly assigned to treatment groups with matched tumor sizes based on caliper measurements, with 7 mice assigned per treatment condition. The same day of staging and normalization, engineered T cells and matched RNP controls were thawed and rested overnight in media including 12.5 ng/mL human IL-7 and IL-15. On Day 10 after MSTO implantation, for each donor all engineered T cell populations were normalized to the lowest KI % within that donor by adding RNP only cells to dilute engineered populations that were above the lowest KI %. Mice were injected with 2e6, 7e5, or 2.3e5 KI+ T cells i.v. via the tail vein. Tumor volumes were monitored 2-3 times weekly via caliper along with body weight.

Results

The dual flank in vivo experiment models on-target off-tumor toxicity observed clinically with constitutive CAR T cells targeting an tumor antigen that is also expressed by healthy organs, with the tumor that only expresses the cytolytic representing such a normal tissue. In these experiments, the K562$^{MSLN}$ tumor modeled a healthy organ (e.g., the mesothelial lining) that expresses MSLN and the K562$^{ALPG/MSLN}$ tumor on the opposite flank modeled an ovarian cancer tumor. T cells expressing either LG1 or LG3 both showed specific killing of the dual-antigen K562$^{ALPG/MSLN}$ tumor cells with no measurable activity against the off-target K562$^{MSLN}$ tumor cells (FIG. 12A-F). In each figure, the lower line shows the tumor volume after treatment with the indicated T cells, and the higher line shows the tumor volume after treatment with control T cells. Tumor volume in the in K562$^{MSLN}$ tumor and K562$^{ALPG/MSLN}$ tumor after treatment with the constitutive CAR is shown in FIGS. 12A and 12B, respectively. Tumor volume in the K562$^{MSLN}$ tumor and K562$^{ALPG/MSLN}$ tumor after treatment with LG1 is shown in FIGS. 12C and 12D, respectively. Tumor volume in the K562 mm-N tumor and K562$^{ALPG/MSLN}$ tumor after treatment with LG3 is shown in FIGS. 12E and 12F, respectively. LG1 T cells demonstrated more potent on-target anti-tumor activity than LG3 T cells. Thus, both LG1 and LG3 directed engineered T cells to specifically target and kill ALPG+/MSLN+ tumors and ignore MSLN+ tumors present just a few centimeters away in the same mice. The results of these experiments show how logic gate T cells can be used to specifically target dual-antigen tumors in vivo.

Figure 13B:
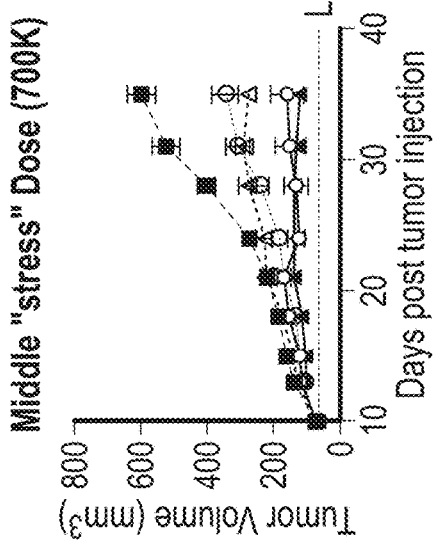
FIG. 13B shows tumor volume after treatment with a middle "stress" dose of the indicated engineered T cells.
Figure 13D:
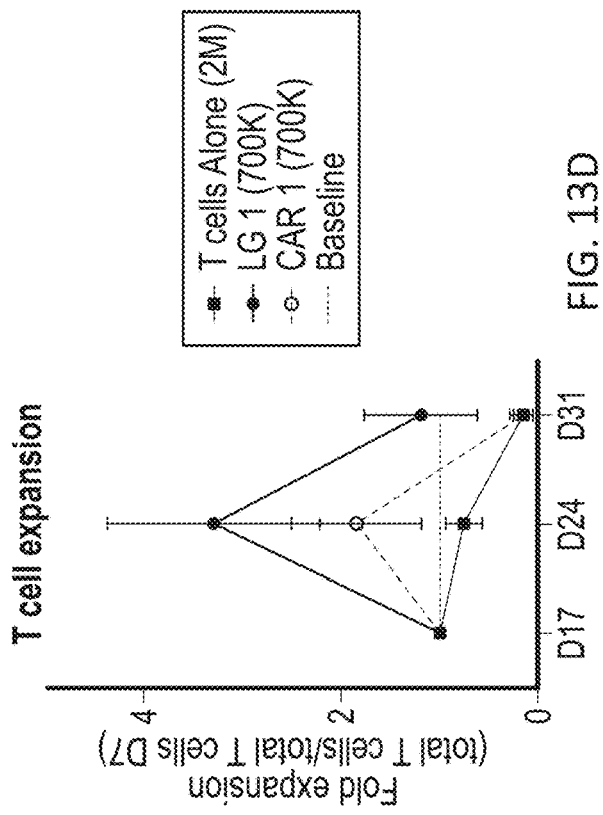
FIG. 13D shows T cell expansion in blood samples after treatment with the indicated T cells.
Figure 13A:
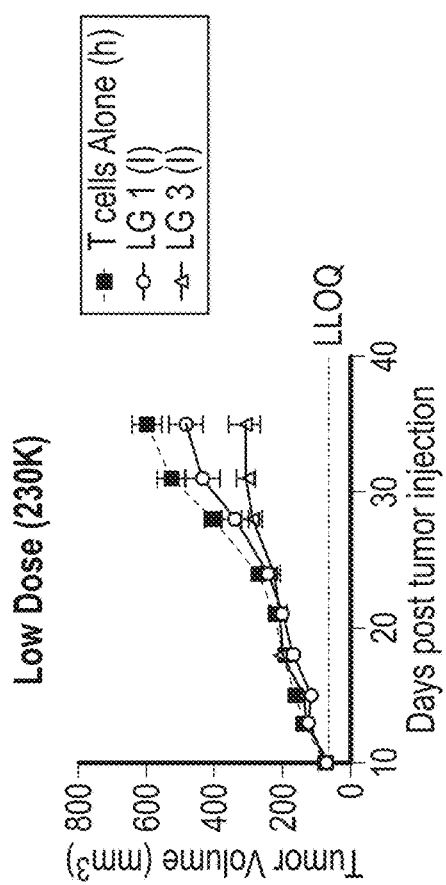
FIG. 13A shows tumor volume in the MSTO model after treatment with a low dose of the indicated engineered T cells.
Figure 13C:
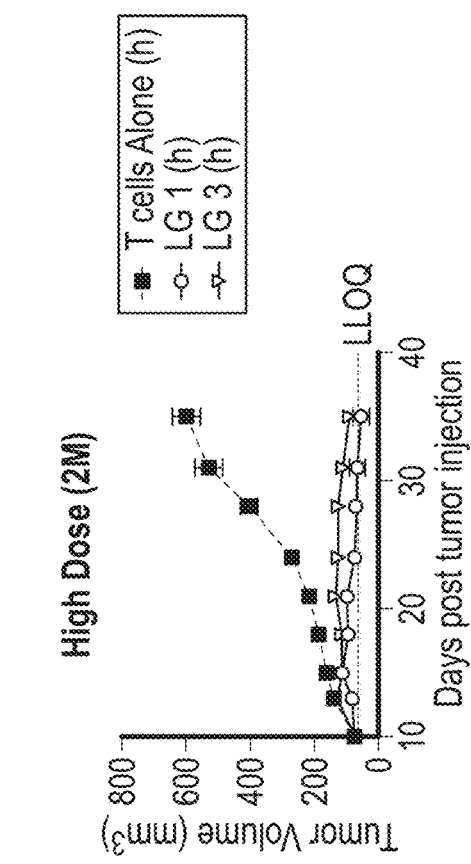
Figure 14A:
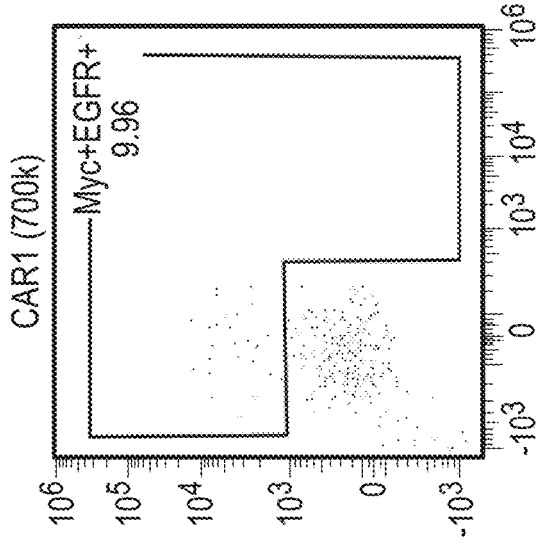
FIG. 14A shows flow analysis of T cells found in the peripheral blood after treatment with control T cells.
Figure 14B:
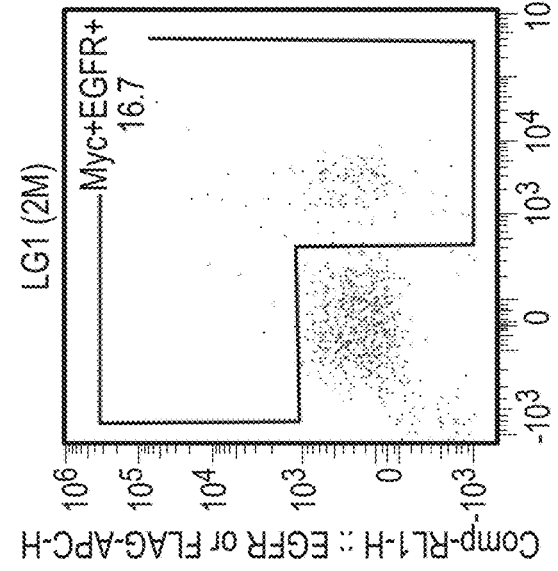
FIG. 14B shows flow analysis of T cells found in the peripheral blood after treatment with the middle dose of CAR 1-expressing T cells.
Figure 14C:
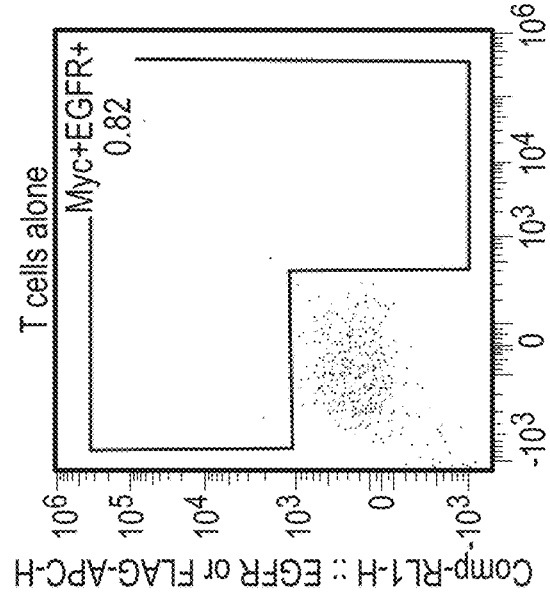
FIG. 14C shows flow analysis of T cells found in the peripheral blood after treatment with the middle dose of LG1-expressing T cells.
Figure 14D:
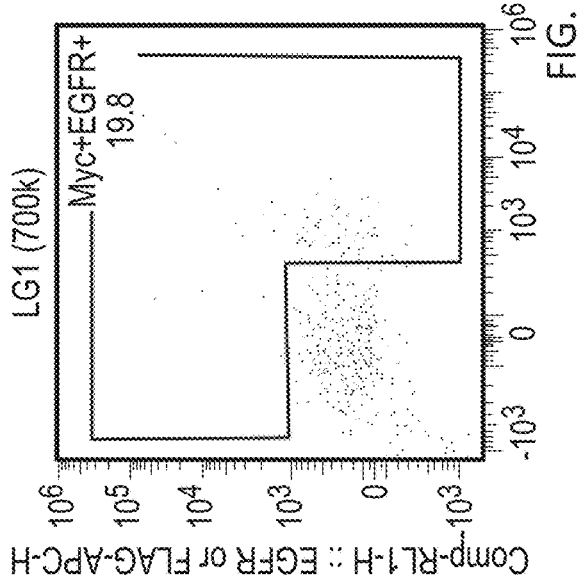
FIG. 14D shows flow analysis of T cells found in the peripheral blood after treatment with the high dose of LG1-expressing T cells, CAR-expressing-T cells, or negative control cells.

The dose of 2e6 LG1 or LG3 T cells induced potent tumor killing and complete responses in the engineered MSTO-2H11ALPG/MSLN xenograft tumor model. CAR potency against solid tumors was enhanced with the LG1 or LG3 logic gate T cells. Low dose, stress dose, and high dose T cell dosing responses are shown in FIGS. 13A, 13B, and 13C, respectively. At the stress-test dose of 7e5 conventional CAR-T cells with constitutive LG1 MSLN-CAR expression, tumor growth was only partially inhibited (FIG. 13B). In contrast, ALPG PrimeR logic-gated T cells (either LG1 or LG3 T cells) resulted in superior tumor growth inhibition at the same dose (FIG. 13B). Additionally, logic gate-expressing T cells showed more robust expansion in blood samples compared to constitutively expressing CAR-T based on counts of engineered T cells in the blood taken via flow cytometry (FIG. 13D). Flow analysis of T cells found in the peripheral blood showed minimal CAR expression from logic gate T cells, demonstrating the fidelity of the logic gate to restrict CAR expression and activity to the on-target tumor (FIG. 14A-14D). Thus, the logic gates not only enhanced specificity and safety of CAR T cells by gating their activity on the presence of a priming antigen but also increased the potency of T cell therapies relative to constitutive CARs.

Example 3: Characterization of shRNA In Vitro

Materials
mRNA-Level Knockdown (qPCR)

T cells from at least 2 donors were engineered to express FMC63 CAR alone or with the indicated FAS, TOX, PTPN2 or ZC3H12A shRNA modules. T cells from donors were isolated from leukopacks and activated (Day 0). 48 hours post-activation, T cells were engineered (Day 2). To engineer the T cells, sgRNA targeting GS94 was complexed with sNLS-SpCas9-sNLS Nuclease at room temperature for 10 minutes forming the ribonucleoprotein mix. Plasmids containing the FMC63 CAR alone or the FAS, TOX, PTPN2 or ZC3H12A shRNA modules and supplemented Primary P3 Solution were added to the ribonucleoprotein and mixed. The mix was added to activated T cells and electroporated. After electroporation, the engineered T cells were recovered using fresh media supplemented with 12.5 ng/mL of IL-7 and IL-15. The engineered T cells were replenished with fresh media supplemented with 12.5 ng/mL of IL-7 and IL-15 on Day 3 and 5.

Six days post-editing, magnetic enrichment was performed using Dynabeads MyOne Streptavidin T1 and a biotinylated anti-EGFRt antibody. The highly pure populations of edited T cells was lysed and mRNA extracted using the Dynabeads mRNA Direct Purification Kit. Once extracted, the mRNA was quantified using the Quant-it RiboGreen RNA Assay Kit, and used to synthesize cDNA with the SuperScript IV First-Strand Synthesis kit. The cDNA was then used to perform real-time Quantitative Reverse Transcription PCR with the TaqMan Fast Advanced Master Mix and the RPL13A, FAS, PTPN2, ZC3H12A and TOX TaqMan assays.

Protein-Level Knockdown (Flow Cytometry)

T cells from at least 2 donors were engineered to express FMC63 CAR alone or with the indicated FAS shRNA module using the R&D manufacturing process. Six days post-editing, T cells were stained for EGFRt and FAS expression using anti-EGFRt PE and anti-FAS AF647, respectively, and analyzed by flow cytometry on an Attune NxT flow cytometer. Relative FAS expression was quantified by taking the ratio of the gMFI of FAS for EGFRt+ cells divided by EGFRt− cells. This value was then normalized to the relative FAS expression of the control group to calculate knockdown.

T Cell Engineering for Dual shRNA Knockdown

T-cells were enriched from peripheral blood mononuclear cells (PBMCs) obtained from normal donor Leukopaks (STEMCELL Technologies) using Lymphoprep (STEMCELL Technologies) and the EasySep Human T-Cell Isolation Kit (STEMCELL Technologies). T-cells were subsequently activated with CD3/CD28 Dynabeads at 1:1 bead to cell ratio (ThermoFisher, 40203D) in TexMACS medium (Miltenyi 130-197-196) supplemented with 3% human AB serum (Gemini Bio) and 12.5 ng/ml human IL-7 and IL-15 (Miltenyi premium grade) and cultured at 37° C., 5% CO2 for 48 hours before electroporation.

CRISPR RNP were prepared by combining 120 µM sgRNA (Synthego) targeting DNA sequence GAGCCATGCTTGGCTTACGA (GS94, SEQ ID NO: 307), 62.5 µM sNLS-SpCas9-sNLS (Aldevron) and P3 buffer (Lonza) at a volume ratio of 5:1:3:6, and incubated for 15 minutes at room temperature. An optimized amount of plasmid DNA encoding the shRNA sequence(s) of interest, determined by dose titration experiments (ranging from 0.5-3 micrograms) was mixed with 3.5 µl of RNP. T-cells were counted, debeaded, centrifuged at 90×G for 10 minutes and resuspended at 10^6 cells/14.5 µl of P3 with supplement added (Lonza). 14.5 µl of T-cell suspension was added to the DNA/RNP mixture, transferred to Lonza 384-well nucleocuvette plate, and pulsed in a Lonza HT Nucleofector System with code EH-115. Cells were allowed to rest for 15 minutes at room temperature before transfer to 96-well plates (Sarstedt) in TexMACS medium supplemented with 12.5 ng/ml human IL-7 and IL-15 (Miltenyi premium grade).

T cells from three donors were engineered to express an anti-mesothelin (MSLN) CAR alone or with either a dual luciferase control shRNA module, FAS shRNA, FAS-TOX shRNA, TOX-PTPN2 shRNA, FAS-PTPN2 shRNA, ZC3H12A-PTPN2, or FAS-NR4A1 shRNA using the non-viral electroporation method described above. Cells were frozen and cryobanked at Day 9 after initial activation. Prior to cryopreservation, an aliquot of cells from each condition was taken and the T cells were stained for EGFRt and CAR expression using anti-EGFRt and anti-myc, respectively, and analyzed by flow cytometry on an Attune NxT.

Sequences of the shRNA and an exemplary shRNA-mir module are provided below and in the sequence listing:

```
FAS_11:
                           (SEQ ID NO: 49)
TTAAGAATCTTTTCAAACACTA

FAS_13:
                           (SEQ ID NO: 51)
TAATCTTAATCTTTCATCCTCT

PTPN2_14:
                           (SEQ ID NO: 82)
TCTGACAAGAGCTTCACACTGA

PTPN2_1:
                           (SEQ ID NO: 72)
TATAATACGACTTCACATCTTC

TOX_9:
                           (SEQ ID NO: 104)
TAGGTGAGGATTCATTCCCGGT

TOX_4:
                           (SEQ ID NO: 99)
TATGACTGCTACATCAAGCCAT

ZC3H12A:
                           (SEQ ID NO: 126)
TTATTAAGAAGCATCTTGCTTA

NR4A1:
                           (SEQ ID NO: 144)
TTAATCAGAAAAGTCACATACT
```

```
FAS_11-PTPN_14 shRNA-miR module:
                                 (SEQ ID NO: 157)
GTAAGTCGACTCGTTGGATCCCCACTACCCGGATCAACGCC

CTAGGTTTATGTTTGGATGAACTGACATACGCGTATCCGT

CTTAAGAATCTTTTCAAACACTAGTAGTGAAATATATATT

AAACTAGTGTTTGAAAAGATTCTTATTACGGTAACGCGGA

ATTCGCAACTATTTTATCAATTTTTTGCGTCGACACTTCA

AGGGGCTTGCGGCCGCAACCATCTCCATGGCTGTTTGAAT

GAGGCTTCAGTACTTTACAGAATCGTTGCCTGCACATCTT

GGAAACACTTGCTGGGATTACTTCGACTTCTTAACCCAAC

AGAAGGCTGAGAAGGTATATTGCTGTTGACAGTGAGCGC

CAGTGTGAAGCTCTTGTCAGATAGTGAAGCCACAGATGTA

TCTGACAAGAGCTTCACACTGATGCCTACTGCCTCGGACT

TCAAGGGGCTAGAATTCGAGCAATTATCTTGTTTACTAAA

ACTGAATACCTTGCTATCTCTTTGATACATTTTTACAAAG

CTGAATTAAAATGGTATAAATTAAATCACTTTTTCATCTG

ACCAGTAGTGGACTAGTGTGACGCTGCTGACCCCTTTCTT

TCCCTTCTACAG
```

Additional shRNA miR modules are provided in the sequence listing.

T cells were also engineered to have a double FAS and PTPN2 knockout.

mRNA Knockdown in Resting Conditions

T cells from four donors were engineered to express MSLN CAR alone or with either a dual luciferase control shRNA, FAS-NR4A1 shRNA, FAS-TOX shRNA, FAS-PTPN2 shRNA, PTPN2-TOX shRNA, or PTPN2-ZC3H12A shRNA modules using the manufacturing process described above. Six days post-editing, magnetic enrichment was performed using Dynabeads MyOne Streptavidin Ti and a biotinylated anti-EGFRt antibody. The highly pure populations of edited T cells were lysed and mRNA extracted using the Dynabeads mRNA Direct Purification Kit. Once extracted, the mRNA was quantified using the Quant-it RiboGreen RNA Assay Kit, and used to synthesize cDNA with the SuperScript IV First-Strand Synthesis kit. The cDNA was then used to perform real-time Quantitative Reverse Transcription PCR (RT-qPCR) with the TaqMan Fast Advanced Master Mix and TaqMan assays for RPL13A, FAS, PTPN2, TOX, and ZC3H12A.

Protein Knockdown in Resting Conditions

Flow Cytometry: T cells from 2 donors were engineered to express MSLN CAR alone or with either a dual luciferase control shRNA, FAS-NR4A1 shRNA, FAS-TOX shRNA, FAS-PTPN2 shRNA, PTPN2-TOX shRNA, or PTPN2-ZC3H12A shRNA modules using the manufacturing process. Six days post-editing and once a week for 6 weeks thereafter, cells were stained for EGFRt and FAS expression using anti-EGFRt PE and anti-FAS FITC, respectively, and analyzed by flow cytometry on an Attune NxT. Relative FAS expression was quantified by taking the ratio of the gMF1 of FAS for EGFRt+ cells divided by EGFRt− cells. This value was then normalized to the relative FAS expression of the control group.

Western Blot: T cells from 4 donors were engineered to express MSLN CAR alone or with either a dual luciferase control shRNA, the FAS-NR4A1 shRNA, FAS-TOX shRNA, FAS-PTPN2 shRNA, PTPN2-TOX shRNA, or PTPN2-ZC3H12A shRNA modules using the manufacturing process. Six days post-editing, magnetic enrichment was performed using Dynabeads MyOne Streptavidin T1 and a biotinylated anti-EGFRt antibody. The highly pure populations of edited T cells were then lysed and boiled to reduce and denature proteins. Total protein was quantified using the Pierce BCA Protein Assay Kit. Normalized lysates were then loaded into an SDS-PAGE gel and run. Protein was then transferred from the gel to a PVDF membrane, blocked, and stained for RPL13A (control), FAS, NR4A1, or PTPN2 primary antibody and HRP conjugated secondary antibody. The blot was then imaged with the Bio-Rad ChemiDoc and relative PTPN2 expression was quantified.

mRNA Knockdown Under Chronic Stimulation Conditions

Edited CD3+ T cells were subjected to 14 days of repetitive stimulation with MSLN+K562 and rested 48 hours before RNA-seq.

FAS-Mediated Apoptosis

T cells from 6 donors were engineered to express MSLN CAR alone or with either a dual luciferase control shRNA, the FAS-NR4A1 shRNA, FAS-TOX shRNA, FAS-PTPN2 shRNA, PTPN2-TOX shRNA, or PTPN2-ZC3H12A shRNA modules using the manufacturing process. Six days post-editing T cells were cultured with 0, 0.2, 2, or 20 ug/mL of anti-FAS activating antibody for 24 hours. T cells were stained with EGFRt, live/dead, and Apotracker and analyzed by flow cytometry on an Attune NxT. The frequency of viable edited cells was calculated as the percent live/dead—Apotracker—among EGFRt+ cells and these frequencies were then normalized to the percent viable cells in the control condition with 0 ug/mL anti-FAS activating antibody.

Cytokine-Independent Growth Assay

T cells from 2 donors were engineered to express MS LN CAR alone or with either a dual luciferase control shRNA, the FAS-NR4A1 shRNA, FAS-TOX shRNA, FAS-PTPN2 shRNA, PTPN2-TOX shRNA, or PTPN2-ZC3H12A shRNA modules using the manufacturing process. Eleven days post-editing T cells were cultured with 12.5 ng/mL of IL-7 and IL-15 or in the absence of exogenous cytokines and the frequency of edited cells and absolute number of viable cells was quantified on day 0, 2, 4, and 8 post cytokine withdrawal. The fold-change in viable edited cells from day 0 was used to normalize each condition.

Cytotoxicity Assays

Incucyte: T cells from three donors were engineered to express MSLN CAR alone or with either a dual luciferase control shRNA, the FAS-NR4A1 shRNA, FAS-TOX shRNA, FAS-PTPN2 shRNA, PTPN2-TOX shRNA, or PTPN2-ZC3H12A shRNA modules using the manufacturing process and were frozen and cryobanked at Day 9 after initial activation. Prior to performing the assay, cells were thawed and recovered in media containing 12.5 ng/mL of IL-7 and IL-15. Edited cell frequencies were normalized to the lowest editing efficiency by adding back RNP only edited T cells. T cells were then co-cultured with K562 cells with and without engineering to express the CAR target antigen, MSLN at a one to one ratio. Over the course of 48 hours, the cell cultures were imaged using the Incucyte and percent killing was calculated by dividing the number of viable K562 cells by the total number of K562 cells, subtracting the quotient from 1 and multiplying by 100.

Lucifersase: T cells from three donors were engineered to express SS1 CAR alone or with either a dual luciferase control shRNA module or the FAS-PTPN2 shRNA module using the CiTE manufacturing process and were frozen and cryobanked at Day 9 after initial activation. Prior to performing the assay, cells were thawed and recovered in media containing 12.5 ng/mL of IL-7 and IL-15. Edited cell frequencies were normalized to the lowest editing efficiency by adding back RNP only edited T cells. T cells were then co-cultured with MSTO cells engineered to express the CAR target antigen, MSLN at the indicated ratios. After 48 hours, the Luc-Screen assay was performed and percent target cell killing was calculated by dividing the luminescence values for each sample by the luminescence values of tumor only control wells, subtracting the quotient from 1, and multiplying by 100.

RSA

T cells from three donors were engineered to express MSLN CAR alone or with either a dual luciferase control shRNA, the FAS-NR4A1 shRNA, FAS-TOX shRNA, FAS-PTPN2 shRNA, PTPN2-TOX shRNA, or PTPN2-ZC3H12A shRNA modules using the manufacturing process and were frozen and cryobanked at Day 9 after initial activation. Prior to performing the assay, cells were thawed and recovered in media containing 12.5 ng/mL of IL-7 and IL-15. Six days post-editing, magnetic enrichment was performed using Dynabeads MyOne Streptavidin T1 and a biotinylated anti-EGFRt antibody. Enriched edited cells were counted by flow cytometry on a Attune NxT with CountBright Plus Absolute counting beads. 85,000 edited T cells were dispensed into wells of a 96 well flat bottom plate and co-cultures were initiated by dispensing K562 at a defined effector:target ratio. At days 2, 5, 7, 9, and 12 after the initial enrichment T cells were quantified by flow cytometry and co-cultures were re-set to the desired E:T ratio by dispensing K562 cells using a TTP LabTech Dragonfly liquid handler, At day 14 after the initial enrichment RNAseq was performed on edited T cells by performing an anti-EGFRt antibody based enrichment as above, using flow cytometry to dispense 20,000 T cells into wells of a 384 well plate, and then using an in house 3' barcode counting bulk RNAseq prep. Sample barcoding oligo-dT reverse transcription primers were dispensed using a Beckman Echo acoustic liquid handler; reverse transcription was performed and RT-PCR products were converted to sequencing libraries using Illumina Nextera XT tagmentation kit and sequenced on an Illumina NovaSeq DNA sequencer. Cytokine production from day 14 supernatants was quantified by EMD Millipore Luminex multiplex cytokine kits.

Figure 36A:
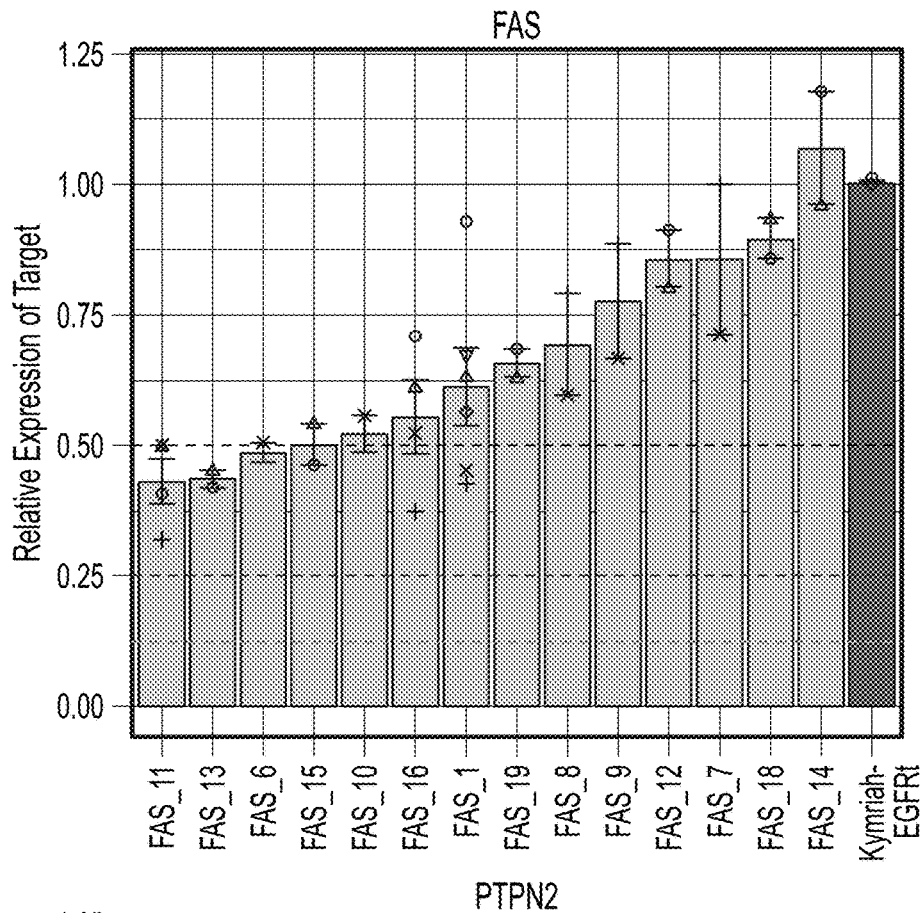
FIG. 36A shows FAS mRNA levels after shRNA knockdown.
Figure 36B:
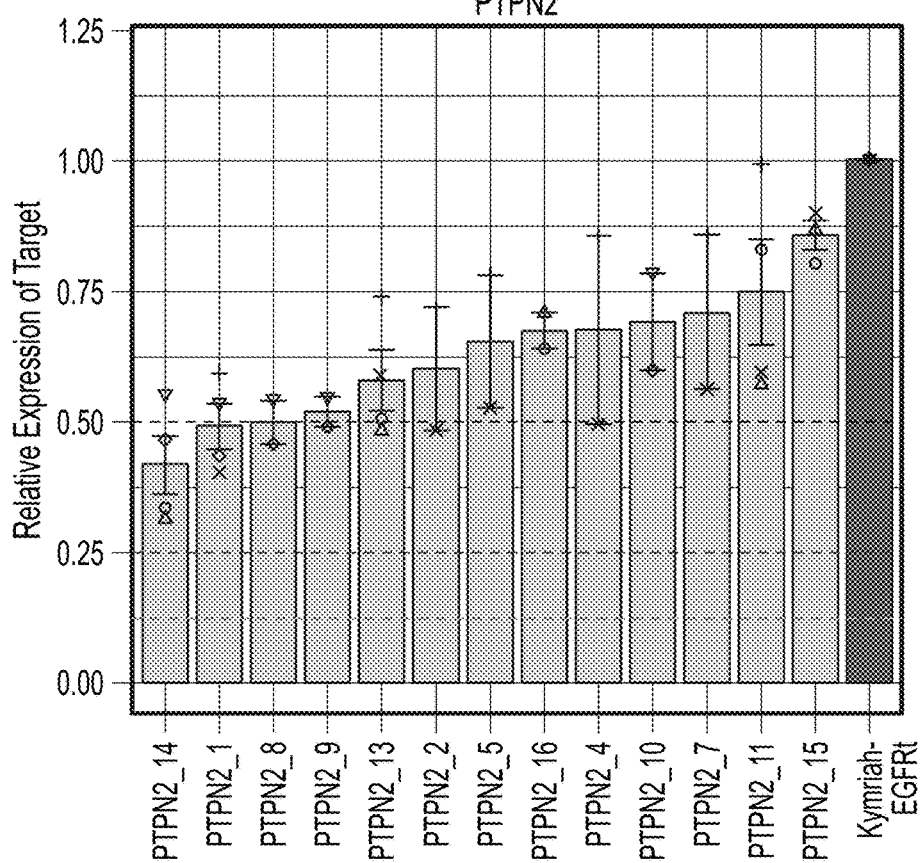
FIG. 36B shows PTPN2 mRNA levels after shRNA knockdown.
Figure 36C:
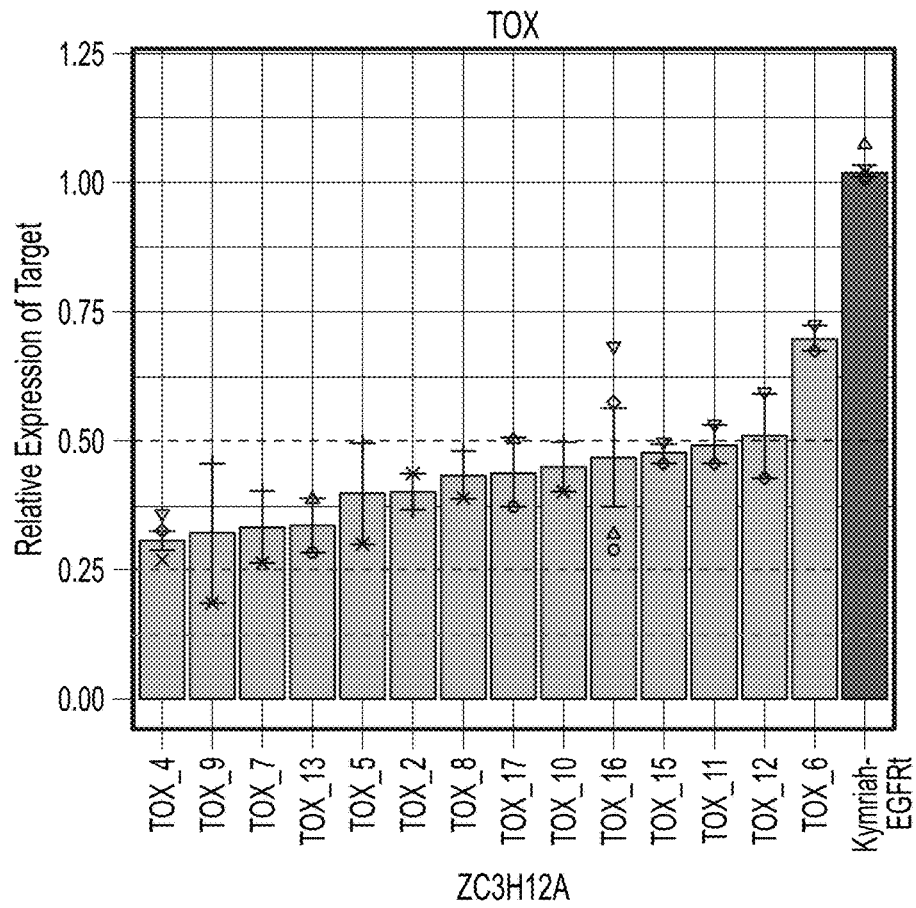
FIG. 36C shows TOX mRNA levels after shRNA knockdown.
Figure 36D:
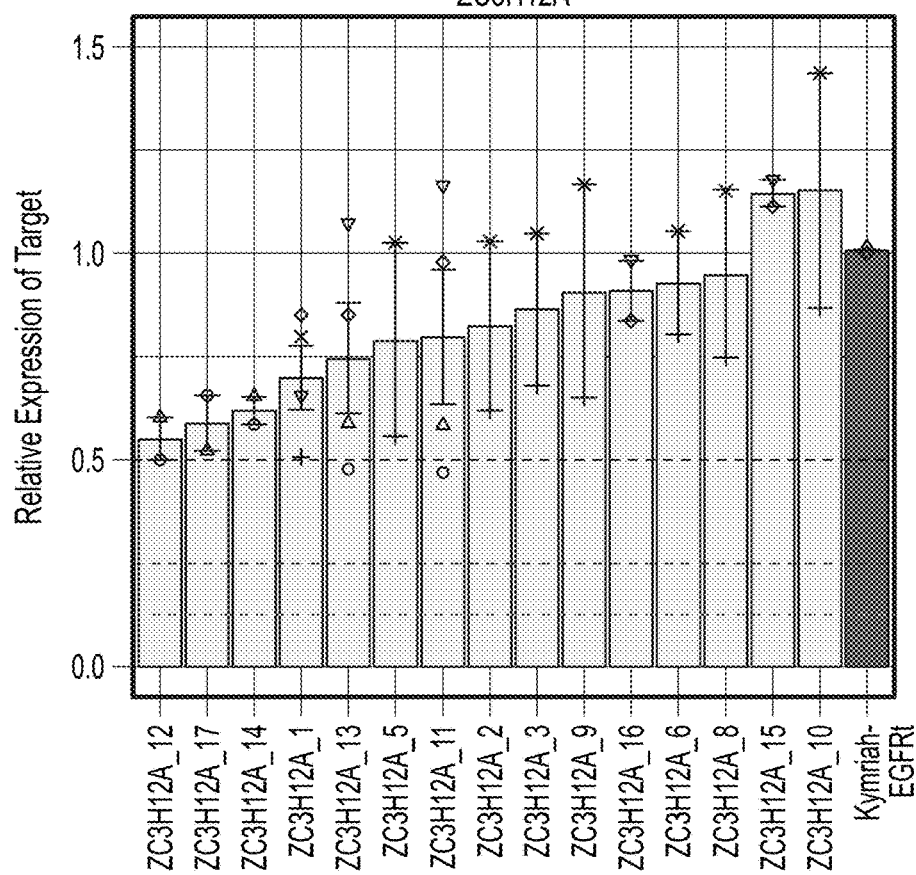
FIG. 36D shows ZC3H12A mRNA levels after shRNA knockdown.

Results mRNA-Level Knockdown (qPCR)

mRNA knock down of FAS, PTPN2, TOX, and ZC3H12A are shown in FIGS. 18A-D. Real-time Quantitative Reverse Transcription PCR results show that the shRNA sequences against FAS (FIG. 36A), TOX (FIG. 36B), and PTPN2 (FIG. 36C) provide greater than 50% knockdown in edited cells at the end of manufacturing. Maximum knockdown of ZC3H12A was approximately 55% (FIG. 36D). shRNA sequences FAS_11, FAS_13, PTPN2_1, PTPN2_14, TOX_9, TOX_4, ZC3H12A_12, ZC3H12A_1, NR4A1_12, and NR4A1_19 (not shown) were selected for additional characterization.

Protein-Level Knockdown (Flow Cytometry)

Figure 37:
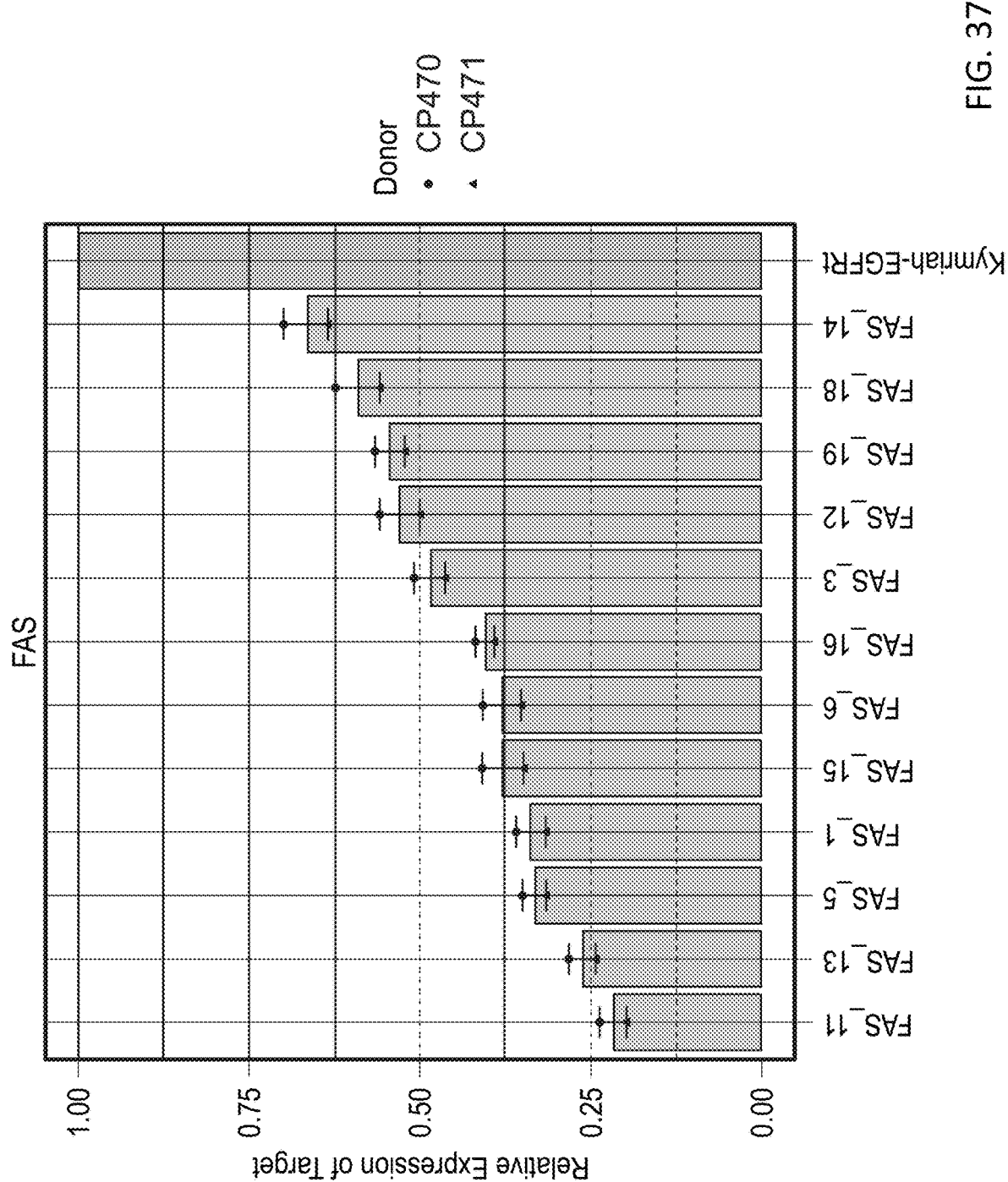
FIG. 37 shows FAS protein levels after shRNA knockdown.

The shRNA module targeting FAS provided greater than 50% knockdown of FAS protein in edited cells at the end of manufacturing (FIG. 37).

T Cell Engineering for Dual shRNA Knockdown

Figure 15A:
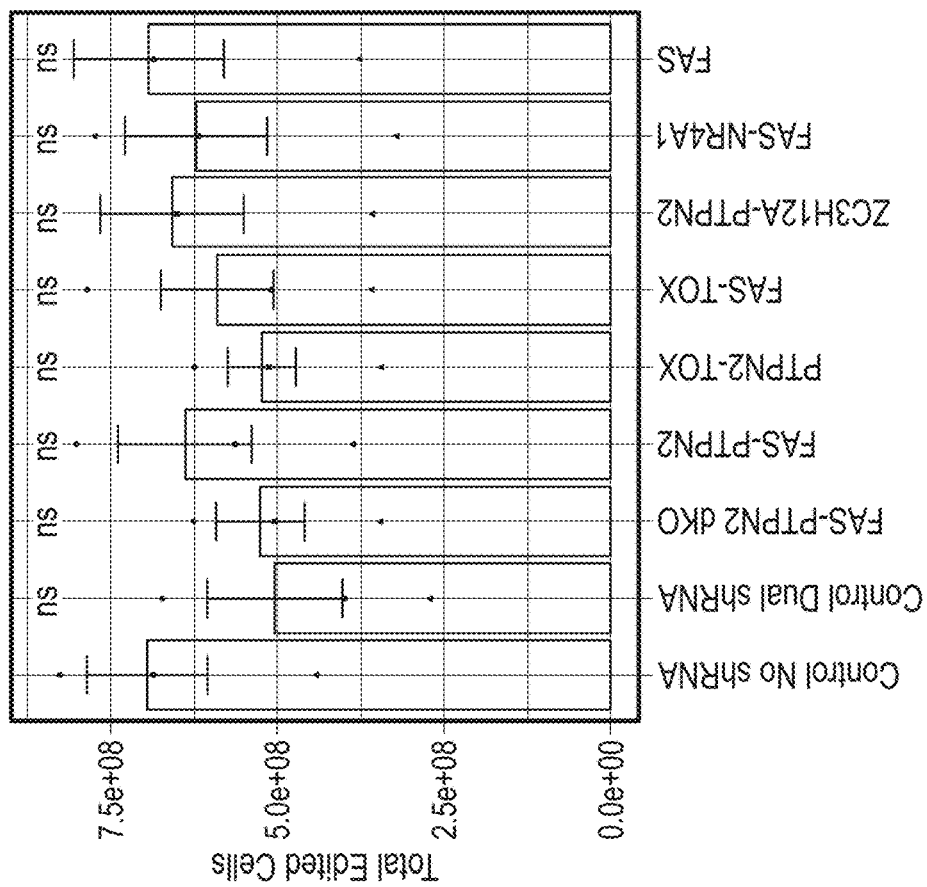
FIG. 15A shows the percent of edited cells with the indicated shRNA after a 9-day expansion.
Figure 15B:
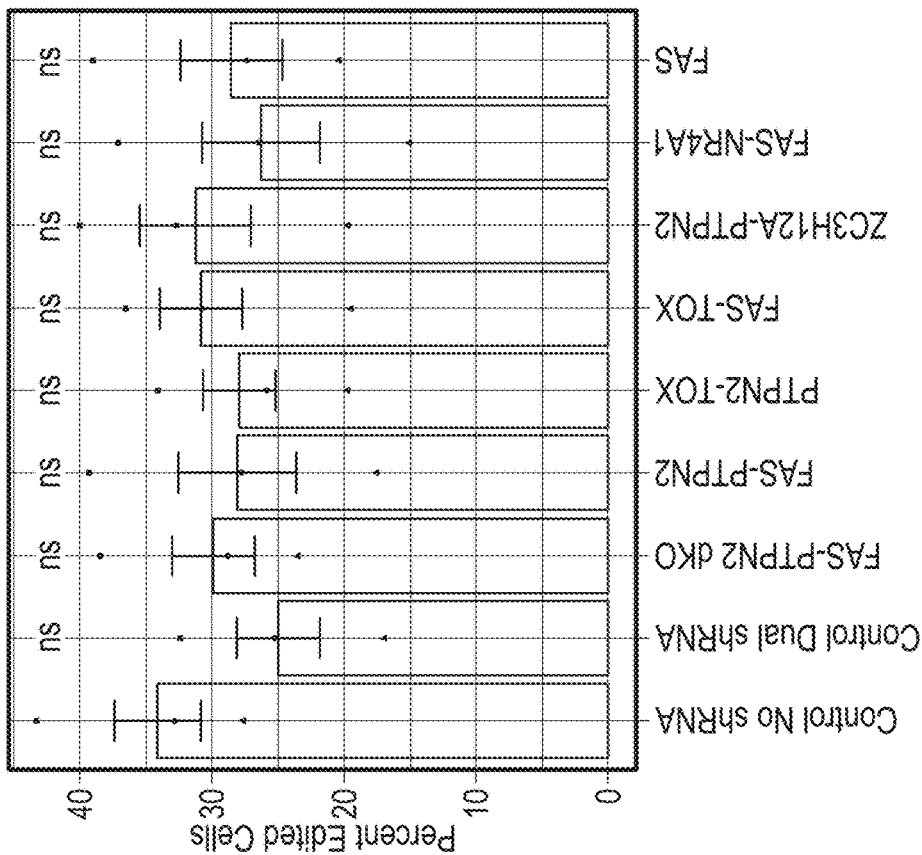
FIG. 15B shows the total edited cells with the indicated shRNA after a 9-day expansion.

No differences in editing efficiency or edited cell yield were observed at the end of manufacturing. The shRNA-miR module did not impact cell expansion during 9-day cell production (FIGS. 15A and 15B).

mRNA Knockdown in Resting Conditions

Figure 16:
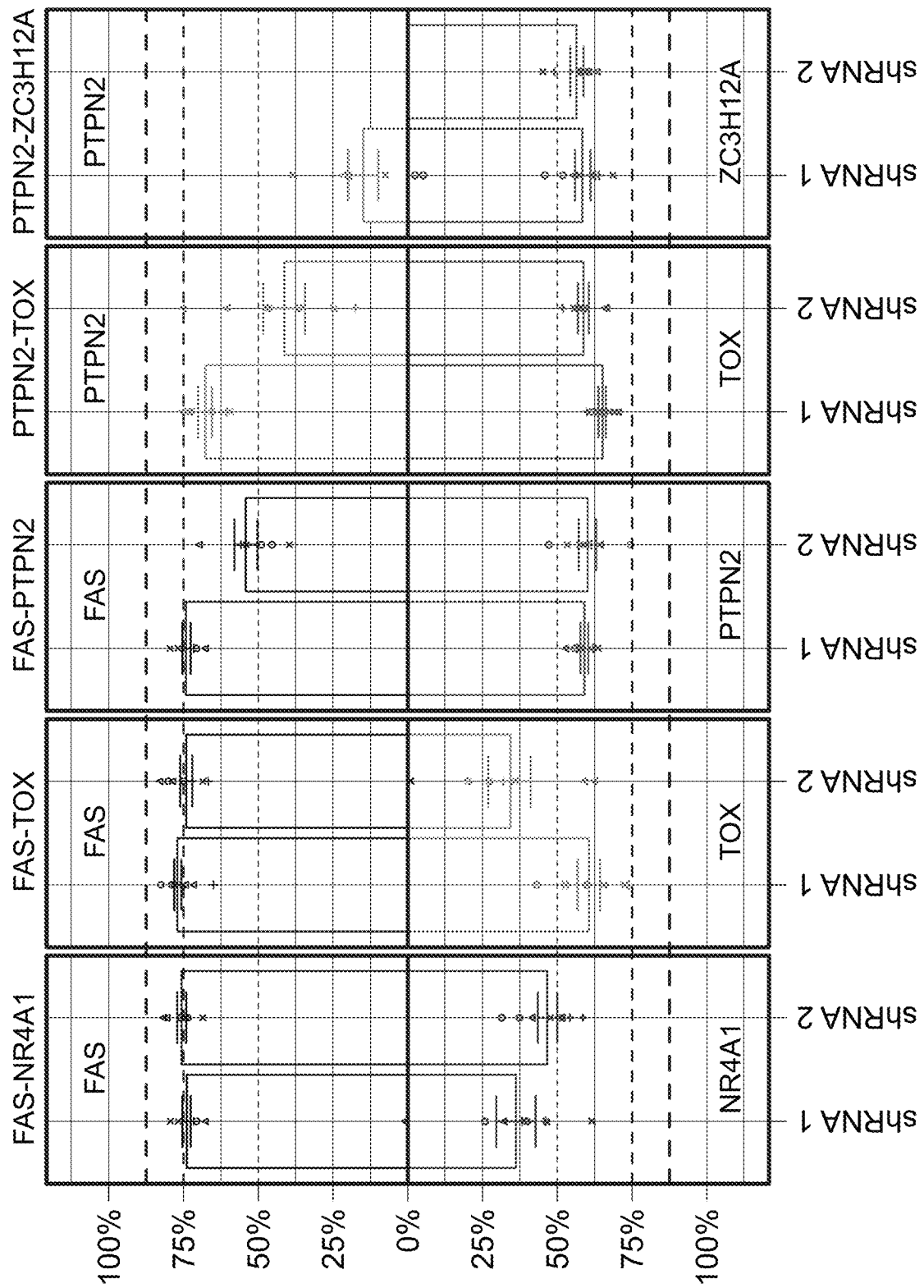
FIG. 16 shows the target gene knock down of both indicated genes when used in combination.

Multiple shRNAs demonstrate robust target gene knock down of both genes when used in combination (FIG. 16). The FAS-PTPN2 module provided greater than 50% knockdown of both FAS and PTPN2 mRNA in edited cells under resting conditions (FIG. 16).

Protein Knockdown in Resting Conditions

The shRNA module targeting FAS, PTPN2, and TOX provides stable knockdown of FAS for at least 7 weeks after editing under resting conditions (FIG. 17A). FAS, PTPN2, and NR4A1 protein levels were also significantly reduced 6 days post editing (FIG. 17B). FAS protein was reduced to less than 25% when the FAS shRNA was combined with PTPN2 or TOX, NR4A1 protein was reduced to less than 50% when the NR4A1 shRNA was combined with FAS, and PTPN2 protein was reduced to about or less than 12% when the PTPN2 shRNA was combined with FAS, TOX, or ZC3H12A shRNA. Thus, shRNA gene knockdown for FAS, PTPN2, and NR4A1 was robust and durable under homeostatic conditions.

mRNA Knockdown Under Chronic Stimulation Conditions

Figure 18:
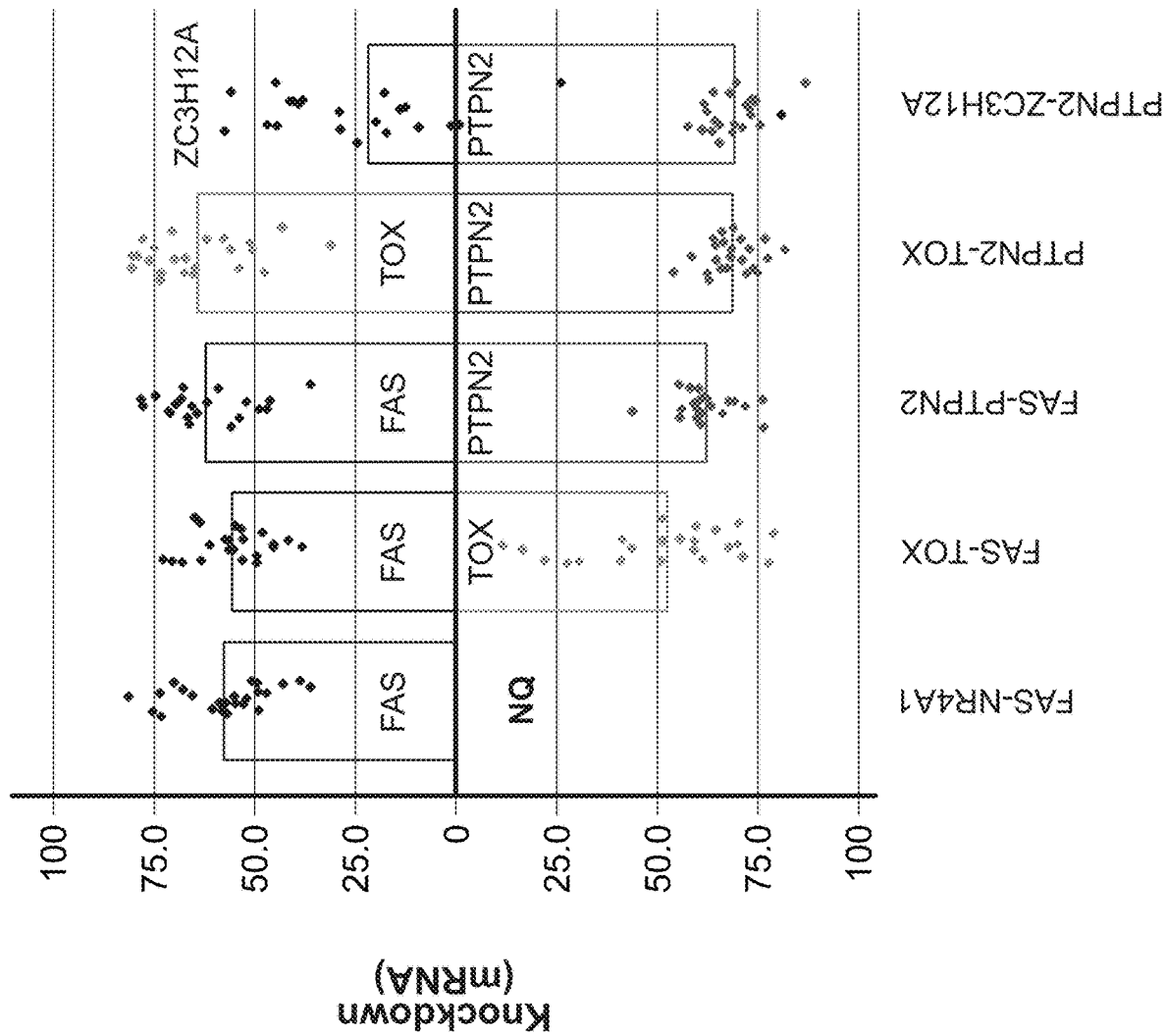
FIG. 18 shows that target gene knockdown in T cells was maintained throughout chronic stimulation.

Target gene knockdown was maintained throughout chronic stimulation (FIG. 18). Thus, the shRNA gene knockdown for FAS, PTPN2, and NR4A1 was robust and durable under chronic stimulation conditions.

FAS-Mediated Apoptosis

Figure 19B:
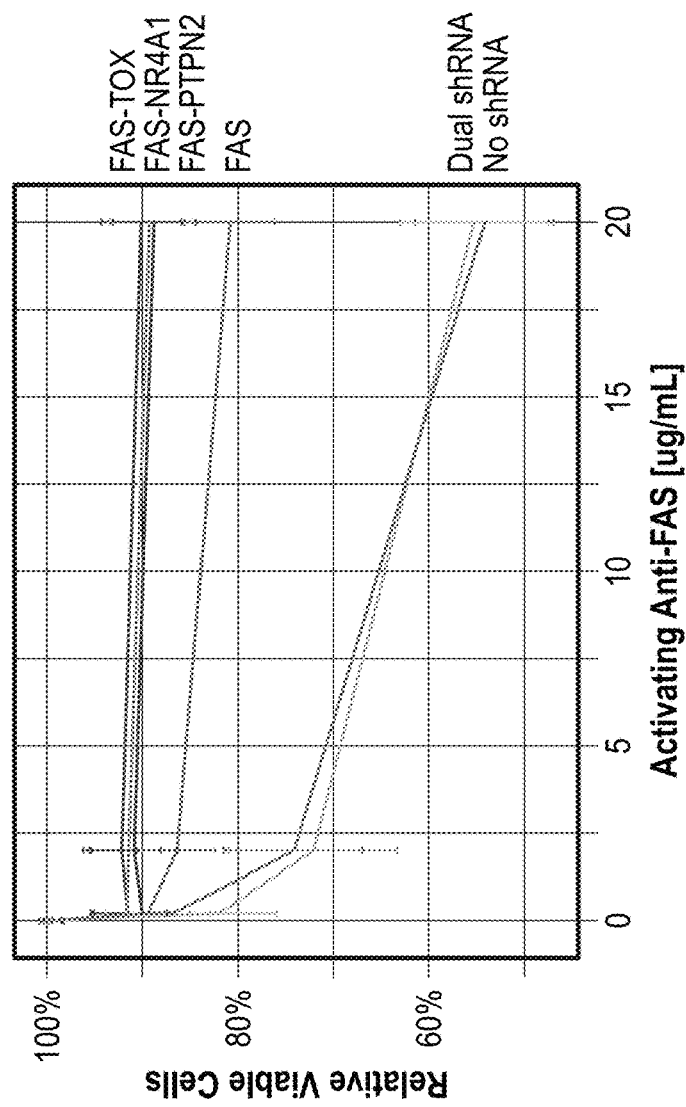
FIG. 19B shows that T cells with FAS knockdown retained greater than 80% viability as normalized to T cells with only the control shRNA after treatment with an anti-FAS activating antibody for 24 hours.
Figure 19A:
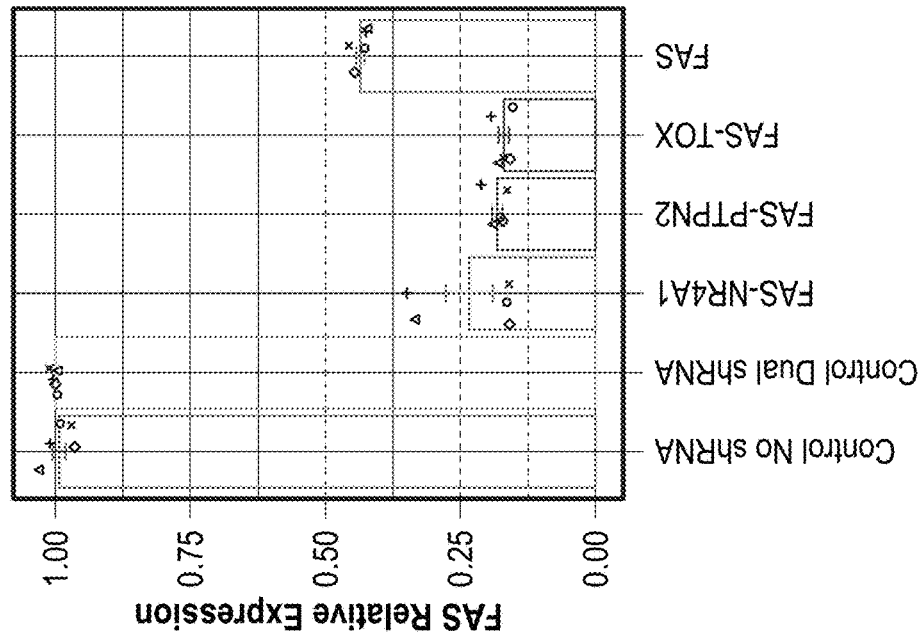
FIG. 19A shows there was strong FAS knockdown in cells from the shRNA.

The shRNA module targeting FAS leads to sufficient knockdown to provide at least 100-fold reduced sensitivity to FAS-mediated apoptosis (FIGS. 19A and 19B). FIG. 19A shows there was strong FAS knockdown in cells from the shRNA. FIG. 19B shows that T cells with FAS knockdown retained greater than 80% viability as normalized to T cells with only the control shRNA after treatment with an anti-FAS activating antibody for 24 hours. Thus, FAS shRNA-miR protected against FAS-mediated apoptosis of T cells.

Cytokine-Independent Growth Assay

Figure 20:
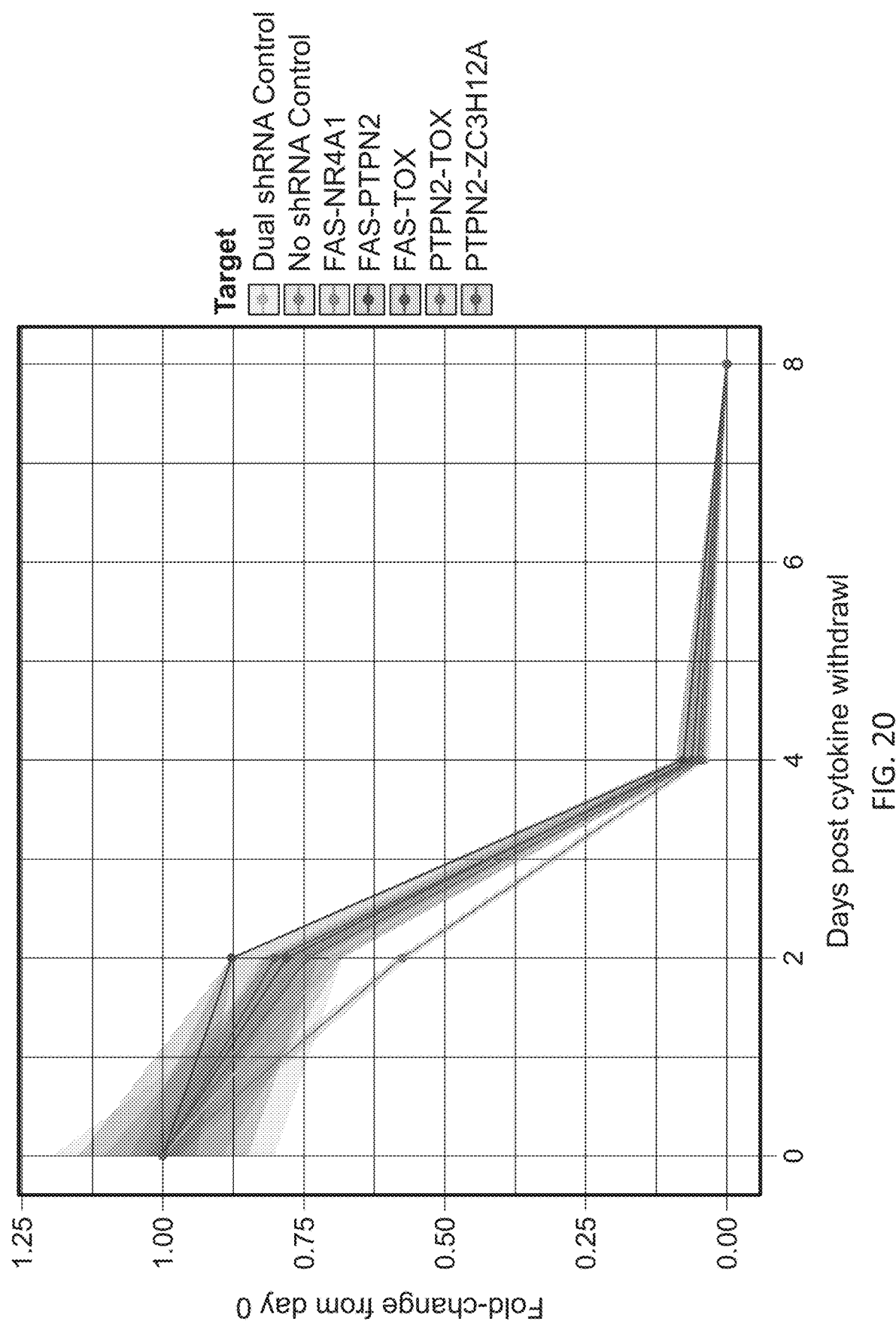
FIG. 20 shows that T cells engineered with the combination shRNA modules did not exhibit evidence of increased risk of transformation.

All engineered T cells died in the absence of cytokine support and no cytokine-independent growth was observed. Thus, T cells engineered with the combination shRNA modules did not exhibit evidence of increased risk of transformation (FIG. 20) as indicated by the death of the engineered T cells after cytokine withdrawal.

Cytotoxicity Assays

Figure 21:
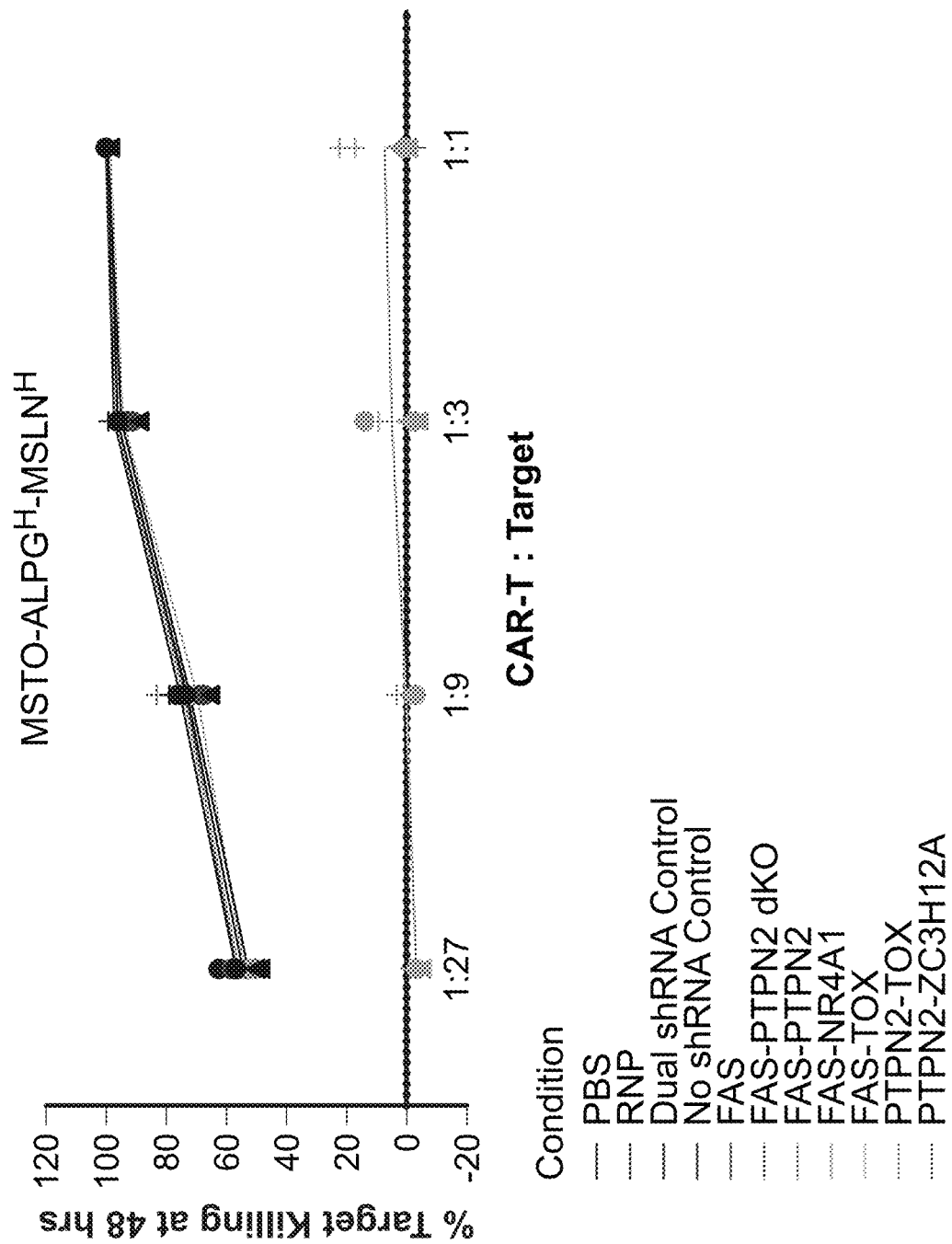
FIG. 21 shows that T cells engineered with the combination shRNA modules did not exhibit evidence of reduced cytotoxic activity over the 48 hour luciferase assay with target antigen expressing K562 cell line.

All knockdown combinations demonstrated identical target cell killing in vitro. T cells engineered with the combination shRNA modules or the control FAS-PTPN2 knockout cells (FAS-PTPN2 dKO) did not exhibit evidence of reduced cytotoxic activity over the 48 hour incucyte assay with target antigen expressing K562 cell line (FIG. 21).

Figure 22:
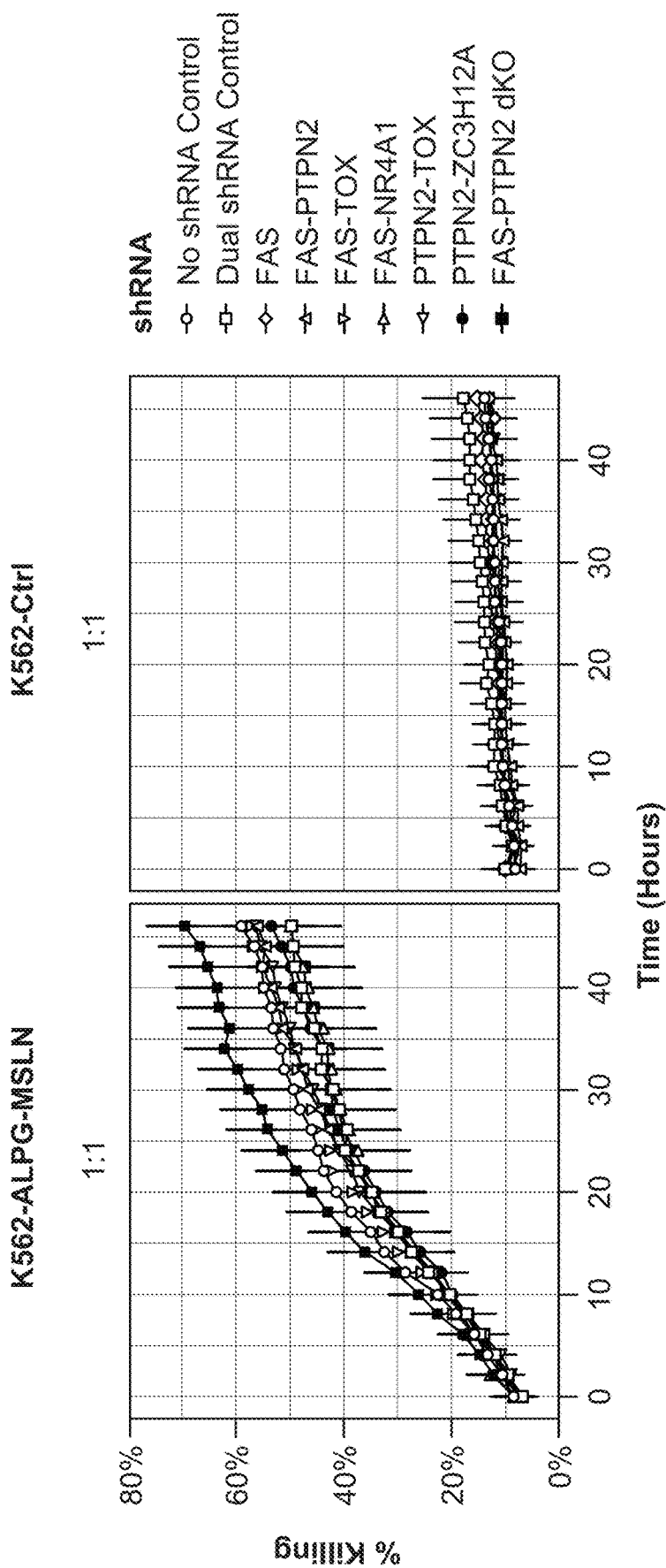
FIG. 22 shows that T cells engineered with the shRNA knockdown modules did not exhibit evidence of reduced cytotoxic activity over the 48 hour incucyte assay with target antigen expressing MSTO cell line.

In addition, all shRNA knockdown combinations demonstrated comparable killing kinetics in vitro. The T cells engineered with the shRNA knockdown modules did not exhibit evidence of reduced cytotoxic activity over the 48 hour luciferase assay with target antigen expressing MSTO cell line (FIG. 22).

RSA

Figure 23:
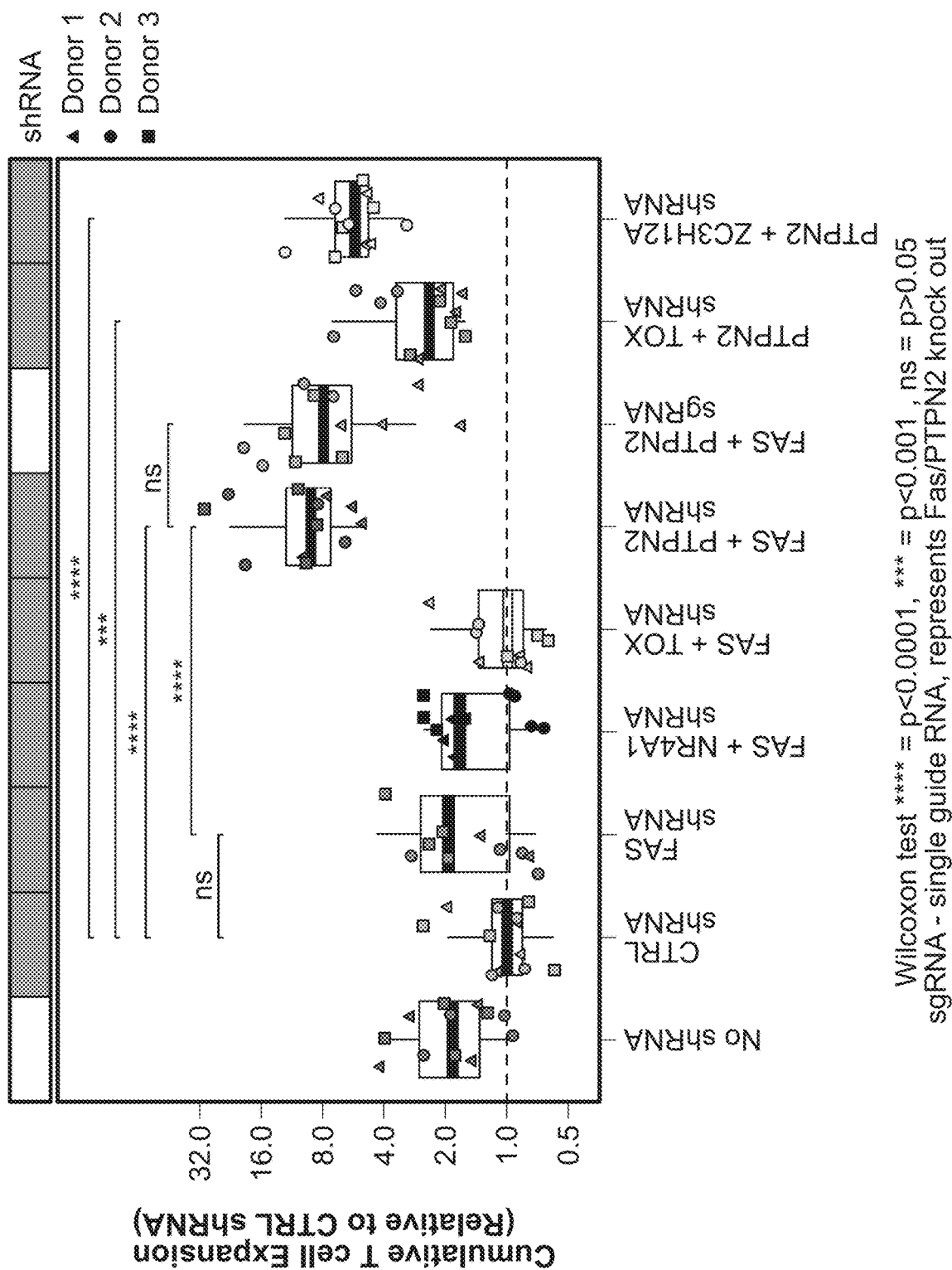
FIG. 23 shows cumulative T cell expansion during chronic antigen stimulation after shRNA knockdown of the indicated target.
Figure 24B:
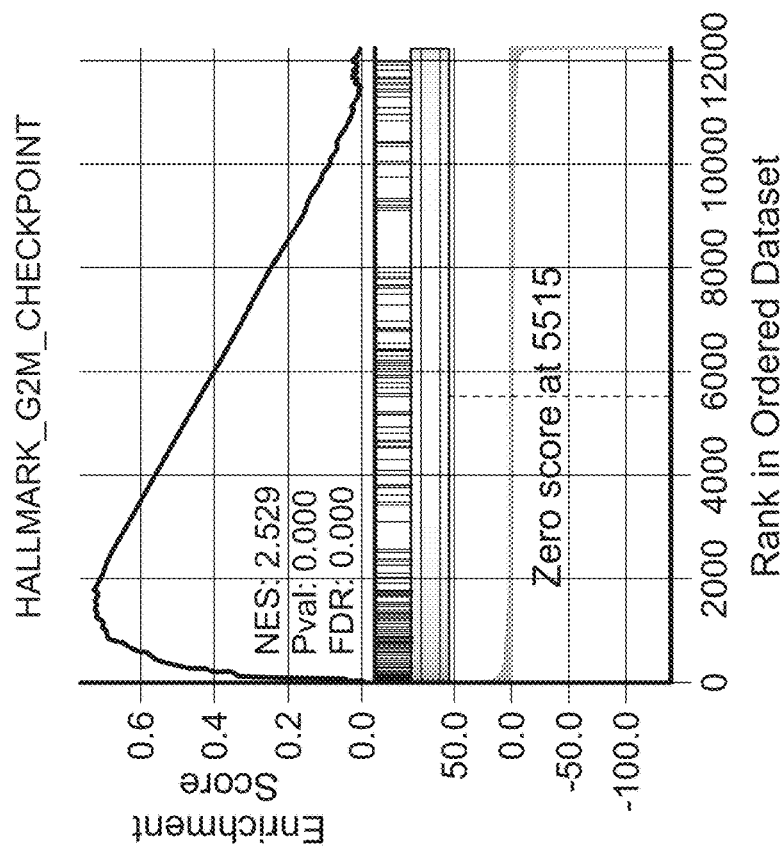
FIG. 24B shows that T cells engineered with a shRNA module targeting PTPN2 exhibited cell cycle signatures after chronic antigen stimulation.
Figure 24A:
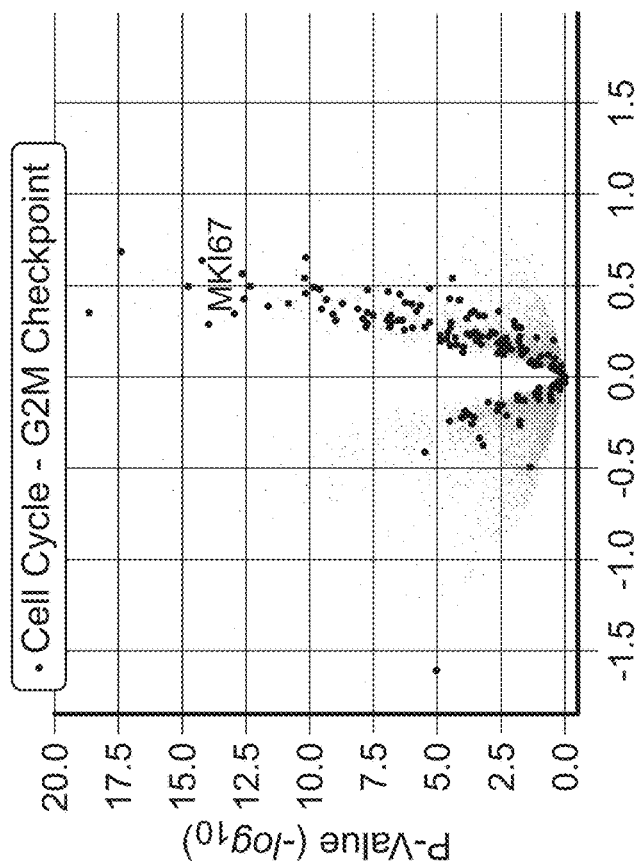
FIG. 24A shows that T cells engineered with a shRNA module targeting PTPN2 exhibited cell cycle signatures after chronic antigen stimulation.
Figure 25:
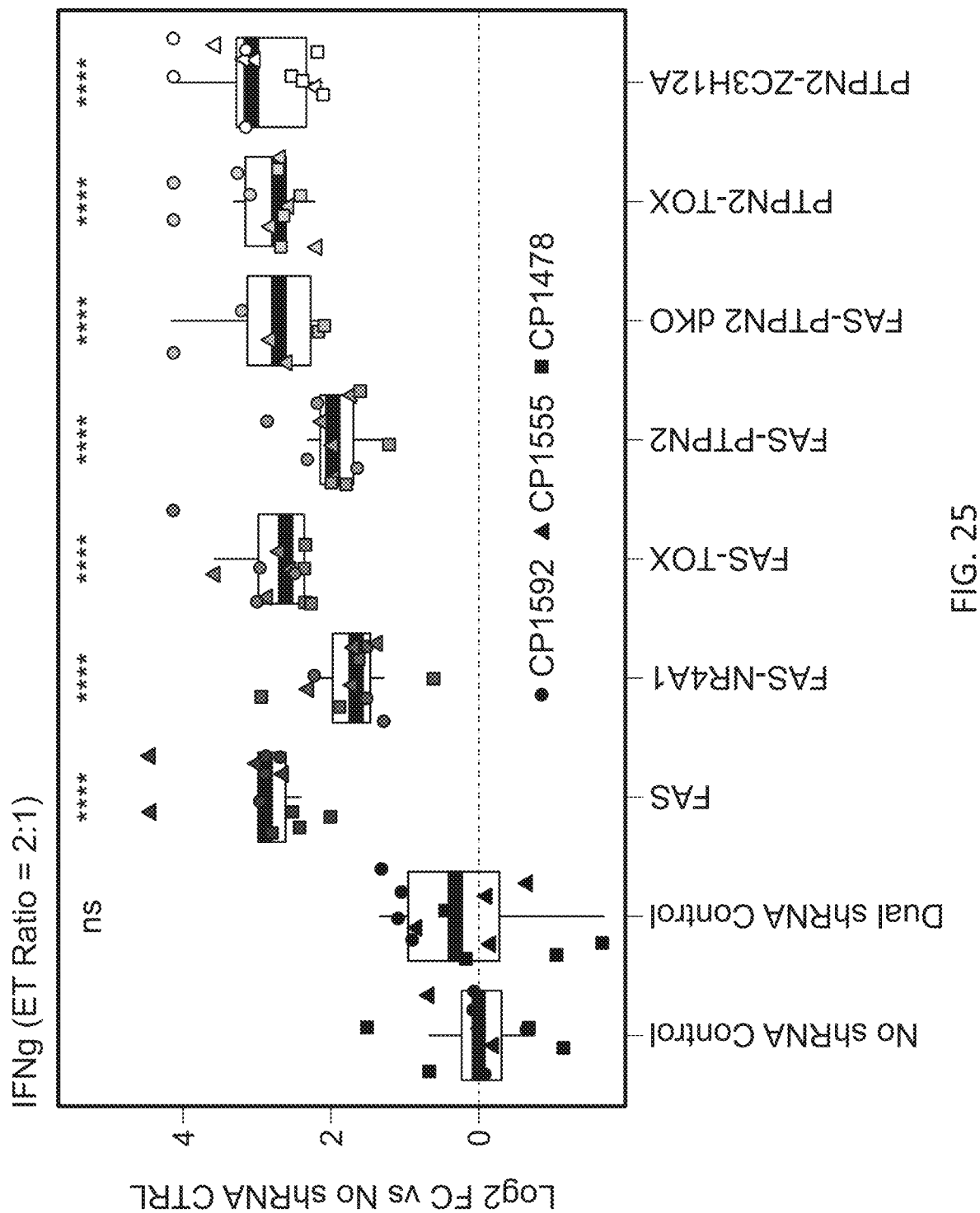
FIG. 25 shows interferon gamma expression in T cells after shRNA knockdown of the indicated target.
Figure 26B:
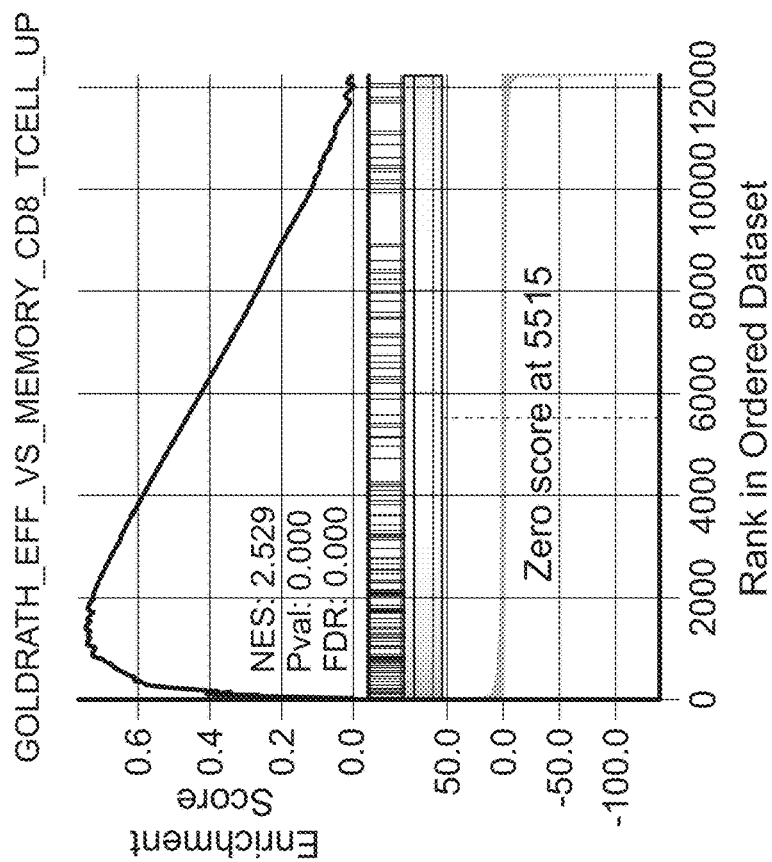
FIG. 26B shows that T cells engineered with a shRNA module targeting PTPN2 retained effector signatures after chronic antigen stimulation.
Figure 26A:
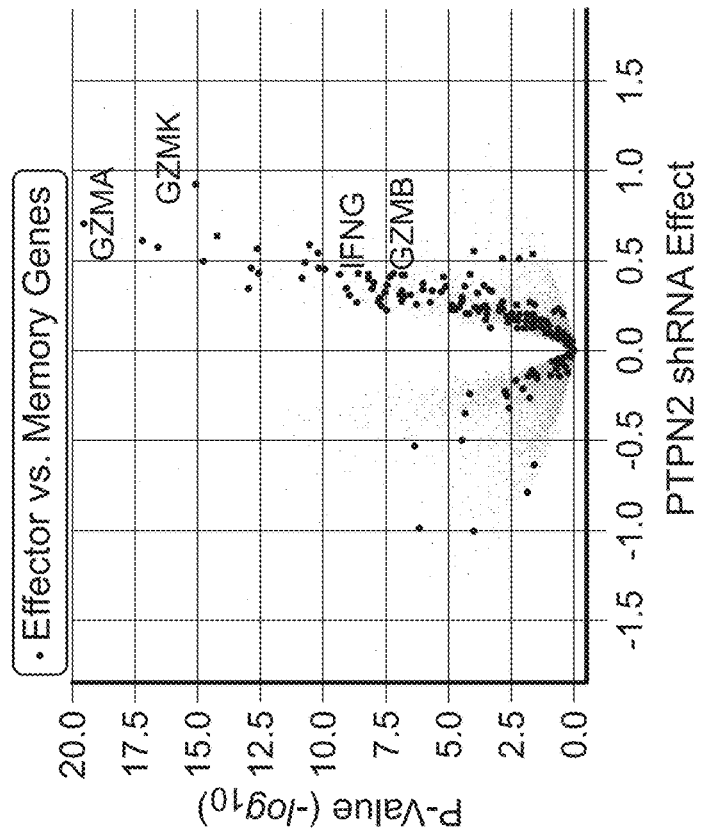
FIG. 26A shows that T cells engineered with a shRNA module targeting PTPN2 retained effector signatures after chronic antigen stimulation.

PTPN2 knockdown via shRNA increased T cell expansion during chronic antigen stimulation (FIG. 23). All dual shRNA modules increase IFNγ production during chronic antigen stimulation, Wilcoxon test **=p<0.0001, *=p<0.001, ns=p>0.05 (FIG. 25). PTPN2 knockdown T cells also exhibited cell cycle signatures after chronic antigen stimulation (FIGS. 24A and 24B), and retained effector signature after chronic antigen stimulation (FIGS. 26A and 26B).

Thus, T cells engineered with FAS-PTPN2 shRNA module exhibited ~8 fold greater expansion (FIG. 23), ~2 fold greater interferon gamma expression (FIG. 25) and strong signatures of effector T cell function (FIGS. 26A and 26B) and cell cycle (FIGS. 24A and 24B) relative to control engineered T cells expressing an shRNA module targeting irrelevant control genes. Wilcoxon test **=p<0.0001, *=p<0.001, ns=p>0.05.

Example 4: Characterization of shRNA In Vivo

Materials

T cells from three donors were engineered to express an MSLN CAR alone or with either a dual luciferase control shRNA module or the FAS-PTPN2 shRNA module using the manufacturing process described above and were frozen and cryobanked at Day 9 after initial activation. Prior to performing the assay, cells were thawed and recovered in media and normalized to the lowest editing efficiency with RNP only edited T cells. To evaluate the efficacy of T cells engineered with MSLN CAR alone or with either a dual luciferase control shRNA module or the FAS-PTPN2 shRNA module in vivo assay were performed in a subcutaneous model of mesothelioma. NSG-MHC I/II dKO mice were injected with MSTO211H cells overexpressing MSLN. MSTO211H cells were injected in 100 uL 1:1 suspension of phosphate-buffered saline (PBS) and Matrigel into the right flank of mice. Animals were randomized into treatment groups according to tumor volumes and were injected into the tail vein with T sells at $0.25 \times 10^6$, $0.5 \times 10^6$ and $2 \times 10^6$ doses. Tumor volumes were measured before and twice per week after treatment was started and calculated as V=(length×width2)/2.

The presence, expansion and persistence of SS1 CAR-T cells in peripheral blood of treated mice were monitored by multiparametric flow cytometry. Fifty uL of blood was collected from each mouse on day 7, 14, 21 and 28 post treatment. Blood was lysed with ACK lysis buffer to remove red blood cells and stained with fluorescently-labeled antibodies against: murine CD45 and GR1; human CD3, CD4, CD8a, CCR7, CD27, CD45RA, EGFR, CD95, and flag. Next, labeled samples were added with counting beads for normalization prior to flow cytometry analysis by the Attune flow cytometer. Collected FACS data were analyzed using FlowJo software.

Spleen and tumors were isolated from subsets (n=3) of mice in each group injected with the high CAR-T dose on day 14, and FACs was performed to characterize and quantify CAR-T phenotypes.

Results

Figure 27:
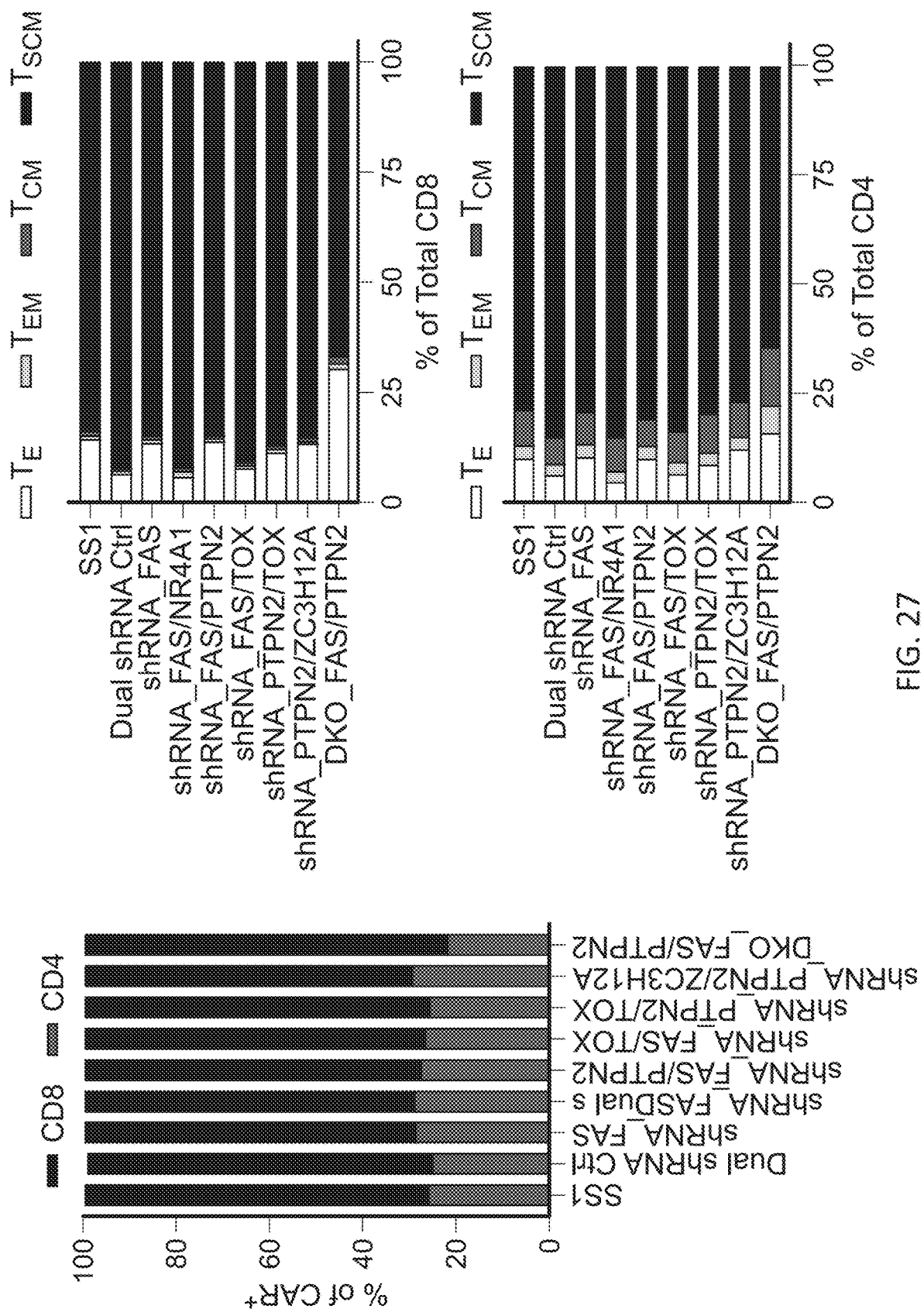
FIG. 27 shows CD4 or CD8% T cell percentages in the engineered T cell populations, and the relative amounts of T effector cells (Te), T effector memory cells (Tem), T central memory cells (Tcm), or memory stem T cells (Tscm) after shRNA knockdown of the indicated target.

In parallel to infusing the animals, a phenotypic analysis of each condition was performed to compare the differentiation states of the cells. As shown in FIG. 13, expression of the shRNA in T cells did not alter the CD4 or CD8% T cell percentages in the engineered T cell populations, or the relative amounts of T effector cells (Te), T effector memory cells (Tem), T central memory cells (Tcm), or memory stem T cells (Tscm), with the exception of the DKO FAS/PTPN2 modification (FIG. 27). Thus, the shRNA modules did not alter the differentiation state of the pre-infusion T cells.

Figures 28A, 28B:
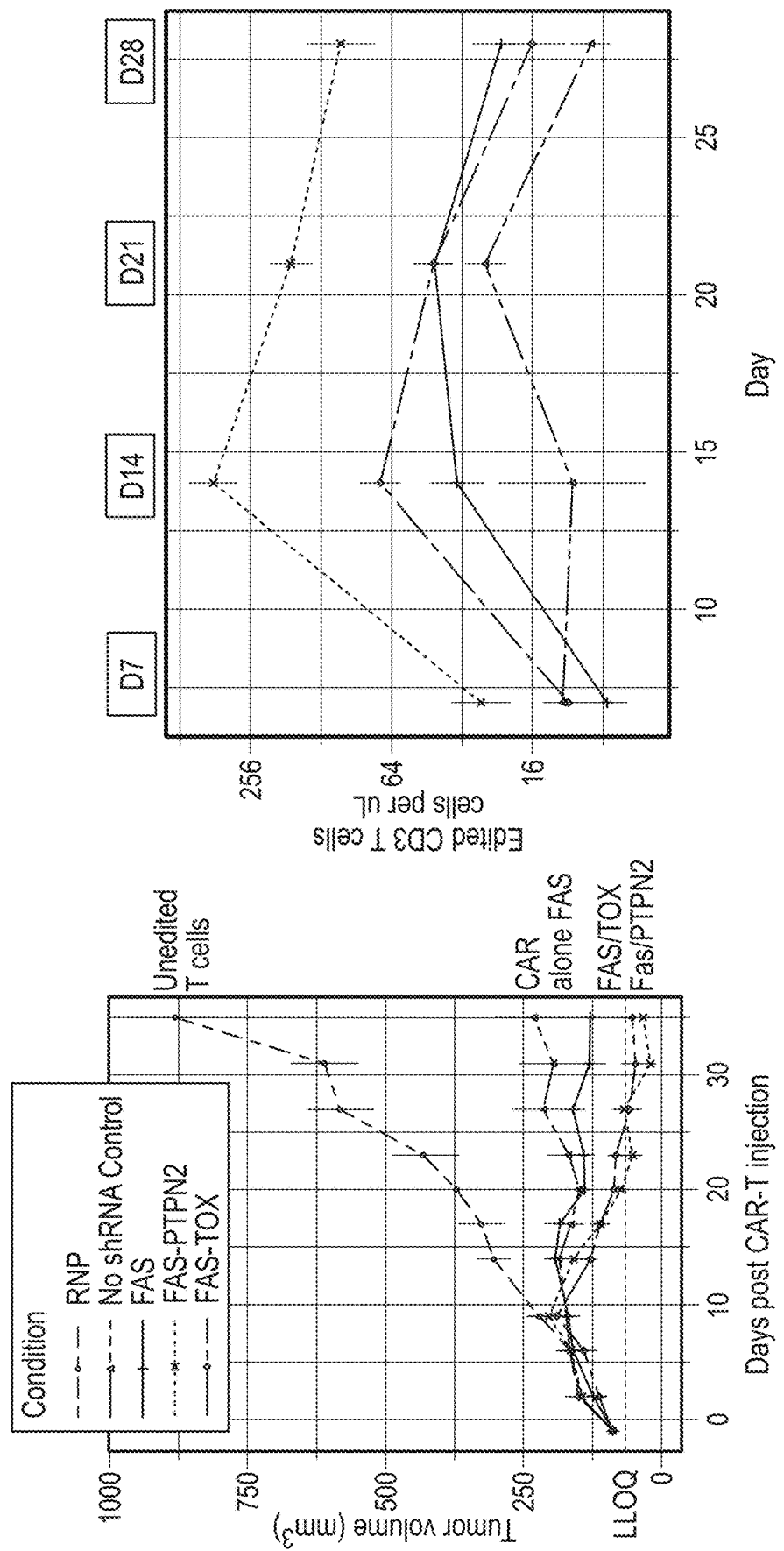
FIG. 28A shows tumor growth in mice after treatment with the indicated CAR T cell or control T cells.
FIG. 28B shows T cell expansion in peripheral blood after treatment with the indicated CAR T cell or control T cells.

After in vivo treatment, the T cells engineered with the FAS-PTPN2 shRNA-miR module exhibit improved tumor control (FIG. 28A) and increased edited T cell accumulation in the periphery (FIG. 28B) and within the tumor. Edited T cells expressing the CAR, or the FAS, FAS/TOX, or FS/PTPN2 shRNA significantly reduced tumor volume in vivo (FIG. 28A). The FAS-PTPN2 shRNA T cells also showed 10 times greater expansion and enhanced persistence in the peripheral blood as compared to the CAR T cells alone without shRNA (FIG. 28B). Thus, FAS-PTPN2 knock down increased T cell expansion and tumor control.

Figure 29:
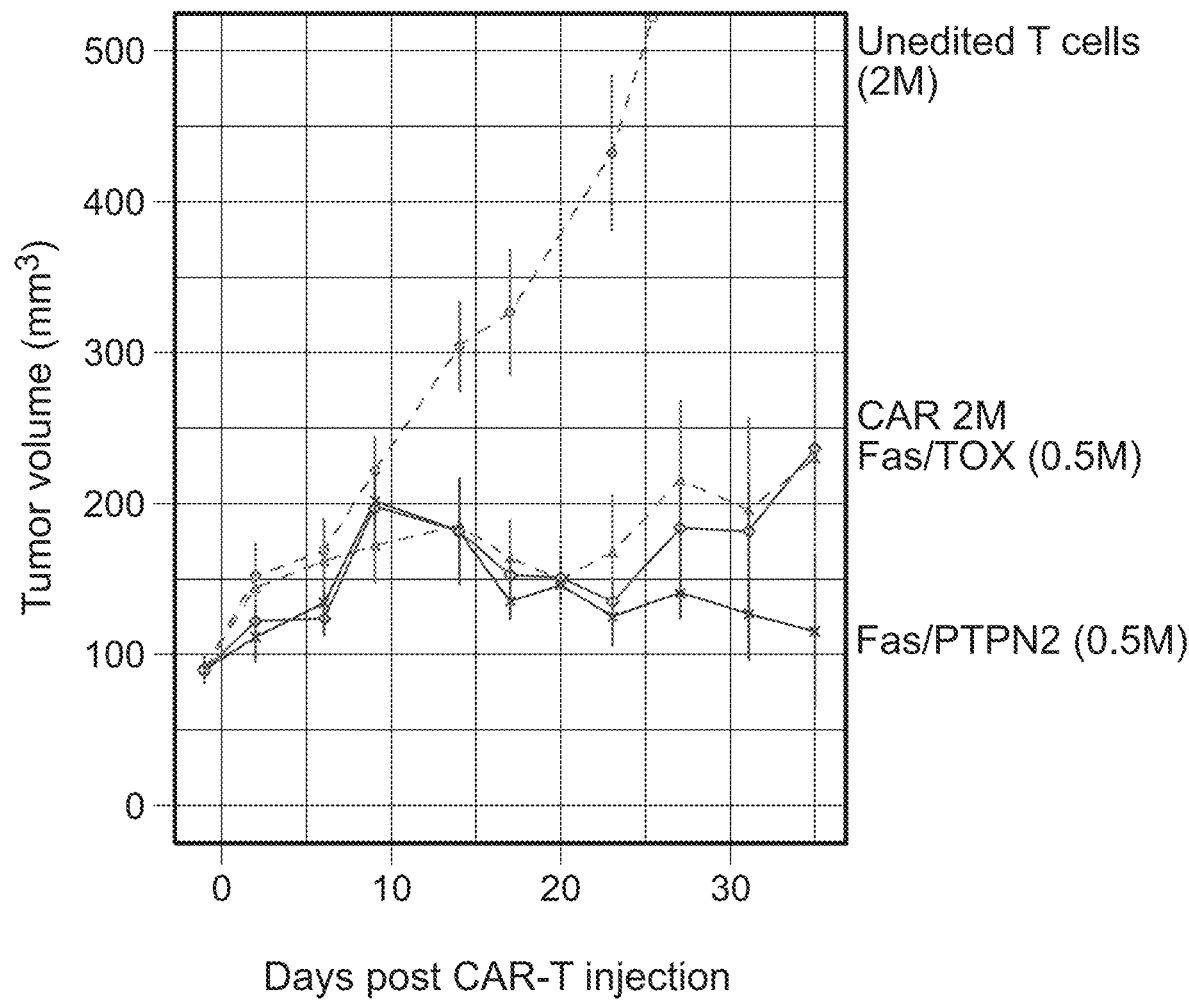
FIG. 29 shows tumor volume after tumor growth in mice after treatment with the indicated amounts of CART cell or control T cells.

In the dose experiments, the $0.5 \times 10^6$ dose FAS-PTPN2 shRNA knockdown T cells and FAS-TOX shRNA knockdown T cells showed better or comparable tumor control to the $2 \times 10^6$ CAR alone, indicating that comparable control of the tumor was observed at a quarter of the dose (FIG. 29). Thus, the knockdown of FAS and PTPN2 or TOX enables lower dosing for similar tumor treatment.

Figure 30B:
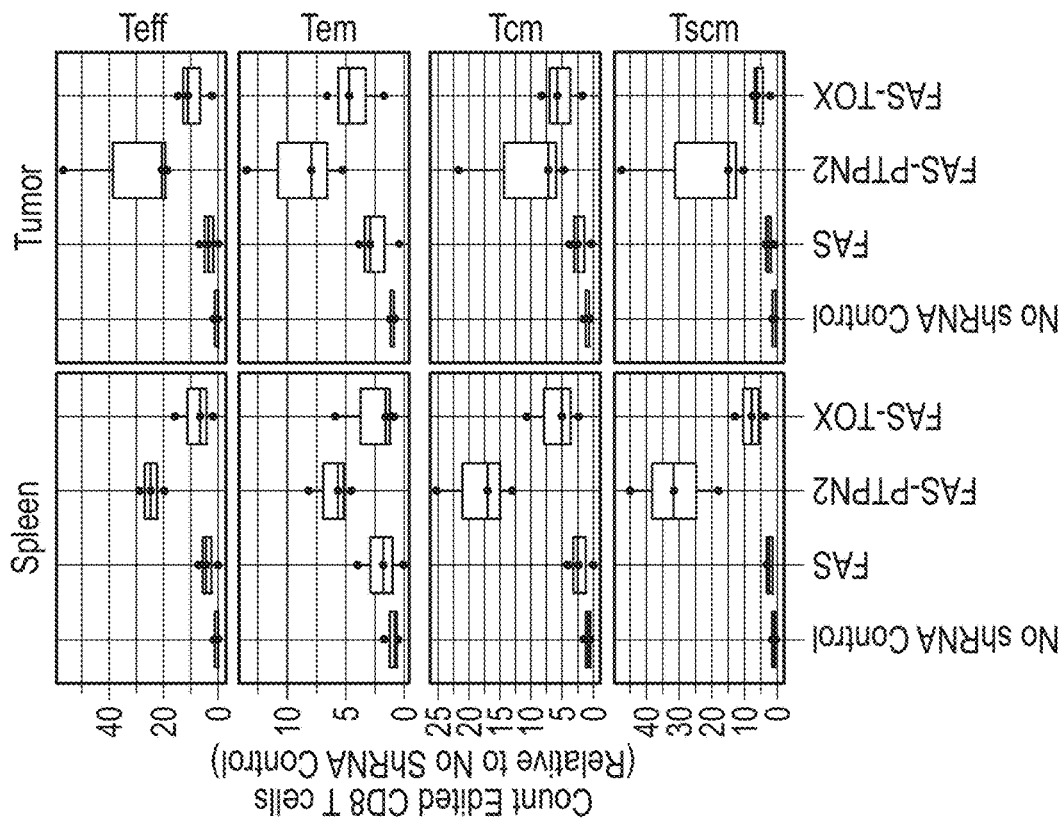
FIG. 30B shows the number of edited T cells in the mice tumor or spleen after treatment with T cells with shRNA knockdown of the indicated target.
Figure 30A:
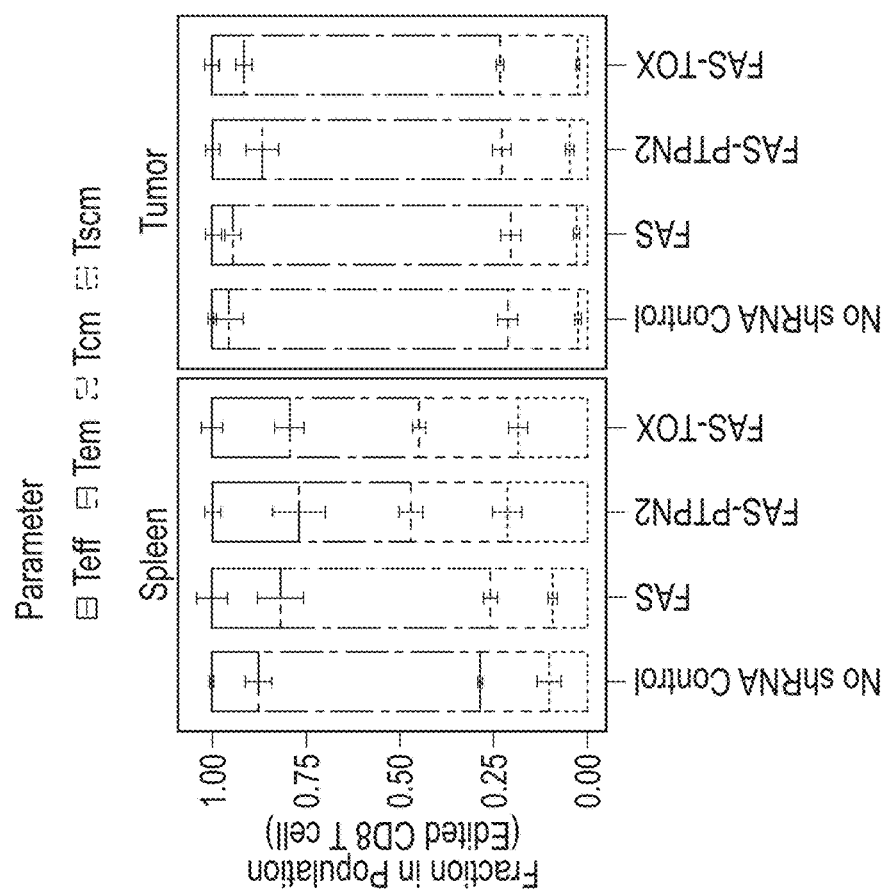
FIG. 30A shows quantification of the types of T cells in the edited CD8 T cell population after treatment with T cells with shRNA knockdown of the indicated target.

FAS-PTPN2 drove expansion of all T cell subsets, including effector and progenitor cells. The FAS-PTPN2 and FAS-TOX combinations resulted in a higher frequency of cells with a memory phenotype in the spleen and similar proportions of subsets in the tumor (FIGS. 30A and 30B).

Figure 31:
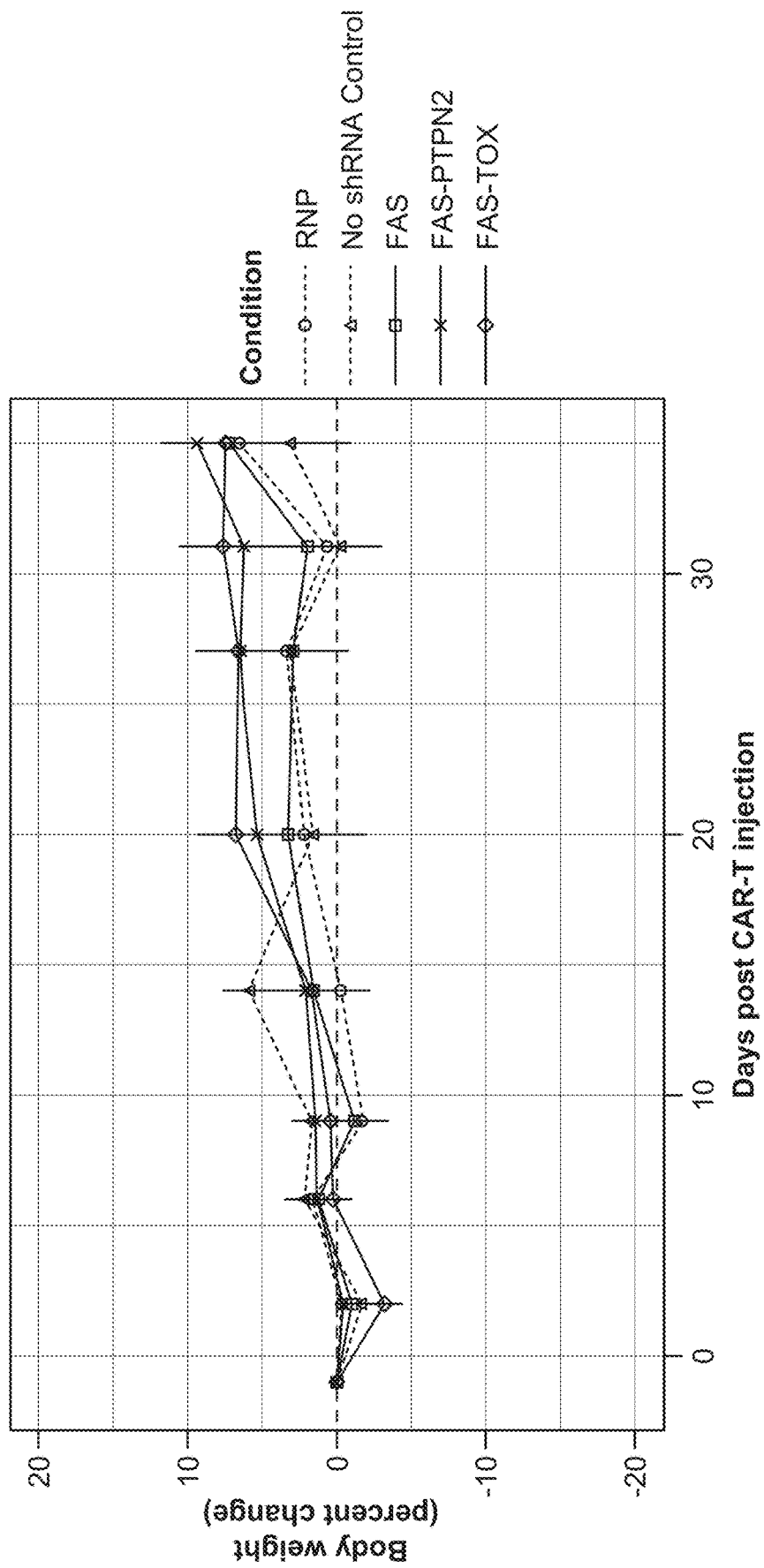
FIG. 31 shows mouse body weight after treatment with T cells with shRNA knockdown of the indicated target.

Furthermore, there was no evidence of gross toxicity associated with increased T cell expansion (FIG. 31) as shown by the mouse weight over the course of the trial. None of the experimental conditions resulted in weight loss of the mice.

Example 5: Co-Expression of shRNA and ALPG/P and MSLN Logic Gate in Vitro

Materials and Methods
Dual Antigen-Dependent Cytotoxicity Assay

T cells from four donors were engineered to express Logic Gate 1 alone without shRNA or a full optimized lead Integrated Circuit T cell (ICT) combining Logic Gate 1 with a FAS/PTPN2 shRNA cassette (AB-1015, SEQ ID NO: 168) using the non-viral manufacturing process and were frozen and cryobanked at Day 9 after initial activation. Prior to the assay, engineered T cells and RNP only control T cells from the same donors were thawed and rested overnight in media including 12.5 ng/mL human IL-7 and IL-15. On the day of the assay, engineered T cells were counted and stained for PrimeR and CAR expression using anti-myc PE and anti-FLAG APC, respectively, and analyzed by flow cytometry. For each donor, all engineered T cell populations were normalized to the lowest KI % within that donor by adding RNP only cells to dilute engineered populations that were above the lowest KI %. After normalization, T cells were resuspended in medium without IL-7 and IL-15 and serially diluted prior to being added to 96-well flat-bottom, white-walled assay plates. The serial dilution of T cells results in the following co-culture KI+ effector:target (E:T) ratios once 1e4 target cells were added/well: 3:1, 1:1, 1:3, 1:9, and 1:27 in technical duplicates. Each T cell population was co-cultured with K562-MSLN, and K562-ALPG/MSLN. Prepared plates with T cells and target cells were spun down for 2 min at 300 g prior to incubation at 37° C. for 72 hours with a breathable membrane on each plate. Cytotoxicity at the end of the 72 hour co-culture was measured using an end-point luciferase assay. PrimeR and CAR expression were quantified using primary staining with a tagged version of each receptor's antigen that was then detected with a fluorescently-conjugated secondary antibody, and analyzed by flow cytometry.

Protein Knockdown in Resting Conditions

Figure 32:
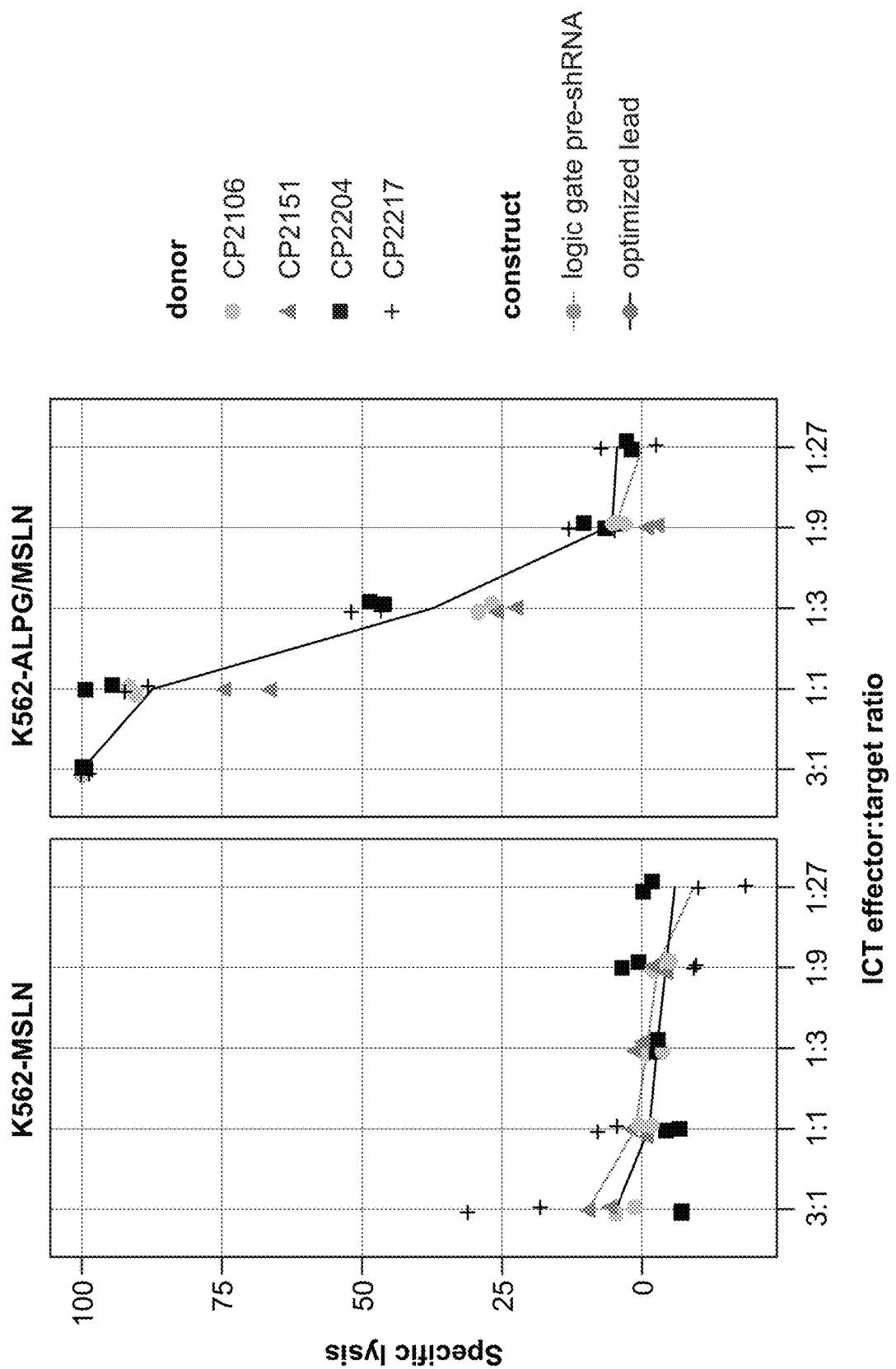
FIG. 32 shows lysis of target cells expressing MSLN or ALPG and MSLN after incubation with T cells expressing a logic gate and FAS/PTPN2 shRNA.

Flow Cytometry: T cells from 2 donors were engineered to express LG1 (ALPG/P priming receptor and MSLN CAR) alone (LG1 HTLV control) or with the FAS-PTPN2 shRNA module using the manufacturing process. T cells were stained for ALPG/P and FAS expression five days post-editing using ALPG-AF647 and anti-FAS FITC, respectively, and analyzed by flow cytometry on an Attune NxT. Relative FAS expression is shown in the flow cytometry histograms, Results Co-expression of the ALPG/P and MSLN logic gate and FAS/PTPN2 shRNA maintained the logic gate fidelity and potency in vitro. As shown in FIG. 32, incubation of the T cells expressing the logic gate and shRNA did not induce lysis of K562-MSLN cells expressing only the CAR antigen. However, incubation with K562 cells expressing the priming receptor target ALPG resulted in significant dose-dependent lysis of the target cells, with 100% of target cells lysed at the highest ratio. Thus, the co-expression of shRNA with the logic gate did not affect the function of the priming receptor and CAR.

Figure 33:
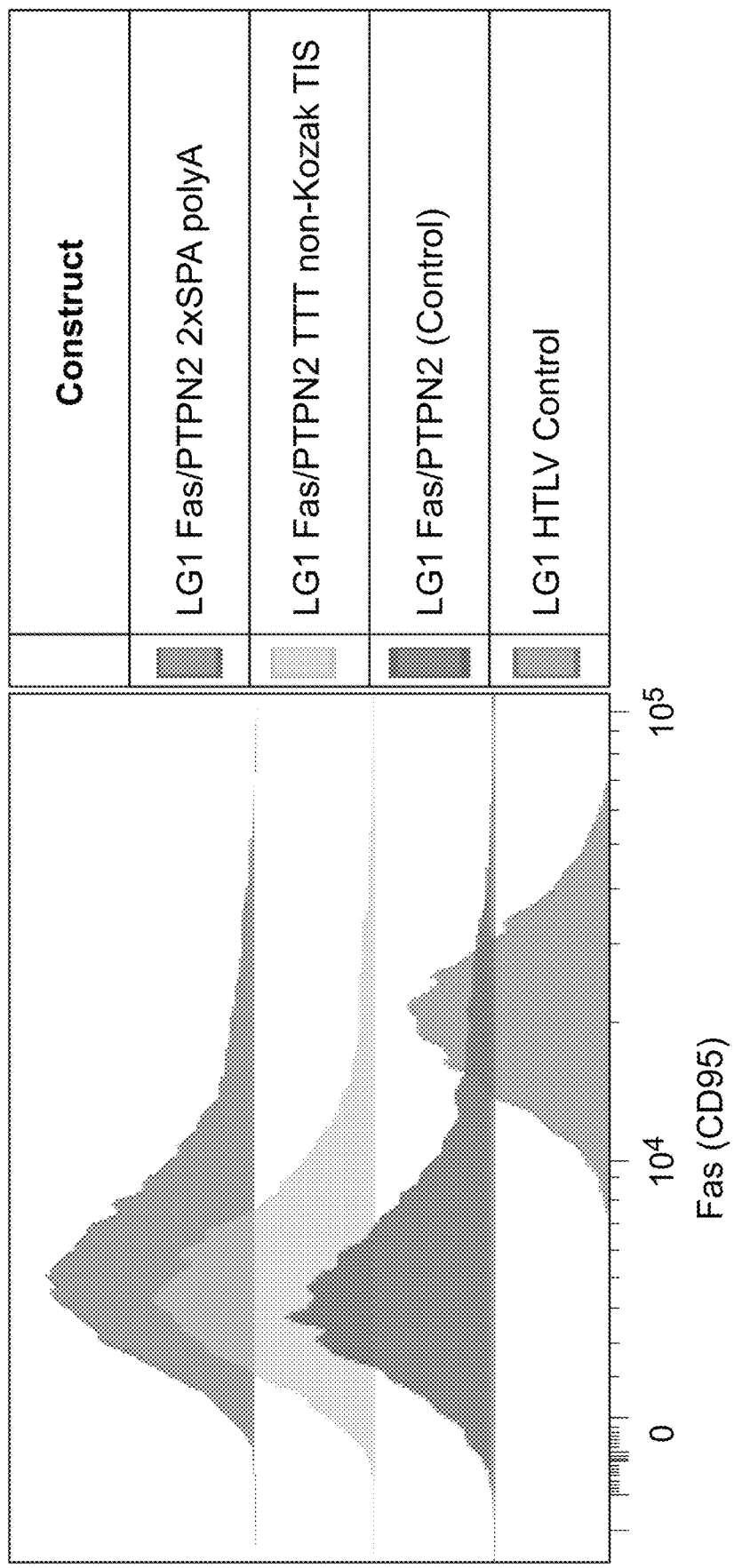
FIG. 33 shows relative FAS expression in T cells expressing an ALPG/MSLN logic gate and FAS/PTPN2 shRNA as compared to control cells expressing the ALPG/MSLN logic gate alone.

In addition, the shRNA also demonstrated strong FAS knock-down relative to LG1 control cells without shRNA (FIG. 33). Thus, Thus, the co-expression of the priming receptor and CAR with the shRNA did not affect the function of the shRNA.

Example 6: Co-Expression of shRNA and ALPG/P and MSLN Logic Gate In Vivo

Materials and Methods

T cells from two donors were engineered to express LG1 and FAS/PTPN2 shRNA (AB-1015, SEQ ID NO: 168) or LG1 and FAS/TOX shRNA using the engineering methods described above in Example 1. Cells were frozen and cryobanked at Day 9 after initial activation. For quality control (QC) assays, RNP only control T cells from the same donors were thawed and rested overnight in media including 12.5 ng/mL human IL-7 and IL-15. The next, engineered T cells were counted and stained for PrimeR and CAR expression using anti-myc PE and anti-FLAG APC, respectively, and analyzed by flow cytometry to assess KI %.

K526 Dual Flank In Vivo Study

NSG double MHC KO (NSG DKO) strain (Jackson Laboratories, 025216) were implanted with 1e6 each of K562-MSLN cells on the left flank and K562-ALPG/MSLN cells on the right flank, both in 50% Matrigel solution. Three days after K562 cell inoculation, mice were randomly assigned to treatment groups with matched tumor sizes using bioluminescent imaging (BLI) to measure luciferase signal to quantify engineered tumor cells, with 7 mice assigned per treatment condition. The same day of staging and normalization, engineered T cells and matched RNP controls were thawed and rested overnight in media including 12.5 ng/mL human IL-7 and IL-15. On Day 4 after K562 implantation, for each donor all engineered T cell populations were normalized to the lowest KI % within that donor by adding RNP only cells to dilute engineered populations that were above the lowest KI %. Mice were injected with 5e6 KI+ T cells i.v. via the tail vein. Bilateral tumor volumes were monitored twice weekly via caliper along with body weight.

Results

Figures 34A, 34B:
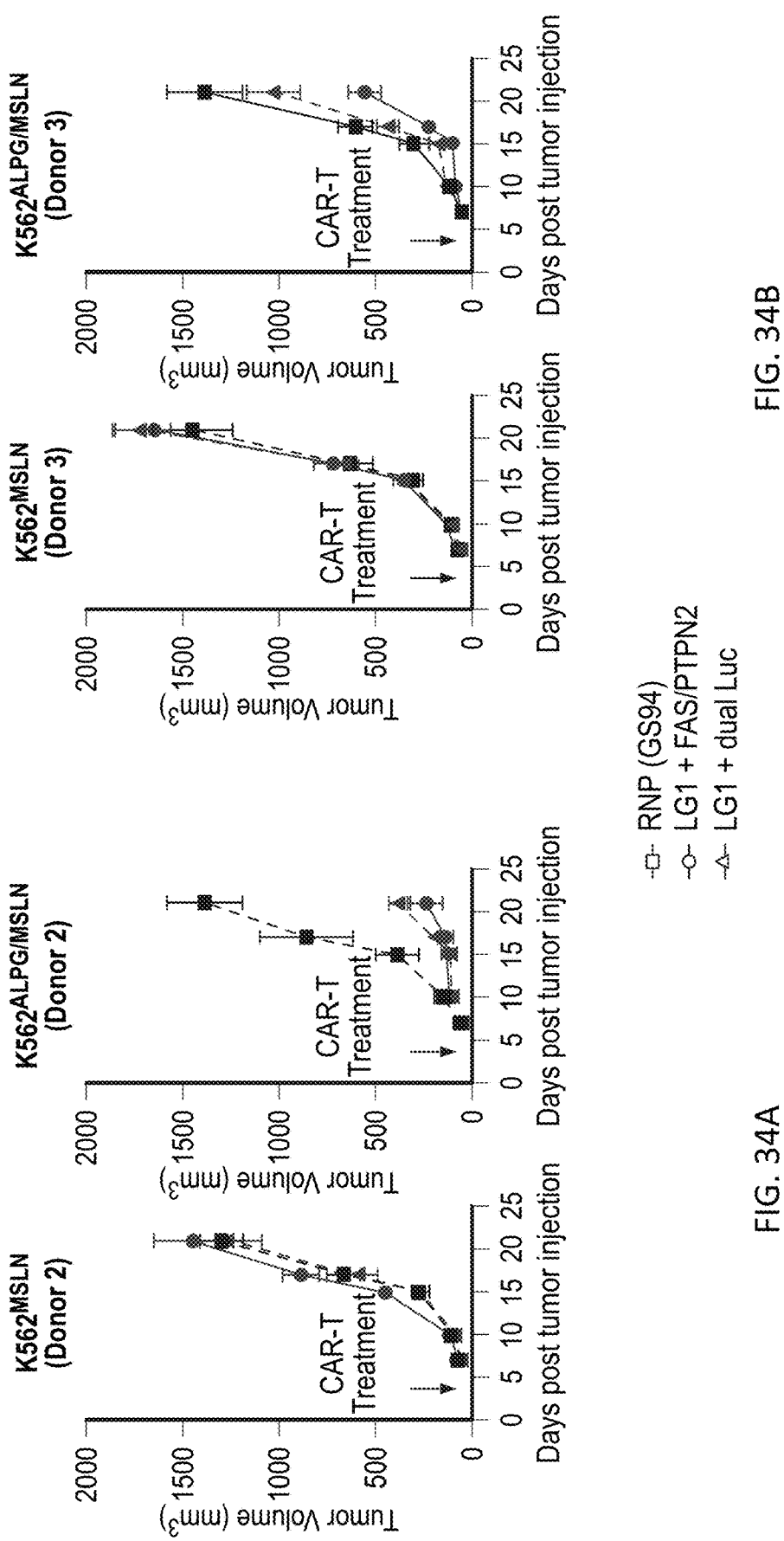
FIG. 34A shows tumor volume in vivo after treatment with T cells from donor two expressing an ALPG/MSLN logic gate and FAS/PTPN2 shRNA as compared to control T cells expressing the ALPG/MSLN logic gate alone.
FIG. 34B shows tumor volume in vivo after treatment with T cells from donor three expressing an ALPG/MSLN logic gate and FAS/PTPN2 shRNA as compared to control T cells expressing the ALPG/MSLN logic gate alone.

Incorporation of FAS/PTPN2 shRNA into the LG1 circuit resulted in greater anti-tumor potency with equivalent fidelity relative to the LG1+dualLuc shRNA control circuit in vivo in the dual-tumor NSG model (FIGS. 34A (donor two) and 34B (donor three)). No tumor reduction was observed against cells expressing only the CAR antigen MSLN. Reductions in tumor volume were observed when the tumor cells expressed both ALPG and MSLN. A greater tumor volume reduction as observed when the engineered T cells co-expressed the FAS/PTPN2 sRNA as compared to only the ALPG/MSLN logic gate (FIGS. 34A and 34B).

Figures 35A, 35B:
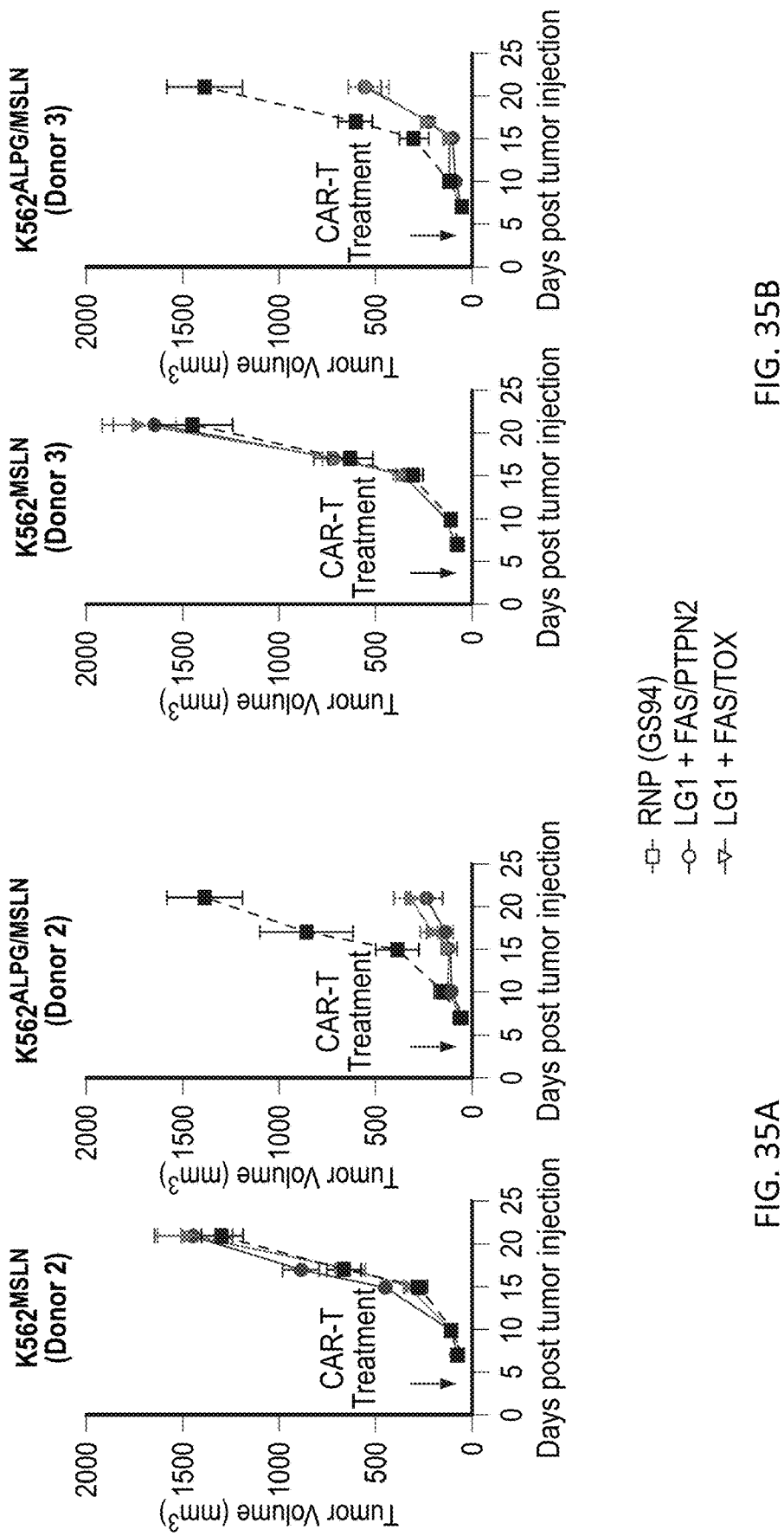
FIG. 35A shows tumor volume in vivo after treatment with T cells from donor two expressing an ALPG/MSLN logic gate and FAS/PTPN2 or FAS/TOX shRNA as compared to control T cells (RNP).
FIG. 35B shows tumor volume in vivo after treatment with T cells from donor three expressing an ALPG/MSLN logic gate and FAS/PTPN2 or FAS/TOX shRNA as compared to control T cells (RNP).

The LG1+FAS/TOX shRNA circuit showed similar fidelity and anti-tumor potency to the LG1+FAS/PTPN2 circuit in in vivo in the dual-tumor NSG model (FIGS. 35A (donor two) and 35B (donor three)). No tumor reduction was observed against cells expressing only the CAR antigen MSLN. Reductions in tumor volume were observed when the tumor cells expressed both ALPG and MSLN. A greater tumor volume reduction as observed when the engineered T cells co-expressed the FAS/TOX shRNA or FAS/PTPN2 sRNA. Similar tumor volume reductions were observed after treatment with T cells co-expressing either FAS/TOX shRNA or FAS/PTPN2 sRNA (FIGS. 35A and 35B).

Example 7: In Vivo Assay in Ovarian Tumor Model

T cells from 3 donors were engineered to express the AB-1015 cassette, which includes LG1 (ALP G/P priming receptor and MSLN CAR) with the FAS-PTPN2 shRNA module, using the engineering methods described above in Example 1. Cells were frozen and cryobanked at Day 9 after initial activation. For quality control (QC) assays, RNP only control T cells from the same donors were thawed and rested overnight in media including 12.5 ng/mL human IL-7 and IL-15. Engineered T cells were counted and stained for priming receptor and CAR expression using ALPG-AF647 and MSLN-Bio primary/streptavidin-PE secondary, respectively, and analyzed by flow cytometry to assess KI %.

NSG double MHC KO (NSG DKO) strain (Jackson Laboratories, 025216) were implanted intraperitoneally with 1e7 cells each of the OVCAR3-ALPG ovarian cancer indication specific cell line that expresses ALPG and MSLN. As shown in FIG. 56A, five days after tumor cell inoculation, mice were randomly assigned to treatment groups with matched tumor sizes based on bioluminescence measurements of the luciferase expressed by the OVCAR3-ALPG target cells, with 10 mice assigned per treatment condition. The same day of staging and normalization, engineered T cells and matched RNP controls were thawed and rested overnight in media including 12.5 ng/mL human IL-7 and IL-15. On Day six after ovarian cancer cell line implantation, mice were injected with 7.5e6 KI+ T cells (or the matched total number of RNP control cells) i.v. via the tail vein. Tumor volumes were monitored 2-3 times weekly via luminescence measurement along with body weight.

As shown in FIG. 56B, AB-1015 T cells (LG1+FAS-PTPN2 shRNA module) induced tumor killing and inhibition of tumor growth in the ovarian cancer cell line tumor model. AB-1015 T cells resulted in increased tumor growth inhibition as compared to RNP control cells. Additionally, FIG. 56C shows that treatment with AB-1015 T cells did not result in body weight loss and was well tolerated by the mice. Without wishing to be bound by theory, T cells engineered with the full LG1+FAS/PTPN2 circuit drive potent responses against an ovarian cancer specific model in in vivo mouse xenograft tumor experiments.

Example 8: Knockdown and Knockout of FAS and Other Genes Improves Profile of Engineered Hematopoietic Cells Methods FAS Knockout (KO) in Combination with Additional Gene Assay CD8 T cells were stimulated with CD3/CD28 magnetic beads for 48 hours. 500,000 cells were transfected with complexed Cas9/crRNA/tracrRNA RNPs targeting the first coding exon of a single gene or a combination of two genes using the Lonza 384 well Nucleofector system according to the manufacturer's instructions. The crRNA library targeted a total of 18 individual genes that were run in all pairwise combinations for a total of 171 independent conditions. Each condition was run in technical duplicate in two independent donors and the experiment was performed twice. Data shown are the cumulative results from both experiments. After transfection with RNP the cells were rested for 4 days then stimulated with CD3/CD28 magnetic beads at a 5:1 bead to cell ratio. 2, 5, 7, 9 and 12 days after the first stimulation post-transfection the cells were de-beaded, counted by flow cytometry, and re-plated with CD3/CD28 beads at a 5:1 bead to cell ratio. At the end of the assay the amount of viable T cells were quantified by flow cytometry and levels of cytokines and other effector molecules in the supernatant were quantified by nPlex ELISA.

shRNA Knockdown Assay

CAR T cells were enriched using biotinylated anti-EGFRt (clone 528 Thermo) and streptavidin conjugated magnetic beads (MyOne T1 Dynabeads). Enriched T cells (>=70% EGFRt+) were subsequently lysed and total RNA was extracted using Dynabeads mRNA DIRECT Kit per the manufacturer's protocol. Purified RNA was quantified using Ribogreen Quant-IT and normalized prior to cDNA synthesis using SuperScript IV First-Strand Synthesis System. Synthesized cDNA was then used to perform qRT-PCR using TaqMan Fast Advanced Master Mix and TaqMan probes for each respective shRNA target. TaqMan probes for RPL13A were used to further normalize cDNA input. Cq values were captured and the delta-delta method was employed to quantify expression. Percent knockdown was calculated as ((1−ddCq)*100).

FAS-Mediated Apoptosis Assay

ICT cells were thawed and enriched using ALPG-Fc reagent and Protein G binding magnetic beads. Enriched T cells (~50% PrimeR+) were subsequently cultured with increasing concentrations (0, 0.2, 2, 20 ug/mL) of the FAS cross-linking antibody, clone CH11, for 22 hours. ICT cells were stained with ALPG, Apotracker, and a viability dye, and viable cell frequency was quantified by flow cytometry. The relative frequency of viable cells was calculated by normalizing the viability at each dose to the sample at 0 ug/mL activating anti-FAS antibody.

In Vivo Dual Knockdown Assay

Figure 38:
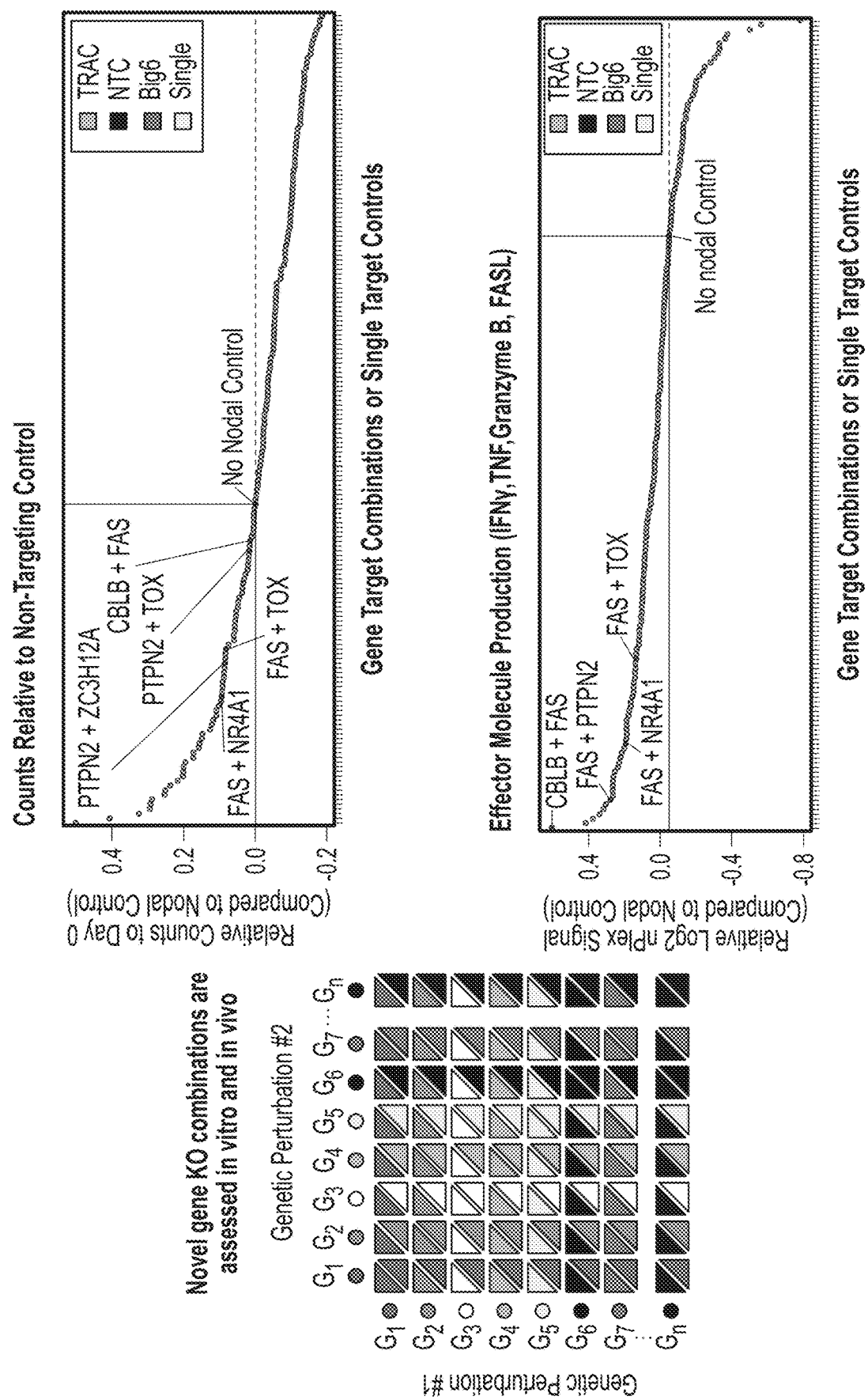
FIG. 38 shows that knocking out FAS improved cell proliferation and effector function.

Bulk T cells were activated for 2 days in CTS expansion beads and electroporated with CAS9 protein, crRNA: tracrRNA complexes, and CD19 (FMC63-41BBz) HDR template to generate TRAC KI CAR T cells with or without combinatorial deletions of FAS and another gene of interest. Following electroporation, cells were expanded for 8 days in TexMACs containing 3% human serum and recombinant IL-7 and IL-15 cytokines. Residual CD3$^+$ cells were depleted from all conditions on the 4th day of expansion. On day 10 post-activation, cells were collected, normalized with CD3$^{Neg}$ T cells, and resuspended in TexMACs media to ensure equivalent cell densities and CAR$^+$ frequencies across conditions. 2.5e5 CAR T cells were adoptively transferred, intravenously, into male NSG animals (n=7/condition) inoculated with 0.5e6 NALM6 leukemic cells harboring a firefly reporter gene 4 days earlier. NALM6 inoculated animals were assessed for tumor burden via bioluminescent imaging (BLI) 1 day prior to infusion of CAR T cells to appropriately randomize cohorts. Animals were monitored daily for signs of well-being and BLIs were measured twice weekly using an IVIS Spectrum instrument. Mice were euthanized when found moribund in accordance with IACUC guidelines Results As shown in FIG. 38, knocking out FAS improved proliferation and effector function. Combination knockouts with FAS and additional genes also improved proliferation and effector function either relative to FAS alone (e.g., effector molecule production of FAS+Gene A/B/C/D relative to FAS alone) or relative to the additional gene (e.g., proliferation of FAS+Gene A/B/C relative to Gene A/B/C alone).

As shown in FIG. 39B robust dual knockdown (>50%) of FAS and additional targets using shRNA was demonstrated together with maintained transgene expression. The shRNA-miR modules provided greater than 50% knockdown for each target of interest with no deleterious effects on the expression of the EGFRt transgene. FIG. 39A provides a diagram of the knockdown system and a diagram of an exemplary shRNA-CAR dual construct.

As shown in FIG. 40B, FAS knockdown provided >2-fold improved protection from FAS-mediated apoptosis. The shRNA-miR module provided nearly complete protection from FAS-mediated apoptosis in this assay. Mean and SEM shown for three representative donors. A diagram of exemplary control and shFAS systems are provided in FIG. 40A.

Figure 41:
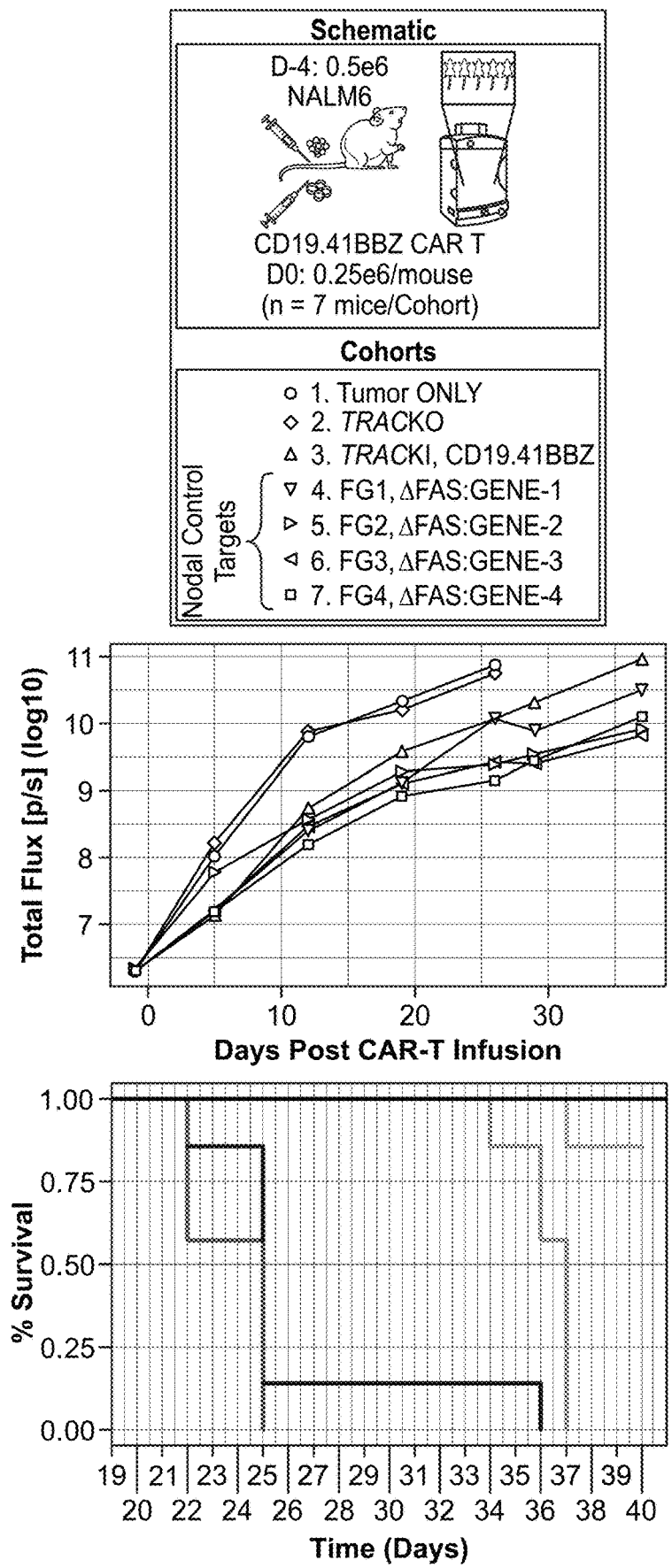
FIG. 41 shows that dual knockdowns with FAS and additional genes enhanced the in vivo efficacy of CART cells (CD19-41BBZ knocked into TRAC locus) in a systemic NALM6 model.

As shown in FIG. 41, dual knockdowns with FAS and additional genes enhanced in vivo efficacy of CART cells (CD19-41BBZ knocked into TRAC locus) in a systemic NALM6 model. Treatment of mice with the dual knockdowns with FAS and additional genes resulted in increased mouse survival as compared to control CAR T cells alone.

Example 9: Characterization of Additional shRNA and Logic Gate Constructs

Materials and Methods

T cells from three donors (ABXFC_ICT 6, 9, 10) were engineered to express three LG1 and FAS/PTPN2 shRNA constructs using the engineering methods described above in Examples 1, 3 and 4. Control cells expressing SS1-CAR, and TC-210, control CAR benchmarks, were produced via lentivirus engineering. Untreated cells (UNT) were used as a negative control, Cells were frozen and cryobanked at Day 9 after initial activation. For quality control (QC) assays, engineered T cells and control T cells from the same donors were thawed and rested overnight in media including 12.5 ng/mL human IL-7 and IL-15. The next day, T cells were counted, washed, stained with Zombie-Aqua viability dye, stained for PrimeR and CAR expression using ALPG-AF647 and MSLN-Bio primary/streptavidin-PE secondary, respectively, and analyzed by flow cytometry with an Attune NxT to assess KI %. Results of the flow cytometry assay demonstrate that after manufacturing the AB-X logic gate/shRNA constructs were expressed in 10-20% of live T cells in the three donors tested.

Figure 42A:
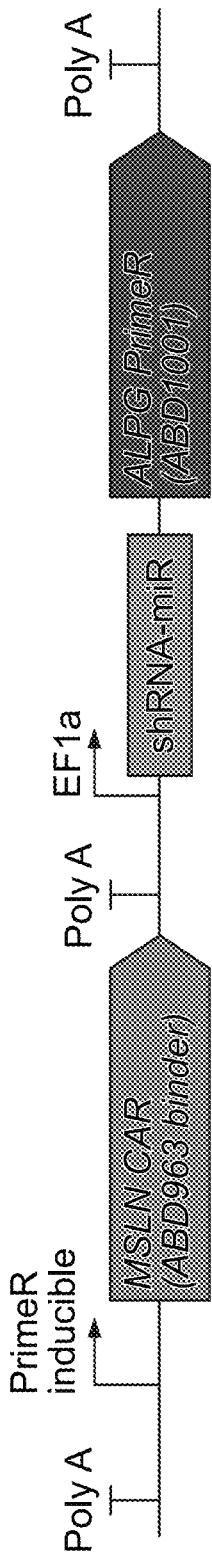
FIG. 42A provides a schematic of an exemplary full shRNA and Logic Gate construct.

Constructs were constructed as described in Table 1 below. FIG. 42A provides a diagram of the construct layout.

TABLE 1

| Construct name | Alias | Description | SEQ ID NO |
|---|---|---|---|
| AB-1013 | LG1_2 × SPA_ Fas + PTPN2 | 2 × SPA polyA reduces PrimeR MFI relative to AB-1015 | 166 |

TABLE 1-continued

| Construct name | Alias | Description | SEQ ID NO |
|---|---|---|---|
| AB-1014 | LG1_TTT_Fas + PTPN2 | TTT translation initiation site reduces PrimeR MFI relative to AB-1015 | 167 |
| AB-1015 | LG1_Fas + PTPN2 | | 168 | mRNA Knockdown in Resting Conditions

Six days post-editing, magnetic enrichment was performed using Dynabeads MyOne Streptavidin T1 and a biotinylated anti-EGFRt antibody. The highly pure populations of edited T cells were lysed and mRNA extracted using the Dynabeads mRNA Direct Purification Kit. Once extracted, the mRNA was quantified using the Quant-it RiboGreen RNA Assay Kit, and used to synthesize cDNA with the SuperScript IV First-Strand Synthesis kit. The cDNA was then used to perform real-time Quantitative Reverse Transcription PCR (RT-qPCR) with the TaqMan Fast Advanced Master Mix and TaqMan assays for FAS and PTPN2.

Protein-Level Knockdown (Flow Cytometry)

Six days post-editing, T cells were stained for EGFRt and FAS expression using anti-EGFRt PE and anti-FAS AF647, respectively, and analyzed by flow cytometry on an Attune NxT flow cytometer. Relative FAS expression was quantified by taking the ratio of the gMFI of FAS for EGFRt+ cells divided by EGFRt– cells. This value was then normalized to the relative FAS expression of the control group to calculate knockdown.

Protein-Level Knockdown (Western Blot)

Six days post-editing, magnetic enrichment was performed using Dynabeads MyOne Streptavidin T1 and a biotinylated anti-EGFRt antibody. The highly pure populations of edited T cells were then lysed and boiled to reduce and denature proteins. Total protein was quantified using the Pierce BCA Protein Assay Kit. Normalized lysates were then loaded into an SDS-PAGE gel and run. Protein was then transferred from the gel to a PVDF membrane, blocked, and stained for PTPN2 primary antibody and HRP conjugated secondary antibody. The blot was then imaged with the Bio-Rad ChemiDoc and relative PTPN2 expression was quantified.

CD4 and CD8 Ratio and Expansion

Cryobanked T cells made according to the method above were thawed and rested overnight in media including 12.5 ng/mL human IL-7 and IL-15. The next day, T cells were counted, washed, stained with Zombie-Aqua viability dye, stained for CD4 and CD8 with FMOs used as controls for gating, and analyzed by flow cytometry with an Attune NxT.

Memory Phenotyping

Donor T cells edited as described above with the shRNA and logic gate circuit were phenotypically profiled with cell surface T cell subset markers by flow cytometry. Cryobanked T cells were thawed, counted, washed, and stained with Zombie-Aqua viability dye, or for CD4, CD8, CD45RA, and CCR7 with FMOs used as controls for gating. Cells were analyzed by flow cytometry with an Attune NxT. In FlowJo, single, viable lymphocytes were selected by SSC and FSC and subset profiling by a combination of CCR7 and CD45RA were used to identify stem cell memory—(SCM: CD45RA+CCR7+), central memory—(CD45RA–CCR7+), effector memory—(CD45RA–CCR7–), or terminal effector—(TEMRA: CD45RA+CCR7–) T cells on CD4+ and CD8+ subpopulations.

CAR Conversion

T cells from two donors (ABXFC_ICT 9, 10) were engineered to express the three LG1 and FAS/PTPN2 shRNA constructs using the manufacturing process described above. Cells were frozen and cryobanked at Day 9 after initial activation, Prior to the assay, engineered T cells were thawed and rested overnight in media including 12.5 ng/mL human IL-7 and IL-15. The PrimeR+ T cells were then enriched to >95% purity via a two day MACS-based process. T cells were then counted and 5e4 T cells were plated per well of a 96-well flat-bottom plate in 200 uL media with 500 pg/mL IL-7 and IL-15 prior to the addition of K562$^{ALPG}$ cells at a 1:1 E:T ratio in technical duplicates. Samples of the T cells alone prior to PrimeR antigen stimulation via the K562$^{ALPG}$ cells as well as samples collected after 24, 96, and 144 hours of co-culture in the conditions above (with ½ media changes every 2-3 days) were washed, stained with Zombie-Aqua viability dye, stained for PrimeR and CAR expression using ALPG-AF647 and MSLN-Bio primary/streptavidin-PE secondary, respectively, and analyzed by flow cytometry with an Attune NxT. % CAR Conversion=(% CAR+ at $t_x$/% PrimeR+ at $t_0$)*100

Heterogeneity Cytotoxicity Assay

T cells from three donors (ABXFC_ICT 9, 10) were engineered to express the three LG1 and FAS/PTPN2 shRNA constructs using the manufacturing process described above. Cells were frozen and cryobanked at Day 9 after initial activation. Prior to the assay, engineered T cells and RNP alone control T cells from the same donors were thawed and rested overnight in media including 12.5 ng/mL human IL-7 and IL-15. On the day of the assay, engineered T cells were counted and stained for PrimeR and CAR expression using ALPG-AF647 and MSLN-Bio primary/streptavidin-PE secondary, respectively, and analyzed by flow cytometry with an Attune NxT. For each donor, all engineered T cell populations were normalized to the lowest KI % within that donor by adding RNP only cells to dilute engineered populations that were above the lowest KI %. After normalization, T cells were resuspended in medium without IL-7 and IL-15 and added to 96-well flat-bottom, white-walled assay plates at 1:1 KI+E:T with 1×10$^4$ K562$^{MSLN}$ and K562$^{ALPG/MSLN}$ mixed at various ratios to model different levels of priming antigen heterogeneity. Prepared plates with T cells and target cells were spun down for 2 min at 300 g prior to incubation at 37° C. for 72 hours with a breathable membrane on each plate. Cytotoxicity at the end of the 72 hour co-culture was measured using an end-point luciferase assay.

Results

Figure 42B:
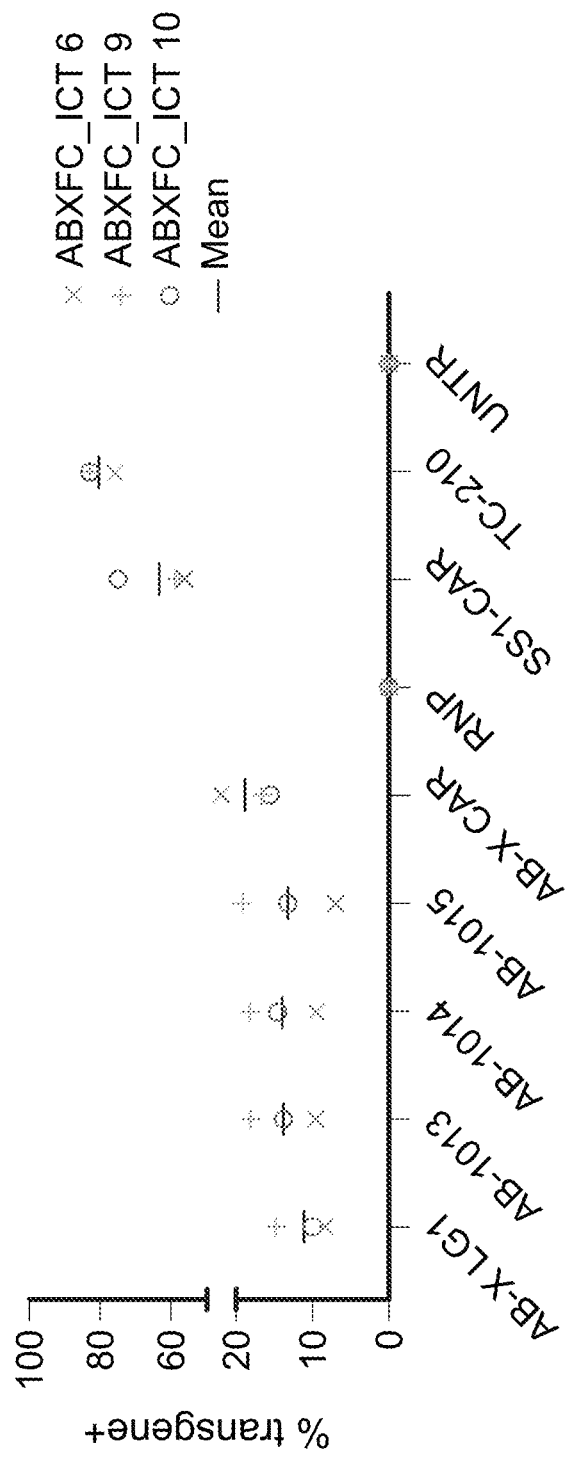
FIG. 42B shows that similar transgene knock-in efficiency was observed with each of the constructs.
Figure 42C:
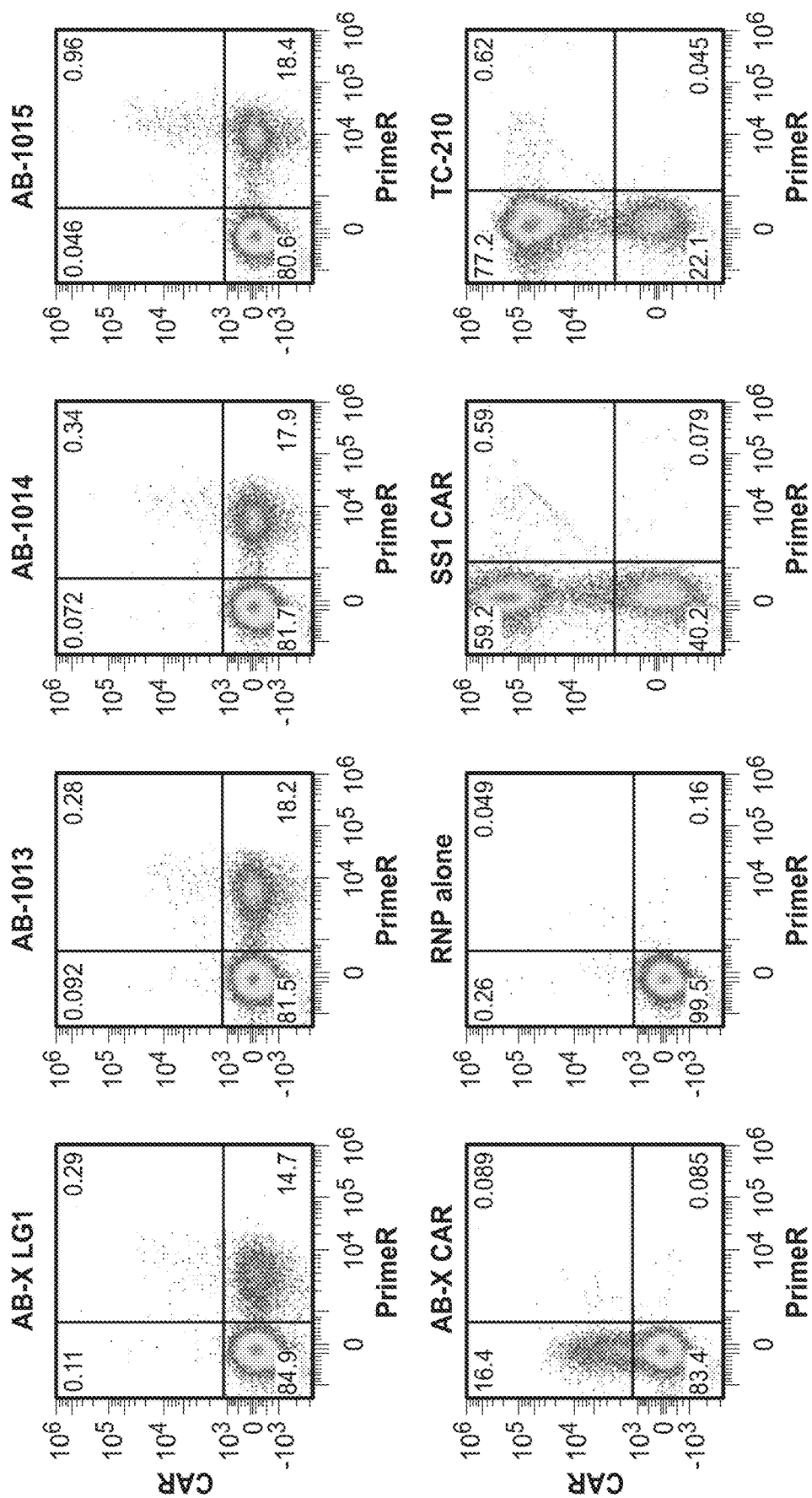
FIG. 42C shows that T cells expressing the PrimeR had minimal CAR expression, due to the function of the logic gate to gate CAR expression on exposure to ALPG+ target cells.

Similar transgene knock-in efficiency was observed with each of the constructs (FIG. 42B). T cells expressing the PrimeR had minimal CAR expression, due to the function of the logic gate to gate CAR expression on exposure to ALPG+ target cells (FIG. 42C). These results indicate that T cells expressing the AB-X logic gate/shRNA circuit constructs were robustly generated using the described manufacturing process.

Figure 42D:
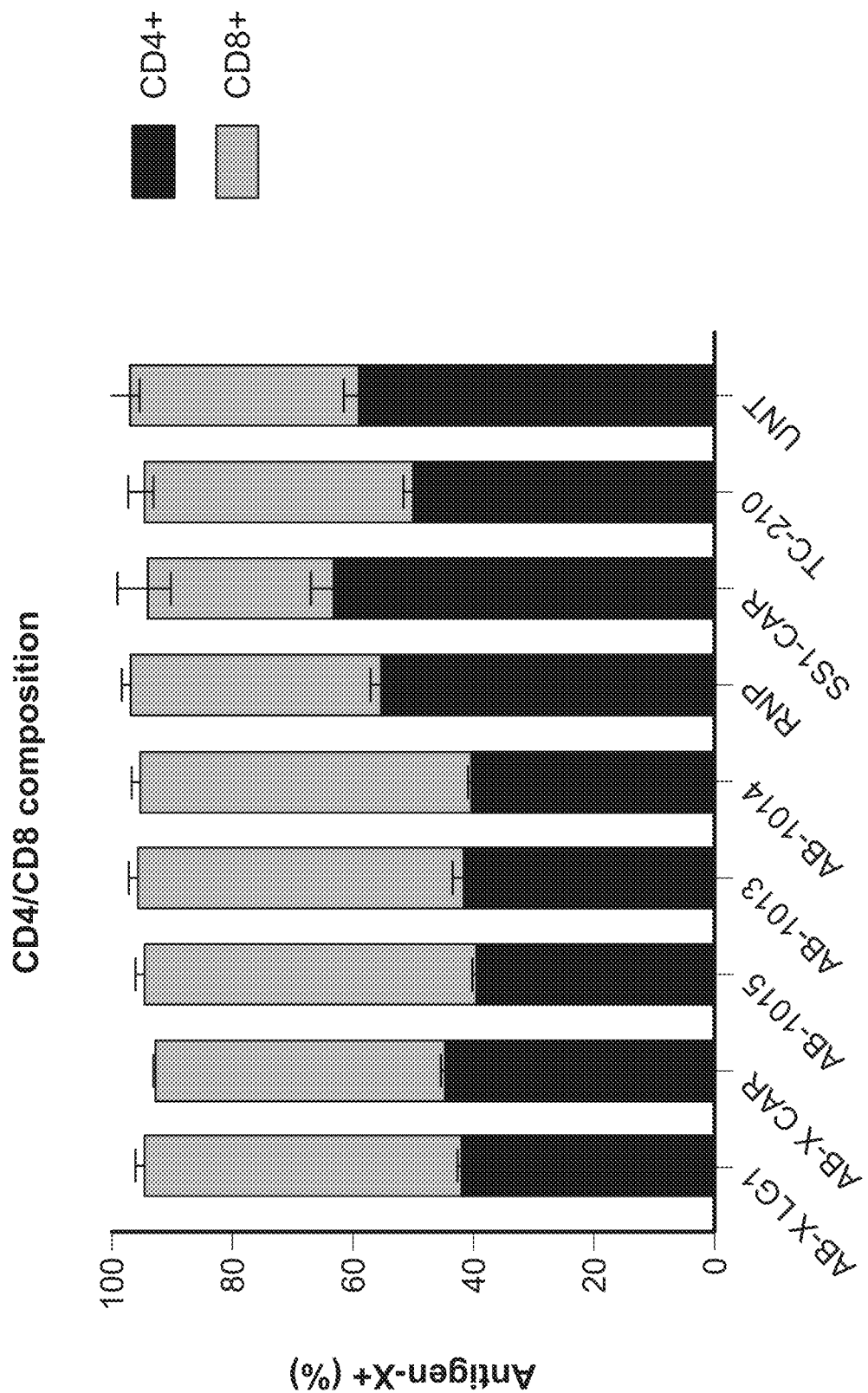
FIG. 42D shows the CD4/CD8 composition of the KI+ population (or transduced for the lentiviral populations) for all engineered T cells and the bulk T cell population for the RNP and untransduced (TNT) cells.

The CD4/CD8 composition of the KI+ population (or transduced for the lentiviral populations) for all engineered T cells and the bulk T cell population for the RNP and untransduced (UNT) controls are shown in FIG. 42D. The CD4:CD8 ratio was similar for all logic gate/shRNA circuits and the logic gate alone. These results indicate that integration of the logic gate and shRNA modules did not alter the CD4/CD8 composition or expansion kinetics of T cells expressing the logic gate/shRNA full circuit candidates compared to the logic gate alone (FIG. 42D).

Figure 43:
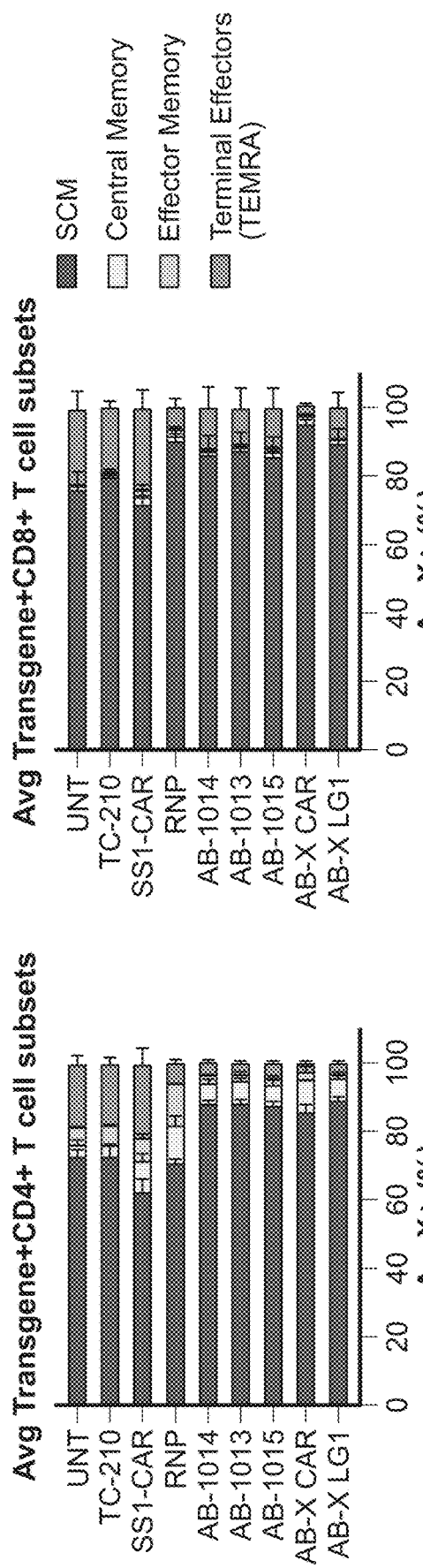
FIG. 43 shows memory phenotyping of the LG1 and FAS/PTPN2 shRNA circuits.

Memory phenotyping showed consistent phenotypes for the LG1 and FAS/PTPN2 shRNA circuits with less differentiation than lentiviral benchmarks (UNT, TC-210, and SSI-CAR samples) (FIG. 43). In all three donors, the editing did not contribute to an expansion of terminally differentiated T cells, as the major subset of T cells in both subpopulations retained positive expression of CD45RA and CCR7 (FIG. 43). This indicates that the edited T cells have the capacity to expand, survive and persist in vivo. The results also indicate that integration of the logic gate and shRNA modules did not alter the memory phenotype composition of T cells expressing the logic gate/shRNA full circuit candidates compared to the logic gate alone. Thus, the edited T cells have the capacity to expand, survive and persist in vivo.

All constructs displayed equivalent knockdown of both FAS (FIG. 44A) and PTPN2 (FIG. 44B).

Figure 45:
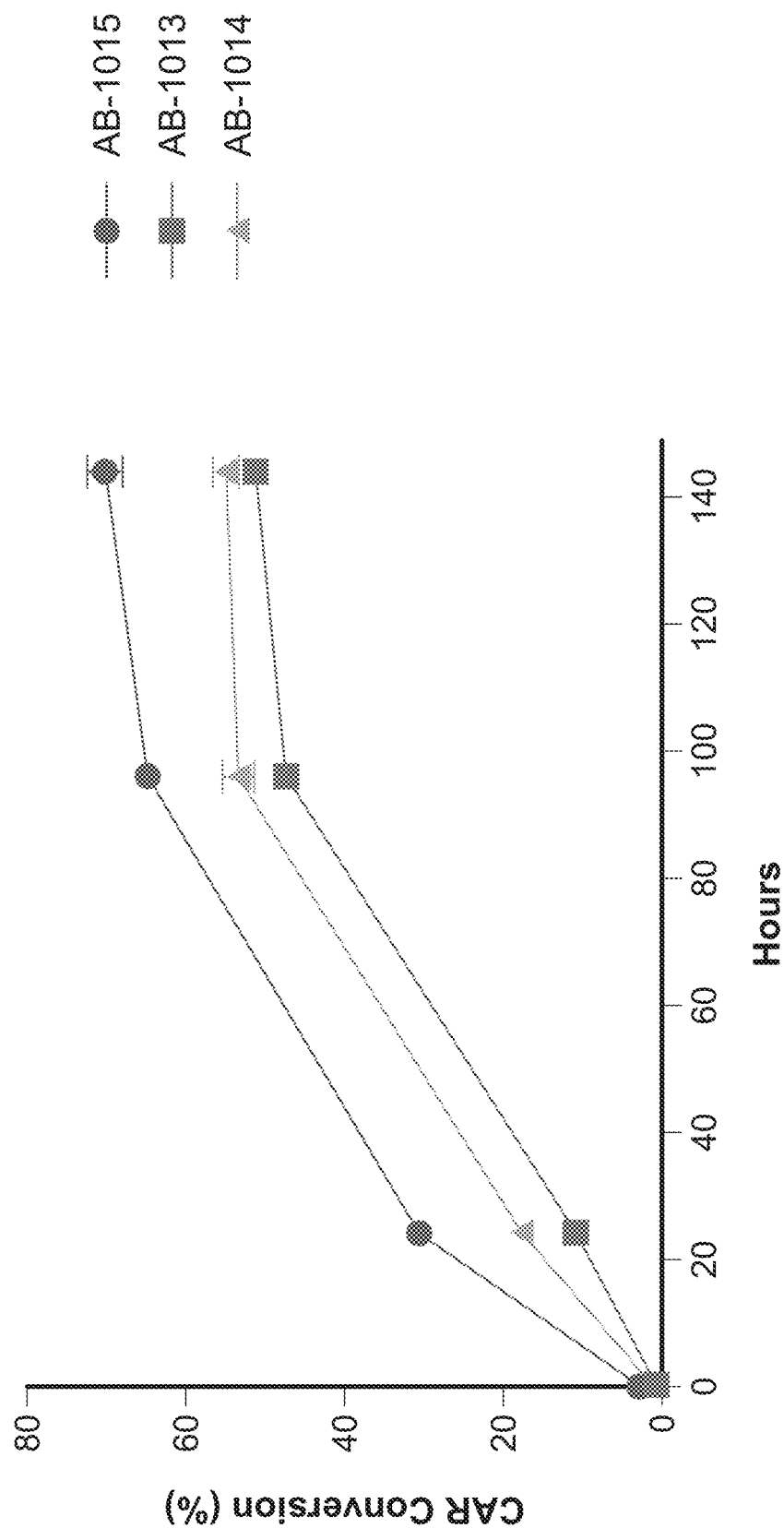
FIG. 45 shows that AB-1013, AB-1014, and AB-1015 induced PG-dependent CAR expression.

The three logic gate/shRNA circuits (AB-1013, AB-1014, and AB-1015) induced ALPG-dependent CAR expression (FIG. 45). ALPG-dependent CAR conversion by the AB-X logic gate/shRNA circuit reached a peak after around 100 hours of stimulation with the PrimeR antigen, with a similar activation kinetic but different magnitude of CAR induction observed for the different candidates. AB-1015 demonstrated the greatest relative conversion of PrimeR signal to CAR expression after ALPG engagement (FIG. 45).

Figure 46:
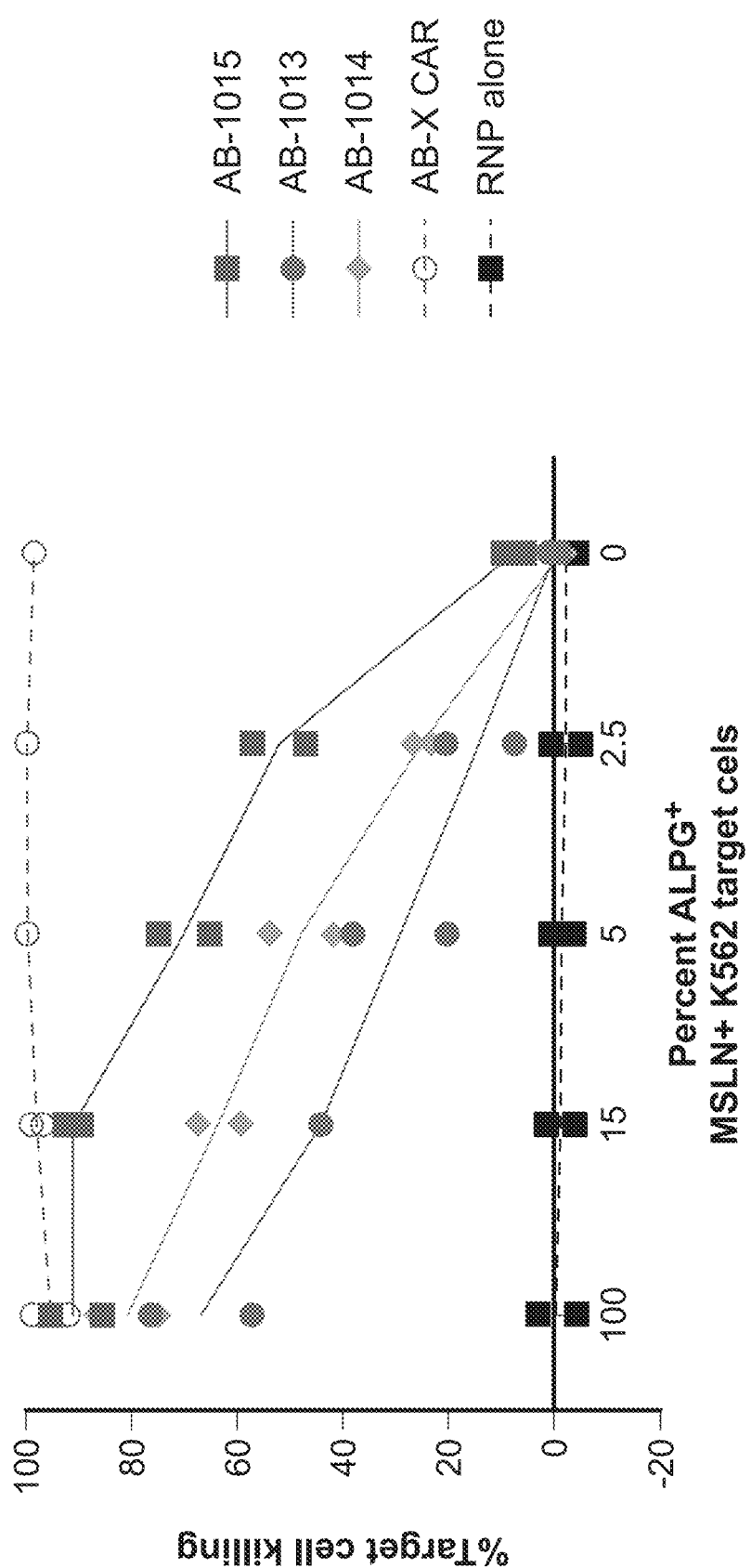
FIG. 46 shows that AB-1013, AB-1014, and AB-1015 killed the priming antigen heterogenous target cell populations.

In the heterogeneity assay, the three logic gate/shRNA circuits killed the priming antigen heterogenous target cell populations with varied potency (FIG. 46). For example, AB-1015 showed the most potent response in the presence of the least priming antigen (FIG. 46). The constitutive CAR control T cells killed all MSLN+ target cell conditions equally-well regardless of ALPG expression. No cytotoxicity was observed from the negative control RNP-only T cells. Taken together with the IHC data analyzing antigen expression in ovarian cancer patient samples and the results of the priming antigen heterogeneity cytotoxicity assay, demonstrate that the logic gate/shRNA T cells were capable of eliminating heterogenous populations of cancer cells that express the priming antigen on only a small minority of cells.

Example 10: In Vivo Characterization of Additional shRNA and LG Circuits

Materials and Methods

T cells from two donors were engineered to express the three LG1 and FAS/PTPN2 shRNA circuits as described in Example 9 using the engineering methods described above in Example 1. Cells were frozen and cryobanked at Day 9 after initial activation. For quality control (QC) assays, RNP only control T cells from the same donors were thawed and rested overnight in media including 12.5 ng/mL human IL-7 and IL-15. The next, engineered T cells were counted and stained for PrimeR and CAR expression using anti-myc PE and anti-FLAG APC, respectively, and analyzed by flow cytometry to assess KI %.

K526 Dual Flank In Vivo Study

NSG double MHC KO (NSG DKO) strain (Jackson Laboratories, 025216) were implanted with 1e6 each of K562-MSLN cells on the left flank and K562-ALPG/MSLN cells on the right flank, both in 50% Matrigel solution. Three days after K562 cell inoculation, mice were randomly assigned to treatment groups with matched tumor sizes using bioluminescent imaging (BLI) to measure luciferase signal to quantify engineered tumor cells, with 7 mice assigned per treatment condition. The same day of staging and normalization, engineered shRNA+LG1 circuit T cells and matched CAR only T cells, logic gate only T cells, or RNP controls were thawed and rested overnight in media including 12.5 ng/mL human IL-7 and IL-15. On Day 4 after K562 implantation, for each donor all engineered T cell populations were normalized to the lowest KI % within that donor by adding RNP only cells to dilute engineered populations that were above the lowest KI %. Mice were injected with $7.5 \times 10^6$ shRNA+LG1 circuit T cells, CAR only T cells or logic gate only T cells i.v. via the tail vein on Day 4. Bilateral tumor volumes were monitored twice weekly via caliper along with body weight. The study was terminated at day 24.

Results

As shown in FIGS. 47A and 47B, the CAR only T cells inhibited the growth of MSLN/ALPG (FIG. 47B) and MSLN only tumors (FIG. 47A). Thus, the MSLN CAR targeted cells express MSLN.

In addition, each of the full shRNA+LG1 circuit T cells were specific in vivo and inhibited tumor growth of $K562^{MSLN/ALPG}$ tumors (FIG. 47D). The full circuit T cells did not inhibit growth of the MSLN only tumor cells (FIG. 47C), and thus showed selectivity to the dual MSLN and ALPG expressing cells.

Example 11: Additional In Vitro Characterization

Materials and Methods

Continuous Stimulation Assay

Edited T cells expressing the LG1 circuit, the full shRNA+Logic Gate circuit, or the controls SS1-CAR or TC-210 were enriched using ALPG-Fc reagent and Protein G Dynabeads to >70% purity. Edited T cells were normalized to a concentration of $8.5 \times 10^4$ T cells/well and plated in 96 well plates in 250 uL of TexMacs media (Miltenyi) supplemented to 3% human serum and 50 U/mL of human IL-2 and were co-cultured with ALPG and MSLN overexpressing K562 at an effector:target ratio of 2:1. At days 2, 5, 7, 9, and 12 after the initiation of culture, T cells and targets were counted by flow cytometry and wells were diluted to reset the T cell number to $8.5 \times 10^4$ and fresh target cells were added as needed to reset the 2:1 E:T ratio. T cell expansion and target control were quantified as the cumulative fold expansion of T cells and K562 cells in the co-culture, respectively. Values are median±sem. Wilcoxon test ****<0.0001, ns>0.05

Comparison Assay with CAR T Cells

T cells from three donors (ABXFC_ICT 6, 9, 10) were engineered to express the three LG1 and FAS/PTPN2 shRNA circuits as described in Example 9 using the engineering methods described above in Example 1. Cells were frozen and cryobanked at Day 9 after initial activation. Prior to the assay, engineered T cells and control T cells from the same donors were thawed and rested overnight in media including 12.5 ng/mL human IL-7 and IL-15. On the day of the assay, engineered T cells were counted and stained for PrimeR and CAR expression using ALPG-AF647 and MSLN-Bio primary/streptavidin-PE secondary, respectively, and analyzed by flow cytometry with an Attune NxT. After normalization, T cells were resuspended in medium without IL-7 and IL-15 and serially diluted prior to being added to 96-well flat-bottom, white-walled assay plates. The serial dilution of T cells results in the following co-culture KI+ effector:target (E:T) ratios once 1e4 target cells were added/well: 3:1, 1:1, 1:3, 1:9, 1:27, and 1:81 in technical duplicates. Each T cell population is co-cultured separately with $K562^{MSLN}$ and $K562^{ALPG/MSLN}$ target cells. Prepared plates with T cells and target cells were spun down for 2 min at 300 g prior to incubation at 37° C. for 72 hours with a breathable membrane on each plate. Cytotoxicity at the end of the 72 hour co-culture was measured using an end-point luciferase assay.

To further demonstrate the specificity and functional activity of the logic gate/shRNA circuit T cells, cytokine production was evaluated in supernatants taken from co-culture wells of the cytotoxicity assay with K562 tumor cells engineered to express different combinations of ALPG and MSLN (described above). Supernatants collected at 72 hours from the 1:1 KI+E:T wells in the cytotoxicity assay mentioned above are analyzed for IFNγ production using a Luminex assay. In agreement with the cytotoxicity data, IFNγ production from AB-X logic gate/shRNA candidate T cells was limited to wells where the dual-antigen K562$^{ALPG/MSLN}$ target cells were present. In contrast, T cells bearing the constitutive CAR control produced IFNγ when co-cultured with either K562$^{MSLN}$ or K562$^{ALPG/MSLN}$ target cells. These data further support the notion that the functional output of the AB-X logic gate/shRNA candidate T cells is limited to conditions where both the priming and cytolytic antigens are present.

Cytokine Assay

Cytokine production was evaluated in supernatants taken from co-culture wells of the cytotoxicity assay with K562 tumor cells engineered to express different combinations of ALPG and MSLN (described above). Supernatants were collected at 72 hours from the 1:1 KI+ E:T wells in the cytotoxicity assay mentioned above and were analyzed for IFNγ production using a Luminex assay.

Multiple Cell Line Cytotoxicity Assay

Each T cell population was co-cultured separately with K562-ALPG/MSLN, MSTO-ALPG/MSLN, and SKOV3-ALPG/MSLN target cells, in order to assess the potency of T cell response against these three different on-target cell lines. T cells were serially diluted resulted in the following co-culture KI+ effector:target (E:T) ratios once 1e4 target cells were added; well: 3:1, 1:1, 1:3, 1:9, 1:27, and 1:81 in technical duplicates. Prepared plates with '1' cells and target cells were spun down for 2 min at 300 g prior to incubation at 37° C. for 72 hours with a breathable membrane on each plate. Cytotoxicity at the end of the 72 hour co-culture was measured using an end-point luciferase assay.

Cell Transformation Assay

1×106 T cells expressing the AB-1014, AB-1013, or AB-1015 shRNA+LG1 circuits were seeded in one well of a 24 well-GRex plate at a density of 0.56/ml. Cells were cultured for 5 days in the TexMACS complete medium (+3% HS) with or without cytokines. Cell number and viability were recorded at days 0, 3, 5 and 7. As a positive control, 1×10$^6$ Jurkat cells were cultured in the medium without cytokines in parallel.

Results

Figure 48:
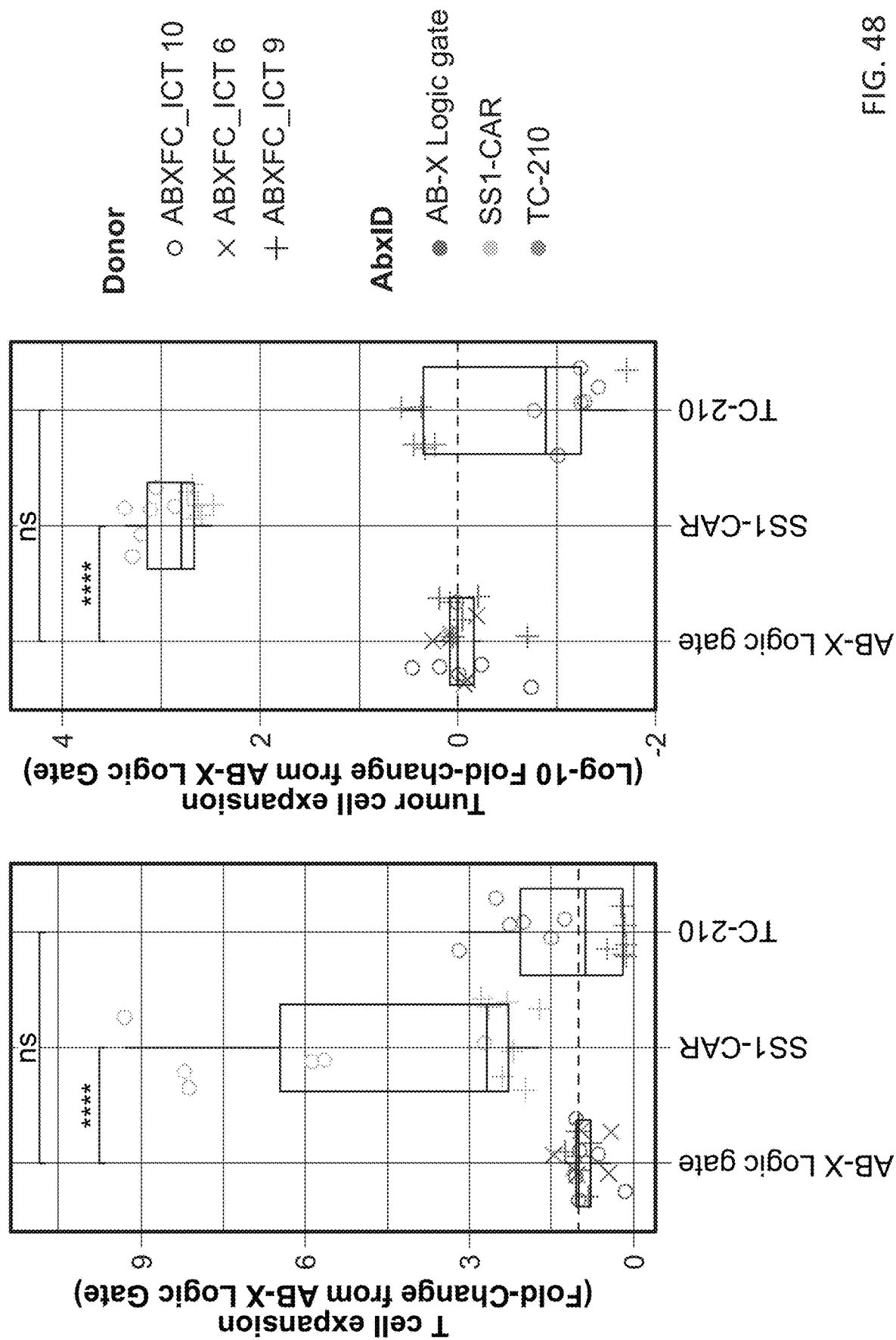
FIG. 48 shows that cells expressing just LG1 (AB-X Logic Gate) showed better tumor control than the SS1-CAR and equivalent tumor control as TC-210.
Figure 49:
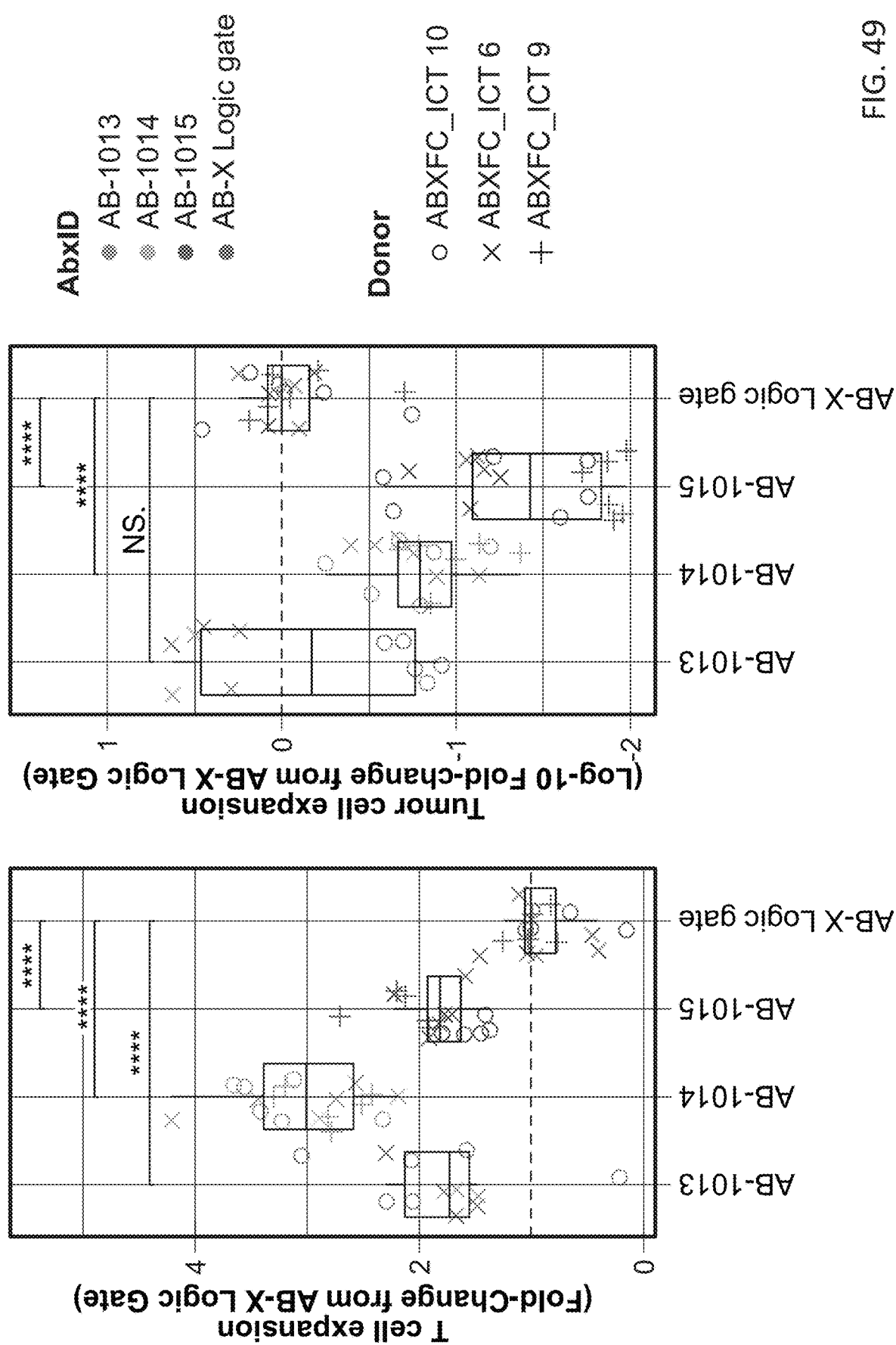
FIG. 49 shows that the three shRNA+LG1 circuit T cells (AB-1013, AB-1014, and AB-1015) showed improved T cell expansion and tumor control (e.g., less tumor expansion) in the continuous stimulation assay as compared to the LG1 T cells.

Cells expressing just LG1 (AB-X Logic Gate) showed better tumor control than the SS1-CAR and equivalent tumor control as TC-210 (FIG. 48). However, the three shRNA+LG1 circuit T cells (AB-1013, AB-1014, and AB-1015) showed improved T cell expansion and tumor control (e.g., less tumor expansion) in the continuous stimulation assay as compared to the LG1 T cells (FIG. 49). Each donor was normalized to the median value of the AB-X Logic Gate.

Figure 50A:
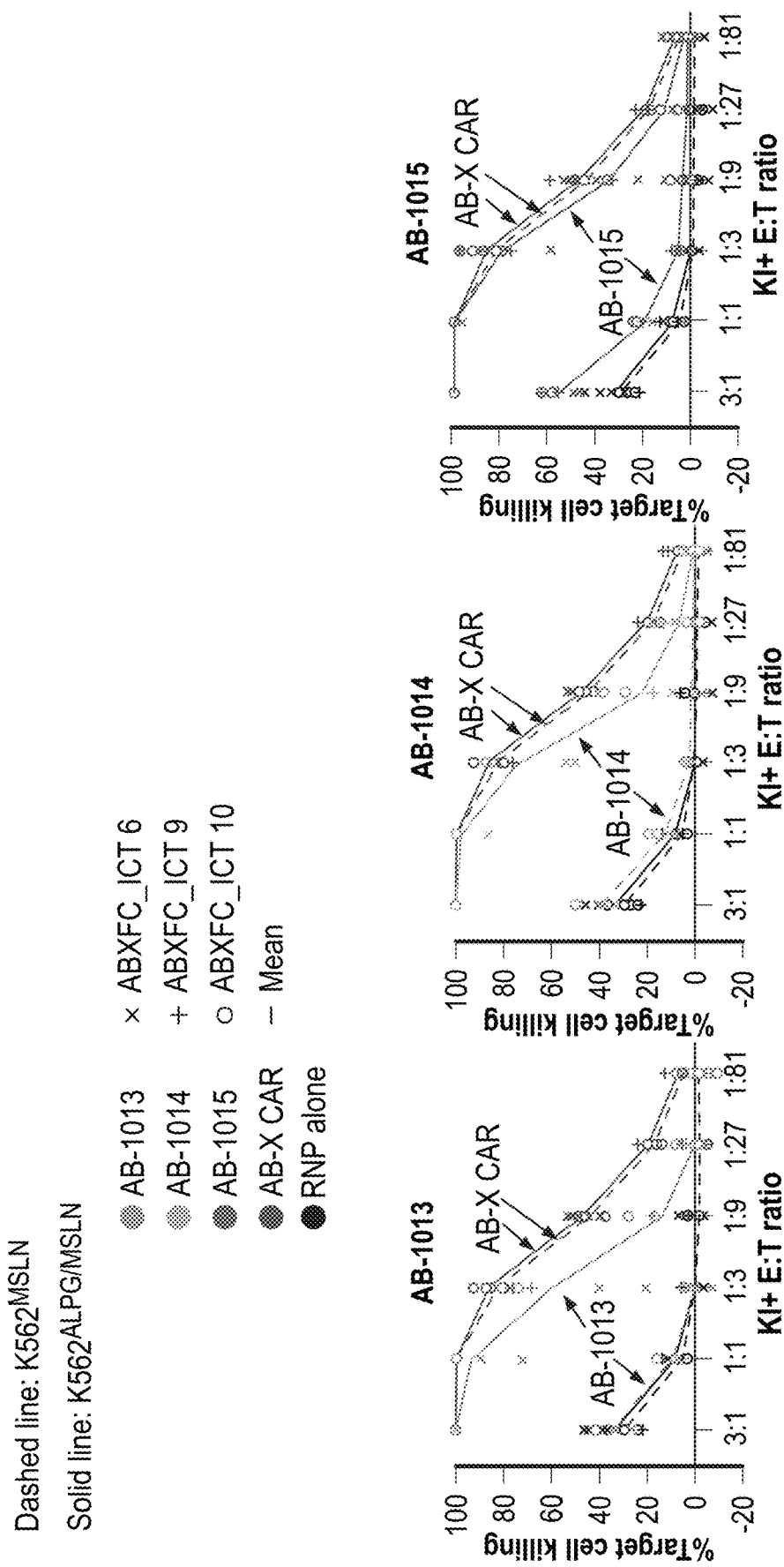
FIG. 50A shows that T cells expressing the constitutive anti-MSLN CARs killed both $K562^{MSLN}$ and $K562^{ALPG/MSLN}$ cells and that cytotoxicity from shRNA+ logic gate T cells (AB-1013, AB-1014, and AB-1015) was specific for dual-antigen $K562^{ALPG/MSLN}$ cells only.

FIG. 50A shows that while T cells expressing the constitutive anti-MSLN CARs killed both K562$^{MSLN}$ and K562$^{ALPG/MSLN}$ cells, cytotoxicity from shRNA+logic gate T cells (AB-1013, AB-1014, and AB-1015) was specific for dual-antigen K562$^{ALPG/MSLN}$ cells only. In FIG. 50A cytotoxicity against K562$^{MSLN}$ cells is shown with dashed lines, cytotoxicity against K562$^{ALPG/MSLN}$ cells is shown with solid lines. No cytotoxicity was observed from the negative control RNP-only T cells. Thus, cytotoxicity from the logic gate T cells against cytolytic antigen positive cells was restricted to conditions where the priming antigen was also present. In addition, incorporation of the shRNA module with the logic gate in a full circuit did not lead to a loss of specificity from the logic gate to bind its target antigens.

Figure 50B:
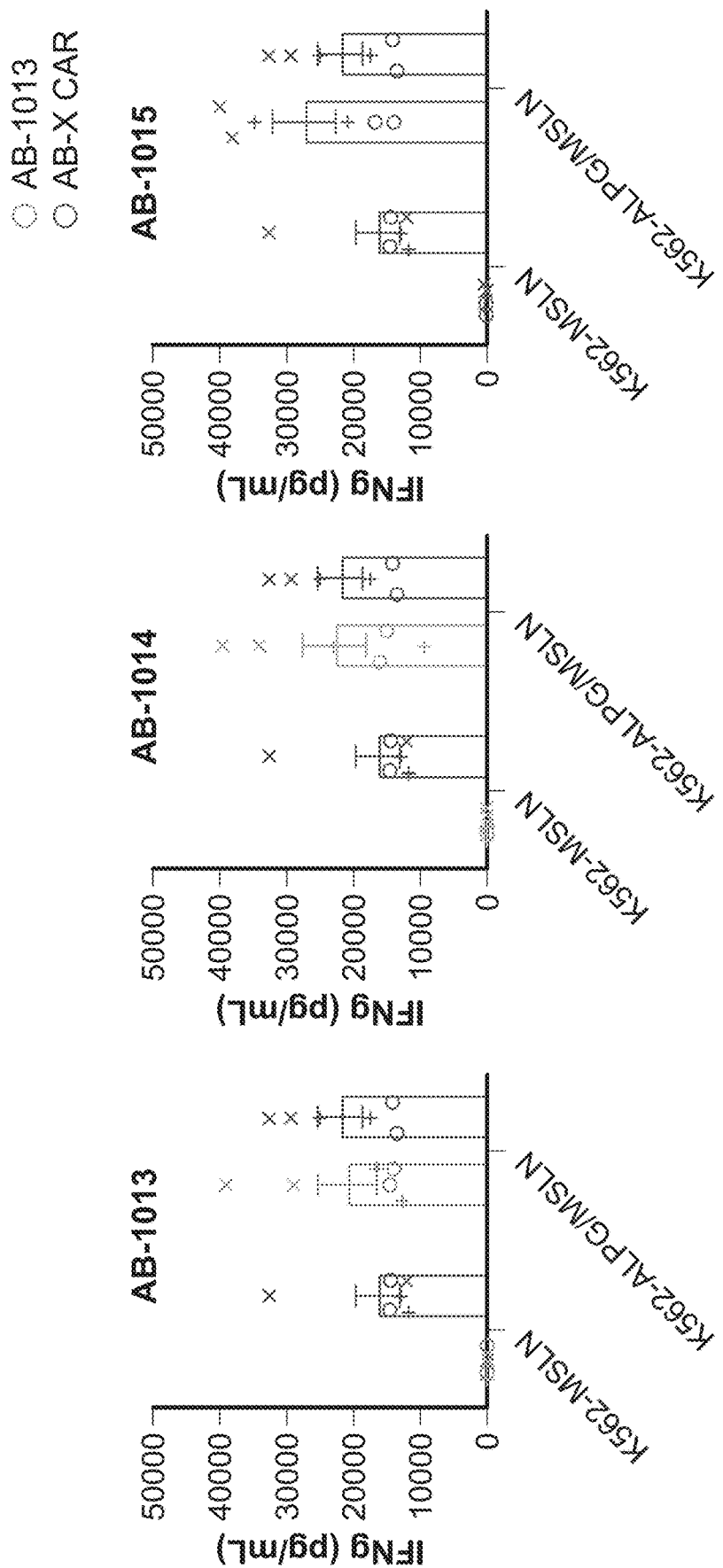
FIG. 50B shows that IFNγ production from the logic gate/shRNA circuit T cells was limited to samples with the dual-antigen $K562^{ALPG/MSLN}$ target cells.

In agreement with the cytotoxicity data. IFNγ production from the logic gate/shRNA circuit T cells was limited to samples with the dual-antigen K562$^{ALPG/MSLN}$ target cells (FIG. 50B). In contrast, T cells bearing the constitutive CAR control produced IFNγ when co-cultured with either K562$^{MSLN}$ or K562$^{ALPG/MSLN}$ target cells. No IFNγ expression was observed after incubation of the three shRNA+LG1 circuits, the CART cells, the LG1 T cells, or the control T cells after incubation with control K562 or K652$^{ALPG}$ cells (data not shown). Thus, the logic gate/shRNA circuit T cells demonstrate an improved safety profile relative to CAR T cells in both cytotoxicity and cytokine assays. Without wishing to be bound by theory, the functional output of the logic gate/shRNA circuit 1 cells is indicated by this data to be limited to conditions where both the priming and cytolytic antigens are present.

The increased potency from AB-1015 was associated with a modest increase in ALPG-independent killing activity in K562$^{MSLN}$ cells and increased IFNγ expression as compared to AB-1013 and AB-1014 (FIG. 51). Comparison of the cytotoxicity assay data for the different T cell populations against K562-MSLN target cells shows the significant reduction in killing of these prime antigen negative target cells by the WI T cells relative to the constitutive CAR T cents. A consistent increase in killing of the K562-MSLN targets by AB-1015 relative to the other AB-X logic gate/ shRNA candidates at the highest E:T of 3:1 was observed. Similarly, both AB-1015 and AB-1014 showed small but significant increases in IFNγ secretion at an E:T of 1:1 with K562-MSLN targets; however, the levels reached were ~100-fold lower than those produced by the constitutive CAR control. Together, these results demonstrate the significant improvement in the therapeutic window (the difference in activity against K562-ALPG/MSLN target cells versus K562-MSLN target cells) shown by the logic gate/ shRNA circuit relative to the constitutive CAR controls.

Figure 52:
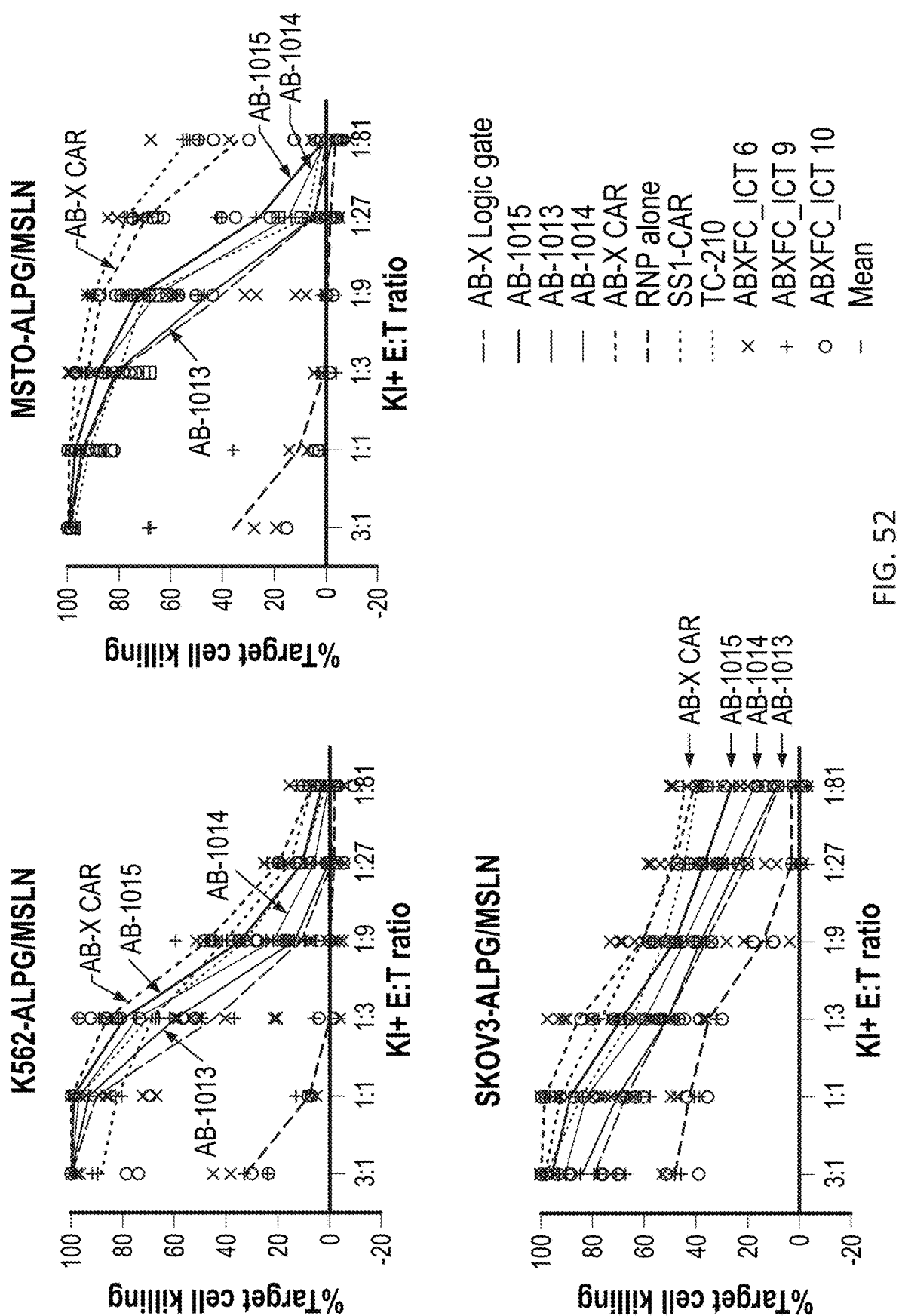
FIG. 52 shows that all three shRNA+logic gate circuit T cells induced target killing.

Activity of the three shRNA+LG1 circuit T cells was also assessed in additional cell lines (MSTO$^{ALPG/MSLN}$ and SKOV3$^{ALPG/MSLN}$ cells). The results of this cytotoxicity assay demonstrate a clear rank-order of on-target potency (as calculated by EC50 of T cell dose) of the three logic gate/shRNA circuits. As shown in FIG. 52, all three shRNA+ logic gate circuit T cells induced target killing. However, the most potent in vitro cytotoxicity was observed with the AB-1015 construct against multiple target cell lines. Across the different on-target cell lines, AB-1015 T cells were consistently ~2-3-fold more potent than AB-1013 T cells, with AB-1014 showing relative intermediate potency. Together, these results demonstrate that the logic gate/ shRNA circuits could be engineered to have tuneable on-target potency.

Figure 53:
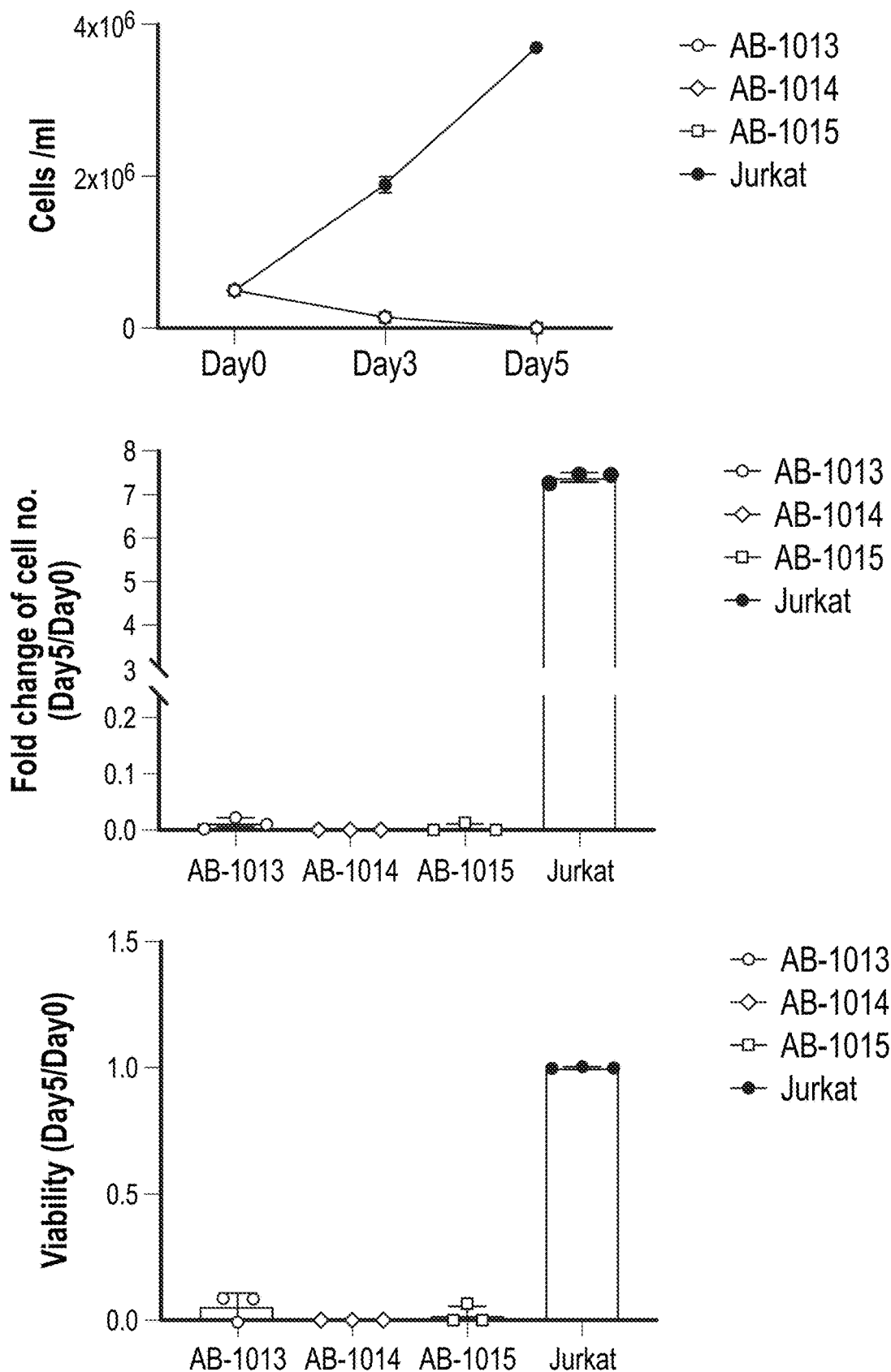
FIG. 53 shows that no cell transformation was observed in T cells edited with the three shRNA+LG1 circuits (AB-1013, AB-1014, or AB-1015).

In addition, no cell transformation was observed in T cells edited with the three shRNA+LG1 circuits (AB-1013, AB-1014, or AB-1015) (FIG. 53). While the positive control Jurkat cells maintained good viability and expansion without cytokine throughout the assay, the shRNA+LG1 circuit T cells did not proliferate or survive beyond day 3, demonstrating that shRNA+LG1 circuit T cells were not transformed.

Example 12: MSLN CAR T Cell Binding Specificity

Methods

Cytotoxicity Assays

T cells from four donors were engineered to constitutively express the MSLN CAR (LG1 CAR) using the manufacturing process described in Example 1 and were frozen and cryobanked at Day 9 after initial activation. Prior to the assay, engineered T cells or RNP only control were thawed and rested overnight in media including 12.5 ng/mL human IL-7 and IL-15. On the day of the assay, MSLN CAR and RNP only control T cells were counted and resuspended in medium without IL-7 and IL-15 and serially diluted and added to 96-well flat-bottom, white-walled assay plates. The serial dilution of T cells results in the following co-culture effector:target (E:T) ratios once 1e4 THP-1 or K562 (negative control), K562-MSLN (positive control) and K562-GP2 target cells were added/well: 3:1, 1:1, 1:3 in technical duplicates. Prepared plates with T cells and target cells were incubated at 37° C. for 24 hours with a breathable membrane on each plate. Cytotoxicity at the end of the 24 hour co-culture was measured using an end-point luciferase assay.

Polyreactivity Assay

T cells from four donors were engineered to express the MSLN CAR as described above. CAR T cells were co-cultured with three different cell lines: A498 and H1975 at final effector:target (E:T) ratios of 3:1, 1:1, 1:3 in technical duplicates. Prepared plates with T cells and target cells were incubated at 37° C. for 24 hours with a breathable membrane on each plate. Cytotoxicity at the end of the 24 hour co-culture was measured using an end-point luciferase assay.

Results

Figure 54A:
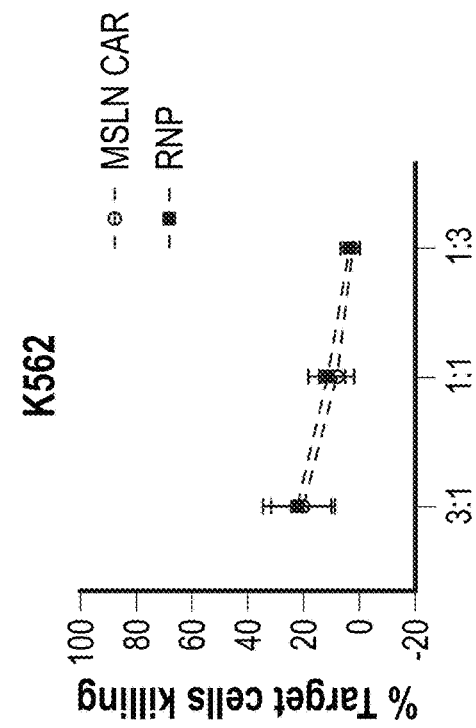
FIG. 54A shows that the MSLN CART cells did not recognize SLC2A9+ cells (THP-1 cells).
Figure 54B:
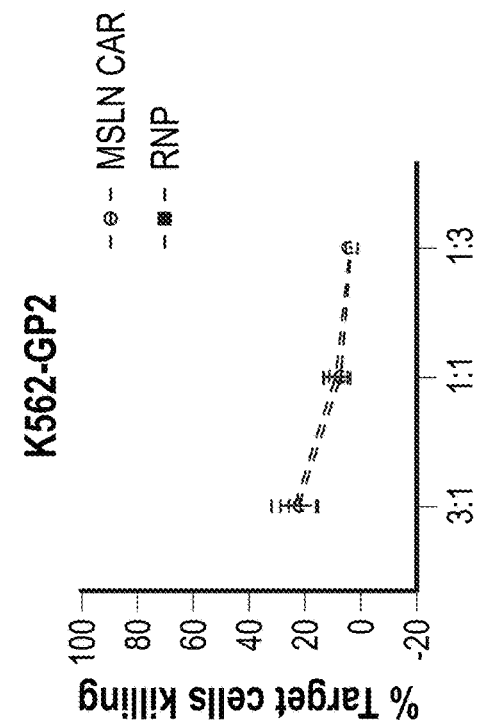
FIG. 54B shows that the MSLN CART cells did not recognize K562 negative control cells.
Figure 54C:
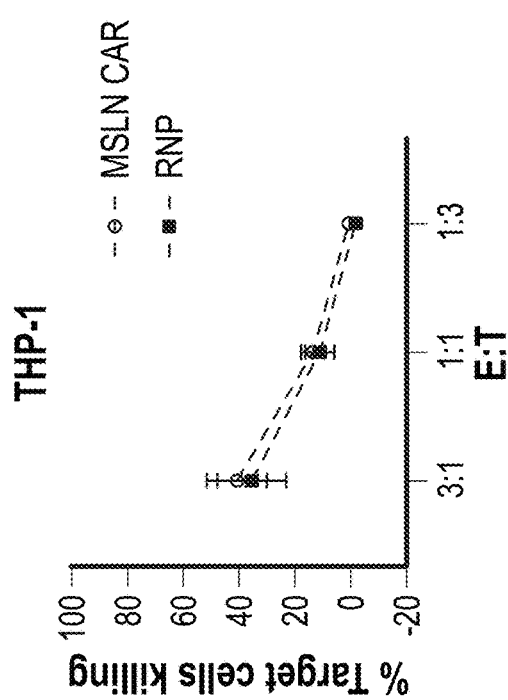
FIG. 54C shows that the MSLN CAR T cells did bind to the positive control MSLN-expressing cells.
Figure 54D:
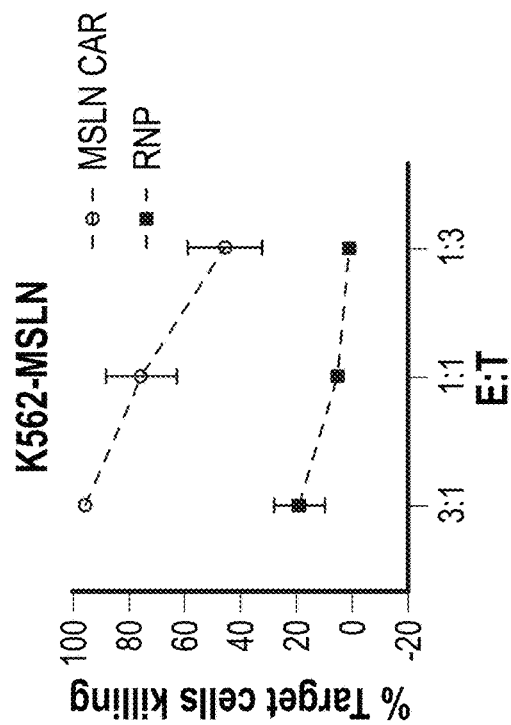
FIG. 54D shows that the MSLN CAR T cells did not recognize GP2+ cells
Figure 55:
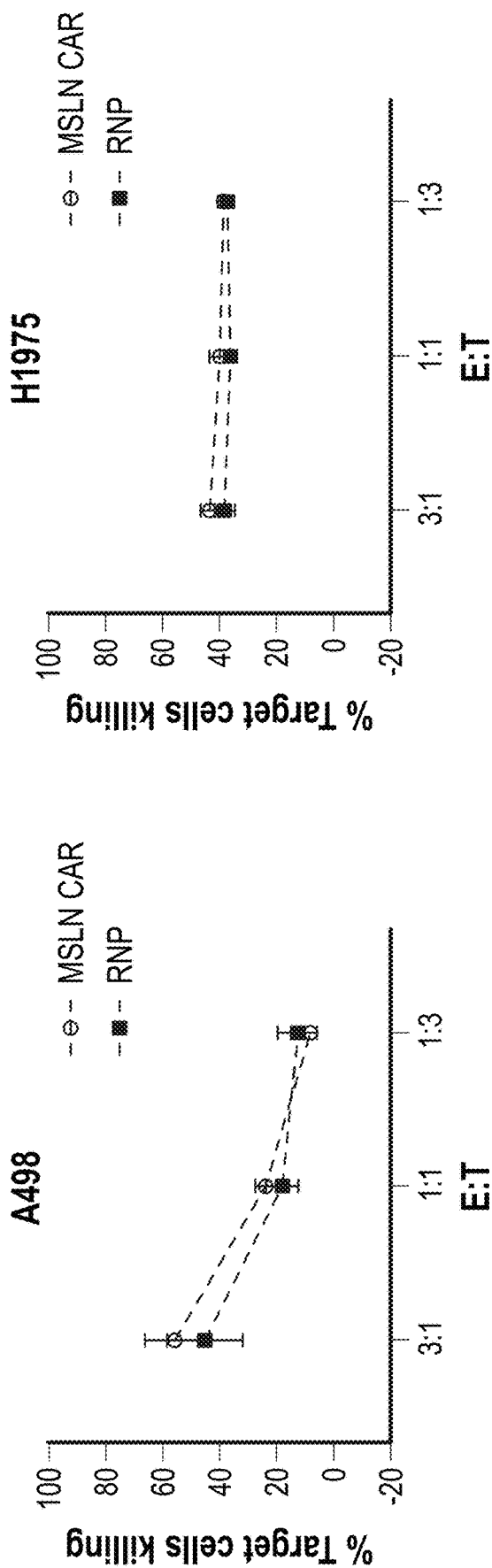
FIG. 55 shows that no evidence of polyreactivity was observed with the MSLN CAR cells against A498 cells or H1975 cells.

As shown in FIG. 54A, the MSLN CAR T cells did not recognize SLC2A9+ cells (THP-1 cells). In addition, as shown in FIG. 54D, the MSLN CAR T cells did not recognize GP2+ cells or the K562 negative control cells (FIG. 54B), but did bind to the positive control MSLN-expressing cells (FIG. 54C). Furthermore, no evidence of polyreactivity was observed with the MSLN CAR cells against A498 cells or H1975 cells (FIG. 55).

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

INFORMAL SEQUENCE LISTING

| SEQ ID NO | Name | Sequence |
|---|---|---|
| 1 | ALPG/P CDR H1 | GFSLTSY |
| 2 | ALPG/P CDR H2 | WEDGS |
| 3 | ALPG/P CDR H3 | PHYGSSYVGAMEY |
| 4 | ALPG/P CDR L1 | RASENTYSYVA |
| 5 | ALPG/P CDR L2 | NAKSLAS |
| 6 | ALPG/P CDR L3 | QHHYVSPWT |
| 7 | ALPG/P VH | QVQLQESGPGLVKPSETLSLTCTVSGFSLTSYGVSWIRQPAGKGLEWIGVIWEDGSTNYHSALISRVTMSVDTSKNQFSLKLSSVTAADTAVYYCARPHYGSSYVGAMEYWGAGTTVTVSS |
| 8 | ALPG/P VL | DIQMTQSPSSLSASVGDRVTITCRASENIYSYVAWYQQKPGKAPKLLIYNAKSLASGVPSRFSGSGSGTDFTLTISSLQPEDFATYYCQHHYVSPWTFGGGTKLEIK |
| 9 | primeR ALPG/P full binder ECD scFv | DIQMTQSPSSLSASVGDRVTITCRASENIYSYVAWYQQKPGKAPKLLIYNAKSLASGVPSRFSGSGSGTDFTLTISSLQPEDFATYYCQHHYVSPWTFGGGTKLEIKGGGSGGGGSGGGGSQVQLQESGPGLVKPSETLSLTCTVSGFSLTSYGVSWIRQPAGKGLEWIGVIWEDGSTNYHSALISRVTMSVDTSKNQFSLKLSSVTAADTAVYYCARPHYGSSYVGAMEYWGAGTTVTVSS |
| 10 | MSLN LG3 CDR H1 | GIDLSLY |
| 11 | MSLN LG3 CDR H2 | TDDGT |
| 12 | MSLN LG3 CDR H3 | ETPLSPVNY |
| 13 | MSLN LG3 VHH | EVQLVESGGGLVQPGGSLRLSCAASGIDLSLYRMRWYRQAPGKGLELVALITDDGTSYYADSVKGRFTISRDNAKNSVYLQMNSLRAEDTAVYYCNAETPLSPVNYWGQGTTVTVSS |
| 14 | MSLN LG1 CDR H1 | GGSISNSY |
| 15 | MSLN LG1 CDR H2 | YHSGN |

INFORMAL SEQUENCE LISTING

| SEQ ID NO | Name | Sequence |
|---|---|---|
| 16 | MSLN LG1 CDR H3 | QDGVGATTTEEY |
| 17 | MSLN LG1 VH | QLQLQESGPGLVKPSETLSLTCTVSGGSISNSYYWGWIRQPPGKGLEWIGSIYH SGNTYYNPSLKSRVTISVDTSKNQFSLKLSSVTAADTAVYYCVTQDGVGATTTE EYWGQGTLVTVSS |
| 18 | primeR CD8Hinge2 | TTTPAPRPPTPAPTIASQPLSLRPEAC |
| 19 | primeR TMD | FMYVAAAAFVLLFFVGCGVLLS |
| 20 | primeR STS | RKRRRQHGQLWFPEGFKVSEASKKKRREPLGEDSVGLKPLKNA |
| 21 | primeR HNF1a DBD | MVSKLSQLQTELLAALLESGLSKEALLQALGEPGPYLLAGEGPLDKGESCGGGR GELAELPNGLGETRGSEDETDDDGEDFTPPILKELENLSPEEAAHQKAVVETLL QEDPWRVAKMVKSYLQQHNIPQREVVDTTGLNQSHLSQHLNKGTPMKTQKRAAL YTWYVRKQREVAQQFTHAGQGGLIEEPTGDELPTKKGRRNRFKWGPASQQILFQ AYERQKNPSKEERETLVEECNRAECIQRGVSPSQAQGLGSNLVTEVRVYNWFAN RRKEEAFRHKLAM |
| 22 | primeR p65 TAD | DEFPTMVFPSGQISQASALAPAPPQVLPQAPAPAPAPAMVSALAÇAPAPVPVLA PGPPQAVAPPAPKPTQAGEGTLSEALLQLQFDDEDLGALLGNSTDPAVFTDLAS VDNSEFQQLLNQGIPVAPHTTEPMLMEYPEAITRLVTGAQRPPDPAPAPLGAPG LPNGLLSGDEDFSSIADMDFSALLSQISS |
| 23 | primeR HNF1a-p65 TAD | MVSKLSQLQTELLAALLESGLSKEALLQALGEPGPYLLAGEGPLDKGESCGGGR GELAELPNGLGETRGSEDETDDDGEDFTPPILKELENLSPEEAAHQKAVVETLL QEDPWRVAKMVKSYLQQHNIPQREVVDTTGLNQSHLSQHLNKGTPMKTQKRAAL YTWYVRKQREVAQQFTHAGQGGLIEEPTGDELPTKKGRRNRFKWGPASQQILFQ AYERQKNPSKEERETLVEECNRAECIQRGVSPSQAQGLGSNLVTEVRVYNWFAN RRKEEAFRHKLAMTCRDEFPTMVFPSGQISQASALAPAPPQVLPQAPAPAPAPA MVSALAQAPAPVPVLAPGPPQAVAPPAPKPTQAGEGTLSEALLQLQFDDEDLGA LLGNSTDPAVFTDLASVDNSEFQQLLNQGIPVAPHTTEPMLMEYPEAITRLVTG AQRPPDPAPAPLGAPGLPNGLLSGDEDFSSIADMDFSALLSQISS |
| 24 | ALPG primeR protein full sequence | DIQMTQSPSSLSASVGDRVTITCRASENIYSYVAWYQQKPGKAPKLLIYNAKSL ASGVPSRFSGSGSGTDFTLTISSLQPEDFATYYCQHHYVSPWTFGGGTKLEIKG GGGSGGGGSGGGGSQVQLQESGPGLVKPSETLSLTCTVSGFSLTSYGVSWIRQP AGKGLEWIGVIWEDGSTNYHSALISRVTMSVDTSKNQFSLKLSSVTAADTAVYY CARPHYGSSYVGAMEYWGAGTTVTVSSATTTPAPRPPTPAPTIASQPLSLRPEA CFMYVAAAAFVLLFFVGCGVLLSRKRRRQHGQLWFPEGFKVSEASKKKRREPLG EDSVGLKPLKNAMVSKLSQLQTELLAALLESGLSKEALLQALGEPGPYLLAGEG PLDKGESCGGGRGELAELPNGLGETRGSEDETDDDGEDFTPPILKELENLSPEE AAHQKAVVETLLQEDPWRVAKMVKSYLQQHNIPQREVVDTTGLNQSHLSQHLNK GTPMKTQKRAALYTWYVRKQREVAQQFTHAGQGGLIEEPTGDELPTKKGRRNRF KWGPASQQILFQAYERQKNPSKEERETLVEECNRAECIQRGVSPSQAQGLGSNL VTEVRVYNWFANRRKEEAFRHKLAMTCRDEFPTMVFPSGQISQASALAPAPPQV LPQAPAPAPAPAMVSALAQAPAPVPVLAPGPPQAVAPPAPKPTQAGEGTLSEAL LQLQFDDEDLGALLGNSTDPAVFTDLASVDNSEFQQLLNQGIPVAPHTTEPMLM EYPEAITRLVTGAQRPPDPAPAPLGAPGLPNGLLSGDEDFSSIADMDFSALLSQ ISS |
| 25 | ALPG primeR protein full sequence with CD8 signal sequence | MALPVTALLLPLALLLHAARPDIQMTQSPSSLSASVGDRVTITCRASENIYSYV AWYQQKPGKAPKLLIYNAKSLASGVPSRFSGSGSGTDFTLTISSLQPEDFATYY CQHHYVSPWTFGGGTKLEIKGGGGSGGGGSGGGGSQVQLQESGPGLVKPSETLS LTCTVSGFSLTSYGVSWIRQPAGKGLEWIGVIWEDGSTNYHSALISRVTMSVDT SKNQFSLKLSSVTAADTAVYYCARPHYGSSYVGAMEYWGAGTTVTVSSATTTPA PRPPTPAPTIASQPLSLRPEACFMYVAAAAFVLLFFVGCGVLLSRKRRRQHGQL WFPEGFKVSEASKKKRREPLGEDSVGLKPLKNAMVSKLSQLQTELLAALLESGL SKEALLQALGEPGPYLLAGEGPLDKGESCGGGRGELAELPNGLGETRGSEDETD DDGEDFTPPILKELENLSPEEAAHQKAVVETLLQEDPWRVAKMVKSYLQQHNIP QREVVDTTGLNQSHLSQHLNKGTPMKTQKRAALYTWYVRKQREVAQQFTHAGQG GLIEEPTGDELPTKKGRRNRFKWGPASQQILFQAYERQKNPSKEERETLVEECN RAECIQRGVSPSQAQGLGSNLVTEVRVYNWFANRRKEEAFRHKLAMTCRDEFPT MVFPSGQISQASALAPAPPQVLPQAPAPAPAPAMVSALAQAPAPVPVLAPGPPQ AVAPPAPKPTQAGEGTLSEALLQLQFDDEDLGALLGNSTDPAVFTDLASVDNSE FQQLLNQGIPVAPHTTEPMLMEYPEAITRLVTGAQRPPDPAPAPLGAPGLPNGL LSGDEDFSSIADMDFSALLSQISS |
| 26 | MSLN Hinge CD8a | TTTPAPRPPTPAPTIASQPLSLRPEACRPAAGGAVHTRGLDFACD |
| 27 | MSLN TMD CD8a | IYIWAPLAGTCGVLLLSLVITLYC |
| 28 | MSLN Co-stim 4-1BB | KRGRKKLLYIFKQPFMRPVQTTQEEDGCSCRFPEEEEGGCEL |

| SEQ ID NO | Name | Sequence |
|---|---|---|
| 29 | MSLN Activation CD3z | RVKFSRSADAPAYQQGQNQLYNELNLGRREEYDVLDKRRGRDPEMGGKPRRKNP QEGLYNELQKDKMAEAYSEIGMKGERRRGKGHDGLYQGLSTATKDTYDALHMQA LPPR |
| 30 | MSLN LG1 CAR protein full sequence | QLQLQESGPGLVKPSETLSLTCTVSGGSISNSYYWGWIRQPPKGLEWIGSIYH SGNTYYNPSLKSRVTISVDTSKNQFSLKLSSVTAADTAVYYCVTQDGVGATTTE EYWGQGTLVTVSSAAATTTPAPRPPTPAPTIASQPLSLRPEACRPAAGGAVHTR GLDFACDIYIWAPLAGTCGVLLLSLVITLYCKRGRKKLLYIFKQPFMRPVQTTQ EEDGCSCRFPEEEEGGCELRVKFSRSADAPAYQQGQNQLYNELNLGRREEYDVL DKRRGRDPEMGGKPRRKNPQEGLYNELQKDKMAEAYSEIGMKGERRRGKGHDGL YQGLSTATKDTYDALHMQALPPR |
| 31 | MSLN LG3 CAR protein full sequence | EVQLVESGGGLVQPGGSLRLSCAASGIDLSLYRMRWYRQAPGKGLELVALITDD GTSYYADSVKGRFTISRDNAKNSVYLQMNSLRAEDTAVYYCNAETPLSPVNYWG QGTTVTVSSAAATTTPAPRPPTPAPTIASQPLSLRPEACRPAAGGAVHTRGLDF ACDIYIWAPLAGTCGVLLLSLVITLYCKRGRKKLLYIFKQPFMRPVQTTQEEDG CSCRFPEEEEGGCELRVKFSRSADAPAYQQGQNQLYNELNLGRREEYDVLDKRR GRDPEMGGKPRRKNPQEGLYNELQKDKMAEAYSEIGMKGERRRGKGHDGLYQGL STATKDTYDALHMQALPPR |
| 32 | MSLN LG1 CAR protein full sequence with signal sequence | MALPVTALLLPLALLLHAARPQLQLQESGPGLVKPSETLSLTCTVSGGSISNSY YWGWIRQPPKGLEWIGSIYHSGNTYYNPSLKSRVTISVDTSKNQFSLKLSSVT AADTAVYYCVTQDGVGATTTEEYWGQGTLVTVSSAAATTTPAPRPPTPAPTIAS QPLSLRPEACRPAAGGAVHTRGLDFACDIYIWAPLAGTCGVLLLSLVITLYCKR GRKKLLYIFKQPFMRPVQTTQEEDGCSCRFPEEEEGGCELRVKFSRSADAPAYQ QGQNQLYNELNLGRREEYDVLDKRRGRDPEMGGKPRRKNPQEGLYNELQKDKMA EAYSEIGMKGERRRGKGHDGLYQGLSTATKDTYDALHMQALPPR |
| 33 | MSLN LG3 CAR protein full sequence with signal sequence | MALPVTALLLPLALLLHAARPEVQLVESGGGLVQPGGSLRLSCAASGIDLSLYR MRWYRQAPGKGLELVALITDDGTSYYADSVKGRFTISRDNAKNSVYLQMNSLRA EDTAVYYCNAETPLSPVNYWGQGTTVTVSSAAATTTPAPRPPTPAPTIASQPLS LRPEACRPAAGGAVHTRGLDFACDIYIWAPLAGTCGVLLLSLVITLYCKRGRKK LLYIFKQPFMRPVQTTQEEDGCSCRFPEEEEGGCELRVKFSRSADAPAYQQGQN QLYNELNLGRREEYDVLDKRRGRDPEMGGKPRRKNPQEGLYNELQKDKMAEAYS EIGMKGERRRGKGHDGLYQGLSTATKDTYDALHMQALPPR |
| 34 | CD8α signal sequence | MALPVTALLLPLALLLHAARP |
| 35 | Myc Tag | EQKLISEEDL |
| 36 | ALPG primeR nucleic acid full sequence | gacatacagatgacacagagccctagcagtctgagcgccagtgtgggcgataga gttactatcacttgtagagcatccgagaacatatacagttacgtggcctggtat cagcaaaaacctggcaaagctcccaagttattgatttacaatgctaagagcttg gcctctggggtgccatcgaggttcagcggtagcgggagcgggaccgacttcact ctgaccatctcgagtctccagccggaggactttgcgacatactattgtcaacac cattacgtatcaccctggaccttcggcggcgggactaagttagagatcaaggg ggaggaggatcaggcggcggtggatcaggaggaggaggtcacaagtgcagtta caggaatcagggcccggctggtgaagccaagtgaaaccctgagtctgacgtgc acggtttcaggattagcctcacttcctacggtgtctcttggattcggcagcca gccggcaaagggctcgagtggattggggtgatctgggaagatggctcaacaaac tatcattctgcactaatctctcgcgtgacaatgtcggtggacacgtccaagaat caattttcccttaaactgtcctccgtgaccgcagccgatacagcggtatattat tgcgcgcgacctcactacggatctagctatgtcggcgcgatggagtattgggc gctggcacaaccgtcaccgtttcttccgcaaccacgacgccagccgccgacca ccaacaccggcgcccaccatcgcgtcgcagccctgtccctgcgccctgaggcg tgcttcatgtacgtggcggcggccgcctttgtgcttctgttcttcgtgggctgc ggggtgctgctgtcccgtaaacgcagacgtcaacacggtcaactgtggtttcca gaaggttttaaggtctccgaagcaagtaagaagaaaagacgtgaaccactggga gaagatagcgtcggtctgaaaccactcaagaatgccatggtttctaaactgagc cagctgcagacggagctcctggcggccctgctggagtcagggctgagcaaagag gcactgctccaggcactgggcgagccggggccctacctcctggctggagaaggc cccctgacaaggggggagtcctgcggcggcggtcgagggggagctggctgagctg cccaatgggctgggggagactcggggctccgaggacgagaccgacgacgatggg gaagacttcacgccacccatcctcaaagagctggagaacctcagccctgaggag gcggccaccagaaagccgtggtggagacccttctgcaggaggacccgtggcgt gtggcgaagatggtcaagtcctacctgcagcagcacaacatcccacagcgggag gtggtcgataccactggcctcaaccagtcccacctgtcccaacacctcaacag ggcactccatgaagacgcagaagcgggccgccctgtacacctggtatgtccgc aagcagcgagaggtggcgcagcagttcacccatgcagggcagggagggctgatt gaagagcccacaggagatgagctaccaaccaagaaggggcggaggaaccgtttc aagtgggcccagcatcccagcagatcctgttccaggcctatgagaggcagaag aaccctagcaaggaggagcgagaaacgctagtggaggagtgcaataggggcggaa |

INFORMAL SEQUENCE LISTING

| SEQ ID NO | Name | Sequence |
|---|---|---|
| | | tgcatccagagaggtgtgtcaccatcacaagcacaaggtctgggctccaacctc<br>gtcacgaggtgcgtgtctacaactggtttgccaaccggcgcaaagaagaagcc<br>ttccggcacaagctggccatgacctgcagggatgagtttcccaccatggtgttt<br>ccttctgggcagatcagccaggcctcggcccttggccccggccccctccccaagtc<br>ctgcccaggctccagcccctgcccctgctccagccatggtatcagctctggcc<br>caggccccagccctgtcccagtcctagcccagccctcctcaagctgtggcc<br>ccacctgccccaagcccacccaagctggggaaggaacgctgtcagaggccctg<br>ctgcagctgcagtttgatgatgaagacttgggggccttgcttggcaacagcaca<br>gacccagctgtgttcacagacctggcatccgtcgacaactccgagtttcagcag<br>ctgctgaaccagggcatacctgtggcccccacacaactgagcccatgctgatg<br>gagtaccctgaggctataactcgcctagtgacaggggcccagaggccccccgac<br>ccagctcctgctccactggggccccggggctccccaatggcctcctttcagga<br>gatgaagacttctcctccattgcggacatggacttctcagccctgctgagtcag<br>atcagctcc |
| 37 | MSLN LG1 CAR nucleic acid full sequence | CAGTTGCAGTTACAGGAGAGCGGACCCGGTCTGGTTAAACCGTCTGAAACACTG<br>AGTTTGACATGTACAGTGTCCGGCGGCTCGATTTCAAACTCTTACTATTGGGGC<br>TGGATTAGGCAGCCTCCCGGGAAAGGGCTCGAGTGGATCGGGTCCATATATCAC<br>TCAGGAAATACCTACTACAACCCAAGTCTTAAGTCTAGAGTGACAATCAGTGTG<br>GATACGTCCAAGAATCAATTCTCCCTGAAGCTCTCAAGCGTGACCGCCGCCGAC<br>ACCGCAGTGTATTATTGCGTAACTCAAGACGGTGTGGGCGCTACCACTACCGAA<br>GAGTATTGGGGACAAGGCACTCTTGTCACAGTCTCCAGCGCGGCAGCAaccacg<br>acgccagcgccgcgaccaccaacaccggcgcccaccatcgcgtcgcagccactg<br>acgccagcgccgcgaccaccaacaccggcgcccaccatcgcgtcgcagccactg<br>gggctggacttcgcctgtgatatctacatctgggcgcccttggccgggacttgt<br>aaactcctgtatatattcaaacaaccatttatgagaccagtacaaactactcaa<br>gaagaggacggctgtagctgccgatttccagaagaagaagaaggaggatgtgaa<br>ctgagagtgaagttcagcaggagcgcagacgcccccgcgtaccagcagggccag<br>aaccagctctataacgagctcaatctaggacgaagagaggagtacgatgttttg<br>gacaagaggcgtggccgggaccctgagatgggggaaagccgagaaggaagaac<br>cctcaggaaggcctgtacaatgaactgcagaaagataagatggcggaggcctac<br>agtgagattgggatgaaaggcgagcgccggaggggcaaggggcacgatggcctt<br>taccagggtctcagtacagccaccaaggacacctacgacgcccttcacatgcag<br>gccctgccccctagg |
| 38 | MSLN LG3 CAR nucleic acid full sequence | GAAGTTCAGCTCGTGGAGAGTGGAGGCGGGTTAGTGCAACCCGGCGGGTCTTTG<br>AGATTGAGTTGTGCTGCGTCTGGAATTGACCTGTCCCTGTACCGAATGAGGTGG<br>TATCGACAAGCACCGGGCAAAGGGCTGGAACTCGTGGCTCTAATCACCGATGAC<br>GGTACAAGCTACTACGCAGACTCCGTCAAGGGCCGTTTCACAATATCACGCGAT<br>AACGCCAAAAATAGCGTGTATCTACAGATGAACAGTCTGCGAGCCGAGGATACC<br>GCCGTGTATTACTGCAATGCCGAGACCACCTCTGTCGCCAGTTAACTATTGGGT<br>CAGGGAACTACGGTAACTGTCTCAAGCGCGGCAGCAaccacgacgccagcgccg<br>cgaccaccaacaccggcgcccaccatcgcgtcgcagCCActgTCActgcgccca<br>GAAgcgtgccgccagcggcgggggcgcagtgcacacgaggggctggacttc<br>gcctgtgatatctacatctgggcgcccttggccgggacttgtgggtccttctc<br>ctgtcactggttatcaccctttactgcaaacggggcagaaagaaactcctgtat<br>atattcaaacaaccatttatgagaccagtacaaactactcaagaagaggacggc<br>tgtagctgccgatttccagaagaagaagaaggaggatgtgaactgAGAGTGAAG<br>TTCAGCAGGAGCGCAGACGCCCCCGCGTACCAGCAGGGCCAGAACCAGCTCTAT<br>AACGAGCTCAATCTAGGACGAAGAGAGGAGTACGATGTTTTGGACAAGAGGcgt<br>GGCCGGGACCCTGAGATGGGGGGAAAGCCGAGAAGGAAGAACCCTCAGGAAGGC<br>CTGTACAATGAACTGCAGAAAGATAAGATGGCGGAGGCCTACAGTGAGATTGGG<br>ATGAAAGGCGAGCGCCGGAGGGGCAAGGGGCACGATGGCCTTTACCAGGGTCTC<br>AGTACAGCCACCAAGGACACCTACGACGCCCTTCACATGCAGGCCCTGCCCCCT<br>AGG |
| 39 | FAS_mRNA NCBI NM_000043-6 | CTCTTCTCCCGCGGGTTGGTGGACCCGCTCAGTACGGAGTTGGGGAAGCTCTTT<br>CACTTCGGAGGATTGCTCAACAACCATGCTGGGCATCTGGACCCTCCTACCTCT<br>GGTTCTTACGTCTGTTGCTAGATTATCGTCCAAAAGTGTTAATGCCCAAGTGAC<br>TGACATCAACTCCAAGGGATTGGAATTGAGGAAGACTGTTACTACAGTTGAGAC<br>TCAGAACTTGGAAGGCCTGCATCATGATGGCCAATTCTGCCATAAGCCCTGTCC<br>TCCAGGTGAAAGGAAAGCTAGGGACTGCACAGTCAATGGGGATGAACCAGACTG<br>CGTGCCCTGCCAAGAAGGGAAGGAGTACACAGACAAAGCCCATTTTTCTTCCAA<br>ATGCAGAAGATGTAGATTGTGTGATGAAGGACATGGCTTAGAAGTGGAAATAAA<br>CTGCACCCGGACCCAGAATACCAAGTGCAGATGTAAACCAAACTTTTTTTGTAA<br>CTCTACTGTATGTGAACACTGTGACCCTTGCACCAAATGTGAACATGGAATCAT<br>CAAGGAATGCACACTCACCAGCAACACCAAGTGCAAAGAGGAAGGATCCAGATC<br>TAACTTGGGGTGGCTTTGTCTTCTTCTTTTGCCAATTCCACTAATTGTTTGGGT<br>GAAGAGAAAGGAAGTACAGAAAACATGCAGAAAGCACAGAAAGGAAAACCAAGG<br>TTCTCATGAATCTCCAACTTTAAATCCTGAAACAGTGGCAATAAATTTATCTGA<br>TGTTGACTTGAGTAAATATATCACCACTATTGCTGGAGTCATGACACTAAGTCA<br>AGTTAAAGGCTTTGTTCGAAAGAATGTGTCAATGAAGCCAAAATAGATGAGAT<br>CAAGAATGACAATGTCCAAGACACAGCAGAACAGAAAGTTCAACTGCTTCGTAA |

| SEQ ID NO | Name | Sequence |
|---|---|---|
| | | TTGGCATCAACTTCATGGAAAGAAAGAAGCGTATGACACATTGATTAAAGATCT<br>CAAAAAAGCCAATCTTTGTACTCTTGCAGAGAAAATTCAGACTATCATCCTCAA<br>GGACATTACTAGTGACTCAGAAAATTCAAACTTCAGAAATGAAATCCAAAGCTT<br>GGTCTAGAGTGAAAAACAACAAATTCAGTTCTGAGTATATGCAATTAGTGTTTG<br>AAAAGATTCTTAATAGCTGGCTGTAAATACTGCTTGGTTTTTTACTGGGTACAT<br>TTTATCATTTATTAGCGCTGAAGAGCCAACATATTTGTAGATTTTTAATATCTC<br>ATGATTCTGCCTCCAAGGATGTTTAAAATCTAGTTGGGAAAACAAACTTCATCA<br>AGAGTAAATGCAGTGGCATGCTAAGTACCCAAATAGGAGTGTATGCAGAGGATG<br>AAAGATTAAGATTATGCTCTGGCATCTAACATATGATTCTGTAGTATGAATGTA<br>ATCAGTGTATGTTAGTACAAATGTCTATCCACAGGCTAACCCCACTCTATGAAT<br>CAATAGAAGAAGCTATGACCTTTTGCTGAAATATCAGTTACTGAACAGGCAGGC<br>CACTTTGCCTCTAAATTACCTCTGATAATTCTAGAGATTTTACCATATTTCTAA<br>ACTTTGTTTATAACTCTGAGAAGATCATATTTATGTAAAGTATATGTATTTGAG<br>TGCAGAATTTAAATAAGGCTCTACCTCAAAGACCTTTGCACAGTTTATTGGTGT<br>CATATTATACAATATTTCAATTGTGAATTCACATAGAAAACATTAAATTATAAT<br>GTTTGACTATTATATATGTGTATGCATTTTGCTGGCTCAAAACTACCTACTTCT<br>TTCTCAGGCATCAAAAGCATTTTGAGCAGGAGAGTATTACTAGAGCTTTGCCAC<br>CTCTCCATTTTTGCCTTGGTGCTCATCTTAATGGCCTAATGCACCCCAAACAT<br>GGAAATATCACCAAAAATACTTAATAGTCCACCAAAAGGCAAGACTGCCCTTA<br>GAAATTCTAGCCTGGTTTGGAGATACTAACTGCTCTCAGAGAAAGTAGCTTTGT<br>GACATGTCATGAACCCATGTTTGCAATCAAAGATGATAAAATAGATTCTTATTT<br>TTCCCCCACCCCCGAAAATGTTCAATAATGTCCCATGTAAAACCTGCTACAAAT<br>GGCAGCTTATACATAGCAATGGTAAAATCATCATCTGGATTTAGGAATTGCTCT<br>TGTCATACCCCCAAGTTTCTAAGATTTAAGATTCTCCTTACTACTATCCTACGT<br>TTAAATATCTTTGAAAGTTTGTATTAAATGTGAATTTTAAGAAATAATATTTAT<br>ATTTCTGTAAATGTAAACTGTGAAGATAGTTATAAACTGAAGCAGATACCTGGA<br>ACCACCTAAAGAACTTCCATTTATGGAGGATTTTTTTGCCCCTTGTGTTTGGAA<br>TTATAAAAATATAGGTAAAAGTACGTAATTAAATAATGTTTTTGGTATTTCTGGT<br>TTTCTCTTTTTTGGTAGGGGCTTGCTTTTTGGTTTTGTCTTCCTTTTCTCTAAC<br>TGATGCTAAATATAACTTGTCTTTAATGCTTCTTGGATCCCTTAGAAGGTACTT<br>CCTTTTTAACCTTAACCCTTTTAGTAGTTAAATAATTATTTCCATAGGTTGCTA<br>TTGCCAAGAAGACCTCTTCCAAACAGCACATGATTATTCGTCAAACAGTTTCGT<br>ATTCCAGATACTGGAATGTGGATAAGAAAGTATACATTTCAAGGGGTAGGTTTT<br>ATTATTAAGAAAGCCAAATGAGGATTTTGAAATATTCTTTCCTGCATATTATCC<br>ATTCTAGCTACATGCTGGCCAGTGGGCCACCTTTCTTTTCTGCAATTTAATGCT<br>AGTAATATATTCTATTTAACCCATGAGTCCCAAAGTATTAGCATTTCAACATGT<br>AAGCATGTCGGTAAGATAGTTGTGCTTTGCTTAGGGTTCCCTCCTGTGTTATGG<br>TCTGGAAAGTGTCTTTAGGCAGAAAGTCTGAGTGATCACAGGGTTCACTCATTA<br>ATTTCTCTTTTCTGAGCCATCATAGTCTGTGCTGTCTGCTCTCCAGTTTTCTAT<br>TTCTAGACAGAAGTAGGGCAAGTTAGGTACTAGTTATTCTTCATGGCCAGAAGT<br>GCAAGTTCTACTTTGCAAGCAAGATTAAGTTAGAGAACACCCTATTCCACTTT<br>GGTGAACTCAGAGCAAGAACTTTGAGTTCCTTTGGGAGGAAGACAGTGGAGAAG<br>TCTTTGTACTTGGTGATGTGGTTTTTTTCCTCATGGCTTCACCTAGTGGCCCCA<br>AGCATGACTTCTCCCATGTCAATGAGCACAGCCACATTCCCGAGTTGAGGTGAC<br>CCCACGGTCCAGAATCATCCTCATTCTGGTGAACCTGGTTCTCTTTGTGGTGGG<br>CATACTGGGTAGGAGAATCACCCAAAGGTCACCCATGAGCTGCAGAAAAAAAGG<br>CTATTTGCAGAAGGAGCTCACAGATCACATTGAAAGCATTGCATATTCAAACAT<br>CTTGGTCTTCTTTATTGGCATGCCCACAGGGTCTTCTGACCTCTGATTAGATCA<br>GACACTTTTTAGATATTGAATCATCAGTTTCTGTACAACTATCTGAATAAGGTA<br>TATAATCAATGAAATTTAGAATTTTTTCTATGCTTACTCCTGATTGGTAATTT<br>GTTTGGGTTTAGAATTCTATACAAGGCCATTTGTAATTTTCCTCAGCACTTTAA<br>AAATATTAAACCATGTTTTCTTAA |
| 40 | PTPN2_mRNA NCBI<br>NM_002828-4 | GCATGCGCCGCAGCGCCAGCGCTCTCCCCGGATCGTGCGGGGCCTGAGCCTCTC<br>CGCCGGCGCAGGCTCTGCTCGCGCCAGCTCGCTCCCGCAGCCATGCCCACCACC<br>ATCGAGCGGGAGTTCGAAGAGTTGGATACTCAGCGTCGCTGGCAGCCGCTGTAC<br>TTGGAAATTCGAAATGAGTCCCATGACTATCCTCATAGAGTGGCCAAGTTTCCA<br>GAAAACAGAAATCGAAACAGATACAGAGATGTAAGCCCATATGATCACAGTCGT<br>GTTAAACTGCAAATGCTGAGAATGATTATATTAATGCCAGTTTAGTTGACATA<br>GAAGAGGCACAAAGGAGTTACATCTTAACACAGGGTCCACTTCCTAACACATGC<br>TGCCATTTCTGGCTTATGGTTTGGCAGCAGAAGACCAAAGCAGTTGTCATGCTG<br>AACCGCATTGTGGAGAAAGAATCGGTTAAATGTGCACAGTACTGGCCAACAGAT<br>GACCAAGAGATGCTGTTTAAAGAAACAGGATTCAGTGTGAAGCTCTTGTCAGAA<br>GATGTGAAGTCGTATTATACAGTACATCTACTACAATTAGAAAATATCAATAGT<br>GGTGAAACCAGAACAATATCTCACTTTCATTATACTACCTGGCCAGATTTTGGA<br>GTCCCTGAATCACCAGCTTCATTTCTCAATTTCTTGTTTAAAGTGAGAGAATCT<br>GGCTCCTTGAACCCTGACCATGGGCCTGCGGTGATCCACTGTAGTGCAGGCATT<br>GGGCGCTCTGGCACCTTCTCTCTGGTAGACACTTGTCTTGTTTTGATGGAAAAA<br>GGAGATGATATTAACATAAAACAAGTGTTACTGAACATGAGAAAATACCGAATG<br>GGTCTTATTCAGACCCCAGATCAACTGAGATTCTCATACATGGCTATAATAGAA<br>GGAGCAAAATGTATAAAGGGAGATTCTAGTATACAGAAACGATGGAAAGAACTT<br>TCTAAGGAAGACTTATCTCCTGCCTTTGATCATTCACCAAACAAAATAATGACT<br>GAAAAATACAATGGGAACAGAATAGGTCTAGAAGAAGAAAAACTGACAGGTGAC |

INFORMAL SEQUENCE LISTING

| SEQ ID NO | Name | Sequence |
|---|---|---|
| | | CGATGTACAGGACTTTCCTCTAAAATGCAAGATACAATGGAGGAGAACAGTGAG AGTGCTCTACGGAAACGTATTCGAGAGGACAGAAAGGCCACCACAGCTCAGAAG GTGCAGCAGATGAAACAGAGGCTAAATGAGAATGAACGAAAAAGAAAAAGGTGG TTATATTGGCAACCTATTCTCACTAAGATGGGGTTTATGTCAGTCATTTTGGTT GGCGCTTTTGTTGGCTGGACACTGTTTTTTCAGCAAAATGCCCTATAAACAATT AATTTTGCCCAGCAAGCTTCTGCACTAGTAACTGACAGTGCTACATTAATCATA GGGGTTTGTCTGCAGCAAACGCCTCATATCCCAAAAACGGTGCAGTAGAATAGA CATCAACCAGATAAGTGATATTTACAGTCACAAGCCCAACATCTCAGGACTCTT GACTGCAGGTTCCTCTGAACCCCAAACTGTAAATGGCTGTCTAAAATAAAGACA TTCATGTTTGTTAAAAACTGGTAAATTTTGCAACTGTATTCATACATGTCAAAC ACAGTATTTCACCTGACCAACATTGAGATATCCTTTATCACAGGATTTGTTTTT GGAGGCTATCTGGATTTTAACCTGCACTTGATATAAGCAATAAATATTGTGGTT TTATCTACGTTATTGGAAAGAAAATGACATTTAAATAATGTGTGTAATGTATAA TGTACTATTGACATGGGCATCAACACTTTTATTCTTAAGCATTTCAGGGTAAAT ATATTTTATAAGTATCTATTTAATCTTTTGTAGTTAACTGTACTTTTTAAGAGC TCAATTTGAAAAATCTGTTACTAAAAAAATAAATTGTATGTCGATTGAATTGTA CTGGATACATTTTCCATTTTTCTAAAGAGAAGTTTGATATGAGCAGTTAGAAGT TGGAATAAGCAATTTCTACTATATATTGCATTTCTTTTATGTTTTACAGTTTTC CCCATTTTAAAAGAAAAGCAAACAAAGAAACAAAAGTTTTTCCTAAAAATATC TTTGAAGGAAAATTCTCCTTACTGGGATAGTCAGGTAAACAGTTGGTCAAGACT TTGTAAAGAAATTGGTTTCTGTAAATCCCATTATTGATATGTTTATTTTTCATG AAAATTTCAATGTAGTTGGGGTAGATTATGATTTAGGAAGCAAAAGTAAGAAGC AGCATTTTATGATTCATAATTTCAGTTTACTAGACTGAAGTTTTGAAGTAAACA CTTTTCAGTTTCTTTCTACTTCAATAAATAGTATGATTATATGCAAACCTTACA TTGTCATTTTAACTTAATGAATATTTTTTAAAGCAAACTGTTTAATGAATTTAA CTGCTCATTTGAATGCTAGCTTTCCTCAGATTTCAACATTCCATTCAGTGTTTA ATTTGTCTTACTTAAACTTGAAATTGTTGTTACAAATTTAATTGCTAGGAGGCA TGGATAGCATACATTATTATGGATAGCATACCTTATTTCAGTGGTTTTCAAACT ATGCTCATTGGATGTCCAGGTGGGTCAAGAGGTTACTTTCAACCACAGCATCTC TGCCTTGTCTCTTTATATGCCACATAAGATTTCTGCATAAGGCTTAAGTATTTT AAAGGGGGCAGTTATCATTTAAAAACAGTTTGGTCGGGCGCGGTGGCTCATGCC TGTAATCCCAGCACTTTGGGAGGCTGAAGTGGGCAGATCACCTGAGGTCAGGAG TTCAAGACCAGCCTGGCCAACGTGGTGAAACACCATCTCTACTAAAAATGCAAA AATTAGCTGGGCATGGTGGAGGGCACCTGTAATCTCAGCTACTCAGGAGGCTGA GGTAGGAGAATTGCTTGAACCCAGGAGATGGAGGTTGCAGTGAGCTGAGATCAC GTCACTGCACTCCAGCCAGGGCGACAGAGCGAGACTCCATCTCAAAAGAAACAA ACAAAAAAAACAGTTTGGGCCGGGTGTGGTGGCTCACGCTTGTAATCCCAGCAC TTCGGAAGGCCAAGGCGGGCGGATCACGAGGTCAAGAGATGGAGACTGTCCTGG CCAACATGGTGAAATCCCTTCTTTACTAAAAATACAAAAATTATCTGGGCGTGG TGGTGCATGCCTGTAGTCCCAGCTCCTTGGGAGGCTAAGGCAGGAGAATCACTT GAACCCGGGAGGCAGAGGTTGCAGTGAGCCGAGATTGCACCACTGCACTCCAGC CTGGCAACAGAGCAAGACTTCGTCTCAAAAAAAAAAAAAAAAAAAGTTTGAAAA CCATTGGTATAGATAGATATTTTGAATTGATTTGCATAGTCTCCTTGAATGTGT TAAATTATGTTGAAAGTATGAAAGCAGGATGTAGGTGGTACTACATATTAAATA AGATTTATATAACA |
| 41 | TOX_mRNA NCBI NM_014729-3 | CTCTTCTTCTTAAACAAACCACAAACGGATGTGAGGGAAGGAAGGTGTTTCTTT TACTCCTGAGCCCAGACACCTCACTCTGTTCCGTCTAAGCTTGTTTTGCTGAAC ACTTTTTTTAAAAAAGGAAAAAGAAAAGGAGTTGCTTGATGTGAGAGTGAAAT GGACGTAAGATTTTATCCACCTCCAGCCCAGCCCGCCGCTGCGCCCGACGCTCC CTGTCTGGGACCTTCTCCCTGCCTGGACCCCTACTATTGCAACAAGTTTGACGG TGAGAACATGTATATGAGCATGACAGAGCCGAGCCAGGACTATGTGCCAGCCAG CCAGTCCTACCCTGGTCCAAGCCTGGAAAGTGAAGACTTCAACATTCCACCCAAT TACTCCTCCTTCCCTCCCAGACCACTCGCTGGTGCACCTGAATGAAGTTGAGTC TGGTTACCATTCTCTGTGTCACCCCATGAACCATAATGGCCTGCTACCATTTCA TCCACAAAACATGGACCTCCCTGAAATCACAGTCTCCAATATGCTGGGCCAGGA TGGAACACTGCTTTCTAATTCCATTTCTGTGATGCCAGATATACGAAACCCAGA AGGAACTCAGTACAGTTCCCATCCTCAGATGGCAGCCATGAGACCAAGGGGCCA GCCTGCAGACATCAGGCAGCAGCCAGGAATGATGCCACATGGCCAGCTGACTAC CATTAACCAGTCACAGCTAAGTGCTCAACTTGGTTTGAATATGGGAGGAAGCAA TGTTCCCCACAACTCACCATCTCCACCTGGAAGCAAGTCTGCAACTCCTTCACC ATCCAGTTCAGTGCATGAAGATGAAGGCGATGATACCTCTAAGCATCAATGGTGG AGAGAAGCGGCCTGCCTCTGATATGGGGAAAAAACCAAAAACTCCCAAAAAGAA GAAGAAGAAGGATCCCAATGAGCCCCAGAAGCCTGTGTCTGCCTATGCGTTATT CTTTCGTGATACTCAGGCCGCCATCAAGGGCAAAATCCAAACGCTACCTTTGG CGAAGTCTCTAAATTGTGGCTTCAATGTGGGACGGTTTAGGAGAAGAGCAAAA ACAGGTCTATAAAAGAAAACCGAGGCTGCGAAGAAGGAGTACCTGAAGCAACT CGCAGCATACAGAGCCAGCCTTGTATCCAAGAGCTACAGTGAACCTGTTGACGT GAAGACATCTCAACCTCCTCAGCTGATCAATTCGAAGCCGTCGGTGTTCCATGG GCCCAGCCAGGCCCACTCGGCCCTGTACCTAAGTTCCCACTATCACCAACAACC GGGAATGAATCCTCACCTAACTGCCATGCATCCTAGTCTCCCCAGGAACATAGC CCCCAAGCCGAATAACCAAATGCCAGTGACTGTCTCTATAGCAAACATGGCTGT GTCCCCTCCTCCTCCCCTCCAGATCAGCCCGCCTCTTCACCAGCATCTCAACAT |

INFORMAL SEQUENCE LISTING

| SEQ ID NO | Name | Sequence |
|---|---|---|
| | | GCAGCAGCACCAGCCGCTCACCATGCAGCAGCCCCTTGGGAACCAGCTCCCCAT
GCAGGTCCAGTCTGCCTTACACTCACCCACCATGCAGCAAGGATTTACTCTTCA
ACCCGACTATCAGACTATTATCAATCCTACATCTACAGCTGCACAAGTTGTCAC
CCAGGCAATGGAGTATGTGCGTTCGGGGTGCAGAAATCCTCCCCCACAACCGGT
GGACTGGAATAACGACTACTGCAGTAGTGGGGGCATGCAGAGGGACAAAGCACT
GTACCTTACTTGAGAATCTGAACACCTCTTCTTTCCACTGAGGAATTCAGGGAA
GTGTTTTCACCATGGATTGCTTTGTACAGTCAAGGCAGTTCTCCATTTTATTAG
AAAATACAAGTTGCTAAGCACTTAGGACCATTTGAGCTTGTGGGTCACCCACTC
TGGAAGAAATAGTCATGCTTCTTTATTATTTTTTTAATCCTTTATGGACATTGT
TTTTCTTCTTCCCTGAAGGAAATTTGGACCATTCAGATTTTATGTTGGTTTTTT
GCTGTGAAGTGCTGCGCTCTAGTAACTGCCTTAGCAACTGTAGATGTCTCGGAT
AAAAGTCCTGGATTTTCCATTGGTTTTCATAATGGGTGTTTATATGAAACTACT
AAAGACTTTTTAAATGGCTTGATGTAGCAGTCATAGCAAGTTTGTAAATAGCAT
CTATGTTACACTCTCCTAGAGTATAAAATGTGAATGTTTTTGTAGCTAAATTGT
AATTGAAACTGGCTCATTCCAGTTTATTGATTTCACAATAGGGGTTAAATTGGC
AAACATTCATATTTTTACTTCATTTTTAAAACAACTGACTGATAGTTCTATATT
TTCAAAATATTTGAAAATAAAAAGTATTCCCAAGTGATTTTAATTTAAAAACAA
ATTGGCTTTGTCTCATTGATCAGACAAAAAGAAACTAGTATTAAGGGAAGCGCA
AACACATTTATTTTGTACTGCAGAAAAATTGCTTTTTGTATCACTTTTTGTGT
AATGGTTAGTAAATGTCATTTAAGTCCTTTTATGTATAAAACTGCCAAATGCTT
ACCTGGTATTTTATTAGATGCAGAAACAGATTGGAAACAGCTAAATTACAACTT
TTACATATGGCTCTGTCTTATTGTTCTTCATACTGTGTCTGTATTTAATCTTT
TTTTATGGAACCTGTTGCGCCTATTTATGAAATAATAAATATAGGTGTTTGTAA
GTAAATTTGTTAGTATTTGAAAGAGGTTTCTTTGATGTTTTAACTTTTGCTGGC
AAAAAAAAAATTCACGCTTGGTGTGAATACTTTATTATTTAGTTTTTACAGTAAC
ATGAATAAAGCCAAACCTGCTTTTCATTTAGCAGCAAATTAAAGTAACCAGTCC
TTATTTCTGCATTTCTTTGGTTGATGCAAACAAAAAACTATTATATTTAAGAAC
TTTATTTCTTCATACGACATAACAGAATTGCCCTCCAAGTCACACAAGCTCCAA
GACTAAACAAACAGACAGGTCCTCTGTCTTAAAAAGGTTACTTCTTGGTTCTCA
GCTGGTTCTAGTCAATTCTGAACCACCACCCCCGCCCCCGCAAAAAGTAAA
AGTCAAACCAAACTTCCTCAAGCTGCATGCTTTTCACAAAATCCAGAAAGCATT
TAAGAATTGAACTAGGGGCTGGAAGAAGTGAAAGGGAAGCATCTAAAAATGAAA
GGTGAGTAACCAGATAGCAAAAGAAAAGGGAAAGCCATCCAAATTTGAAAGCTG
TTGATAGAAATTGAGATTCTTGCTGTCTTTTGTGCCTCTACAAGCTACTACTCA
TTCCAGAATTCCTGGGTCTTCAAGAGGATTCTTAAGGTACCAGAGATTTGCTA
GGGAACCAAAAGTGCTTGAGAATCTGCCTGAGGGCTTGCATAGCTTTCACATTA
AAAAAAGAAAAAGCTAGCAGATTTACTCCTTTTTAGGGGATCATATCAAGAAAG
TTAGTCTGGTTGGAAACCAAGAGAATGGCTGATGTCTCTTTCTTGGAATATGTG
AAATAAATTTAGCAGTTTAACTAAATACAAATATATGCATTGTGTAATCCACTC
AGAATTAAACAGACAAAAGGTATGCTTGCTTTGGAATGATTTTAGGCATTGTAC
AACCTTGAATCACTTGAGCATGTAATAACTAATAAATAATGCAGATCCATGTGA
TTATTAAAATGACTGTAGCTGAGAGCTCTAATTTTCCTGTCTTGAAACTGTATA
AGAACTCATGTGATTAAGTTCACAGTTTATTGTTTGTCTGTTTAGTATTTTAGA
AATATACCAGCACTACTAATTAACTAATGTCTTTTATTTATTATATTATGATAA
AGTAAAAATTTCACTTGCATTAAGTCTAAACTGAGAAGGTAATTACTGGGAGGA
GAATGAGCAGCTTTGACTTTGACAGGCGGTTTGTGCAGGAAAGCACAGTGCCGT
GTTGTTTACAGCTTTTCTAGAGCAGCTGTGCGACCAGGGTAGAGAGTGTTGAAA
TTCAATACCAAATACAGTAAAAACAAATGTAAATAAAAGAAAACACATCATCAA
TAAAACTGTTATTATGCGTGACCGTA |
| 42 | FAS_1 guide | TAGATTTTAAACATCCTTGGAG |
| 43 | FAS_1 guide | TAGATTTTAAACATCCTTGGAG |
| 44 | FAS_6 guide | TTACTCTTGATGAAGTTTGTTT |
| 45 | FAS_7 guide | TTGAACTTTCTGTTCTGCTGTG |
| 46 | FAS_8 guide | TTGTCTGTGTACTCCTTCCCTT |
| 47 | FAS_9 guide | TCTTTGATTGCAAACATGGGTT |
| 48 | FAS_10 guide | TTGATCTCATCTATTTTGGCTT |
| 49 | FAS_11 guide | TTAAGAATCTTTTCAAACACTA |
| 50 | FAS_12 guide | TTCTATTGATTCATAGAGTGGG |
| 51 | FAS_13 guide | TAATCTTAATCTTTCATCCTCT |
| 52 | FAS_14 guide | TTAACTTGACTTAGTGTCATGA |
| 53 | FAS_15 guide | TTACATAAATATGATCTTCTCA |

| | | INFORMAL SEQUENCE LISTING |
|---|---|---|
| SEQ ID NO | Name | Sequence |
| 54 | FAS_16 guide | TACATAAATATGATCTTCTCAG |
| 55 | FAS_18 guide | TAAAAATCTACAAATATGTTGG |
| 56 | FAS_19 guide | TTTGGTTTACATCTGCACTTGG |
| 57 | FAS_1 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGATCCAAGGATGTTTAAAATCTATAGTGAAGCCAC<br>AGATGTATAGATTTTAAACATCCTTGGAGTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 58 | FAS_1 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGATCCAAGGATGTTTAAAATCTATAGTGAAGCCAC<br>AGATGTATAGATTTTAAACATCCTTGGAGTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 59 | FAS_6 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCAACAAACTTCATCAAGAGTAATAGTGAAGCCAC<br>AGATGTATTACTCTTGATGAAGTTTGTTTTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 60 | FAS_7 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGAACAGCAGAACAGAAAGTTCAATAGTGAAGCCAC<br>AGATGTATTGAACTTTCTGTTCTGCTGTGTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 61 | FAS_8 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCAGGGAAGGAGTACACAGACAATAGTGAAGCCAC<br>AGATGTATTGTCTGTGTACTCCTTCCCTTTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 62 | FAS_9 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCACCCATGTTTGCAATCAAAGATAGTGAAGCCAC<br>AGATGTATCTTTGATTGCAAACATGGGTTTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 63 | FAS_10 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCAGCCAAAATAGATGAGATCAATAGTGAAGCCAC<br>AGATGTATTGATCTCATCTATTTTGGCTTTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 64 | FAS_11 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCAGTGTTTGAAAAGATTCTTAATAGTGAAGCCAC<br>AGATGTATTAAGAATCTTTTCAAACACTATGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 65 | FAS_12 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGACCACTCTATGAATCAATAGAATAGTGAAGCCAC<br>AGATGTATTCTATTGATTCATAGAGTGGGTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 66 | FAS_13 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCGAGGATGAAAGATTAAGATTATAGTGAAGCCAC |

| SEQ ID NO | Name | Sequence |
|---|---|---|
| | | AGATGTATAATCTTAATCTTTCATCCTCTTGCCTACTGCCTCGGACTTCAAGGG GCTAGAATTCGAGCAATTATCTTGTTTACTAAAACTGAATACCTTGCTATCTCT TTGATACATTTTTACAAAGCTGAATTAAAATGGTATAAATTAAATCACTTT |
| 67 | FAS_14 full | TGTTTGAATGAGGCTTCAGTACTTTACAGAATCGTTGCCTGCACATCTTGGAAA CACTTGCTGGGATTACTTCGACTTCTTAACCCAACAGAAGGCTCGAGAAGGTAT ATTGCTGTTGACAGTGAGCGCCATGACACTAAGTCAAGTTAATAGTGAAGCCAC AGATGTATTAACTTGACTTAGTGTCATGATGCCTACTGCCTCGGACTTCAAGGG GCTAGAATTCGAGCAATTATCTTGTTTACTAAAACTGAATACCTTGCTATCTCT TTGATACATTTTTACAAAGCTGAATTAAAATGGTATAAATTAAATCACTTT |
| 68 | FAS_15 full | TGTTTGAATGAGGCTTCAGTACTTTACAGAATCGTTGCCTGCACATCTTGGAAA CACTTGCTGGGATTACTTCGACTTCTTAACCCAACAGAAGGCTCGAGAAGGTAT ATTGCTGTTGACAGTGAGCGCGAGAAGATCATATTTATGTAATAGTGAAGCCAC AGATGTATTACATAAATATGATCTTCTCATGCCTACTGCCTCGGACTTCAAGGG GCTAGAATTCGAGCAATTATCTTGTTTACTAAAACTGAATACCTTGCTATCTCT TTGATACATTTTTACAAAGCTGAATTAAAATGGTATAAATTAAATCACTTT |
| 69 | FAS_16 full | TGTTTGAATGAGGCTTCAGTACTTTACAGAATCGTTGCCTGCACATCTTGGAAA CACTTGCTGGGATTACTTCGACTTCTTAACCCAACAGAAGGCTCGAGAAGGTAT ATTGCTGTTGACAGTGAGCGATGAGAAGATCATATTTATGTATAGTGAAGCCAC AGATGTATACATAAATATGATCTTCAGTGCCTACTGCCTCGGACTTCAAGGG GCTAGAATTCGAGCAATTATCTTGTTTACTAAAACTGAATACCTTGCTATCTCT TTGATACATTTTTACAAAGCTGAATTAAAATGGTATAAATTAAATCACTTT |
| 70 | FAS_18 full | TGTTTGAATGAGGCTTCAGTACTTTACAGAATCGTTGCCTGCACATCTTGGAAA CACTTGCTGGGATTACTTCGACTTCTTAACCCAACAGAAGGCTCGAGAAGGTAT ATTGCTGTTGACAGTGAGCGACAACATATTTGTAGATTTTTATAGTGAAGCCAC AGATGTATAAAAATCTACAAATATGTTGGTGCCTACTGCCTCGGACTTCAAGGG GCTAGAATTCGAGCAATTATCTTGTTTACTAAAACTGAATACCTTGCTATCTCT TTGATACATTTTTACAAAGCTGAATTAAAATGGTATAAATTAAATCACTTT |
| 71 | FAS_19 full | TGTTTGAATGAGGCTTCAGTACTTTACAGAATCGTTGCCTGCACATCTTGGAAA |
| 72 | PTPN2_1 guide | CACTTGCTGGGATTACTTCGACTTCTTAACCCAACAGAAGGCTCGAGAAGGTAT ATTGCTGTTGACAGTGAGCGACAAGTGCAGATGTAAACCAAATAGTGAAGCCAC AGATGTATTTGGTTTACATCTGCACTTGGTGCCTACTGCCTCGGACTTCAAGGG GCTAGAATTCGAGCAATTATCTTGTTTACTAAAACTGAATACCTTGCTATCTCT TTGATACATTTTTACAAAGCTGAATTAAAATGGTATAAATTAAATCACTTT TATAATACGACTTCACATCTTC |
| 73 | PTPN2_2 guide | TAGAAAGTTCTTTCCATCGTTT |
| 74 | PTPN2_4 guide | TTCTATGTCAACTAAACTGGCA |
| 75 | PTPN2_5 guide | TTAAACAGCATCTCTTGGTCAT |
| 76 | PTPN2_7 guide | TCGAATTTCCAAGTACAGCGGC |
| 77 | PTPN2_8 guide | TTAGAAAGTTCTTTCCATCGTT |
| 78 | PTPN2_9 guide | TAGATGTACTGTATAATACGAC |
| 79 | PTPN2_10 guide | TCTGTATACTAGAATCTCCCTT |
| 80 | PTPN2_11 guide | TTTTATGTTAATATCATCTCCT |
| 81 | PTPN2_13 guide | TGAGAATCTCAGTTGATCTGGG |
| 82 | PTPN2_14 guide | TCTGACAAGAGCTTCACACTGA |
| 83 | PTPN2_15 guide | TTCTATTATAGCCATGTATGAG |
| 84 | PTPN2_16 guide | TGATATTTCTAATTGTAGTAG |
| 85 | PTPN2_1 full | TGTTTGAATGAGGCTTCAGTACTTTACAGAATCGTTGCCTGCACATCTTGGAAA CACTTGCTGGGATTACTTCGACTTCTTAACCCAACAGAAGGCTCGAGAAGGTAT ATTGCTGTTGACAGTGAGCGAAAGATGTGAAGTCGTATTATATAGTGAAGCCAC AGATGTATATAATACGACTTCACATCTTCTGCCTACTGCCTCGGACTTCAAGGG GCTAGAATTCGAGCAATTATCTTGTTTACTAAAACTGAATACCTTGCTATCTCT TTGATACATTTTTACAAAGCTGAATTAAAATGGTATAAATTAAATCACTTT |

-continued

INFORMAL SEQUENCE LISTING

| SEQ ID NO | Name | Sequence |
|---|---|---|
| 86 | PTPN2_2 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCAACGATGGAAAGAACTTTCTATAGTGAAGCCAC<br>AGATGTATAGAAAGTTCTTTCCATCGTTTTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 87 | PTPN2_4 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCGCCAGTTTAGTTGACATAGAATAGTGAAGCCAC<br>AGATGTATTCTATGTCAACTAAACTGGCATGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 88 | PTPN2_5 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCTGACCAAGAGATGCTGTTTAATAGTGAAGCCAC<br>AGATGTATTAAACAGCATCTCTTGGTCATTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 89 | PTPN2_7 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGACCGCTGTACTTGGAAATTCGATAGTGAAGCCAC<br>AGATGTATCGAATTTCCAAGTACAGCGGCTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 90 | PTPN2_8 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCACGATGGAAAGAACTTTCTAATAGTGAAGCCAC<br>AGATGTATTAGAAAGTTCTTTCCATCGTTTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 91 | PTPN2_9 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGATCGTATTATACAGTACATCTATAGTGAAGCCAC<br>AGATGTATAGATGTACTGTATAATACGACTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 92 | PTPN2_10 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCAGGGAGATTCTAGTATACAGATAGTGAAGCCAC<br>AGATGTATCTGTATACTAGAATCTCCCTTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 93 | PTPN2_11 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCGGAGATGATATTAACATAAAATAGTGAAGCCAC<br>AGATGTATTTTATGTTAATATCATCTCCTTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 94 | PTPN2_13 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGACCAGATCAACTGAGATTCTCATAGTGAAGCCAC<br>AGATGTATGAGAATCTCAGTTGATCTGGGTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 95 | PTPN2_14 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCCAGTGTGAAGCTCTTGTCAGATAGTGAAGCCAC<br>AGATGTATCTGACAAGAGCTTCACACTGATGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 96 | PTPN2_15 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT |

INFORMAL SEQUENCE LISTING

| SEQ ID NO | Name | Sequence |
|---|---|---|
|  |  | ATTGCTGTTGACAGTGAGCGATCATACATGGCTATAATAGAATAGTGAAGCCAC<br>AGATGTATTCTATTATAGCCATGTATGAGTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 97 | PTPN2_16 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGATACTACAATTAGAAAATATCATAGTGAAGCCAC<br>AGATGTATGATATTTTCTAATTGTAGTAGTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 98 | TOX_2 guide | TAAAGTATTCACACCAAGCGTG |
| 99 | TOX_4 guide | TATGACTGCTACATCAAGCCAT |
| 100 | TOX_5 guide | TTAAATGACATTTACTAACCAT |
| 101 | TOX_6 guide | TTAAATTAAAATCACTTGGGAA |
| 102 | TOX_7 guide | TTTGCTCTTCTCCTAAACCGTC |
| 103 | TOX_8 guide | TTAGTTAATTAGTAGTGCTGGT |
| 104 | TOX_9 guide | TAGGTGAGGATTCATTCCCGGT |
| 105 | TOX_10 guide | TTAGTCTTGGAGCTTGTGTGAC |
| 106 | TOX_11 guide | TTTAAATTAAAATCACTTGGGA |
| 107 | TOX_12 guide | TTTTAAATTAAAATCACTTGGG |
| 108 | TOX_13 guide | TTCAATTACAATTTAGCTACAA |
| 109 | TOX_15 guide | TTTATTATTTCATAAATAGGCG |
| 110 | TOX_16 guide | TTACAAACTTGCTATGACTGCT |
| 111 | TOX_17 guide | TATTATTTCATAAATAGGCGCA |
| 112 | TOX_2 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGAACGCTTGGTGTGAATACTTTATAGTGAAGCCAC<br>AGATGTATAAAGTATTCACACCAAGCGTGTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 113 | TOX_4 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCTGGCTTGATGTAGCAGTCATATAGTGAAGCCAC<br>AGATGTATATGACTGCTACATCAAGCCATTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 114 | TOX_5 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCTGGTTAGTAAATGTCATTTAATAGTGAAGCCAC<br>AGATGTATTAAATGACATTTACTAACCATTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 115 | TOX_6 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCTCCCAAGTGATTTTAATTTAATAGTGAAGCCAC<br>AGATGTATTAAATTAAAATCACTTGGGAATGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 116 | TOX_7 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGAACGGTTTAGGAGAAGAGCAAATAGTGAAGCCAC<br>AGATGTATTTGCTCTTCTCCTAAACCGTCTGCCTACTGCCTCGGACTTCAAGGG |

-continued

INFORMAL SEQUENCE LISTING

| SEQ ID NO | Name | Sequence |
|---|---|---|
| | | GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 117 | TOX_8 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCCCAGCACTACTAATTAACTAATAGTGAAGCCAC<br>AGATGTATTAGTTAATTAGTAGTGCTGGTTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 118 | TOX_9 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCCCGGGAATGAATCCTCACCTATAGTGAAGCCAC<br>AGATGTATAGGTGAGGATTCATTCCCGGTTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 119 | TOX_10 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGATCACACAAGCTCCAAGACTAATAGTGAAGCCAC<br>AGATGTATTAGTCTTGGAGCTTGTGTGACTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 120 | TOX_11 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCCCCAAGTGATTTTAATTTAAATAGTGAAGCCAC<br>AGATGTATTTAAATTAAAATCACTTGGGATGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 121 | TOX_12 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGACCAAGTGATTTTAATTTAAATAGTGAAGCCAC<br>AGATGTATTTTAAATTAAAATCACTTGGGTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 122 | TOX_13 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCTGTAGCTAAATTGTAATTGAATAGTGAAGCCAC<br>AGATGTATTCAATTACAATTTAGCTACAATGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 123 | TOX_15 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGAGCCTATTTATGAAATAATAAATAGTGAAGCCAC<br>AGATGTATTTATTATTTCATAAATAGGCGTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 124 | TOX_16 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCGCAGTCATAGCAAGTTTGTAATAGTGAAGCCAC<br>AGATGTATTACAAACTTGCTATGACTGCTTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 125 | TOX_17 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCGCGCCTATTTATGAAATAATATAGTGAAGCCAC<br>AGATGTATATTATTTCATAAATAGGCGCATGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 126 | ZC3H12A_1 guide | TTATTAAGAAGCATCTTGCTTA |
| 127 | ZC3H12A_2 guide | TTGCTTACTGACATGAAGCCAC |
| 128 | ZC3H12A_3 guide | TTGTAGGAGAGGATCTCGGCAG |
| 129 | ZC3H12A_5 guide | TGTATCAACAGGGTGATCGCTT |

| INFORMAL SEQUENCE LISTING | | |
|---|---|---|
| SEQ ID NO | Name | Sequence |
| 130 | ZC3H12A_1 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCAAGCAAGATGCTTCTTAATAATAGTGAAGCCAC<br>AGATGTATTATTAAGAAGCATCTTGCTTATGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 131 | ZC3H12A_2 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGATGGCTTCATGTCAGTAAGCAATAGTGAAGCCAC<br>AGATGTATTGCTTACTGACATGAAGCCACTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 132 | ZC3H12A_3 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGATGCCGAGATCCTCTCCTACAATAGTGAAGCCAC<br>AGATGTATTGTAGGAGAGGATCTCGGCAGTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 133 | ZC3H12A_5 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCAGCGATCACCCTGTTGATACATAGTGAAGCCAC<br>AGATGTATGTATCAACAGGGTGATCGCTTTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 134 | NR4A1_4 guide | TCTGTCATTTGTCTTCTTCCTA |
| 135 | NR4A1_7 guide | TTGAGGTAGAAGATGCGCTGCA |
| 136 | NR4A1_9 guide | TCCTCGAACTTGAAGGAGGCAG |
| 137 | NR4A1_10 guide | TTTTCAGTTCCAACTACATGTC |
| 138 | NR4A1_11 guide | TTACAAAAAACATAAAGGCCGG |
| 139 | NR4A1_12 guide | TATAAATGTCAGAATCTGTCAT |
| 140 | NR4A1_13 guide | TATATTAATCAGAAAAGTCACA |
| 141 | NR4A1_14 guide | ATATTAATCAGAAAAGTCACAT |
| 142 | NR4A1_15 guide | TAATCAGAAAAGTCACATACTA |
| 143 | NR4A1_17 guide | TATTAATCAGAAAAGTCACATA |
| 144 | NR4A1_19 guide | TTAATCAGAAAAGTCACATACT |
| 145 | NR4A1_4 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCAGGAAGAAGACAAATGACAGATAGTGAAGCCAC<br>AGATGTATCTGTCATTTGTCTTCTTCCTATGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 146 | NR4A1_7 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCGCAGCGCATCTTCTACCTCAATAGTGAAGCCAC<br>AGATGTATTGAGGTAGAAGATGCGCTGCATGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 147 | NR4A1_9 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGATGCCTCCTTCAAGTTCGAGGATAGTGAAGCCAC<br>AGATGTATCCTCGAACTTGAAGGAGGCAGTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |

INFORMAL SEQUENCE LISTING

| SEQ ID NO | Name | Sequence |
|---|---|---|
| 148 | NR4A1_10 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGAACATGTAGTTGGAACTGAAAATAGTGAAGCCAC<br>AGATGTATTTTCAGTTCCAACTACATGTCTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 149 | NR4A1_11 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGACGGCCTTTATGTTTTTTGTAATAGTGAAGCCAC<br>AGATGTATTACAAAAAACATAAAGGCCGGTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 150 | NR4A1_12 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCTGACAGATTCTGACATTTATATAGTGAAGCCAC<br>AGATGTATATAAATGTCAGAATCTGTCATTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 151 | NR4A1_13 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCGTGACTTTTCTGATTAATATATAGTGAAGCCAC<br>AGATGTATATATTAATCAGAAAAGTCACATGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 152 | NR4A1_14 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCTGTGACTTTTCTGATTAATATTAGTGAAGCCAC<br>AGATGTAATATTAATCAGAAAAGTCACATTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 153 | NR4A1_15 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCAGTATGTGACTTTTCTGATTATAGTGAAGCCAC<br>AGATGTATAATCAGAAAGTCACATACTATGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 154 | NR4A1_17 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCATGTGACTTTTCTGATTAATATAGTGAAGCCAC<br>AGATGTATATTAATCAGAAAAGTCACATATGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 155 | NR4A1_19 full | TGTTTGAATGAGGCTTCAGTACTTTACAGAATCGTTGCCTGCACATCTTGGAAA<br>CACTTGCTGGGATTACTTCGACTTCTTAACCCAACAGAAGGCTCGAGAAGGTAT<br>ATTGCTGTTGACAGTGAGCGCGTATGTGACTTTTCTGATTAATAGTGAAGCCAC<br>AGATGTATTAATCAGAAAAGTCACATACTTGCCTACTGCCTCGGACTTCAAGGG<br>GCTAGAATTCGAGCAATTATCTTGTTTACTAAAACTGAATACCTTGCTATCTCT<br>TTGATACATTTTTACAAAGCTGAATTAAAATGGTATAAATTAAATCACTTT |
| 156 | FAS_11 miR3G-NR4A1_19 miRE Module | GTAAGTCGACTCGTTGGATCCCCACTACCCGGATCAACGCCCTAGGTTTATGTT<br>TGGATGAACTGACATACGCGTATCCGTCTTAAGAATCTTTTCAAACACTAGTAG<br>TGAAATATATATTAAACTAGTGTTTGAAAAGATTCTTATTCGGTAACGCGGAA<br>TTCGCAACTATTTTATCAATTTTTTGCGTCGACACTTCAAGGGGCTTGCGGCCG<br>CAACCATCTCCATGGCTGTTTGAATGAGGCTTCAGTACTTTACAGAATCGTTGC<br>CTGCACATCTTGGAAACACTTGCTGGGATTACTTCGACTTCTTAACCCAACAGA<br>AGGCTCGAGAAGGTATATTGCTGTTGACAGTGAGCGCGTATGTGACTTTTCTGA<br>TTAATAGTGAAGCCACAGATGTATTAATCAGAAAAGTCACATACTTGCCTACTG<br>CCTCGGACTTCAAGGGGCTAGAATTCGAGCAATTATCTTGTTTACTAAAACTGA<br>ATACCTTGCTATCTCTTTGATACATTTTTACAAAGCTGAATTAAAATGGTATAA<br>ATTAAATCACTTTTTCATCTGACCAGTAGTGGACTAGTGTGACGCTGCTGACCC<br>CTTTCTTTCCCTTCTACAG |

INFORMAL SEQUENCE LISTING

| SEQ ID NO | Name | Sequence |
|---|---|---|
| 157 | FAS_11 miR3G-PTPN2_14 miRE Module | GTAAGTCGACTCGTTGGATCCCCACTACCCGGATCAACGCCCTAGGTTTATGTT<br>TGGATGAACTGACATACGCGTATCCGTCTTAAGAATCTTTTCAAACACTAGTAG<br>TGAAATATATATTAAACTAGTGTTTGAAAAGATTCTTATTACGGTAACGCGGAA<br>TTCGCAACTATTTTATCAATTTTTTGCGTCGACACTTCAAGGGGCTTGCGGCCG<br>CAACCATCTCCATGGCTGTTTGAATGAGGCTTCAGTACTTTACAGAATCGTTGC<br>CTGCACATCTTGGAAACACTTGCTGGGATTACTTCGACTTCTTAACCCAACAGA<br>AGGCTCGAGAAGGTATATTGCTGTTGACAGTGAGCGCCAGTGTGAAGCTCTTGT<br>CAGATAGTGAAGCCACAGATGTATCTGACAAGAGCTTCACACTGATGCCTACTG<br>CCTCGGACTTCAAGGGGCTAGAATTCGAGCAATTATCTTGTTTACTAAAACTGA<br>ATACCTTGCTATCTCTTTGATACATTTTTACAAAGCTGAATTAAAATGGTATAA<br>ATTAAATCACTTTTTCATCTGACCAGTAGTGGACTAGTGTGACGCTGCTGACCC<br>CTTTCTTTCCCTTCTACAG |
| 158 | FAS_11 miR3G-TOX_4 miRE Module | GTAAGTCGACTCGTTGGATCCCCACTACCCGGATCAACGCCCTAGGTTTATGTT<br>TGGATGAACTGACATACGCGTATCCGTCTTAAGAATCTTTTCAAACACTAGTAG<br>TGAAATATATATTAAACTAGTGTTTGAAAAGATTCTTATTACGGTAACGCGGAA<br>TTCGCAACTATTTTATCAATTTTTTGCGTCGACACTTCAAGGGGCTTGCGGCCG<br>CAACCATCTCCATGGCTGTTTGAATGAGGCTTCAGTACTTTACAGAATCGTTGC<br>CTGCACATCTTGGAAACACTTGCTGGGATTACTTCGACTTCTTAACCCAACAGA<br>AGGCTCGAGAAGGTATATTGCTGTTGACAGTGAGCGCTGGCTTGATGTAGCAGT<br>CATATAGTGAAGCCACAGATGTATATGACTGCTACATCAAGCCATTGCCTACTG<br>CCTCGGACTTCAAGGGGCTAGAATTCGAGCAATTATCTTGTTTACTAAAACTGA<br>ATACCTTGCTATCTCTTTGATACATTTTTACAAAGCTGAATTAAAATGGTATAA<br>ATTAAATCACTTTTTCATCTGACCAGTAGTGGACTAGTGTGACGCTGCTGACCC<br>CTTTCTTTCCCTTCTACAG |
| 159 | PTPN2_14 miR3G-TOX_4 miRE Module | GTAAGTCGACTCGTTGGATCCCCACTACCCGGATCAACGCCCTAGGTTTATGTT<br>TGGATGAACTGACATACGCGTATCCGTCTCTGACAAGAGCTTCACACTGAGTAG<br>TGAAATATATATTAAACTCAGTGTGAAGCTCTTGTCAGTTACGGTAACGCGGAA<br>TTCGCAACTATTTTATCAATTTTTTGCGTCGACACTTCAAGGGGCTTGCGGCCG<br>CAACCATCTCCATGGCTGTTTGAATGAGGCTTCAGTACTTTACAGAATCGTTGC<br>CTGCACATCTTGGAAACACTTGCTGGGATTACTTCGACTTCTTAACCCAACAGA<br>AGGCTCGAGAAGGTATATTGCTGTTGACAGTGAGCGCTGGCTTGATGTAGCAGT<br>CATATAGTGAAGCCACAGATGTATATGACTGCTACATCAAGCCATTGCCTACTG<br>CCTCGGACTTCAAGGGGCTAGAATTCGAGCAATTATCTTGTTTACTAAAACTGA<br>ATACCTTGCTATCTCTTTGATACATTTTTACAAAGCTGAATTAAAATGGTATAA<br>ATTAAATCACTTTTTCATCTGACCAGTAGTGGACTAGTGTGACGCTGCTGACCC<br>CTTTCTTTCCCTTCTACAG |
| 160 | ZC3H12A_12 miR3G-PTPN2_14 miRE Module | GTAAGTCGACTCGTTGGATCCCCACTACCCGGATCAACGCCCTAGGTTTATGTT<br>TGGATGAACTGACATACGCGTATCCGTCTTAAGAAGCATCTTGCTTACTGGTAG<br>TGAAATATATATTAAACCAGTAAGCAAGATGCTTCTTATTCGGTAACGCGGAA<br>TTCGCAACTATTTTATCAATTTTTTGCGTCGACACTTCAAGGGGCTTGCGGCCG<br>CAACCATCTCCATGGCTGTTTGAATGAGGCTTCAGTACTTTACAGAATCGTTGC<br>CTGCACATCTTGGAAACACTTGCTGGGATTACTTCGACTTCTTAACCCAACAGA<br>AGGCTCGAGAAGGTATATTGCTGTTGACAGTGAGCGCCAGTGTGAAGCTCTTGT<br>CAGATAGTGAAGCCACAGATGTATCTGACAAGAGCTTCACACTGATGCCTACTG<br>CCTCGGACTTCAAGGGGCTAGAATTCGAGCAATTATCTTGTTTACTAAAACTGA<br>ATACCTTGCTATCTCTTTGATACATTTTTACAAAGCTGAATTAAAATGGTATAA<br>ATTAAATCACTTTTTCATCTGACCAGTAGTGGACTAGTGTGACGCTGCTGACCC<br>CTTTCTTTCCCTTCTACAG |
| 161 | FAS_11 miR3G-NR4A1_12 miRE Module | GTAAGTCGACTCGTTGGATCCCCACTACCCGGATCAACGCCCTAGGTTTATGTT<br>TGGATGAACTGACATACGCGTATCCGTCTTAAGAATCTTTTCAAACACTAGTAG<br>TGAAATATATATTAAACTAGTGTTTGAAAAGATTCTTATTACGGTAACGCGGAA<br>TTCGCAACTATTTTATCAATTTTTTGCGTCGACACTTCAAGGGGCTTGCGGCCG<br>CAACCATCTCCATGGCTGTTTGAATGAGGCTTCAGTACTTTACAGAATCGTTGC<br>CTGCACATCTTGGAAACACTTGCTGGGATTACTTCGACTTCTTAACCCAACAGA<br>AGGCTCGAGAAGGTATATTGCTGTTGACAGTGAGCGCTGACAGATTCTGACATT<br>TATATAGTGAAGCCACAGATGTATATAAATGTCAGAATCTGTCATTGCCTACTG<br>CCTCGGACTTCAAGGGGCTAGAATTCGAGCAATTATCTTGTTTACTAAAACTGA<br>ATACCTTGCTATCTCTTTGATACATTTTTACAAAGCTGAATTAAAATGGTATAA<br>ATTAAATCACTTTTTCATCTGACCAGTAGTGGACTAGTGTGACGCTGCTGACCC<br>CTTTCTTTCCCTTCTACAG |
| 162 | FAS_13 miR3G-PTPN2_14 miRE Module | GTAAGTCGACTCGTTGGATCCCCACTACCCGGATCAACGCCCTAGGTTTATGTT<br>TGGATGAACTGACATACGCGTATCCGTCTAATCTTAATCTTTCATCCTCTGTAG<br>TGAAATATATATTAAACAGAGGATGAAAGATTAAGATTTTACGGTAACGCGGAA<br>TTCGCAACTATTTTATCAATTTTTTGCGTCGACACTTCAAGGGGCTTGCGGCCG<br>CAACCATCTCCATGGCTGTTTGAATGAGGCTTCAGTACTTTACAGAATCGTTGC<br>CTGCACATCTTGGAAACACTTGCTGGGATTACTTCGACTTCTTAACCCAACAGA<br>AGGCTCGAGAAGGTATATTGCTGTTGACAGTGAGCGCCAGTGTGAAGCTCTTGT |

-continued

INFORMAL SEQUENCE LISTING

| SEQ ID NO | Name | Sequence |
|---|---|---|
| | | CAGATAGTGAAGCCACAGATGTATCTGACAAGAGCTTCACACTGATGCCTACTG<br>CCTCGGACTTCAAGGGGCTAGAATTCGAGCAATTATCTTGTTTACTAAAACTGA<br>ATACCTTGCTATCTCTTTGATACATTTTTACAAAGCTGAATTAAAATGGTATAA<br>ATTAAATCACTTTTTCATCTGACCAGTAGTGGACTAGTGTGACGCTGCTGACCC<br>CTTTCTTTCCCTTCTACAG |
| 163 | FAS_11 miR3G-TOX_9 miRE Module | GTAAGTCGACTCGTTGGATCCCCACTACCCGGATCAACGCCCTAGGTTTATGTT<br>TGGATGAACTGACATACGCGTATCCGTCTTAAGAATCTTTTCAAACACTAGTAG<br>TGAAATATATATTAAACTAGTGTTTGAAAAGATTCTTATTACGGTAACGCGGAA<br>TTCGCAACTATTTTATCAATTTTTTGCGTCGACACTTCAAGGGGCTTGCGGCCG<br>CAACCATCTCCATGGCTGTTTGAATGAGGCTTCAGTACTTTACAGAATCGTTGC<br>CTGCACATCTTGGAAACACTTGCTGGGATTACTTCGACTTCTTAACCCAACAGA<br>AGGCTCGAGAAGGTATATTGCTGTTGACAGTGAGCGCCCGGGAATGAATCCTCA<br>CCTATAGTGAAGCCACAGATGTATAGGTGAGGATTCATTCCCGGTTGCCTACTG<br>CCTCGGACTTCAAGGGGCTAGAATTCGAGCAATTATCTTGTTTACTAAAACTGA<br>ATACCTTGCTATCTCTTTGATACATTTTTACAAAGCTGAATTAAAATGGTATAA<br>ATTAAATCACTTTTTCATCTGACCAGTAGTGGACTAGTGTGACGCTGCTGACCC<br>CTTTCTTTCCCTTCTACAG |
| 164 | PTPN2_14 miR3G-TOX_9 miRE Module | GTAAGTCGACTCGTTGGATCCCCACTACCCGGATCAACGCCCTAGGTTTATGTT<br>TGGATGAACTGACATACGCGTATCCGTCTCTGACAAGAGCTTCACACTGAGTAG<br>TGAAATATATATTAAACTCAGTGTGAAGCTCTTGTCAGTTACGGTAACGCGGAA<br>TTCGCAACTATTTTATCAATTTTTTGCGTCGACACTTCAAGGGGCTTGCGGCCG<br>CAACCATCTCCATGGCTGTTTGAATGAGGCTTCAGTACTTTACAGAATCGTTGC<br>CTGCACATCTTGGAAACACTTGCTGGGATTACTTCGACTTCTTAACCCAACAGA<br>AGGCTCGAGAAGGTATATTGCTGTTGACAGTGAGCGCCCGGGAATGAATCCTCA<br>CCTATAGTGAAGCCACAGATGTATAGGTGAGGATTCATTCCCGGTTGCCTACTG<br>CCTCGGACTTCAAGGGGCTAGAATTCGAGCAATTATCTTGTTTACTAAAACTGA<br>ATACCTTGCTATCTCTTTGATACATTTTTACAAAGCTGAATTAAAATGGTATAA<br>ATTAAATCACTTTTTCATCTGACCAGTAGTGGACTAGTGTGACGCTGCTGACCC<br>CTTTCTTTCCCTTCTACAG |
| 165 | PTPN2_1 miR3G-ZC3H12A_1 miRE Module | GTAAGTCGACTCGTTGGATCCCCACTACCCGGATCAACGCCCTAGGTTTATGTT<br>TGGATGAACTGACATACGCGTATCCGTCTATAATACGACTTCACATCTTCGTAG<br>TGAAATATATATTAAACGAAGATGTGAAGTCGTATTATTTACGGTAACGCGGAA<br>TTCGCAACTATTTTATCAATTTTTTGCGTCGACACTTCAAGGGGCTTGCGGCCG<br>CAACCATCTCCATGGCTGTTTGAATGAGGCTTCAGTACTTTACAGAATCGTTGC<br>CTGCACATCTTGGAAACACTTGCTGGGATTACTTCGACTTCTTAACCCAACAGA<br>AGGCTCGAGAAGGTATATTGCTGTTGACAGTGAGCGCAAGCAAGATGCTTCTTA<br>ATAATAGTGAAGCCACAGATGTATTATTAAGAAGCATCTTGCTTATGCCTACTG<br>CCTCGGACTTCAAGGGGCTAGAATTCGAGCAATTATCTTGTTTACTAAAACTGA<br>ATACCTTGCTATCTCTTTGATACATTTTTACAAAGCTGAATTAAAATGGTATAA<br>ATTAAATCACTTTTTCATCTGACCAGTAGTGGACTAGTGTGACGCTGCTGACCC<br>CTTTCTTTCCCTTCTACAG |
| 166 | AB-1013: LG1_2xSPA_Fas + PTPN2 | TAaGGTAcgactgtgccttctagttgccagccatctgttgtttgccctccccc<br>gtgccttccttgaccctggaaggtgccactcccactgtcctttcctaataaaat<br>gaggaaattgcatcgcattgtctgagtaggtgtcattctattctgggggtggg<br>gtggggcaggacagcaaggggaggattgggaagacaatagcaggcatgctggg<br>gatgcggtgggctctatgggataagcttgatatcgaattcatcgatgttaataa<br>ttaacatatatgttaatcattaacatatagttaattattaaccgctatgttaat<br>gattaacaacggttaataattaacatatatgttaatcattaacatataactagt<br>ctagagggtatataatgggggccactagtctactaccagagTtcatcgctagcg<br>ctaccggatccgccaccATGGCCCTGCCAGTAACGGCTCTGCTGCTGCCACTTG<br>CTCTGCTCCTCCATGCAGCCAGGCCTCAGTTGCAGTTACAGGAGAGCGGACCCG<br>GTCTGGTTAAACCGTCTGAAACACTGAGTTTGACATGTACAGTGTCCGGCGGCT<br>CGATTTCAAACTCTTACTATTGGGGCTGGATTAGGCAGCCTCCCGGGAAAGGGC<br>TCGAGTGGATCGGGTCCATATATCACTCAGGAAATACCTACTACAACCCAAGTC<br>TTAAGTCTAGAGTGACAATCAGTGTGGATACGTCCAAGAATCAATTCTCCCTGA<br>AGCTCTCAAGCGTGACCGCCGCCGACACCGCAGTGTATTATTGCGTAACTCAAG<br>ACGGTGTGGGCGCTACCACTACCGAAGAGTATTGGGACAAGGCACTCTTGTCA<br>CAGTCTCCAGCGCGGCAGCAaccacgacgccagcgccgcgaccaccaacaccgg<br>cgcccaccatcgcgtcgcagccactgtcactgcgcccagaagcgtgccggccag<br>tctgggcgcccttggccgggacttgtggggtccttctcctgtcactggttatca<br>cccttttactgcaaacggggcagaaagaaactcctgtatatattcaaacaaccat<br>ttatgagaccagtacaaactactcaagaagaggacggctgtagctgccgatttc<br>cagaagaagaagaaggaggatgtgaactgagagtgaagttcagcaggagcgcag<br>acgccccgcgtaccagcagggccagaaccagctctataacgagctcaatctag<br>gacgaagagaggagtacgatgttttggacaagaggcgtggccgggaccctgaga<br>agaaagataagatggcggaggcctacagtgagattgggatgaaaggcgagcgcc<br>ggaggggcaaggggcacgatggcctttaccagggtctcagtacagccaccaagg<br>acacctacgacgcccttcacatgcaggccctgccccctaggtaaaatcaacctc<br>tggattacaaaatttgtgaaagattgactggtattcttaactatgttgctccctt |

-continued

| INFORMAL SEQUENCE LISTING | | |
|---|---|---|
| SEQ ID NO | Name | Sequence |
| | | ttacgctatgtggatacgctgctttaatgcctttgtatcatgctattgcttccc |
| | | gtatggctttcattttctcctccttgtataaatcctggttgctgtctctttatg |
| | | aggagttgtgggcccgttgtcaggcaacgtggcgtggtgtgcactgtgtttgctg |
| | | acgcaaccccccactggttggggcattgccaccacctgtcagctccttccggga |
| | | ctttcgctttcccccctcccctattgccacggcggaactcatcgccgcctgccttg |
| | | cccgctgctggacagggctcggctgttgggcactgacaattccgtggtgttgt |
| | | cggggaaatcatcgtcctttccttggctgctcgcctgtgttgccacctggattc |
| | | tgcgcgggacgtccttctgctacgtccctcggccctcaatccagcggaccttc |
| | | cttcccgcggcctgctgccggctctgcggcctcttccgcgtcttcgccttcgcc |
| | | ctcagacgagtcggatctccctttgggccgcctccccgcctggatccttgactt |
| | | gcggccaacttgttttattgcagcttataatggttacaaataaagcaatagcatc |
| | | acaaatttcacaaataaagcattttttcactgcattctagttgtggtttgtcc |
| | | aaactcatcaatgtatcttatcatgtctgggatccttgacttgcggccgcaact |
| | | cccacctgcaacatgcgtgactgactgaggccgcgactctagagtcgaccggat |
| | | ctgcgatcgctccggtgcccgtcagtgggcagagcgcacatcgcccacagtccc |
| | | cgagaagttggggggaggggtcggcaattgaacgggtgcctagagaaggtggcg |
| | | cggggtaaactgggaaagtgatgtcgtgtactggctccgcctttttcccgaggg |
| | | tgggggagaaccgtatataagtgcagtagtcgccgtgaacgttcttttttcgcaa |
| | | cgggtttgccgccagaacacagctgaagcttcgagggctcgcatctctccttc |
| | | acgcgcccgccgccctacctgaggccgccatccacgccggttgagtcgcgttct |
| | | gccgcctcccgcctgtggtgcctcctgaactgcgtccgccgtctaggtaaGTcg |
| | | actcgttggatccCCACTACCCGGATCAACGCCCTAGGTTTATGTTTGGATGAA |
| | | CTGACATACGCGTATCCGTCTTAAGAATCTTTTCAAACACTAGTAGTGAAATAT |
| | | ATATTAAACTAGTGTTTGAAAAGATTCTTATTACGGTAACGCGGAATTCGCAAC |
| | | TATTTTATCAATTTTTTGCGTCGACACTTCAAGGGGCTTGCGGCCGCAACCATC |
| | | TCCATGGCTGTTTGAATGAGGCTTCAGTACTTTACAGAATCGTTGCCTGCACAT |
| | | CTTGGAAACACTTGCTGGGATTACTTCGACTTCTTAACCCAACAGAAGGCTCGA |
| | | GAAGGTATATTGCTGTTGACAGTGAGCGCCAGTGTGAAGCTCTTGTCAGATAGT |
| | | GAAGCCACAGATGTATCTGACAAGAGCTTCACACTGATGCCTACTGCCTCGGAC |
| | | TTCAAGGGGCTAGAATTCGAGCAATTATCTTGTTTACTAAAACTGAATACCTTG |
| | | CTATCTCTTTGATACATTTTTACAAAGCTGAATTAAAATGGTATAAATTAAATC |
| | | ACTTTTTCATCTGACCAGTAGTGGactagtgtgacgctgctgacccctttctttt |
| | | cccttctACAGatccaagctgtgaccggcgcctacacctgcagcccaagcttac |
| | | catggccttaccagtgaccgccttgctcctgccgctggccttgctgctccacgc |
| | | cgccaggcctgacatacagatgacacagagccctagcagtctgagcgccagtgt |
| | | gggcgatagagttactatcacttgtagagcatccgagaacatatacagttacgt |
| | | ggcctggtatcagcaaaaacctggcaaagctcccaagttattgatttacaatgc |
| | | taagagcttggcctctggggtgccatcgaggttcagcggtagcgggagcgggac |
| | | cgacttcactctgaccatctcgagtctccagccgaggactttgcgacatacta |
| | | ttgtcaacaccattacgtatcaccctggaccttcggcggcgggactaagttaga |
| | | gatcaagggtggaggaggatcaggcggcggtggatcaggaggaggagggtcaca |
| | | agtgcagttacaggaatcagggcccggcctggtgaagccaagtgaaaccctgag |
| | | tctgacgtgcacggtttcaggatttagcctcacttcctacggtgtctcttggat |
| | | tcggcagccagccggcaaagggctcgagtggattgggtgatctgggaagatgg |
| | | ctcaacaaactatcattctgcactaatctctcgcgtgacaatgtcggtggacac |
| | | gtccaagaatcaattttcccttaaactgtcctccgtgaccgcagccgatacagc |
| | | ggtatattattgcgcgcgacctcactacggatctagctatgtcggcgcgatgga |
| | | gtattggggcgctggcacaaccgtcaccgtttcttccgcaaccacgacgccagc |
| | | gccgcgaccaccaacaccggcgcccaccatcgcgtcgcagccccctgtccctgcg |
| | | ccctgaggcgtgcttcatgtacgtggcggcggccgcctttgtgcttctgttctt |
| | | cgtgggctgcggggtgctgctgtcccgtaaacgcagacgtcaacacggtcaact |
| | | gtggtttccagaaggttttaaggtctccgaagcaagtaagaagaaaagacgtga |
| | | accactgggagaagatagcgtcggtctgaaaccactcaagaatgccatggtttc |
| | | taaactgagccagctgcagacggagctcctggcggccctgctggagtcagggct |
| | | gagcaaagaggcactgctccaggcactgggcgagccgggccctacctcctggc |
| | | tggagaaggcccctggacaagggggagtcctgcggcggcggtcgaggggagct |
| | | ggctgagctgcccaatgggctggggagactcgggctccgaggacgagaccga |
| | | cgacgatggggaagacttcacgccacccatcctcaaagagctggagaacctcag |
| | | ccctgaggaggcggccaccagaaagccgtggtggagacccttctgcaggagga |
| | | cccgtggcgtgtggcgaagatggtcaagtcctacctgcagcagcacaacatccc |
| | | acagcgggaggtggtcgataccactggcctcaaccagtcccacctgtcccaaca |
| | | cctcaacaagggcactcccatgaagacgcagaagcgggccgccctgtacacctg |
| | | gtatgtccgcaagcagcgagaggtggcgcagcagtttcaccatgcagggcaggg |
| | | agggctgattgaagagcccacaggagatgagctaccaaccaagaagggcggag |
| | | gaaccgtttcaagtggggcccagcatcccagcagatcctgttccaggcctatga |
| | | gaggcagaagaaccctagcaaggaggagcgagaaacgctagtggaggagtgcaa |
| | | tagggcggaatgcatccagagaggtgtgtcaccatcacaagcacaaggtctggg |
| | | ctccaacctcgtcacggaggtgcgtgtcacaactggtttgcaaccggcgcaa |
| | | agaagaagccttccggcacaagctggccatgacctgcagggatgagtttcccac |
| | | catggtgtttccttctgggcagatcagccaggcctcggccttggccccggcccc |
| | | tccccaagtcctgcccaggctccagccctgccctgctccagccatggtatc |
| | | agctctggcccaggcccagccctgtcccagtcctagccccaggccctcctca |
| | | agctgtggccccacctgccccaagcccacccaagctggggaaggaacgctgtc |

INFORMAL SEQUENCE LISTING

| SEQ ID NO | Name | Sequence |
|---|---|---|
| | | agaggccctgctgcagctgcagtttgatgatgaagacctgggggccttgcttgg caacagcacagacccagctgtgttcacagacctggcatccgtcgacaactccga gtttcagcagctgctgaaccagggcatacctgtggcccccccacacaactgagcc catgctgatggagtaccctgaggctataactcgcctagtgacaggggcccagag catgctgatggagtaccctgaggctataactcgcctagtgacaggggcccagag gccccccgacccagctcctgctccactgggggccccggggctcccccaatggcct cctttcaggagatgaagacttctcctccattgcggacatggacttctcagccct gctgagtcagatcagctcctaaAGGAaataaaaagatctttaatgaaaatAGATC TGTGTGTTGGTTTTTTGTGTGaataaaaagatccagagctctagAGATCTGTGTG TTGGTTTTTTGTGTG |
| 167 | AB-1014: LG1_TTT_Fas PTPN2 | TAaGGTAcgactgtgccttctagttgccagccatctgttgtttgccctccccc gtgccttccttgacctggaaggtgccactcccactgtcctttcctaataaaat gaggaaattgcatcgcattgtctgagtaggtgtcattctattctgggggtggg gtggggcaggacagcaaggggaggattgggaagacaatagcaggcatgctggg gatgcggtgggctctatgggataagcttgatatcgaattcatcgatgttaataa ttaacatatatgttaatcattaacatatagttaattattaaccgctatgttaat gattaacaacggttaataattaacatatatgttaatcattaacatataactagt ctagagggtatataatgggggccactagtctactaccagagTtcatcgctagcg ctaccggatccgcaccATGGCCCTGCCAGTAACGGCTCTGCTGCTGCCACTTG CTCTGCTCCTCCATGCAGCCAGGCCTCAGTTGCAGTTACAGGAGAGCGGACCCG GTCTGGTTAAACCGTCTGAAACACTGAGTTTGACATGTACAGTGTCCGGCGGCT CGATTTCAAACTCTTACTATTGGGGCTGGATTAGGCAGCCTCCCGGGAAAGGGC TCGAGTGGATCGGGTCCATATATCACTCAGGAAATACCTACTACAACCCAAGTC TTAAGTCTAGAGTGACAATCAGTGTGGATACGTCCAAGAATCAATTCTCCCTGA AGCTCTCAAGCGTGACCGCCGCCGACACCGCAGTGTATTATTGCGTAACTCAAG ACGGTGTGGGCGCTACCACTACCGAAGAGTATTGGGACAAGGCACTCTTGTCA CAGTCTCCAGCGCGGCAGCAaccacgacgccagcgccgcgaccaccaacaccgg cgcccaccatcgcgtcgcagccactgtcactgcgcccagaagcgtgccggccag cggcgggggcgcagtgcacacgagggggctggacttcgcctgtgatatctaca cccttactgcaaacggggcagaaagaaactcctgtatatattcaaacaaccat ttatgagaccagtacaaactactcaagaagaggacggctgtagctgccgatttc cagaagaagaagaaggaggatgtgaactgagagtgaagttcagcaggagcgcag acgcccccgcgtaccagcagggccagaaccagctctataacgagctcaatctag gacgaagagaggagtacgatgtttggacaagaggcgtggccgggaccctgaga tgggggggaaagccgagaaggaagaaccctcaggaaggcctgtacaatgaactgc agaaagataagatggcggaaggcctacagtgagattgggatgaaaggcgagcgcc ggaggggcaaggggcacgatggcctttaccagggtctcagtacagccaccaagg acacctacgacgcccttcacatgcaggccctgcccctaggtaaaatcaacctc tggattacaaaatttgtgaaagattgactggtattcttaactatgttgctcctt ttacgctatgtggatacgctgctttaatgcctttgtatcatgctattgcttccc gtatggctttcatttctcctccttgtataaatcctggttgctgtctctttatg aggagttgtggcccgttgtcaggcaacgtggcgtggtgtgcactgtgtttgctg acgcaaccccccactggttggggcattgccaccacctgtcagctcctttccggga ctttcgctttccccctcccctattgccacggcggaactcatcgccgcctgccttg cccgctgctggacaggggctcggctgttgggcactgacaattccgtggtgttgt cggggaaatcatcgtcctttccttggctgctcgcctgtgttgccacctggattc tgcgcgggacgtccttctgctacgtcccttcggccctcaatccagcggaccttc cttcccgcgccctgctgccggctctgcggcctcttccgcgtcttcgccttcgcc ctcagacgagtcggatctccctttgggccgcctcccgcctggatccttgactt gcggccaacttgtttattgcagcttataatggttacaaataaagcaatagcatc acaaatttcacaaataaagcatttttttcactgcattctagttgtggtttgtcc aaactcatcaatgtatcttatcatgtctgggatccttgacttgcggccgcaact cccacctgcaacatgcgtgactgactgaggccgcgactctagagtcgaccggat ctgcgatcgctccggtgcccgtcagtgggcagagcgcacatcgcccacagtccc cgagaagttgggggaggggtcggcaattgaacgggtgcctagagaaggtggcg cggggtaaactgggaaagtgatgtcgtgtactggctccgccttttcccgaggg tgggggagaaccgtatataagtgcagtagtcgccgtgaacgttcttttcgcaa cgggtttgccgccagaacacagctgaagcttcgaggggctcgcatctctccttc acgcgcccgccgccctacctgaggccgccatccacgccggttgagtcgcgttct gccgcctccgcctgtggtgcctcctgaactgcgtccgccgtctaggtaaGTCg actcgttggatccCCACTACCCGGATCAACGCCCTAGGTTTATGTTTGGATGAA CTGACATACGCGTATCCGTCTTAAGAATCTTTTCAAACACTAGTAGTGAAATAT ATATTAAACTAGTGTTTGAAAAGATTCTTATTACGGTAACGCGGAATTCGCAAC TATTTTATCAATTTTTTGCGTCGACACTTCAAGGGGCTTGCGGCCGCAACCATC TCCATGGCTGTTTGAATGAGGCTTCAGTACTTTACAGAATCGTTGCCTGCACAT CTTGGAAACACTTGCTGGGATTACTTCGACTTCTTAACCCAACAGAAGGCTCGA GAAGGTATATTGCTGTTGACAGTGAGCGCCAGTGTGAAGCTCTTGTCAGATAGT GAAGCCACAGATGTATCTGACAAGAGCTTCACACTGATGCCTACTGCCTCGGAC TTCAAGGGGCTAGAATTCGAGCAATTATCTTGTTTACTAAAACTGAATACCTTG CTATCTCTTTGATACATTTTTACAAAGCTGAATTAAAATGGTATAAATTAAATC ACTTTTTCATCTGACCAGTAGTGGactagtgtgacgctgctgacccctttcttt cccttctACAGatccaagctgtgaccggcgcctacacctgcagcccaagctttTT |

INFORMAL SEQUENCE LISTING

| SEQ ID NO | Name | Sequence |
|---|---|---|
| | | Tatggccttaccagtgaccgccttgctcctgccgctggccttgctgctccacgc<br>cgccaggcctgacatacagatgacacagagccctagcagtctgagcgccagtgt<br>gggcgatagagttactatcacttgtagagcatccgagaacatatacagttacgt<br>ggcctggtatcagcaaaaacctggcaaagctcccaagttattgatttacaatgc<br>taagagcttggcctctggggtgccatcgaggttcagcggtagcgggagcgggac<br>cgacttcactctgaccatctcgagtctccagccgaggactttgcgacatacta<br>ttgtcaacaccattacgtatcaccctggaccttcggcggcgggactaagttaga<br>gatcaagggtggaggaggatcaggcggcggtggatcaggaggaggaggtcaca<br>agtgcagttacaggaatcagggcccggcctggtgaagccaagtgaaaccctgag<br>tctgacgtgcacggtttcaggatttagcctcacttcctacggtgtctcttggat<br>tcggcagccagccggcaaagggctcgagtggattgggtgatctgggaagatgg<br>ctcaacaaactatcattctgcactaatctctcgcgtgacaatgtcggtggacac<br>gtccaagaatcaattttcccttaaactgtcctccgtgaccgcagccgatacagc<br>ggtatattattgcgcgcgacctcactacggatctagctatgtcggcgcgatgga<br>gtattggggcgctggcacaaccgtcaccgtttcttccgcaaccacgacgccagc<br>gccgcgaccaccaacaccggcgcccaccatcgcgtcgcagccctgtccctgcg<br>ccctgaggcgtgcttcatgtacgtggcggcggccgcctttgtgcttctgttctt<br>cgtgggctgcggggtgctgctgtcccgtaaacgcagacgtcaacacggtcaact<br>gtggtttccagaaggttttaaggtctccgaagcaagtaagaagaaaagacgtga<br>accactgggagaagatagcgtcggtctgaaaccactcaagaatgccatggtttc<br>taaactgagccagctgcagacggagctcctggcggccctgctggagtcagggct<br>gagcaaagaggcactgctccaggcactgggcgagccggggccctacctcctggc<br>tggagaaggcccctggacaagggggagtcctgcggcggcggtcgaggggagct<br>ggctgagctgcccaatgggctgggggagactcggggctccgaggacgagaccga<br>cgacgatggggaagacttcacgccacccatcctcaaagagctggagaacctcag<br>ccctgaggaggcggccaccagaaagccgtggtggagacccttctgcaggagga<br>cccgtggcgtgtggcgaagatggtcaagtcctacctgcagcagcacaacatccc<br>acagcgggaggtggtcgataccactggcctcaaccagtcccacctgtcccaaca<br>cctcaacaagggcactcccatgaagacgcagaagcgggccgccctgtacacctg<br>gtatgtccgcaagcagcgagaggtggcgcagcagttcacccatgcagggcaggg<br>agggctgattgaagagcccacaggagatgagctaccaaccaagaaggggcggag<br>gaaccgtttcaagtggggcccagcatcccagcagatcctgttccaggcctatga<br>gaggcagaagaaccctagcaaggaggagcgagaaacgctagtggaggagtgcaa<br>tagggcggaatgcatccagagaggtgtgtcaccatcacaagcacaaggtctggg<br>ctccaacctcgtcacggaggtgcgtgtctacaactggtttgccaaccggcgcaa<br>agaagaagccttccggcacaagctggccatgacctgcagggatgagtttcccac<br>catggtgtttccttctgggcagatcagccaggcctcggccttggcccggccc<br>tccccaagtcctgccccaggctccagcccctgcccctgctccagccatggtatc<br>agctctggcccaggccccagcccctgtcccagtcctagccccaggccctcctca<br>agctgtggccccacctgcccccaagcccacccaagctggggaaggaacgctgtc<br>agaggccctgctgcagctgcagtttgatgatgaagacctgggggccttgcttgg<br>caacagcacagacccagctgtgttcacagacctggcatccgtcgacaactccga<br>gtttcagcagctgctgaaccagggcatacctgtgcccccacacaactgagcc<br>catgctgatggagtaccctgaggctataactcgcctagtgacaggggcccagag<br>cctttcaggagatgaagactttctcctccattgcggacatggacttctcagccct<br>gctgagtcagatcagctcctaaAGGACGGGTGGCATCCCTGTGACCCCTCCCCA<br>GTGCCTCTCCTGGCCCTGGAAGTTGCCACTCCAGTGCCCACCAGCCTTGTCCTA<br>ATAAAATTAAGTTGCATCATTTTGTCTGACTAGGTGTCCTTCTATAATATTATG<br>GGGTGGAGGGGGGTGGTATGGAGCAAGGGGCAAGTTGGGAAGACAACCTGTAGG<br>GCCTGCGGGGTCTATTGGGAACCAAGCTGGAGTGCAGTGGCACAATCTTGGCTC<br>ACTGCAATCTCCGCCTCCTGGGTTCAAGCGATTCTCCTGCCTCAGCCTCCCGAG<br>TTGTTGGGATTCCAGGCATGCATGACCAGGCTCAGCTAATTTTGTTTTTTTGG<br>TAGAaACGGGGTTTCACCATATTGGCCAGGCTGGTCTCCAACTCCTAATCTCAG<br>GTGATCTACCCACCTTGGCCTCCCAAATTGCTGGGATTACAGGCGTGAACCACT<br>GCTCCCttccctgtccttc |
| 168 | AB-1015: LG1_Fas + PTPN2 | TAaGGTAcgactgtgccttctagttgccagccatctgttgtttgcccctccccc<br>gtgccttccttgacccctggaaggtgccactcccactgttccttccctaataaaat<br>gaggaaattgcatcgcattgtctgagtaggtgtcattctattctgggggtggg<br>gtggggcaggacagcaaggggggaggattgggaagacaatagcaggcatgctggg<br>gatgcggtgggctctatgggataagcttgatatcgaattcatcgatgttaataa<br>ttaacatatatgttaatcattaacatatagttaattattaaccgctatgttaat<br>gattaacaacggttaataattaacatatatgttaatcattaacatataactagt<br>ctagagggtatataatgggggccactagtctactaccagagTtcatcgctagcg<br>ctaccggatccgccaccATGGCCCTGCCAGTAACGGCTCTGCTGCTGCCACTTG<br>CTCTGCTCCTCCATGCAGCCAGGCCTCAGTTGCAGTTACAGGAGAGCGGACCCG<br>GTCTGGTTAAACCGTCTGAAACACTGAGTTTGACATGTACAGTGTCCGGCGGCT<br>CGATTTCAAACTCTTACTATTGGGGCTGGATTAGGCAGCCTCCCGGGAAGGGC<br>TCGAGTGGATCGGGTCCATATATCACTCAGGAAATACCTACTACAACCCAAGTC<br>TTAAGTCTAGAGTGACAATCAGTGTGGATACGTCCAAGAATCAATTCTCCCTGA<br>AGCTCTCAAGCGTGACCGCCGCCGACACCGCAGTGTATTATTGCGTAACTCAAG<br>ACGGTGTGGGCGCTACCACTACCGAAGAGTATTGGGACAAGGCACTCTTGTCA<br>CAGTCTCCAGCGCGGCAGCAaccacgacgccagccgccgcgaccaccaacaccgg |

-continued

| INFORMAL SEQUENCE LISTING | | |
|---|---|---|
| SEQ ID NO | Name | Sequence |
| | | cgcccaccatcgcgtcgcagccactgtcactgcgcccagaagcgtgccggccag<br>ccctttactgcaaacggggcagaaagaaactcctgtatatattcaaacaaccat<br>ttatgagaccagtacaaactactcaagaagaggacggctgtagctgccgatttc<br>cagaagaagaagaaggaggatgtgaactgagagtgaagttcagcaggagcgcag<br>acgccccgcgtaccagcagggccagaaccagctctataacgagctcaatctag<br>gacgaagagaggagtacgatgttttggacaagaggcgtggccgggaccctgaga<br>agaaagataagatggcggaggcctacagtgagattgggatgaaaggcgagcgcc<br>ggaggggcaaggggcacgatggcctttaccagggtctcagtacagccaccaagg<br>acacctacgacgcccttcacatgcaggccctgcccccctaggtaaaatcaacctc<br>tggattacaaaatttgtgaaagattgactggtattcttaactatgttgctcctt<br>ttacgctatgtggatacgctgctttaatgcctttgtatcatgctattgcttccc<br>gtatggctttcattttctcctccttgtataaatcctggttgctgtctctttatg<br>aggagttgtggcccgttgtcaggcaacgtggcgtggtgtgcactgtgtttgctg<br>acgcaacccccactggttggggcattgccaccacctgtcagctccttccggga<br>ctttcgctttccccctccctattgccacggcggaactcatcgccgcctgccttg<br>cccgctgctggacaggggctcggctgttggggcactgacaattccgtggtgttgt<br>cggggaaatcatcgtcctttccttggctgctcgcctgtgttgccacctggattc<br>tgcgcgggacgtccttctgctacgtcccttcggccctcaatccagcggaccttc<br>cttcccgcgcctgctgccggctctgcggctcttccgcgtcttcgccttcgcc<br>ctcagacgagtcggatctccctttgggccgcctccccgcctggatccttgactt<br>gcggccaacttgtttattgcagcttataatggttacaaataaagcaatagcatc<br>acaaatttcacaaataaagcattttttcactgcattctagttgtggtttgtcc<br>aaactcatcaatgtatcttatcatgtctgggatccttgacttgcggccgcaact<br>cccacctgcaacatgcgtgactgactgaggccgcgactctagagtcgaccggat<br>ctgcgatcgctccggtgcccgtcagtgggcagagcgcacatcgcccacagtccc<br>cgagaagttggggggagggtcggcaattgaacgggtgcctagagaaggtggcg<br>cggggtaaactgggaaagtgatgtcgtgtactggctccgccttttcccgagggg<br>tggggagaaccgtatataagtgcagtagtcgccgtgaacgttcttttttcgcaa<br>cgggtttgccgccagaacacagctgaagcttcgaggggctcgcatctctcctc<br>acgcgcccgccgccctacctgaggccgccatccacgccggttgagtcgcgttct<br>gccgcctcccgcctgtggtgcctcctgaactgcgtccgccgtctaggtaaGTcg<br>actcgttggatccCCACTACCCGGATCAACGCCCTAGGTTTATGTTTGGATGAA<br>CTGACATACGCGTATCCGTCTTAAGAATCTTTTCAAACACTAGTAGTGAAATAT<br>ATATTAAACTAGTGTTTGAAAAGATTCTTATTACGGTAACGCGGAATTCGCAAC<br>TATTTTATCAATTTTTTGCGTCGACACTTCAAGGGGCTTGCGGCCGCAACCATC<br>TCCATGGCTGTTTGAATGAGGCTTCAGTACTTTACAGAATCGTTGCCTGCACAT<br>CTTGGAAACACTTGCTGGGATTACTTCGACTTCTTAACCCAACAGAAGGCTCGA<br>GAAGGTATATTGCTGTTGACAGTGAGCGCAGTGTGAAGCTCTTGTCAGATAGT<br>GAAGCCACAGATGTATCTGACAAGAGCTTCACACTGATGCCTACTGCCTCGGAC<br>TTCAAGGGGCTAGAATTCGAGCAATTATCTTGTTTACTAAAACTGAATACCTTG<br>CTATCTCTTTGATACATTTTTACAAAGCTGAATTAAAATGGTATAAATTAAATC<br>ACTTTTTCATCTGACCAGTAGTGGactagtgtgacgctgctgaccccttctctt<br>cccttctACAGatccaagctgtgaccggcgcctacacctgcagcccaagcttac<br>catggccttaccagtgaccgccttgctcctgccgctggccttgctgctccacgc<br>cgccaggcctgacatacagatgacacagagccctagcagtctgagcgccagtgt<br>gggcgatagagttactatcacttgtagagcatccgagaacatatacagttacgt<br>ggcctggtatcagcaaaaacctggcaaagctcccaagttattgatttacaatgc<br>taagagcttggcctctggggtgccatcgaggttcagcggtagcgggagcgggac<br>cgacttcactctgaccatctcgagtctccagccggaggactttgcgacatacta<br>ttgtcaacaccattacgtatcaccctggaccttcggcggcgggactaagttaga<br>gatcaagggtggaggaggatcaggcggcggtggatcaggaggaggagggtcaca<br>agtgcagttacaggaatcagggcccggcctggtgaagccaagtgaaaccctgag<br>tctgacgtgcacggtttcaggatttagcctcacttcctacggtgtctcttggat<br>tcggcagccagccggcaaagggctcgagtggattggggtgatctgggaagatgg<br>ctcaacaaactatcattctgcactaatctctcgcgtgacaatgtcggtggacac<br>gtccaagaatcaattttcccttaaactgtcctccgtgaccgcagccgatacagc<br>ggtatattattgcgcgcgacctcactacggatctagctatgtcggcgcgatgga<br>gtattgggcgctggcaacaccgtcaccgttcttccgcaaccacgacgccagc<br>gccgcgaccaccaacaccggcgcccaccatcgcgtcgcagcccctgtccctgcg<br>ccctgaggcgtgcttcatgtacgtggcggcggccgcctttgtgcttctgttctt<br>cgtgggctgcggggtgctgctgtcccgtaaacgcagacgtcaacacggtcaact<br>gtggtttccagaagggttttaaggtctccgaagcaagtaagaagaaaagacgtga<br>accactgggagaagatagcgtcggtctgaaaccactcaagaatgccatggtttc<br>taaactgagccagctgcagacggagctcctggcggccctgctggagtcagggct<br>gagcaaagaggcactgctccaggcactgggcgagccggggccctacctcctggc<br>tggagaaggcccctggacaaggggggagtcctgcggcggcggtcgaggggagct<br>ggctgagctgcccaatgggctggggagactcggggctccgaggacgagaccga<br>cgacgatggggaagacttcacgccaccccatcctcaaagagctggagaacctcag<br>ccctgaggaggcggccaccagaaagccgtggtggagaccttctgcaggagga<br>cccgtggcgtgtggcgaagatggtcaagtcctacctgcagcagcacaacatccc<br>acagcgggaggtggtcgataccactggcctcaaccagtcccacctgtcccaaca<br>cctcaacaagggcactcccatgaagacgcagaagcgggccgcctgtacacctg<br>gtatgtccgcaagcagcgagaggtggcgcagcagttcacccatgcagggcaggg |

-continued

| SEQ ID NO | Name | Sequence |
|---|---|---|
| | | agggctgattgaagagcccacaggagatgagctaccaaccaagaaggggcggag gaaccgtttcaagtgggcccagcatcccagcagatcctgttccaggcctatga gaggcagaagaaccctagcaaggaggagcgagaaacgctagtggaggagtgcaa tagggcggaatgcatccagagaggtgtgtcaccatcacaagcacaaggtctggg ctccaacctcgtcacggaggtgcgtgtctacaactggtttgccaaccggcgcaa agaagaagccttccggcacaagctggccatgacctgcagggatgagtttcccac catggtgtttccttctgggcagatcagccaggcctcggccttggcccggcccc tccccaagtcctgccccaggctccagccctgcccctgctccagccatggtatc agctctggcccaggccccagccctgtcccagtcctagccccaggccctcctca agctgtggcccacctgccccaagcccaccaagctggggaaggaacgctgtc agaggccctgctgcagctgcagtttgatgatgaagacctgggggccttgcttgg caacagcacagaccagctgtgttcacagacctggcatccgtcgacaactccga gtttcagcagctgctgaaccagggcatacctgtggcccccacacaactgagcc catgctgatggagtaccctgaggctataactcgcctagtgacaggggcccagag cctttcaggagatgaagacttctcctccattgcggacatggacttctcagccct gctgagtcagatcagctcctaaAGGAcgggtggcatccctgtgacccctcccca gtgcctctcctggccctggaagttgccactccagtgccaccagccttgtccta ataaaattaagttgcatcattttgtctgactaggtgtccttctataatattatg gcctgcgggtctattgggaaccaagctggagtgcagtggcacaatcttggctc actgcaaatctccgcctcctgggttcaagcgattctcctgcctcagcctcccgag ttgttgggattccaggcatgcatgaccaggctcagctaattttttgttttttgg tagaaacgggtttcaccatattggccaggctggtctccaactcctaatctcag gtgatctacccaccttggcctcccaaattgctgggattacaggcgtgaaccact gctcccttccctgtccttc |
| 169 | AB-1013:<br>LG1_2xSPA_Fas + PTPN2<br>with flanking<br>CDL and homology<br>arms | GAGCCATGCTTGGCTTACGAGGGCGACCAACCCATCAAACTCCCCGCCCCCAGC ACTTTTATTTCTCCTCTTTAGGAAGTACACTTCAGTATCTTTGGCACAGTGCAT GAGCACGACTAAAGTAAAACATCGCAGAAAACATAGCTTTAGTCTACCCTTCGT GTCCTAAAAGGAAAACCAGTAGCTTCCCAGGCCACCGGAAGGGCAACACATGTC CTCTGCAGTTTCTGCACACGGGAAGGTAAAGACAGAGAGAGGACCTACTCCTCA ACACAGAAACATTTCAAATCTTTCCTCGCCTGCAACCCAAGCTGAAGTCATTC TCCCCAGAAATAACAAAAGTTGGAAGAGAAGCCGGAGACAGGATAGGTGCAGGA AGCCCACACTTTGAGGGCAGCACTCAGACACCCTCTCCTGTGTGCAGGACGTGC CGAATGTTCAGGTGCAATGAGAATGAGCCATGCTTGGCTTATAaGGTAcgactg tgccttctagttgccagccatctgttgtttgccctcccccgtgccttccttga ccctggaaggtgccactcccactgtcctttcctaataaaatgaggaaattgcat cgcattgtctgagtaggtgtcattctattctggggggtgggtggggcaggaca gcaaggggggaggattgggaagacaatagcaggcatgctggggatgcggtgggct ctatgggataagcttgatatcgaattcatcgatgttaataattaacatatatgt taatcattaacatatagttaattattaaccgctatgttaatgattaacaacggt taataattaacatatatgttaatcattaacatataactagtctagagggtatat aatgggggccactagtctactaccagagTtcatcgctagcgctaccggatccgc caccATGGCCCTGCCAGTAACGGCTCTGCTGCTGCCACTTGCTCTGCTCCTCCA TGCAGCCAGGCCTCAGTTGCAGTTACAGGAGAGCGGACCCGGTCTGGTTAAACC GTCTGAAACACTGAGTTTGACATGTACAGTGTCCGGCGGCTCGATTTCAAACTC TTACTATTGGGGCTGGATTAGGCAGCCTCCCGGGAAAGGGCTCGAGTGGATCGG GTCCATATATCACTCAGGAAATACCTACTACAACCCAAGTCTTAAGTCTAGAGT GACAATCAGTGTGGATACGTCCAAGAATCAATTCTCCCTGAAGCTCTCAAGCGT GACCGCCGCCGACACCGCAGTGTATTATTGCGTAACTCAAGACGGTGTGGGCGC TACCACTACCGAAGAGTATTGGGACAAGGCACTCTTGTCACAGTCCCAGCGC GGCAGCAaccacgacgccagcgccgcgaccaccaacaccggcgcccaccatcgc gtcgcagccactgtcactgcgcccagaagcgtgccggccagcggcggggggcgc agtgcacacgaggggggctggacttcgcctgtgtgatatctacatctgggcgccctt acggggcagaaagaaactcctgtatatattcaaacaaccatttatgagaccagt acaaactactcaagaagaggacggctgtagctgccgatttccagaagaagaaga aggaggatgtgaactgagagtgaagttcagcaggagcgcagacgcccccgcgta ccagcagggccagaaccagctctataacgagctcaatctaggacgaagagagga gtacgatgttttgacaagaggcgtggccgggaccctgcagtgggggaaagcc gagaaggaagaaccctcaggaaggcctgtacaatgaactgcagaaagataagat ggcggaggcctacagtgagattgggatgaaaggcgagcgccggaggggcaaggg gcacgatggcctttaccagggtctcagtacagccaccaaggacacctacgacgc ccttcacatgcaggccctgccccctaggtaaaatcaacctctggattacaaaat ttgtgaaagattgactggtattcttaactatgttgctccttttacgctatgtgg atacgctgcttaaatgcctttgtatcatgctattgcttcccgtatggctttcat tttctcctccttgtataaatcctggttgctgtctctttatgaggagttgtggcc cgttgtcaggcaacgtggcgtggtgtgcactgtgtttgctgacgcaaccccac tggttggggcattgccaccacctgtcagctcctttccgggactttcgctttccc cctccctattgccacggcggaactcatccgcgctgccttgcctgccttgcgtgctggaa aggggctcggctgttgggcactgacaattccgtggtgttgtcggggaaatcatc gtccttttccttggctgctcgcctgtgttgccacctggattctgcgcgggacgtc cttctgctacgtcccttcggccctcaatccagcggaccttccttcccgcggcct gctgccggctctgcggcctcttccgcgtcttcgccttcgccctcagacgagtcg gatctcccttttgggccgcctccccgcctggatccttgacttgcggccaacttgt |

| INFORMAL SEQUENCE LISTING | | |
|---|---|---|
| SEQ ID NO | Name | Sequence |
| | | ttattgcagcttataatggttacaaataaagcaatagcatcacaaatttcacaa
ataaagcattttttcactgcattctagttgtggtttgtccaaactcatcaatg
tatcttatcatgtctgggatccttgacttgcggccgcaactcccacctgcaaca
tgcgtgactgactgaggccgcgactctagagtcgaccggatctgcgatcgctcc
ggtgcccgtcagtgggcagagcgcacatcgcccacagtccccgagaagttgggg
ggaggggtcggcaattgaacgggtgcctagagaaggtggcgcggggtaaactgg
gaaagtgatgtcgtgtactggctccgccttttcccgagggtgggggagaaccg
tatataagtgcagtagtcgccgtgaacgttcttttcgcaacgggtttgccgcc
agaacacagctgaagcttcgaggggctcgcatctctccttcacgcgcccgccgc
cctacctgaggcgccatccacgccggttgagtcgcgttctgccgcctcccgcc
tgtggtgcctcctgaactgcgtccgccgtctaggtaaGTcgactcgttggatcc
CCACTACCCGGATCAACGCCCTAGGTTTATGTTTGGATGAACTGACATACGCGT
ATCCGTCTTAAGAATCTTTTCAAACACTAGTAGTGAAATATATATTAAACTAGT
GTTTGAAAAGATTCTTATTACGGTAACGCGGAATTCGCAACTATTTTATCAATT
TTTTGCGTCGACACTTCAAGGGGCTTGCGGCCGCAACCATCTCCATGGCTGTTT
GAATGAGGCTTCAGTACTTTACAGAATCGTTGCCTGCACATCTTGGAAACACTT
GCTGGGATTACTTCGACTTCTTAACCCAACAGAAGGCTCGAGAAGGTATATTGC
TGTTGACAGTGAGCGCCAGTGTGAAGCTCTTGTCAGATAGTGAAGCCACAGATG
TATCTGACAAGAGCTTCACACTGATGCCTACTGCCTCGGACTTCAAGGGGCTAG
AATTCGAGCAATTATCTTGTTTACTAAAACTGAATACCTTGCTATCTCTTTGAT
ACATTTTTACAAAGCTGAATTAAAATGGTATAAATTAAATCACTTTTTCATCTG
ACCAGTAGTGGactagtgtgacgctgctgaccccttctttcccttctACAGat
ccaagctgtgaccggcgcctacacctgcagcccaagcttaccatggccttacca
gtgaccgccttgctcctgccgctggccttgctgctccacgccgccaggcctgac
atacagatgacacagagccctagcagtctgagcgccagtgtgggcgatagagtt
actatcacttgtagagcatccgagaacatatacagttacgtggcctggtatcag
caaaaacctggcaaagctcccaagttattgatttacaatgctaagagcttggcc
tctggggtgccatcgaggttcagcggtagcgggagcgggaccgacttcactctg
accatctcgagtctccagccggaggactttgcgacatactattgtcaacaccat
tacgtatcaccctggaccttcggcggcgggactaagttagagatcaagggtgga
ggaggatcaggcggcggtggatcaggaggaggagggtcacaagtgcagttacag
gaatcagggcccggcctggtgaagccaagtgaaaccctgagtctgacgtgcacg
gtttcaggatttagcctcacttcctacggtgtctcttggattcggcagccagcc
cattctgcactaatctctcgcgtgacaatgtcggtggacacgtccaagaatcaa
ttttcccttaaactgtcctccgtgaccgcagccgatacagcggtatattattgc
gcgcgacctcactacggatctagctatgtcggcgcgatggagtattgggcgct
ggcacaaccgtcaccgtttcttccgcaaccacgacgccagcgccgcgaccacca
acaccggcgcccaccatcgcgtcgcagcccctgtccctgcgccctgaggcgtgc
gtgctgctgtcccgtaaacgcagacgtcaacacggtcaactgtggtttccagaa
ggttttaaggtctccgaagcaagtaagaagaaaagacgtgaaccactgggagaa
gatagcgtcggtctgaaaccactcaagaatgccatggtttctaaactgagccag
ctgcagacggagctcctggcggccctgctggagtcaggggagcaaagagaggca
ctgctccaggcactgggcgagccggggccctacctcctggctggagaaggcccc
ctggacaaggggagtcctgcggcggcggtcgaggggagctggctgagctgccc
aatgggctgggggagactcggggctccgaggacgagaccgacgacgatgggaa
gacttcacgccaccatcctcaaagagctggagaacctcagccctgaggaggcg
gcccaccagaaagccgtggtggagaccctttctgcaggaggacccgtggcgtgtg
gcgaagatggtcaagtcctacctgcagcagcacaacatcccacagcgggaggtg
gtcgataccactggcctcaaccagtccacctgtcccaacacctcaacaagggc
actcccatgaagacgcagaagcgggccgccctgtacacctggtatgtccgcaag
cagcgagaggtggcgcagcagttcacccatgcagggcaggagggctgattgaa
gagcccacaggagatgagctaccaaccaagaaggggcggaggaaccgtttcaag
tggggccagcatcccagcagatcctgttccaggcctatgagaggcagaagaac
cctagcaaggaggagcgagaaacgctagtggaggagtgcaatagggcggaatgc
atccagagaggtgtgtcaccatcacaagcacaaggtctgggctccaacctcgtc
acggaggtgcgtgtctacaactggtttgccaaccggcgcaaagaagaagccttc
cggcacaagctggccatgacctgcagggatgagtttcccaccatggtgtttcct
tctgggcagatcagccaggcctcggccttggcccgggccctcccaagtcctg
cccaggctccagcccctgccctgctccagccatggtatcagctctggcccag
gccccagcccctgtcccagtcctagcccaggccctcctcaagctgtggcccca
cctgcccaagcccacccaagctggggaaggaacgctgtcagaggcctgctg
cagctgcagtttgatgatgaagacctgggggccttgcttggcaacagcacagac
ccagctgtgttcacagacctggcatccgtcgacaactccgagtttcagcagctg
ctgaaccagggcataccctgtggcccccacacaactgagcccatgctgatggag
taccctgaggctataactcgcctagtgacaggggcccagaggccccccgaccca
gaagacttctcctccattgcggacatggacttctcagccctgctgagtcagatc
agctcctaaaggAaataaaagatctttaatgaaaatAGATCTGTGTGTTGGTTT
TTTGTGTGaataaaaagatccagagctctagAGATCTGTGTGTTGGTTTTTTGTG
TGCGAGGGCAATCTGGCCCATCAAGTGGCCTTCGCCTCTGGGAGTAACAAAAAT
GCACTTCAAAATAGCTTCTGTAATCAAGCTGCATGGGTGGAGTACTCCCAGCT
GACTCCAGGAAGTTCTCTATCCAAAGCTATTCATTAGGCCAGAGCTGTGCAAAT
AATTAGTCACCCACTTGCTCCATAACCCTCCATGACAGCCCAGGCATTGAGTCC
AGGTGGGACCATCAAGCCATGCTCTGGTGGCTCATGCATTATCATAGAAATGGG |

| SEQ ID NO | Name | Sequence |
|---|---|---|
| | | AGGCTTTATTTATTTTACTAAAAAGAACAAAAACAACAGACTGCTGTCCTTTAG<br>ACAATAGGATCACGTCATCTGAGCCCTCTGTGCCCCAGGTGACAAGCCCAGCCC<br>CAAGTTCTCTTTCCTCAGCCTCCCCACACATGTTCTGGAGGAGATGGGCCCAGC<br>AGGCTGCTCTGAGGCCTGGCCCCTCGTAAGCCAAGCATGGCTC |
| 170 | AB-1014:<br>LG1_TTT_Fas + PTPN2<br>with flanking CDL<br>and homology arms | GAGCCATGCTTGGCTTACGAGGGCGACCAACCCATCAAACTCCCCGCCCCCAGC<br>ACTTTTATTTCTCCTCTTTAGGAAGTACACTTCAGTATCTTTGGCACAGTGCAT<br>GAGCACGACTAAAGTAAAACATCGCAGAAAACATAGCTTTAGTCTACCCTTCGT<br>GTCCTAAAAGGAAAACCAGTAGCTTCCCAGGCCACCGGAAGGGCAACACATGTC<br>CTCTGCAGTTTCTGCACACGGGAAGGTAAAGACAGAGAGAGGACCTACTCCTCA<br>ACACAGAAACATTTCAAAATCTTTCCTCGCCTGCAACCCAAGCTGAAGTCATTC<br>TCCCCAGAAATAACAAAAGTTGGAAGAGAAGCCGGAGACAGGATAGGTGCAGGA<br>AGCCCACACTTTGAGGGCAGCACTCAGACACCCTCTCCTGTGTGCAGGACGTGC<br>CGAATGTTCAGGTGCAATGAGAATGAGCCATGCTTGGCTTATAaGGTAcgactg<br>tgccttctagttgccagccatctgttgtttgccctccccgtgccttccttga<br>ccctggaaggtgccactcccactgtcctttcctaataaaatgaggaaattgcat<br>cgcattgtctgagtaggtgtcattctattctgggggtgggtgggcaggaca<br>gcaaggggaggattgggaagacaatagcaggcatgctggggatgcggtgggct<br>ctatgggataagcttgatatcgaattcatcgatgttaataattaacatatatgt<br>taatcattaacatatagttaattattaaccgctatgttaatgattaacaacggt<br>taataattaacatatatgttaatcattaacatataactagtctagagggtatat<br>aatgggggccactagtctactaccagagTtcatcgctagcgctaccggatccgc<br>caccATGGCCCTGCCAGTAACGGCTCTGCTGCTGCCACTTGCTCTGCTCCTCCA<br>TGCAGCCAGGCCTCAGTTGCAGTTACAGGAGAGCGGACCCGGTCTGGTTAAACC<br>GTCTGAAACACTGAGTTTGACATGTACAGTGTCCGGCGGCTCGATTTCAAACTC<br>TTACTATTGGGGCTGGATTAGGCAGCCTCCCGGGAAAGGGCTCGAGTGGATCGG<br>GTCCATATATCACTCAGGAAATACCTACTACAACCCAAGTCTTAAGTCTAGAGT<br>GACAATCAGTGTGGATACGTCCAAGAATCAATTCTCCCTGAAGCTCTCAAGCGT<br>GACCGCCGCCGACACCGCAGTGTATTATTGCGTAACTCAAGACGGTGTGGGCGC<br>TACCACTACCGAAGAGTATTGGGACAAGGCACTCTTGTCACAGTCTCCAGCGC<br>GGCAGCAaccacgacgccagcgccgcgaccaccaacaccggcgcccaccatcgc<br>gtcgcagccactgtcactgcgcccagaagcgtgccggccagcggcgggggcgc<br>agtgcacacgagggggctggacttcgcctgtgatatctacatctgggcgccctt<br>acggggcagaaagaaactcctgtatatattcaaacaaccatttatgagaccagt<br>acaaactactcaagaagaggacggctgtagctgccgatttccagaagaagaaga<br>aggaggatgtgaactgagagtgaagttcagcaggagcgcagacgcccccgcgta<br>ccagcagggccagaaccagctctataacgagctcaatctaggacgaagagagga<br>gtacgatgttttggacaagaggcgtggccgggaccctgagatgggggaaagcc<br>gagaaggaagaaccctcaggaaggcctgtacaatgaactgcagaaagataagat<br>gcacgatggcctttaccagggtctcagtacagccaccaaggacacctacgacgc<br>ccttcacatgcaggccctgcccctaggtaaaatcaacctctggattacaaaat<br>tgtgaaagattgactggtattcttaactatgttgctccttttacgctatgtgg<br>atacgctgctttaatgcctttgtatcatgctattgcttcccgtatggctttcat<br>tttctcctccttgtataaatcctggttgctgtctctttatgaggagttgtggcc<br>cgttgtcaggcaacgtggcgtggtgtgcactgtgtttgctgacgcaaccccac<br>tggttggggcattgccaccacctgtcagctccttccgggactttcgctttccc<br>cctccctattgccacggcggaactcatcgccgcctgccttgcccgctgctggac<br>aggggctcggctgttgggcactgacaattccgtggtgttgtcggggaaatcatc<br>gtccttttccttggctgctcgcctgtgttgccacctggattctgcgcgggacgtc<br>cttctgctacgtcccttcggccctcaatccagcggaccttccttcccgcggcct<br>gctgccggctctgcggcctcttccgcgtcttcgcttcgccctcagacgagtcg<br>gatctcccttgggccgcctccccgcctggatccttgacttgcggccaacttgt<br>ttattgcagcttataatggttacaaataaagcaatagcatcacaaatttcacaa<br>ataaagcatttttttcactgcattctagttgtggtttgtccaaactcatcaatg<br>tatcttatcatgtctgggatccttgacttgcggccgcaactccacctgcaaca<br>tgcgtgactgactgaggccgcgactctagagtcgaccggatctgcgatcgctcc<br>ggtgcccgtcagtgggcagagcgcacatcgcccacagtccccgagaagttgggg<br>ggaggggtcggcaattgaacgggtgcctagagaaggtggcgcggggtaaactgg<br>gaaagtgatgtcgtgtactggctccgccttttccccgagggtgggggagaaccg<br>tatataagtgcagtagtcgccgtgaacgttctttttcgcaacgggtttgccgcc<br>agaacacagctgaagcttcgaggggctcgcatctctccttcacgcgcccgccgc<br>cctacctgaggccgccatccacgccggttgagtcgcgttctgccgcctcccgcc<br>tgtggtgcctcctgaactgcgtccgccgtctaggtaaGTcgactcgttggatcc<br>CCACTACCCGGATCAACGCCCTAGGTTTATGTTTGGATGAACTGACATACGCGT<br>ATCCGTCTTAAGAATCTTTTCAAACACTAGTAGTGAAATATATATTTAAACTAGT<br>GTTTGAAAAGATTCTTATTACGGTAACGCGGAATTCGCAACTATTTTATCAATT<br>TTTTGCGTCGACACTTCAAGGGGCTTGCGGCCGCAACCATCTCCATGGCTGTTT<br>GAATGAGGCTTCAGTACTTTACAGAATCGTTGCCTGCACATCTTGGAAACACTT<br>GCTGGGATTACTTCGACTTCTTAACCCAACAGAAGGCTCGAGAAGGTATATTGC<br>TGTTGACAGTGAGCGCCAGTGTGAAGCTCTTGTCAGATAGTGAAGCCACAGATG<br>TATCTGACAAGAGCTTCACACTGATGCCTACTGCCTCGGACTTCAAGGGGCTAG<br>AATTCGAGCAATTATCTTGTTTACTAAAACTGAATACCTTGCTATCTCTTTGAT<br>ACATTTTTACAAAGCTGAATTAAAATGGTATAAATTAAATCACTTTTTCATCTG |

-continued

| SEQ ID NO | Name | Sequence |
|---|---|---|
| | | ACCAGTAGTGGactagtgtgacgctgctgaccccttttcttttcccttctACAGat<br>ccaagctgtgaccggcgcctacacctgcagcccaagcttTTTatggccttacca<br>gtgaccgccttgctcctgccgctggccttgctgctccacgccgccaggcctgac<br>atacagatgacacagagccctagcagtctgagcgcgccagtgtgggcgatagagtt<br>actatcacttgtagagcatccgagaacatatacagttacgtggcctggtatcag<br>caaaaacctggcaaagctcccaagttattgatttacaatgctaagagcttggcc<br>tctggggtgccatcgaggttcagcggtagcgggagcgggaccgacttcactctg<br>accatctcgagtctccagccggaggactttgcgacatactattgtcaacaccat<br>tacgtatcaccctggaccttcggcggcgggactaagttagagatcaagggtgga<br>ggaggatcaggcggcggtggatcaggaggaggagggtcacaagtgcagttacag<br>gaatcagggcccggcctggtgaagccaagtgaaaccctgagtctgacgtgcacg<br>gtttcaggatttagcctcacttcctacggtgtctcttggattcggcagccagcc<br>ggcaaagggctcgagtggattggggtgatctgggaagatggctcaacaaactat<br>cattctgcactaatctctcgcgtgacaatgtcggtggacacgtccaagaatcaa<br>ttttcccttaaactgtcctccgtgaccgcagccgatacagcggtatattattgc<br>gcgcgacctcactacggatctagctatgtcggcgcgatggtattggggcgct<br>ggcacaaccgtcaccgtttcttccgcaaccacgacgccagccgccgcgaccacca<br>acaccggcgccaccatcgcgtcgcagcccctgtccctgcgccctgaggcgtgc<br>ttcatgtacgtggcggcggccgcctttgtgcttctgttcttcgtgggctgcggg<br>gtgctgctgtcccgtaaacgcagacgtcaacacggtcaactgtggttccagaa<br>ggttttaaggtctccgaagcaagtaagaagaaaagacgtgaaccactgggagaa<br>gatagcgtcggtctgaaaccactcaagaatgccatggtttctaaactgagccag<br>ctgcagacggagctcctggcggccctgctggagtcagggctgagcaaagaggca<br>ctgctccaggcactgggcgagccgggcccctacctcctggctggagaaggcccc<br>ctggacaaggggagtcctgcggcggcggtcgaggggagctggctgagctgccc<br>aatgggctggggagactcggggctccgaggacgagaccgacgacgatggggaa<br>gacttcacgccacccatcctcaaagagctggagaacctcagccctgaggaggcg<br>gcccaccagaaagccgtggtggagaccctctgcaggaggacccgtggcgtgtg<br>gcgaagatggtcaagtcctacctgcagcagcacaacatcccacagcgggaggtg<br>gtcgataccactggcctcaaccagtcccacctgtcccaacacctcaacaagggc<br>actcccatgaagacgcagaagcgggccgccctgtacacctggtatgtccgcaag<br>cagcgagaggtggcgcagcagttcacccatgcagggcaggagggctgattgaa<br>gagcccacaggagatgagctaccaaccaagaaggggcggaggaaccgtttcaag<br>tggggcccagcatcccagcagatcctgttccaggcctatgagaggcagaagaac<br>cctagcaaggaggagcgagaaacgctagtggaggagtgcaatagggcggaatgc<br>atccagagaggtgtgtcaccatcacaagcacaaggtctgggctccaacctcgtc<br>acggaggtgcgtgtctacaactggtttgccaaccggcgcaaagaagaagccttc<br>cggcacaagctggccatgacctgcagggatgagtttcccaccatggtgtttcct<br>tctgggcagatcagccaggcctcggccttggcccggcccctccccaagtcctg<br>ccccaggctccagcccctgccctgctccagccatggtatcagctctggcccag<br>gccccagccctgtcccagtcctagccccaggccctcctcaagctgtggcccca<br>cctgccccaagcccacccaagctggggaaggaacgctgtcagaggccctgctg<br>cagctgcagtttgatgatgaagacctgggggccttgcttggcaacagcacagac<br>ccagctgtgttcacagacctggcatccgtcgacaactccgagtttcagcagctg<br>ctgaaccagggcatacctgtggccccccacacaactgagcccatgctgatgag<br>taccctgaggctataactcgcctagtgacaggggcccagaggcccccgaccca<br>gctcctgctccactgggggccccggggctcccaatggcctccttcaggagatg<br>gaagacttctcctccattgcggacatggacttctcagccctgctgagtcagatc<br>agctcctaaAGGACGGGTGGCATCCCTGTGACCCCTCCCCAGTGCCTCTCCTGG<br>CCCTGGAAGTTGCCACTCCAGTCCCACCAGCCTTGTCCTAATAAAATTAAGTT<br>GCATCATTTTGTCTGACTAGGTGTCCTTCTATAATATTATGGGTGGAGGGGGG<br>TGGTATGGAGCAAGGGGCAAGTTGGGAAGACAACCTGTAGGGCCTGCGGGGTCT<br>ATTGGGAACCAAGCTGGAGTGCAGTGGCACAATCTTGGCTCACTGCAATCTCCG<br>CCTCCTGGGTTCAAGCGATTCTCCTGCCTCAGCCTCCCGAGTTGTTGGGATTCC<br>AGGCATGCATGACCAGGCTCAGCTAATTTTTGTTTTTTTGGTAGAaACGGGGTT<br>TCACCATATTGGCCAGGCTGGTCTCCAACTCCTAATCTCAGGTGATCTACCCAC<br>CTTGGCCTCCCAAATTGCTGGGATTACAGGCGTGAACCACTGCTCCCttccctg<br>tccttcCGAGGGCAATCTGGCCCATCAAGTGGCCTTCGCCTCTGGGAGTAACAA<br>AAATGCACTTCAAAATAGCTTCTGTAATCAAGCTGCATGGGTGGAGTACTCCCC<br>AGCTGACTCCAGGAAGTTCTCTATCCAAAGCTATTCATTAGGCCAGAGCTGTGC<br>AAATAATTAGTCACCCACTTGCTCCATAACCCTCCATGACAGCCCAGGCATTGA<br>GTCCAGGTGGGACCATCAAGCCATGCTCTGGTGGCTCATGCATTATCATAGAAA<br>TGGGAGGCTTTATTTATTTTACTAAAAAGAACAAAAACAACAGACTGCTGTCCT<br>TTAGACAATAGGATCACGTCATCTGAGCCCTCTGTGCCCCAGGTGACAAGCCCA<br>GCCCCAAGTTCTCTTTCCTCAGCCTCCCCACACATGTTCTGGAGGAGATGGGCC<br>CAGCAGGCTGCTCTGAGGCCTGGCCCCTCGTAAGCCAAGCATGGCTCatcccaa<br>tggcgcgccgagcttggcgtaatcatggtcatagctgtt |
| 171 | AB-1015: LG1_Fas + PTPN2 with flanking CDL and homology arms | GAGCCATGCTTGGCTTACGAGGGCGACCAACCCATCAAACTCCCCGCCCCCAGC<br>ACTTTTATTTCTCCTCTTTAGGAAGTACACTTCAGTATCTTTGGCACAGTGCAT<br>GAGCACGACTAAAGTAAAACATCGCAGAAAACATAGCTTTAGTCTACCCTTCGT<br>GTCCTAAAAGGAAAACCAGTAGCTTCCCAGGCCACCGGAAGGGCAACACATGTC<br>CTCTGCAGTTTCTGCACACGGGAAGGTAAAGACAGAGAGAGGACCTACTCCTCA |

INFORMAL SEQUENCE LISTING

| SEQ ID NO | Name | Sequence |
|---|---|---|
| | | ACACAGAAACATTTCAAAATCTTTCCTCGCCTGCAACCCAAGCTGAAGTCATTC
TCCCCAGAAATAACAAAAGTTGGAAGAGAAGCCGGAGACAGGATAGGTGCAGGA
AGCCCACACTTTGAGGGCAGCACTCAGACACCCTCTCCTGTGTGCAGGACGTGC
CGAATGTTCAGGTGCAATGAGAATGAGCCATGCTTGGCTTATAaGGTAcgactg
tgccttctagttgccagccatctgttgtttgccccctccccgtgccttccttga
ccctggaaggtgccactcccactgtccttccctaataaaatgaggaaattgcat
cgcattgtctgagtaggtgtcattctattctggggggtggggtggggcaggaca
gcaaggggaggattgggaagacaatagcaggcatgctggggatgcggtgggct
ctatgggataagcttgatatcgaattcatcgatgttaataattaacatatatgt
taatcattaacatatagttaattattaaccgctatgttaatgattaacaacggt
taataattaacatatatgttaatcattaacatataactagtctagagggtatat
aatggggccactagtctactaccagagTtcatcgctagcgctaccggatccgc
caccATGGCCCTGCCAGTAACGGCTCTGCTGCTGCCACTTGCTCTGCTCCTCCA
TGCAGCCAGGCCTCAGTTGCAGTTACAGGAGAGCGGACCCGGTCTGGTTAAACC
GTCTGAAACACTGAGTTTGACATGTACAGTGTCCGGCGGCTCGATTTCAAACTC
TTACTATTGGGGCTGGATTAGGCAGCCTCCCGGGAAAGGGCTCGAGTGGATCGG
GTCCATATATCACTCAGGAAATACCTACTACAACCCAAGTCTTAAGTCTAGAGT
GACAATCAGTGTGGATACGTCCAAGAATCAATTCTCCCTGAAGCTCTCAAGCGT
GACCGCCGCCGACACCGCAGTGTATTATTGCGTAACTCAAGACGGTGTGGGCGC
TACCACTACCGAAGAGTATTGGGGACAAGGCACTCTTGTCACAGTCTCCAGCGC
GGCAGCAaccacgacgccagcgccgcgaccaccaacaccggcgccaccatcgc
gtcgcagccactgtcactgcgcccagaagcgtgccggccagcggcgggggcgc
agtgcacacgaggggggctggacttcgcctgtgatatctacatctgggcgcctt
ggccgggacttgtggggtccttctcctgtcactggttatcaccctttactgcaa
acggggcagaaagaaactcctgtatatattcaaacaaccatttatgagaccagt
acaaactactcaagaagaggacggctgtagctgccgatttccagaagaagaaga
aggaggatgtgaactgagagtgaagttcagcaggagcgcagacgcccccgcgta
ccagcagggccagaaccagctctataacgagctcaatctaggacgaagagagga
gtacgatgttttggacaagaggcgtggccgggaccctgagatgggggaaagcc
gagaaggaagaaccctcaggaaggcctgtacaatgaactgcagaaagataagat
ggccgaggcctacagtgagattgggatgaaaggcgagcgccggaggggcaaggg
gcacgatggcctttaccagggtctcagtacagccaccaaggacacctacgacgc
ccttcacatgcaggccctgccccctaggtaaaatcaacctctggattacaaaat
ttgtgaaagattgactggtattcttaactatgttgctcctttacgctatgtgg
atacgctgctttaatgcctttgtatcatgctattgcttcccgtatggctttcat
tttctcctccttgtataaatcctggttgctgtctctttatgaggagttgtggcc
tggttggggcattgccaccacctgtcagctccttccgggactttcgctttccc
cctcccattgccacggcggaactcatcgccgcctgccttgcccgctgctggac
aggggctcggctgttgggcactgacaattccgtggtgttgtcggggaaatcatc
gtcctttccttggctgctcgcctgtgttgccacctggattctgcgcgggacgtc
cttctgctacgtcccttcggccctcaatccagcggaccttccttcccgcggcct
gctgccggctctgcggcctcttccgcgtcttcgccttcgccctcagacgagtcg
gatctccctttgggccgcctccccgcctggatccttgacttgcggccaacttgt
ttattgcagcttataatggttacaaataaagcaatagcatcacaaatttcacaa
ataaagcatttttttcactgcattctagttgtggtttgtccaaactcatcaatg
tatcttatcatgtctgggatccttgacttgcggccgcaactcccacctgcaaca
tgcgtgactgactgaggccgcgactctagagtcgaccggatctgcgatcgctcc
ggtgcccgtcagtgggcagagcgcacatcgcccacagtccccgagaagttgggg
ggaggggtcggcaattgaacgggtgcctagagaaggtggcgcggggtaaactgg
gaaagtgatgtcgtgtactggctccgccttttcccgagggtggggagaaccg
tatataagtgcagtagtcgccgtgaacgttctttttcgcaacgggtttgccgcc
agaacacagctgaagcttcgaggggctcgcatctctccttcacgcgcccgccgc
cctacctgaggccgccatccacgccggttgagtcgcgttctgccgcctcccgc
tgtggtgcctcctgaactgcgtccgccgtctaggtaaGTcgactcgttggatcc
CCACTACCCGGATCAACGCCCTAGGTTTATGTTTGGATGAACTGACATACGCGT
ATCCGTCTTAAGAATCTTTTCAAACACTAGTAGTGAAATATATATTAAACTAGT
GTTTGAAAAGATTCTTATTACGGTAACGCGGAATTCGCAACTATTTTATCAATT
TTTTGCGTCGACACTTCAAGGGGCTTGCGGCCGCAACCATCTCCATGGCTGTTT
GAATGAGGCTTCAGTACTTTACAGAATCGTTGCCTGCACATCTTGGAAACACTT
GCTGGGATTACTTCGACTTCTTAACCCAACAGAAGGCTCGAGAAGGTATATTGC
TGTTGACAGTGAGCGCCAGTGTGAAGCTCTTGTCAGATAGTGAAGCCACAGATG
TATCTGACAAGAGCTTCACACTGATGCCTACTGCCTCGGACTTCAAGGGGCTAG
AATTCGAGCAATTATCTTGTTTACTAAAACTGAATACCTTGCTATCTCTTTGAT
ACATTTTTACAAAGCTGAATTAAAATGGTATAAATTAAATCACTTTTTCATCTG
ACCAGTAGTGGactagtgtgacgctgctgaccccttcttttcccttctACAGat
ccaagctgtgaccggcgcctacacctgcagcccaagcttaccatggccttacca
gtgaccgccttgctcctgccgctggccttgctgctccacgccgcaggcctgac
atacagatgacacagagccctagcagtctgagcgccagtgtgggcgatagagtt
actatcacttgtagagcatccgagaacatatacagttacgtggcctggtatcag
caaaaacctggcaaagctcccaagttattgatttacaatgctaagagcttggcc
tctggggtgccatcgaggttcagcggtagcgggagcgggaccgacttcactctg
accatctcgagtctccagccggaggactttgcgacatactattgtcaacaccat
tacgtatcacctggaccttcggcggcgggactaagttagagatcaagggtgga |

INFORMAL SEQUENCE LISTING

| SEQ ID NO | Name | Sequence |
|---|---|---|
| | | ggaggatcaggcggcggtggatcaggaggaggagggtcacaagtgcagttacag |
| | | gaatcagggcccggcctggtgaagccaagtgaaaccctgagtctgacgtgcacg |
| | | gtttcaggatttagcctcacttcctacggtgtctcttggattcggcagccagcc |
| | | ggcaaagggctcgagtggattgggtgatctgggaagatggctcaacaaactat |
| | | cattctgcactaatctctcgcgtgacaatgtcggtggacacgtccaagaatcaa |
| | | ttttcccttaaactgtcctccgtgaccgcagccgatacagcggtatattattgc |
| | | gcgcgacctcactacggatctagctatgtcggcgcgatggagtattgggcgct |
| | | ggcacaaccgtcaccgtttcttccgcaaccacgacgccagcgccgcgaccacca |
| | | acaccggcgcccaccatcgcgtcgcagcccctgtccctgcgcctgaggcgtgc |
| | | ttcatgtacgtggcggcggccgcctttgtgcttctgttcttcgtgggctgcggg |
| | | gtgctgctgtcccgtaaacgcagacgtcaacacggtcaactgtggtttccagaa |
| | | ggttttaaggtctccgaagcaagtaagaagaaaagacgtgaaccactgggagaa |
| | | gatagcgtcggtctgaaaccactcaagaatgccatggtttctaaactgagccag |
| | | ctgcagacggagctcctggcggccctgctggagtcagggctgagcaaagaggca |
| | | ctgctccaggcactgggcgagccggggccctacctcctggctggagaaggcccc |
| | | ctggacaaggggagtcctgcggcggcggtcgaggggagctggctgagctgccc |
| | | aatgggctgggggagactcggggctccgaggacgagaccgacgacgatgggga |
| | | gacttcacgccaccatcctcaaagagctggagaacctcagccctgaggaggcg |
| | | gcccaccagaaagccgtggtggagaccttctgcaggaggacccgtggcgtgtg |
| | | gcgaagatggtcaagtcctacctgcagcagcacaacatcccacagcgggaggtg |
| | | gtcgataccactggcctcaaccagtcccacctgtcccaacacctcaacaagggc |
| | | actcccatgaagacgcagaagcgggccgccctgtacacctggtatgtccgcaag |
| | | cagcgagaggtggcgcagcagttcacccatgcagggcagggagggctgattgaa |
| | | gagcccacaggagatgagctaccaaccaagaaggggcggaggaaccgtttcaag |
| | | tggggcccagcatcccagcagatcctgttccaggcctatgagaggcagaagaac |
| | | cctagcaaggaggagcgagaaacgctagtggaggagtgcaatagggcggaatgc |
| | | atccagagaggtgtgtcaccatcacaagcacaaggtctgggctccaacctcgtc |
| | | acggaggtgcgtgtctacaactggtttgccaaccggcgcaaagaagaagccttc |
| | | cggcacaagctggccatgacctgcagggatgagtttccaccatggtgtttcct |
| | | cccccaggctccagcccctgccctgctccagccatggtatcagctctggcccag |
| | | gccccagcccctgtcccagtcctagccccaggccctcctcaagctgtggcccca |
| | | cctgcccccaagcccacccaagctggggaaggaacgctgtcagaggccctgctg |
| | | cagctgcagtttgatgatgaagacctgggggccttgcttggcaacagcacagac |
| | | ccagctgtgttcacagacctggcatccgtcgacaactccgagtttcagcagctg |
| | | ctgaaccagggcatacctgtggcccccacacaactgagcccatgctgatggag |
| | | taccctgaggctataactcgcctagtgacaggggcccagaggccccccgaccca |
| | | gaagacttctcctccattgctggacatggacttctcagccctgctgagtcagatc |
| | | agctcctaaAGGAcgggtggcatccctgtgacccctccccagtgcctctcctgg |
| | | ccctggaagttgccactccagtgcccaccagccttgtcctaataaaattaagtt |
| | | gcatcattttgtctgactaggtgtccttctataatattatgggtggaggggg |
| | | tggtatggagcaaggggcaagttgggaagacaacctgtagggcctgcggggtct |
| | | attgggaaccaagctggagtgcagtggcacaatcttggctcactgcaatctccg |
| | | cctcctgggttcaagcgattctcctgcctcagcctcccgagttgttgggattcc |
| | | aggcatgcatgaccaggctcagctaattttgtttttttggtagaaacggggttt |
| | | tcaccatattggccaggctggtctccaactcctaatctcaggtgatctacccac |
| | | cttggcctcccaaattgctgggattacaggcgtgaaccactgctcccttccctg |
| | | tccttcCGAGGGCAATCTGGCCCATCAAGTGGCCTTCGCCTCTGGGAGTAACAA |
| | | AAATGCACTTCAAAATAGCTTCTGTAATCAAGCTGCATGGGTGGAGTACTCCCC |
| | | AGCTGACTCCAGGAAGTTCTCTATCCAAAGCTATTCATTAGGCCAGAGCTGTGC |
| | | AAATAATTAGTCACCCACTTGCTCCATAACCCTCCATGACAGCCCAGGCATTGA |
| | | GTCCAGGTGGGACCATCAAGCCATGCTCTGGTGGCTCATGCATTATCATAGAAA |
| | | TGGGAGGCTTTATTTATTTTACTAAAAAGAACAAAAACAACAGACTGCTGTCCT |
| | | TTAGACAATAGGATCACGTCATCTGAGCCCTCTGTGCCCCAGGTGACAAGCCCA |
| | | GCCCCAAGTTCTCTTTCCTCAGCCTCCCCACACATGTTCTGGAGGAGATGGGCC |
| | | CAGCAGGCTGCTCTGAGGCCTGGCCCCTCGTAAGCCAAGCATGGCTC |

---

SEQUENCE LISTING

Sequence total quantity: 333

```
SEQ ID NO: 1          moltype = AA  length = 7
FEATURE               Location/Qualifiers
source                1..7
                      mol_type = protein
                      organism = synthetic construct
SEQUENCE: 1
GFSLTSY                                                                    7

SEQ ID NO: 2          moltype = AA  length = 5
FEATURE               Location/Qualifiers
```

```
                        -continued source                  1..5
                        mol_type = protein
                        organism = synthetic construct
SEQUENCE: 2
WEDGS                                                               5

SEQ ID NO: 3            moltype = AA  length = 13
FEATURE                 Location/Qualifiers
source                  1..13
                        mol_type = protein
                        organism = synthetic construct
SEQUENCE: 3
PHYGSSYVGA MEY                                                      13

SEQ ID NO: 4            moltype = AA  length = 11
FEATURE                 Location/Qualifiers
source                  1..11
                        mol_type = protein
                        organism = synthetic construct
SEQUENCE: 4
RASENIYSYV A                                                        11

SEQ ID NO: 5            moltype = AA  length = 7
FEATURE                 Location/Qualifiers
source                  1..7
                        mol_type = protein
                        organism = synthetic construct
SEQUENCE: 5
NAKSLAS                                                             7

SEQ ID NO: 6            moltype = AA  length = 9
FEATURE                 Location/Qualifiers
source                  1..9
                        mol_type = protein
                        organism = synthetic construct
SEQUENCE: 6
QHHYVSPWT                                                           9

SEQ ID NO: 7            moltype = AA  length = 121
FEATURE                 Location/Qualifiers
source                  1..121
                        mol_type = protein
                        organism = synthetic construct
SEQUENCE: 7
QVQLQESGPG LVKPSETLSL TCTVSGFSLT SYGVSWIRQP AGKGLEWIGV IWEDGSTNYH    60
SALISRVTMS VDTSKNQFSL KLSSVTAADT AVYYCARPHY GSSYVGAMEY WGAGTTTVS    120
S                                                                   121

SEQ ID NO: 8            moltype = AA  length = 107
FEATURE                 Location/Qualifiers
source                  1..107
                        mol_type = protein
                        organism = synthetic construct
SEQUENCE: 8
DIQMTQSPSS LSASVGDRVT ITCRASENIY SYVAWYQQKP GKAPKLLIYN AKSLASGVPS    60
RFSGSGSGTD FTLTISSLQP EDFATYYCQH HYVSPWTFGG GTKLEIK                 107

SEQ ID NO: 9            moltype = AA  length = 243
FEATURE                 Location/Qualifiers
source                  1..243
                        mol_type = protein
                        organism = synthetic construct
SEQUENCE: 9
DIQMTQSPSS LSASVGDRVT ITCRASENIY SYVAWYQQKP GKAPKLLIYN AKSLASGVPS    60
RFSGSGSGTD FTLTISSLQP EDFATYYCQH HYVSPWTFGG GTKLEIKGGG GSGGGGSGGG   120
GSQVQLQESG PGLVKPSETL SLTCTVSGFS LTSYGVSWIR QPAGKGLEWI GVIWEDGSTN   180
YHSALISRVT MSVDTSKNQF SLKLSSVTAA DTAVYYCARP HYGSSYVGAM EYWGAGTTVT   240
VSS                                                                 243

SEQ ID NO: 10           moltype = AA  length = 7
FEATURE                 Location/Qualifiers
source                  1..7
                        mol_type = protein
                        organism = synthetic construct
SEQUENCE: 10
GIDLSLY                                                             7

SEQ ID NO: 11           moltype = AA  length = 5
FEATURE                 Location/Qualifiers
```

```
source                          1..5
                                mol_type = protein
                                organism = synthetic construct
SEQUENCE: 11
TDDGT                                                                        5

SEQ ID NO: 12                   moltype = AA   length = 9
FEATURE                         Location/Qualifiers
source                          1..9
                                mol_type = protein
                                organism = synthetic construct
SEQUENCE: 12
ETPLSPVNY                                                                    9

SEQ ID NO: 13                   moltype = AA   length = 117
FEATURE                         Location/Qualifiers
source                          1..117
                                mol_type = protein
                                organism = synthetic construct
SEQUENCE: 13
EVQLVESGGG LVQPGGSLRL SCAASGIDLS LYRMRWYRQA PGKGLELVAL ITDDGTSYYA           60
DSVKGRFTIS RDNAKNSVYL QMNSLRAEDT AVYYCNAETP LSPVNYWGQG TTVTVSS             117

SEQ ID NO: 14                   moltype = AA   length = 8
FEATURE                         Location/Qualifiers
source                          1..8
                                mol_type = protein
                                organism = synthetic construct
SEQUENCE: 14
GGSISNSY                                                                     8

SEQ ID NO: 15                   moltype = AA   length = 5
FEATURE                         Location/Qualifiers
source                          1..5
                                mol_type = protein
                                organism = synthetic construct
SEQUENCE: 15
YHSGN                                                                        5

SEQ ID NO: 16                   moltype = AA   length = 12
FEATURE                         Location/Qualifiers
source                          1..12
                                mol_type = protein
                                organism = synthetic construct
SEQUENCE: 16
QDGVGATTTE EY                                                               12

SEQ ID NO: 17                   moltype = AA   length = 121
FEATURE                         Location/Qualifiers
source                          1..121
                                mol_type = protein
                                organism = synthetic construct
SEQUENCE: 17
QLQLQESGPG LVKPSETLSL TCTVSGGSIS NSYYWGWIRQ PPGKGLEWIG SIYHSGNTYY           60
NPSLKSRVTI SVDTSKNQFS LKLSSVTAAD TAVYYCVTQD GVGATTTEEY WGQGTLVTVS          120
S                                                                          121

SEQ ID NO: 18                   moltype = AA   length = 27
FEATURE                         Location/Qualifiers
source                          1..27
                                mol_type = protein
                                organism = synthetic construct
SEQUENCE: 18
TTTPAPRPPT PAPTIASQPL SLRPEAC                                               27

SEQ ID NO: 19                   moltype = AA   length = 22
FEATURE                         Location/Qualifiers
source                          1..22
                                mol_type = protein
                                organism = synthetic construct
SEQUENCE: 19
FMYVAAAAFV LLFFVGCGVL LS                                                    22

SEQ ID NO: 20                   moltype = AA   length = 43
FEATURE                         Location/Qualifiers
source                          1..43
                                mol_type = protein
                                organism = synthetic construct
SEQUENCE: 20
```

```
RKRRRQHGQL WFPEGFKVSE ASKKKRREPL GEDSVGLKPL KNA              43

SEQ ID NO: 21              moltype = AA  length = 283
FEATURE                    Location/Qualifiers
source                     1..283
                           mol_type = protein
                           organism = synthetic construct
SEQUENCE: 21
MVSKLSQLQT ELLAALLESG LSKEALLQAL GEPGPYLLAG EGPLDKGESC GGGRGELAEL  60
PNGLGETRGS EDETDDDGED FTPPILKELE NLSPEEAAHQ KAVVETLLQE DPWRVAKMVK 120
SYLQQHNIPQ REVVDTTGLN QSHLSQHLNK GTPMKTQKRA ALYTWYVRKQ REVAQQFTHA 180
GQGGLIEEPT GDELPTKKGR RNRFKWGPAS QQILFQAYER QKNPSKEERE TLVEECNRAE 240
CIQRGVSPSQ AQGLGSNLVT EVRVYNWFAN RRKEEAFRHK LAM                  283

SEQ ID NO: 22              moltype = AA  length = 191
FEATURE                    Location/Qualifiers
source                     1..191
                           mol_type = protein
                           organism = synthetic construct
SEQUENCE: 22
DEFPTMVFPS GQISQASALA PAPPQVLPQA PAPAPAPAMV SALAQAPAPV PVLAPGPPQA  60
VAPPAPKPTQ AGEGTLSEAL LQLQFDDEDL GALLGNSTDP AVFTDLASVD NSEFQQLLNQ 120
GIPVAPHTTE PMLMEYPEAI TRLVTGAQRP PDPAPAPLGA PGLPNGLLSG DEDFSSIADM 180
DFSALLSQIS S                                                   191

SEQ ID NO: 23              moltype = AA  length = 477
FEATURE                    Location/Qualifiers
source                     1..477
                           mol_type = protein
                           organism = synthetic construct
SEQUENCE: 23
MVSKLSQLQT ELLAALLESG LSKEALLQAL GEPGPYLLAG EGPLDKGESC GGGRGELAEL  60
PNGLGETRGS EDETDDDGED FTPPILKELE NLSPEEAAHQ KAVVETLLQE DPWRVAKMVK 120
SYLQQHNIPQ REVVDTTGLN QSHLSQHLNK GTPMKTQKRA ALYTWYVRKQ REVAQQFTHA 180
GQGGLIEEPT GDELPTKKGR RNRFKWGPAS QQILFQAYER QKNPSKEERE TLVEECNRAE 240
CIQRGVSPSQ AQGLGSNLVT EVRVYNWFAN RRKEEAFRHK LAMTCRDEFP TMVFPSGQIS 300
QASALAPAPP QVLPQAPAPA PAPAMVSALA QAPAPVPVLA PGPPQAVAPP APKPTQAGEG 360
TLSEALLQLQ FDDEDLGALL GNSTDPAVFT DLASVDNSEF QQLLNQGIPV APHTTEPMLM 420
EYPEAITRLV TGAQRPPDPA PAPLGAPGLP NGLLSGDEDF SSIADMDFSA LLSQISS    477

SEQ ID NO: 24              moltype = AA  length = 813
FEATURE                    Location/Qualifiers
source                     1..813
                           mol_type = protein
                           organism = synthetic construct
SEQUENCE: 24
DIQMTQSPSS LSASVGDRVT ITCRASENIY SYVAWYQQKP GKAPKLLIYN AKSLASGVPS  60
RFSGSGSGTD FTLTISSLQP EDFATYYCQH HYVSPWTFGG GTKLEIKGGG GSGGGGSGGG 120
GSQVQLQESG PGLVKPSETL SLTCTVSGFS LTSYGVSWIR QPAGKGLEWI GVIWEDSTN  180
YHSALISRVT MSVDTSKNQF SLKLSSVTAA DTAVYYCARP HYGSSYVGAM EYWGAGTTVT 240
VSSATTTPAP RPPTPAPTIA SQPLSLRPEA CFMYVAAAAF VLLFFVGCGV LLSRKRRRQH 300
GQLWFPEGFK VSEASKKKRR EPLGEDSVGL KPLKNAMVSK LSQLQTELLA ALLESGLSKE 360
ALLQALGEPG PYLLAGEGPL DKGESCGGGR GELAELPNGL GETRGSEDET DDDGEDFTPP 420
ILKELENLSP EEAAHQKAVV ETLLQEDPWR VAKMVKSYLQ QHNIPQREVV DTTGLNQSHL 480
SQHLNKGTPM KTQKRAALYT WYVRKQREVA QQFTHAGQGG LIEEPTGDEL PTKKGRRNRF 540
KWGPASQQIL FQAYERQKNP SKEERETLVE ECNRAECIQR GVSPSQAQGL GSNLVTEVRV 600
YNWFANRRKE EAFRHKLAMT CRDEFPTMVF PSGQISQASA LAPAPPQVLP QAPAPAPAPA 660
MVSALAQAPA PVPVLAPGPP QAVAPPAPKP TQAGEGTLSE ALLQLQFDDE DLGALLGNST 720
DPAVFTDLAS VDNSEFQQLL NQGIPVAPHT TEPMLMEYPE AITRLVTGAQ RPPDPAPAPL 780
GAPGLPNGLL SGDEDFSSIA DMDFSALLSQ ISS                            813

SEQ ID NO: 25              moltype = AA  length = 834
FEATURE                    Location/Qualifiers
source                     1..834
                           mol_type = protein
                           organism = synthetic construct
SEQUENCE: 25
MALPVTALLL PLALLLHAAR PDIQMTQSPS SLSASVGDRV TITCRASENI YSYVAWYQQK  60
PGKAPKLLIY NAKSLASGVP SRFSGSGSGT DFTLTISSLQ PEDFATYYCQ HHYVSPWTFG 120
GGTKLEIKGG GGSGGGGSGG GGSQVQLQES GPGLVKPSET LSLTCTVSGF SLTSYGVSWI 180
RQPAGKGLEW IGVIWEDGST NYHSALISRV TMSVDTSKNQ FSLKLSSVTA ADTAVYYCAR 240
PHYGSSYVGA MEYWGAGTTV TVSSATTTPA PRPPTPAPTI ASQPLSLRPE ACFMYVAAAA 300
FVLLFFVGCG VLLSRKRRRQ HGQLWFPEGF KVSEASKKKR REPLGEDSVG LKPLKNAMVS 360
KLSQLQTELL AALLESGLSK EALLQALGEP GPYLLAGEGP LDKGESCGGG RGELAELPNG 420
LGETRGSEDE TDDDGEDFTP PILKELENLS PEEAAHQKAV VETLLQEDPW RVAKMVKSYL 480
QQHNIPQREV VDTTGLNQSH LSQHLNKGTP MKTQKRAALY TWYVRKQREV AQQFTHAGQG 540
GLIEEPTGDE LPTKKGRRNR FKWGPASQQI LFQAYERQKN PSKEERETLV EECNRAECIQ 600
RGVSPSQAQG LGSNLVTEVR VYNWFANRRK EEAFRHKLAM TCRDEFPTMV FPSGQISQAS 660
ALAPAPPQVL PQAPAPAPAP AMVSALAQAP APVPVLAPGP PQAVAPPAPK PTQAGEGTLS 720
```

```
EALLLQLQFDD EDLGALLGNS TDPAVFTDLA SVDNSEFQQL LNQGIPVAPH TTEPMLMEYP   780
EAITRLVTGA QRPPDPAPAP LGAPGLPNGL LSGDEDFSSI ADMDFSALLS QISS         834

SEQ ID NO: 26           moltype = AA  length = 45
FEATURE                 Location/Qualifiers
source                  1..45
                        mol_type = protein
                        organism = synthetic construct
SEQUENCE: 26
TTTPAPRPPT PAPTIASQPL SLRPEACRPA AGGAVHTRGL DFACD                   45

SEQ ID NO: 27           moltype = AA  length = 24
FEATURE                 Location/Qualifiers
source                  1..24
                        mol_type = protein
                        organism = synthetic construct
SEQUENCE: 27
IYIWAPLAGT CGVLLLSLVI TLYC                                          24

SEQ ID NO: 28           moltype = AA  length = 42
FEATURE                 Location/Qualifiers
source                  1..42
                        mol_type = protein
                        organism = synthetic construct
SEQUENCE: 28
KRGRKKLLYI FKQPFMRPVQ TTQEEDGCSC RFPEEEEGGC EL                      42

SEQ ID NO: 29           moltype = AA  length = 112
FEATURE                 Location/Qualifiers
source                  1..112
                        mol_type = protein
                        organism = synthetic construct
SEQUENCE: 29
RVKFSRSADA PAYQQGQNQL YNELNLGRRE EYDVLDKRRG RDPEMGGKPR RKNPQEGLYN    60
ELQKDKMAEA YSEIGMKGER RRGKGHDGLY QGLSTATKDT YDALHMQALP PR           112

SEQ ID NO: 30           moltype = AA  length = 347
FEATURE                 Location/Qualifiers
source                  1..347
                        mol_type = protein
                        organism = synthetic construct
SEQUENCE: 30
QLQLQESGPG LVKPSETLSL TCTVSGGSIS NSYYWGWIRQ PPGKGLEWIG SIYHSGNTYY    60
NPSLKSRVTI SVDTSKNQFS LKLSSVTAAD TAVYYCVTQD GVGATTTEEY WGQGTLVTVS   120
SAAATTTPAP RPPTPAPTIA SQPLSLRPEA CRPAAGGAVH TRGLDFACDI YIWAPLAGTC   180
GVLLLSLVIT LYCKRGRKKL LYIFKQPFMR PVQTTQEEDG CSCRFPEEEE GGCELRVKFS   240
RSADAPAYQQ GQNQLYNELN LGRREEYDVL DKRRGRDPEM GGKPRRKNPQ EGLYNELQKD   300
KMAEAYSEIG MKGERRRGKG HDGLYQGLST ATKDTYDALH MQALPPR                 347

SEQ ID NO: 31           moltype = AA  length = 343
FEATURE                 Location/Qualifiers
source                  1..343
                        mol_type = protein
                        organism = synthetic construct
SEQUENCE: 31
EVQLVESGGG LVQPGGSLRL SCAASGIDLS LYRMRWYRQA PGKGLELVAL ITDDGTSYYA    60
DSVKGRFTIS RDNAKNSVYL QMNSLRAEDT AVYYCNAETP LSPVNYWGQG TTVTVSSAAA   120
TTTPAPRPPT PAPTIASQPL SLRPEACRPA AGGAVHTRGL DFACDIYIWA PLAGTCGVLL   180
LSLVITLYCK RGRKKLLYIF KQPFMRPVQT TQEEDGCSCR FPEEEEGGCE LRVKFSRSAD   240
APAYQQGQNQ LYNELNLGRR EEYDVLDKRR GRDPEMGGKP RRKNPQEGLY NELQKDKMAE   300
AYSEIGMKGE RRRGKGHDGL YQGLSTATKD TYDALHMQAL PPR                     343

SEQ ID NO: 32           moltype = AA  length = 368
FEATURE                 Location/Qualifiers
source                  1..368
                        mol_type = protein
                        organism = synthetic construct
SEQUENCE: 32
MALPVTALLL PLALLLHAAR PQLQLQESGP GLVKPSETLS LTCTVSGGSI SNSYYWGWIR    60
QPPGKGLEWI GSIYHSGNTY YNPSLKSRVT ISVDTSKNQF SLKLSSVTAA DTAVYYCVTQ   120
DGVGATTTEE YWGQGTLVTV SSAAATTTPA PRPPTPAPTI ASQPLSLRPE ACRPAAGGAV   180
HTRGLDFACD IYIWAPLAGT CGVLLLSLVI TLYCKRGRKK LLYIFKQPFM RPVQTTQEED   240
GCSCRFPEEE EGGCELRVKF SRSADAPAYQ QGQNQLYNEL NLGRREEYDV LDKRRGRDPE   300
MGGKPRRKNP QEGLYNELQK DKMAEAYSEI GMKGERRRGK GHDGLYQGLS TATKDTYDAL   360
HMQALPPR                                                            368

SEQ ID NO: 33           moltype = AA  length = 364
FEATURE                 Location/Qualifiers
source                  1..364
```

```
                            mol_type = protein
                            organism = synthetic construct
SEQUENCE: 33
MALPVTALLL PLALLLHAAR PEVQLVESGG GLVQPGGSLR LSCAASGIDL SLYRMRWYRQ      60
APGKGLELVA LITDDGTSYY ADSVKGRFTI SRDNAKNSVY LQMNSLRAED TAVYYCNAET     120
PLSPVNYWGQ GTTVTVSSAA ATTTPAPRPP TPAPTIASQP LSLRPEACRP AAGGAVHTRG     180
LDFACDIYIW APLAGTCGVL LLSLVITLYC KRGRKKLLYI FKQPFMRPVQ TTQEEDGCSC     240
RFPEEEGGC ELRVKFSRSA DAPAYQQGQN QLYNELNLGR REEYDVLDKR RGRDPEMGGK      300
PRRKNPQEGL YNELQKDKMA EAYSEIGMKG ERRRGKGHDG LYQGLSTATK DTYDALHMQA     360
LPPR                                                                 364

SEQ ID NO: 34               moltype = AA  length = 21
FEATURE                     Location/Qualifiers
source                      1..21
                            mol_type = protein
                            organism = synthetic construct
SEQUENCE: 34
MALPVTALLL PLALLLHAAR P                                               21

SEQ ID NO: 35               moltype = AA  length = 10
FEATURE                     Location/Qualifiers
source                      1..10
                            mol_type = protein
                            organism = synthetic construct
SEQUENCE: 35
EQKLISEEDL                                                            10

SEQ ID NO: 36               moltype = DNA  length = 2439
FEATURE                     Location/Qualifiers
source                      1..2439
                            mol_type = other DNA
                            organism = synthetic construct
SEQUENCE: 36
gacatacaga tgacacagag ccctagcagt ctgagcgcca gtgtgggcga tagagttact      60
atcacttgta gagcatccga gaacatatac agttacgtgg cctgtatca gcaaaaacct     120
ggcaaagctc ccaagttatt gatttacaat gctaagagct tggcctctgg ggtgccatcg    180
aggttcagcg gtagcgggag cgggaccgac ttcactctga ccatctcgag tctccagccg    240
gaggactttg cgacatacta ttgtcaacac cattacgtat caccctggac cttcggcggc    300
gggactaagt tagagatcaa gggtggagga ggatcaggtg gcggtggatc aggaggagga    360
gggtcacaag tgcagttaca ggaatcaggg cccggcctgg tgaagccaag tgaaaccctg    420
agtctgacgt gcacggtttc aggatttagc ctcacttcct acggtgtctc ttggattcgg    480
cagccagccg gcaaagggct cgagtggatt ggggtgatct gggaagatgg ctcaacaaac    540
tatattctg cactaatctc tcgcgtgaca atgtcggtgg acacgtccaa gaatcaattt     600
tcccttaaac tgtcctccgt gaccgcagcc gatacagcgg tatattattg cgcgcgacct    660
cactacggat ctagctatgt cggcgcgatg gagtattggg gcgctggcac aaccgtcacc    720
gttcttccg caaccacgac gccagcgccg cgaccaccaa caccggcgcc caccatcgcg     780
tcgcagcccc tgtccctgcg ccctgaggcg tgcttcatgt acgtggcgga ggccgccttt    840
gtgcttctgt tcttcgtggg ctgcggggtg ctgctgtccc gtaaacgcag acgtcaacac    900
ggtcaactgt ggtttccaga aggttttaag gtctccgaag caagtaagaa gaaaagacgt    960
gaaccactgg gagaagatag cgtcggtctg aaaccactca gaatgccat ggtttctaaa    1020
ctgagccagc tgcagacgga gctcctgagc gccctgctgg agtcagggct gagcaaagag   1080
gcactgctcc aggcactggg cgagccgggg ccctacctcc tggctggaga aggcccctg    1140
gacaagggg agtcctgcgg cggcggtcga ggggagctgg ctgagctgcc caatgggctg    1200
ggggagactc ggggctccga ggacgagacc gacgacgatg ggaagacttc cacgccaccc   1260
atcctcaaag agctggagaa cctcagccct gaggaggcgg cccaccagaa agccgtggtg   1320
gagacccttc tgcaggagga cccgtggcgt gtggcgaaga tggtcaagtc ctacctgcag   1380
cagcacaaca tccacagcg ggaggtggtc gataccactg gcctcaacca gtcccacctg    1440
tcccaacacc tcaacaaggg cactcccatg aagacgcaga agcgggccgc cctgtacacc   1500
tggtatgtcc gcaagcagcg agaggtggcg cagcagttca ccatgcgcag gcagggaggg   1560
ctgattgaag agcccacagg agatgagcta ccaaccaaga agggggcggaa gaaccgtttc   1620
aagtgggcc cagcatccca gcagatcctg ttccaggcct atgagaggca gaagaaccct   1680
agcaaggagg agcgagaaac gctagtggag gagtgcaata gggcggaatg catccagaga   1740
ggtgtgtcac catcacaagc acaaggtctg gctccaacc tcgtcacgga ggtgcgtgtc    1800
tacaactggt ttgccaaccg gcgcaaagaa gaagccttca agtggcaagt gccatgaac    1860
tgcagggatg agtttcccac catggtgttt ccttctgggc agatcagcca ggcctcggcc   1920
ttggccccgg ccctcccca gtcctgccc caggctccag ccctgcccc tgctccagcc     1980
atggtatcag ctctggccca ggcccagcc cctgtcccag tcctagcccc aggccctcct    2040
caagctgtgg cccacctgc ccccaagccc acccaagctg gggaaggaac gctgtcgag    2100
gccctgctgc agctgcagtt tgatgatgaa gacctggggc ccttgcttgg caacagcaca   2160
gacccagctg tgttcacaga cctggcatcc gtcgacaact ccgagtttca gcagctgctg   2220
aaccagggca tacctgtggc ccccacaca actgagccca tgctgatgga gtaccctgag   2280
gctataactc gcctagtgac agggggccag aggccccg acccagctcc tgctccactg    2340
ggggccccgg ggctcccaaa tggcctcctt tcaggagatg aagacttctc ctccattgcg   2400
gacatggact tctcagccct gctgagtcag atcagctcc                          2439

SEQ ID NO: 37               moltype = DNA  length = 1041
FEATURE                     Location/Qualifiers
source                      1..1041
                            mol_type = other DNA
```

```
                        organism = synthetic construct
SEQUENCE: 37
cagttgcagt tacaggagag cggacccggt ctggttaaac cgtctgaaac actgagtttg    60
acatgtacag tgtccggcgg ctcgatttca aactcttact attggggctg gattaggcag   120
cctcccggga aagggctcga gtggatcggg tccatatatc actcaggaaa tacctactac   180
aacccaagtc ttaagtctag agtgacaatc agtgtggata cgtccaagaa tcaattctcc   240
ctgaagctct caagcgtgac cgccgccgac accgcagtgt attattgcgt aactcaagac   300
ggtgtgggcg ctaccactac cgaagagtat tggggacaag cactcttgt cacagtctcc    360
agcgcggcag caaccacgac gccagcgccg cgaccaccaa caccggcgcc caccatccgg   420
tcgcagccac tgtcactgcg cccagaagcg tgccggccag cggcggggg cgcagtgcac    480
acgagggggc tggacttcgc ctgtgatatc tacatctggg cgcccttggc cgggacttgt   540
ggggtccttc tcctgtcact ggttatcacc ctttactgca aacggggcag aaagaaactc   600
ctgtatatat tcaaacaacc atttatgaga ccagtacaaa ctactcaaga agaggacggc   660
tgtagctgcc gatttccaga agaagaagaa ggaggatgtg aactgagagt gaagttcagc   720
aggagcgcag acgccccgc gtaccagcag ggccagaacc agctctataa cgagctcaat    780
ctaggacgaa gagaggagta cgatgttttg gacaagaggc gtggccggga ccctgagatg   840
gggggaaagc cgagaaggaa gaaccctcag gaaggcctgt acaatgaact gcagaaagat   900
aagatggcgg aggcctacag tgagattggg atgaaaggcg agcgccggag gggcaagggg   960
cacgatggcc tttaccaggg tctcagtaca gccaccaagg acacctacga cgcccttcac  1020
atgcaggccc tgccccctag g                                            1041

SEQ ID NO: 38              moltype = DNA  length = 1029
FEATURE                    Location/Qualifiers
source                     1..1029
                           mol_type = other DNA
                           organism = synthetic construct
SEQUENCE: 38
gaagttcagc tcgtggagag tggaggcggg ttagtgcaac ccggcgggtc tttgagattg    60
agttgtgctg cgtctggaat tgacctgtcc ctgtaccgaa tgaggtggta tcgacaagca   120
ccgggcaaag ggctggaact cgtggctcta atcaccgatg acgtacaag ctactactg    180
gactccgtca agggccgttt cacaatatca cgcgataacg ccaaaaatag cgtgtatcta   240
cagatgaaca gtctgcgagc cgaggatacc gccgtgtatt actgcaatgc cgagacacct   300
ctgtcgccag ttaactattg gggtcaggga actacggtaa ctgtctcaag cgcggcagca   360
accacgacgc cagcgccgcg accaccaaca ccggcgccca ccatcgcgtc gcagccactg   420
tcactgcgcc cagaagcgtg ccggccagca cggcggggcg cagtgcacac gaggggctg    480
gacttcgcct gtgatatcta catctgggcg cccttggccg gacttgtgg ggtccttctc    540
ctgtcactgg ttatcaccct ttactgcaaa cggggcagaa agaaactcct gtatatattc   600
aaacaaccat ttatgagacc agtacaaact actcaagaag aggacggctg tagctgccga   660
tttccagaag aagaaggagg atgtgaactg agagtgagtt cagcag gagcgcagac      720
gccccgcgt accagcaggg ccagaaccag ctctataacg agctcaatct aggacgaaga   780
gaggagtacg atgttttgga caagaggcgt ggccgggacc ctgagatggg ggaaagccg    840
agaaggaaga accctcagga aggcctgtac aatgaactgc agaaagataa gatggcggag   900
gcctacagtg agattgggat gaaaggcgag cgccggaggg gcaaggggca cgatggcctt   960
taccagggtc tcagtacagc caccaaggac acctacgacg cccttcacat gcaggccctg  1020
cccccctagg                                                         1029

SEQ ID NO: 39              moltype = RNA  length = 3696
FEATURE                    Location/Qualifiers
source                     1..3696
                           mol_type = mRNA
                           organism = Homo sapiens
SEQUENCE: 39
ctcttctccc gcgggttggt ggacccgctc agtacggagt tggggaagct ctttcacttc    60
ggaggattgc tcaacaacca tgctgggcat ctggaccctc ctacctctgg ttcttacgtc   120
tgttgctaga ttatcgtcca aaagtgttaa tgcccaagtg actgacatca actccaaggg   180
attggaattg aggaagactg ttactacagt tgagactcag aacttggaag gcctgcatca   240
tgatggccaa ttctgccata gccctgtcc tccaggtgaa aggaaagcta gggactgcac   300
agtcaatggg gatgaaccag actgcgtgcc ctgccagaa gggaaggagt acacagacaa    360
agcccatttt tcttccaaat gcagaagatg tagattgtgt gatgaaggac atggcttaga   420
agtggaaata aactgcaccc ggaccccagaa taccaagtgc agatgtaaac caaacttttt  480
ttgtaactct actgtatgtg aacactgtga cccttgcacc aaatgtgaac atggaatcat   540
caaggaatgc acactcacca gcaacaccaa gtgcaaagag aaggatcca gatctaactt    600
ggggtggctt tgtcttcttc ttttgccaat tccactaatt gttttggtga agagaaagga   660
agtacagaaa acatgcagaa aggaaacc aagttctcatg aatctccaac                720
tttaaatcct gaaacagtgg caataaattt atctgatgtt gacttgagta atatatatca   780
cactattgct ggagtcatga cactaagtca agttaaaggc tttgttcgaa agaatggtgt   840
caatgaagcc aaaatagatg agatcaagaa tgacaatgtc caagacacag cagaacagaa   900
agttcaactg cttcgtaatt ggcatcaact tcatggaaaa aagaagct atgacacatt    960
gattaaagat ctcaaaaaag ccaatctttg tactcttgca gagaaaattc agactatcat  1020
cctcaaggac attactagtg actcagaaaa ttcaaacttc agaaatgaaa tccaaagctt  1080
ggtctagagt gaaaaacaac aaattcagtt ctgagtatat gcaattagtg tttgaaagaa  1140
ttcttaatag ctggctgtaa atactgcttg gttttttact gggtacattt tatcatttat  1200
tagcgctgaa gagccaacat atttgtgat ttttaatatc tcatgattct gcctccaagg   1260
atgttttaaa tctagttggg aaaacaaact tcatcaagaa taaatgcagt ggcatgctaa  1320
gtacccaaat aggagtgtat gcagaggatg aaagattaag attatgctct ggcatctaac  1380
atatgattct gtagtatgaa tgtaatcagt gtatgttagt acaaatgtct atccacaggc  1440
taacccccact ctatgaatca atagaagaag ctatgacctt tgctgaaat atcagttact   1500
gaacaggcag gccactttgc ctctaaatta cctctgataa ttctagagat tttaccatat  1560
ttctaaactt tgtttataac tctgagaaga tcatatttat gtaaagtata tgtatttgag  1620
```

```
tgcagaattt aaataaggct ctacctcaaa gaccttttgca cagtttattg gtgtcatatt   1680
atacaatatt tcaattgtga attcacatag aaaacattaa attataatgt ttgactatta   1740
tatatgtgta tgcattttac tggctcaaaa ctacctactt ctttctcagg catcaaaagc   1800
attttgagca ggagagtatt actagagctt tgccacctct ccattttttgc cttggtgctc   1860
atcttaatgg cctaatgcac ccccaaacat ggaaatatca ccaaaaaata cttaatagtc   1920
caccaaaagg caagactgcc cttagaaatt ctagcctggt ttggagatac taactgctct   1980
cagagaaagt agctttgtga catgtcatga acccatgttt gcaatcaaag atgataaaat   2040
agattcttat ttttccccca cccccgaaaa tgttcaataa tgtcccatgt aaaacctgct   2100
acaaatggca gcttatacat agcaatggta aaatcatcat ctggatttag gaattgctct   2160
tgtcataccc ccaagtttct aagatttaag attctcctta ctactatcct acgtttaaat   2220
atctttgaaa gtttgtatta aatgtgaatt ttaagaaata atatttatat ttctgtaaat   2280
gtaaactgtg aagatagtta taaactgaag cagatacctg gaaccaccta agaacttcc    2340
atttatggag gatttttttg ccccttgtgt ttggaattat aaaatatagg taaaagtacg   2400
taattaaata atgtttttgg tatttctggt tttctcttt ttggtagggg cttgcttttt    2460
ggttttgtct tccttttctc taactgatgc taaatataac ttgtctttaa tgcttcttgg   2520
atcccttaga aggtacttcc ttttttaacct taacccttt agtagttaaa taattatttc    2580
cataggttgc tattgccaag aagacctctt ccaaacagca catgattatt cgtcaaacag   2640
tttcgtattc cagatactgg aatgtggata agaaagtata catttcaagg ggtaggtttt   2700
attattaaga aagccaaatg aggattttga aatattcttt cctgcatatt atccattcta   2760
gctacatgct ggccagtggg ccaccttttct tttctgcaat ttaatgctag taatatattc    2820
tatttaaccc atgagtccca aagtattagc atttcaacat gtaagcatgt cggtaagata   2880
gttgtgcttt gcttagggtt ccctcctgtg ttatgtctg gaaagtgtct ttaggcagaa     2940
agtctgagtg atcacagggt tcactcatta atttctcttt tctgagccat catagtctgt   3000
gctgtctgct ctccagttttt ctatttctag acagaagtag ggcaagttag gtactagtta  3060
ttcttcatgg ccagaagtgc aagttctact ttgcaagaca agattaagtt agagaacacc   3120
ctattccact ttggtgaact cagagcaaga actttggtt cctttgggag gaagacagtg    3180
gagaagtctt tgtacttggt gatgtggttt ttttcctcat ggcttcacct agtggcccca   3240
agcatgactt ctcccatgtc aatgagcaca gccacattcc cgagttgagg tgaccccacg   3300
gtccagaatc atcctcattc tggtgaacct ggttctcttt gtggtgggca tactgggtag   3360
gagaatcacc caaaggtcac cctgagctg cagaaaaaaa cctatttgc agaaggagct     3420
cacagatcac attgaaagca ttgcatattc aaacatcttg gtcttcttta ttggcatgcc   3480
cacagggtct tctgacctct gattagatca gacactttt agatattgaa tcatcagttt    3540
ctgtacaact atctgaataa ggtatataat caatgaaatt tagaattttt ttctatgctt   3600
actcctgatt ggtaatttgt ttgggtttag aattctatac aaggccattt gtaattttcc   3660
tcagcacttt aaaaatatta aaccatgttt tcttaa                             3696
```

```
SEQ ID NO: 40          moltype = RNA   length = 3470
FEATURE                Location/Qualifiers
source                 1..3470
                       mol_type = mRNA
                       organism = Homo sapiens
SEQUENCE: 40
gcatgcgccg cagcgccagc gctctccccg gatcgtgcgg ggcctgagcc tctccgccgg   60
cgcaggctct gctcgcgcca gctcgctccc gcagccatgc ccaccaccat cgagcgggag   120
ttcgaagagt tggatactca gcgtcgctgg cagccgctgt acttggaaat tcgaaatgag   180
tcccatgact atcctcatag agtggccaag tttccagaaa acagaaatcg aaacagatac   240
agagatgtaa gcccatatga tcacagtcgt gttaaactgc aaaatgctga gaatgattat   300
attaatgcca gtttagttga catagaagag gcacaaagga gttacatctt aacacagggt   360
ccacttccta cacacatgctg ccattttctgg cttatgggttt ggcagcagaa gaccaaagca   420
gttgtcatgc tgaaccgcat tgtggagaaa gaatcggtta atgtgcaca gtactggcca   480
acagatgacc aagagatgct gtttaaagaa acaggattca gtgtgaagct cttgtcagaa   540
gatgtgaagt cgtattatac agtacatcta ctacaattag aaaatatcaa tagtggtgaa   600
accagaacaa tatctcactt tcattatact acctggccag attttggagt ccctgaatca   660
ccagcttcat ttctcaattt cttgttaaa gtgagagaat ctggctcctt gaaccctgac   720
catgggcctg cggtgatcca ctgtagtgca ggcattgggc gctctggcac cttctctctg   780
gtagacactt gtcttgtttt gatggaaaaa ggagatgata ttaacataaa acaagtgtta   840
ctgaacatga gaaaataccg aatgggtctt attcagaccc cagatcaact gagattctca   900
tacatggcta aatagaaggg agcaaaatgt ataagggag attctagtat acagaaacga   960
tggaaagaac tttctaagga agacttatct cctgcctttg atcattccac aaacaaaata   1020
atgactgaaa aatacaatgg gaacagaata ggtctagaag aagaaaaact gacaggtgac   1080
cgatgtacag gactttcctc taaaatgcaa gatacaatgg aggagaacag tgagagtgct   1140
ctacggaaac gtattcgaga ggacagaaag gccaccacag ctcagaaggt gcagcagatg   1200
aaacagaggc taaatgagaa tgaacgaaaa agaaaaaggt ggtatattg gcaacctatt   1260
ctcactaaga tgggggttat gtcagtcatt ttggttggcg cttttgttgg ctggacactg   1320
ttttttcagc aaaatgccct ataaacaatt aattttgccc agcaagcttc tgcactagta   1380
actgacagtg ctacattaat catagggttt tgtctgcagc aaacgcctca tatcccaaaa   1440
acggtgcagt agaatagaca tcaaccagat aagtgatatt tacagtcaca agcccaacat   1500
ctcaggactc ttgactgcag gttcctctga accccaaact gtaaatggct gtctaaaata   1560
aagacattca tgtttgttaa aaactggtaa attttgcaac tgtattcata catgtcaaac   1620
acagtatttc acctgaccaa cattgagata tcctttatca caggatttgt ttttggaggc   1680
tatctggatt ttaacctgca cttgatataa gcaataaata ttgtggtttt atctacgtta   1740
ttggaaagaa aatgacattt aaataatgtg tgtaatgtat aatgtactat tgacatgggc   1800
atcaaacactt ttattcttaa gcatttcagg gtaaatatat tttataagta tctatttaat    1860
cttttgtagt taactgtact tttaagagc tcaatttgaa aatctgtta ctaaaaaaat     1920
aaattgtatg tcgattgaat tgtactggat acattttcca tttttctaaa gagaagtttg   1980
atatgagcag ttagaagttg gaataagcaa tttctactat atattgcatt tctttttatgt   2040
tttacagttt tccccatttt aaaagaaaa gcaaacaaag aaacaaagt ttttcctaaa      2100
aatatctttg aaggaaaatt ctccttactg ggatagtcag gtaaacagtt ggtcaagact   2160
ttgtaaagaa attggtttct gtaaatccca ttattgatat gtttattttt catgaaaatt   2220
```

```
tcaatgtagt tggggtagat tatgatttag gaagcaaaag taagaagcag catttttatga  2280
ttcataattt cagtttacta gactgaagtt ttgaagtaaa cacttttcag tttcttttcta  2340
cttcaataaa tagtatgatt atatgcaaac cttacattgt cattttaact taatgaatat  2400
ttttttaaagc aaactgttta atgaatttaa ctgctcattt gaatgctagc tttcctcaga  2460
tttcaacatt ccattcagtg tttaatttgt cttacttaaa cttgaaattg ttgttacaaa  2520
tttaattgct aggaggcatg gatagcatac attattatgg atagcatacc ttatttcagt  2580
ggttttcaaa ctatgctcat tggatgtcca ggtgggtcaa gaggtacctt tcaaccacag  2640
catctctgcc ttgtctcttt atatgccaca taagatttct gcataaggct taagtatttt  2700
aaaggggggca gttatcattt aaaaacagtt tggtcgggcg cggtggctca tgcctgtaat  2760
cccagcactt tgggaggctg aagtgggcag atcacctgag gtcaggagtt caagaccagc  2820
ctggccaacg tggtgaaaca ccatctctac taaaaatgca aaaattagct gggcatggtg  2880
gagggcacct gtaatctcag ctactcagga ggctgaggta ggagaattgc ttgaacccag  2940
gagatggagg ttgcagtgag ctgagatcac gtcactgcac tccagccagg gcgacagagc  3000
gagactccat ctcaaaagaa acaaacaaaa aaaacagttt gggccgggtg tggtggctca  3060
cgcttgtaat cccagcactt cggaaggcca aggcgggcgg atcacgaggt caagagatgg  3120
agactgtcct ggccaacatg gtgaaatccc ttctttacta aaaatacaaa aattatctgg  3180
gcgtggtggt gcatgcctgt agtcccagct ccttgggagg ctaaggcagg agaatcactt  3240
gaacccggga ggcagaggtt gcagtgagcc gagattgcac cactgcactc cagcctggca  3300
acagagcaag acttcgtctc aaaaaaaaaa aaaaaaaaag tttgaaaacc attggtatag  3360
atagatattt tgaattgatt tgcatagtct ccttgaatgt gttaaattat gttgaaagta  3420
tgaaagcagg atgtaggtgg tactacatat taaataagat ttatataaca              3470

SEQ ID NO: 41        moltype = RNA   length = 4076
FEATURE              Location/Qualifiers
source               1..4076
                     mol_type = mRNA
                     organism = Homo sapiens
SEQUENCE: 41
ctcttcttct taaacaaacc acaaacggat gtgagggaag gaaggtgttt cttttactcc  60
tgagcccaga cacctcactc tgttccgtct aagcttgttt tgctgaacac ttttttttaa  120
aaaaggaaaa agaaaaggag ttgcttgatg tgagagtgaa atggacgtaa gattttatcc  180
acctccagcc cagcccgccg ctgcgcccga cgctccctgt ctgggacctt ctccctgcct  240
ggaccctac tattgcaaca gtttgacgg tgagaacatg tatatgagca tgacagagcc  300
gagccggac tatgtgccag ccagccagtc ctaccctggt ccaagcctgg aaagtgaaga  360
cttcaacatt ccaccaatta ctcctccttc cctcccagac cactcgctgg tgcacctgga  420
tgaagttgag tctggttacc attctctgtg tcacccatg aaccataatg gcctgctacc  480
atttcatcca caaaacatgg acctccctga aatcacagtc tccaatatgc tgggccagga  540
tggaacactg ctttctaatt ccatttctgt gatgccagat atacgaaacc cagaaggaac  600
tcagtacagt tcccatcctc agatggcagc catgagccta agggccagc ctgcagacat  660
caggcagcag ccaggaatga tgccacatgg ccagctgact accattaacc agtcacagct  720
aagtgctcaa cttggtttga atatgggagg aagcaatgtt ccccacaact caccatctcc  780
acctggaagc aagtctgcaa ctccttcacc atccagttca gtgcatgaag atgaaggcga  840
tgatacctct aagatcaatg gtggagaaa gcggcctgcc tctgatatgg ggaaaaaacc  900
aaaaactccc aaaaagaaga agaagaagga tcccaatgaa ccccagaagc ctgtgtctgc  960
ctatgcgtta ttctttcgtg atactcaggc cgccatcaag ggccaaaatc caaacgctac  1020
cttttggcgaa gtctctaaaa ttgtggcttc aatgtgggac ggtttaggag aagagcaaaa  1080
acaggtctat aaaaagaaaa ccgaggctgc gaagaaggat tacctgaaga aactcgcaga  1140
atacagagcc agccttgtat ccaagagcta cagtgaacct gttgacgtga agacatctca  1200
acctcctcag ctgatcaatt cgaagccgtc ggtgttccat gggcccagcc aggcccactc  1260
ggccctgtac ctaagttccc actatcacca caaccgggga atgaatcctc acctaactgc  1320
catgcatcct agtctcccca ggaacatagc ccccaagccg aataaccaaa tgccagtgac  1380
tgtctctata gcaaacatgg ctgtgtcccc tcctcctccc ctccagatca gcccgcctct  1440
tcaccagcat ctcaacatgc agcagcacca gccgctcacc atgcagcagc ccttgggaa  1500
ccagctcccc atgcaggtcc agtctgcctt acactcaccc accatgcagc aaggattac  1560
tcttcaaccc gactatcaga ctattatcaa tcctacatct cagctgcac aagttgtcac  1620
ccaggcaatg gagtatgtgc gttcggggtg cagaaatcct ccccacaac cggtggactg  1680
gaataacgac tactcagta gtgggggcat cagagggac aaagcactgt accttactgg  1740
agaatctgaa cacctcttct ttccactgag gaattcaggg aagtgtttc accatggatt  1800
gcttgtgaca gtcaaggcag ttctccattt tattagaaaa tacaagttgc taagcactta  1860
ggaccatttg agcttgtggg tcacccactc tggaagaaat agtcatgctt ctttattatt  1920
ttttttaatcc tttatggaca ttgtttttct tctccctga aggaaatttg gaccattcag  1980
attttatgtt ggttttttgc tgtgaagtgc tgcgctctag taactgcctt agcaactgta  2040
gatgtctcgg ataaaagtcc tggattttcc attggttttc ataatgggtg tttatatgaa  2100
actactaaag acttttttaaa tggcttgatg tagcagtcat agcaagttg taaatagcat  2160
ctatgttaca ctctcctaga gtataaaatg tgaatgtttt tgtagctaaa ttgtaattga  2220
aactggctca ttccagtttta ttgatttcac aatagggg aaattggcaa acattcatat  2280
ttttacttca ttttttaaaac aactgactga tagttctata ttttcaaaat atttgaaaat  2340
aaaaagtatt cccaagtgat tttaatttaa aaacaaattg gctttgtctc attgatcaga  2400
caaaaagaaa ctagtattaa gggaagcgca aacacattta ttttgtactg cagaaaaatt  2460
gcttttttgt atcactttt gtgtaatggt tagtaaatgt catttaagtc cttttatgta  2520
taaaactgcc aaatgcttac ctggtatttt attagatgca gaaacagatt ggaaacagct  2580
aaattacaac ttttacatat ggctctgtct tattgtttct tcatactgtg tctgtattta  2640
atcttttttt atggaacctg ttgcgcctat ttatgaaata taaatatag gtgttgtaa  2700
gtaaatttgt tagtatttga aagaggtttc ttgttttgtc taacttttgc tggcaaaaaa  2760
aaattcacgc ttggtgtgaa actttattta tttagttttt acagtaacat gaataaagcc  2820
aaacctgctt tcattttagc agcaaattaa agtaaccagt cctatttcct gcatttcttt  2880
ggttgatgca aacaaaaaac tattatatttt aagaacttta tttcttcata cgacataaca  2940
gaattgccct ccagtcaca caagctccaa gactaaacaa acagacaggt cctctgtctt  3000
aaaaaaggtta cttcttggtt ctcagctggt tctagtcaat tctgaaccac cacccccgc  3060
```

```
cccccgcaaa aaagtaaaag tcaaaccaaa cttcctcaag ctgcatgctt ttcacaaaat   3120
ccagaaagca tttaagaatt gaactagggg ctggaagaag tgaaaggaa gcatctaaaa    3180
atgaaaggtg agtaaccaga tagcaaaaga aaagggaaag ccatccaaat ttgaaagctg   3240
ttgatagaaa ttgagattct tgctgtcttt tgtgcctcta caagctacta ctcattccag   3300
aattcctggg tcttccaaga ggattcttaa ggtaccaaga atttgctagg gaaccaaaag   3360
tgcttgagaa tctgcctgag ggcttgcata gcttccacat taaaaaaaga aaaagctagc   3420
agatttactc cttttaggg gatcatatca agaaagttag tctggttgga aaccaagaga    3480
atggctgatg tctctttctt ggaatatgtg aaataaattt agcagtttaa ctaaatacaa   3540
atatatgcat tgtgtaatcc actcagaatt aaacagacaa aaggtatgct tgctttggaa   3600
tgatttagg cattgtacaa ccttgaatca cttgagcatg taataactaa taaataatgc    3660
agatccatgt gattattaaa atgactgtag ctgagagctc taattttcct gtcttgaaac   3720
tgtataagaa ctcatgtgat taagttcaca gtttattgtt tgtctgttta gtattttaga   3780
aatataccag cactactaat taactaatgt cttttattta ttatattatg ataaagtaaa   3840
aatttcactt gcattaagtc taaactgaga aggtaattac tgggaggaa atgagcagct    3900
ttgactttga caggcggttt gtgcaggaaa gcacagtgcc gtgttgttta cagctttct    3960
agcagctg tgcgaccagg gtagagagtg ttgaaattca ataccaaata cagtaaaaac     4020
aaatgtaaat aaaagaaaac acatcatcaa taaaactgtt attatgcgtg accgta       4076

SEQ ID NO: 42           moltype = DNA   length = 22
FEATURE                 Location/Qualifiers
source                  1..22
                        mol_type = other DNA
                        organism = synthetic construct
SEQUENCE: 42
tagatttaa acatccttgg ag                                             22

SEQ ID NO: 43           moltype = DNA   length = 22
FEATURE                 Location/Qualifiers
source                  1..22
                        mol_type = other DNA
                        organism = synthetic construct
SEQUENCE: 43
tagatttaa acatccttgg ag                                             22

SEQ ID NO: 44           moltype = DNA   length = 22
FEATURE                 Location/Qualifiers
source                  1..22
                        mol_type = other DNA
                        organism = synthetic construct
SEQUENCE: 44
ttactcttga tgaagtttgt tt                                            22

SEQ ID NO: 45           moltype = DNA   length = 22
FEATURE                 Location/Qualifiers
source                  1..22
                        mol_type = other DNA
                        organism = synthetic construct
SEQUENCE: 45
ttgaactttc tgttctgctg tg                                            22

SEQ ID NO: 46           moltype = DNA   length = 22
FEATURE                 Location/Qualifiers
source                  1..22
                        mol_type = other DNA
                        organism = synthetic construct
SEQUENCE: 46
ttgtctgtgt actccttccc tt                                            22

SEQ ID NO: 47           moltype = DNA   length = 22
FEATURE                 Location/Qualifiers
source                  1..22
                        mol_type = other DNA
                        organism = synthetic construct
SEQUENCE: 47
tctttgattg caaacatggg tt                                            22

SEQ ID NO: 48           moltype = DNA   length = 22
FEATURE                 Location/Qualifiers
source                  1..22
                        mol_type = other DNA
                        organism = synthetic construct
SEQUENCE: 48
ttgatctcat ctattttggc tt                                            22

SEQ ID NO: 49           moltype = DNA   length = 22
FEATURE                 Location/Qualifiers
source                  1..22
                        mol_type = other DNA
                        organism = synthetic construct
```

```
SEQUENCE: 49
ttaagaatct tttcaaacac ta                                                    22

SEQ ID NO: 50           moltype = DNA   length = 22
FEATURE                 Location/Qualifiers
source                  1..22
                        mol_type = other DNA
                        organism = synthetic construct
SEQUENCE: 50
ttctattgat tcatagagtg gg                                                    22

SEQ ID NO: 51           moltype = DNA   length = 22
FEATURE                 Location/Qualifiers
source                  1..22
                        mol_type = other DNA
                        organism = synthetic construct
SEQUENCE: 51
taatcttaat ctttcatcct ct                                                    22

SEQ ID NO: 52           moltype = DNA   length = 22
FEATURE                 Location/Qualifiers
source                  1..22
                        mol_type = other DNA
                        organism = synthetic construct
SEQUENCE: 52
ttaacttgac ttagtgtcat ga                                                    22

SEQ ID NO: 53           moltype = DNA   length = 22
FEATURE                 Location/Qualifiers
source                  1..22
                        mol_type = other DNA
                        organism = synthetic construct
SEQUENCE: 53
ttacataaat atgatcttct ca                                                    22

SEQ ID NO: 54           moltype = DNA   length = 22
FEATURE                 Location/Qualifiers
source                  1..22
                        mol_type = other DNA
                        organism = synthetic construct
SEQUENCE: 54
tacataaata tgatcttctc ag                                                    22

SEQ ID NO: 55           moltype = DNA   length = 22
FEATURE                 Location/Qualifiers
source                  1..22
                        mol_type = other DNA
                        organism = synthetic construct
SEQUENCE: 55
taaaaatcta caaatatgtt gg                                                    22

SEQ ID NO: 56           moltype = DNA   length = 22
FEATURE                 Location/Qualifiers
source                  1..22
                        mol_type = other DNA
                        organism = synthetic construct
SEQUENCE: 56
tttggtttac atctgcactt gg                                                    22

SEQ ID NO: 57           moltype = DNA   length = 321
FEATURE                 Location/Qualifiers
source                  1..321
                        mol_type = other DNA
                        organism = synthetic construct
SEQUENCE: 57
tgtttgaatg aggcttcagt actttacaga atcgttgcct gcacatcttg gaaacacttg            60
ctgggattac ttcgacttct aacccaaca gaaggctcga gaaggtatat tgctgttgac            120
agtgagcgat ccaaggatgt ttaaaatcta tagtgaagcc acagatgtat agattttaaa           180
catccttgga gtgcctactg cctcggactt caaggggcta gaattcgagc aattatcttg           240
tttactaaaa ctgaatacct tgctatctct ttgatacatt tttacaaagc tgaattaaaa           300
tggtataaat taaatcactt t                                                     321

SEQ ID NO: 58           moltype = DNA   length = 321
FEATURE                 Location/Qualifiers
source                  1..321
                        mol_type = other DNA
                        organism = synthetic construct
SEQUENCE: 58
tgtttgaatg aggcttcagt actttacaga atcgttgcct gcacatcttg gaaacacttg            60
```

```
ctgggattac ttcgacttct taacccaaca gaaggctcga gaaggtatat tgctgttgac    120
agtgagcgat ccaaggatgt ttaaaatcta tagtgaagcc acagatgtat agattttaaa    180
catccttgga gtgcctactg cctcggactt caaggggcta gaattcgagc aattatcttg    240
tttactaaaa ctgaatacct tgctatctct ttgatacatt tttacaaagc tgaattaaaa    300
tggtataaat taaatcactt t                                              321

SEQ ID NO: 59          moltype = DNA   length = 321
FEATURE                Location/Qualifiers
source                 1..321
                       mol_type = other DNA
                       organism = synthetic construct
SEQUENCE: 59
tgtttgaatg aggcttcagt actttacaga atcgttgcct gcacatcttg gaaacacttg     60
ctgggattac ttcgacttct taacccaaca gaaggctcga gaaggtatat tgctgttgac    120
agtgagcgca acaaacttca tcaagagtaa tagtgaagcc acagatgtat tactcttgat    180
gaagtttgtt ttgcctactg cctcggactt caaggggcta gaattcgagc aattatcttg    240
tttactaaaa ctgaatacct tgctatctct ttgatacatt tttacaaagc tgaattaaaa    300
tggtataaat taaatcactt t                                              321

SEQ ID NO: 60          moltype = DNA   length = 321
FEATURE                Location/Qualifiers
source                 1..321
                       mol_type = other DNA
                       organism = synthetic construct
SEQUENCE: 60
tgtttgaatg aggcttcagt actttacaga atcgttgcct gcacatcttg gaaacacttg     60
ctgggattac ttcgacttct taacccaaca gaaggctcga gaaggtatat tgctgttgac    120
agtgagcgaa cagcagaaca gaaagttcaa tagtgaagcc acagatgtat tgaactttct    180
gttctgctgt gtgcctactg cctcggactt caaggggcta gaattcgagc aattatcttg    240
tttactaaaa ctgaatacct tgctatctct ttgatacatt tttacaaagc tgaattaaaa    300
tggtataaat taaatcactt t                                              321

SEQ ID NO: 61          moltype = DNA   length = 321
FEATURE                Location/Qualifiers
source                 1..321
                       mol_type = other DNA
                       organism = synthetic construct
SEQUENCE: 61
tgtttgaatg aggcttcagt actttacaga atcgttgcct gcacatcttg gaaacacttg     60
ctgggattac ttcgacttct taacccaaca gaaggctcga gaaggtatat tgctgttgac    120
agtgagcgca gggaaggagt acacagacaa tagtgaagcc acagatgtat tgtctgtgta    180
ctccttccct ttgcctactg cctcggactt caaggggcta gaattcgagc aattatcttg    240
tttactaaaa ctgaatacct tgctatctct ttgatacatt tttacaaagc tgaattaaaa    300
tggtataaat taaatcactt t                                              321

SEQ ID NO: 62          moltype = DNA   length = 321
FEATURE                Location/Qualifiers
source                 1..321
                       mol_type = other DNA
                       organism = synthetic construct
SEQUENCE: 62
tgtttgaatg aggcttcagt actttacaga atcgttgcct gcacatcttg gaaacacttg     60
ctgggattac ttcgacttct taacccaaca gaaggctcga gaaggtatat tgctgttgac    120
agtgagcgca cccatgtttg caatcaaaga tagtgaagcc acagatgtat ctttgattgc    180
aaacatgggt tgcctactg cctcggactt caaggggcta gaattcgagc aattatcttg     240
tttactaaaa ctgaatacct tgctatctct ttgatacatt tttacaaagc tgaattaaaa    300
tggtataaat taaatcactt t                                              321

SEQ ID NO: 63          moltype = DNA   length = 321
FEATURE                Location/Qualifiers
source                 1..321
                       mol_type = other DNA
                       organism = synthetic construct
SEQUENCE: 63
tgtttgaatg aggcttcagt actttacaga atcgttgcct gcacatcttg gaaacacttg     60
ctgggattac ttcgacttct taacccaaca gaaggctcga gaaggtatat tgctgttgac    120
agtgagcgca gccaaaatag atgagatcaa tagtgaagcc acagatgtat tgatctcatc    180
tattttggct ttgcctactg cctcggactt caaggggcta gaattcgagc aattatcttg    240
tttactaaaa ctgaatacct tgctatctct ttgatacatt tttacaaagc tgaattaaaa    300
tggtataaat taaatcactt t                                              321

SEQ ID NO: 64          moltype = DNA   length = 321
FEATURE                Location/Qualifiers
source                 1..321
                       mol_type = other DNA
                       organism = synthetic construct
SEQUENCE: 64
tgtttgaatg aggcttcagt actttacaga atcgttgcct gcacatcttg gaaacacttg     60
ctgggattac ttcgacttct taacccaaca gaaggctcga gaaggtatat tgctgttgac    120
```

```
agtgagcgca gtgtttgaaa agattcttaa tagtgaagcc acagatgtat taagaatctt   180
ttcaaacact atgcctactg cctcggactt caaggggcta gaattcgagc aattatcttg   240
tttactaaaa ctgaatacct tgctatctct ttgatacatt tttacaaagc tgaattaaaa   300
tggtataaat taaatcactt t                                              321

SEQ ID NO: 65           moltype = DNA   length = 321
FEATURE                 Location/Qualifiers
source                  1..321
                        mol_type = other DNA
                        organism = synthetic construct
SEQUENCE: 65
tgtttgaatg aggcttcagt actttacaga atcgttgcct gcacatcttg gaaacacttg    60
ctgggattac ttcgacttct aacccaaca gaaggctcga aaggtatat tgctgttgac    120
agtgagcgac cactctatga atcaataga tagtgaagcc acagatgtat tctattgatt   180
catagagtgg gtgcctactg cctcggactt caaggggcta gaattcgagc aattatcttg   240
tttactaaaa ctgaatacct tgctatctct ttgatacatt tttacaaagc tgaattaaaa   300
tggtataaat taaatcactt t                                              321

SEQ ID NO: 66           moltype = DNA   length = 321
FEATURE                 Location/Qualifiers
source                  1..321
                        mol_type = other DNA
                        organism = synthetic construct
SEQUENCE: 66
tgtttgaatg aggcttcagt actttacaga atcgttgcct gcacatcttg gaaacacttg    60
ctgggattac ttcgacttct aacccaaca gaaggctcga aaggtatat tgctgttgac    120
agtgagcgcg aggatgaaag attaagatta tagtgaagcc acagatgtat aatcttaatc   180
tttcatcctc ttgcctactg cctcggactt caaggggcta gaattcgagc aattatcttg   240
tttactaaaa ctgaatacct tgctatctct ttgatacatt tttacaaagc tgaattaaaa   300
tggtataaat taaatcactt t                                              321

SEQ ID NO: 67           moltype = DNA   length = 321
FEATURE                 Location/Qualifiers
source                  1..321
                        mol_type = other DNA
                        organism = synthetic construct
SEQUENCE: 67
tgtttgaatg aggcttcagt actttacaga atcgttgcct gcacatcttg gaaacacttg    60
ctgggattac ttcgacttct aacccaaca gaaggctcga aaggtatat tgctgttgac    120
agtgagcgcc atgacactaa gtcaagtaa tagtgaagcc acagatgtat taacttgact   180
tagtgtcatg atgcctactg cctcggactt caaggggcta gaattcgagc aattatcttg   240
tttactaaaa ctgaatacct tgctatctct ttgatacatt tttacaaagc tgaattaaaa   300
tggtataaat taaatcactt t                                              321

SEQ ID NO: 68           moltype = DNA   length = 321
FEATURE                 Location/Qualifiers
source                  1..321
                        mol_type = other DNA
                        organism = synthetic construct
SEQUENCE: 68
tgtttgaatg aggcttcagt actttacaga atcgttgcct gcacatcttg gaaacacttg    60
ctgggattac ttcgacttct aacccaaca gaaggctcga aaggtatat tgctgttgac    120
agtgagcgcg agaagatcat atttatgtaa tagtgaagcc acagatgtat tacataaata   180
tgatcttctc atgcctactg cctcggactt caaggggcta gaattcgagc aattatcttg   240
tttactaaaa ctgaatacct tgctatctct ttgatacatt tttacaaagc tgaattaaaa   300
tggtataaat taaatcactt t                                              321

SEQ ID NO: 69           moltype = DNA   length = 321
FEATURE                 Location/Qualifiers
source                  1..321
                        mol_type = other DNA
                        organism = synthetic construct
SEQUENCE: 69
tgtttgaatg aggcttcagt actttacaga atcgttgcct gcacatcttg gaaacacttg    60
ctgggattac ttcgacttct aacccaaca gaaggctcga aaggtatat tgctgttgac    120
agtgagcgat gagaagatca tatttatgta tagtgaagcc acagatgtat acataaatat   180
gatcttctca gtgcctactg cctcggactt caaggggcta gaattcgagc aattatcttg   240
tttactaaaa ctgaatacct tgctatctct ttgatacatt tttacaaagc tgaattaaaa   300
tggtataaat taaatcactt t                                              321

SEQ ID NO: 70           moltype = DNA   length = 321
FEATURE                 Location/Qualifiers
source                  1..321
                        mol_type = other DNA
                        organism = synthetic construct
SEQUENCE: 70
tgtttgaatg aggcttcagt actttacaga atcgttgcct gcacatcttg gaaacacttg    60
ctgggattac ttcgacttct aacccaaca gaaggctcga aaggtatat tgctgttgac    120
agtgagcgac aacatatttg tagattttta tagtgaagcc acagatgtat aaaaatctac   180
```

```
aaatatgttg gtgcctactg cctcggactt caaggggcta gaattcgagc aattatcttg    240
tttactaaaa ctgaatacct tgctatctct tgatacatt  tttacaaagc tgaattaaaa   300
tggtataaat taaatcactt t                                              321

SEQ ID NO: 71           moltype = DNA  length = 321
FEATURE                 Location/Qualifiers
source                  1..321
                        mol_type = other DNA
                        organism = synthetic construct
SEQUENCE: 71
tgtttgaatg aggcttcagt actttacaga atcgttgcct gcacatcttg gaaacacttg    60
ctgggattac ttcgacttct taacccaaca gaaggctcga gaaggtatat tgctgttgac   120
agtgagcgac aagtgcagat gtaaaccaaa tagtgaagcc acagatgtat ttggtttaca   180
tctgcacttg gtgcctactg cctcggactt caaggggcta gaattcgagc aattatcttg   240
tttactaaaa ctgaatacct tgctatctct tgatacatt  tttacaaagc tgaattaaaa   300
tggtataaat taaatcactt t                                              321

SEQ ID NO: 72           moltype = DNA  length = 22
FEATURE                 Location/Qualifiers
source                  1..22
                        mol_type = other DNA
                        organism = synthetic construct
SEQUENCE: 72
tataatacga cttcacatct tc                                             22

SEQ ID NO: 73           moltype = DNA  length = 22
FEATURE                 Location/Qualifiers
source                  1..22
                        mol_type = other DNA
                        organism = synthetic construct
SEQUENCE: 73
tagaaagttc tttccatcgt tt                                             22

SEQ ID NO: 74           moltype = DNA  length = 22
FEATURE                 Location/Qualifiers
source                  1..22
                        mol_type = other DNA
                        organism = synthetic construct
SEQUENCE: 74
ttctatgtca actaaactgg ca                                             22

SEQ ID NO: 75           moltype = DNA  length = 22
FEATURE                 Location/Qualifiers
source                  1..22
                        mol_type = other DNA
                        organism = synthetic construct
SEQUENCE: 75
ttaaacagca tctcttggtc at                                             22

SEQ ID NO: 76           moltype = DNA  length = 22
FEATURE                 Location/Qualifiers
source                  1..22
                        mol_type = other DNA
                        organism = synthetic construct
SEQUENCE: 76
tcgaatttcc aagtacagcg gc                                             22

SEQ ID NO: 77           moltype = DNA  length = 22
FEATURE                 Location/Qualifiers
source                  1..22
                        mol_type = other DNA
                        organism = synthetic construct
SEQUENCE: 77
ttagaaagtt ctttccatcg tt                                             22

SEQ ID NO: 78           moltype = DNA  length = 22
FEATURE                 Location/Qualifiers
source                  1..22
                        mol_type = other DNA
                        organism = synthetic construct
SEQUENCE: 78
tagatgtact gtataatacg ac                                             22

SEQ ID NO: 79           moltype = DNA  length = 22
FEATURE                 Location/Qualifiers
source                  1..22
                        mol_type = other DNA
                        organism = synthetic construct
SEQUENCE: 79
```

```
tctgtatact agaatctccc tt                                              22

SEQ ID NO: 80            moltype = DNA   length = 22
FEATURE                  Location/Qualifiers
source                   1..22
                         mol_type = other DNA
                         organism = synthetic construct
SEQUENCE: 80
ttttatgtta atatcatctc ct                                              22

SEQ ID NO: 81            moltype = DNA   length = 22
FEATURE                  Location/Qualifiers
source                   1..22
                         mol_type = other DNA
                         organism = synthetic construct
SEQUENCE: 81
tgagaatctc agttgatctg gg                                              22

SEQ ID NO: 82            moltype = DNA   length = 22
FEATURE                  Location/Qualifiers
source                   1..22
                         mol_type = other DNA
                         organism = synthetic construct
SEQUENCE: 82
tctgacaaga gcttcacact ga                                              22

SEQ ID NO: 83            moltype = DNA   length = 22
FEATURE                  Location/Qualifiers
source                   1..22
                         mol_type = other DNA
                         organism = synthetic construct
SEQUENCE: 83
ttctattata gccatgtatg ag                                              22

SEQ ID NO: 84            moltype = DNA   length = 22
FEATURE                  Location/Qualifiers
source                   1..22
                         mol_type = other DNA
                         organism = synthetic construct
SEQUENCE: 84
tgatattttc taattgtagt ag                                              22

SEQ ID NO: 85            moltype = DNA   length = 321
FEATURE                  Location/Qualifiers
source                   1..321
                         mol_type = other DNA
                         organism = synthetic construct
SEQUENCE: 85
tgtttgaatg aggcttcagt actttacaga atcgttgcct gcacatcttg gaaacacttg     60
ctgggattac ttcgacttct aacccaaca gaaggctcga gaaggtatat tgctgttgac     120
agtgagcgaa agatgtgaag tcgtattata tagtgaagcc acagatgtat ataatacgac    180
ttcacatctt ctgcctactg cctcggactt caaggggcta gaattcgagc aattatcttg    240
tttactaaaa ctgaatacct tgctatctct ttgatacatt tttacaaagc tgaattaaaa    300
tggtataaat taaatcactt t                                              321

SEQ ID NO: 86            moltype = DNA   length = 321
FEATURE                  Location/Qualifiers
source                   1..321
                         mol_type = other DNA
                         organism = synthetic construct
SEQUENCE: 86
tgtttgaatg aggcttcagt actttacaga atcgttgcct gcacatcttg gaaacacttg     60
ctgggattac ttcgacttct aacccaaca gaaggctcga gaaggtatat tgctgttgac     120
agtgagcgca acgatggaaa gaactttcta tagtgaagcc acagatgtat agaaagttct    180
ttccatcgtt ttgcctactg cctcggactt caaggggcta gaattcgagc aattatcttg    240
tttactaaaa ctgaatacct tgctatctct ttgatacatt tttacaaagc tgaattaaaa    300
tggtataaat taaatcactt t                                              321

SEQ ID NO: 87            moltype = DNA   length = 321
FEATURE                  Location/Qualifiers
source                   1..321
                         mol_type = other DNA
                         organism = synthetic construct
SEQUENCE: 87
tgtttgaatg aggcttcagt actttacaga atcgttgcct gcacatcttg gaaacacttg     60
ctgggattac ttcgacttct aacccaaca gaaggctcga gaaggtatat tgctgttgac     120
agtgagcgcg ccagtttagt tgacatagaa tagtgaagcc acagatgtat tctatgtcaa    180
ctaaactggc atgcctactg cctcggactt caaggggcta gaattcgagc aattatcttg    240
tttactaaaa ctgaatacct tgctatctct ttgatacatt tttacaaagc tgaattaaaa    300
```

SEQ ID NO: 88          moltype = DNA   length = 321
FEATURE                Location/Qualifiers
source                 1..321
                       mol_type = other DNA
                       organism = synthetic construct
SEQUENCE: 88
tgtttgaatg aggcttcagt actttacaga atcgttgcct gcacatcttg gaaacacttg   60
ctgggattac ttcgacttct aacccaaca gaaggctcga gaaggtatat tgctgttgac   120
agtgagcgct gaccaagaga tgctgtttaa tagtgaagcc acagatgtat aaacagcat   180
ctcttggtca ttgcctactg cctcggactt caaggggcta gaattcgagc aattatcttg   240
tttactaaaa ctgaatacct tgctatctct tgatacatt tttacaaagc tgaattaaaa   300
tggtataaat taaatcactt t                                             321

SEQ ID NO: 89          moltype = DNA   length = 321
FEATURE                Location/Qualifiers
source                 1..321
                       mol_type = other DNA
                       organism = synthetic construct
SEQUENCE: 89
tgtttgaatg aggcttcagt actttacaga atcgttgcct gcacatcttg gaaacacttg   60
ctgggattac ttcgacttct aacccaaca gaaggctcga gaaggtatat tgctgttgac   120
agtgagcgac cgctgtactt ggaaattcga tagtgaagcc acagatgtat cgaatttcca   180
agtacagcgg ctgcctactg cctcggactt caaggggcta gaattcgagc aattatcttg   240
tttactaaaa ctgaatacct tgctatctct tgatacatt tttacaaagc tgaattaaaa   300
tggtataaat taaatcactt t                                             321

SEQ ID NO: 90          moltype = DNA   length = 321
FEATURE                Location/Qualifiers
source                 1..321
                       mol_type = other DNA
                       organism = synthetic construct
SEQUENCE: 90
tgtttgaatg aggcttcagt actttacaga atcgttgcct gcacatcttg gaaacacttg   60
ctgggattac ttcgacttct aacccaaca gaaggctcga gaaggtatat tgctgttgac   120
agtgagcgca cgatggaaag aactttctaa tagtgaagcc acagatgtat tagaaagttc   180
tttccatcgt ttgcctactg cctcggactt caaggggcta gaattcgagc aattatcttg   240
tttactaaaa ctgaatacct tgctatctct tgatacatt tttacaaagc tgaattaaaa   300
tggtataaat taaatcactt t                                             321

SEQ ID NO: 91          moltype = DNA   length = 321
FEATURE                Location/Qualifiers
source                 1..321
                       mol_type = other DNA
                       organism = synthetic construct
SEQUENCE: 91
tgtttgaatg aggcttcagt actttacaga atcgttgcct gcacatcttg gaaacacttg   60
ctgggattac ttcgacttct aacccaaca gaaggctcga gaaggtatat tgctgttgac   120
agtgagcgat cgtattatac agtacatcta tagtgaagcc acagatgtat agatgtactg   180
tataatacga ctgcctactg cctcggactt caaggggcta gaattcgagc aattatcttg   240
tttactaaaa ctgaatacct tgctatctct tgatacatt tttacaaagc tgaattaaaa   300
tggtataaat taaatcactt t                                             321

SEQ ID NO: 92          moltype = DNA   length = 321
FEATURE                Location/Qualifiers
source                 1..321
                       mol_type = other DNA
                       organism = synthetic construct
SEQUENCE: 92
tgtttgaatg aggcttcagt actttacaga atcgttgcct gcacatcttg gaaacacttg   60
ctgggattac ttcgacttct aacccaaca gaaggctcga gaaggtatat tgctgttgac   120
agtgagcgca gggagattct agtatacaga tagtgaagcc acagatgtat ctgtatacta   180
gaatctccct tgcctactg cctcggactt caaggggcta gaattcgagc aattatcttg   240
tttactaaaa ctgaatacct tgctatctct tgatacatt tttacaaagc tgaattaaaa   300
tggtataaat taaatcactt t                                             321

SEQ ID NO: 93          moltype = DNA   length = 321
FEATURE                Location/Qualifiers
source                 1..321
                       mol_type = other DNA
                       organism = synthetic construct
SEQUENCE: 93
tgtttgaatg aggcttcagt actttacaga atcgttgcct gcacatcttg gaaacacttg   60
ctgggattac ttcgacttct aacccaaca gaaggctcga gaaggtatat tgctgttgac   120
agtgagcgcg gagatgatat taacataaaa tagtgaagcc acagatgtat tttatgttaa   180
tatcatctcc ttgcctactg cctcggactt caaggggcta gaattcgagc aattatcttg   240
tttactaaaa ctgaatacct tgctatctct tgatacatt tttacaaagc tgaattaaaa   300
tggtataaat taaatcactt t                                             321

```
SEQ ID NO: 94          moltype = DNA   length = 321
FEATURE                Location/Qualifiers
source                 1..321
                       mol_type = other DNA
                       organism = synthetic construct
SEQUENCE: 94
tgtttgaatg aggcttcagt actttacaga atcgttgcct gcacatcttg gaaacacttg   60
ctgggattac ttcgacttct taacccaaca gaaggctcga gaaggtatat tgctgttgac  120
agtgagcgac cagatcaact gagattctca tagtgaagcc acagatgtat gagaatctca  180
gttgatctgg gtgcctactg cctcggactt caagggcta gaattcgagc aattatcttg   240
tttactaaaa ctgaataacct tgctatctct ttgatacatt tttacaaagc tgaattaaaa  300
tggtataaat taaatcactt t                                             321

SEQ ID NO: 95          moltype = DNA   length = 321
FEATURE                Location/Qualifiers
source                 1..321
                       mol_type = other DNA
                       organism = synthetic construct
SEQUENCE: 95
tgtttgaatg aggcttcagt actttacaga atcgttgcct gcacatcttg gaaacacttg   60
ctgggattac ttcgacttct taacccaaca gaaggctcga gaaggtatat tgctgttgac  120
agtgagcgcc agtgtgaagc tcttgtcaga tagtgaagcc acagatgtat ctgacaagag  180
cttcacactg atgcctactg cctcggactt caagggcta gaattcgagc aattatcttg   240
tttactaaaa ctgaataacct tgctatctct ttgatacatt tttacaaagc tgaattaaaa  300
tggtataaat taaatcactt t                                             321

SEQ ID NO: 96          moltype = DNA   length = 321
FEATURE                Location/Qualifiers
source                 1..321
                       mol_type = other DNA
                       organism = synthetic construct
SEQUENCE: 96
tgtttgaatg aggcttcagt actttacaga atcgttgcct gcacatcttg gaaacacttg   60
ctgggattac ttcgacttct taacccaaca gaaggctcga gaaggtatat tgctgttgac  120
agtgagcgat catacatggc tataatagaa tagtgaagcc acagatgtat tctattatag  180
ccatgtatga gtgcctactg cctcggactt caagggcta gaattcgagc aattatcttg   240
tttactaaaa ctgaataacct tgctatctct ttgatacatt tttacaaagc tgaattaaaa  300
tggtataaat taaatcactt t                                             321

SEQ ID NO: 97          moltype = DNA   length = 321
FEATURE                Location/Qualifiers
source                 1..321
                       mol_type = other DNA
                       organism = synthetic construct
SEQUENCE: 97
tgtttgaatg aggcttcagt actttacaga atcgttgcct gcacatcttg gaaacacttg   60
ctgggattac ttcgacttct taacccaaca gaaggctcga gaaggtatat tgctgttgac  120
agtgagcgat actacaatta gaaaatatca tagtgaagcc acagatgtat gatatttct   180
aattgtagta gtgcctactg cctcggactt caagggcta gaattcgagc aattatcttg   240
tttactaaaa ctgaataacct tgctatctct ttgatacatt tttacaaagc tgaattaaaa  300
tggtataaat taaatcactt t                                             321

SEQ ID NO: 98          moltype = DNA   length = 22
FEATURE                Location/Qualifiers
source                 1..22
                       mol_type = other DNA
                       organism = synthetic construct
SEQUENCE: 98
taaagtattc acaccaagcg tg                                             22

SEQ ID NO: 99          moltype = DNA   length = 22
FEATURE                Location/Qualifiers
source                 1..22
                       mol_type = other DNA
                       organism = synthetic construct
SEQUENCE: 99
tatgactgct acatcaagcc at                                             22

SEQ ID NO: 100         moltype = DNA   length = 22
FEATURE                Location/Qualifiers
source                 1..22
                       mol_type = other DNA
                       organism = synthetic construct
SEQUENCE: 100
ttaaatgaca tttactaacc at                                             22

SEQ ID NO: 101         moltype = DNA   length = 22
FEATURE                Location/Qualifiers
```

```
source                  1..22
                        mol_type = other DNA
                        organism = synthetic construct
SEQUENCE: 101
ttaaattaaa atcacttggg aa                                              22

SEQ ID NO: 102          moltype = DNA  length = 22
FEATURE                 Location/Qualifiers
source                  1..22
                        mol_type = other DNA
                        organism = synthetic construct
SEQUENCE: 102
tttgctcttc tcctaaaccg tc                                              22

SEQ ID NO: 103          moltype = DNA  length = 22
FEATURE                 Location/Qualifiers
source                  1..22
                        mol_type = other DNA
                        organism = synthetic construct
SEQUENCE: 103
ttagttaatt agtagtgctg gt                                              22

SEQ ID NO: 104          moltype = DNA  length = 22
FEATURE                 Location/Qualifiers
source                  1..22
                        mol_type = other DNA
                        organism = synthetic construct
SEQUENCE: 104
taggtgagga ttcattcccg gt                                              22

SEQ ID NO: 105          moltype = DNA  length = 22
FEATURE                 Location/Qualifiers
source                  1..22
                        mol_type = other DNA
                        organism = synthetic construct
SEQUENCE: 105
ttagtcttgg agcttgtgtg ac                                              22

SEQ ID NO: 106          moltype = DNA  length = 22
FEATURE                 Location/Qualifiers
source                  1..22
                        mol_type = other DNA
                        organism = synthetic construct
SEQUENCE: 106
tttaaattaa aatcacttgg ga                                              22

SEQ ID NO: 107          moltype = DNA  length = 22
FEATURE                 Location/Qualifiers
source                  1..22
                        mol_type = other DNA
                        organism = synthetic construct
SEQUENCE: 107
ttttaaatta aaatcacttg gg                                              22

SEQ ID NO: 108          moltype = DNA  length = 22
FEATURE                 Location/Qualifiers
source                  1..22
                        mol_type = other DNA
                        organism = synthetic construct
SEQUENCE: 108
ttcaattaca atttagctac aa                                              22

SEQ ID NO: 109          moltype = DNA  length = 22
FEATURE                 Location/Qualifiers
source                  1..22
                        mol_type = other DNA
                        organism = synthetic construct
SEQUENCE: 109
tttattattt cataaatagg cg                                              22

SEQ ID NO: 110          moltype = DNA  length = 22
FEATURE                 Location/Qualifiers
source                  1..22
                        mol_type = other DNA
                        organism = synthetic construct
SEQUENCE: 110
ttacaaactt gctatgactg ct                                              22

SEQ ID NO: 111          moltype = DNA  length = 22
```

```
FEATURE             Location/Qualifiers
source              1..22
                    mol_type = other DNA
                    organism = synthetic construct
SEQUENCE: 111
tattatttca taaataggcg ca                                          22

SEQ ID NO: 112      moltype = DNA  length = 321
FEATURE             Location/Qualifiers
source              1..321
                    mol_type = other DNA
                    organism = synthetic construct
SEQUENCE: 112
tgtttgaatg aggcttcagt actttacaga atcgttgcct gcacatcttg gaaacacttg   60
ctgggattac ttcgacttct taacccaaca gaaggctcga gaaggtatat tgctgttgac  120
agtgagcgaa cgcttggtgt gaatacttta tagtgaagcc acagatgtat aaagtattca  180
caccaagcgt gtgcctactg cctcggactt caaggggcta gaattcgagc aattatcttg  240
tttactaaaa ctgaatacct tgctatctct ttgatacatt tttacaaagc tgaattaaaa  300
tggtataaat taaatcactt t                                           321

SEQ ID NO: 113      moltype = DNA  length = 321
FEATURE             Location/Qualifiers
source              1..321
                    mol_type = other DNA
                    organism = synthetic construct
SEQUENCE: 113
tgtttgaatg aggcttcagt actttacaga atcgttgcct gcacatcttg gaaacacttg   60
ctgggattac ttcgacttct taacccaaca gaaggctcga gaaggtatat tgctgttgac  120
agtgagcgct ggcttgatgt agcagtcata tagtgaagcc acagatgtat atgactgcta  180
catcaagcca ttgcctactg cctcggactt caaggggcta gaattcgagc aattatcttg  240
tttactaaaa ctgaatacct tgctatctct ttgatacatt tttacaaagc tgaattaaaa  300
tggtataaat taaatcactt t                                           321

SEQ ID NO: 114      moltype = DNA  length = 321
FEATURE             Location/Qualifiers
source              1..321
                    mol_type = other DNA
                    organism = synthetic construct
SEQUENCE: 114
tgtttgaatg aggcttcagt actttacaga atcgttgcct gcacatcttg gaaacacttg   60
ctgggattac ttcgacttct taacccaaca gaaggctcga gaaggtatat tgctgttgac  120
agtgagcgct ggttagtaaa tgtcatttaa tagtgaagcc acagatgtat taaatgacat  180
ttactaacca ttgcctactg cctcggactt caaggggcta gaattcgagc aattatcttg  240
tttactaaaa ctgaatacct tgctatctct ttgatacatt tttacaaagc tgaattaaaa  300
tggtataaat taaatcactt t                                           321

SEQ ID NO: 115      moltype = DNA  length = 321
FEATURE             Location/Qualifiers
source              1..321
                    mol_type = other DNA
                    organism = synthetic construct
SEQUENCE: 115
tgtttgaatg aggcttcagt actttacaga atcgttgcct gcacatcttg gaaacacttg   60
ctgggattac ttcgacttct taacccaaca gaaggctcga gaaggtatat tgctgttgac  120
agtgagcgct cccaagtgat tttaatttaa tagtgaagcc acagatgtat taaattaaaa  180
tcacttggga atgcctactg cctcggactt caaggggcta gaattcgagc aattatcttg  240
tttactaaaa ctgaatacct tgctatctct ttgatacatt tttacaaagc tgaattaaaa  300
tggtataaat taaatcactt t                                           321

SEQ ID NO: 116      moltype = DNA  length = 321
FEATURE             Location/Qualifiers
source              1..321
                    mol_type = other DNA
                    organism = synthetic construct
SEQUENCE: 116
tgtttgaatg aggcttcagt actttacaga atcgttgcct gcacatcttg gaaacacttg   60
ctgggattac ttcgacttct taacccaaca gaaggctcga gaaggtatat tgctgttgac  120
agtgagcgaa cggtttagga gaagagcaaa tagtgaagcc acagatgtat ttgctcttct  180
cctaaaccgt ctgcctactg cctcggactt caaggggcta gaattcgagc aattatcttg  240
tttactaaaa ctgaatacct tgctatctct ttgatacatt tttacaaagc tgaattaaaa  300
tggtataaat taaatcactt t                                           321

SEQ ID NO: 117      moltype = DNA  length = 321
FEATURE             Location/Qualifiers
source              1..321
                    mol_type = other DNA
                    organism = synthetic construct
SEQUENCE: 117
tgtttgaatg aggcttcagt actttacaga atcgttgcct gcacatcttg gaaacacttg   60
```

```
ctgggattac ttcgacttct aacccaaca gaaggctcga gaaggtatat tgctgttgac    120
agtgagcgcc cagcactact aattaactaa tagtgaagcc acagatgtat tagttaatta    180
gtagtgctgg ttgcctactg cctcggactt caaggggcta gaattcgagc aattatcttg    240
tttactaaaa ctgaataccT tgctatctct ttgatacatt tttacaaagc tgaattaaaa    300
tggtataaat taaatcactt t                                              321

SEQ ID NO: 118           moltype = DNA   length = 321
FEATURE                  Location/Qualifiers
source                   1..321
                         mol_type = other DNA
                         organism = synthetic construct
SEQUENCE: 118
tgtttgaatg aggcttcagt actttacaga atcgttgcct gcacatcttg gaaacacttg    60
ctgggattac ttcgacttct aacccaaca gaaggctcga gaaggtatat tgctgttgac    120
agtgagcgcc cgggaatgaa tcctcaccta tagtgaagcc acagatgtat aggtgaggat    180
tcattcccgg ttgcctactg cctcggactt caaggggcta gaattcgagc aattatcttg    240
tttactaaaa ctgaataccT tgctatctct ttgatacatt tttacaaagc tgaattaaaa    300
tggtataaat taaatcactt t                                              321

SEQ ID NO: 119           moltype = DNA   length = 321
FEATURE                  Location/Qualifiers
source                   1..321
                         mol_type = other DNA
                         organism = synthetic construct
SEQUENCE: 119
tgtttgaatg aggcttcagt actttacaga atcgttgcct gcacatcttg gaaacacttg    60
ctgggattac ttcgacttct aacccaaca gaaggctcga gaaggtatat tgctgttgac    120
agtgagcgat cacacaagct ccaagactaa tagtgaagcc acagatgtat tagtcttgga    180
gcttgtgtga ctgcctactg cctcggactt caaggggcta gaattcgagc aattatcttg    240
tttactaaaa ctgaataccT tgctatctct ttgatacatt tttacaaagc tgaattaaaa    300
tggtataaat taaatcactt t                                              321

SEQ ID NO: 120           moltype = DNA   length = 321
FEATURE                  Location/Qualifiers
source                   1..321
                         mol_type = other DNA
                         organism = synthetic construct
SEQUENCE: 120
tgtttgaatg aggcttcagt actttacaga atcgttgcct gcacatcttg gaaacacttg    60
ctgggattac ttcgacttct aacccaaca gaaggctcga gaaggtatat tgctgttgac    120
agtgagcgcc ccaagtgatt ttaatttaaa tagtgaagcc acagatgtat ttaaattaaa    180
atcacttggg atgcctactg cctcggactt caaggggcta gaattcgagc aattatcttg    240
tttactaaaa ctgaataccT tgctatctct ttgatacatt tttacaaagc tgaattaaaa    300
tggtataaat taaatcactt t                                              321

SEQ ID NO: 121           moltype = DNA   length = 321
FEATURE                  Location/Qualifiers
source                   1..321
                         mol_type = other DNA
                         organism = synthetic construct
SEQUENCE: 121
tgtttgaatg aggcttcagt actttacaga atcgttgcct gcacatcttg gaaacacttg    60
ctgggattac ttcgacttct aacccaaca gaaggctcga gaaggtatat tgctgttgac    120
agtgagcgac caagtgattt taatttaaaa tagtgaagcc acagatgtat tttaaattaa    180
aatcacttgg gtgcctactg cctcggactt caaggggcta gaattcgagc aattatcttg    240
tttactaaaa ctgaataccT tgctatctct ttgatacatt tttacaaagc tgaattaaaa    300
tggtataaat taaatcactt t                                              321

SEQ ID NO: 122           moltype = DNA   length = 321
FEATURE                  Location/Qualifiers
source                   1..321
                         mol_type = other DNA
                         organism = synthetic construct
SEQUENCE: 122
tgtttgaatg aggcttcagt actttacaga atcgttgcct gcacatcttg gaaacacttg    60
ctgggattac ttcgacttct aacccaaca gaaggctcga gaaggtatat tgctgttgac    120
agtgagcgct gtagctaaat tgtaattgaa tagtgaagcc acagatgtat tcaattacaa    180
tttagctaca atgcctactg cctcggactt caaggggcta gaattcgagc aattatcttg    240
tttactaaaa ctgaataccT tgctatctct ttgatacatt tttacaaagc tgaattaaaa    300
tggtataaat taaatcactt t                                              321

SEQ ID NO: 123           moltype = DNA   length = 321
FEATURE                  Location/Qualifiers
source                   1..321
                         mol_type = other DNA
                         organism = synthetic construct
SEQUENCE: 123
tgtttgaatg aggcttcagt actttacaga atcgttgcct gcacatcttg gaaacacttg    60
ctgggattac ttcgacttct aacccaaca gaaggctcga gaaggtatat tgctgttgac    120
```

```
agtgagcgag cctatttatg aaataataaa tagtgaagcc acagatgtat ttattatttc   180
ataaataggc gtgcctactg cctcggactt caaggggcta gaattcgagc aattatcttg   240
tttactaaaa ctgaatacct tgctatctct ttgatacatt tttacaaagc tgaattaaaa   300
tggtataaat taaatcactt t                                             321

SEQ ID NO: 124          moltype = DNA   length = 321
FEATURE                 Location/Qualifiers
source                  1..321
                        mol_type = other DNA
                        organism = synthetic construct
SEQUENCE: 124
tgtttgaatg aggcttcagt actttacaga atcgttgcct gcacatcttg gaaacacttg   60
ctgggattac ttcgacttct taacccaaca gaaggctcga gaaggtatat tgctgttgac   120
agtgagcgcg cagtcatagc aagtttgtaa tagtgaagcc acagatgtat acaaacttga   180
ctatgactgc ttgcctactg cctcggactt caaggggcta gaattcgagc aattatcttg   240
tttactaaaa ctgaatacct tgctatctct ttgatacatt tttacaaagc tgaattaaaa   300
tggtataaat taaatcactt t                                             321

SEQ ID NO: 125          moltype = DNA   length = 321
FEATURE                 Location/Qualifiers
source                  1..321
                        mol_type = other DNA
                        organism = synthetic construct
SEQUENCE: 125
tgtttgaatg aggcttcagt actttacaga atcgttgcct gcacatcttg gaaacacttg   60
ctgggattac ttcgacttct taacccaaca gaaggctcga gaaggtatat tgctgttgac   120
agtgagcgcg cgcctattta tgaaataata tagtgaagcc acagatgtat attatttcat   180
aaataggcgc atgcctactg cctcggactt caaggggcta gaattcgagc aattatcttg   240
tttactaaaa ctgaatacct tgctatctct ttgatacatt tttacaaagc tgaattaaaa   300
tggtataaat taaatcactt t                                             321

SEQ ID NO: 126          moltype = DNA   length = 22
FEATURE                 Location/Qualifiers
source                  1..22
                        mol_type = other DNA
                        organism = synthetic construct
SEQUENCE: 126
ttattaagaa gcatcttgct ta                                            22

SEQ ID NO: 127          moltype = DNA   length = 22
FEATURE                 Location/Qualifiers
source                  1..22
                        mol_type = other DNA
                        organism = synthetic construct
SEQUENCE: 127
ttgcttactg acatgaagcc ac                                            22

SEQ ID NO: 128          moltype = DNA   length = 22
FEATURE                 Location/Qualifiers
source                  1..22
                        mol_type = other DNA
                        organism = synthetic construct
SEQUENCE: 128
ttgtaggaga ggatctcggc ag                                            22

SEQ ID NO: 129          moltype = DNA   length = 22
FEATURE                 Location/Qualifiers
source                  1..22
                        mol_type = other DNA
                        organism = synthetic construct
SEQUENCE: 129
tgtatcaaca gggtgatcgc tt                                            22

SEQ ID NO: 130          moltype = DNA   length = 321
FEATURE                 Location/Qualifiers
source                  1..321
                        mol_type = other DNA
                        organism = synthetic construct
SEQUENCE: 130
tgtttgaatg aggcttcagt actttacaga atcgttgcct gcacatcttg gaaacacttg   60
ctgggattac ttcgacttct taacccaaca gaaggctcga gaaggtatat tgctgttgac   120
agtgagcgca agcaagatgc ttcttaataa tagtgaagcc acagatgtat tattaagaag   180
catcttgctt atgcctactg cctcggactt caaggggcta gaattcgagc aattatcttg   240
tttactaaaa ctgaatacct tgctatctct ttgatacatt tttacaaagc tgaattaaaa   300
tggtataaat taaatcactt t                                             321

SEQ ID NO: 131          moltype = DNA   length = 321
FEATURE                 Location/Qualifiers
source                  1..321
```

```
                        mol_type = other DNA
                        organism = synthetic construct
SEQUENCE: 131
tgtttgaatg aggcttcagt actttacaga atcgttgcct gcacatcttg gaaacacttg    60
ctgggattac ttcgacttct taacccaaca gaaggctcga gaaggtatat tgctgttgac   120
agtgagcgat ggcttcatgt cagtaagcaa tagtgaagcc acagatgtat tgcttactga   180
catgaagcca ctgcctactg cctcggactt caaggggcta gaattcgagc aattatcttg   240
tttactaaaa ctgaatacct tgctatctct ttgatacatt tttacaaagc tgaattaaaa   300
tggtataaat taaatcactt t                                             321

SEQ ID NO: 132          moltype = DNA   length = 321
FEATURE                 Location/Qualifiers
source                  1..321
                        mol_type = other DNA
                        organism = synthetic construct
SEQUENCE: 132
tgtttgaatg aggcttcagt actttacaga atcgttgcct gcacatcttg gaaacacttg    60
ctgggattac ttcgacttct taacccaaca gaaggctcga gaaggtatat tgctgttgac   120
agtgagcgat gccgagatcc tctcctacaa tagtgaagcc acagatgtat tgtaggagag   180
gatctcggca gtgcctactg cctcggactt caaggggcta gaattcgagc aattatcttg   240
tttactaaaa ctgaatacct tgctatctct ttgatacatt tttacaaagc tgaattaaaa   300
tggtataaat taaatcactt t                                             321

SEQ ID NO: 133          moltype = DNA   length = 321
FEATURE                 Location/Qualifiers
source                  1..321
                        mol_type = other DNA
                        organism = synthetic construct
SEQUENCE: 133
tgtttgaatg aggcttcagt actttacaga atcgttgcct gcacatcttg gaaacacttg    60
ctgggattac ttcgacttct taacccaaca gaaggctcga gaaggtatat tgctgttgac   120
agtgagcgca gcgatcaccc tgttgataca tagtgaagcc acagatgtat gtatcaacag   180
ggtgatcgct ttgcctactg cctcggactt caaggggcta gaattcgagc aattatcttg   240
tttactaaaa ctgaatacct tgctatctct ttgatacatt tttacaaagc tgaattaaaa   300
tggtataaat taaatcactt t                                             321

SEQ ID NO: 134          moltype = DNA   length = 22
FEATURE                 Location/Qualifiers
source                  1..22
                        mol_type = other DNA
                        organism = synthetic construct
SEQUENCE: 134
tctgtcattt gtcttcttcc ta                                             22

SEQ ID NO: 135          moltype = DNA   length = 22
FEATURE                 Location/Qualifiers
source                  1..22
                        mol_type = other DNA
                        organism = synthetic construct
SEQUENCE: 135
ttgaggtaga agatgcgctg ca                                             22

SEQ ID NO: 136          moltype = DNA   length = 22
FEATURE                 Location/Qualifiers
source                  1..22
                        mol_type = other DNA
                        organism = synthetic construct
SEQUENCE: 136
tcctcgaact tgaaggaggc ag                                             22

SEQ ID NO: 137          moltype = DNA   length = 22
FEATURE                 Location/Qualifiers
source                  1..22
                        mol_type = other DNA
                        organism = synthetic construct
SEQUENCE: 137
ttttcagttc caactacatg tc                                             22

SEQ ID NO: 138          moltype = DNA   length = 22
FEATURE                 Location/Qualifiers
source                  1..22
                        mol_type = other DNA
                        organism = synthetic construct
SEQUENCE: 138
ttacaaaaaa cataaaggcc gg                                             22

SEQ ID NO: 139          moltype = DNA   length = 22
FEATURE                 Location/Qualifiers
source                  1..22
```

```
                        mol_type = other DNA
                        organism = synthetic construct
SEQUENCE: 139
tataaatgtc agaatctgtc at                                                22

SEQ ID NO: 140          moltype = DNA   length = 22
FEATURE                 Location/Qualifiers
source                  1..22
                        mol_type = other DNA
                        organism = synthetic construct
SEQUENCE: 140
tatattaatc agaaaagtca ca                                                22

SEQ ID NO: 141          moltype = DNA   length = 22
FEATURE                 Location/Qualifiers
source                  1..22
                        mol_type = other DNA
                        organism = synthetic construct
SEQUENCE: 141
atattaatca gaaaagtcac at                                                22

SEQ ID NO: 142          moltype = DNA   length = 22
FEATURE                 Location/Qualifiers
source                  1..22
                        mol_type = other DNA
                        organism = synthetic construct
SEQUENCE: 142
taatcagaaa agtcacatac ta                                                22

SEQ ID NO: 143          moltype = DNA   length = 22
FEATURE                 Location/Qualifiers
source                  1..22
                        mol_type = other DNA
                        organism = synthetic construct
SEQUENCE: 143
tattaatcag aaaagtcaca ta                                                22

SEQ ID NO: 144          moltype = DNA   length = 22
FEATURE                 Location/Qualifiers
source                  1..22
                        mol_type = other DNA
                        organism = synthetic construct
SEQUENCE: 144
ttaatcagaa aagtcacata ct                                                22

SEQ ID NO: 145          moltype = DNA   length = 321
FEATURE                 Location/Qualifiers
source                  1..321
                        mol_type = other DNA
                        organism = synthetic construct
SEQUENCE: 145
tgtttgaatg aggcttcagt actttacaga atcgttgcct gcacatcttg gaaacacttg        60
ctgggattac ttcgacttct taacccaaca gaaggctcga gaaggtatat tgctgttgac       120
agtgagcgca ggaagaagac aaatgacaga tagtgaagcc acagatgtat ctgtcatttg       180
tcttcttcct atgcctactg cctcggactt caaggggcta gaattcgagc aattatcttg       240
tttactaaaa ctgaatacct tgctatctct ttgatacatt tttacaaagc tgaattaaaa       300
tggtataaat taaatcactt t                                                 321

SEQ ID NO: 146          moltype = DNA   length = 321
FEATURE                 Location/Qualifiers
source                  1..321
                        mol_type = other DNA
                        organism = synthetic construct
SEQUENCE: 146
tgtttgaatg aggcttcagt actttacaga atcgttgcct gcacatcttg gaaacacttg        60
ctgggattac ttcgacttct taacccaaca gaaggctcga gaaggtatat tgctgttgac       120
agtgagcgcg cagcgcatct tctacctcaa tagtgaagcc acagatgtat tgaggtgaaa       180
gatgcgctgc atgcctactg cctcggactt caaggggcta gaattcgagc aattatcttg       240
tttactaaaa ctgaatacct tgctatctct ttgatacatt tttacaaagc tgaattaaaa       300
tggtataaat taaatcactt t                                                 321

SEQ ID NO: 147          moltype = DNA   length = 321
FEATURE                 Location/Qualifiers
source                  1..321
                        mol_type = other DNA
                        organism = synthetic construct
SEQUENCE: 147
tgtttgaatg aggcttcagt actttacaga atcgttgcct gcacatcttg gaaacacttg        60
ctgggattac ttcgacttct taacccaaca gaaggctcga gaaggtatat tgctgttgac       120
```

```
agtgagcgat gcctccttca agttcgagga tagtgaagcc acagatgtat cctcgaactt    180
gaaggaggca gtgcctactg cctcggactt caaggggcta gaattcgagc aattatcttg    240
tttactaaaa ctgaatacct tgctatctct ttgatacatt tttacaaagc tgaattaaaa    300
tggtataaat taaatcactt t                                              321

SEQ ID NO: 148         moltype = DNA   length = 321
FEATURE                Location/Qualifiers
source                 1..321
                       mol_type = other DNA
                       organism = synthetic construct
SEQUENCE: 148
tgtttgaatg aggcttcagt actttacaga atcgttgcct gcacatcttg gaaacacttg     60
ctgggattac ttcgacttct taacccaaca gaaggctcga gaaggtatat tgctgttgac    120
agtgagcgaa catgtagttg gaactgaaaa tagtgaagcc acagatgtat tttcagttcc    180
aactacatgt ctgcctactg cctcggactt caaggggcta gaattcgagc aattatcttg    240
tttactaaaa ctgaatacct tgctatctct ttgatacatt tttacaaagc tgaattaaaa    300
tggtataaat taaatcactt t                                              321

SEQ ID NO: 149         moltype = DNA   length = 321
FEATURE                Location/Qualifiers
source                 1..321
                       mol_type = other DNA
                       organism = synthetic construct
SEQUENCE: 149
tgtttgaatg aggcttcagt actttacaga atcgttgcct gcacatcttg gaaacacttg     60
ctgggattac ttcgacttct taacccaaca gaaggctcga gaaggtatat tgctgttgac    120
agtgagcgac ggcctttatg ttttttgtaa tagtgaagcc acagatgtat tacaaaaaac    180
ataaaggccg gtgcctactg cctcggactt caaggggcta gaattcgagc aattatcttg    240
tttactaaaa ctgaatacct tgctatctct ttgatacatt tttacaaagc tgaattaaaa    300
tggtataaat taaatcactt t                                              321

SEQ ID NO: 150         moltype = DNA   length = 321
FEATURE                Location/Qualifiers
source                 1..321
                       mol_type = other DNA
                       organism = synthetic construct
SEQUENCE: 150
tgtttgaatg aggcttcagt actttacaga atcgttgcct gcacatcttg gaaacacttg     60
ctgggattac ttcgacttct taacccaaca gaaggctcga gaaggtatat tgctgttgac    120
agtgagcgct gacagattct gacatttata tagtgaagcc acagatgtat ataaatgtca    180
gaatctgtca ttgcctactg cctcggactt caaggggcta gaattcgagc aattatcttg    240
tttactaaaa ctgaatacct tgctatctct ttgatacatt tttacaaagc tgaattaaaa    300
tggtataaat taaatcactt t                                              321

SEQ ID NO: 151         moltype = DNA   length = 321
FEATURE                Location/Qualifiers
source                 1..321
                       mol_type = other DNA
                       organism = synthetic construct
SEQUENCE: 151
tgtttgaatg aggcttcagt actttacaga atcgttgcct gcacatcttg gaaacacttg     60
ctgggattac ttcgacttct taacccaaca gaaggctcga gaaggtatat tgctgttgac    120
agtgagcgcg tgacttttct gattaatata tagtgaagcc acagatgtat atattaatca    180
gaaaagtcac atgcctactg cctcggactt caaggggcta gaattcgagc aattatcttg    240
tttactaaaa ctgaatacct tgctatctct ttgatacatt tttacaaagc tgaattaaaa    300
tggtataaat taaatcactt t                                              321

SEQ ID NO: 152         moltype = DNA   length = 321
FEATURE                Location/Qualifiers
source                 1..321
                       mol_type = other DNA
                       organism = synthetic construct
SEQUENCE: 152
tgtttgaatg aggcttcagt actttacaga atcgttgcct gcacatcttg gaaacacttg     60
ctgggattac ttcgacttct taacccaaca gaaggctcga gaaggtatat tgctgttgac    120
agtgagcgct gtgactttc tgattaatat tagtgaagcc acagatgtaa tattaatcag    180
aaaagtcaca ttgcctactg cctcggactt caaggggcta gaattcgagc aattatcttg    240
tttactaaaa ctgaatacct tgctatctct ttgatacatt tttacaaagc tgaattaaaa    300
tggtataaat taaatcactt t                                              321

SEQ ID NO: 153         moltype = DNA   length = 321
FEATURE                Location/Qualifiers
source                 1..321
                       mol_type = other DNA
                       organism = synthetic construct
SEQUENCE: 153
tgtttgaatg aggcttcagt actttacaga atcgttgcct gcacatcttg gaaacacttg     60
ctgggattac ttcgacttct taacccaaca gaaggctcga gaaggtatat tgctgttgac    120
agtgagcgca gtatgtgact tttctgatta tagtgaagcc acagatgtat aatcagaaaa    180
```

```
gtcacatact atgcctactg cctcggactt caaggggcta gaattcgagc aattatcttg    240
tttactaaaa ctgaatacct tgctatctct ttgatacatt tttacaaagc tgaattaaaa    300
tggtataaat taaatcactt t                                              321

SEQ ID NO: 154          moltype = DNA   length = 321
FEATURE                 Location/Qualifiers
source                  1..321
                        mol_type = other DNA
                        organism = synthetic construct
SEQUENCE: 154
tgtttgaatg aggcttcagt actttacaga atcgttgcct gcacatcttg gaaacacttg    60
ctgggattac ttcgacttct taacccaaca gaaggctcga gaaggtatat tgctgttgac    120
agtgagcgca tgtgactttt ctgattaata tagtgaagcc acagatgtat attaatcaga    180
aaagtcacat atgcctactg cctcggactt caaggggcta gaattcgagc aattatcttg    240
tttactaaaa ctgaatacct tgctatctct ttgatacatt tttacaaagc tgaattaaaa    300
tggtataaat taaatcactt t                                              321

SEQ ID NO: 155          moltype = DNA   length = 321
FEATURE                 Location/Qualifiers
source                  1..321
                        mol_type = other DNA
                        organism = synthetic construct
SEQUENCE: 155
tgtttgaatg aggcttcagt actttacaga atcgttgcct gcacatcttg gaaacacttg    60
ctgggattac ttcgacttct taacccaaca gaaggctcga gaaggtatat tgctgttgac    120
agtgagcgcg tatgtgactt ttctgattaa tagtgaagcc acagatgtat taatcagaa    180
agtcacatac ttgcctactg cctcggactt caaggggcta gaattcgagc aattatcttg    240
tttactaaaa ctgaatacct tgctatctct ttgatacatt tttacaaagc tgaattaaaa    300
tggtataaat taaatcactt t                                              321

SEQ ID NO: 156          moltype = DNA   length = 613
FEATURE                 Location/Qualifiers
source                  1..613
                        mol_type = other DNA
                        organism = synthetic construct
SEQUENCE: 156
gtaagtcgac tcgttggatc cccactaccc ggatcaacgc cctaggttta tgtttggatg    60
aactgacata cgcgtatccg tcttaagaat cttttcaaac actagtagtg aaatatatat    120
taaactagtg tttgaaaaga ttcttattac ggtaacgcgg aattcgcaac тattтттatca    180
attttttgcg tcgacacttc aaggggcttg cggccgcaac catctccatg gctgtttgaa    240
tgaggcttca gtactttaca gaatcgttgc ctgcacatct tggaaacact tgctgggatt    300
acttcgactt cttaacccaa cagaaggctc gagaaggtat attgctgttg acagtgagcg    360
cgtatgtgac ttttctgatt aaтaгтgaag ccacagatgt attaatcaga aaagtcacat    420
acttgcctac tgcctcggac ttcaagggc tagaattcga gcaattatct tgtttactaa    480
aactgaatac cttgctatct ctttgataca ttttacaaa gctgaattaa aтгgтатaa    540
attaaatcac ttttcatct gaccagtagt ggactagtgt gacgctgctg accccttct    600
ttcccttcta cag                                                       613

SEQ ID NO: 157          moltype = DNA   length = 613
FEATURE                 Location/Qualifiers
source                  1..613
                        mol_type = other DNA
                        organism = synthetic construct
SEQUENCE: 157
gtaagtcgac tcgttggatc cccactaccc ggatcaacgc cctaggttta tgtttggatg    60
aactgacata cgcgtatccg tcttaagaat cttttcaaac actagtagtg aaatatatat    120
taaactagtg tttgaaaaga ttcttattac ggtaacgcgg aattcgcaac тaтттттaтca    180
atttttgcg tcgacacttc aaggggcttg cggccgcaac catctccatg gctgtttgaa    240
tgaggcttca gtactttaca gaatcgttgc ctgcacatct tggaaacact tgctgggatt    300
acttcgactt cttaacccaa cagaaggctc gagaaggtat attgctgttg acagtgagcg    360
ccagtgtgaa gctcttgtca gatagtgaag ccacagatgt atctgacaag agcttcacac    420
tgatgcctac tgcctcggac ttcaagggc tagaattcga gcaattatct tgtttactaa    480
aactgaatac cttgctatct ctttgataca ttttacaaa gctgaattaa aтгgтатaa    540
attaaatcac ttttcatct gaccagtagt ggactagtgt gacgctgctg accccttct    600
ttccttcta cag                                                        613

SEQ ID NO: 158          moltype = DNA   length = 613
FEATURE                 Location/Qualifiers
source                  1..613
                        mol_type = other DNA
                        organism = synthetic construct
SEQUENCE: 158
gtaagtcgac tcgttggatc cccactaccc ggatcaacgc cctaggttta tgtttggatg    60
aactgacata cgcgtatccg tcttaagaat cttttcaaac actagtagtg aaatatatat    120
taaactagtg tttgaaaaga ttcttattac ggtaacgcgg aattcgcaac тaтттттaтca    180
atttttgcg tcgacacttc aaggggcttg cggccgcaac catctccatg gctgtttgaa    240
tgaggcttca gtactttaca gaatcgttgc ctgcacatct tggaaacact tgctgggatt    300
acttcgactt cttaacccaa cagaaggctc gagaaggtat attgctgttg acagtgagcg    360
ctggcttgat gtagcagtca tatagtgaag ccacagatgt atatgactgc tacatcaagc    420
```

Note: Due to character recognition limitations in rendering, sequences above may contain visual substitutions; the authoritative content is the original patent sequence listing (DNA bases: a, c, g, t).

```
cattgcctac tgcctcggac ttcaaggggc tagaattcga gcaattatct tgtttactaa   480
aactgaatac cttgctatct ctttgataca ttttacaaa gctgaattaa aatggtataa     540
attaaatcac tttttcatct gaccagtagt ggactagtgt gacgctgctg accccttct    600
ttcccttcta cag                                                        613

SEQ ID NO: 159         moltype = DNA   length = 613
FEATURE                Location/Qualifiers
source                 1..613
                       mol_type = other DNA
                       organism = synthetic construct
SEQUENCE: 159
gtaagtcgac tcgttggatc cccactaccc ggatcaacgc cctaggttta tgtttggatg   60
aactgacata cgcgtatccg tctctgacaa gagcttcaca ctgagtagtg aaatatatat   120
taaactcagt gtgaagctct tgtcagttac ggtaacgcgg aattcgcaac tatttttatca  180
atttttgcg tcgacacttc aaggggcttg cggccgcaac catctccatg gctgtttgaa    240
tgaggcttca gtactttaca gaatcgttgc ctgcacatct tggaaacact tgctgggatt   300
acttcgactt cttaacccaa cagaaggctc gagaaggtat attgctgttg acagtgagcg   360
ctggcttgat gtagcagtca tatagtgaag ccacagatgt atatgactgc tacatcaagc   420
cattgcctac tgcctcggac ttcaaggggc tagaattcga gcaattatct tgtttactaa   480
aactgaatac cttgctatct ctttgataca ttttacaaa gctgaattaa aatggtataa    540
attaaatcac tttttcatct gaccagtagt ggactagtgt gacgctgctg accccttct    600
ttcccttcta cag                                                        613

SEQ ID NO: 160         moltype = DNA   length = 613
FEATURE                Location/Qualifiers
source                 1..613
                       mol_type = other DNA
                       organism = synthetic construct
SEQUENCE: 160
gtaagtcgac tcgttggatc cccactaccc ggatcaacgc cctaggttta tgtttggatg   60
aactgacata cgcgtatccg tcttaagaag catcttgctt actggtagtg aaatatatat   120
taaaccagta agcaagatgc ttcttattac ggtaacgcgg aattcgcaac tatttttatca  180
atttttgcg tcgacacttc aaggggcttg cggccgcaac catctccatg gctgtttgaa    240
tgaggcttca gtactttaca gaatcgttgc ctgcacatct tggaaacact tgctgggatt   300
acttcgactt cttaacccaa cagaaggctc gagaaggtat attgctgttg acagtgagcg   360
ccagtgtgaa gctcttgtca gatagtgaag ccacagatgt atctgacaag agcttcacac   420
tgatgcctac tgcctcggac ttcaaggggc tagaattcga gcaattatct tgtttactaa   480
aactgaatac cttgctatct ctttgataca ttttacaaa gctgaattaa aatggtataa    540
attaaatcac tttttcatct gaccagtagt ggactagtgt gacgctgctg accccttct    600
ttcccttcta cag                                                        613

SEQ ID NO: 161         moltype = DNA   length = 613
FEATURE                Location/Qualifiers
source                 1..613
                       mol_type = other DNA
                       organism = synthetic construct
SEQUENCE: 161
gtaagtcgac tcgttggatc cccactaccc ggatcaacgc cctaggttta tgtttggatg   60
aactgacata cgcgtatccg tcttaagaat cttttcaaac actagtagtg aaatatatat   120
taaactagtg tttgaaaaga ttcttattac ggtaacgcgg aattcgcaac tatttttatca  180
atttttgcg tcgacacttc aaggggcttg cggccgcaac catctccatg gctgtttgaa    240
tgaggcttca gtactttaca gaatcgttgc ctgcacatct tggaaacact tgctgggatt   300
acttcgactt cttaacccaa cagaaggctc gagaaggtat attgctgttg acagtgagcg   360
ctgacagatt ctgacattta tatagtgaag ccacagatgt atataaatgt cagaatctgt   420
cattgcctac tgcctcggac ttcaaggggc tagaattcga gcaattatct tgtttactaa   480
aactgaatac cttgctatct ctttgataca ttttacaaa gctgaattaa aatggtataa    540
attaaatcac tttttcatct gaccagtagt ggactagtgt gacgctgctg accccttct    600
ttcccttcta cag                                                        613

SEQ ID NO: 162         moltype = DNA   length = 613
FEATURE                Location/Qualifiers
source                 1..613
                       mol_type = other DNA
                       organism = synthetic construct
SEQUENCE: 162
gtaagtcgac tcgttggatc cccactaccc ggatcaacgc cctaggttta tgtttggatg   60
aactgacata cgcgtatccg tctaatctta atctttcatc ctctgtagtg aaatatatat   120
taaacagagg atgaaagatt aagatttac ggtaacgcgg aattcgcaac tatttttatca   180
atttttgcg tcgacacttc aaggggcttg cggccgcaac catctccatg gctgtttgaa    240
tgaggcttca gtactttaca gaatcgttgc ctgcacatct tggaaacact tgctgggatt   300
acttcgactt cttaacccaa cagaaggctc gagaaggtat attgctgttg acagtgagcg   360
ccagtgtgaa gctcttgtca gatagtgaag ccacagatgt atctgacaag agcttcacac   420
tgatgcctac tgcctcggac ttcaaggggc tagaattcga gcaattatct tgtttactaa   480
aactgaatac cttgctatct ctttgataca ttttacaaa gctgaattaa aatggtataa    540
attaaatcac tttttcatct gaccagtagt ggactagtgt gacgctgctg accccttct    600
ttcccttcta cag                                                        613

SEQ ID NO: 163         moltype = DNA   length = 613
FEATURE                Location/Qualifiers
```

```
source                  1..613
                        mol_type = other DNA
                        organism = synthetic construct
SEQUENCE: 163
gtaagtcgac tcgttggatc cccactaccc ggatcaacgc cctaggttta tgtttggatg   60
aactgacata cgcgtatccg tcttaagaat cttttcaaac actagtagtg aaatatatat  120
taaactagtt tttgaaaaga ttcttattac ggtaacgcgg aattcgcaac tattttatca  180
atttttgcg  tcgacacttc aaggggcttg cggccgcaac catctccatg gctgtttgaa  240
tgaggcttca gtactttaca gaatcgttgc ctgcacatct tggaaacact tgctgggatt  300
acttcgactt cttaacccaa cagaaggctc gagaaggtat attgctgttg acagtgagcg  360
cccgggaatg aatcctcacc tatagtgaag ccacagatgt ataggtgagg attcattccc  420
ggttgcctac tgcctcggac ttcaagggcc tagaattcga gcaattatct tgtttactaa  480
aactgaatac cttgctatct ctttgataca ttttacaaa  gctgaattaa aatggtataa  540
attaaatcac ttttcatct  gaccagtagt ggactagtgt gacgctgctg accccttttct 600
ttcccttcta cag                                                     613

SEQ ID NO: 164          moltype = DNA  length = 613
FEATURE                 Location/Qualifiers
source                  1..613
                        mol_type = other DNA
                        organism = synthetic construct
SEQUENCE: 164
gtaagtcgac tcgttggatc cccactaccc ggatcaacgc cctaggttta tgtttggatg   60
aactgacata cgcgtatccg tctctgacaa gagcttcaca ctgagtagtg aaatatatat  120
taaactcagt gtgaagctct tgtcagttac ggtaacgcgg aattcgcaac tattttatca  180
atttttgcg  tcgacacttc aaggggcttg cggccgcaac catctccatg gctgtttgaa  240
tgaggcttca gtactttaca gaatcgttgc ctgcacatct tggaaacact tgctgggatt  300
acttcgactt cttaacccaa cagaaggctc gagaaggtat attgctgttg acagtgagcg  360
cccgggaatg aatcctcacc tatagtgaag ccacagatgt ataggtgagg attcattccc  420
ggttgcctac tgcctcggac ttcaagggcc tagaattcga gcaattatct tgtttactaa  480
aactgaatac cttgctatct ctttgataca ttttacaaa  gctgaattaa aatggtataa  540
attaaatcac ttttcatct  gaccagtagt ggactagtgt gacgctgctg accccttttct 600
ttcccttcta cag                                                     613

SEQ ID NO: 165          moltype = DNA  length = 613
FEATURE                 Location/Qualifiers
source                  1..613
                        mol_type = other DNA
                        organism = synthetic construct
SEQUENCE: 165
gtaagtcgac tcgttggatc cccactaccc ggatcaacgc cctaggttta tgtttggatg   60
aactgacata cgcgtatccg tctataatac gacttcacat cttcgtagtg aaatatatat  120
taaacgaaga tgtgaagtcg tattatttac ggtaacgcgg aattcgcaac tattttatca  180
atttttgcg  tcgacacttc aaggggcttg cggccgcaac catctccatg gctgtttgaa  240
tgaggcttca gtactttaca gaatcgttgc ctgcacatct tggaaacact tgctgggatt  300
acttcgactt cttaacccaa cagaaggctc gagaaggtat attgctgttg acagtgagcg  360
caagcaagat gcttcttaat aatagtgaag ccacagatgt attattaaga agcatcttgc  420
ttatgcctac tgcctcggac ttcaagggcc tagaattcga gcaattatct tgtttactaa  480
aactgaatac cttgctatct ctttgataca ttttacaaa  gctgaattaa aatggtataa  540
attaaatcac ttttcatct  gaccagtagt ggactagtgt gacgctgctg accccttttct 600
ttcccttcta cag                                                     613

SEQ ID NO: 166          moltype = DNA  length = 6009
FEATURE                 Location/Qualifiers
source                  1..6009
                        mol_type = other DNA
                        organism = synthetic construct
SEQUENCE: 166
taaggtacga ctgtgccttc tagttgccag ccatctgttg tttgcccctc cccgtgcctt    60
ccttgacccc tggaaggtgc cactcccact gtcctttcct aataaaatga ggaaattgca  120
tcgcattgtc tgagtaggtg tcattctatt ctggggggtg gggtggggca ggacagcaag  180
ggggaggatt gggaagacaa tagcaggcat gctggggatg cggtgggctc tatgggataa  240
gcttgatatc gaattcatcg atgttaataa ttaacatata tgttaatcat taacatatag  300
ttaattatta accgctatgt taatgattaa caacggttaa taattaacat atatgttaat  360
cattaacata taactagtct agagggtata taatgggggc cactagtcta ctaccagagt  420
tcatcgctag cgctaccgga tccgccacca tggcctgcc agtaacggct ctgctgctgc  480
cacttgctct gctcctccat gcagccaggc tcagttgca gttacaggag agcggacccg  540
gtctggttaa accgtctgaa acactgagtt tgacatgtac agtgtccggc ggctcgattt  600
caaactctta ctattgggc tggattaggc agccccggg gaaagggctc gagtggatcg  660
ggtccatata tcactcagga aatacctact acaacccaag tcttaagtct agagtgacaa  720
tcagtgtgga tacgtccaag aatcaattct ccctgaagct ctcaagcgtg accgccgccg  780
acaccgcagt gtattattgc gtaactcaag acggtgtggg cgctaccact accgaagagt  840
attgggggaca aggcactctt gtcacagtct ccagcgcggc agcaaccacg acgccagcgc  900
cgcgaccacc aaccaccgcg cccacatccg tccggacgc actgtcagct gcgcccagaag  960
cgtgccggcc agcggcgggg ggcgcagtgc acacgagggg gctggacttc gcctgtgata 1020
tctacatctg ggcgcccttg gccgggactt gtggggtcct tctcctgtca ctggttatca 1080
ccctttactg caaacggggc agaaagaaac tcctgtatat attcaaacaa ccatttatga 1140
gaccagtaca aactactcaa gaagaggacg gctgtagctg ccgatttcca gaagaagaag 1200
aaggaggatg tgaactgaga gtgaagttca gcaggagcgc agacgccccc gcgtaccagc 1260
```

```
agggccagaa ccagctctat aacgagctca atctaggacg aagagaggag tacgatgttt  1320
tggacaagag gcgtggccgg gaccctgaga tgggggggaaa gccgagaagg aagaaccctc  1380
aggaaggcct gtacaatgaa ctgcagaaag ataagatggc ggaggcctac agtgagattg  1440
ggatgaaagg cgagcgccgg aggggcaagg ggcacgatgg cctttaccag ggtctcagta  1500
cagccaccaa ggacacctac gacgcccttc acatgcaggc cctgcccct aggtaaaatc  1560
aacctctgga ttacaaaatt tgtgaaagat tgactggtat tcttaactat gttgctcctt  1620
ttacgctatg tggatacgct gctttaatgc cttttgtatca tgctattgct tcccgtatgg  1680
cttttcatttt ctcctccttg tataaatcct ggttgctgtc tctttatgag gagttgtggc  1740
ccgttgtcag gcaacgtggc gtggtgtgca ctgtgtttgc tgacgcaacc cccactggtt  1800
ggggcattgc caccacctgt cagctccttt ccgggacttt cgctttcccc ctccctattg  1860
ccacggcgga actcatcgcc gcctgccttg cccgctgctg gacagggggct cggctgttgg  1920
gcactgacaa ttccgtggtg ttgtcgggga aatcatcgtc cttccttgg ctgctcgcct  1980
gtgttgccac ctggattctg cgcgggacgt ccttctgcta cgtcccttcg gccctcaatc  2040
cagcggacct tccttcccgc ggcctgctgc cggctctgcg gcctcttccg cgtcttcgcc  2100
ttcgccctca gacgagtcgg atctccttt gggccgcctc cccgcctgga tccttgactt  2160
gcggccaact tgtttattgc agcttataat ggttacaaat aaagcaatag catcacaaat  2220
ttcacaaata aagcattttt ttcactgcat tctagttgtg gtttgtccaa actcatcaat  2280
gtatcttatc atgtctggga tccttgactt gcggccgcaa ctcccacctg caacatgcgt  2340
gactgactga ggccgcgact ctagagtcga ccggatctgc gatcgctccg gtgcccgtca  2400
gtgggcagag cgcacatcgc ccacagtccc gagaagttgg gggggagggg tcggcaattg  2460
aacgggtgcc tagagaaggt ggcgcggggt aaactgggaa agtgatgtcg tgtactggct  2520
ccgccttttt cccgagggtg ggggagaacc gtatataagt gcagtagtcg ccgtgaacgt  2580
tctttttcgc aacgggtttg ccgccagaac acagctgaag cttcgagggg ctcgcatctc  2640
tccttcacgc gcccgccgcc ctacctgagg ccgccatcca cgccggttga gtcgcgttct  2700
gccgcctccc gcctgtggtg cctcctgaac tgcgtccgcc gtctaggtaa gtcgactcgt  2760
tggatcccca ctacccggat caacgcccta ggtttatgtt tggataagct gacatacgcg  2820
tatccgtctt aagaatcttt tcaaacacta gtagtgaaat atatattaaa ctagtgttg  2880
aaaagattct tattacggta acgcggaatt cgcaactatt ttatcaattt tttgcgtcga  2940
cacttcaagg ggcttgcggc cgcaaccatc tccatggctg tttgaatgag gcttcagtac  3000
tttacagaat cgttgcctgc acatcttgga aacacttgct gggattactt cgacttctta  3060
acccaacaga aggctcgaga aggtatattg ctgttgacga tgagcgccag tgtgaagctc  3120
ttgtcagata gtgaagccac agatgtatct gacaagagct tcacactgat gcctactgcc  3180
tcggacttca aggggctaga attcgagcaa ttatcttgtt tactaaaact gaataccttg  3240
ctatctcttt gatacatttt tacaaagctg aattaaaatg tataaatta aatcacttt  3300
tcatctgacc agtagtggac tagtgtgacg ctgctgaccg cttctttccc cttctacaga  3360
tccaagctgt gaccggcgcc tacacctgca gcccaagctt accatggcct taccagtgac  3420
cgccttgctc ctgccgctgg ccttgctgct ccacgccgcc aggcctgaca tacagatgac  3480
acagagccct agcagtctga gcgccagtgt gggcgataga gttactatca cttgtagagc  3540
atccgagaac atatacagtt acgtggcctg gtatcagcaa aaacctggac aagctcccaa  3600
gttattgatt tacaatgcta agagcttggc ctctggggtg ccatcgaggt tcagcggtag  3660
cgggagcggg accgacttca ctctgaccat ctcgagtctc cagccggagg actttgcgac  3720
atactattgt caacaccatt acgtatcacc ctggaccttc ggcggcggga ctaagttaga  3780
gatcaagggt ggaggaggat caggcggcgg tggatcagga ggagggggt cacaagtgca  3840
gttacaggaa tcagggcccg gcctggtgaa gccaagtgaa accctgagtc tgacgtgcac  3900
ggtttcagga tttagcctca cttcctacgg tgtctcttgg attcggcagc cagccggcaa  3960
agggctcgag tggattgggg tgatctggga agatggctca acaaactatc attctgcact  4020
aatctctcgc gtgacaatgt cggtgacac gtccaagaat caattttccc ttaaactgct  4080
ctccgtgacc gcagccgata cagcggtata ttattgcgcg cgacctcact acggatctag  4140
ctatgtcggc gcgatggagt attggggcgc tggcacaacc gtcaccgttt cttccgcaac  4200
cacgacgcca gcgccgcgac caccaacacc ggcgcccacc atcgcgtcgc agcccctgtc  4260
cctgcgccct gaggcgtgct tcatgtacgt ggcggcgggc gcctttgtgc ttctgttctt  4320
cgtgggctgc ggggtgctgc tgtcccgtaa acgcagacgt caaacacgtc aactgtggtt  4380
tccagaaggt tttaaggtct ccgaagcaag taagaagaaa agacgtgaac cactgggaga  4440
agatagcgtc ggtctgaaac cactcaagaa tgccatggtt tctaaactga ccagctgca  4500
gacggagctc ctggcgcccc tgctggagtc agggctgagc aaagaggcac tgctccaggc  4560
actgggcgag ccggggccct acctcctggc tggagaaggc cccctggaca aggggagtc  4620
ctgcggcggc ggtcgagggg agctggctga gctgcccaat gggctggggg agactcgggg  4680
ctccgaggac gagaccgacg acgatgggga agacttcacg ccacccatcc tcaaagagct  4740
ggagaacctc agccctgagg aggcggccca ccagaaagcc gtggtggaga cccttctgca  4800
ggaggacccg tggcgtgtgg cgaagatggt caagtcctac ctgcagcagc acaacatccc  4860
acagcgggag gtggtcgata ccactggcct caaccagtcc cacctgtccc aacacctcaa  4920
caagggcact cccatgaaga cgcagaagcg ggccgccctg tacacctggt atgtccgcaa  4980
gcagcgagag gtggcgcagc agttcaccca tgcagggcag ggagggctga ttgaagagcc  5040
cacaggagat gagctaccaa ccaagaaggg gcggaggaac cgtttcaagt gggccccagc  5100
atcccagcag atcctgttcc aggcctatga gaggcagaag aaccctagca aggaggagc  5160
agaaacgcta gtggaggagt gcaatagggc ggaatgcatc cagagaggtg tgtcaccatc  5220
acaagcacaa ggtctgggct ccaacctcgt cacgaggtg cgtgtctaca actgtttgc  5280
caaccggcgc aaagaagaag ccttccggca caagctggcc atgacctgca gggatgagtt  5340
tcccaccatg gtgttttcctt ctgggcagat cagccaggcc tcggccttgg ccgggccatc  5400
tccccaagtc ctgccccagg ctccagcccc tgcccctgct ccagccatgg tatcagctct  5460
ggcccaggcc ccagccccctg tccagtcct agccccaggc cctcctcaag ctgtggcccc  5520
acctgccccc aagcccaccc aagctgggga aggaacgctg tcagaggccc tgctgcagct  5580
gcagtttgat gatgaagacc tggggggcctt gcttggcaac agcacagacc cagctgtgtt  5640
cacagacctg gcatccgtcg acaactccga gttctgcaac ctgctgaccc agggcatacc  5700
tgtggccccc cacacaactg agcccatgct gatggagtac cctgaggcta taactcgcct  5760
agtgacaggg gccagaggc ccccgacccc agctcctgct ccactgggg ccccggggct  5820
ccccaatggc ctcctttcag gagatgaaga cttctcctcc attgcggaca tggacttctc  5880
agccctgctg agtcagatca gctccctaag gaaataaaag atctttaatg aaaatagatc  5940
tgtgtgttgg ttttttgtgt gaataaaaga tccagagctc tagagatctg tgtgttggtt  6000
``` ttttgtgtg                                                                          6009

SEQ ID NO: 167          moltype = DNA   length = 6391
FEATURE                 Location/Qualifiers
source                  1..6391
                        mol_type = other DNA
                        organism = synthetic construct SEQUENCE: 167
taaggtacga ctgtgccttc tagttgccag ccatctgttg tttgcccctc ccccgtgcct    60
tccttgaccc tggaaggtgc cactcccact gtcctttcct aataaaatga ggaaattgca   120
tcgcattgtc tgagtaggtg tcattctatt ctggggggtg gggtggggca ggacagcaag   180
ggggaggatt gggaagacaa tagcaggcat gctgggggatg cggtgggctc tatgggataa   240
gcttgatatc gaattcatcg atgttaataa ttaacatata tgttaatcat taacatatag   300
ttaattatta accgctatgt taatgattaa caacggttaa taattaacat atatgttaat   360
cattaacata taactagtct agagggtata taatgggggc cactagtcta ctaccagagt   420
tcatcgctag cgctaccgga tccgccacca tggcctgcc agtaacggct ctgctgctgc    480
cacttgctct gctcctccat gcagccaggc ctcagttgca gttacaggag agcggacccg    540
gtctggttaa accgtctgaa acactgagtt tgacatgtac agtgtccggc ggctcgattt   600
caaactctta ctattgggggc tggattaggc agcctcccgg gaaagggctc gagtggatcg   660
ggtccatata tcactcagga aatacctact acaacccaag tcttaagtct agagtgacaa    720
tcagtgtgga tacgtccaag aatcaattct ccctgaagct ctcaagcgtg accgccgccg   780
acaccgcagt gtattattgc gtaactcaag acggtgtggg cgctaccact accgaagagt   840
attgggggaca aggcactctt gtcacagtct ccagcgcggc agcaaccacg acgcagcgc    900
cgcgaccacc aacaccggcg cccaccatcg cgtcgcagcc actgtcactg cgcccagaag   960
cgtgccggca gcggcggggg ggcgcagtgc acacgagggg gctggacttc gcctgtgata  1020
tctacatctg ggcgcccttg gccggacttt gtgggggtcct tctcctgtca ctggttatca  1080
cccttttactg caaacggggc agaaagaaac tcctgtatat attcaaacaa ccatttatga  1140
gaccagtaca aactactcaa gaagaggacg gctgtagctg ccgatttcca gaagaagaag  1200
aaggaggatg tgaactgaga gtgaagttca gcaggagcgc agacgcccc gcgtaccagc   1260
agggccagaa ccagctctat aacgagctca tctaggacg aagagaggag tacgatgttt   1320
tggacaagag gcgtgccggg gaccctgaga tgggggggaaa gccgagaagg aagaaccctc  1380
aggaaggcct gtacaatgaa ctgcagaaag ataagatggc ggaggcctac agtgagattg  1440
ggatgaaagg cgagcgccgg aggggcaagg ggcacgatgg cctttaccag ggtctcagta  1500
cagccaccaa ggacacctac gacgcccttc acatgcaggc cctgcccct aggtaaaatc    1560
aacctctgga ttacaaaatt tgtgaaagat tgactggtat tcttaactat gttgctcctt  1620
ttacgctatg tggatacgct gctttaatgc ctttgtatca tgctattgct tcccgtatgg  1680
ctttcatttt ctcctccttg tataaatcct ggttgctgtc tctttatgag gagttgtggc  1740
ccgttgtcag gcaacgtggc gtggtgtgca ctgtgtttgc tgacgcaacc cccactggtt   1800
ggggcattgc caccacctgt cagctccttt ccgggacttt cgctttcccc ctccctattg   1860
ccacggcgga actcatcgcc gcctgccttg cccgctgctg gacaggggct cggctgttgg   1920
gcactgacaa ttccgtggtg ttgtcgggga atcatcgtc ctttccttgg ctgctcgcct   1980
gtgttgccac ctggattctg cgcggacgt ccttctgcta cgtcccttcg gccctcaatc    2040
cagcggacct tccttcccgc ggcctgctgc cggctctgcg gcctcttccg cgtcttcgcc   2100
ttcgccctca gacgagtcgg atctcccttt gggccgcctc cccgcctgga tccttgactt   2160
gcggccaact tgtttattgc agcttataat ggttacaaat aaagcaatag catcacaaat   2220
ttcacaaata agcattttt ttcactgcat tctagttgtg gtttgtccaa actcatcaat    2280
gtatcttatc atgtctggga tccttgactt gcggccgcaa ctccccacctg caacatgcgt   2340
gactgactga ggccgcgact ctagagtcga ccggatctgc gatcgctccg gtgcccgtca  2400
gtgggcagag cgcacatcgc ccacagtccc cgagaagttg ggggggaggg tcggcaattg  2460
aacgggtgcc tagagaaggt ggcgcggggt aaactgggaa agtgatgtcg tgtactggct  2520
ccgcctttt cccgagggtg ggggagaacc gtatataagt gcagtagtcg ccgtgaacgt  2580
tctttttcgc aacgggtttg ccgccagaac acagctgaag cttcgagggg ctcgcatctc  2640
tccttcacgc gcccgccgcc ctacctgagg ccgccatcca cgccggttga gtcgcgttct  2700
gccgcctccc gcctgtggtg cctcctgaac tgcgtccgcc gtctaggtaa gtcgactcgt  2760
tggatcccca ctacccggat caacgcccta ggtttatgtt tggatgaact gacatacgcg  2820
tatccgtctt aagaatcttt tcaaacacta gtagtgaaat atatattaaa ctagtgtttg  2880
aaaagattct tattacggta acgcggaatt cgcaactatt ttatcaattt tttgcgtcga  2940
cacttcaagg ggcttgcggc cgcaaccatc tccatggctg tttgaatgag gcttcagtac  3000
tttacagaat cgttgcctgc acatcttgga aacacttgct gggattactt cgacttctta  3060
acccaacaga aggctcgaga aggtatattg ctgttgacag tgagcgccag tgtgaagctc  3120
ttgtcagata gtgaagccac agatgtatct gacaagagct tcacactgat gcctactgcc  3180
tcggacttca aggggctaga attcgagcaa ttatcttgtt tactaaaact gaatacctg   3240
ctatctcttt gatacatttt tacaaagctg aattaaaatg gtataaatta aatcacttt   3300
tcatctgacc agtagtggaa tagtgtgacg tgctgaccc cttttcttc cttctacaga   3360
tccaagctgt gaccggcgcc tacacctgca gcccaagctt tttatggcct taccagtgac   3420
cgccttgctc ctgccgctgg ccttgctgct ccacgccgcc aggcctgaca tacagatgac  3480
acagagccct agcagtctga gcgccagtgt gggcgataga gttactatca cttgtagagc   3540
atccagagaac atatacagtt acgtggcctg tatcagcaa aaacctggca agctcccaa    3600
gttattgatt tacaatgcta agagcttggc ctctggggtg ccatcgaggt tcagcggtag  3660
cgggagcggg accgacttca ctctgaccat ctcgagtctc cagccggagg acttttgcgac  3720
atactattgt caacaccatt acgtatcacc ctggaccttc ggcggcggga ctaagttaga  3780
gatcaaggggt ggaggaggat caggcggcgg tggatcagga ggagggt cacaagtgca    3840
gttacaggaa tcagggccg gcctggtgaa gccaagtgaa accctgagtc tgacgtgcac   3900
ggtttcagga tttagcctca cttcctacgg tgtctcttgg atcggcagc cagccggaaa   3960
agggctcgag tggattgggg tgatctggga agatgctca acaaactatc attctgcact   4020
aatctctcgc gtgacaatgt cggtggacac gtccaagaat caattttccc ttaaactgtc   4080
ctccgtgacc gcagccgata cagcggtata tttattgcgcg cgacctcact acggatctag   4140
ctatgtcggc gcgatggagt attggggcgc tggcacaacc gtcaccgttt cttccgcaac   4200
cacgacgcca gcgccgcgac caccaacacc ggcgcccacc atcgcgtcgc agcccctgtc   4260

```
cctgcgccct gaggcgtgct tcatgtacgt ggcggcggcc gccttttgtgc ttctgttctt   4320
cgtgggctgc ggggtgctgc tgtcccgtaa acgcagacgt caaacacggtc aactgtggtt   4380
tccagaaggt tttaaggtct ccgaagcaag taagaagaaa agacgtgaac cactgggaga   4440
agatagcgtc ggtctgaaac cactcaagaa tgccatggtt tctaaactga gccagctgca   4500
gacggagctc ctggcggccc tgctggagtc agggctgacg aaagaggcac tgctccaggc   4560
actgggcgag ccggggccct acctcctggc tggagaaggc cccctgggaca aggggggagtc   4620
ctgcggcggc ggtcgagggg agctggctga gctgcccaat gggctggggg agactcgggg   4680
ctccgaggac gagaccgacg acgatgggga agacttcacg ccacccatcc tcaaagagct   4740
ggagaacctc agccctgagg aggcggccca ccagaaagcc gtggtggaa cccttctgca   4800
ggaggacccg tggcgtgtgg cgaagatggt caagtcctac ctgcagcagc acaacatccc   4860
acagcgggag gtggtcgata ccactggcct caaccagtcc cacctgtccc aacacctcaa   4920
caagggcact cccatgaaga cgcagaagcg ggccgccctg tacacctggt atgtccgcaa   4980
gcagcgagag gtggcgcagc agttcaccca tgcagggcag ggagggctga ttgaagagcc   5040
cacaggagat gagctaccaa ccaagagggg gcggaggaac cgtttcaagt ggggcccaac   5100
atcccagcag atcctgttcc aggcctatga gaggcagaaa acccctagca aggaggagc   5160
agaaacgcta gtggaggagt gcaataggg ggaatgcatc cagagaggtg tgtcaccatc   5220
acaagcacaa ggtctgggct ccaacctcgt cacgaggtg cgtgtctaca actggtttgc   5280
caaccggcgc aaagaagaag ccttccggca caagctggca atgacctgca gggatgagtt   5340
tcccaccatg gtgttttcctt ctgggcagat cagccaggcc tcggcttgg ccccggcccc   5400
tccccaagtc ctgccccagg ctccagcccc tgccctgct ccagccatgg tatcagctct   5460
ggcccaggcc ccagccctg tcccagtcct agccccagge cctcctcaag ctgtggcccc   5520
acctgccccc aagcccaccc aagctgggga aggaacgctc tcagaggccc tgctgcagct   5580
gcagtttgat gatgaagacc tgggggcctt gcttggcaac agcacagacc cagctgtgtt   5640
cacagacctg gcatccgtcg acaactccga gtttcagcag ctgctgaacc agggcatacc   5700
tgtgggccccc cacacaactg agcccatgct gatggagtac cctgaggcta taactcgcct   5760
agtgacaggg gcccagaggc cccccgaccc agctcctgcc ccactggggca cccgcccccg   5820
ccccaatggc ctccttttcag gagatgaaga cttctcctcc attgcggaca tggacttctc   5880
agccctgctg agtcagatca gctcctaaag gacgggtggc atccctgtga cccctcccca   5940
gtgcctctcc tggccctgga agttgccact ccagtgccca ccagccttgt cctaataaaa   6000
ttaagttgca tcattttgtc tgactaggtg tccttctata atatttatgg gtggagggg   6060
gtggtatgga gcaagggca agttgggaag acaacctgta gggctgcggg ggtctattgg   6120
gaaccaagct ggagtgcagt ggcacaatct tggctcactg caatcctccg ctcctgggtt   6180
caagcgattc tcctgcctca gcctcccgag ttgttgggat tccaggcatg catgaccagg   6240
ctcagctaat ttttgttttt tggtagaaa cggggttttca ccatattggc caggctggtc   6300
tccaactcct aatctcaggt gatctaccca ccttggcctc ccaaattgct gggattacag   6360
gcgtgaacca ctgctccctt ccctgtcctt c                                  6391

SEQ ID NO: 168         moltype = DNA  length = 6391
FEATURE                Location/Qualifiers
source                 1..6391
                       mol_type = other DNA
                       organism = synthetic construct
SEQUENCE: 168
taaggtacga ctgtgccttc tagttgccag ccatctgttg tttgcccctc ccccgtgcct   60
tccttgaccc tggaaggtgc cactcccact gtcctttcct aataaaatga ggaaattgca   120
tcgcattgtc tgagtaggtg tcattctatt ctgggggtg gggtgggca ggacagcaag   180
ggggaggatt gggaagacaa tagcaggcat gctgggggatg cggtgggctc tatgggataa   240
gcttgatatc gaattcatcg atgttaataa ttaacatata tgttaatcat taacatatag   300
ttaattatta accgctatgt taatgattaa caacggttaa taattaacat atatgttaat   360
cattaacata taactagtct agagggtata taatgggggc cactagtcta ctaccagagt   420
tcatcgctag cgctaccgga tccgccacca tggcccctgcc agtaacggct ctgctgctgc   480
cacttgctct gctcctccat gcagccaggc ctcagttgca gttacaggag agcggacccg   540
gtctggttaa accgtctgaa acactgagtt tgacatgtac agtgtccggc ggctcgattt   600
caaactctta ctattgggggc tggattaggc agcctcccgg gaaagggctc gagtggatcg   660
ggtccatata tcactcagga aatacctact acaacccagc cttaagtct agagtgacaa   720
tcagtgtgga tacgtccaag aatcaattcc ccctgaagct ctcaagcgtg accgccgccg   780
acaccgcagt gtattattgc gtaactcaag acggtgtggg cgctaccact accgaagagt   840
attgggggaca aggcactctt gtcacagtct ccagcgcggc agcaaccacg acgccagcgc   900
cgcgaccacc aacaccggcg cccaccatcg cctcgcagcc actgtcactg cgcccagaag   960
cgtgccggcc agcggcgggg ggcgcagtgc acacgagggg gctggacttc gcctcgtgata   1020
tctacatctg ggcgcccttg gccgggactt gtggggtcct tctcctgtca ctggttatca   1080
cccttttactg caaacggggc agaaagaaac tcctgtatat attcaaacaa ccatttatga   1140
gaccagtaca aactactcaa gaagaggacg gctgtagctg ccgatttcca gaagaagaag   1200
aaggaggatg tgaactgaga gtgaagttca gcaggagcgc agacgccccc gcgtaccagc   1260
agggccagaa ccagctctat aacgagctca atctaggacg aagagaggag tacgatgttt   1320
tggacaagag gcgtggccgg accctgaga tggggggaaa gccgagaagg aagaaccctc   1380
aggaaggcct gtacaatgaa ctgcagaaag ataagatggc ggaggcctac agtgagattg   1440
ggatgaaagg cgagcgccgg aggggcaagg ggcacgatgg cctttaccag ggtctcagta   1500
cagccaccaa ggacacctac gacgcccttc acatgcaggc cctgccccct aggtaaaatc   1560
aacctctgga ttacaaaatt tgtgaaagat tgactggtat tcttaactat gttgctcctt   1620
ttacgctatg tggatacgct gctttaatgc ctttgtatca tgctattgct tcccgtatgg   1680
cttttcatttt ctcctccttg tataaatcct ggttgctgtc tctttatgag gagttgtggc   1740
ccgttgtcag gcaacgtggc gtggtgtgca ctgtgtttgc tgacgcaacc cccactggtt   1800
ggggcattgc caccacctgt cagctccttt ccgggacttt cgctttcccc tccctattg   1860
ccacggcgga actcatcgcc gcctgccttg cccgctgctg acagggggct cggctgttgg   1920
gcactgacaa ttccgtggtg ttgtcgggga atcatcgtc ctttccttgg ctgctcgcct   1980
gtgttgccac ctggattctg cgcgggacgt ccttctgcta cgtcccttcg ccctcaatc   2040
cagcggacct tccttcccgc ggcctgctgc cggctctgcg gcctcttccg cgtcttcgcc   2100
ttcgccctca gacgagtcgg atctcccttt gggccgcctc ccgcctgga tccttgactt   2160
```

```
gcggccaact tgtttattgc agcttataat ggttacaaat aaagcaatag catcacaaat    2220
ttcacaaata aagcatttttt ttcactgcat tctagttgtg gtttgtccaa actcatcaat    2280
gtatcttatc atgtctggga tccttgactt gcggccgcaa ctcccacctg caacatgcgt    2340
gactgactga ggccgcgact ctagagtcga ccggatctgc gatcgctccg gtgcccgtca    2400
gtgggcagag cgcacatcgc ccacagtccc cgagaagttg ggggagggg tcggcaattg    2460
aacgggtgcc tagagaaggt ggcgcgggt aaactgggaa agtgatgtcg tgtactggct    2520
ccgccttttt cccgagggtg ggggagaacc gtatataagt gcagtagtcg ccgtgaacgt    2580
tcttttttcgc aacgggtttg ccgccagaac acagctgaag cttcgagggg ctcgcatctc    2640
tccttcacgc gcccgccgcc ctacctgagg ccgccatcca cgccggttga gtcgcgttct    2700
gccgcctccc gcctgtggtg cctcctgaac tgcgtccgcc gtctaggtaa gtcgactcgt    2760
tggatcccca ctaccggat caacgccta ggtttatgtt tggatgaact gacatacgcg    2820
tatccgtctt aagaatcttt tcaaacacta gtagtgaaat atatattaaa ctagtgtttg    2880
aaaagattct tattacggta acgcggaatt cgcaactatt ttatcaattt tttgcgtcga    2940
cacttcaagg ggcttgcggc cgcaaccatc tccatggctg tttgaatgag gcttcagtac    3000
tttacagaat cgttgcctgc acatcttgga aacacttgct gggattactt cgacttctta    3060
acccaacaga aggctcgaga aggtatattg ctgttgacag tgagcgccag tgtgaagctc    3120
ttgtcagata gtgaagccac agatgtatct gacaagagct tcacactgat gcctactgcc    3180
tcggacttca aggggctaga attcgagcaa ttatcttgtt tactaaaact gaataccttg    3240
ctatctcttt gatacatttt tacaaagctg aattaaaatg gtataaatta aatcactttt    3300
tcatctgacc agtagtggac tagtgtgacg ctgctgaccc cttctcttcc cttctacaga    3360
tccaagctgt gaccggcgcc tacacctgca gcccaagctt accatggcct taccagtgac    3420
cgccttgctc ctgccgctgg ccttgctgct ccacgccgcc aggcctgaca tacagatgac    3480
acagagccct agcagtctga gcgccagtgt gggcgataga gttactatca cttgtagagc    3540
atccgagaac atatacagtt acgtggcctg gtatcagcaa aaacctgcaa agctcccaa    3600
gttattgatt tacaatgcta agagcttggc ctctggggtg ccatcgaggt tcagcggtag    3660
cgggacgggg accgacttca ctctgaccat ctcgagtctc cagccggagg actttgcgac    3720
atactattgt caacaccatt acgtatcacc ctgaccttc ggcggcggga ctaagttaga    3780
gatcaagggt ggaggaggat caggcggcgg tggatcagga ggaggggt cacaagtgca    3840
gttacaggaa tcagggcccg gcctggtgaa gccaagtgaa accctgagtc tgacgtgcac    3900
ggtttcagga tttagcctca cttcctacgg tgtctcttgg attcggcagc cagccggcaa    3960
aggggctcgag tggattgggg tgatctggga agatgctca acaaactatc attctgcact    4020
aatctctcgc gtgacaatgt cggtggacac gtccaagaat caattttccc ttaaactgtc    4080
ctccgtgacc gcagccgata cagcggtata ttattgcgcg cgacctcact acggatctag    4140
ctatgtcggc gcgatggagt attgggggcgc tggcacaacc gtcaccgttt cttccgcaac    4200
cacgacgcca gcgccgcgac caccaacacc ggcgcccacc atcgcgtcgc agccctgtc    4260
cctgcgccct gaggcgtgct tcatgtacgt ggcggcggcc gcctttgtgc ttctgttctt    4320
cgtgggctgc ggggtgctgc tgtcccgtaa acgcagacgt caacacggtc aactgtggtt    4380
tccagaaggt tttaaggtct ccgaagcaag taagaagaaa agacgtgaac cactgggaga    4440
agatagcgtc ggtctgaaac cactcaagaa tgccatggtt tctaaactga gccagctgca    4500
gacggagctc ctggcggccc tgctggagtc agggcgtgagc aaagaggcac tgctccaggc    4560
actgggcgag ccggggccct acctcctggc tggagaaggc ccctggaca aggggagtc    4620
ctgcggcggc ggtcgagggg agctggctga gctgcccaat gggctggggg agactcgggg    4680
ctccgaggac gagaccgacg acgatgggga agacttcacg ccacccatcc tcaaagagct    4740
ggagaacctc agccctgagg aggcggccca ccagaaagcc gtggtggaga ccttctcga    4800
ggaggacccg tggcgtgtgg cgaagatggt caagtcctac ctgcagcagc acaacatccc    4860
acagcgggag gtggtcgata ccactggcct caaccagtcc cacctgtccc aacacctcaa    4920
caagggcct cccatgaaga cgcagaagcg ggccgccctg tacacctggt atgtccgcaa    4980
gcagcgagag gtgcgcagc agttcaccca tgcagggcag ggagggctga ttgaagagcc    5040
cacaggagat gagctaccaa ccaagaaggg gcggaggaac cgtttcaagt ggggcccagc    5100
atcccagcag atcctgttcc aggcctatga gaggcagaag aaccctagca aggaggagcg    5160
agaaacgcta gtggagagt gcaatagggc ggaatgcatc cagagaggtg tgtcaccatc    5220
acaagcacaa ggtctgggct ccaacctcgt cacggaggtg cgtgtctaca actggttgc    5280
caaccggcgc aaagaagaag ccttccggca caagctggcc atgacctgca gggatgagtt    5340
tcccaccatg gtgtttcctt ctgggcagat cagccaggcc tcggccttgg ccccggcccc    5400
tccccaagtc ctgcccagg ctccagcccc tgccctgtc cagccatgg tatcagctct    5460
ggcccaggcc ccagcccctg tccagtcctt agcccaggcc cctcctcaag ctgtggcccc    5520
acctgccccc aagcccaccc aagctgggga ggaacgctg tcagaggccc tgctgcagct    5580
gcagtttgat gatgaagacc tgggggcctt gcttggcaac agcacagacc cagctgtgtt    5640
cacagacctg gcatccgtcg acaactccga gttcagcag ctgctgaacc agggcatacc    5700
tgtggccccc cacacaactg agcccatgct gatggagtac cctgaggcta taactcgcct    5760
agtgacaggg gcccagaggc ccccgacc agctcctgct ccactgggg ccccggggct    5820
ccccaatggc ctcctttcag gagatgaaga cttctcctcc attgcggaca tggacttctc    5880
agccctgctg agtcagatca gctcctaaag gacgggtggc atccctgtga cccctcccca    5940
gtgcctctcc tggccctgga agttgccact ccagtgccat cccgccttgt cctaatdaaa    6000
ttaagttgca tcatttgtc tgactaggtg tccttctata atatattggg gtgaggggg    6060
gtggtatgga gcaaggggca agttgggaag acaacctgta gggcctgcgg ggtctattgg    6120
gaaccaagct ggagtgcagt ggcacaatct ggctcactg caatctccgc ctcctgggtt    6180
caagcgatc tcctgcctca gcctcccgag ttgttgggat tccaggcatg catgaccagg    6240
ctcagctaat tttgttttt tggtagaaa cggggtttca ccatgttggc caggctggtc    6300
tccaactcct aatctcaggt gatctaccca ccttggcctc ccaaattgct gggattacag    6360
gcgtgaacca ctgctccctt ccctgtcctt c                                   6391

SEQ ID NO: 169        moltype = DNA  length = 6955
FEATURE               Location/Qualifiers
source                1..6955
                      mol_type = other DNA
                      organism = synthetic construct
SEQUENCE: 169
gagccatgct tggcttacga gggcgaccaa cccatcaaac tccccgcccc cagcactttt    60
```

```
atttctcctc tttaggaagt acacttcagt atctttggca cagtgcatga gcacgactaa  120
agtaaaacat cgcagaaaac atagctttag tctacccttc gtgtcctaaa aggaaaaacca 180
gtagcttccc aggccaccgg aagggcaaca catgtcctct gcagtttctg cacacgggaa  240
ggtaaagaca gagagaggac ctactcctca acacagaaac atttcaaaat ctttcctcgc  300
ctgcaaccca agctgaagtc attctcccca gaaataacaa aagttggaag agaagccgga  360
gacaggatag gtgcaggaag cccacacttt gagggcagca ctcagacacc ctctcctgtg  420
tgcaggacgt gccgaatgtt caggtgcaat gagaatgagc catgcttggc ttataaggta  480
cgactgtgcc ttctagttgc cagccatctg ttgtttgccc ctccccgtg ccttcctga   540
ccctggaagg tgccactccc actgtccttt cctaataaaa tgaggaaatt gcatcgcatt  600
gtctgagtag gtgtcattct attctggggg gtgggggtggg gcaggacagc aaggggggagg 660
attgggaaga caatagcagg catgctgggg atgcggtggg ctctatggga taagcttgat  720
atcgaattca tcgatgttaa taattaacat atatgttaat cattaacata tagttaatta  780
ttaaccgcta tgttaatgat taacaacggt taataattaa catatatgtt aatcattaac  840
ataaactag tctagagggt ctataatggg ggcactagt ctactaccag agttcatcgc   900
tagcgctacc ggatccgcca ccatggccct gccagtaacg gctctgctgc tgccacttgc  960
tctgctcctc catgcagcca ggcctcagtt gcagttacag gagagcggac ccggtctggt 1020
taaaccgtct gaaacactga gtttgacatg tacagtgtcc ggcggctcga tttcaaactc 1080
ttactattgg ggctggatta ggcagcctcc cgggaaaggg ctcgagtgga tcgggtccat 1140
atatcactca ggaaatacct actacaaccc aagtcttaag tctagagtga caatcagtgt 1200
ggatacgtcc aagaatcaat tctccctgaa gctctcaagc gtgaccgccg ccgacaccgc 1260
agtgtattat tgcgtaactc aagacggtgt gggcgctacc actaccgaag agtattgggg 1320
acaaggcact cttgtcacag tctccagcgc ggcagcaacc acgccgccag cgccgcgacc 1380
accaacaccg gcgcccacca tcgcgtcgca gccactgtca ctgcgcccag aagcgtgccg 1440
gccagcggcg gggggcgcag tgcacacgag ggggctggac ttcgcctgtg atatctacat 1500
ctgggcgccc ttggccggga cttgtggggt ccttctcctg tcactggtta tcacccttta 1560
ctgcaaacgg ggcagaaaga aactcctgta tatattcaaa caaccattta tgagaccagt 1620
acaaactact caagaagagg acggctgtag ctgccgattt ccagaagaag aagaaggagg 1680
atgtgaactg agagtgaagt tcagcaggag cgcagacgcc cccgcgtacc agcagggcca 1740
gaaccagctc tataacgagc tcaatctagg acgaagagag gagtacgatg ttttggacaa 1800
gaggcgtggc cgggacccctg agatgggggg aaagccagga ggaagaacc ctcaggaagg 1860
cctgtacaat gaactgcaga agataagat ggcggaggcc tacagtgaga ttgggatgaa 1920
aggcgagcgc cggaggggca agggacga tggcctttac cagggtctca gtacagccac 1980
caaggacacc tacgacgccc ttcacatgca ggccctgccc cctaggtaaa atcaacctct 2040
ggattacaaa atttgtgaaa gattgactgg tattcttaac tatgttgctc cttttacgct 2100
atgtggatac gctgctttaa tgcctttgta tcatgctatt gcttcccgta tggctttcat 2160
tttctcctcc ttgtataaat cctggttgct gtctctttat gaggagttgt ggcccgttgt 2220
caggcaacgt ggcgtggtgt gcactgtgtt tgctgacgca accccactg gttggggcat 2280
tgccaccacc tgtcagctcc tttccgggac tttcgctttc cccctcccta ttgccacggc 2340
ggaactcatc gccgcctgcc ttgcccgctg ctggacaggg gctcggctgt tgggcactga 2400
caattccgtg gtgttgtcgg ggaaatcatc gtcctttcct ggctgctcg cctgtgttgc 2460
cacctcggat ctgcgcggga cgtccttctg ctacgtccct tcggccctca atccagcgga 2520
ccttccttcc cgcggcctgc tgccggctct gcggcctctt ccgcgtcttc gccttcgccc 2580
tcagacgagt cggatctccc tttgggccgc ctccccgcct ggatccttga cttgcggcca 2640
acttgtttat tgcagcttat aatggttaca aataaagcaa tagcatcaca aatttcacaa 2700
ataaagcatt ttttcactg cattctagtt gtggtttgtc caaactcatc aatgtatctt 2760
atcatgtctg gatccttga cttgcggccg caactcccac ctgcaacatg cgtgactgac 2820
tgaggccgcg actctagagt cgaccggatc tgcgatcgct ccggtgcccg tcagtgggca 2880
gagcgcacat cgcccacagt ccccgagaag ttggggggag gggtcggcaa ttgaacgggt 2940
gcctagagaa ggtggcgcgg ggtaaactgg gaaagtgatg tcgtgtactg gctccgcctt 3000
tttcccgagg gtgggggaga accgtatata agtgcagtag tcgccgtgaa cgttctttt 3060
cgcaacgggt ttgccgccag aacacagctg aagcttcgag gggctcgcat ctctccttca 3120
cgcgcccgcc gccctacctg aggccgccat ccacgccggt tgagtcgcgt tctgccgcct 3180
cccgcctgtg gtgcctcctg aactgcgtcc gccgtctagg taagtcgact cgttggatcc 3240
ccactacccg gatcaacgcc ctaggtttat gtttggatga actgacatac gcgtatccgt 3300
cttaagaatc ttttcaaaca ctagtagtga aatatatatt aaactagtgt ttgaaaagat 3360
tcttattacg gtaacgcgga attcgcaact attttatcaa ttttttgcgt cgacacttca 3420
aggggcttgc ggccgcaacc atctccatgg ctgtttgaat gaggcttcag tactttacag 3480
aatcgttgcc tgcacatctt ggaaacactt gctgggatta cttcgacttc ttaacccaac 3540
agaaggctcg agaaggtata ttgctgttga cagtgagcgc cagtgtgaag ctcttgtcag 3600
atagtgaagc cacagatgta tctgacaaga gcttcacact gatgcctact gcctcggact 3660
tcaaggggct agaattcgag caattatctt gtttactaaa actgaatacc ttgctatctc 3720
tttgatacat ttttacaaag ctgaattaaa atggtataaa ttaaatcact ttttcatctg 3780
accagtagtg gactagtgtg acgctgctga ccccttctt tccttctac agatccaagc 3840
tgtgaccggc gcctacacct gcagccaag cttaccatgg acctgccttg 3900
ctcctgccgc tggccttgct gctccacgcc gccaggcctg acatacagat gacacagagc 3960
cctagcagtc tgagcgccag tgtgggcgat agagttacta tcacttgtag agcatccgag 4020
aacatataca gttacgtggc ctggtatcag caaaaacctg gcaaagctcc caagttattg 4080
atttacaatg ctaagagctt ggcctctggg gtgccatcga ggttcagcgg tagcgggagc 4140
gggaccgact tcactctgac catctcgagt ctccagccgg aggactttgc gacatactat 4200
tgtcaacacc attacgtatc accctggacc ttcggcggcg ggactaagtt agagatcaag 4260
ggtgaggag atcaggcgg cggtggatca ggaggaggag ggtcacaagt gcagttacag 4320
gaatcagggc ccgcctggt gaagccagt gaaaccctga gtctgacgtg cacggtttca 4380
ggatttagcc tcacttccta cggtgtctct tggattcggc agccagccgg caaagggctc 4440
gagtggattg gggtattgg gaagatggc tcaacaaact atcattctgc actaatctct 4500
cgcgtgacaa tgtcggtgga cacgtccaag aatcaatttt cccttaaact gtcctccgtg 4560
accgcagccc atacagcggt atattattgc gcgcgacctc actacggatc tagctatgtc 4620
ggcgcgatgg agtattgggg cgctggcaca accgtcaccg tttcttccgc aaccacgacg 4680
ccagcgccgc gaccaccaac accggcgccc accatcgcgt cgcagcccct gtccctgcgc 4740
cctgaggcgt gcttcatgta cgtggcggcg gccgcctttg tgcttctgtt cttcgtgggc 4800
```

```
tgcgggtgc tgctgtcccg taaacgcaga cgtcaacacg gtcaactgtg gtttccagaa    4860
ggttttaagg tctccgaagc aagtaagaag aaaagacgtg aaccactggg agaagatagc    4920
gtcggtctga aaccactcaa gaatgccatg gtttctaaac tgagccagct gcagacggag    4980
ctcctggcgc cctgctgga gtcagggctg agcaaagagg cactgctcca ggcactgggc    5040
gagccggggc cctacctcct ggctggagaa ggcccccctg acaagggga gtcctgcgcc    5100
ggcggtcgag gggagctggc tgagctgccc aatgggctgg gggagactcg gggctccgag    5160
gacgagaccg acgacgatgg ggaagacttc acgccaccca tcctcaaaga gctggagaac    5220
ctcagccctg aggaggcggc ccaccagaaa gccgtggtgg agacccttct gcaggaggac    5280
ccgtggcgtg tggcgaagat ggtcaagtcc tacctgcagc agcacaacat cccacagcgg    5340
gaggtggtcg ataccactgg cctcaaccag tcccacctgt cccaacacct caacaagggc    5400
actcccatga agacgcagaa gcgggccgcc ctgtacacct ggtatgtccg caagcagcga    5460
gaggtggcgc agcagttcac ccatgcaggg cagggagggc tgattgaaga gcccacagga    5520
gatgagctac caaccaagaa ggggcggagg aaccgtttca gtgggggccc agcatcccag    5580
cagatcctgt tccaggccta tgagaggcag aagaaccc ta gcaaggagga gcgagaaacg    5640
ctagtggagg agtgcaatag gcggaatgc atccagagag gtgtgtcacc atcacaagca    5700
caaggtctgg gctccaacct cgtcacggag gtgcgtgtct acaactggtt tgccaaccgg    5760
cgcaaagaag aagccttccg gcacaagctg gccatgacct gcagggatga gtttcccacc    5820
atggtgtttc cttctgggca gatcagccag gcctcggcct tggcccggc ccctcccaa    5880
gtcctgcccc aggctccagc ccctgcccct gctccagcca tggtatcagc tctggcccag    5940
gccccagccc ctgtcccagt cctagcccca ggccctcctc aagctgtggc cccacctgcc    6000
cccaagccca cccaagctgg ggaaggaacg ctgtcagagg ccctgctgca gctgcagttt    6060
gatgatgaag acctgggggc cttgcttggc aacagcacag acccagctgt gttcacagac    6120
ctggcatccg tcgacaactc cgagtttcag cagctgctga accagggcat acctgtggcc    6180
ccccacacaa ctgagcccat gctgatggag taccctgagg ctataactcg cctagtgaca    6240
gggggcccaga ggcccccga cccagctcct gctccactgg ggccccggg gctccccaat    6300
ggcctcccttt caggagatga agacttctcc tccattgcgg acttctcagc ccctg         6360
ctgagtcaga tcagctccta aaggaaataa aagatcttta tgaaaatag atctgtgtgt    6420
tggtttttg tgtgaataaa agatccagg ctctagagat ctgtgtgttg gttttttgtg    6480
tgcgagggca atctggccca tcaagtggcc ttcgcctctg ggagtaacaa aaatgcactt    6540
caaaatagct tctgtaatca agctgcatgg gtggagtact ccccagctga ctccaggaag    6600
ttctctatcc aaagctattc attaggccag agctgtgcaa ataattagtc acccacttgc    6660
tccataaccc tccatgacag cccaggcatt gagtccaggt gggaccatca agccatgctc    6720
tggtggctca tgcattatca tagaaatggg aggctttatt tattttacta aaagaacaa    6780
aaacaacaga ctgctgtcct ttagacaata ggatcacgtc atctgagcc tctgtgcccc    6840
aggtgacaag cccagcccca agttctcttt cctcagcctc cccacacatg ttctggagga    6900
gatggcccca gcaggctgct ctgaggcctg gccccctcgta agccaagcat ggctc         6955

SEQ ID NO: 170       moltype = DNA  length = 7383
FEATURE              Location/Qualifiers
source               1..7383
                     mol_type = other DNA
                     organism = synthetic construct
SEQUENCE: 170
gagccatgct tggcttacga gggcgaccaa cccatcaaac tccccgcccc cagcacttt    60
atttctcctc tttaggaagt acacttcagt atctttggca cagtgcatga gcacgactaa    120
agtaaaacat cgcagaaaac atagctttag tctacccttc gtgtcctaaa aggaaaacca    180
gtagcttccc aggccaccgg aagggcaaca catgtcctct gcagtttctg cacacgggaa    240
ggtaaagaca gagagaggac ctactcctca acacagaaac atttcaaaat ctttcctcgc    300
ctgcaaccca agctgaagtc attctcccca gaaataacaa aagttggaag agaagccgga    360
gacaggatag tgtcaggaag cccacacttt gagggcagca ctcagacacc ctctcctgtg    420
tgcaggacgt gccgaatgtt caggtgcaat gagaatgagc catgcttggc ttataaggta    480
cgactgtgcc ttctagttgc cagccatctg ttgtttgccc ctcccccgtg ccttccttga    540
ccctggaagg tgccactccc actgtccttt cctaataaaa tgaggaaatt gcatcgcatt    600
gtctgagtag tgtgtcattct attctggggg gtggggtggg gcaggacagc aagggggagg    660
attgggaaga caatagcagg catgctgggg atgcggttgg ctctatggga taagcttgat    720
atcgaattca tcgatgttaa taattaacat atatgttaat cattaacata tagttaatta    780
ttaaccgcta tgttaatgat taacaacggt taataattaa catatatgtt aatcattaac    840
atataactag tctagagggt atataatggg ggccactagt ctactaccag agttcatcgc    900
tagcgctacc ggatccgcca ccatgggcct gccagtaacg gctctgctgc tgccacttga    960
tctgctcctc catgcagcca ggcctcagtt gcagttacga gagagcggac ccggtctggt    1020
taaaccgtct gaaacactga gtttgacatg tacagtgtcc ggcggctcga tttcaaactc    1080
ttactattgg ggctggatta ggcagcctcc cgggaagggg ctcgagtgga tcgggtccat    1140
atcactca ggaaatacct actacaaccc aagtcttaag tctagagtga caatcagtgt    1200
ggatacgtcc aagaatcaat tctccctgaa gctctcaagc gtgaccgccg ccgacacgc    1260
agtgtattat tgcgtaactc aagacggtgt gggcgctacc actaccgaag agtattggg    1320
acaaggcact cttgtcacag tctccagcgc ggcagcaacc acgacgccag cgccgcgacc    1380
accaacaccg gcgcccacca tcgcgtcgca gccactgtca ctgcgccag aagcgtgccg    1440
gccagcggc gggggcgcag tgcacgagg ggctggac ttcgcctgtg atatctacat    1500
ctgggcgcc ttgcccggga cttgtgggt ccttctcctg tcactggtta tcacccttta    1560
ctgcaaacgg ggcagaaaga aactcctgta tattcaaaa caaccattta tgagaccagt    1620
acaaactact caagaagagg acggctgtag ctgccgattt ccagaagaag aagaggagg    1680
atgtgaactg agagtgaagt tcagcaggag cgcagacgcc ccgcgtacc agcagggcca    1740
gaaccagctc tataacgagc tcaatctagg acgaagagag gagtacgatg ttttggacaa    1800
gaggcgtggc cgggaccctg agatgggggg aaagccgaga aggaagaacc ctcaggaagg    1860
cctgtacaat gaactgcaga agataagat ggcggaggcc tacagtgaga ttgggatgaa    1920
aggcgagcgc cggaggggca aggggcacga tggcctttac cagggtctca gtacagccac    1980
caaggacacc tacgacgccc ttcacatgca ggccctgccc cctaggtaaa atcaacctct    2040
ggattacaaa atttgtgaaa gattgactgg tattcttaac tatgttgctc cttttacgct    2100
atgtggatac gctgctttaa tgcctttgta tcatgcatt gcttcccgta tggctttcat    2160
```

```
tttctcctcc ttgtataaat cctggttgct gtctctttat gaggagttgt ggcccgttgt 2220
caggcaacgt ggcgtggtgt gcactgtgtt tgctgacgca accccactg gttgggcat   2280
tgccaccacc tgtcagctcc tttccgggac tttcgctttc cccctcccta ttgccacggc 2340
ggaactcatc gccgcctgcc ttgcccgctg ctggacaggg gctcggctgt gggcactga  2400
caattccgtg gtgttgtcgg ggaaatcatc gtcctttcct tggctgtcg cctgtgttgc  2460
cacctggatt ctgcgcggga cgtccttctg ctacgtccct tcggccctca atccagcgga 2520
ccttccttcc cgcggcctgc tgccggctct gcggcctctt ccgcgtcttc gccttcgccc 2580
tcagacgagt cggatctccc tttgggccgc ctccccgcct ggatccttga cttgcggcca 2640
acttgtttat tgcagcttat aatggttaca aataaagcaa tagcatcaca aatttcacaa 2700
ataaagcatt ttttcactg cattctagtt gtggtttgtc caaactcatc aatgtatctt   2760
atcatgtctg ggatccttga cttgcggccg caactcccac ctgcaacatg cgtgactgac 2820
tgaggccgcg actctagagt cgaccggatc tgcgatcgct ccggtgcccg tcagtgggca 2880
gagcgcacat cgcccacagt ccccgagaag ttgggggaga gggtcggcaa ttgaacgggt 2940
gcctagagaa ggtggcgcgg ggtaaactgg gaaagtgatg tcgtgtactg gctccgcctt 3000
tttcccgagg gtgggggaga accgtatata agtgcagtag tcgccgtgaa cgttctttt   3060
cgcaacgggt ttgccgccag aacacagctg aagcttcgag gggctcgcat ctctccttca 3120
cgcgcccgcc gccctacctg aggccgccat ccacgccggt tgagtcgcgt tctgccgcct  3180
cccgcctgtg gtgcctcctg aactgcgtcc gccgtctagg taagtcgact cgttggatcc 3240
ccactacccg gatcaacgcc ctaggtttat gtttggatga actgacatac gcgtatccgt 3300
cttaagaatc ttttcaaaca ctagtagtga aatatatatt aaactagtgt ttgaaaagat 3360
tcttattacg gtaacgcgga attcgcaact atttttatcaa ttttttgcgt cgacacttca  3420
aggggcttgc ggccgcaacc atctccatgg ctgtttgaat gaggcttcag tactttacag 3480
aatcgttgcc tgcacatctt ggaaacactt gctggatta cttcgacttc ttaacccaac   3540
agaaggctcg agaaggtata ttgctgttga cagtgagcgc cagtgtgaag ctcttgtcag 3600
atagtgaagc cacagatgta tctgacaaga gcttcacact gatgcctact gcctcggact  3660
tcaaggggct agaattcgag caattatctt gtttactaaa actgaatacc ttgctatctc  3720
tttgatacat ttttacaaag ctgaattaaa atggtataaa ttaaatcact ttttcatctg 3780
accagtagtg gactagtgtg acgctgctga ccccttttctt tcccttctac agatccaagc  3840
tgtgaccggc gcctacacct gcagcccaag cttttttatgg ccttaccagt gaccgccttg 3900
ctcctgccgc tggccttgct gctccacgcc gccaggcctg acatacagat gacacagagc 3960
cctagcagtc tgagcgccag tgtgggcgat agagttacta tcacttgtag agcatccgaa 4020
aacatataca gttacgtggc ctggtatcag caaaaacctg gcaaagctcc caagttattg 4080
atttacaatg ctaagagctt ggcctctggg gtgccatcga ggttcagcgg tagcgggagc 4140
gggaccgact tcactctgac catctcgagt ctccagccgg aggactttgc gacatactat 4200
tgtcaacacc attacgtatc accctggacc ttcggccggg ggactaagtt agagatcaag 4260
ggtggaggag gatcaggcgg cggtggatca ggaggaggag ggtcacaagt gcagttacag 4320
gaatcagggc ccggcctggt gaagccaagt gaaaccctga gtctgacgtg cacggtttca 4380
ggatttagcc tcacttccta cggtgtctct tggattcggc agccagccgg caaagggctc 4440
gagtggattg gggtgatctg ggaagatggc tcaacaaact atcattctgc actaatctct 4500
cgcgtgacaa tgtcggtgga cacgtccaag aatcaattt cccttaaact gtcctccgtg  4560
accgcagccg atacagcggt atattattgc gcgcgacctc actacggatc tagctatgtc 4620
ggcgcgatgg agtattgggg cgctggcaca accgtcaccg tttcttccgc aaccacgacg 4680
ccagcgccgc gaccaccaac accggcgccc accatccgct gcagccccct gtccctgcgg 4740
cctgaggcgt gcttcatgta cgtgcgcgcg gccgcctttg tgcttctgtt cttcgtgggc 4800
tgcggggtgc tgctgtcccg taaacgcaga cgtcaacacg gtcaactgtg gtttccagaa 4860
ggttttaagg tctccgaagc aagtaagaag aaaaagacgtg aaccactggg agaagatagc 4920
gtcggtctga aaccactcaa gaatgccatg gtttctaaac tgagccagct acgagcggag 4980
ctcctggcgg ccctgctgga gtcagggctg agcaaagagg cactgctcca ggcactgggc 5040
gagccggggc cctacctcct ggctggagaa ggccccctgg acaaggggga gtcctgcggc 5100
ggcggtcgag gggagctggc tgagctgccc aatgggctgg gggagactcg gggctccgag 5160
gacgagaccg acgacgatgg ggaagacttc acgccaccca tcctcaaaga gctggagaac 5220
ctcagccctg aggaggcggc ccaccagaaa gccgtggtgg agaccttct gcaggaggac 5280
ccgtggcgtg tggcgaagat ggtcaagtcc tacctgcagc agcacaacat cccacagcgg 5340
gaggtggtcg ataccactgg cctcaaccag tcccacctgt cccaacacct caacaagggc 5400
actccatga agacgcagaa gcgggccgcc ctgtacaccg ggtatgtccg caagcagcga 5460
gaggtggcgc agcagttcac ccatgcaggg caggggaggc tgattgaaga gcccacagga 5520
gatgagctac caaccaagaa ggggcggagg aaccgtttca gtgggggccc agcatcccag 5580
cagatcctgt tccaggccta tgagaggcag aagaaccccta gcaaggagga gcgagaaacg 5640
ctagtggagg agtgcaatag ggcggaatgc atccaagaga gtgtgtcacc atcacaagca 5700
caaggtctgg gctcaaacct cgtcacggag gtgcgtgtct acaactggtt tgccaaccgg 5760
cgcaaagaag aagccttccg gcacaagctg gccatgacct gcaggatga gtttcccacc 5820
atggtgtttc cttctgggca gatcagccag gcctcggcct tggccccggc ccctccccaa 5880
gtcctgcccc aggctccagc ccctgcccct gctccagcca tggtatcagc tctgcccag  5940
gcccagccc ctgtcccagt cctagcccca ggccctcctc agctgtggcc cccacctccc 6000
cccaagccca cccaagctgg ggaaggaacg ctgtcagagg ccctgctgca gctgcagttt 6060
gatgatgaag acctggggc cttgcttggc aacagcacag acccagctgt gttcacagac 6120
ctggcatccg tcgacaactc cgagtttcag cagctgctga accagggcat acctgtggcc 6180
ccccacacaa ctgagcccca gctgatggag tacctgaagg ctataactcg cctagtgaca 6240
ggggcccaga ggccccccga cccagctcct gctccactgg gccccccggg gctccccaat 6300
ggcctccttt caggagatga agacttctcc tccattgcgg acatggactt ctcagccctg 6360
ctgagtcaga tcagctccta aaggacgggt ggcatccctg tgaccctcc ccagtgcctc  6420
tcctggcccct ggaagttgcc actccagtgc ccaccagcct tgtcctaata aaattaagtt 6480
gcatcatttt gtctgactag gtgtccttct ataaatattat ggggtggagg gggtggtat   6540
ggagcaaggg gcaagttggg aagacaacct gtaggggtct tgggaaccaa 6600
gctggagtgc agtggcacaa tcttggctca ctgcaatctc cgcctcctgg gttcaagcga 6660
ttctcctgcc tcagcctccc gagttgttgg gattccaggc atgcatgacc aggctcagct 6720
aattttttgtt ttttggtag aaacggggtt tcaccatatt ggccaggctg gtctccaact 6780
cctaatctca ggtgatctac ccaccttggc ctcccaaatt gctgggatta caggcgtgaa 6840
ccactgctcc cttccctgtc cttccgaggg caatctggcc catcaagtgg ccttcgcctc 6900
```

```
tgggagtaac aaaaatgcac ttcaaaatag cttctgtaat caagctgcat gggtggagta   6960
ctccccagct gactccagga agttctctat ccaaagctat tcattaggcc agagctgtgc   7020
aaataattag tcacccactt gctccataac cctccatgac agcccaggca ttgagtccag   7080
gtgggaccat caagccatgc tctggtggct catgcattat catagaaatg ggaggcttta   7140
tttattttac taaaaagaac aaaaacaaca gactgctgtc ctttagacaa taggatcacg   7200
tcatctgagc cctctgtgcc ccaggtgaca agcccagccc caagttctct ttcctcagcc   7260
tccccacaca tgttctggag gagatgggcc cagcaggctg ctctgaggcc tggcccctcg   7320
taagccaagc atggctcatc ccaatggcgc gccgagcttg gcgtaatcat ggtcatagct   7380
gtt                                                                7383

SEQ ID NO: 171        moltype = DNA   length = 7337
FEATURE               Location/Qualifiers
source                1..7337
                      mol_type = other DNA
                      organism = synthetic construct
SEQUENCE: 171
gagccatgct tggcttacga gggcgaccaa cccatcaaac tccccgcccc cagcactttt    60
atttctcctc tttaggaagt acacttcagt atctttggca cagtgcatga gcacgactaa   120
agtaaaacat cgcagaaaac atagctttag tctaccttc gtgtcctaaa aggaaaacca   180
gtagcttccc aggccaccgg aagggcaaca catgtcctct gcagtttctg cacacgggaa   240
ggtaaagaca gagagaggac ctactcctca acacagaaac atttcaaaat cttctcctcgc  300
ctgcaaccca agctgaagtc attctcccca gaaataacaa aagttggaag agaagccgga   360
gacaggatag gtgcaggaag cccacacttt gagggcagca ctcagacacc ctctcctgtg   420
tgcaggacgt gccgaatgtt caggtgcaat gagaatgagc catgcttggc ttataaggta   480
cgactgtgcc ttctagttgc cagccatctg ttgtttgccc ctccccgtg ccttccttga   540
ccctgaaagg tgccactccc actgtccttt cctaataaaa tgggaaatt gcatcgcatt   600
gtctgagtag gtgtcattct attctggggg gtgggtggg gcaggacagc aaggggagg   660
attgggaaga caatagcagg catgctgggg atgcggtggg ctctatggga taagcttgat   720
atcgaattca tcgatgttaa taattaacat atatgttaat cattaacata tagttaatta   780
ttaaccgcta tgttaatgat taacaacggt taataattaa catatatgtt aatcattaac   840
atataactag tctagagggt atataatggg ggccactagt ctactaccag agttcatcgc   900
tagcgctacc ggatccgcca ccatggccct gccagtaacg gctctgctgc tgccacttgc   960
tctgctcctc catgcagcca ggcctcagtt gcagttacag gagagcggac ccggtctggt  1020
taaaccgtct gaaacactga gtttgacatg tacagtgtcc ggcggctcga tttcaaactc  1080
ttactattgg ggctggatta ggcagcctcc cgggaaaggg ctcgagtgta tcggtcccca  1140
atatcactca ggaaatacct actacaaccc aagtcttaag tctagagtga caatcagtgt  1200
ggatacgtcc aagaatcaat tctccctgaa gctctcaagc gtgaccgccg ccgacaccgc  1260
agtgtattat tgcgtaactc aagacggtgt gggcgctacc actaccgaag agtattggg  1320
acaaggcact cttgtcacag tctccagcgc ggcagcaatc acgacgccag cgccgccca  1380
accaacaccg gcgcccacca tcgcgtcgca gccactgtca ctgcgcccag aagcgtgccg  1440
gccagcggcg gggggcgcag tgcacacgag ggggctggac ttcgcctgtg atatctacat  1500
ctgggcgccc ttggccggga cttgtggggt ccttctcctg tcactggtta tcaccctta  1560
ctgcaaacgg ggcagaaaga aactcctgta tatattcaaa caaccattta tgagaccagt  1620
acaaactact caagaagagg acggctgtag ctgccgattt ccagaagaag aagaaggagg  1680
atgtgaactg agagtgaagt tcagcaggag cgcagacgcc cccgcgtacc agcagggcca  1740
gaaccagctc tataacgagc tcaatctagg acgaagagag gagtacgatg tttttgggaca  1800
gaggcgtggc cgggaccctg agatgggggg aaagccgaga aggaagaacc ctcaggaagg  1860
cctgtacaat gaactgcaga aagataagat ggcggaggcc tacagtgaga ttgggatgaa  1920
aggcgagcgc cggaggggca aggggcacga tggcctttac caggtctca gtacagccac  1980
caaggacacc tacgacgccc ttcacatgca ggccctgccc cctaggtaaa atcaacctct  2040
ggattacaaa atttgtgaaa gattgactgg tattcttaac tatgttgctc cttttacgct  2100
atgtggatac gctgctttaa tgcctttgta tcatgctatt gcttcccgta tggctttcat  2160
tttctcctcc ttgtataaat cctggttgct gtctctttat gaggagttgt ggcccgttgt  2220
caggcaacgt ggcgtggtgt gcactgtgtt tgctgacgca accccactg gttggggcat  2280
tgccaccacc tgtcagctcc tttccgggac tttcgctttc ccctccccta tgccacggc  2340
ggaactcatc gccgcctgcc ttgcccgctg ctggacaggg gctcggctgt tgggcactga  2400
caattccgtg gtgttgtcgg ggaaatcatc gtcctttcct tggctgctcg cctgtgttgc  2460
cacctggatt ctgcgcggga cgtccttctg ctacgtccct tcggccctca atccagcgga  2520
ccttccttcc cgcggcctgc tgccgctct gcggcctctt ccgcgtcttc gccttcgccc  2580
tcagacgagt cggatctccc tttgggccgc ctccccgcct ggatccttga cttgcggcca  2640
acttgtttat tgcagcttat aatggttaca aataaagcaa tagcatcaca aatttcacaa  2700
ataaagcatt ttttcactg cattctagtt gtggtttgtc caaactcatc aatgtatctt  2760
atcatgtctg gatccttga cttgcggccg caactccac ctgcaacatg cgtgactgac  2820
tgaggcgcg actctagagt cgaccggatc tgcgatcgct ccggtgcccg tcagtgggca  2880
gagcgcacat cgcccacagt ccccgagaag ttggggggag gggtcggcaa ttgaacgggt  2940
gcctagagaa ggtggcgcgg ggtaaactgg gaaagtgatg tcgtgtactg gctccgcctt  3000
tttcccgagg gtgggggaga accgtatata agtgcagtag tcgccgtgaa cgttctttttc  3060
cgcaacgggt ttgccgccag aacacagctg aagcttcgag gggctcgcat ctctccttca  3120
cgcgcccgcc gccctacctg aggccgccat ccacgccggt tgagtcgcgt tctgccgcct  3180
cccgcctgtg tgtgcctctg aactgcgtcc gccgtctagg taagtcgact cgttggatcc  3240
ccactacccg gatcaacgcc ctaggtttat gtttggatga actgacatac gcgtatccgt  3300
cttaagaatc ttttcaaaca ctagtagtga aatatatatt aaactagtgt ttgaaaagat  3360
tcttattacg gtaacgcgga attcgcaact attttatcaa tttttttgcgt cgacacttca  3420
aggggcttgc ggccgaaca atctccatgg ctgtttgaat gaggcttcag tacttacag  3480
aatcgttgcc tgcacatctt ggaaacactt gctgggatta cttcgacttc ttaacccaac  3540
agaaggctcg agaaggtata ttgctgttga cagtgagcgc cagtgtgaag ctcttgtcag  3600
atagtgaagc cacagatgta tctgacaaga gcttcacact gatgcctact gcctcggact  3660
tcaagggact agaattcgag caattatctt gtttactaaa actgaatacc ttgctatctc  3720
tttgatacat ttttacaaag ctgaattaaa atggtataaa ttaaatcact ttttcatctg  3780
```

```
accagtagtg gactagtgtg acgctgctga ccccttctt tccctctac agatccaagc  3840
tgtgaccggc gcctacacct gcagcccaag cttaccatgg ccttaccagt gaccgcttg   3900
ctcctgccgc tggccttgct gctccacgcc gccaggcctg acatacagat gacacagagc  3960
cctagcagtc tgagcgccag tgtgggcgat agagttacta tcacttgtag agcatccgag  4020
aacatataca gttacgtggc ctggtatcag caaaaacctg gcaaagctcc caagttattg  4080
atttacaatg ctaagagctt ggcctctggg gtgccatcga ggttcagcgg tagcgggagc  4140
gggaccgact tcactctgac catctcgagt ctccagccgg aggactttgc gacatactat  4200
tgtcaacacc attacgtatc accctggacc ttcggcggcg ggactaagtt agagatcaag  4260
ggtggaggag gatcaggcgg cggtggatca ggaggaggag ggtcacaagt gcagttacag  4320
gaatcagggc ccggcctggt gaagccaagt gaaaccctga gtctgacgtg cacggtttca  4380
ggatttagcc tcacttccta cggtgtctct tggattcggc agccagccgg caaagggctc  4440
gagtggattg gggtgatctg ggaagatggc tcaacaaact atcattctgc actaatctct  4500
cgcgtgacaa tgtcggtgga cacgtccaag aatcaatttt cccttaaact gtcctccgtg  4560
accgcagccg atacagcggt atattattgc gcgcgacctc actacggatc tagctatgtc  4620
ggcgcgatgg agtattgggg cgctggcaca accgtcaccg tttcttccgc aaccacgacg  4680
ccagcgccgc gaccaccaac accggcgccc accatcgcgt cgcagcccct gtccctgcgc  4740
cctgaggcgt gcttcatgta cgtggcgcg gccgcctttg tgcttctgtt cttcgtgggc  4800
tgcgggtgca tgctgtcccg taaacgcaga cgtcaacacg gtcaactgtg gtttccagaa  4860
ggttttaagg tctccgaagc aagtaagaag aaaagacgtg aaccactggg agaagatagc  4920
gtcggtctga aaccactcaa gaatgccatg gtttctaaac tgagccagct gcagacggag  4980
ctcctggcgg ccctgctgga gtcagggctg agcaaagagg cactgctcca ggcactgggc  5040
gagccgggcc cctacctcct ggctggagaa ggccccctgg acaaggggga ggcgctgcgg  5100
ggcggtcgag gggagctggc tgagctgccc aatgggctgg gggagactcg gggctccgag  5160
gacgagaccg acgacgatgg ggaagacttc acgccaccca tcctcaaaga gctggagaac  5220
ctcagccctg aggaggcggc ccaccagaaa gccgtggtgg agacccttct gcaggaggac  5280
ccgtggcgtg tggcgaagat ggtcaagtcc tacctgcagc agcacaacat ccacacgag   5340
gaggtggtcg ataccactgg cctcaaccag tcccaccctg tcccaacacct caacaagggc  5400
actcccatga agacgcagaa gcgggccgcc ctgtacacct ggtatgtccg caagcagcga  5460
gaggtggcgc agcagttcac ccatgcaggg cagggagggc tgattgaaga gcccacagga  5520
gatgagctac caaccaagaa ggggcggagg aaccgtttca agtgggccc agcatcccag  5580
cagatcctgt tccaggccta tgagaggcag aagaaccct gcaaggagga gcgagaaacg  5640
ctagtggagg agtgcaatag gcggaatgc atccagagag tgtgtcacc atcacaagca  5700
caaggtctgg gctccaacct cgtcacggag gtgcgtgtct acaactggtt tgccaaccgg  5760
cgcaaagaag aagccttccg gcacaagctg gccatgaact gcagggatga gtttcccctg  5820
atggtgtttc cttctgggca gatcagccag gcctcggcct tggccccggc ccctccccaa  5880
gtcctgcccc aggctccagc ccctgcccct gctccagcca tggtatcagc tctggccag   5940
gccccagccc ctgtcccagt cctagcccca ggccctcctc aagctgtggc cccacctgcc  6000
cccaagccca cccaagctgg ggaaggaacg ctgtcagagg ccctgctgca gctgcagttt  6060
gatgatgaag acctgggggc cttgcttggc aacagcagg acccagctgt gttcacagac  6120
ctggcatccg tcgacaactc cgagtttcag cagctgctga accagggcat acctgtggcc  6180
ccccacacaa ctgagcccat gctgatggag taccctgagg ctataactcg cctagtgaca  6240
ggggcccaga ggcccccga cccagctcct gctccactgg ggccccggg gctcccaat   6300
ggcctccttt caggagatga agacttctcc tccattgcgg acatggactt ctcagccctg  6360
ctgagtcaga tcagctccta aaggacgggt ggcatccctg tgaccctcc ccagtgcctc   6420
tcctggcct ggaagttgcc actccagtgc ccaccagcct tgtcctaata aaattaagtt  6480
gcatcattt gtctgactag gtgtccttct ataatattat ggggtggagg gggtggtat   6540
ggagcaaggg gcaagttggg aagacaacct gtaggggctct tgggaaccaa            6600
gctggagtgc agtggcacaa tcttggctca ctgcaatctc gcctcctgg ttcaagcga   6660
ttctctgcc tcagcctccc gagttgttgg gattccaggc atgcatgacc aggctcagct  6720
aattttgtt tttggtag aaacggggtt tcaccatatt ggccaggctg gtctccaact   6780
cctaatctca ggtgatctac ccaccttggc ctcccaaatt gctgggatta caggcgtgag  6840
ccactgctcc cttccctgtc cttccgaggg caatctggcc catcaagtgg ccttcgcctc  6900
tgggagtaac aaaaatgcac ttcaaaatag cttctgtaat caagctgcat gggtggagta  6960
ctccccagct gactccagga agttctctat ccaaagctat tcattaggcc agagctgtgc  7020
aaataattag tcacccactt gctccataac cctccatgac agcccaggca ttgagtccag  7080
gtgggaccat caagccatgc tctggtggct catgcattat catagaaatg ggaggcttta  7140
tttattttac taaaaagaac aaaaacaaca gactgctgtc ctttagacaa taggatcacg  7200
tcatctgagc cctctgtgcc ccaggtgaca agcccagccc caagttctct ttcctcagcc  7260
tccccacaca tgttctggag gagatgggcc cagcaggctg ctctgaggcc tggcccctcg  7320
taagccaagc atggctc                                                  7337

SEQ ID NO: 172        moltype =    length =
SEQUENCE: 172
000

SEQ ID NO: 173        moltype = AA  length = 10
FEATURE               Location/Qualifiers
source                1..10
                      mol_type = protein
                      organism = synthetic construct
SEQUENCE: 173
GFSLTSYGVS                                                           10

SEQ ID NO: 174        moltype = AA  length = 5
FEATURE               Location/Qualifiers
source                1..5
                      mol_type = protein
                      organism = synthetic construct
SEQUENCE: 174
```

```
SYGVS                                                                           5

SEQ ID NO: 175         moltype = AA  length = 6
FEATURE                Location/Qualifiers
source                 1..6
                       mol_type = protein
                       organism = synthetic construct
SEQUENCE: 175
TSYGVS                                                                          6

SEQ ID NO: 176         moltype = AA  length = 8
FEATURE                Location/Qualifiers
source                 1..8
                       mol_type = protein
                       organism = synthetic construct
SEQUENCE: 176
GFSLTSYG                                                                        8

SEQ ID NO: 177         moltype = AA  length = 9
FEATURE                Location/Qualifiers
source                 1..9
                       mol_type = protein
                       organism = synthetic construct
SEQUENCE: 177
VIWEDGSTN                                                                       9

SEQ ID NO: 178         moltype = AA  length = 16
FEATURE                Location/Qualifiers
source                 1..16
                       mol_type = protein
                       organism = synthetic construct
SEQUENCE: 178
VIWEDGSTNY HSALIS                                                              16

SEQ ID NO: 179         moltype = AA  length = 12
FEATURE                Location/Qualifiers
source                 1..12
                       mol_type = protein
                       organism = synthetic construct
SEQUENCE: 179
WIGVIWEDGS TN                                                                  12

SEQ ID NO: 180         moltype = AA  length = 7
FEATURE                Location/Qualifiers
source                 1..7
                       mol_type = protein
                       organism = synthetic construct
SEQUENCE: 180
IWEDGST                                                                         7

SEQ ID NO: 181         moltype = AA  length = 14
FEATURE                Location/Qualifiers
source                 1..14
                       mol_type = protein
                       organism = synthetic construct
SEQUENCE: 181
ARPHYGSSYV GAME                                                                14

SEQ ID NO: 182         moltype = AA  length = 15
FEATURE                Location/Qualifiers
source                 1..15
                       mol_type = protein
                       organism = synthetic construct
SEQUENCE: 182
ARPHYGSSYV GAMEY                                                               15

SEQ ID NO: 183         moltype = AA  length = 7
FEATURE                Location/Qualifiers
source                 1..7
                       mol_type = protein
                       organism = synthetic construct
SEQUENCE: 183
YSYVAWY                                                                         7

SEQ ID NO: 184         moltype = AA  length = 6
FEATURE                Location/Qualifiers
source                 1..6
                       mol_type = protein
                       organism = synthetic construct
```

```
SEQUENCE: 184
ENIYSY                                                                        6

SEQ ID NO: 185          moltype = AA  length = 10
FEATURE                 Location/Qualifiers
source                  1..10
                        mol_type = protein
                        organism = synthetic construct
SEQUENCE: 185
LLIYNAKSLA                                                                   10

SEQ ID NO: 186          moltype =    length =
SEQUENCE: 186
000

SEQ ID NO: 187          moltype = AA  length = 8
FEATURE                 Location/Qualifiers
source                  1..8
                        mol_type = protein
                        organism = synthetic construct
SEQUENCE: 187
QHHYVSPW                                                                      8

SEQ ID NO: 188          moltype = AA  length = 7
FEATURE                 Location/Qualifiers
source                  1..7
                        mol_type = protein
                        organism = Tobacco etch virus
SEQUENCE: 188
ENLYTQS                                                                       7

SEQ ID NO: 189          moltype = AA  length = 5
FEATURE                 Location/Qualifiers
source                  1..5
                        mol_type = protein
                        organism = synthetic construct
SEQUENCE: 189
DDDDK                                                                         5

SEQ ID NO: 190          moltype = AA  length = 4
FEATURE                 Location/Qualifiers
source                  1..4
                        mol_type = protein
                        organism = synthetic construct
SEQUENCE: 190
LVPR                                                                          4

SEQ ID NO: 191          moltype = AA  length = 4
FEATURE                 Location/Qualifiers
source                  1..4
                        mol_type = protein
                        organism = synthetic construct
SEQUENCE: 191
CPPC                                                                          4

SEQ ID NO: 192          moltype = AA  length = 10
FEATURE                 Location/Qualifiers
source                  1..10
                        mol_type = protein
                        organism = synthetic construct
SEQUENCE: 192
GIDLSLYRMR                                                                   10

SEQ ID NO: 193          moltype = AA  length = 5
FEATURE                 Location/Qualifiers
source                  1..5
                        mol_type = protein
                        organism = synthetic construct
SEQUENCE: 193
LYRMR                                                                         5

SEQ ID NO: 194          moltype = AA  length = 6
FEATURE                 Location/Qualifiers
source                  1..6
                        mol_type = protein
                        organism = synthetic construct
SEQUENCE: 194
SLYRMR                                                                        6
```

```
SEQ ID NO: 195          moltype = AA   length = 8
FEATURE                 Location/Qualifiers
source                  1..8
                        mol_type = protein
                        organism = synthetic construct
SEQUENCE: 195
GIDLSLYR                                                                    8

SEQ ID NO: 196          moltype = AA   length = 9
FEATURE                 Location/Qualifiers
source                  1..9
                        mol_type = protein
                        organism = synthetic construct
SEQUENCE: 196
LITDDGTSY                                                                   9

SEQ ID NO: 197          moltype = AA   length = 16
FEATURE                 Location/Qualifiers
source                  1..16
                        mol_type = protein
                        organism = synthetic construct
SEQUENCE: 197
LITDDGTSYY ADSVKG                                                          16

SEQ ID NO: 198          moltype = AA   length = 12
FEATURE                 Location/Qualifiers
source                  1..12
                        mol_type = protein
                        organism = synthetic construct
SEQUENCE: 198
LVALITDDGT SY                                                              12

SEQ ID NO: 199          moltype = AA   length = 7
FEATURE                 Location/Qualifiers
source                  1..7
                        mol_type = protein
                        organism = synthetic construct
SEQUENCE: 199
ITDDGTS                                                                     7

SEQ ID NO: 200          moltype = AA   length = 10
FEATURE                 Location/Qualifiers
source                  1..10
                        mol_type = protein
                        organism = synthetic construct
SEQUENCE: 200
NAETPLSPVN                                                                 10

SEQ ID NO: 201          moltype = AA   length = 11
FEATURE                 Location/Qualifiers
source                  1..11
                        mol_type = protein
                        organism = synthetic construct
SEQUENCE: 201
NAETPLSPVN Y                                                               11

SEQ ID NO: 202          moltype = AA   length = 11
FEATURE                 Location/Qualifiers
source                  1..11
                        mol_type = protein
                        organism = synthetic construct
SEQUENCE: 202
GGSISNSYYW G                                                               11

SEQ ID NO: 203          moltype = AA   length = 6
FEATURE                 Location/Qualifiers
source                  1..6
                        mol_type = protein
                        organism = synthetic construct
SEQUENCE: 203
NSYYWG                                                                      6

SEQ ID NO: 204          moltype = AA   length = 7
FEATURE                 Location/Qualifiers
source                  1..7
                        mol_type = protein
                        organism = synthetic construct
SEQUENCE: 204
SNSYYWG                                                                     7
```

```
SEQ ID NO: 205          moltype = AA  length = 9
FEATURE                 Location/Qualifiers
source                  1..9
                        mol_type = protein
                        organism = synthetic construct
SEQUENCE: 205
GGSISNSYY                                                                    9

SEQ ID NO: 206          moltype = AA  length = 9
FEATURE                 Location/Qualifiers
source                  1..9
                        mol_type = protein
                        organism = synthetic construct
SEQUENCE: 206
SIYHSGNTY                                                                    9

SEQ ID NO: 207          moltype = AA  length = 16
FEATURE                 Location/Qualifiers
source                  1..16
                        mol_type = protein
                        organism = synthetic construct
SEQUENCE: 207
SIYHSGNTYY NPSLKS                                                           16

SEQ ID NO: 208          moltype = AA  length = 12
FEATURE                 Location/Qualifiers
source                  1..12
                        mol_type = protein
                        organism = synthetic construct
SEQUENCE: 208
WIGSIYHSGN TY                                                               12

SEQ ID NO: 209          moltype = AA  length = 7
FEATURE                 Location/Qualifiers
source                  1..7
                        mol_type = protein
                        organism = synthetic construct
SEQUENCE: 209
IYHSGNT                                                                      7

SEQ ID NO: 210          moltype = AA  length = 13
FEATURE                 Location/Qualifiers
source                  1..13
                        mol_type = protein
                        organism = synthetic construct
SEQUENCE: 210
VTQDGVGATT TEE                                                              13

SEQ ID NO: 211          moltype = AA  length = 14
FEATURE                 Location/Qualifiers
source                  1..14
                        mol_type = protein
                        organism = synthetic construct
SEQUENCE: 211
VTQDGVGATT TEEY                                                             14

SEQ ID NO: 212          moltype = DNA  length = 103
FEATURE                 Location/Qualifiers
source                  1..103
                        mol_type = other DNA
                        organism = synthetic construct
SEQUENCE: 212
ggggccacta gggacaggat gttttagagc tagaaatagc aagttaaaat aaggctagtc           60
cgttatcaac ttgaaaaagt ggcaccgagt cggtgctttt ttt                            103

SEQ ID NO: 213          moltype = DNA  length = 20
FEATURE                 Location/Qualifiers
source                  1..20
                        mol_type = genomic DNA
                        organism = Adeno-associated virus
SEQUENCE: 213
ggggccacta gggacaggat                                                       20

SEQ ID NO: 214          moltype = DNA  length = 20
FEATURE                 Location/Qualifiers
source                  1..20
                        mol_type = other DNA
                        organism = synthetic construct
```

SEQUENCE: 214
gcacctgaat accacgcctg                                                    20

SEQ ID NO: 215      moltype = DNA   length = 20
FEATURE             Location/Qualifiers
source              1..20
                    mol_type = other DNA
                    organism = synthetic construct
SEQUENCE: 215
cgcctgcgat gtagtcgatg                                                    20

SEQ ID NO: 216      moltype = DNA   length = 20
FEATURE             Location/Qualifiers
source              1..20
                    mol_type = other DNA
                    organism = synthetic construct
SEQUENCE: 216
caggacgggc gagatgtccc                                                    20

SEQ ID NO: 217      moltype = DNA   length = 20
FEATURE             Location/Qualifiers
source              1..20
                    mol_type = other DNA
                    organism = synthetic construct
SEQUENCE: 217
ctgaatcttt ggagtacctg                                                    20

SEQ ID NO: 218      moltype = DNA   length = 20
FEATURE             Location/Qualifiers
source              1..20
                    mol_type = other DNA
                    organism = synthetic construct
SEQUENCE: 218
ggccacggag cgagacatct                                                    20

SEQ ID NO: 219      moltype = DNA   length = 20
FEATURE             Location/Qualifiers
source              1..20
                    mol_type = other DNA
                    organism = synthetic construct
SEQUENCE: 219
aagtcaactt caatgtcgga                                                    20

SEQ ID NO: 220      moltype = DNA   length = 20
FEATURE             Location/Qualifiers
source              1..20
                    mol_type = other DNA
                    organism = synthetic construct
SEQUENCE: 220
gcttggaggc ctgatcagcg                                                    20

SEQ ID NO: 221      moltype = DNA   length = 20
FEATURE             Location/Qualifiers
source              1..20
                    mol_type = other DNA
                    organism = synthetic construct
SEQUENCE: 221
cttatctctt cgcagcgagg                                                    20

SEQ ID NO: 222      moltype = DNA   length = 20
FEATURE             Location/Qualifiers
source              1..20
                    mol_type = other DNA
                    organism = synthetic construct
SEQUENCE: 222
cacacattac tccaacattg                                                    20

SEQ ID NO: 223      moltype = DNA   length = 20
FEATURE             Location/Qualifiers
source              1..20
                    mol_type = other DNA
                    organism = synthetic construct
SEQUENCE: 223
ttccgcaaaa tagagcccca                                                    20

SEQ ID NO: 224      moltype = DNA   length = 20
FEATURE             Location/Qualifiers
source              1..20
                    mol_type = other DNA -continued

```
SEQUENCE: 224
tgcacagaac tatcgtacca                                          20

SEQ ID NO: 225         moltype = DNA  length = 20
FEATURE                Location/Qualifiers
source                 1..20
                       mol_type = other DNA
                       organism = synthetic construct
SEQUENCE: 225
gcaataagac tctttaaaga                                          20

SEQ ID NO: 226         moltype = DNA  length = 20
FEATURE                Location/Qualifiers
source                 1..20
                       mol_type = other DNA
                       organism = synthetic construct
SEQUENCE: 226
caaagagatt acgaatgcct                                          20

SEQ ID NO: 227         moltype = DNA  length = 20
FEATURE                Location/Qualifiers
source                 1..20
                       mol_type = other DNA
                       organism = synthetic construct
SEQUENCE: 227
caaggcaccc caggtttcca                                          20

SEQ ID NO: 228         moltype = DNA  length = 20
FEATURE                Location/Qualifiers
source                 1..20
                       mol_type = other DNA
                       organism = synthetic construct
SEQUENCE: 228
ttacgaatgc cttggaaacc                                          20

SEQ ID NO: 229         moltype = DNA  length = 20
FEATURE                Location/Qualifiers
source                 1..20
                       mol_type = other DNA
                       organism = synthetic construct
SEQUENCE: 229
cagagacgca tctgaccctc                                          20

SEQ ID NO: 230         moltype = DNA  length = 20
FEATURE                Location/Qualifiers
source                 1..20
                       mol_type = other DNA
                       organism = synthetic construct
SEQUENCE: 230
catgcagttc tcacacactg                                          20

SEQ ID NO: 231         moltype = DNA  length = 20
FEATURE                Location/Qualifiers
source                 1..20
                       mol_type = other DNA
                       organism = synthetic construct
SEQUENCE: 231
gtgtgagaac tgcatggaga                                          20

SEQ ID NO: 232         moltype = DNA  length = 20
FEATURE                Location/Qualifiers
source                 1..20
                       mol_type = other DNA
                       organism = synthetic construct
SEQUENCE: 232
tctcatttca ggaaaccact                                          20

SEQ ID NO: 233         moltype = DNA  length = 20
FEATURE                Location/Qualifiers
source                 1..20
                       mol_type = other DNA
                       organism = synthetic construct
SEQUENCE: 233
agtcatacac cttaaccaag                                          20

SEQ ID NO: 234         moltype = DNA  length = 20
FEATURE                Location/Qualifiers
source                 1..20
```

```
                        mol_type = other DNA
                        organism = synthetic construct
SEQUENCE: 234
ttcaaggaaa ccagttgagg                                               20

SEQ ID NO: 235          moltype = DNA   length = 20
FEATURE                 Location/Qualifiers
source                  1..20
                        mol_type = other DNA
                        organism = synthetic construct
SEQUENCE: 235
gagccttgcc tggaaatctg                                               20

SEQ ID NO: 236          moltype = DNA   length = 20
FEATURE                 Location/Qualifiers
source                  1..20
                        mol_type = other DNA
                        organism = synthetic construct
SEQUENCE: 236
aagcgtcaaa agtctgccag                                               20

SEQ ID NO: 237          moltype = DNA   length = 20
FEATURE                 Location/Qualifiers
source                  1..20
                        mol_type = other DNA
                        organism = synthetic construct
SEQUENCE: 237
cgttccaact cgaagtgcca                                               20

SEQ ID NO: 238          moltype = DNA   length = 20
FEATURE                 Location/Qualifiers
source                  1..20
                        mol_type = other DNA
                        organism = synthetic construct
SEQUENCE: 238
gagcgactgg gacacggtga                                               20

SEQ ID NO: 239          moltype = DNA   length = 20
FEATURE                 Location/Qualifiers
source                  1..20
                        mol_type = other DNA
                        organism = synthetic construct
SEQUENCE: 239
gctgcgcaag aagggcccta                                               20

SEQ ID NO: 240          moltype = DNA   length = 20
FEATURE                 Location/Qualifiers
source                  1..20
                        mol_type = other DNA
                        organism = synthetic construct
SEQUENCE: 240
ttgttctggc cagcagcccc                                               20

SEQ ID NO: 241          moltype = DNA   length = 20
FEATURE                 Location/Qualifiers
source                  1..20
                        mol_type = other DNA
                        organism = synthetic construct
SEQUENCE: 241
cttccagagc cacatcatcg                                               20

SEQ ID NO: 242          moltype = DNA   length = 20
FEATURE                 Location/Qualifiers
source                  1..20
                        mol_type = other DNA
                        organism = synthetic construct
SEQUENCE: 242
gggactcacc agagagaggt                                               20

SEQ ID NO: 243          moltype = DNA   length = 20
FEATURE                 Location/Qualifiers
source                  1..20
                        mol_type = other DNA
                        organism = synthetic construct
SEQUENCE: 243
cggtcgaaat agaagcccta                                               20

SEQ ID NO: 244          moltype = DNA   length = 20
FEATURE                 Location/Qualifiers
```

```
source                  1..20
                        mol_type = other DNA
                        organism = synthetic construct
SEQUENCE: 244
aaaaggatat tgtgcaactg                                                    20

SEQ ID NO: 245          moltype = DNA   length = 20
FEATURE                 Location/Qualifiers
source                  1..20
                        mol_type = other DNA
                        organism = synthetic construct
SEQUENCE: 245
tgtgcatatt tattacatcg                                                    20

SEQ ID NO: 246          moltype = DNA   length = 20
FEATURE                 Location/Qualifiers
source                  1..20
                        mol_type = other DNA
                        organism = synthetic construct
SEQUENCE: 246
tttgtgaaga tcttgaccaa                                                    20

SEQ ID NO: 247          moltype = DNA   length = 20
FEATURE                 Location/Qualifiers
source                  1..20
                        mol_type = other DNA
                        organism = synthetic construct
SEQUENCE: 247
tgtcatgctg aaccgcattg                                                    20

SEQ ID NO: 248          moltype = DNA   length = 20
FEATURE                 Location/Qualifiers
source                  1..20
                        mol_type = other DNA
                        organism = synthetic construct
SEQUENCE: 248
ccactctatg aggatagtca                                                    20

SEQ ID NO: 249          moltype = DNA   length = 20
FEATURE                 Location/Qualifiers
source                  1..20
                        mol_type = other DNA
                        organism = synthetic construct
SEQUENCE: 249
ttgacataga agaggcacaa                                                    20

SEQ ID NO: 250          moltype = DNA   length = 20
FEATURE                 Location/Qualifiers
source                  1..20
                        mol_type = other DNA
                        organism = synthetic construct
SEQUENCE: 250
gagtactaca ctcagcagca                                                    20

SEQ ID NO: 251          moltype = DNA   length = 20
FEATURE                 Location/Qualifiers
source                  1..20
                        mol_type = other DNA
                        organism = synthetic construct
SEQUENCE: 251
tcacgcacaa gaaacgtcca                                                    20

SEQ ID NO: 252          moltype = DNA   length = 20
FEATURE                 Location/Qualifiers
source                  1..20
                        mol_type = other DNA
                        organism = synthetic construct
SEQUENCE: 252
aggtctcggt gaaaccacct                                                    20

SEQ ID NO: 253          moltype = DNA   length = 20
FEATURE                 Location/Qualifiers
source                  1..20
                        mol_type = other DNA
                        organism = synthetic construct
SEQUENCE: 253
agcattatcc aaagagtccg                                                    20

SEQ ID NO: 254          moltype = DNA   length = 20
```

```
FEATURE              Location/Qualifiers
source               1..20
                     mol_type = other DNA
                     organism = synthetic construct
SEQUENCE: 254
atattaattc ttaccagtgg                                                    20

SEQ ID NO: 255       moltype = DNA   length = 20
FEATURE              Location/Qualifiers
source               1..20
                     mol_type = other DNA
                     organism = synthetic construct
SEQUENCE: 255
agctttaaat caaggttcat                                                    20

SEQ ID NO: 256       moltype = DNA   length = 20
FEATURE              Location/Qualifiers
source               1..20
                     mol_type = other DNA
                     organism = synthetic construct
SEQUENCE: 256
atcccgagcc ctaaggtgca                                                    20

SEQ ID NO: 257       moltype = DNA   length = 20
FEATURE              Location/Qualifiers
source               1..20
                     mol_type = other DNA
                     organism = synthetic construct
SEQUENCE: 257
ggcagcgcgg aggacagcgt                                                    20

SEQ ID NO: 258       moltype = DNA   length = 20
FEATURE              Location/Qualifiers
source               1..20
                     mol_type = other DNA
                     organism = synthetic construct
SEQUENCE: 258
ctcaggggc tactaccacc                                                     20

SEQ ID NO: 259       moltype = DNA   length = 20
FEATURE              Location/Qualifiers
source               1..20
                     mol_type = other DNA
                     organism = synthetic construct
SEQUENCE: 259
gtcaccgacg agaccagaag                                                    20

SEQ ID NO: 260       moltype = DNA   length = 20
FEATURE              Location/Qualifiers
source               1..20
                     mol_type = other DNA
                     organism = synthetic construct
SEQUENCE: 260
gtcgtggact tcgtactgct                                                    20

SEQ ID NO: 261       moltype = DNA   length = 20
FEATURE              Location/Qualifiers
source               1..20
                     mol_type = other DNA
                     organism = synthetic construct
SEQUENCE: 261
taatttttag gcaagtgtcg                                                    20

SEQ ID NO: 262       moltype = DNA   length = 20
FEATURE              Location/Qualifiers
source               1..20
                     mol_type = other DNA
                     organism = synthetic construct
SEQUENCE: 262
ttagctgtta gacttgaata                                                    20

SEQ ID NO: 263       moltype = DNA   length = 20
FEATURE              Location/Qualifiers
source               1..20
                     mol_type = other DNA
                     organism = synthetic construct
SEQUENCE: 263
cgagagccgt caacttgcgt                                                    20
```

-continued

| | | |
|---|---|---|
| SEQ ID NO: 264 | moltype = DNA  length = 20 | |
| FEATURE | Location/Qualifiers | |
| source | 1..20<br>mol_type = other DNA<br>organism = synthetic construct | |
| SEQUENCE: 264<br>cggcttcaac tgcaaaggtg | | 20 |
| SEQ ID NO: 265 | moltype = DNA  length = 20 | |
| FEATURE | Location/Qualifiers | |
| source | 1..20<br>mol_type = other DNA<br>organism = synthetic construct | |
| SEQUENCE: 265<br>tatgaaaaag cagagcgact | | 20 |
| SEQ ID NO: 266 | moltype = DNA  length = 20 | |
| FEATURE | Location/Qualifiers | |
| source | 1..20<br>mol_type = other DNA<br>organism = synthetic construct | |
| SEQUENCE: 266<br>tctggcgggc gagctcacgc | | 20 |
| SEQ ID NO: 267 | moltype = DNA  length = 20 | |
| FEATURE | Location/Qualifiers | |
| source | 1..20<br>mol_type = other DNA<br>organism = synthetic construct | |
| SEQUENCE: 267<br>ctcacgctgg ttaccgccta | | 20 |
| SEQ ID NO: 268 | moltype = DNA  length = 20 | |
| FEATURE | Location/Qualifiers | |
| source | 1..20<br>mol_type = other DNA<br>organism = synthetic construct | |
| SEQUENCE: 268<br>aaagattacg aacttccctg | | 20 |
| SEQ ID NO: 269 | moltype = DNA  length = 20 | |
| FEATURE | Location/Qualifiers | |
| source | 1..20<br>mol_type = other DNA<br>organism = synthetic construct | |
| SEQUENCE: 269<br>gttaaaaaca gacatgccta | | 20 |
| SEQ ID NO: 270 | moltype = DNA  length = 20 | |
| FEATURE | Location/Qualifiers | |
| source | 1..20<br>mol_type = other DNA<br>organism = synthetic construct | |
| SEQUENCE: 270<br>atgcctaagg aggttgtacc | | 20 |
| SEQ ID NO: 271 | moltype = DNA  length = 20 | |
| FEATURE | Location/Qualifiers | |
| source | 1..20<br>mol_type = other DNA<br>organism = synthetic construct | |
| SEQUENCE: 271<br>ctccaggtat cccatcgaaa | | 20 |
| SEQ ID NO: 272 | moltype = DNA  length = 20 | |
| FEATURE | Location/Qualifiers | |
| source | 1..20<br>mol_type = other DNA<br>organism = synthetic construct | |
| SEQUENCE: 272<br>caccaaatac gatagatcag | | 20 |
| SEQ ID NO: 273 | moltype = DNA  length = 20 | |
| FEATURE | Location/Qualifiers | |
| source | 1..20<br>mol_type = other DNA<br>organism = synthetic construct | |
| SEQUENCE: 273<br>tggcggcgtg aatggcaaga | | 20 |

```
SEQ ID NO: 274              moltype = DNA  length = 20
FEATURE                     Location/Qualifiers
source                      1..20
                            mol_type = other DNA
                            organism = synthetic construct
SEQUENCE: 274
taggatggta gcacacaacc                                                   20

SEQ ID NO: 275              moltype = DNA  length = 20
FEATURE                     Location/Qualifiers
source                      1..20
                            mol_type = other DNA
                            organism = synthetic construct
SEQUENCE: 275
cagcagcaga gccccgacgg                                                   20

SEQ ID NO: 276              moltype = DNA  length = 20
FEATURE                     Location/Qualifiers
source                      1..20
                            mol_type = other DNA
                            organism = synthetic construct
SEQUENCE: 276
cggcgtgcga acggaatgtg                                                   20

SEQ ID NO: 277              moltype = DNA  length = 20
FEATURE                     Location/Qualifiers
source                      1..20
                            mol_type = other DNA
                            organism = synthetic construct
SEQUENCE: 277
tatagacgct gcccgacgtc                                                   20

SEQ ID NO: 278              moltype = DNA  length = 20
FEATURE                     Location/Qualifiers
source                      1..20
                            mol_type = other DNA
                            organism = synthetic construct
SEQUENCE: 278
tccaaagaag ggtactgtgg                                                   20

SEQ ID NO: 279              moltype = DNA  length = 20
FEATURE                     Location/Qualifiers
source                      1..20
                            mol_type = other DNA
                            organism = synthetic construct
SEQUENCE: 279
acagtaccct tctttggaat                                                   20

SEQ ID NO: 280              moltype = DNA  length = 20
FEATURE                     Location/Qualifiers
source                      1..20
                            mol_type = other DNA
                            organism = synthetic construct
SEQUENCE: 280
gcgacgggcg catctacgtg                                                   20

SEQ ID NO: 281              moltype = DNA  length = 20
FEATURE                     Location/Qualifiers
source                      1..20
                            mol_type = other DNA
                            organism = synthetic construct
SEQUENCE: 281
cccgacctcc ataagtcctg                                                   20

SEQ ID NO: 282              moltype = DNA  length = 20
FEATURE                     Location/Qualifiers
source                      1..20
                            mol_type = other DNA
                            organism = synthetic construct
SEQUENCE: 282
ggggtcctcg aagcgcacga                                                   20

SEQ ID NO: 283              moltype = DNA  length = 20
FEATURE                     Location/Qualifiers
source                      1..20
                            mol_type = other DNA
                            organism = synthetic construct
SEQUENCE: 283
```

```
tgctctgttt agaagatgac                                              20

SEQ ID NO: 284          moltype = DNA   length = 20
FEATURE                 Location/Qualifiers
source                  1..20
                        mol_type = other DNA
                        organism = synthetic construct
SEQUENCE: 284
atattctttt ctagttaaag                                              20

SEQ ID NO: 285          moltype = DNA   length = 20
FEATURE                 Location/Qualifiers
source                  1..20
                        mol_type = other DNA
                        organism = synthetic construct
SEQUENCE: 285
cctgtaaaga aacaaaagac                                              20

SEQ ID NO: 286          moltype = DNA   length = 20
FEATURE                 Location/Qualifiers
source                  1..20
                        mol_type = other DNA
                        organism = synthetic construct
SEQUENCE: 286
tggagaaaga cgtaacttcg                                              20

SEQ ID NO: 287          moltype = DNA   length = 20
FEATURE                 Location/Qualifiers
source                  1..20
                        mol_type = other DNA
                        organism = synthetic construct
SEQUENCE: 287
tctgccctga ggtatgcgat                                              20

SEQ ID NO: 288          moltype = DNA   length = 20
FEATURE                 Location/Qualifiers
source                  1..20
                        mol_type = other DNA
                        organism = synthetic construct
SEQUENCE: 288
attccgcttg gtgaaaacga                                              20

SEQ ID NO: 289          moltype = DNA   length = 20
FEATURE                 Location/Qualifiers
source                  1..20
                        mol_type = other DNA
                        organism = synthetic construct
SEQUENCE: 289
caggcacaat agaaacaacg                                              20

SEQ ID NO: 290          moltype = DNA   length = 20
FEATURE                 Location/Qualifiers
source                  1..20
                        mol_type = other DNA
                        organism = synthetic construct
SEQUENCE: 290
ccatttgtaa tgctgacttg                                              20

SEQ ID NO: 291          moltype = DNA   length = 20
FEATURE                 Location/Qualifiers
source                  1..20
                        mol_type = other DNA
                        organism = synthetic construct
SEQUENCE: 291
ctgggtcact tgtgccgtgg                                              20

SEQ ID NO: 292          moltype = DNA   length = 20
FEATURE                 Location/Qualifiers
source                  1..20
                        mol_type = other DNA
                        organism = synthetic construct
SEQUENCE: 292
gtcagggttc tggatatctg                                              20

SEQ ID NO: 293          moltype = DNA   length = 20
FEATURE                 Location/Qualifiers
source                  1..20
                        mol_type = other DNA
                        organism = synthetic construct
```

| | | |
|---|---|---|
| SEQUENCE: 293 tggatttaga gtctctcagc | | 20 |
| SEQ ID NO: 294 FEATURE source | moltype = DNA  length = 20 Location/Qualifiers 1..20 mol_type = other DNA organism = synthetic construct | |
| SEQUENCE: 294 ctgcggctgt ggtccagctg | | 20 |
| SEQ ID NO: 295 FEATURE source | moltype = DNA  length = 20 Location/Qualifiers 1..20 mol_type = other DNA organism = synthetic construct | |
| SEQUENCE: 295 acaaaactgt gctagacatg | | 20 |
| SEQ ID NO: 296 FEATURE source | moltype = DNA  length = 20 Location/Qualifiers 1..20 mol_type = other DNA organism = synthetic construct | |
| SEQUENCE: 296 ttcttcccca gcccaggtaa | | 20 |
| SEQ ID NO: 297 FEATURE source | moltype = DNA  length = 20 Location/Qualifiers 1..20 mol_type = other DNA organism = synthetic construct | |
| SEQUENCE: 297 cgtcatgagc agattaaacc | | 20 |
| SEQ ID NO: 298 FEATURE source | moltype = DNA  length = 20 Location/Qualifiers 1..20 mol_type = other DNA organism = synthetic construct | |
| SEQUENCE: 298 gagagcgcct gcgacccgag | | 20 |
| SEQ ID NO: 299 FEATURE source | moltype = DNA  length = 20 Location/Qualifiers 1..20 mol_type = other DNA organism = synthetic construct | |
| SEQUENCE: 299 ccagcgggtg aagtacacca | | 20 |
| SEQ ID NO: 300 FEATURE source | moltype = DNA  length = 20 Location/Qualifiers 1..20 mol_type = other DNA organism = synthetic construct | |
| SEQUENCE: 300 ggagcgcttt tcgccgccag | | 20 |
| SEQ ID NO: 301 FEATURE source | moltype = DNA  length = 20 Location/Qualifiers 1..20 mol_type = other DNA organism = synthetic construct | |
| SEQUENCE: 301 tgaggcctgg accttatgca | | 20 |
| SEQ ID NO: 302 FEATURE source | moltype = DNA  length = 20 Location/Qualifiers 1..20 mol_type = other DNA organism = synthetic construct | |
| SEQUENCE: 302 cctggtggag tgaaccatga | | 20 |
| SEQ ID NO: 303 FEATURE source | moltype = DNA  length = 20 Location/Qualifiers 1..20 mol_type = other DNA | |

```
                              -continued organism = synthetic construct
SEQUENCE: 303
caagcactta ggttcccctg                                             20

SEQ ID NO: 304        moltype = DNA  length = 20
FEATURE               Location/Qualifiers
source                1..20
                      mol_type = other DNA
                      organism = synthetic construct
SEQUENCE: 304
ggtctcccta caattcagcg                                             20

SEQ ID NO: 305        moltype = DNA  length = 20
FEATURE               Location/Qualifiers
source                1..20
                      mol_type = other DNA
                      organism = synthetic construct
SEQUENCE: 305
cacagcgcgt gactgcaatg                                             20

SEQ ID NO: 306        moltype = DNA  length = 20
FEATURE               Location/Qualifiers
source                1..20
                      mol_type = other DNA
                      organism = synthetic construct
SEQUENCE: 306
tctggggcac caattctagg                                             20

SEQ ID NO: 307        moltype = DNA  length = 20
FEATURE               Location/Qualifiers
source                1..20
                      mol_type = other DNA
                      organism = synthetic construct
SEQUENCE: 307
gagccatgct tggcttacga                                             20

SEQ ID NO: 308        moltype = DNA  length = 20
FEATURE               Location/Qualifiers
source                1..20
                      mol_type = other DNA
                      organism = synthetic construct
SEQUENCE: 308
gtacaagtac ttatctcatg                                             20

SEQ ID NO: 309        moltype = DNA  length = 20
FEATURE               Location/Qualifiers
source                1..20
                      mol_type = other DNA
                      organism = synthetic construct
SEQUENCE: 309
gagataacaa cataacaaca                                             20

SEQ ID NO: 310        moltype = DNA  length = 20
FEATURE               Location/Qualifiers
source                1..20
                      mol_type = other DNA
                      organism = synthetic construct
SEQUENCE: 310
catattccat agtctttggg                                             20

SEQ ID NO: 311        moltype = DNA  length = 20
FEATURE               Location/Qualifiers
source                1..20
                      mol_type = other DNA
                      organism = synthetic construct
SEQUENCE: 311
ctgcccctta gcaacttagg                                             20

SEQ ID NO: 312        moltype = DNA  length = 20
FEATURE               Location/Qualifiers
source                1..20
                      mol_type = other DNA
                      organism = synthetic construct
SEQUENCE: 312
tgtttaaaaa tatgttgaca                                             20

SEQ ID NO: 313        moltype = DNA  length = 20
FEATURE               Location/Qualifiers
source                1..20
```

```
                            mol_type = other DNA
                            organism = synthetic construct
SEQUENCE: 313
ccaggaatgg aaactcacgc                                                    20

SEQ ID NO: 314              moltype = DNA   length = 20
FEATURE                     Location/Qualifiers
source                      1..20
                            mol_type = other DNA
                            organism = synthetic construct
SEQUENCE: 314
gaggccgctg aattaacccg                                                    20

SEQ ID NO: 315              moltype = DNA   length = 20
FEATURE                     Location/Qualifiers
source                      1..20
                            mol_type = other DNA
                            organism = synthetic construct
SEQUENCE: 315
atacacgcac acttgcagaa                                                    20

SEQ ID NO: 316              moltype = DNA   length = 20
FEATURE                     Location/Qualifiers
source                      1..20
                            mol_type = other DNA
                            organism = synthetic construct
SEQUENCE: 316
gagcagacag aaacccaggg                                                    20

SEQ ID NO: 317              moltype = DNA   length = 20
FEATURE                     Location/Qualifiers
source                      1..20
                            mol_type = other DNA
                            organism = synthetic construct
SEQUENCE: 317
tgagtctcca aacagaacag                                                    20

SEQ ID NO: 318              moltype = DNA   length = 20
FEATURE                     Location/Qualifiers
source                      1..20
                            mol_type = other DNA
                            organism = synthetic construct
SEQUENCE: 318
taatatcact gacttcacgg                                                    20

SEQ ID NO: 319              moltype = DNA   length = 20
FEATURE                     Location/Qualifiers
source                      1..20
                            mol_type = other DNA
                            organism = synthetic construct
SEQUENCE: 319
tacacacaat gtaagcagca                                                    20

SEQ ID NO: 320              moltype = DNA   length = 20
FEATURE                     Location/Qualifiers
source                      1..20
                            mol_type = other DNA
                            organism = synthetic construct
SEQUENCE: 320
gggagctcaa ttcgaaacca                                                    20

SEQ ID NO: 321              moltype = DNA   length = 20
FEATURE                     Location/Qualifiers
source                      1..20
                            mol_type = other DNA
                            organism = synthetic construct
SEQUENCE: 321
ttggacaggt gagacagtcg                                                    20

SEQ ID NO: 322              moltype = DNA   length = 20
FEATURE                     Location/Qualifiers
source                      1..20
                            mol_type = other DNA
                            organism = synthetic construct
SEQUENCE: 322
aagctcactc agatagtgtg                                                    20

SEQ ID NO: 323              moltype = DNA   length = 20
FEATURE                     Location/Qualifiers
```

```
source                  1..20
                        mol_type = other DNA
                        organism = synthetic construct
SEQUENCE: 323
caggagaacc accttacacg                                                       20

SEQ ID NO: 324          moltype = DNA   length = 20
FEATURE                 Location/Qualifiers
source                  1..20
                        mol_type = other DNA
                        organism = synthetic construct
SEQUENCE: 324
ggacagaccc tgattcacaa                                                       20

SEQ ID NO: 325          moltype = DNA   length = 20
FEATURE                 Location/Qualifiers
source                  1..20
                        mol_type = other DNA
                        organism = synthetic construct
SEQUENCE: 325
acatggcagt ctatgaacag                                                       20

SEQ ID NO: 326          moltype = DNA   length = 20
FEATURE                 Location/Qualifiers
source                  1..20
                        mol_type = other DNA
                        organism = synthetic construct
SEQUENCE: 326
cctatagaga gtactacttg                                                       20

SEQ ID NO: 327          moltype = DNA   length = 20
FEATURE                 Location/Qualifiers
source                  1..20
                        mol_type = other DNA
                        organism = synthetic construct
SEQUENCE: 327
ccaaccgggt cttcattacg                                                       20

SEQ ID NO: 328          moltype = DNA   length = 20
FEATURE                 Location/Qualifiers
source                  1..20
                        mol_type = other DNA
                        organism = synthetic construct
SEQUENCE: 328
tcaagcgtag agttccgagt                                                       20

SEQ ID NO: 329          moltype = DNA   length = 20
FEATURE                 Location/Qualifiers
source                  1..20
                        mol_type = other DNA
                        organism = synthetic construct
SEQUENCE: 329
tcatgcaatt atggacccag                                                       20

SEQ ID NO: 330          moltype = DNA   length = 20
FEATURE                 Location/Qualifiers
source                  1..20
                        mol_type = other DNA
                        organism = synthetic construct
SEQUENCE: 330
cgggaaagtg actggccatg                                                       20

SEQ ID NO: 331          moltype = DNA   length = 20
FEATURE                 Location/Qualifiers
source                  1..20
                        mol_type = other DNA
                        organism = synthetic construct
SEQUENCE: 331
tgagattgaa atcaaatcgg                                                       20

SEQ ID NO: 332          moltype = DNA   length = 20
FEATURE                 Location/Qualifiers
source                  1..20
                        mol_type = other DNA
                        organism = synthetic construct
SEQUENCE: 332
tatgcaatat tcatcacgcg                                                       20

SEQ ID NO: 333          moltype = DNA   length = 20
```

-continued

```
FEATURE          Location/Qualifiers
source           1..20
                 mol_type = other DNA
                 organism = synthetic construct
SEQUENCE: 333
aatgtgttaa atcaaatgca                                    20
```

The invention claimed is:

1. One or more recombinant nucleic acid molecule(s), wherein the one or more recombinant nucleic acid molecules(s) encode:
   a. a first chimeric polypeptide comprising a priming receptor comprising a first extracellular antigen-binding domain that specifically binds to Alkaline Phosphatase, Germ Cell (ALPG/P), wherein the first extracellular antigen-binding domain comprises a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3, wherein:
      i. CDR-H1 comprises the sequence set forth in SEQ ID NO: 1,
      ii. CDR-H2 comprises the sequence set forth in SEQ ID NO: 2,
      iii. CDR-H3 comprises the sequence set forth in SEQ ID NO: 3,
      iv. CDR-L1 comprises the sequence set forth in SEQ ID NO: 4,
      v. CDR-L2 comprises the sequence set forth in SEQ ID NO: 5, and
      vi. CDR-L3 comprises the sequence set forth in SEQ ID NO: 6; and
   b. a second chimeric polypeptide comprising a chimeric antigen receptor (CAR) comprising a second extracellular antigen-binding domain that specifically binds to mesothelin (MSLN), wherein the second extracellular antigen-binding domain comprises a VHH comprising a variable heavy (VH) chain sequence comprising three heavy chain CDR sequences, CDR-H1, CDR-H2, and CDR-H3, wherein:
      i. CDR-H1 comprises the sequence set forth in SEQ ID NO: 14,
      ii. CDR-H2 comprises the sequence set forth in SEQ ID NO: 15, and
      iii. CDR-H3 comprises the sequence set forth in SEQ ID NO: 16.

2. One or more expression vector(s) comprising the recombinant nucleic acid molecule(s) of claim 1.

3. A cell comprising the one or more recombinant nucleic acid molecule(s) of claim 1.

4. A pharmaceutical composition comprising the cell of claim 3, and a pharmaceutically acceptable excipient.

5. The cell of claim 3, wherein the cell is a primary human immune cell.

6. The cell of claim 5, wherein the primary human immune cell is a primary human T cell that is a CD8+ T cell or a CD4+ T cell.

7. The recombinant nucleic acid molecule(s) of claim 1, wherein the first extracellular antigen-binding domain VH chain sequence comprises the sequence as set forth in SEQ ID NO: 7 and the VL chain sequence comprises the sequence as set forth in SEQ ID NO: 8.

8. One or more expression vector(s) comprising the recombinant nucleic acid molecule(s) of claim 7.

9. A cell comprising the one or more recombinant nucleic acid molecule(s) of claim 7.

10. A pharmaceutical composition comprising the cell of claim 9, and a pharmaceutically acceptable excipient.

11. The recombinant nucleic acid molecule(s) of claim 1, wherein the first extracellular antigen-binding domain comprises the sequence set forth in SEQ ID NO: 9.

12. The recombinant nucleic acid molecule(s) of claim 1, wherein the second extracellular antigen-binding domain VH chain sequence comprises the sequence as set forth in SEQ ID NO: 17.

13. One or more expression vector(s) comprising the recombinant nucleic acid molecule(s) of claim 12.

14. A cell comprising the one or more recombinant nucleic acid molecule(s) of claim 12.

15. A pharmaceutical composition comprising the cell of claim 14, and a pharmaceutically acceptable excipient.

16. The recombinant nucleic acid molecule(s) of claim 1, wherein the first extracellular antigen-binding domain VH chain sequence comprises the sequence as set forth in SEQ ID NO: 7, and the VL chain sequence comprises the sequence as set forth in SEQ ID NO: 8, and wherein the second extracellular antigen-binding domain VH chain sequence comprises the sequence as set forth in SEQ ID NO: 17.

17. One or more expression vector(s) comprising the recombinant nucleic acid molecule(s) of claim 16.

18. A cell comprising the one or more recombinant nucleic acid molecule(s) of claim 16.

19. A pharmaceutical composition comprising the cell of claim 18, and a pharmaceutically acceptable excipient.

20. The recombinant nucleic acid molecule(s) of claim 1, wherein the priming receptor comprises the sequence as set forth in SEQ ID NO: 24.

21. The recombinant nucleic acid molecule(s) of claim 1, wherein the chimeric antigen receptor (CAR) comprises the sequence as set forth in SEQ ID NO: 30.

22. The recombinant nucleic acid molecule(s) of claim 1, wherein the priming receptor comprises the sequence as set forth in SEQ ID NO: 24 and the chimeric antigen receptor (CAR) comprises the sequence as set forth in SEQ ID NO: 30.

23. A polypeptide system comprising
   a. a first chimeric polypeptide comprising a priming receptor comprising a first extracellular antigen-binding domain that specifically binds to Alkaline Phosphatase, Germ Cell (ALPG/P), wherein the first extracellular antigen-binding domain comprises a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3, wherein:

i. CDR-H1 comprises the sequence set forth in SEQ ID NO: 1,
ii. CDR-H2 comprises the sequence set forth in SEQ ID NO: 2,
iii. CDR-H3 comprises the sequence set forth in SEQ ID NO: 3,
iv. CDR-L1 comprises the sequence set forth in SEQ ID NO: 4,
v. CDR-L2 comprises the sequence set forth in SEQ ID NO: 5, and
vi. CDR-L3 comprises the sequence set forth in SEQ ID NO: 6; and
b. a second chimeric polypeptide comprising a chimeric antigen receptor (CAR) comprising a second extracellular antigen-binding domain that specifically binds to mesothelin (MSLN), wherein the second extracellular antigen-binding domain comprises a VHH comprising a variable heavy (VH) chain sequence comprising three heavy chain CDR sequences, CDR-H1, CDR-H2, and CDR-H3, wherein:
i. CDR-H1 comprises the sequence set forth in SEQ ID NO: 14,
ii. CDR-H2 comprises the sequence set forth in SEQ ID NO: 15, and
iii. CDR-H3 comprises the sequence set forth in SEQ ID NO: 16.

24. The system of claim 23, wherein the first extracellular antigen-binding domain VH chain sequence comprises the sequence as set forth in SEQ ID NO: 7 and the VL chain sequence comprises the sequence as set forth in SEQ ID NO: 8.

25. The system of claim 23, wherein the first extracellular antigen-binding domain comprises the sequence set forth in SEQ ID NO: 9.

26. The system of claim 23, wherein the second extracellular antigen-binding domain VH chain sequence comprises the sequence as set forth in SEQ ID NO: 17.

27. The system of claim 23, wherein the first extracellular antigen-binding domain VH chain sequence comprises the sequence as set forth in SEQ ID NO: 7, and the VL chain sequence comprises the sequence as set forth in SEQ ID NO: 8, and wherein the second extracellular antigen-binding domain VH chain sequence comprises the sequence as set forth in SEQ ID NO: 17.

28. The system of claim 23, wherein the priming receptor comprises the sequence as set forth in SEQ ID NO: 24.

29. The system of claim 23, wherein the chimeric antigen receptor (CAR) comprises the sequence as set forth in SEQ ID NO: 30.

30. A cell comprising the system of claim 23.

31. A pharmaceutical composition comprising the cell of claim 30, and a pharmaceutically acceptable excipient.

32. The polypeptide system of claim 23, wherein the priming receptor comprises, from N-terminus to C-terminus,
a. the first extracellular antigen-binding domain;
b. a first transmembrane domain comprising one or more ligand-inducible proteolytic cleavage sites; and
c. an intracellular domain comprising a human or humanized transcriptional effector, wherein binding of ALPG/P by the first extracellular antigen-binding domain results in cleavage at the one or more ligand-inducible proteolytic cleavage sites.

33. The polypeptide system of claim 32, wherein the priming receptor further comprises a first hinge domain positioned between the first extracellular antigen-binding domain and the first transmembrane domain wherein the first hinge comprises the sequence as set forth in SEQ ID NO: 18.

34. The polypeptide system of claim 32, wherein the first transmembrane domain comprises the sequence as set forth in SEQ ID NO: 19.

35. The polypeptide system of claim 32, wherein the intracellular domain comprises the sequence as set forth in SEQ ID NO: 23.

36. The polypeptide system of claim 32, wherein the priming receptor further comprises a stop-transfer-sequence between the first transmembrane domain and the intracellular domain and wherein the stop-transfer-sequence comprises the sequence as set forth in SEQ ID NO: 20.

37. The polypeptide system of claim 23, wherein the CAR comprises, from N-terminus to C-terminus,
a. a second extracellular antigen-binding domain;
b. a second transmembrane domain;
c. an intracellular co-stimulatory domain; and
d. an intracellular activation domain.

38. The polypeptide system of claim 37, wherein the CAR further comprises a second hinge domain positioned between the second extracellular antigen-binding domain and the second transmembrane domain and wherein the second hinge domain comprises the sequence as set forth in SEQ ID NO: 26.

39. The polypeptide system of claim 37, wherein the second transmembrane domain comprises the sequence as set forth in SEQ ID NO: 27.

40. The polypeptide system of claim 37, wherein the intracellular co-stimulatory domain comprises a 4-1BB domain comprising the sequence as set forth in SEQ ID NO: 28.

41. The polypeptide system of claim 37, wherein the intracellular activation domain comprises a CD3ζ domain comprising the sequence as set forth in SEQ ID NO: 29.

42. The recombinant nucleic acid molecule(s) of claim 1, wherein the priming receptor comprises, from N-terminus to C-terminus,
a. the first extracellular antigen-binding domain;
b. a first transmembrane domain comprising one or more ligand-inducible proteolytic cleavage sites; and
c. an intracellular domain comprising a human or humanized transcriptional effector, wherein binding of ALPG/P by the first extracellular antigen-binding domain results in cleavage at the one or more ligand-inducible proteolytic cleavage sites.

43. The recombinant nucleic acid molecule(s) of claim 42, wherein the priming receptor further comprises a first hinge domain positioned between the first extracellular antigen-binding domain and the first transmembrane domain and wherein the hinge comprises the sequence as set forth in SEQ ID NO: 18.

44. The recombinant nucleic acid molecule(s) of claim 42, wherein the first transmembrane domain comprises the sequence as set forth in SEQ ID NO: 19.

45. The recombinant nucleic acid molecule(s) of claim 42, wherein the intracellular domain comprises the sequence as set forth in SEQ ID NO: 23.

46. The recombinant nucleic acid molecule(s) of claim 42, wherein the priming receptor further comprises a stop-transfer-sequence between the first transmembrane domain and the intracellular domain and wherein the stop-transfer-sequence comprises the sequence as set forth in SEQ ID NO: 20.

47. The recombinant nucleic acid molecule(s) of claim 1, wherein the recombinant nucleic acid molecule(s) encoding the priming receptor comprises the sequence set forth in SEQ ID NO: 36.

48. The recombinant nucleic acid molecule(s) of claim 1, wherein the CAR comprises, from N-terminus to C-terminus,
   a. a second extracellular antigen-binding domain;
   b. a second transmembrane domain;
   c. an intracellular co-stimulatory domain; and
   d. an intracellular activation domain.

49. The recombinant nucleic acid molecule(s) of claim 48, wherein the CAR comprises a second hinge domain positioned between the second extracellular antigen-binding domain and the second transmembrane domain and wherein the second hinge domain comprises the sequence as set forth in SEQ ID NO: 26.

50. The recombinant nucleic acid molecule(s) of claim 48, wherein the second transmembrane domain comprises the sequence as set forth in SEQ ID NO: 27.

51. The recombinant nucleic acid molecule(s) of claim 48, wherein the intracellular co-stimulatory domain comprises a 4-1BB domain comprising the sequence as set forth in SEQ ID NO: 28.

52. The recombinant nucleic acid molecule(s) of claim 48, wherein the intracellular activation domain comprises a CD35 domain comprising the sequence as set forth in SEQ ID NO: 29.

53. The recombinant nucleic acid molecule(s) of claim 1, wherein the recombinant nucleic acid molecule(s) encoding the chimeric antigen receptor comprises the sequence set forth in SEQ ID NO: 37.

54. The recombinant nucleic acid molecule(s) of claim 1, wherein the recombinant nucleic acid molecule(s) further comprises an inducible promoter operably linked to the nucleotide sequence encoding the CAR.

55. The recombinant nucleic acid molecule(s) of claim 1, wherein the recombinant nucleic acid molecule(s) further comprises a first constitutive promoter operably linked to the nucleotide sequence encoding the priming receptor.

56. A polypeptide system comprising
   a. a first chimeric polypeptide comprising a priming receptor comprising a first extracellular antigen-binding domain that specifically binds to Alkaline Phosphatase, Germ Cell (ALPG/P), wherein the priming receptor comprises the sequence as set forth in SEQ ID NO: 24; and
   b. a second chimeric polypeptide comprising a chimeric antigen receptor (CAR) comprising a second extracellular antigen-binding domain that specifically binds to mesothelin (MSLN), wherein the chimeric antigen receptor (CAR) comprises the sequence as set forth in SEQ ID NO: 30.

57. A cell comprising the system of claim 56.

58. The cell of claim 57, wherein the cell is a primary human T cell that is a CD8+ T cell or a CD4+ T cell.

59. A pharmaceutical composition comprising the cell of claim 57, and a pharmaceutically acceptable excipient.

60. One or more recombinant nucleic acid molecule(s), wherein the one or more recombinant nucleic acid molecule(s) encode:
   a. a first chimeric polypeptide comprising a priming receptor comprising a first extracellular antigen-binding domain that specifically binds to Alkaline Phosphatase, Germ Cell (ALPG/P), wherein the priming receptor comprises the sequence as set forth in SEQ ID NO: 24; and
   b. a second chimeric polypeptide comprising a chimeric antigen receptor (CAR) comprising a second extracellular antigen-binding domain that specifically binds to mesothelin (MSLN), wherein the chimeric antigen receptor (CAR) comprises the sequence as set forth in SEQ ID NO: 30.

61. The recombinant nucleic acid molecule(s) of claim 60, wherein the recombinant nucleic acid molecule(s) further comprises an inducible promoter operably linked to the nucleotide sequence encoding the CAR.

62. The recombinant nucleic acid molecule(s) of claim 60, wherein the recombinant nucleic acid molecule(s) further comprises a first constitutive promoter operably linked to the nucleotide sequence encoding the priming receptor.

63. One or more expression vector(s) comprising the recombinant nucleic acid molecule(s) of claim 60.

64. A cell comprising the one or more recombinant nucleic acid molecule(s) of claim 60.

65. The cell of claim 64, wherein the cell is a primary human T cell that is a CD8+ T cell or a CD4+ T cell.

66. A primary human T cell comprising one or more recombinant nucleic acid molecule(s), wherein the one or more recombinant nucleic acid molecule(s) encode:
   a. a first chimeric polypeptide comprising a priming receptor comprising a first extracellular antigen-binding domain that specifically binds to Alkaline Phosphatase, Germ Cell (ALPG/P), wherein the first extracellular antigen-binding domain comprises a variable heavy (VH) chain sequence comprising three heavy chain CDR sequences, CDR-H1, CDR-H2, and CDR-H3, and a variable light (VL) chain sequence comprising three light chain CDR sequences, CDR-L1, CDR-L2, and CDR-L3, wherein:
      i. CDR-H1 comprises the sequence set forth in SEQ ID NO: 1,
      ii. CDR-H2 comprises the sequence set forth in SEQ ID NO: 2,
      iii. CDR-H3 comprises the sequence set forth in SEQ ID NO: 3,
      iv. CDR-L1 comprises the sequence set forth in SEQ ID NO: 4,
      v. CDR-L2 comprises the sequence set forth in SEQ ID NO: 5, and
      vi. CDR-L3 comprises the sequence set forth in SEQ ID NO: 6; and
   b. a second chimeric polypeptide comprising a chimeric antigen receptor (CAR) comprising a second extracellular antigen-binding domain that specifically binds to mesothelin (MSLN), wherein the second extracellular antigen-binding domain comprises a VHH comprising a variable heavy (VH) chain sequence comprising three heavy chain CDR sequences, CDR-H1, CDR-H2, and CDR-H3, wherein:
      i. CDR-H1 comprises the sequence set forth in SEQ ID NO: 14,
      ii. CDR-H2 comprises the sequence set forth in SEQ ID NO: 15, and
      iii. CDR-H3 comprises the sequence set forth in SEQ ID NO: 16.

67. The primary human T cell of claim 66, wherein the first extracellular antigen-binding domain VH chain sequence comprises the sequence as set forth in SEQ ID NO: 7, and the VL chain sequence comprises the sequence as set forth in SEQ ID NO: 8, and wherein the second extracellular antigen-binding domain VH chain sequence comprises the sequence as set forth in SEQ ID NO: 17.

68. The primary human T cell of claim 67, wherein the priming receptor comprises the sequence as set forth in SEQ ID NO: 24 and the chimeric antigen receptor (CAR) comprises the sequence as set forth in SEQ ID NO: 30.

69. The primary human T cell of claim 66, wherein the T cell is a CD8+ T cell or a CD4+ T cell.

70. A population of cells comprising a plurality of the primary human T cell of claim 66, wherein the population comprises CD8+ T cells and CD4+ T cells.

71. A pharmaceutical composition comprising the population of cells of claim 70, and a pharmaceutically acceptable excipient.

* * * * *